(12) United States Patent
Heiser et al.

(10) Patent No.: US 8,486,940 B2
(45) Date of Patent: Jul. 16, 2013

(54) INHIBITORS

(75) Inventors: Ulrich Heiser, Halle/Saale (DE); Daniel Ramsbeck, Halle/Saale (DE); Robert Sommer, Halle/Saale (DE); Antje Meyer, Halle/Saale (DE); Torsten Hoffmann, Halle/Saale (DE); Livia Boehme, Halle/Saale (DE); Hans-Ulrich Demuth, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 146 days.

(21) Appl. No.: 12/880,369

(22) Filed: Sep. 13, 2010

(65) Prior Publication Data

US 2011/0092501 A1 Apr. 21, 2011

Related U.S. Application Data

(60) Provisional application No. 61/241,432, filed on Sep. 11, 2009.

(51) Int. Cl.
| | |
|---|---|
| A61K 31/535 | (2006.01) |
| A61K 31/497 | (2006.01) |
| A61K 31/42 | (2006.01) |
| A61K 31/415 | (2006.01) |
| A61K 31/40 | (2006.01) |
| C07D 211/06 | (2006.01) |
| C07D 265/30 | (2006.01) |
| C07D 241/02 | (2006.01) |
| C07D 263/02 | (2006.01) |
| C07D 233/02 | (2006.01) |

(52) U.S. Cl.
USPC ............... 514/234.5; 514/252.12; 514/374; 514/385; 514/408; 544/106; 544/336; 546/195; 548/215; 548/300.1

(58) Field of Classification Search
USPC .. 514/234.5, 252.12, 385, 374, 408; 544/106, 544/336; 546/195; 548/215, 300.1
See application file for complete search history.

(56) References Cited

U.S. PATENT DOCUMENTS

2004/0209865 A1  10/2004  Stenkamp et al.

FOREIGN PATENT DOCUMENTS

| WO | 2005/075436 | 8/2005 |
| WO | 2006/128692 | 12/2006 |
| WO | 2008/151927 | 12/2008 |
| WO | 2009/042907 | 4/2009 |
| WO | 2009/134750 | 11/2009 |
| WO | 2010/026212 | 3/2010 |
| WO | 2008/055947 | 12/2010 |

OTHER PUBLICATIONS

Ramla et al., Synthesis and inhibitory activity of new benzimidazole derivatives against Burkitt's lymphoma promotion, Bioorganic & Medicinal Chemistry, 2007, 15:6489-6496.
CAplus accession RN 948885-28-7, citing document dated 2007.
CAplus accession RN 948885-29-8, citing document dated 2007.
CAplus accession RN 948885-30-1, citing document dated 2007.
CAplus accession RN 948885-31-2, citing document dated 2007.
CAplus accession RN 948885-32-3, citing document dated 2007.
CAplus accession RN 948885-33-4, citing document dated 2007.
CAplus accession RN 916253-13-9, citing document dated 2006.

*Primary Examiner* — Paul Zarek
(74) *Attorney, Agent, or Firm* — Dentons US LLP

(57) ABSTRACT

The invention relates to novel pyrrolidine derivatives of formula (I):

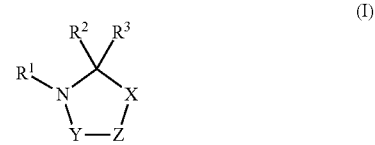

wherein $R^1$, $R^2$ and $R^3$ are as defined herein, as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

33 Claims, No Drawings

INHIBITORS

CROSS-REFERENCE TO RELATED APPLICATIONS

This application claims priority from U.S. Provisional Application Ser. No. 61/241,432 filed on Sep. 11, 2009, which is incorporated herein by reference in its entirety.

MATERIAL INCORPORATED BY REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The invention relates to novel pyrrolidine derivatives as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Inhibitors of QC are described in WO 2004/098625, WO 2004/098591, WO 2005/039548, WO 2005/075436, WO 2008/055945, WO 2008/055947, WO 2008/055950, WO2008/065141, WO 2008/110523, WO 2008/128981, WO 2008/128982, WO 2008/128983, WO 2008/128984, WO 2008/128985, WO 2008/128986, WO 2008/128987 and WO 2010/026212.

EP 02 011 349.4 discloses polynucleotides encoding insect glutaminyl cyclase, as well as polypeptides encoded thereby and their use in methods of screening for agents that reduce glutaminyl cyclase activity. Such agents are useful as pesticides.

DEFINITIONS

The terms "$k_i$," or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins where the proline is in amino acid position 3 or higher counted from the N-terminus of a peptide or protein substrate.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC. Examples of QC-like enzymes are the glutaminyl-peptide cyclotransferase-like proteins (QPCTLs) from human (GenBank NM_017659), mouse (GenBank BC058181), *Macaca fascicularis* (GenBank AB168255), *Macaca mulatta* (GenBank XM_001110995), *Canis familiaris* (GenBank XM_541552), *Rattus norvegicus* (GenBank XM_001066591), *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

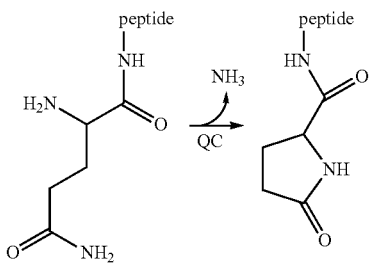

Scheme 2: Cyclization of L-homoglutamine by QC

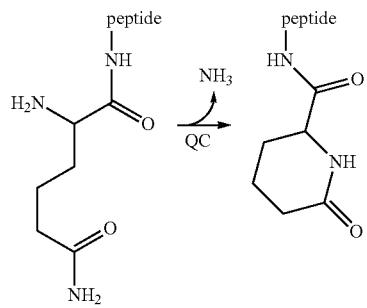

The term "EC" as used herein comprises the activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with an $IC_{50}$ for QC inhibition of 10 μM or less, more preferably of 1 μM or less, even more preferably of 0.1 μM or less or 0.01 μM or less, or most preferably 0.001 μM or less. Indeed, inhibitors with $K_i$ values in the lower micromolar, preferably the nanomolar and even more preferably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, preferably of 350 g/mole or less, and even more preferably of 300 g/mole or less and even of 250 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Throughout the description and the claims the expression "alkyl", unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-pro- Scheme 3: N-terminal cyclization of uncharged glutamyl peptides by QC (EC)

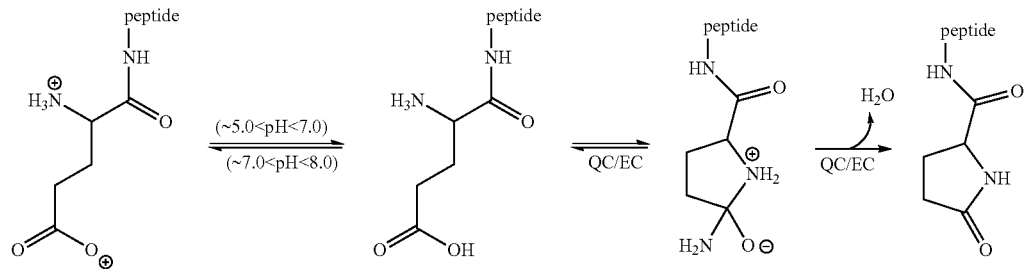

poxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)_n$— wherein n is an integer e.g. 2-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine.

The expression "-alkylaryl", unless specifically limited, denotes an aryl residue which is connected via an alkylene moiety e.g. a $C_{1-4}$alkylene moiety.

The expression "-alkylheteroaryl", unless specifically limited, denotes a heteroaryl residue which is connected via an alkylene moiety e.g. a $C_{1-4}$alkylene moiety.

The term "halogen" or "halo" comprises fluorine (F), chlorine (Cl) and bromine (Br).

The term "amino" refers to the group —$NH_2$.

The term "phenyl substituted by phenyl" refers to biphenyl.

The term " "‿‿‿" " denotes a single bond where the stereochemistry is not defined.

When benzimidazolyl is shown as benzimidazol-5-yl, which is represented as:

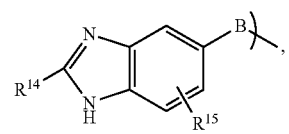

the person skilled in the art will appreciate that benzimidazol-6-yl, which is represented as:

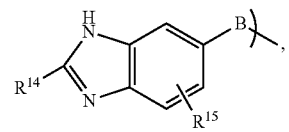

is an equivalent structure. As employed herein, the two forms of benzimidazolyl are covered by the term "benzimidazol-5-yl".

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

A protecting group or protective group is introduced into a molecule by chemical modification of a functional group in order to obtain chemoselectivity in a subsequent chemical reaction. Protecting groups are e.g. alcohol protecting groups, amine protecting groups, carbonyl protecting groups, carboxylic acid protecting groups and phosphate protecting groups.

Examples for alcohol protecting groups are acetyl (Ac), benzoyl (Bz), benzyl (Bn, Bnl) β-methoxyethoxymethyl ether (MEM), mimethoxytrityl [bis-(4-methoxyphenyl)phenylmethyl, DMT], methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), trityl (triphenylmethyl, Tr), silyl ethers (such as trimethylsilyl ether (TMS), tert-butyldimethylsilyl ether (TBDMS), tert-butyldimethylsilyloxymethyl ether (TOM), and triisopropylsilyl ether (TIPS)); methyl ethers and ethoxyethyl ethers (EE).

Suitable amine protecting groups are selected from carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), p-methoxybenzyl (PMB), 3,4-dimethoxybenzyl (DMPM), p-methoxyphenyl (PMP), tosyl (Ts), and other sulfonamides (Nosyl & Nps).

Suitable carbonyl protecting groups are selected from acetals and ketals, acylals and dithianes.

Suitable carboxylic acid protecting groups are selected from methyl esters, benzyl esters, tert-butyl esters, silyl esters, orthoesters, and oxazoline.

Examples for phosphate protecting groups are 2-cyanoethyl and methyl (Me)

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

ABBREVIATIONS (DHQ)$_2$PHAL hydroquinine 1,4-phthalazinediyl diether
AcOH acetic acid
DAD diode array detector
DCC dicyclohexyl carbodiimide
DEA Diethylamine
DHAP/DAHC dihydroxyacetone phosphate/dihydro-5-azacytidine
DMF dimethylformamide
DMSO dimethylsulfoxide
EDTA ethylenediamine-N,N,N',N'-tetraacetic acid
EtOAc ethyl acetate
EtOH ethanol
FPLC fast performance liquid chromatography
HPLC high performance liquid chromatography
IPA isopropanole
LD-TOF laser-desorption time-of-flight mass spectrometry
ML mother lye
MS mass spectromtry
NMR nuclear magnetic resonance
Pd$_2$dba$_3$ tris(dibenzylideneacetone)dipalladium
TEA triethyl amine
TFA trifluoroacetic acid
THF tetrahydrofuran
TLC thin layer chromatography
TMSCN trimethylsilyl cyanide

SUMMARY OF THE INVENTION

According to the invention there are provided a compound of formula (I):

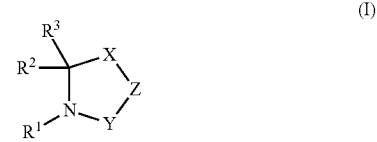

or a pharmaceutically acceptable salt, solvate or polymorph thereof, including all tautomers and stereoisomers thereof wherein:

$R^1$ represents heteroaryl, -carbocyclyl-heteroaryl, —C$_{2-6}$alkenylheteroaryl, —C$_{1-6}$alkylheteroaryl, or (CH$_2$)$_a$CR$^5$R$^6$ (CH$_2$)$_b$heteroaryl wherein a and b independently represent integers 0-5 provided that a+b=0-5 and $R^5$ and $R^6$ are alkylene which together with the carbon to which they are attached form a C$_3$-C$_5$ cycloalkyl group;

in which any of aforesaid heteroaryl groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

and in which any of aforesaid carbocyclyl groups may optionally be substituted by one or more groups selected from C$_{1-4}$alkyl, oxo, halogen and C$_{1-4}$alkoxy;

$R^2$ represents H, C$_{1-8}$alkyl, aryl, heteroaryl, carbocyclyl, heterocyclyl, —C$_{1-4}$alkylaryl, —C$_{1-4}$alkylheteroaryl, —C$_{1-4}$alkylcarbocyclyl or —C$_{1-4}$alkylheterocyclyl;

in which any of aforesaid aryl and heteroaryl groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, C$_{1-6}$alkoxy-C$_{1-6}$alkoxy-, nitro, halogen, haloC$_{1-6}$alkyl, haloC$_{1-6}$alkoxy, cyano, hydroxyl, —C(O)OH, —NH$_2$, —NHC$_{1-4}$alkyl, —N(C$_{1-4}$alkyl)(C$_{1-4}$alkyl, —N(C$_{1-4}$alkyl)(C$_{1-4}$alkyl)-N(C$_{1-4}$alkyl)(C$_{1-4}$alkyl), —C$_{1-4}$alkyl-N(C$_{1-4}$alkyl)(C$_{1-4}$alkyl), —C$_{1-4}$alkoxy-N(C$_{1-4}$alkyl)(C$_{1-4}$alkyl), —N(C$_{3-8}$ cycloalkyll)(C$_{3-8}$cycloalkyl), —N(—C$_{1-6}$alkyl-C$_{1-6}$alkoxy)(—C$_{1-6}$alkyl-C$_{1-6}$alkoxy), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

and in which any of aforesaid carbocyclyl and heterocyclyl groups may optionally be substituted by one or more groups selected from C$_{1-4}$alkyl, oxo, halogen, —C(O)C$_{1-6}$alkyl and C$_{1-4}$alkoxy;

or R² represents phenyl substituted by phenyl, phenyl substituted by a monocyclic heteroaryl group, phenyl substituted by phenoxy, phenyl substituted by heterocyclyl, phenyl substituted by heterocyclyl wherein said heterocyclyl is substituted by phenyl, phenyl substituted by —O—C$_{1-4}$alkyl-heterocyclyl, phenyl substituted by benzyloxy, phenyl substituted by carbocyclyl, phenyl substituted by carbocyclyl wherein said carbocyclyl is substituted by heterocyclyl, phenyl substituted by —O-carbocyclyl, heterocyclyl substituted by phenyl, carbocyclyl substituted by phenyl, phenyl fused to carbocyclyl, phenyl fused to heterocyclyl, —C$_{1-4}$alkyl(phenyl substituted by phenyl), —C$_{1-4}$alkyl(phenyl substituted by a monocyclic heteroaryl group), —C$_{1-4}$alkyl(phenyl substituted by a monocyclic heterocyclyl group), —C$_{1-4}$alkyl(phenyl substituted by an —O-carbocyclyl group), —C$_{1-4}$alkyl(phenyl substituted by benzyloxy), —C$_{1-4}$alkyl(optionally substituted phenyl fused to optionally substituted carbocyclyl or —C$_{1-4}$alkyl (optionally substituted phenyl fused to optionally substituted heterocyclyl);
in which any of aforesaid phenyl, benzyloxy and heteroaryl groups may optionally be substituted by one or more groups selected from C$_{1-4}$alkyl, halogen and C$_{1-4}$alkoxy, and in which any of aforesaid carbocyclyl and heterocyclyl groups may optionally be substituted by one or more groups selected from methyl, phenyl, oxo, halogen, hydroxyl and C$_{1-4}$alkoxy;
R³ represents H, —C$_{1-4}$alkyl or aryl;
in which aforesaid aryl may optionally be substituted by one or more groups selected from C$_{1-6}$alkyl, C$_{2-6}$alkenyl, C$_{2-6}$alkynyl, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and, —C(O)NH(C$_{3-10}$cycloalkyl);
or R² and R³ are joined to form a carbocyclyl ring which is optionally substituted by one or more C$_{1-2}$alkyl groups;
or R² and R³ are joined to form a carbocyclyl ring which is fused to phenyl, wherein aforesaid carbocyclyl and/or phenyl may optionally be substituted by one or more groups selected from C$_{1-4}$alkyl, halogen and C$_{1-4}$alkoxy;
or R² and R³ are joined to form a carbocyclyl ring which is fused to monocyclic heteroaryl, wherein aforesaid carbocyclyl and/or heteroaryl may optionally be substituted by one or more groups selected from C$_{1-4}$alkyl, halogen and C$_{1-4}$alkoxy;
X represents C=O, O, S, CR⁷R⁸, —O—CH$_2$— or —CH$_2$—CH$_2$—;
Y represents CHR⁹, C=O or C=S;
Z represents —N—R⁴, O or CHR¹⁰, such that when X represents O or S, Z must represent CHR¹⁰;
or X and Z represent two adjacent carbon atoms of a phenyl ring which is fused in that position and which is optionally substituted by one or more halogen or C$_{1-2}$alkyl groups;
R⁴ represents H, —C(O)C$_{1-6}$alkyl or —NH$_2$;
R⁷ and R⁸ independently represent H, —C$_{1-4}$ alkyl or aryl;
in which said aforesaid aryl may be optionally substituted by C$_{1-6}$alkyl, C$_{2-6}$alkenyl, C$_{2-6}$alkynyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and, —C(O)NH(C$_{3-10}$cycloalkyl);

R⁹ and R¹⁰ independently represent H or methyl;
provided that the moiety —Y—Z—X— represents a moiety other than —C(=O)—N(—R⁴)—C(=O)— or —C(=S)—N(—R⁴)—C(=O)—.

Other objects and features will be in part apparent and in part pointed out hereinafter.

DETAILED DESCRIPTION OF THE INVENTION

In one particular embodiment of the invention, there is provided a compound of formula (I):

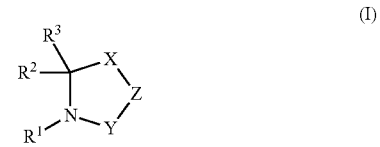

(I)

or a pharmaceutically acceptable salt, solvate or polymorph thereof, including all tautomers and stereoisomers thereof wherein:
R¹ represents heteroaryl, -carbocyclyl-heteroaryl, —C$_{2-6}$alkenylheteroaryl, —C$_{1-6}$alkylheteroaryl, or (CH$_2$)$_a$CR⁵R⁶(CH$_2$)$_b$heteroaryl wherein a and b independently represent integers 0-5 provided that a+b=0-5 and R⁵ and R⁶ are alkylene which together with the carbon to which they are attached form a C$_3$-C$_5$ cycloalkyl group;
in which any of aforesaid heteroaryl groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);
and in which any of aforesaid carbocyclyl groups may optionally be substituted by one or more groups selected from C$_{1-4}$alkyl, oxo, halogen and C$_{1-4}$alkoxy;
R² represents H, C$_{1-8}$alkyl, aryl, heteroaryl, carbocyclyl, heterocyclyl, —C$_{1-4}$alkylaryl, —C$_{1-4}$alkylheteroaryl, —C$_{1-4}$alkylcarbocyclyl or —C$_{1-4}$alkylheterocyclyl;
in which any of aforesaid aryl and heteroaryl groups may optionally be substituted by one or more groups selected from C$_{1-6}$alkyl, C$_{2-6}$alkenyl, C$_{2-6}$alkynyl, C$_{1-6}$haloalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, haloC$_{1-6}$alkyl, haloC$_{1-6}$alkoxy, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);
and in which any of aforesaid carbocyclyl and heterocyclyl groups may optionally be substituted by one or more groups selected from C$_{1-4}$alkyl, oxo, halogen and C$_{1-4}$alkoxy;

or R² represents phenyl substituted by phenyl, phenyl substituted by a monocyclic heteroaryl group, phenyl substituted by phenoxy, phenyl substituted by heterocyclyl, phenyl substituted by —O—C$_{1-4}$alkyl-heterocyclyl, phenyl substituted by benzyloxy, phenyl fused to carbocyclyl, phenyl fused to heterocyclyl, —C$_{1-4}$alkyl(phenyl substituted by phenyl), —C$_{1-4}$alkyl(phenyl substituted by a monocyclic heteroaryl group), —C$_{1-4}$alkyl(phenyl substituted by benzyloxy), —C$_{1-4}$alkyl(optionally substituted phenyl fused to optionally substituted carbocyclyl or —C$_{1-4}$alkyl(optionally substituted phenyl fused to optionally substituted heterocyclyl);
 in which any of aforesaid phenyl, benzyloxy and heteroaryl groups may optionally be substituted by one or more groups selected from C$_{1-4}$alkyl, halogen and C$_{1-4}$alkoxy, and in which any of aforesaid carbocyclyl and heterocyclyl groups may optionally be substituted by one or more groups selected from methyl, phenyl, oxo, halogen and C$_{1-4}$alkoxy;
R³ represents H, —C$_{1-4}$alkyl or aryl;
 in which aforesaid aryl may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-6}$cycloalkyl, C$_{3-6}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and, —C(O)NH(C$_{3-10}$cycloalkyl);
or R² and R³ are joined to form a carbocyclyl ring which is optionally substituted by one or more C$_{1-2}$alkyl groups;
or R² and R³ are joined to form a carbocyclyl ring which is fused to phenyl, wherein aforesaid carbocyclyl and/or phenyl may optionally be substituted by one or more groups selected from C$_{1-4}$alkyl, halogen and C$_{1-4}$alkoxy;
or R² and R³ are joined to form a carbocyclyl ring which is fused to monocyclic heteroaryl, wherein aforesaid carbocyclyl and/or heteroaryl may optionally be substituted by one or more groups selected from C$_{1-4}$alkyl, halogen and C$_{1-4}$alkoxy;
X represents C=O, O, S, CR⁷R⁸, —O—CH$_2$— or —CH$_2$—CH$_2$—;
Y represents CHR⁹, C=O or C=S;
Z represents —N—R⁴, O or CHR¹⁰, such that when X represents O or S, Z must represent CHR¹⁰;
or X and Z represent two adjacent carbon atoms of a phenyl ring which is fused in that position and which is optionally substituted by one or more halogen or C$_{1-2}$alkyl groups;
R⁴ represents H, —C$_{1-6}$alkyl, —C(O)C$_{1-6}$alkyl or —NH$_2$;
R⁷ and R⁸ independently represent H, —C$_{1-4}$ alkyl or aryl;
 in which said aforesaid aryl may be optionally substituted by C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and, —C(O)NH(C$_{3-10}$cycloalkyl);

R⁹ and R¹⁰ independently represent H or methyl;
provided that the moiety —Y—Z—X— represents a moiety other than —C(=O)—N(—R⁴)—C(=O)— or —C(=S)—N(—R⁴)—C(=O)—.

When carbocyclyl and heterocyclyl are substituted, they are typically substituted by 1 or 2 substituents (e.g. 1 substituent). Typically the substituent is methyl. More typically carbocyclyl and heterocyclyl groups are unsubstituted.

When aryl and heteroaryl are substituted, they are typically substituted by 1, 2 or 3 (e.g. 1 or 2) substituents. Substituents for aryl and heteroaryl are selected from C$_{1-6}$alkyl (e.g. methyl), C$_{2-6}$alkenyl (e.g. buten-3-yl), C$_{2-6}$alkynyl (e.g. butyn-3-yl), C$_{1-6}$haloalkyl (e.g. fluoromethyl, trifluoromethyl), —C$_{1-6}$thioalkyl (e.g. —S-methyl), —SOC$_{1-4}$alkyl (e.g. —SOmethyl), —SO$_2$C$_{1-4}$alkyl (e.g. —SO$_2$-methyl), C$_{1-6}$alkoxy- (e.g. methoxy, ethoxy), —O—C$_{3-8}$cycloalkyl (e.g. —O-cyclopentyl), C$_{3-8}$cycloalkyl (e.g. cyclopropyl, cyclohexyl), —SO$_2$C$_{3-8}$cycloalkyl (e.g. —SO$_2$cyclohexyl), —SOC$_{3-6}$cycloalkyl (e.g. —SOcyclopropyl), C$_{3-6}$alkenyloxy- (e.g. —O-buten-2-yl), C$_{3-6}$alkynyloxy- (e.g. —O-buten-2-yl), —C(O)C$_{1-6}$alkyl (e.g. —C(O)ethyl), —C(O)OC$_{1-6}$alkyl (e.g. —C(O)O-methyl), C$_{1-6}$alkoxy-C$_{1-6}$alkyl- (e.g. methoxy-ethyl-), nitro, halogen (e.g. fluoro, chloro, bromo), cyano, hydroxyl, —C(O)OH, —NH$_2$, —NHC$_{1-4}$alkyl (e.g. —NHmethyl), —N(C$_{1-4}$alkyl)(C$_{1-4}$alkyl) (e.g. —N(methyl)$_2$), —C(O)N(C$_{1-4}$alkyl)(C$_{1-4}$alkyl) (e.g. —C(O)N(methyl)$_2$), —C(O)NH$_2$, —C(O)NH(C$_{1-4}$alkyl) (e.g. —C(O)NHmethyl), —C(O)NH(C$_{3-18}$cycloalkyl) (e.g. —C(O)NHcyclopropyl). More typically, substituents will be selected from C$_{1-6}$alkyl (e.g. methyl), C$_{1-6}$haloalkyl (e.g. C$_{1-6}$-fluoroalkyl, e.g. CF$_3$), C$_{1-6}$alkoxy (e.g. OMe), halogen and hydroxy.

When R¹ represents heteroaryl, examples include monocyclic (e.g. 5 and 6 membered) and bicyclic (e.g. 9 and 10 membered, particularly 9 membered) heteroaryl rings, especially rings containing nitrogen atoms (e.g. 1 or 2 nitrogen atoms). A suitable bicyclic heteroaryl ring is a 9-membered heteroaryl ring containing 1 or 2 nitrogen atoms, especially a benzene ring fused to a 5-membered ring containing one or two nitrogen atoms (e.g. 1H-benzoimidazolyl). Most suitably the point of attachment is through a benzene ring, e.g. the group is 1H-benzoimidazol-5-yl. Aforementioned heteroaryl groups may either be unsubstituted (which is more typical) or may suitably be substituted by one or more (e.g. 1 or 2) substituents selected from alkyl (e.g. C$_{1-4}$ alkyl such as Me), alkoxy- (e.g. C$_{1-4}$ alkoxy- such as OMe) and halogen (e.g. F).

When R¹ represents —C$_{3-8}$-carbocyclyl-heteroaryl, examples of carbocyclyl include cycloalkyl (e.g. cyclohexyl) and cycloalkenyl (e.g. cyclohexenyl), examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is more typical) or may suitably be substituted by one or more (e.g. 1 or 2) substituents selected from alkyl (e.g. C$_{1-4}$ alkyl such as Me), alkoxy- (e.g. C$_{1-4}$alkoxy- such as OMe) and halogen (e.g. F). A suitable heteroaryl group is imidazol-1-yl. An exemplary —C$_{3-8}$-carbocyclyl-heteroaryl group is 3-imidazol-1-yl-cyclohexyl-.

When R¹ represents —C$_{2-6}$alkenyheteroaryl, examples of C$_{2-6}$ alkenyl include C$_{2-4}$ alkenyl, in particular propenyl and examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is more typical) or may suitably be substituted by one or more (e.g. 1 or 2) substituents selected from alkyl (e.g.

$C_{1-4}$alkyl such as Me), alkoxy- (e.g. $C_{1-4}$ alkoxy- such as OMe) and halogen (e.g. F). A suitable heteroaryl group is imidazolyl, particularly imidazol-1-yl. An exemplary -alkenylheteroaryl group is 3-imidazol-1-yl-prop-2-enyl-.

When $R^1$ represents —$C_{1-6}$alkylheteroaryl, examples of $C_{1-6}$ alkyl include $C_{1-5}$alkyl or $C_{1-4}$alkyl, especially $C_{2-5}$alkyl or $C_{2-4}$ alkyl, in particular propyl, and examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is most typical) or may suitably be substituted by one or more (e.g. 1 or 2) substituents selected from alkyl (e.g. $C_{1-4}$ alkyl such as Me), alkoxy- (e.g. $C_{1-4}$ alkoxy- such as OMe) and halogen (e.g. F). A suitable heteroaryl group is imidazol-1-yl. A particularly suitable -alkylheteroaryl group is 3-imidazol-1-yl-propyl-.

When $R^1$ represents —$C_{1-6}$alkylheteroaryl, examples wherein alkyl is branched include:

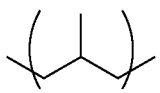
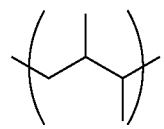
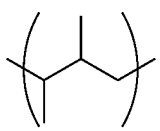

When $R^1$ represents $(CH_2)_aCR^5R^6 (CH_2)_b$heteroaryl wherein a and b independently represent integers 0-5 provided that a+b=0-5 and $R^5$ and $R^6$ are alkylene which together with the carbon to which they are attached form a $C_3$-$C_5$ cycloalkyl group, examples include:

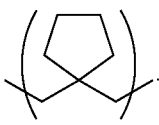

Particular examples of $R^1$ heteroaryl groups include a 5-membered ring containing 2 or 3 nitrogen atoms, which ring may optionally be substituted (e.g. in particular by one or two groups, such as methyl, for example:

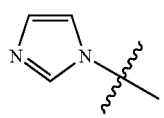
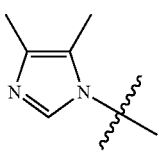
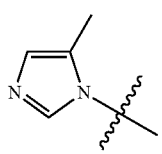
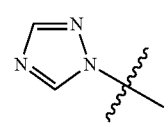

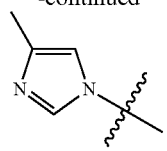

Other examples of $R^1$ heteroaryl groups include a 9-membered bicyclic ring containing 2 nitrogen atoms, which ring may optionally be substituted, for example:

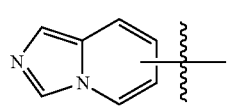
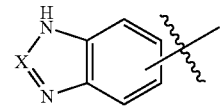

X = O, S

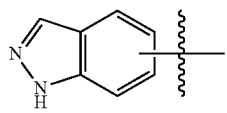
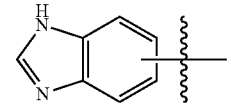

Clearly, the heteroaryl groups shown above may also be present as part of a larger $R^1$ function such as —$C_{3-8}$-carbocyclyl-heteroaryl, —$C_{2-6}$alkenylheteroaryl or —$C_{1-6}$alkylheteroaryl.

When $R^2$ represents —$C_{1-8}$alkyl, examples include methyl, ethyl, propyl (e.g. n-propyl, isopropyl), butyl (e.g. n-butyl- sec-butyl, isobutyl and tert-butyl), pentyl (e.g. n-pentyl, 3,3,-dimethylpropyl), hexyl, heptyl and octyl.

When $R^2$ represents optionally substituted aryl, aryl may typically represent phenyl. Exemplary substituted phenyl groups include 3-methylphenyl-, 2,3-dichlorophenyl-, 2,3-difluorophenyl-, 2,4-dichlorophenyl-, 2,4-difluororophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2,6-difluoro-4-(methoxy)phenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-difluorophenyl-, 3,4-dimethylphenyl-, 3,4,5-trifluorophenyl-, 3,5-bis(trifluororomethyl)phenyl-, 3,5-dimethoxyphenyl-, 2-methoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-, 4-ethoxyphenyl-, 4-propoxyphenyl-, 4-butoxyphenyl-, 4-pentoxyphenyl-, 4-isopropyloxyphenyl-, 4-tetrafluoroethyloxyphenyl-. Alternatively, $R^2$ may represent unsubstituted phenyl-. Further exemplary substituted phenyl groups include 2,3,4-trifluorophenyl, 2,3-difluoro-4-methylphenyl, 2-bromo-4-fluorophenyl-, 2-bromo-5-fluorophenyl-, 2-chlorophenyl-, 2-fluorophenyl-, 2-fluoro-5-(trifluoromethyl)phenyl-, 2-hydroxy-3-methoxyphenyl-, 2-hydroxy-5-methylphenyl-, 3-chlorophenyl-, 3-fluorophenyl-, 3-fluoro-4-(trifluoromethyl)phenyl-, 3-fluoro-5-(trifluoromethyl)phenyl-, 2-fluoro-4-(trifluoromethyl)phenyl-, 3-fluoro-4-(methoxy)phenyl-, 3-hydroxy-4-methoxyphenyl-, 4-bromo-2-fluorophenyl, 4-chloro-3-(trifluoromethyl)phenyl-, 4-chloro-3-methylphenyl, 4-chlorophenyl-, 4-fluorophenyl- and 4-propoxyphenyl-.

When $R^2$ represents optionally substituted aryl and aryl represents naphthyl, examples include unsubstituted naphthyl (e.g. naphthalen-1-yl, naphthalen-2-yl, naphthalen-3-yl) as well as substituted naphthyl (e.g. 4-methyl-naphthalen-2-yl-, 5-methyl-naphthalen-3-yl-, 7-methyl-naphthalen-3-y- and 4-fluoro-naphthalen-2-yl-).

When $R^2$ represents optionally substituted heteroaryl, examples include monocyclic rings (e.g. 5 or 6 membered rings) and bicyclic rings (e.g. 9 or 10 membered rings) which may optionally be substituted. Example 5 membered rings include pyrrolyl (e.g. pyrrol-2-yl) and imidazolyl (e.g. 1H-imidazol-2-yl or 1H-imidazol-4-yl), pyrazolyl (e.g. 1H-pyrazol-3-yl), furanyl (e.g. furan-2-yl), thiazolyl (e.g. thiazol-2-yl), thiophenyl (e.g. thiophen-2-yl, thiophen-3-yl). Example 6 membered rings include pyridinyl (e.g. pyridin-2-yl and pyridin-4-yl). Specific substituents that may be mentioned are one or more e.g. 1, 2 or 3 groups selected from halogen, hydroxyl, alkyl (e.g. methyl) and alkoxy- (e.g. methoxy-). Example substituted 5 membered rings include 4,5-dimethyl-furan-2-yl-, 5-hydroxymethyl-furan-2-yl-, 5-methyl-furan-2-yl- and 6-methyl-pyridin-2-yl-. An example substituted 6-membered ring is 1-oxy-pyridin-4-yl-. Example 9 membered rings include 1H-indolyl (e.g. 1H-indol-3-yl, 1H-indol-5-yl), benzothiophenyl (e.g. benzo[b]thiophen-3-yl, particularly 2-benzo[b]thiophen-3-yl), benzo[1,2,5]-oxadiazolyl (e.g. benzo[1,2,5]-oxadiazol-5-yl), benzo[1,2,5]-thiadiazolyl (e.g. benzo[1,2,5]-thiadiazol-5-yl, benzo[1,2,5]thiadiazol-6-yl). Example 10 membered rings include quinolinyl (e.g. quinolin-3-yl, quinolin-4-yl, quinolin-8-yl). Specific substituents that may be mentioned are one or more e.g. 1, 2 or 3 groups selected from halogen, hydroxyl, alkyl (e.g. methyl) and alkoxy- (e.g. methoxy-). Example substituted 9-membered rings include 1-methyl-1H-indol-3-yl, 2-methyl-1H-indol-3-yl, 6-methyl-1H-indol-3-yl. Example substituted 10 membered rings include 2-chloroquinolin-3-yl, 8-hydroxy-quinolin-2-yl, oxo-chromenyl (e.g. 4-oxo-4H-chromen-3-yl) and 6-methyl-4-oxo-4H-chromen-3-yl.

When $R^2$ represents carbocyclyl, examples include cycloalkyl and cycloalkenyl. Examples of cycloalkyl include cyclopropyl, cyclobutyl, cyclopentyl, cyclohexyl and cycloheptyl. Examples of cycloalkenyl include cyclohexenyl (e.g. cyclohex-2-enyl, cyclohex-3-enyl). Examples of substituted carbocyclyl include 2-methyl-cyclohexyl-, 3-methyl-cyclohexyl-, 4-methyl-cyclohexyl-, 2-methyl-cyclohex-2-enyl, 2-methyl-cyclohex-3-enyl, 3-methyl-cyclohex-3-enyl, 3-methyl-cyclohex-3-enyl.

When $R^2$ represents heterocyclyl (which may optionally be substituted), examples include tetrahydrofuranyl, morpholinyl, piperidinyl, 3,4-dihydro-2H-pyranyl, pyrrolidinyl, methyltetrahydrofuranyl- (e.g. 5-methyltetrahydrofuran-2-yl-).

When $R^2$ represents —$C_{1-4}$alkylaryl, examples include -alkyl(substituted phenyl) e.g. in which phenyl is substituted by one or more groups selected from alkyl, fluoroalkyl, halogen and alkoxy (e.g. methyl, trifluoromethyl, tert-butyl, chloro, fluoro and methoxy) and, for example, alkyl is $C_{1-4}$ alkyl. Another specific group is -alkyl(bicyclic aryl) e.g. wherein bicyclic aryl is optionally substituted naphthyl. A further specific group is benzyl.

When $R^2$ represents —$C_{1-4}$alkylheteroaryl in which heteroaryl is optionally substituted, examples include methylheteroaryl and -ethylheteroaryl (e.g. 1-heteroarylethyl- and 2-heteroarylethyl-), -propylheteroaryl and -butylheteroaryl in which heteroaryl is optionally substituted. Specific examples of -alkylheteroaryl groups include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl-, 4-methyl-pyridin-3-ethyl-.

When $R^2$ represents —$C_{1-4}$alkyl-carbocyclyl (which may optionally be substituted), examples include -methyl-cyclopentyl, -methyl-cyclohexyl, -ethyl-cyclohexyl, -propyl-cyclohexyl, -methyl-cyclohexenyl, -ethyl-cyclohexenyl, -methyl(4-methylcyclohexyl) and -propyl(3-methylcyclyohexyl).

When $R^2$ represents —$C_{1-4}$alkylheterocyclyl (which may optionally be substituted); examples include -methyl-tetrahydrofuranyl (e.g. -methyl-tetrahydrofuran-2-yl, -methyl-tetrahydrofuran-3-yl), -ethyl-tetrahydrofuranyl, -methyl-piperidinyl.

When $R^2$ represents phenyl substituted by phenyl or phenyl substituted by a monocyclic heteroaryl group, in which any of aforesaid phenyl and heteroaryl groups may optionally be substituted, typically the phenyl ring connected directly to the nitrogen atom is unsubstituted and the terminal phenyl ring or the monocyclic heteroaryl ring is optionally substituted by one, two or three substituents (e.g. one or two, e.g. one). Typically the terminal phenyl or monocyclic heteroaryl group is unsubstituted. Typically the terminal phenyl or monocyclic heteroaryl group substitutes the other phenyl group at the 4-position.

When $R^2$ represents phenyl substituted by phenyl in which any of aforesaid phenyl groups may optionally be substituted, examples include -biphenyl-4-yl.

When $R^2$ represents phenyl substituted by a monocyclic heteroaryl group, in which any of aforesaid phenyl and heteroaryl groups may optionally be substituted, examples include 4-(oxazol-5-yl)phenyl-.

When $R^2$ represents phenyl substituted by benzyloxy in which any of aforesaid phenyl and benzyloxy groups may optionally be substituted, examples include 4-benzyloxy-phenyl-, 4-(3-methylbenzyloxy)phenyl- and 4-(4-methylbenzyloxy)phenyl-.

When $R^2$ represents optionally substituted phenyl fused to optionally substituted carbocyclyl, examples include indanyl (e.g. indan-4-yl-, 2-methyl-indan-4-yl-), indenyl and tetralinyl.

When $R^2$ represents optionally substituted phenyl fused to optionally substituted heterocyclyl, examples include benzo[1,3]dioxo-4-yl- and 2,3-dihydro-benzo[1,4]dioxin-4-yl-.

When $R^2$ represents —$C_{1-4}$alkyl(phenyl substituted by phenyl), examples include biphenyl-4-yl-methyl-.

When $R^2$ represents —$C_{1-4}$alkyl(phenyl substituted by a monocyclic heteroaryl group), examples include 4-(oxazol-5-yl)phenyl-methyl-.

When $R^2$ represents —$C_{1-4}$alkyl(phenyl substituted by benzyloxy) in which any of aforesaid phenyl and benzyloxy groups may optionally be substituted, examples include 4-benzyloxy-phenyl-methyl-, 4-(3-methylbenzyloxy)phenyl-methyl- and 4-(4-methylbenzyloxy)phenyl-methyl-.

When $R^2$ represents —$C_{1-4}$alkyl(optionally substituted phenyl fused to optionally substituted carbocyclyl), examples include indanyl-methyl- (e.g. indan-4-yl-methyl-, 2-methyl-indan-4-yl-methyl-), indenyl-methyl- and tetralinyl-methyl-.

When $R^2$ represents —$C_{1-4}$alkyl(optionally substituted phenyl fused to optionally substituted heterocyclyl); examples include benzo[1,3]dioxo-4-yl-methyl- and 2,3-dihydro-benzo[1,4]dioxin-4-yl-methyl-.

When $R^3$ represents —$C_{1-4}$alkyl, examples include methyl, ethyl, propyl (e.g. n-propyl, isopropyl) and butyl (e.g. n-butyl-sec-butyl, isobutyl and tert-butyl).

When R³ represents optionally substituted aryl, aryl may typically represent phenyl. Exemplary substituted phenyl groups include 2,4-dichlorophenyl-, 2,4-difluorophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-dimethylphenyl-, 3,4,5-trifluorophenyl-, 3,5-bis(trifluororomethyl)phenyl-, 3,5-dimethoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-. Alternatively, R³ may represents unsubstituted phenyl-. Further exemplary substituted phenyl groups include 2-bromo-4-fluorophenyl-, 2-bromo-5-fluorophenyl-, 2-chlorophenyl-, 2-fluoro-5-(trifluoromethyl) phenyl-, 2-hydroxy-3-methoxyphenyl-, 2-hydroxy-5-methylphenyl-, 3-chlorophenyl-, 3-fluoro-4-(trifluoromethyl) phenyl-, 3-hydroxy-4-methoxyphenyl-, 4-chloro-3-(trifluoromethyl)phenyl-, 4-chlorophenyl-, 4-fluorophenyl- and 4-propoxyphenyl-.

When R² and R³ are joined to form a carbocyclyl ring, which is optionally substituted by one or more $C_{1-2}$alkyl groups, examples include cycloalkyl (e.g. cyclopropyl, cyclopentyl and cyclohexyl) and cycloalkenyl (e.g. cyclohexenyl).

When R² and R³ are joined to form a carbocyclyl ring which is fused to phenyl; examples include indanyl (e.g. indan-2-yl) and tetralinyl.

When R² and R³ are joined to form a carbocyclyl ring which is fused to monocyclic heteroaryl; examples include 5-membered carbocyclyl fused to 6-membered heteroaryl, 6-membered carbocyclyl fused to 6-membered heteroaryl, 5-membered carbocyclyl fused to 5-membered heteroaryl and 6-membered carbocyclyl fused to 5-membered heteroaryl. The monocyclic heteroaryl to which carbocyclyl is fused contains at least one heteroatom (e.g. one, two or three heteroatoms, e.g. one or two, e.g. one heteroatom).

When R⁴ represents —$C_{1-8}$alkyl examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When R⁴ represents —C(O)$C_{1-6}$alkyl; examples include —C(O)$C_{1-4}$alkyl such as —C(O)methyl, —C(O)ethyl, —C(O)propyl and —C(O)butyl.

Suitably, R¹ represents heteroaryl or —$C_{1-6}$alkylheteroaryl.

In one embodiment, R¹ represents heteroaryl. In a further embodiment, R¹ represents unsubstituted heteroaryl or heteroaryl optionally substituted by one or more $C_{1-6}$ alkyl (e.g. methyl), halogen (e.g. fluorine) or $C_{1-6}$ haloalkyl (e.g. trifluoromethyl) groups. In another embodiment, R¹ represents —$C_{1-6}$alkylheteroaryl.

When R¹ represents heteroaryl, R¹ suitably represents bicyclic heteroaryl, especially 9-membered bicyclic heteroaryl. More suitably, R¹ represents a bicyclic heteroaryl ring system and in particular a phenyl ring fused with a 5 membered heteroaryl ring containing one or more (e.g. one or two, suitably one, more suitably two) nitrogen atoms or a pyridine ring fused with a 5-membered heteroaryl ring containing one or more (e.g. one or two, suitably one, more suitably two) nitrogen atoms. When R¹ represents bicyclic heteroaryl, preferably the heteroaryl group does not contain S atoms. When R¹ represents a phenyl ring fused to a 5-membered heteroaryl ring, preferably R¹ is linked to the core of formula (I) through the phenyl ring. When R¹ represents a pyridine ring fused to a 5-membered heteroaryl ring, preferably R¹ is linked to the core of formula (I) through the pyridine ring. Suitably R¹ represents unsubstituted heteroaryl. In particular, R¹ suitably represents 1H-benzoimidazolyl or imidazo[1,2-a]pyridine, particularly 1H-benzoimidazolyl, especially 1H-benzoimidazol-5-yl.

When R¹ represents —$C_{1-6}$alkylheteroaryl, heteroaryl is suitably monocyclic heteroaryl, especially 5-membered monocyclic heteroaryl. More suitably, when R¹ represents —$C_{1-6}$alkylheteroaryl, heteroaryl is suitably a 5 membered heteroaryl ring containing one or more (e.g. one or two, suitably one, more suitably two) nitrogen atoms. When R¹ represents —$C_{1-6}$alkylheteroaryl, preferably the heteroaryl group does not contain S atoms. When R¹ represents —$C_{1-6}$alkylheteroaryl, heteroaryl represents substituted or unsubstituted imidazolyl. In particular, when R¹ represents —$C_{1-6}$alkylheteroaryl, heteroaryl suitably represents substituted or unsubstituted imidazoly-1-yl. When R¹ represents —$C_{1-6}$alkylheteroaryl and heteroaryl is substituted imidazoly-1-yl, imidazoly-1-yl is suitably substituted by methyl.

In one embodiment R¹ represents

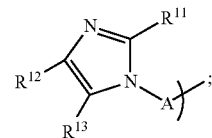

wherein A represents an unbranched $C_{1-6}$alkylene chain (e.g. an unbranched $C_{1-6}$alkylene chain, e.g. an unbranched $C_{1-4}$alkylene chain, e.g. an unbranched $C_{1-3}$alkylene chain) or A represents a branched $C_{1-6}$alkylene chain (e.g. wherein the one or more (e.g. one or two) branches consist of one or more (e.g. one or two) methyl groups at the same or different positions) or A represents $(CH_2)_2CR^5R^6$ $(CH_2)_b$ and $R^{11}$, $R^{12}$ and $R^{13}$ independently represent H or $C_{1-2}$alkyl.

In a second embodiment, R¹ represents

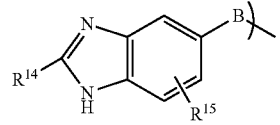

wherein B represents a bond, —$CH_2$—, —$CH_2$—$CH_2$—, —CH(Me)—, —CH(Me)—$CH_2$— or —$CH_2$—CH(Me)— and $R^{14}$ and $R^{15}$ independently represent H, $C_{1-2}$alkyl (e.g. methyl), halogen (e.g. fluorine) or $C_{1-6}$ haloalkyl (e.g. trifluoromethyl).

In a third embodiment, R¹ represents

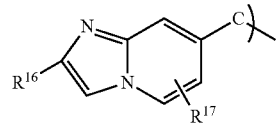

wherein C represents a bond, —$CH_2$—, —$CH_2$—$CH_2$—, —CH(Me)—, —CH(Me)—$CH_2$— or —$CH_2$—CH(Me)— and $R^{16}$ and $R^{17}$ independently represent H, $C_{1-2}$alkyl (e.g. methyl), halogen (e.g. fluorine) or $C_{1-6}$ haloalkyl (e.g. trifluoromethyl).

In a fourth embodiment, $R^1$ represents

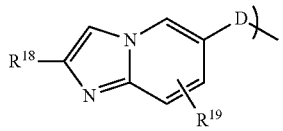

wherein D represents a bond, —$CH_2$—, —$CH_2$—$CH_2$—, —CH(Me)—, —CH(Me)—$CH_2$— or —$CH_2$—CH(Me)— and
$R^{18}$ and $R^{19}$ independently represent H, $C_{1-2}$alkyl (e.g. methyl), halogen (e.g. fluorine) or $C_{1-6}$ haloalkyl (e.g. trifluoromethyl);

Suitably $R^1$ represents

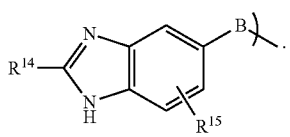

In one embodiment $R^{14}$ represents H and $R^{15}$ represents H. In another embodiment $R^{14}$ represents H and $R^{15}$ represents $C_{1-2}$alkyl. In a third embodiment $R^{14}$ represents $C_{1-2}$alkyl and $R^{15}$ represents H. In a fourth embodiment $R^{14}$ represents methyl and $R^{15}$ represents H. In a further embodiment, $R^{14}$ represents H or methyl and $R^{15}$ represents $C_{1-2}$alkyl (e.g. methyl) or halogen (e.g. fluorine).

Suitably B represents a bond, —$CH_2$— or —$CH_2CH_2$—. In one embodiment B represents a bond.

In another embodiment, B represents —$CH_2$—. In a third embodiment, B represents —$CH_2CH_2$—.

Alternatively $R^1$ represents

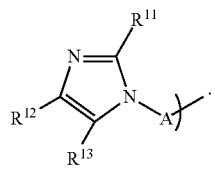

$R^{11}$ suitably represents H,
$R^{12}$ suitably represents H or methyl.
$R^{13}$ suitably represents H or methyl.

In one embodiment of the invention, $R^{12}$ represents H and $R^{13}$ represents methyl. In another embodiment, $R^{12}$ represents methyl and $R^{13}$ represents H. In a third embodiment, $R^{12}$ represents H and $R^{13}$ represents H.

Suitably A represents an unbranched $C_{2-5}$ alkylene chain. In one embodiment, A represents —$(CH_2)_2$—. In another embodiment, A represents —$(CH_2)_3$—. In a third embodiment, A represents —$(CH_2)_4$—. In further embodiment, A represents —$(CH_2)_5$—. More suitably A represents —$(CH_2)_2$—, —$(CH_2)_4$— or —$(CH_2)_5$—. In one embodiment, A represents —$(CH_2)_3$—. In another embodiment, A represents —$(CH_2)_4$—.

Alternatively A represents a branched $C_{2-5}$ alkylene chain.
In one embodiment A does not represent —$(CH_2)_3$—.

When A represents a $C_{2-5}$ alkylene chain, which is substituted by two alkylene substituents at the same position wherein the two alkylene substituents are joined to each other to form a $C_{3-5}$-spiro-cycloalkyl group, the spiro-cycloalkyl group is suitably $C_3$-spiro-cycloalkyl.

Alternatively $R^1$ represents

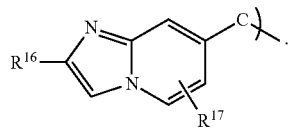

In one embodiment $R^{16}$ represents H and $R^{17}$ represents H. In another embodiment $R^{16}$ represents H and $R^{17}$ represents $C_{1-2}$alkyl. In a third embodiment $R^{16}$ represents $C_{1-2}$alkyl and $R^{17}$ represents H. In a further embodiment, $R^{16}$ represents H or methyl and $R^{17}$ represents $C_{1-2}$alkyl (e.g. methyl) or halogen (e.g. fluorine).

Suitably C represents a bond, —$CH_2$— or —$CH_2CH_2$—. In one embodiment C represents a bond. In another embodiment, C represents —$CH_2$—. In a third embodiment, C represents —$CH_2CH_2$—.

Alternatively $R^1$ represents

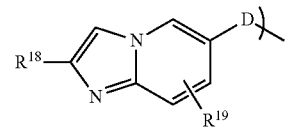

In one embodiment $R^{18}$ represents H and $R^{19}$ represents H. In another embodiment $R^{18}$ represents H and $R^{19}$ represents $C_{1-2}$alkyl. In a third embodiment $R^{18}$ represents $C_{1-2}$alkyl and $R^{19}$ represents H. In a further embodiment, $R^{14}$ represents H or methyl and $R^{15}$ represents $C_{1-2}$alkyl (e.g. methyl) or halogen (e.g. fluorine).

Suitably D represents a bond, —$CH_2$— or —$CH_2CH_2$—. In one embodiment D represents a bond. In another embodiment, D represents —$CH_2$—. In a third embodiment, D represents —$CH_2CH_2$—.

More suitably $R^1$ represents

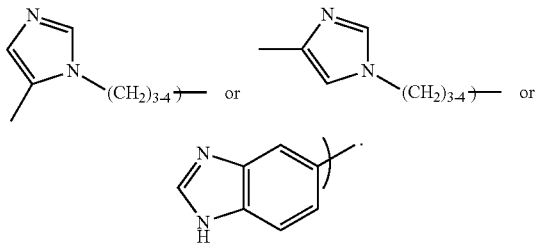

Yet more suitably $R^1$ represents

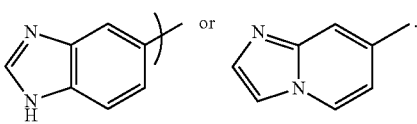

Most suitably, $R^1$ represents

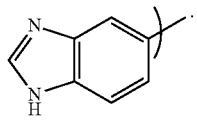

Suitably $R^2$ represents H, $C_{1-8}$alkyl, $C_{3-8}$cycloalkyl, —$C_{1-4}$ alkylcarbocyclyl, aryl, heteroaryl, heterocyclyl, —$C_{1-4}$ alkylaryl, phenyl substituted by phenyl, phenyl substituted by phenoxy, phenyl substituted by heterocyclyl wherein said heterocyclyl group is optionally substituted by a methyl or phenyl group, phenyl substituted by carbocyclyl, phenyl substituted by carbocyclyl wherein said carbocyclyl is substituted by heterocyclyl, phenyl substituted by —O-carbocyclyl, heterocyclyl substituted by phenyl, carbocyclyl substituted by phenyl, —$C_{1-4}$alkyl(phenyl substituted by a monocyclic heterocyclyl group), —$C_{1-4}$alkyl(phenyl substituted by an —O-carbocyclyl group), phenyl substituted by —O—$C_{1-4}$alkyl-heterocyclyl or phenyl fused to heterocyclyl, the aforesaid aryl, heteroaryl, phenyl and heterocyclyl groups optionally being substituted.

More suitably $R^2$ represents H, $C_{1-8}$alkyl, $C_{3-8}$cycloalkyl, aryl, heteroaryl, —$C_{1-4}$alkylaryl, phenyl substituted by phenyl, phenyl substituted by phenoxy, phenyl substituted by heterocyclyl wherein said heterocyclyl group is optionally substituted by a methyl or phenyl group, phenyl substituted by —O—$C_{1-4}$alkyl-heterocyclyl or phenyl fused to heterocyclyl, the aforesaid aryl, heteroaryl, phenyl and heterocyclyl groups optionally being substituted.

Yet more suitably $R^2$ represents $C_{1-8}$alkyl, $C_{3-8}$cycloalkyl, aryl, heteroaryl, —$C_{1-4}$alkylaryl, phenyl substituted by phenyl, phenyl substituted by phenoxy, phenyl substituted by heterocyclyl wherein said heterocyclyl group is optionally substituted by a methyl or phenyl group, phenyl substituted by —O—$C_{1-4}$alkyl-heterocyclyl or phenyl fused to heterocyclyl, the aforesaid aryl, heteroaryl, phenyl and heterocyclyl groups optionally being substituted.

In one embodiment, $R^2$ represent H.

In one embodiment, $R^2$ represents $C_{1-8}$alkyl. When $R^2$ represents $C_{1-8}$alkyl, $R^2$ suitably represents i-propyl or t-butyl.

In one embodiment, $R^2$ represents carbocyclyl. When $R^2$ represents carbocyclyl, $R^2$ suitably represents cyclohexyl.

In one embodiment, $R^2$ represents —$C_{1-4}$alkylcarbocyclyl. When $R^2$ represents —$C_{1-4}$alkylcarbocyclyl, $R^2$ suitably represents —$CH_2$-cyclohexyl.

In one embodiment, $R^2$ represents optionally substituted aryl. When $R^2$ represents optionally substituted aryl, $R^2$ suitably represents optionally substituted phenyl or napthyl.

In one embodiment, $R^2$ represents phenyl optionally substituted by one or more groups selected from $C_{1-6}$ alkyl (e.g. methyl), $C_{1-6}$ alkoxy (e.g. methoxy, ethoxy, propoxy, butoxy, pentoxy or isopropyloxy), hydroxyl, halo$C_{1-6}$ alkyl (e.g. trifluoromethyl), halo$C_{1-6}$ alkoxy (e.g. tetrafluoroethyloxy), halogen (e.g. chlorine or fluorine), $C_{1-6}$alkoxy-$C_{1-6}$alkyl- (e.g. —$(CH_2)_3$—OMe), $C_{1-6}$alkoxy-$C_{1-6}$alkoxy- (e.g. —O—$(CH_2)_2$—OMe), —N($C_{1-4}$alkyl)($C_{1-4}$alkyl)-N($C_{1-4}$alkyl)($C_{1-4}$alkyl) (e.g. —N(Me)—$(CH_2)_2$—N(Me)$_2$), —N($C_{1-4}$alkyl)($C_{1-4}$alkyl) (e.g. —N(ethyl)(ethyl)), —N($C_{3-8}$cycloalkyl)($C_{3-8}$cycloalkyl) (e.g. —N(cyclopropyl)(cyclopropyl)), —$C_{1-4}$alkyl-N($C_{1-4}$alkyl)($C_{1-4}$alkyl) (e.g. —$(CH_2)_3$—N(methyl)(methyl), —$C_{1-4}$alkoxy-N($C_{1-4}$alkyl)($C_{1-4}$alkyl) (e.g. —O$(CH_2)_2$—N(methyl)(methyl)), —N(—$C_{1-6}$alkyl-$C_{1-6}$alkoxy)(—$C_{1-6}$alkyl-$C_{1-6}$alkoxy) (e.g. —N(($CH_2)_2$OMe)($CH_2)_2$OMe)).

In a further embodiment, $R^2$ represents phenyl optionally substituted by one or more groups selected from $C_{1-6}$ alkyl (e.g. methyl), $C_{1-6}$ alkoxy (e.g. methoxy, ethoxy, propoxy, butoxy, pentoxy or isopropyloxy), halo$C_{1-6}$ alkyl (e.g. trifluoromethyl), halo$C_{1-6}$ alkoxy (e.g. tetrafluoroethyloxy) or halogen (e.g. chlorine or fluorine).

In a yet further embodiment, $R^2$ represents phenyl optionally substituted by one or more groups selected from $C_{1-6}$ alkoxy (e.g. methoxy, ethoxy, propoxy, butoxy, pentoxy or isopropyloxy). In a still yet further embodiment, $R^2$ represents phenyl optionally substituted by a propoxy group.

When $R^2$ represents optionally substituted phenyl, $R^2$ suitably represents 3-methylphenyl, 2-methoxyphenyl, 3-methoxyphenyl, 3,4-dimethoxyphenyl, 4-methoxyphenyl, 4-ethoxyphenyl, 4-propoxyphenyl, 4-butoxyphenyl, 4-pentoxyphenyl, 4-isopropyloxyphenyl, 4-tetrafluoroethyloxyphenyl, 2-chlorophenyl, 3-chlorophenyl, 4-chlorophenyl, 2,6-dichlorophenyl, 2,3-dichlorophenyl, 3,4-dichlorophenyl, 2-fluorophenyl, 3-fluorophenyl, 4-fluorophenyl, 2,6-difluorophenyl, 2,3-difluorophenyl, 3,4-difluorophenyl, 3-chloro-5-fluorophenyl, 3,5-difluorophenyl, 2,3,5-trifluorophenyl, 2-fluoro-5-trifluoromethylphenyl, 3-fluoro-5-trifluoromethylphenyl, 2-fluoro-4-trifluoromethylphenyl, 3-fluoro-4-trifluoromethylphenyl, 3-fluoro-4-methoxyphenyl or 2,6-difluoro-4-methoxyphenyl. In an alternative embodiment, $R^2$ represents unsubstituted phenyl. In an alternative embodiment, $R^2$ represents unsubstituted naphthyl.

In one embodiment, $R^2$ represents —$C_{1-4}$alkylaryl, the aforesaid aryl optionally being substituted. When $R^2$ represents —$C_{1-4}$alkylaryl, $R^2$ suitably represents benzyl optionally substituted by one or more $C_{1-6}$alkoxy (e.g. methoxy) or halogen (e.g. chlorine or fluorine) groups. When $R^2$ represents optionally substituted benzyl, $R^2$ suitably represents 4-methoxybenzyl, 4-chlorobenzyl or 4-fluorobenzyl. When $R^2$ represents optionally substituted benzyl, $R^2$ also suitably represents 4-propoxybenzyl or 4-isopropoxybenzyl. In an alternative embodiment, $R^2$ represents unsubstituted benzyl. When $R^2$ represents —$C_{1-4}$alkylaryl, $R^2$ suitably represents —C(H)(Me)-phenyl. When $R^2$ represents —$C_{1-4}$alkylaryl, $R^2$ suitably represents —$(CH_2)_2$-phenyl.

In one embodiment, $R^2$ represents optionally substituted heteroaryl. When $R^2$ represents optionally substituted heteroaryl, $R^2$ suitably represents optionally substituted thiophenyl. In an alternative embodiment, $R^2$ represents unsubstituted thiophenyl.

In one embodiment, $R^2$ represents optionally substituted heterocyclyl. When $R^2$ represents optionally substituted heteroaryl, $R^2$ suitably represents unsubstituted dihydrobenzodioxinyl or piperidinyl substituted by a —C(O)$C_{1-6}$alkyl (i.e. —COMe) group.

In one embodiment, $R^2$ represents phenyl substituted by phenyl, the aforesaid phenyl groups optionally being substituted. When $R^2$ represents phenyl substituted by phenyl, the aforesaid phenyl groups optionally being substituted, $R^2$ suitably represents phenyl substituted by 3-phenyl, phenyl substituted by 4-phenyl, phenyl substituted by 3-(3-chlorophenyl), phenyl substituted by 4-(3-chlorophenyl), phenyl substituted by 4-(3,4-dichlorophenyl) or 3-fluorophenyl substituted by 4-phenyl. In an alternative embodiment, when $R^2$ represents phenyl substituted by phenyl, $R^2$ suitably represents unsubstituted phenyl substituted by unsubstituted phenyl.

In one embodiment, $R^2$ represents optionally substituted phenyl substituted by optionally substituted phenoxy. When $R^2$ represents optionally substituted phenyl substituted by optionally substituted phenoxy, $R^2$ suitably represents phenyl substituted by 4-phenoxy.

In one embodiment, $R^2$ represents optionally substituted phenyl substituted by optionally substituted heterocyclyl. When $R^2$ represents optionally substituted phenyl substituted by optionally substituted heterocyclyl, $R^2$ suitably represents 3-chlorophenyl substituted by 4-morpholinyl, phenyl substituted by 4-piperazinyl substituted by 4N-methyl, 2-chlorophenyl substituted by 6-piperazinyl substituted by 4N-ethyl, phenyl substituted by pyrrolidinyl, phenyl substituted by piperidinyl substituted by 4N-methyl, phenyl substituted by tetrahydropyranyl or phenyl substituted by morpholinyl.

In a further embodiment, $R^2$ represents optionally substituted phenyl substituted by optionally substituted heterocyclyl. When $R^2$ represents optionally substituted phenyl substituted by optionally substituted heterocyclyl, $R^2$ suitably represents 3-chlorophenyl substituted by 4-morpholinyl, phenyl substituted by 4-piperazinyl substituted by 4N-methyl, phenyl substituted by 4-piperazinyl substituted by 4N-phenyl, phenyl substituted by 3-piperazinyl substituted by 4N-phenyl or 2-chlorophenyl substituted by 6-piperazinyl substituted by 4N-ethyl.

In one embodiment, $R^2$ represents optionally substituted phenyl substituted by heterocyclyl wherein said heterocyclyl is substituted by phenyl. When $R^2$ represents optionally substituted phenyl substituted by heterocyclyl wherein said heterocyclyl is substituted by phenyl, $R^2$ suitably represents phenyl substituted by 4-piperazinyl substituted by 4N-phenyl, phenyl substituted by 3-piperazinyl substituted by 4N-phenyl.

In one embodiment, $R^2$ represents optionally substituted phenyl substituted by optionally substituted carbocyclyl wherein said carbocyclyl is substituted by optionally substituted heterocyclyl. When $R^2$ represents optionally substituted phenyl substituted by optionally substituted carbocyclyl wherein said carbocyclyl is substituted by optionally substituted heterocyclyl, $R^2$ suitably represents phenyl substituted by carbocyclyl (i.e. cyclohexyl) substituted by heterocyclyl (i.e. morpholinyl).

In one embodiment, $R^2$ represents optionally substituted phenyl substituted by —O—$C_{1-4}$alkyl-heterocyclyl. When $R^2$ represents optionally substituted phenyl substituted by —O—$C_{1-4}$alkyl-heterocyclyl, $R^2$ suitably represents phenyl substituted by 4-O—$(CH_2)_2$-morpholinyl, 4-O—$(CH_2)_3$-morpholinyl, 2-O—$(CH_2)_2$-morpholinyl or 4-O—$(CH_2)_2$-piperazinyl.

In one embodiment, $R^2$ represents optionally substituted phenyl substituted by optionally substituted carbocyclyl. When $R^2$ represents optionally substituted phenyl substituted by optionally substituted carbocyclyl, $R^2$ suitably represents phenyl substituted by $C_{3-8}$ cycloalkyl (such as cyclohexyl) wherein said $C_{3-8}$ cycloalkyl may be optionally substituted by one or more oxo, halogen (i.e. fluorine), hydroxyl or $C_{1-4}$alkoxy (i.e. methoxy) groups.

In one embodiment, $R^2$ represents optionally substituted phenyl substituted by —O-carbocyclyl. When $R^2$ represents optionally substituted phenyl substituted by —O-carbocyclyl, $R^2$ suitably represents unsubstituted phenyl substituted by an —O—$C_{3-8}$ cycloalkyl group (i.e. —O-cyclohexyl).

In one embodiment, $R^2$ represents optionally substituted heterocyclyl substituted by optionally substituted phenyl. When $R^2$ represents optionally substituted heterocyclyl substituted by optionally substituted phenyl, $R^2$ suitably represents unsubstituted piperidinyl substituted by unsubstituted phenyl.

In one embodiment, $R^2$ represents optionally substituted carbocyclyl substituted by optionally substituted phenyl. When $R^2$ represents optionally substituted carbocyclyl substituted by optionally substituted phenyl, $R^2$ suitably represents unsubstituted $C_{3-8}$ cycloalkyl (i.e. cyclohexyl) substituted by unsubstituted phenyl.

In one embodiment, $R^2$ represents optionally substituted phenyl fused to optionally substituted heterocyclyl. When $R^2$ represents optionally substituted phenyl fused to optionally substituted heterocyclyl, $R^2$ suitably represents benzo-1,3-dioxolanyl, 4-methoxy(benzo-1,3-dioxolanyl), 6-methoxy(benzo-1,3-dioxolanyl), 2,2-difluoro(benzo-1,3-dioxolanyl) or benzo-1,4-dioxanyl.

In one embodiment, $R^2$ represents —$C_{1-4}$alkyl(phenyl substituted by a monocyclic heterocyclyl group). When $R^2$ represents —$C_{1-4}$alkyl(phenyl substituted by a monocyclic heterocyclyl group), $R^2$ suitably represents benzyl substituted by morpholinyl.

In one embodiment, $R^2$ represents —$C_{1-4}$alkyl(phenyl substituted by an —O-carbocyclyl group). When $R^2$ represents —$C_{1-4}$alkyl(phenyl substituted by an —O-carbocyclyl group), $R^2$ suitably represents benzyl substituted by an —O-carbocyclyl group (i.e. —O-cyclohexyl).

Suitably $R^3$ represents H or $R^2$ and $R^3$ are joined to form a carbocyclyl ring which is fused to phenyl. Most suitably $R^3$ represents H.

Suitably $R^4$ represents H, —$C_{1-6}$alkyl or —$C(O)C_{1-6}$alkyl. More suitably $R^4$ represents H or —$C_{1-8}$alkyl, e.g. H or methyl. Most suitably $R^4$ represents H.

In one embodiment, X represents O, S or $CR^7R^8$ or X and Z represent two adjacent carbon atoms of a phenyl ring which is fused in that position and is optionally substituted by one or more halogen or $C_{1-2}$alkyl groups. In a further embodiment, X represents O, S or $CR^7R^8$.

In one embodiment X represents O. In an alternative embodiment X represents S. In an alternative embodiment X represents C=O. In an alternative embodiment, X represents S or $CR^7R^8$. In an alternative embodiment X represents —O—$CH_2$— or —$CH_2$—$CH_2$—. In an alternative embodiment X and Z are joined to form a carbocyclic ring, e.g. a five or six membered carbocyclic ring. In an alternative embodiment, X and Z represent two adjacent carbon atoms of a phenyl ring which is fused in that position and is optionally substituted by one or more halogen or $C_{1-2}$alkyl groups.

In one embodiment, $R^7$ and $R^8$ both represent hydrogen or —$C_{1-4}$alkyl, or one of $R^7$ and $R^8$ represents hydrogen and the other represents —$C_{1-4}$alkyl or an optionally substituted aryl group. When one of $R^7$ and $R^8$ represents a —$C_{1-4}$alkyl group, said group is suitably methyl. When one of $R^7$ and $R^8$ represents an optionally substituted aryl group, said group is suitably unsubstituted phenyl or phenyl substituted by 4-propoxy. In one embodiment, $R^7$ and $R^8$ both represent hydrogen. In an alternative embodiment, $R^7$ and $R^8$ both represent —$C_{1-4}$alkyl. In an alternative embodiment, one of $R^7$ and $R^8$ represents hydrogen and the other represents —$C_{1-4}$alkyl (e.g. methyl). In an alternative embodiment, one of $R^7$ and $R^8$ represents hydrogen and the other represents an optionally substituted aryl group (e.g. unsubstituted phenyl or phenyl substituted by a $C_{1-6}$ alkoxy group).

In one embodiment Y represents C=O, C=S or $CH_2$. In an alternative embodiment, Y represents C=O. In an alternative embodiment Y represents C=S. In an alternative embodiment, Y represents $CH_2$.

In one embodiment, Z represents —N—$R^4$ (e.g. —NH or —N—$NH_2$), O or $CHR^{10}$ (e.g. $CH_2$ or CH-methyl), or X and Z represent two adjacent carbon atoms of a phenyl ring which is fused in that position and is optionally substituted by one or more halogen or $C_{1-2}$alkyl groups. In one embodiment, Z represents —NH. In an alternative embodiment, Z represents —N—NH$_2$. In an alternative embodiment, Z represents O. In an alternative embodiment, Z represents CH$_2$. In an alternative embodiment, Z represents CH-methyl.

In one embodiment, X represents $CR^7R^8$, Y represents C=O and Z represents —N—$R^4$. In a further embodiment, X represents CH$_2$, Y represents C=O and Z represents —NH. In a further embodiment, X represents CH—Me, Y represents C=O and Z represents —NH. In a further embodiment, X represents CH$_2$, Y represents C=O and Z represents —N—NH$_2$.

When X represents $CR^7R^8$, Y represents C=O and Z represents —N—$R^4$, $R^1$ suitably represents 1H-benzo[d]imidazolyl or 1H-imidazo[1,2-a]pyridinyl.

When X represents $CR^7R^8$, Y represents C=O and Z represents —N—$R^4$, $R^2$ suitably represents:
 $C_{1-8}$ alkyl (such as t-butyl);
 carbocyclyl (such as cyclohexyl);
 phenyl optionally substituted by one or more $C_{1-6}$ alkyl (e.g. methyl), $C_{1-6}$ alkoxy (such as methoxy, ethoxy, propoxy, butoxy, pentoxy or isopropoxy), halogen (such as fluorine or chlorine), halo$C_{1-6}$ alkyl (such as trifluoromethyl) or halo$C_{1-6}$ alkoxy groups (such as trifluoromethoxy);
 optionally substituted phenyl fused to optionally substituted heterocyclyl (such as 4-methoxybenzo[d][1,3]dioxol-6-yl, 2,2-difluorobenzo[d][1,3]dioxol-5-yl or 2,3-dihydrobenzo[b][1,4]dioxin-6-yl);
 optionally substituted phenyl substituted by optionally substituted heterocyclyl (such as phenyl substituted by —O—(CH$_2$)$_2$-morpholinyl or phenyl substituted by —O—(CH$_2$)$_3$-morpholinyl);
 optionally substituted phenyl substituted by optionally substituted phenyl; or
 optionally substituted phenyl substituted by optionally substituted heterocyclyl (such as optionally substituted phenyl substituted by morpholinyl, optionally substituted phenyl substituted by piperazinyl substituted by phenyl or optionally substituted phenyl substituted by piperazinyl substituted by ethyl).

When X represents $CR^7R^8$, Y represents C=O and Z represents —N—$R^4$, $R^3$ suitably represents hydrogen.

When X represents $CR^7R^8$, Y represents C=O and Z represents —N—$R^4$, $R^3$, $R^7$ and $R^8$ each suitably represent hydrogen.

In one embodiment, X represents C=O, Y represents $CHR^9$ and Z represents —N—$R^4$. In a further embodiment, X represents C=O, Y represents CH$_2$ and Z represents —NH.

When X represents C=O, Y represents $CHR^9$ and Z represents —N—$R^4$, $R^1$ suitably represents 1H-benzo[d]imidazolyl.

When X represents C=O, Y represents $CHR^9$ and Z represents —N—$R^4$, $R^2$ suitably represents phenyl optionally substituted by one or more halogen atoms (such as unsubstituted phenyl or 2,3,5-trifluorophenyl).

When X represents C=O, Y represents $CHR^9$ and Z represents —N—$R^4$, $R^3$ suitably represents hydrogen.

In an alternative embodiment, X represents $CR^7R^8$, Y represents C=O and Z represents O. In a further embodiment, X represents CH$_2$, Y represents C=O and Z represents O. In a further embodiment, X represents C(Me)$_2$, Y represents C=O and Z represents O. In a further embodiment, X represents CH-phenyl, Y represents C=O and Z represents O.

When X represents $CR^7R^8$, Y represents C=O and Z represents O, $R^1$ suitably represents 1H-benzo[d]imidazolyl or 1H-imidazo[1,2-a]pyridinyl.

When X represents $CR^7R^8$, Y represents C=O and Z represents O, $R^2$ suitably represents:
 $C_{1-8}$ alkyl (such as i-propyl);
 phenyl optionally substituted by one or more halogen (such as fluorine or chlorine), $C_{1-6}$ alkoxy (such as propoxy) or halo$C_{1-6}$ alkyl groups (such as trifluoromethyl);
 —$C_{1-4}$ alkylaryl (such as benzyl);
 optionally substituted phenyl fused to optionally substituted heterocyclyl (such as 2,3-dihydrobenzo[b][1,4]dioxin-6-yl or benzo[d][1,3]dioxol-6-yl);
 optionally substituted phenyl substituted by optionally substituted heterocyclyl (such as phenyl substituted by —O—(CH$_2$)$_2$-piperazinyl or —O—(CH$_2$)$_2$-morpholinyl);
 optionally substituted phenyl substituted by optionally substituted phenyl; or
 optionally substituted phenyl substituted by optionally substituted heterocyclyl (such as optionally substituted phenyl substituted by piperazinyl substituted by phenyl or optionally substituted phenyl substituted by piperazinyl substituted by methyl).

When X represents $CR^7R^8$, Y represents C=O and Z represents O, $R^3$ suitably represents hydrogen.

In an alternative embodiment, X represents $CR^7R^8$, Y represents $CHR^9$ and Z represents $CHR^{10}$. In a further embodiment, X represents CH$_2$, Y represents CH$_2$ and Z represents CH$_2$.

When X represents $CR^7R^8$, Y represents $CHR^9$ and Z represents $CHR^{10}$, $R^1$ suitably represents 1H-benzo[d]imidazolyl.

When X represents $CR^7R^8$, Y represents $CHR^9$ and Z represents $CHR^{10}$, $R^2$ suitably represents:
 hydrogen;
 phenyl optionally substituted by one or more halogen (such as fluorine or chlorine), $C_{1-6}$ alkoxy (such as methoxy); or
 optionally substituted —$C_{1-4}$ alkylaryl (such as unsubstituted benzyl and benzyl substituted a halogen atom, such as fluorine or chlorine or a $C_{1-6}$ alkoxy, such as methoxy).

When X represents $CR^7R^8$, Y represents $CHR^9$ and Z represents $CHR^{10}$, $R^3$ suitably represents hydrogen.

In an alternative embodiment, X represents S, Y represents C=O and Z represents $CHR^{10}$. In a further embodiment, X represents S, Y represents C=O and Z represents CH$_2$. In a further embodiment, X represents S, Y represents C=O and Z represents CH-methyl.

When X represents S, Y represents C=O and Z represents $CHR^{10}$, $R^1$ suitably represents 1H-benzo[d]imidazolyl.

When X represents S, Y represents C=O and Z represents $CHR^{10}$, $R^2$ suitably represents:
 phenyl optionally substituted by one or more halogen (such as fluorine or chlorine);
 optionally substituted naphthyl (such as unsubstituted naphthyl);
 optionally substituted phenyl substituted by optionally substituted phenoxy; or
 optionally substituted heteroaryl (such as unsubstituted thiophenyl).

When X represents S, Y represents C=O and Z represents $CHR^{10}$, $R^3$ suitably represents hydrogen.

In an alternative embodiment, X represents S, Y represents C=S and Z represents $CHR^{10}$. In a further embodiment, X represents S, Y represents C=S and Z represents CH$_2$.

When X represents S, Y represents C=S and Z represents $CHR^{10}$, $R^1$ suitably represents 1H-benzo[d]imidazolyl.

When X represents S, Y represents C=S and Z represents CHR$^{10}$, R$^2$ suitably represents optionally substituted phenyl or optionally substituted phenyl substituted by optionally substituted phenoxy.

When X represents S, Y represents C=S and Z represents CHR$^{10}$, R$^3$ suitably represents hydrogen.

In an alternative embodiment, X represents CR$^7$R$^8$, Y represents C=O and Z represents CHR$^{10}$. In a further embodiment, X represents CH$_2$, Y represents C=O and Z represents CH$_2$.

When X represents CR$^7$R$^8$, Y represents C=O and Z represents CHR$^{10}$, R$^1$ suitably represents 1H-benzo[d]imidazolyl.

When X represents CR$^7$R$^8$, Y represents C=O and Z represents CHR$^{10}$, R$^2$ suitably represents:
phenyl optionally substituted by one or more halogen (such as fluorine), C$_{1-6}$ alkoxy (such as methoxy or propoxy); or
optionally substituted phenyl fused to optionally substituted heterocyclyl (such as 2,3-dihydrobenzo[b][1,4]dioxin-6-yl).

When X represents CR$^7$R$^8$, Y represents C=O and Z represents CHR$^{10}$, R$^3$ suitably represents hydrogen.

In an alternative embodiment, X and Z represent two adjacent carbon atoms of a phenyl ring which is fused in that position and Y represents C=O. In a further embodiment, X and Z represent two adjacent carbon atoms of a phenyl ring which is fused in that position and is substituted by one or more halogen or C$_{1-2}$alkyl groups such as 2,5-dichlorophenyl or 3,4-dichlorophenyl and Y represents C=O.

When X and Z represent two adjacent carbon atoms of a phenyl ring which is fused in that position and Y represents C=O, R$^1$ suitably represents 1H-benzo[d]imidazolyl.

When X and Z represent two adjacent carbon atoms of a phenyl ring which is fused in that position and Y represents C=O, R$^2$ suitably represents:
phenyl optionally substituted by one or more halogen (such as fluorine or chlorine), C$_{1-6}$ alkoxy (such as methoxy or propoxy);
optionally substituted phenyl substituted by optionally substituted phenyl;
optionally substituted phenyl fused to optionally substituted heterocyclyl (such as benzo[d][1,3]dioxol-6-yl); or
optionally substituted phenyl substituted by optionally substituted phenoxy.

When X and Z represent two adjacent carbon atoms of a phenyl ring which is fused in that position and Y represents C=O, R$^3$ suitably represents hydrogen.

In an alternative embodiment, X represents —O—CH$_2$—, Y represents CO and Z represents CHR$^{10}$. In a further embodiment, X represents —O—CH$_2$—, Y represents CO and Z represents CH$_2$ (see e.g. Example 93).

When X represents —O—CH$_2$—, Y represents CO and Z represents CHR$^{10}$, R$^1$ suitably represents 1H-benzo[d]imidazolyl.

When X represents —O—CH$_2$—, Y represents CO and Z represents CHR$^{10}$, R$^2$ suitably represents phenyl optionally substituted by a C$_{1-6}$ alkoxy (such as propoxy).

When X represents —O—CH$_2$—, Y represents CO and Z represents CHR$^{10}$, R$^3$ suitably represents hydrogen.

In an alternative embodiment, X represents —CH$_2$—CH$_2$—, Y represents CO and Z represents O.

When X represents —CH$_2$—CH$_2$—, Y represents CO and Z represents O, R$^1$ suitably represents 1H-benzo[d]imidazolyl or 1H-imidazo[1,2-a]pyridinyl.

When X represents —CH$_2$—CH$_2$—, Y represents CO and Z represents O, R$^2$ suitably represents phenyl optionally substituted by a C$_{1-6}$ alkoxy (such as propoxy).

When X represents —CH$_2$—CH$_2$—, Y represents CO and Z represents O, R$^3$ suitably represents hydrogen.

In one embodiment, the compound of formula (I) is a compound selected from Examples 1 to 235. In a further embodiment, the compound of formula (I) is a compound selected from Examples 1 to 147. In a yet further embodiment, the compound of formula (I) is a compound selected from Examples 12 to 14.

Processes

According to a further aspect of the invention there is provided a process for preparing a compound of formula (I) which comprises:

(a) preparing a compound of formula (I) from a compound of formula (II):

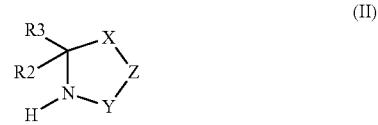

wherein R$^2$, R$^3$, X, Y and Z are as defined above for compounds of formula (I). The process typically involves reacting a compound of formula (II) with a compound of formula R$^1$-L in which L represents a leaving group e.g. a halogen atom such as iodine. A non-limiting example of the methodology of process (a) is described in Methods 5-8 and 12 herein.

(b) preparing a compound of formula (I) wherein R$^3$ represents hydrogen, Y represents CO, Z represents —N—R$^4$ and X represents CR$^7$R$^8$ and R$^8$ represents hydrogen by hydrogenation of a compound of formula (III):

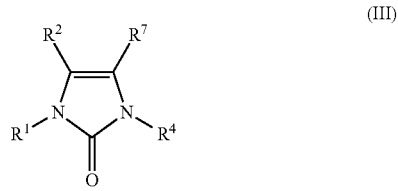

wherein R$^1$, R$^2$, R$^4$ and R$^7$ are as defined above for compounds of formula (I). Process (b) typically comprises hydrogenation under suitable conditions, such as PdC, 10% on charcoal at 4 bar at 40° C. for 4 hours. A non-limiting example of the methodology of process (b) is described in Method 1 herein.

(c) preparing a compound of formula (I) wherein R$^3$ represents hydrogen, Y represents CO, Z represents CH$_2$ and X represents CH$_2$ by hydrogenation of a compound of formula (IV):

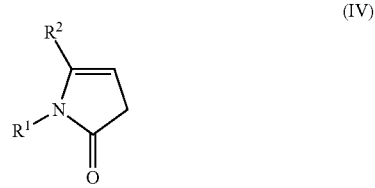

wherein R¹ and R² are as defined above for compounds of formula (I). Process (c) typically comprises hydrogenation under suitable conditions, such as PdC, 10% on charcoal at 1-2 bar at room temperature overnight. A non-limiting example of the methodology of process (c) is described in Method 10 herein.

(d) preparing a compound of formula (I) wherein $R^3$ represents hydrogen, Y represents CO, Z represents —N—$R^4$ and X represents $CH_2$ from a compound of formula (V):

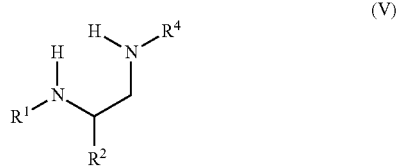

(V)

wherein $R^1$, $R^2$ and $R^4$ are as defined above for compounds of formula (I). Process (d) typically comprises reaction with a suitable reagent, such as a compound of formula LCOL' in which L and L' represent leaving groups. An example reagent is carbonyldiimidazole which may be employed in the presence of a suitable solvent such as dichloromethane. A non-limiting example of the methodology of process (d) is described in Method 2 herein.

(e) preparing a compound of formula (I) wherein $R^3$ represents hydrogen, Y represents $CH_2$, Z represents —N—$R^4$ and X represents CO from a compound of formula (VI):

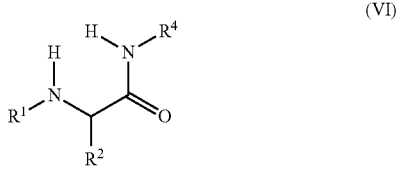

(VI)

wherein $R^1$, $R^2$ and $R^4$ are as defined above for compounds of formula (I). Process (e) typically comprises the use of a suitable reagent, such as an activated formic acid derivative e.g. triethyl-ortho formate under suitable conditions, such as reflux followed by reduction e.g. with sodium borohydride. A non-limiting example of the methodology of process (e) is described in Method 4 herein.

(f) preparing a compound of formula (I) wherein $R^1$ represents 1H-benzo[d]imidazol-5-yl, $R^3$ represents hydrogen, Y represents CO, Z represents —NH and X represents $CH_2$ from a compound of formula (VII):

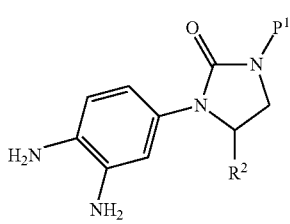

(VII)

wherein $R^2$ is as defined above for compounds of formula (I) and $P^1$ represents a suitable protecting group, such as p-methoxy benzyl. Process (f) typically comprises treatment of the compound of formula (IV) with an activated formic acid derivative, such as triethyl orthoformate. A non-limiting example of the methodology of process (f) is described in Method 3 herein.

(g) preparing a compound of formula (I) wherein $R^3$ represents hydrogen, Y represents CO and X and Z are joined to form a carbocyclic ring or else X and Z represent two adjacent carbon atoms of a phenyl ring which is fused in that position and is optionally substituted by one or more halogen or $C_{1-2}$alkyl groups, from a compound of formula (VIII):

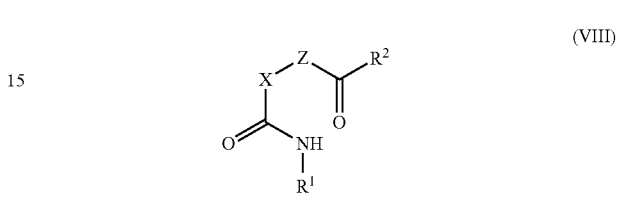

(VIII)

wherein $R^1$, $R^2$, X and Z are as defined above for compounds of formula (I). Process (g) is essentially a dehydration reaction which typically comprises the use of suitable reagents, such as trifluoroacetic acid, triethylsilane and sodium bicarbonate. A non-limiting example of the methodology of process (g) is described in Method 11 herein.

(h) preparing a compound of formula (I) wherein X represents S, for example a compound of formula (I) wherein $R^3$ represents hydrogen, Y represents CO, Z represents —$CH_2$ and X represents S from a corresponding compound in which X represents O. Process (h) typically comprises the use of suitable reagents such as Lawesson's Reagent. A non-limiting example of the methodology of process (h) is described in Method 9 herein.

(i) preparing a compound of formula (I) wherein $R^4$ represents —$NH_2$ from a corresponding compound of formula (I) wherein $R^4$ represents H by treatment with nitrite followed by reduction. Typically the compound of formula (I) wherein $R^4$ represents H is treated with sodium (or potassium) nitrite in the presence of acid (e.g. glacial acetic acid) and then reduced by treatment with zinc powder. A non-limiting example of the methodology of process (i) is described in Example 65 herein.

(j) preparing a compound of formula (I) wherein $R^4$ represents —$C_{1-6}$alkyl or —$C(O)C_{1-6}$alkyl from a corresponding compound of formula (I) wherein $R^4$ represents H by treatment with an alkylating or alkanoylating agent. Typical alkylating agents include compounds of formula $R^4$-L wherein L is a leaving group such as iodine and typical alkanoylating agents include activated acids such as compounds of formula $R^4$-L wherein L is a leaving group such as halogen (e.g. chlorine) or a corresponding acid anhydride.

(k) interconversion of compounds of formula (I). Examples of such an interconversion includes interconversion of a compound of formula (I) wherein Y represents CO to a compound of formula (I) wherein Y represents CS. Such an interconversion may typically comprise the use of suitable reagents, such as toluol and Lawesson's Reagent. A non-limiting example of the methodology of process (k) is described in Method 9 herein; and (l) deprotecting a compound of formula (I) which is protected.

Compounds of formula (I) and intermediate compounds may also be prepared using techniques analogous to those known to a skilled person, or described herein.

Novel intermediates are claimed as an aspect of the present invention.

Therapeutic Uses

Physiological substrates of QC (EC) in mammals are, e.g. amyloid beta-peptides (3-40), (3-42), (11-40 and (11-42), ABri, ADan, Gastrin, Neurotensin, FPP, CCL 2, CCL 7, CCL 8, CCL 16, CCL 18, Fractalkine, Orexin A, [Gln$^3$]-glucagon (3-29), [Gln$^5$]-substance P(5-11) and the peptide QYNAD.

For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which are prone to be cyclized to final pGlu

| Peptide | Amino acid sequence | Function |
|---|---|---|
| Abeta(1-42) (SEQ ID NO: 1) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(1-40) (SEQ ID NO: 2) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta(3-42) (SEQ ID NO: 3) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(3-40) (SEQ ID NO: 4) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta(11-42) (SEQ ID NO: 16) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(11-40) (SEQ ID NO: 17) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| ABri (SEQ ID NO: 18) | EASNCFA IRHFENKFAV ETLIC SRTVKKNIIEEN | Pyroglutamated form plays a role in Familial British Dementia |
| ADan (SEQ ID NO: 19) | EASNCFA IRHFENKFAV ETLIC FNLFLNSQEKHY | Pyroglutamated form plays a role in Familial Danish Dementia |
| Gastrin 17 Swiss-Prot: P01350 (SEQ ID NO: 5) | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin Swiss-Prot: P30990 (SEQ ID NO: 6) | QLYENKPRRP YIL | Neurotensin plays an endocrine or paracrine role in the regulation of fat metabolism. It causes contraction of smooth muscle. |

TABLE 1-continued

Amino acid sequences of physiological active peptides with an N-terminal glutamine residue, which are prone to be cyclized to final pGlu

| Peptide | Amino acid sequence | Function |
| --- | --- | --- |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH Swiss-Prot: P20396 | QHP amide | TRH functions as a regulator of the biosynthesis of TSH in the anterior pituitary gland and as a neurotransmitter/ neuromodulator in the central and peripheral nervous systems. |
| GnRH Swiss-Prot: P01148 (SEQ ID NO: 7) | QHWSYGL RP(G) amide | Stimulates the secretion of gonadotropins; it stimulates the secretion of both luteinizing and follicle-stimulating hormones. |
| CCL16 (small inducible cytokine A16) Swiss-Prot: O15467 (SEQ ID NO: 8) | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8) Swiss-Prot: P80075 (SEQ ID NO: 9) | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (MCP-1, small inducible cytokine A2) Swiss-Prot: P13500 (SEQ ID NO: 10) | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18) Swiss-Prot: P55774 (SEQ ID NO: 11) | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |

TABLE 1-continued

Amino acid sequences of physiological active peptides with an N-terminal glutamine residue, which are prone to be cyclized to final pGlu

| Peptide | Amino acid sequence | Function |
| --- | --- | --- |
| Fractalkine (neurotactin) Swiss-Prot: P78423 (SEQ ID NO: 12) | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |
| CCL7 (small inducible cytokine A7) Swiss-Prot: P80098 (SEQ ID NO: 13) | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot O43612 (SEQ ID NO: 14) | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P (SEQ ID NO: 15) | RPK PQQFFGLM | Belongs to the tachykinins. Tachykinins are active peptides which excite neurons, evoke behavioral responses, are potent vasodilators and secretagogues, and contract (directly or indirectly) many smooth muscles. |
| QYNAD (SEQ ID NO: 20) | Gln-Tyr-Asn-Ala-Asp | Acts on voltage-gated sodium channels. |

Glutamate is found in positions 3, 11 and 22 of the amyloid β-peptide. Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid 0-peptides 1-40 (42/43) (Saido T. C. 2000 Medical Hypotheses 54 (3): 427-429).

The multiple N-terminal variations, e.g. Abeta(3-40), Abeta(3-42), Abeta(11-40) and Abeta (11-42) can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertension, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) *Mol. Cell* 2, 275-281; Gosling, J., et al., (1999) *J Clin. Invest* 103, 773-778); rheumatoid arthritis (Gong, J. H., et al., (1997) *J Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J Oncol.* 22, 773-778; Li, S., et al., (2005) *J Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

MCP-1 levels are increased in CSF of AD patients and patients showing mild cognitive impairment (MCI) (Galimberti, D., et al., (2006) *Arch. Neurol.* 63, 538-543). Furthermore, MCP-1 shows an increased level in serum of patients with MCI and early AD (Clerici, F., et al., (2006) *Neurobiol. Aging* 27, 1763-1768).

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, *J Pept Res* 57 (6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of the compounds of formula (I) for the preparation of a medicament for the prevention or alleviation or treatment of a disease selected from the group consisting of mild cognitive impairment, Alzheimer's disease, Familial British Dementia, Familial Danish Dementia, neurodegeneration in Down Syndrome, Huntington's disease, Kennedy's disease, ulcer disease, duodenal cancer with or w/o *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal diseases, artherosclerosis and multiple sclerosis.

The present invention also provides a method of treatment of the aforementioned diseases comprising the administration of a therapeutically active amount of at least one compound of formula (I) to a mammal, preferably a human.

Most preferably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson's disease and Chorea Huntington, comprising the administration of a therapeutically active amount of at least one compound of formula (I) to a mammal, preferably a human.

Even preferably, the present invention provides a method of treatment and corresponding uses for the treatment of rheumatoid arthritis, atherosclerosis, pancreatitis and restenosis.

Pharmaceutical Combinations

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most preferably, said QC inhibitor is a compound of formula (I) of the present invention.

More specifically, the aforementioned other agent is selected from the group consisting of beta-amyloid antibodies, vaccines, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of (a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene, (b) Selective serotonin re-uptake inhibitors (SSRI's), e.g. citalopram, fluoxetine, fluvoxamine, escitalopram, sertraline, paroxetine, (c) Tricyclic antidepressants, e.g. amitryptiline, clomipramine, desipramine, doxepin, imipramine (d) Monoamine oxidase (MAO) inhibitors, (e) Azapirones, e.g. buspirone, tandopsirone, (f) Serotonin-norepinephrine reuptake inhibitors (SNRI's), e.g. venlafaxine, duloxetine, (g) Mirtazapine, (h) Norepinephrine reuptake inhibitors (NRI's), e.g. reboxetine, (i) Bupropione,
(j) Nefazodone,
(k) beta-blockers,
(l) NPY-receptor ligands: NPY agonists or antagonists.

In a further embodiment, the other agent may be, for example, an anti-multiple sclerosis drug selected from the group consisting of
a) dihydroorotate dehydrogenase inhibitors, e.g. SC-12267, teriflunomide, MNA-715, HMR-1279 (syn. to HMR-1715, MNA-279),
b) autoimmune suppressant, e.g. laquinimod,
c) paclitaxel,
d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
e) peptide nucleic acid (PNA) preparations, e.g. reticulose,
f) interferon alpha, e.g. Alfaferone, human alpha interferon (syn. to Omniferon, Alpha Leukoferon),
g) interferon beta, e.g. Frone, interferon beta-1a like Avonex, Betron (Rebif), interferon beta analogs, interferon beta-transferrin fusion protein, recombinant interferon beta-1 b like Betaseron,
h) interferon tau,
i) peptides, e.g. AT-008, AnergiX.MS, Immunokine (alpha-Immunokine-NNSO3), cyclic peptides like ZD-7349,
j) therapeutic enzymes, e.g. soluble CD8 (sCD8),
k) multiple sclerosis-specific autoantigen-encoding plasmid and cytokine-encoding plasmid, e.g. BHT-3009;
l) inhibitor of TNF-alpha, e.g. BLX-1002, thalidomide, SH-636,
m) TNF antagonists, e.g. solimastat, lenercept (syn. to $R^O$-45-2081, Tenefuse), onercept (sTNFR1), CC-1069,
n) TNF alpha, e.g. etanercept (syn. to Enbrel, TNR-001)
o) CD28 antagonists, e.g. abatacept,
p) Lck tyrosine kinase inhibitors,
q) cathepsin K inhibitors,
r) analogs of the neuron-targeting membrane transporter protein taurine and the plant-derived calpain inhibitor leupeptin, e.g. Neurodur,
s) chemokine receptor-1 (CCR1) antagonist, e.g. BX-471,
t) CCR2 antagonists,
u) AMPA receptor antagonists, e.g. ER-167288-01 and ER-099487, E-2007, talampanel,
v) potassium channel blockers, e.g. fampridine,
w) tosyl-proline-phenylalanine small-molecule antagonists of the VLA-4/VCAM interaction, e.g. TBC-3342,
x) cell adhesion molecule inhibitors, e.g. TBC-772,
y) antisense oligonucleotides, e.g. EN-101,
z) antagonists of free immunoglobulin light chain (IgLC) binding to mast cell receptors, e.g. F-991,
aa) apoptosis inducing antigens, e.g. Apogen MS,
bb) alpha-2 adrenoceptor agonist, e.g. tizanidine (syn. to Zanaflex, Ternelin, Sirdalvo, Sirdalud, Mionidine),
cc) copolymer of L-tyrosine, L-lysine, L-glutamic acid and L-alanine, e.g. glatiramer acetate (syn. to Copaxone, COP-1, copolymer-1),
dd) topoisomerase II modulators, e.g. mitoxantrone hydrochloride,
ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SRI-62-834 (syn. to CRC-8605, NSC-614383),
ii) immunomodulators, e.g. SAIK-MS, PNU-156804, alpha-fetoprotein peptide (AFP), IPDS,
jj) retinoid receptor agonists, e.g. adapalene (syn. to Differin, CD-271),
kk) TGF-beta, e.g. GDF-1 (growth and differentiation factor 1),
ll) TGF-beta-2, e.g. BetaKine,
mm) MMP inhibitors, e.g. glycomed,
nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34, TO-200),
pp) alpha-4/beta-1 integrin antagonists, e.g. ISIS-104278,
qq) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S-inhibitors,
ww) bropirimine analogs, e.g. PNU-56169, PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO/2009/065054, WO/2009/056490, WO/2009/053696, WO/2009/033743, WO/2007/113172, WO/2007/022416, WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/

104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

The beta-amyloid antibodies may be selected from, for example, polyclonal, monoclonal, chimenic or humanized antibodies. Furthermore, said antibodies may be useful to develop active and passive immune therapies, i.e. vaccines and monoclonal antibodies. Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Especially preferred are antibodies, which recognize the N-terminus of the Aβ peptide. A suitable antibody, which recognizes the Aβ-N-Terminus is, for example Acl-24 (AC Immune SA).

Monoclonal antibodies against beta-amyloid peptide are disclosed in WO 2007/068412, WO/2008/156621 and WO/2010/012004. Respective chimeric and humanized antibodies are disclosed in WO 2008/011348 and WO/2008/060364. Vaccine composition for treating an amyloid-associated disease is disclosed in WO/2002/096937, WO/2005/014041, WO 2007/068411, WO/2007/097251, WO/2009/029272, WO/2009/054537, WO/2009/090650 WO/2009/095857, WO/2010/016912, WO/2010/011947, WO/2010/011999, WO/2010/044464.

Suitable vaccines for treating an amyloid-associated disease are, e.g. Affitopes AD-01 and AD-02 (GlaxoSmithKline), ACC-01 and ACC-02 (Elan/Wyeth), CAD-106 (Novartis/Cytos Biotechnology), Suitable cysteine protease inhibitors are inhibitors of cathepsin B. Inhibitors of cathepsin B and compositions containing such inhibitors are described, e.g. in WO/2008/077109, WO/2007/038772, WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b,f]oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO/2010/094242, WO/2010/058333, WO/2010/021680, WO/2009/108550, WO/2009/042694, WO/2008/054698, WO/2007/051333, WO/2007/021793, WO/2007/019080, WO/2007/019078, WO/2007/011810, WO03/059346, WO2006/099352, WO2006/078576, WO2006/060109, WO2006/057983, WO2006/057945, WO2006/055434, WO2006/044497, WO2006/034296, WO2006/034277, WO2006/029850, WO2006/026204, WO2006/014944, WO2006/014762, WO2006/002004, U.S. Pat. No. 7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.), DNP-004089 (De Novo Pharmaceuticals Ltd.) and CT-21166 (CoMentis Inc.).

Inhibitors of gamma secretase and compositions containing such inhibitors are described, e.g. in WO/2010/090954, WO/2009/011851, WO/2009/008980, WO/2008/147800, WO/2007/084595, WO2005/008250, WO2006/004880, U.S. Pat. No. 7,122,675, U.S. Pat. No. 7,030,239, U.S. Pat. No. 6,992,081, U.S. Pat. No. 6,982,264, WO2005/097768, WO2005/028440, WO2004/101562, U.S. Pat. No. 6,756,511, U.S. Pat. No. 6,683,091, WO03/066592, WO03/014075, WO03/013527, WO02/36555, WO01/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO2005/040126, WO2005/030731, WO2005/014553, U.S. Pat. No. 6,890,956, EP 1334085, EP 1263774, WO2004/101538, WO2004/00958, WO2004/089911, WO2004/073630, WO2004/069826, WO2004/039370, WO2004/031139, WO2004/031137, U.S. Pat. No. 6,713,276, U.S. Pat. No. 6,686,449, WO03/091278, U.S. Pat. No. 6,649,196, U.S. Pat. No. 6,448,229, WO01/77144 and WO01/66564. Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); NGX-555 (TorreyPines Therapeutics Inc.) and Semagacestat (Eli Lilly).

DP IV-inhibitors and compositions containing such inhibitors are described, e.g. in U.S. Pat. No. 6,011,155; U.S. Pat. No. 6,107,317; U.S. Pat. No. 6,110,949; U.S. Pat. No. 6,124,305; U.S. Pat. No. 6,172,081; WO99/61431, WO99/67278, WO99/67279, DE19834591, WO97/40832, WO95/15309, WO98/19998, WO00/07617, WO99/38501, WO99/46272, WO99/38501, WO01/68603, WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977, WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352, WO2004/050022, WO2004/052850, WO2004/058266, WO2004/064778, WO2004/069162, WO2004/071454, WO2004/076433, WO2004/076434, WO2004/087053, WO2004/089362, WO2004/099185, WO2004/103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235, WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613; WO2006/009886; WO2006/013104; WO2006/017292; WO2006/019965; WO2006/020017; WO2006/023750; WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo Nordisk A/S).

Other preferred DP IV-inhibitors are
(i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;
(ii) peptide structures, disclosed in WO 03/002593, e.g. tripeptides;
(iii) peptidylketones, disclosed in WO 03/033524;
(vi) substituted aminoketones, disclosed in WO 03/040174;
(v) topically active DP IV-inhibitors, disclosed in WO 01/14318;
(vi) prodrugs of DP IV-inhibitors, disclosed in WO 99/67278 and WO 99/67279; and
(v) glutaminyl based DP IV-inhibitors, disclosed in WO 03/072556 and WO 2004/099134.

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.), RQ-00000009 (RaQualia Pharma Inc).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.), SEN-1176 and SEN-1329 (Senexis Ltd.), AGT-160 (ArmaGen Technologies), Davunetide (Allon Therapeutics), ELND-005 (Elan Corp/Transition Therapeutics) and nilvadipine (Archer Pharmaceuticals).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A preferred PDE-4-inhibitor is Rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157, WO96/20946, WO94/07890 and WO92/21333.

Suitable MAO-inhibitors for the purpose of the present invention are for example Linezolid (Pharmacia Corp.); RWJ-416457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer), NW-1048 (Newron Pharmaceuticals SpA.), EVT-302 (Evotec).

Suitable histamine H3 antagonists for the purpose of the present invention are, e.g. ABT-239, ABT-834 (Abbott Laboratories); 3874-H1 (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262, 431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118, 811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810, 721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221, 752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)—N-2-(diphenylacetyl)-(R)—N-[1-(4-hydroxy-phenyl)ethyl]arginine amide (Example 4 of international patent application WO 99/15498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth), CI-101 7/(PD-151832) (Pfizer Inc.) and MCD-386 (Mitridion Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057, WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.), INM-176

(Whanln), huperzine A (Neuro-Hitech/Xel Pharmaceutical), mimopezil (Debiopharm) and Dimebon (Medivation/Pfizer).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216, WO2004/092189, WO2004/039371, WO2004/028522, WO2004/009062, WO03/010159, WO02/072542, WO02/34718, WO01/98262, WO01/94321, WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416, WO98/50075, WO98/50044, WO98/10757, WO98/05337, WO97/32873, WO97/23216, WO97/23215, WO97/23214, WO96/14318, WO96/08485, WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); Epi-Cept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-Cl-kynurenine (4-Cl-KYN)), 7-chloro-kynurenic acid (7-Cl-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec), neramexane (Merz).

Furthermore, the present invention relates to combination therapies useful for the treatment of atherosclerosis, restenosis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include $AT_1$ receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-41 77 of the formula

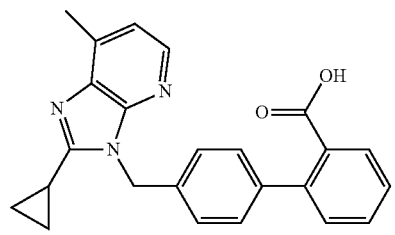 [SMILES: Cc1ccnc2c1nc(C1CC1)n2Cc1ccc(-c2ccccc2C(=O)O)cc1]

the compound with the designation SC-52458 of the following formula

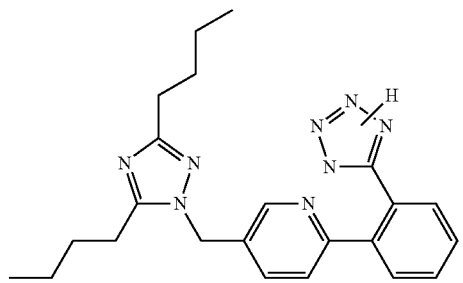

and the compound with the designation the compound ZD-8731 of the formula

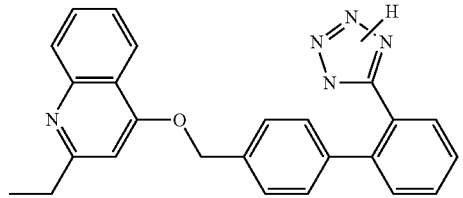

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorothalidon. The most preferred diuretic is hydrochlorothiazide. A diuretic furthermore comprises a potassium sparing diuretic such as amiloride or triameterine, or a pharmaceutically acceptable salt thereof.

The class of CCBs essentially comprises dihydropyridines (DHPs) and non-DHPs, such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Preferably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT705 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serine/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-κB) inhibitors/antibodies, IκB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, preferably in the form of the hemi-fumarate salt thereof.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies.

MCP-1 antagonists and compositions containing such inhibitors are described, e.g. in WO02/070509, WO02/081463, WO02/060900, US2006/670364, US2006/677365, WO2006/097624, US2006/316449, WO2004/056727, WO03/053368, WO00/198289, WO00/157226, WO00/046195, WO00/046196, WO00/046199, WO00/046198, WO00/046197, WO99/046991, WO99/007351, WO98/006703, WO97/012615, WO2005/105133, WO03/037376, WO2006/125202, WO2006/085961, WO2004/024921, WO2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-C5a monoclonal antibodies, e.g. neutrazumab (G2 Therapies Ltd.); AZD-6942 (AstraZeneca plc.); 2-mercaptoimidazoles (Johnson & Johnson); TE1-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most preferably the QC inhibitor is combined with one or more compounds selected from the following group: PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N-2-(diphenylacetyl)-(R)—N-[1-(4-hydroxyphenyl)ethyl]arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:
- a QC inhibitor, preferably a QC inhibitor of formula (I), more preferably a QC inhibitor selected from any one of examples 1-235, in combination with Atorvastatin for the treatment and/or prevention of artherosclerosis,
- a QC inhibitor, preferably a QC inhibitor of formula (I), more preferably a QC inhibitor selected from any one of examples 1-235, in combination with immunosuppressive agents, preferably rapamycin for the prevention and/or treatment of restenosis,
- a QC inhibitor, preferably a QC inhibitor of formula (I), more preferably a QC inhibitor selected from any one of examples 1-235, in combination with immunosuppressive agents, preferably paclitaxel for the prevention and/or treatment of restenosis,
- a QC inhibitor, preferably a QC inhibitor of formula (I), more preferably a QC inhibitor selected from any one of examples 1-235, in combination with AChE inhibitors, preferably Donepezil, for the prevention and/or treatment of Alzheimer's disease,
- a QC inhibitor, preferably a QC inhibitor of formula (I), more preferably a QC inhibitor selected from any one of examples 1-235, in combination with interferones, preferably Aronex, for the prevention and/or treatment of multiple sclerosis,
- a QC inhibitor, preferably a QC inhibitor of formula (I), more preferably a QC inhibitor selected from any one of examples 1-235, in combination with interferones, preferably betaferon, for the prevention and/or treatment of multiple sclerosis,
- a QC inhibitor, preferably a QC inhibitor of formula (I), more preferably a QC inhibitor selected from any one of examples 1-235, in combination with interferones, preferably Rebif, for the prevention and/or treatment of multiple sclerosis
- a QC inhibitor, preferably a QC inhibitor of formula (I), more preferably a QC inhibitor selected from any one of examples 1-235, in combination with Copaxone, for the prevention and/or treatment of multiple sclerosis,
- a QC inhibitor, preferably a QC inhibitor of formula (I), more preferably a QC inhibitor selected from any one of examples 1-235, in combination with dexamethasone, for the prevention and/or treatment of restenosis,
- a QC inhibitor, preferably a QC inhibitor of formula (I), more preferably a QC inhibitor selected from any one of examples 1-235, in combination with dexamethasone, for the prevention and/or treatment of atherosclerosis,
- a QC inhibitor, preferably a QC inhibitor of formula (I), more preferably a QC inhibitor selected from any one of examples 1-235, in combination with dexamethasone, for the prevention and/or treatment of rheumatid arthritis,
- a QC inhibitor, preferably a QC inhibitor of formula (I), more preferably a QC inhibitor selected from any one of examples 1-235, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1-235, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1-235, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1-235, in combination with amyloid-beta antibodies for the prevention and/or treatment of mild cognitive impairment, wherein the amyloid-beta antibody is Act-24,
- a QC inhibitor, preferably a QC inhibitor of formula (I), more preferably a QC inhibitor selected from any one of examples 1-235, in combination with amyloid-beta antibodies for the prevention and/or treatment of Alzheimer's disease, wherein the amyloid-beta antibody is Act-24,
- a QC inhibitor, preferably a QC inhibitor of formula (I), more preferably a QC inhibitor selected from any one of examples 1-235, in combination with amyloid-beta antibodies for the prevention and/or treatment of neurodegeneration in Down Syndrome, wherein the amyloid-beta antibody is Act-24,
- a QC inhibitor, preferably a QC inhibitor of formula (I), more preferably a QC inhibitor selected from any one of examples 1-235, in combination with beta-secretase inhibitors for the prevention and/or treatment of mild cognitive impairment, wherein the beta-secretase inhibitor is selected from WY-25105, GW-840736× and CTS-21166, a QC inhibitor, preferably a QC inhibitor of formula (I), more preferably a QC inhibitor selected from any one of examples 1-235, in combination with beta-secretase inhibitors for the prevention and/or treatment of Alzheimer's disease, wherein the beta-secretase inhibitor is selected from WY-25105, GW-840736× and CTS-21166, a QC inhibitor, preferably a QC inhibitor of formula (I), more preferably a QC inhibitor selected from any one of examples 1-235, in combination with beta-secretase inhibitors for the prevention and/or treatment of neurodegeneration in Down Syndrome, wherein the beta-secretase inhibitor is selected from WY-25105, GW-840736× and CTS-21166, a QC inhibitor, preferably a QC inhibitor of formula (I), more preferably a QC inhibitor selected from any one of examples 1-235, in combination with gamma-secretase inhibitors for the prevention and/or treatment of mild cognitive impairment, wherein the gamma-secretase inhibitor is selected from LY-450139, LY-411575 and AN-37124, a QC inhibitor, preferably a QC inhibitor of formula (I), more preferably a QC inhibitor selected from any one of examples 1-235, in combination with gamma-secretase inhibitors for the prevention and/or treatment of Alzheimer's disease, wherein the gamma-secretase inhibitor is selected from LY-450139, LY-411575 and AN-37124, a QC inhibitor, preferably a QC inhibitor of formula (I), more preferably a QC inhibitor selected from any one of examples 1-235, in combination with gamma-secretase inhibitors for the prevention and/or treatment of neurodegeneration in Down Syndrome, wherein the gamma-secretase inhibitor is selected from LY-450139, LY-411575 and AN-37124.

Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier. The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

The invention embraces all combinations of preferred and more preferred groups and embodiments of groups recited herein.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

| Example | Chemical Name | Structure | Formula | Mol Weight |
|---|---|---|---|---|
| 1 | 5-tert-butyl-1-(1H-benzo[d]imidazol-5-yl)imidazolidin-2-one | 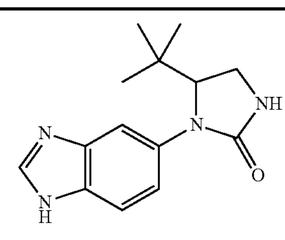 | $C_{14}H_{18}N_4O$ | 258.319 |

-continued

| Example | Chemical Name | Structure | Formula | Mol Weight |
|---|---|---|---|---|
| 2 | 1-(1H-benzo[d]imidazol-5-yl)-5-cyclohexylimidazolidin-2-one | 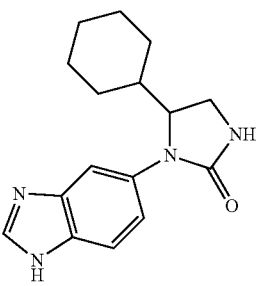 [SMILES: O=C1NCC(C2CCCCC2)N1c1ccc2[nH]cnc2c1] | $C_{16}H_{20}N_4O$ | 284.356 |
| 3 | 1-(1H-benzo[d]imidazol-5-yl)-5-phenylimidazolidin-2-one | 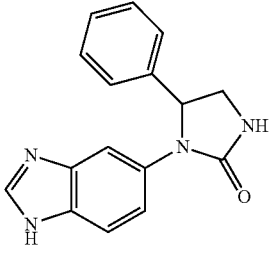 [SMILES: O=C1NCC(c2ccccc2)N1c1ccc2[nH]cnc2c1] | $C_{16}H_{14}N_4O$ | 278.309 |
| 4 | 1-(1H-benzo[d]imidazol-5-yl)-5-m-tolylimidazolidin-2-one | 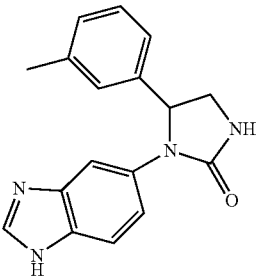 [SMILES: Cc1cccc(C2CNC(=O)N2c2ccc3[nH]cnc3c2)c1] | $C_{17}H_{16}N_4O$ | 292.335 |
| 5 | 1-(1H-benzo[d]imidazol-5-yl)-5-(4-methoxyphenyl)imidazolidin-2-one | 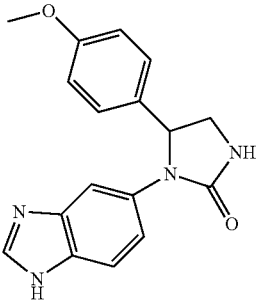 [SMILES: COc1ccc(C2CNC(=O)N2c2ccc3[nH]cnc3c2)cc1] | $C_{17}H_{16}N_4O_2$ | 308.335 |
| 6 | 1-(1H-benzo[d]imidazol-5-yl)-5-(4-methoxyphenyl)imidazolidin-2-one | 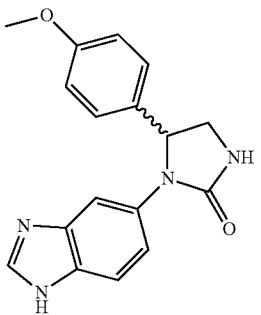<br>enantiomer 1 | $C_{17}H_{16}N_4O_2$ | 308.335 |

-continued

| Example | Chemical Name | Structure | Formula | Mol Weight |
|---|---|---|---|---|
| 7 | 1-(1H-benzo[d]imidazol-5-yl)-5-(4-methoxyphenyl)imidazolidin-2-one | enantiomer 2 | $C_{17}H_{16}N_4O_2$ | 308.335 |
| 8 | (4R,5S)-1-(1H-benzo[d]imidazol-6-yl)-5-(4-methoxyphenyl)-4-methylimidazolidin-2-one | 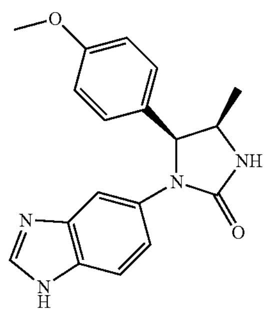 [SMILES: COc1ccc([C@H]2[C@@H](C)NC(=O)N2c2ccc3[nH]cnc3c2)cc1] | $C_{18}H_{18}N_4O_2$ | 322.36 |
| 9 | 1-(1H-benzo[d]imidazol-5-yl)-5-(3-methoxyphenyl)imidazolidin-2-one | 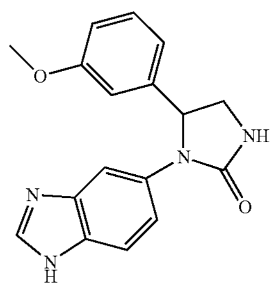 [SMILES: COc1cccc(C2CNC(=O)N2c2ccc3[nH]cnc3c2)c1] | $C_{17}H_{16}N_4O_2$ | 308.335 |
| 10 | 1-(1H-benzo[d]imidazol-5-yl)-5-(2-methoxyphenyl)imidazolidin-2-one | 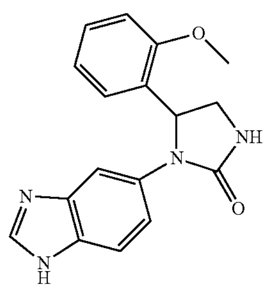 [SMILES: COc1ccccc1C1CNC(=O)N1c1ccc2[nH]cnc2c1] | $C_{17}H_{16}N_4O_2$ | 308.335 |
| 11 | 1-(1H-benzo[d]imidazol-5-yl)-5-(4-ethoxyphenyl)imidazolidin-2-one | 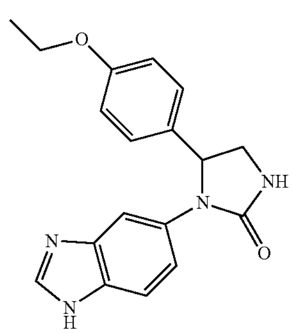 [SMILES: CCOc1ccc(C2CNC(=O)N2c2ccc3[nH]cnc3c2)cc1] | $C_{18}H_{18}N_4O_2$ | 322.361 |

-continued

| Example | Chemical Name | Structure | Formula | Mol Weight |
|---|---|---|---|---|
| 12 | 1-(1H-benzo[d]imidazol-5-yl)-5-(4-propoxyphenyl)imidazolidin-2-one | 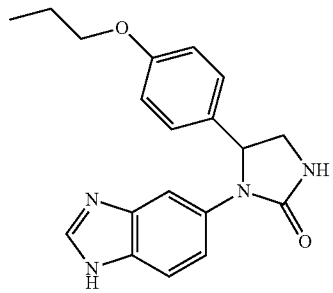 [SMILES: CCCOc1ccc(C2CNC(=O)N2c2ccc3[nH]cnc3c2)cc1] | $C_{19}H_{20}N_4O_2$ | 336.388 |
| 13 | (R)-1-(1H-benzo[d]imidazol-5-yl)-5-(4-propoxyphenyl)imidazolidin-2-one | 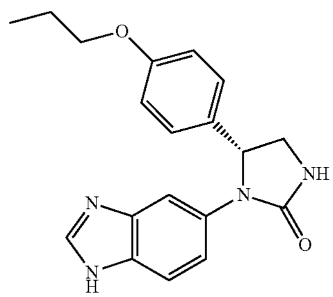 [SMILES: CCCOc1ccc([C@@H]2CNC(=O)N2c2ccc3[nH]cnc3c2)cc1] | $C_{19}H_{20}N_4O_2$ | 336.388 |
| 14 | (S)-1-(1H-benzo[d]imidazol-5-yl)-5-(4-propoxyphenyl)imidazolidin-2-one | 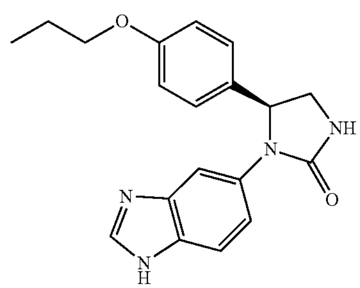 [SMILES: CCCOc1ccc([C@H]2CNC(=O)N2c2ccc3[nH]cnc3c2)cc1] | $C_{19}H_{20}N_4O_2$ | 336.388 |
| 15 | 1-(1H-benzo[d]imidazol-5-yl)-5-(4-butoxyphenyl)imidazolidin-2-one | 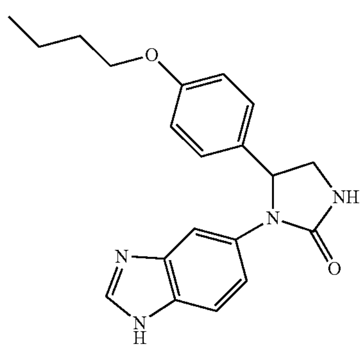 [SMILES: CCCCOc1ccc(C2CNC(=O)N2c2ccc3[nH]cnc3c2)cc1] | $C_{20}H_{22}N_4O_2$ | 350.414 |
| 16 | 1-(1H-benzo[d]imidazol-5-yl)-5-(4-(pentyloxy)phenyl)imidazolidin-2-one | 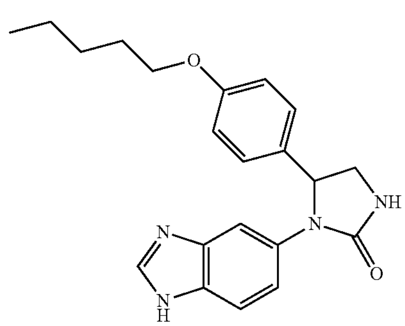 [SMILES: CCCCCOc1ccc(C2CNC(=O)N2c2ccc3[nH]cnc3c2)cc1] | $C_{21}H_{24}N_4O_2$ | 364.441 |

-continued

| Example | Chemical Name | Structure | Formula | Mol Weight |
|---|---|---|---|---|
| 17 | 1-(1H-benzo[d]imidazol-5-yl)-5-(4-isopropoxyphenyl)imidazolidin-2-one | 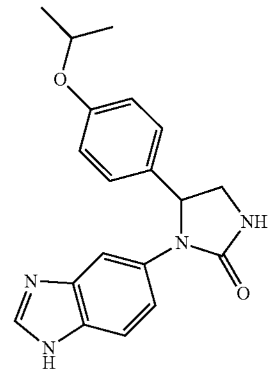 [SMILES: CC(C)Oc1ccc(C2CNC(=O)N2c2ccc3[nH]cnc3c2)cc1] | $C_{19}H_{20}N_4O_2$ | 336.388 |
| 18 | 1-(1H-benzo[d]imidazol-5-yl)-5-(4-methoxybenzo[d][1,3]dioxol-6-yl)imidazolidin-2-one | 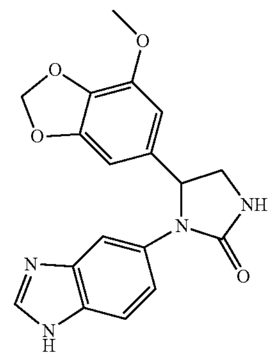 [SMILES: COc1cc(C2CNC(=O)N2c2ccc3[nH]cnc3c2)cc2c1OCO2] | $C_{18}H_{16}N_4O_4$ | 352.344 |
| 19 | 1-(1H-benzo[d]imidazol-5-yl)-5-(2,3-dihydrobenzo[b][1,4]dioxin-6-yl)imidazolidin-2-one | 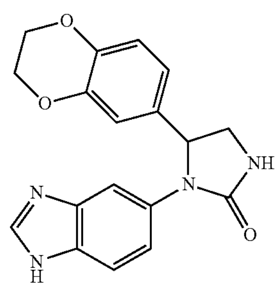 [SMILES: O=C1NCC(c2ccc3c(c2)OCCO3)N1c1ccc2[nH]cnc2c1] | $C_{18}H_{16}N_4O_3$ | 336.345 |
| 20 | 5-(4-(1,1,2,2-tetrafluoroethoxy)phenyl)-1-(1H-benzo[d]imidazol-5-yl)imidazolidin-2-one | 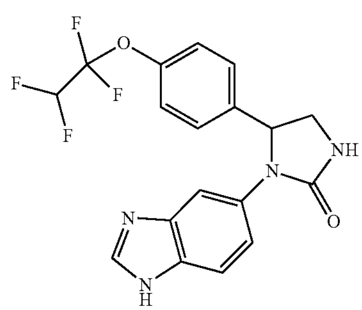 [SMILES: O=C1NCC(c2ccc(OC(F)(F)C(F)F)cc2)N1c1ccc2[nH]cnc2c1] | $C_{18}H_{14}F_4N_4O_2$ | 394.323 |
| 21 | 1-(1H-benzo[d]imidazol-5-yl)-5-(2,2-difluorobenzo[d][1,3]dioxol-5-yl)imidazolidin-2-one | 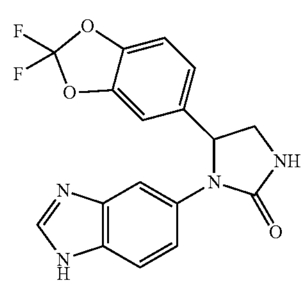 [SMILES: O=C1NCC(c2ccc3c(c2)OC(F)(F)O3)N1c1ccc2[nH]cnc2c1] | $C_{17}H_{12}F_2N_4O_3$ | 358.299 |

-continued

| Example | Chemical Name | Structure | Formula | Mol Weight |
|---|---|---|---|---|
| 22 | 1-(1H-benzo[d]imidazol-5-yl)-5-(3-fluoro-4-methoxyphenyl)imidazolidin-2-one | 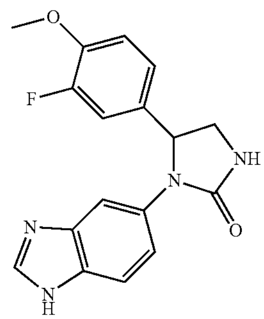 [SMILES: COc1ccc(C2CNC(=O)N2c2ccc3[nH]cnc3c2)cc1F] | $C_{17}H_{15}FN_4O_2$ | 326.325 |
| 23 | 1-(1H-benzo[d]imidazol-5-yl)-5-(2,6-difluoro-4-methoxyphenyl)imidazolidin-2-one | 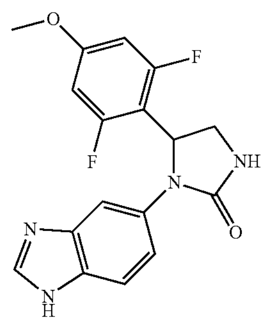 [SMILES: COc1cc(F)c(C2CNC(=O)N2c2ccc3[nH]cnc3c2)c(F)c1] | $C_{17}H_{14}F_2N_4O_2$ | 344.315 |
| 24 | 5-(4-(2-morpholinoethoxy)phenyl)-1-(1H-benzo[d]imidazol-6-yl)imidazolidin-2-one | 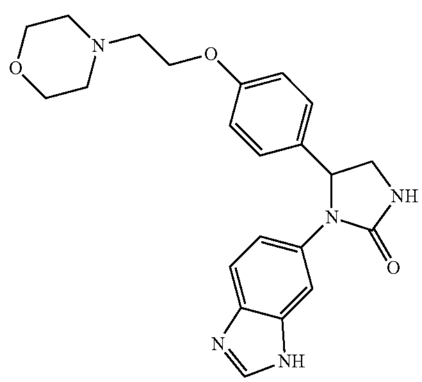 [SMILES: O=C1NCC(c2ccc(OCCN3CCOCC3)cc2)N1c1ccc2nc[nH]c2c1] | $C_{22}H_{25}N_5O_3$ | 407.466 |
| 25 | 5-(4-(3-morpholinopropoxy)phenyl)-1-(1H-benzo[d]imidazol-5-yl)imidazolidin-2-one | 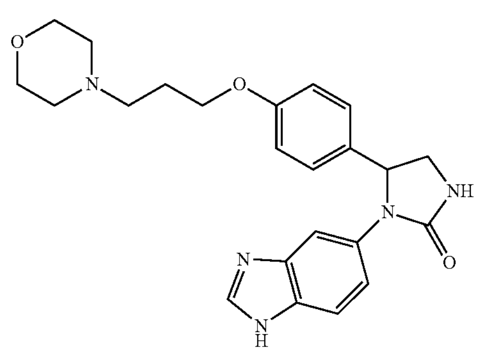 [SMILES: O=C1NCC(c2ccc(OCCCN3CCOCC3)cc2)N1c1ccc2[nH]cnc2c1] | $C_{23}H_{27}N_5O_3$ | 421.492 |

-continued

| Example | Chemical Name | Structure | Formula | Mol Weight |
| --- | --- | --- | --- | --- |
| 26 | 5-(2-(2-morpholinoethoxy)phenyl)-1-(1H-benzo[d]imidazol-5-yl)imidazolidin-2-one | 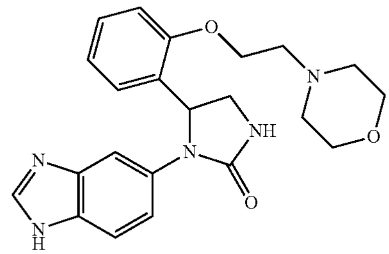 [SMILES: O=C1NCC(c2ccccc2OCCN2CCOCC2)N1c1ccc2[nH]cnc2c1] | $C_{22}H_{25}N_5O_3$ | 407.466 |
| 27 | 1-(1H-benzo[d]imidazol-5-yl)-5-(4-fluorophenyl)imidazolidin-2-one | 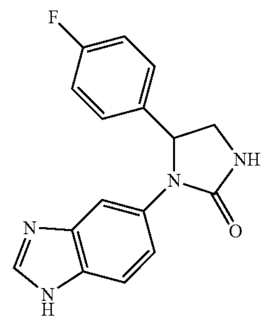 [SMILES: O=C1NCC(c2ccc(F)cc2)N1c1ccc2[nH]cnc2c1] | $C_{16}H_{13}FN_4O$ | 296.299 |
| 28 | 1-(1H-benzo[d]imidazol-5-yl)-5-(2-fluorophenyl)imidazolidin-2-one | 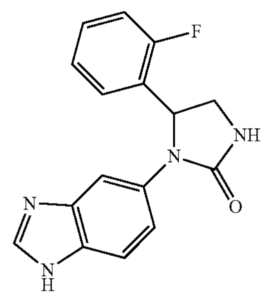 [SMILES: O=C1NCC(c2ccccc2F)N1c1ccc2[nH]cnc2c1] | $C_{16}H_{13}FN_4O$ | 296.299 |
| 29 | 1-(1H-benzo[d]imidazol-5-yl)-5-(3-fluorophenyl)imidazolidin-2-one | 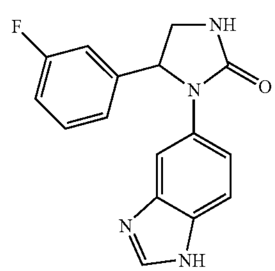 [SMILES: O=C1NCC(c2cccc(F)c2)N1c1ccc2[nH]cnc2c1] | $C_{16}H_{13}FN_4O$ | 296.299 |
| 30 | 1-(1H-benzo[d]imidazol-5-yl)-5-(2,6-difluorophenyl)imidazolidin-2-one | 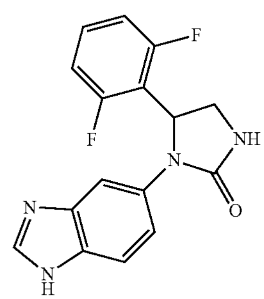 [SMILES: O=C1NCC(c2c(F)cccc2F)N1c1ccc2[nH]cnc2c1] | $C_{16}H_{12}F_2N_4O$ | 314.289 |

| Example | Chemical Name | Structure | Formula | Mol Weight |
|---|---|---|---|---|
| 31 | 1-(1H-benzo[d]imidazol-5-yl)-5-(3,4-difluorophenyl)imidazolidin-2-one | 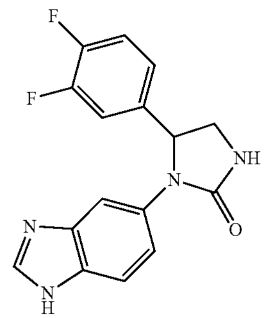 [SMILES: O=C1NCC(c2ccc(F)c(F)c2)N1c1ccc2[nH]cnc2c1] | $C_{16}H_{12}F_2N_4O$ | 314.289 |
| 32 | 1-(1H-benzo[d]imidazol-5-yl)-5-(2-fluoro-5-(trifluoromethyl)phenyl)imidazolidin-2-one | 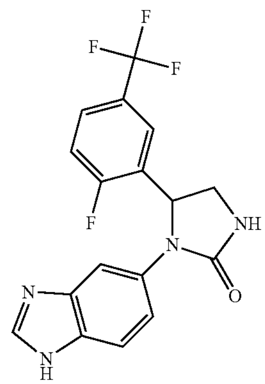 [SMILES: O=C1NCC(c2cc(C(F)(F)F)ccc2F)N1c1ccc2[nH]cnc2c1] | $C_{17}H_{12}F_4N_4O$ | 364.297 |
| 33 | 1-(1H-benzo[d]imidazol-5-yl)-5-(3-fluoro-5-(trifluoromethyl)phenyl)imidazolidin-2-one | 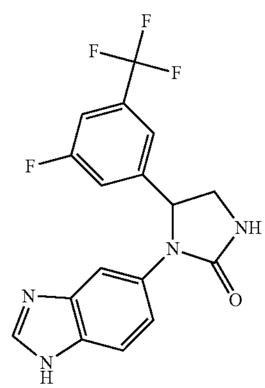 [SMILES: O=C1NCC(c2cc(F)cc(C(F)(F)F)c2)N1c1ccc2[nH]cnc2c1] | $C_{17}H_{12}F_4N_4O$ | 364.297 |
| 34 | 1-(1H-benzo[d]imidazol-5-yl)-5-(2-fluoro-4-(trifluoromethyl)phenyl)imidazolidin-2-one | 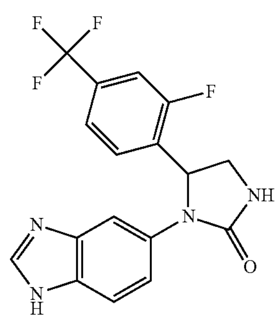 [SMILES: O=C1NCC(c2ccc(C(F)(F)F)cc2F)N1c1ccc2[nH]cnc2c1] | $C_{17}H_{12}F_4N_4O$ | 364.297 |

-continued

| Example | Chemical Name | Structure | Formula | Mol Weight |
|---|---|---|---|---|
| 35 | 1-(1H-benzo[d]imidazol-5-yl)-5-(3-fluoro-4-(trifluoromethyl)phenyl)imidazolidin-2-one | 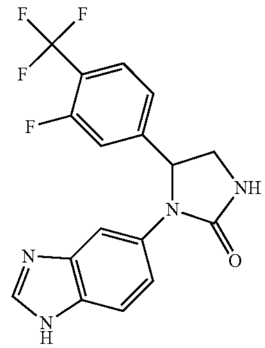 [SMILES: O=C1NCC(c2ccc(C(F)(F)F)c(F)c2)N1c1ccc2[nH]cnc2c1] | $C_{17}H_{12}F_4N_4O$ | 364.297 |
| 36 | 1-(1H-benzo[d]imidazol-5-yl)-5-(2-chlorophenyl)imidazolidin-2-one | 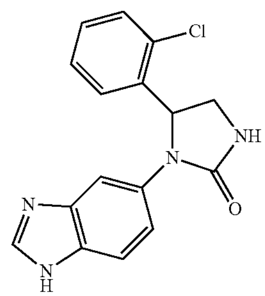 [SMILES: O=C1NCC(c2ccccc2Cl)N1c1ccc2[nH]cnc2c1] | $C_{16}H_{13}ClN_4O$ | 312.754 |
| 37 | 1-(1H-benzo[d]imidazol-5-yl)-5-(3-chlorophenyl)imidazolidin-2-one | 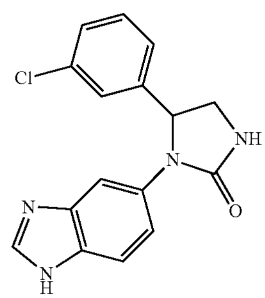 [SMILES: O=C1NCC(c2cccc(Cl)c2)N1c1ccc2[nH]cnc2c1] | $C_{16}H_{13}ClN_4O$ | 312.754 |
| 38 | 1-(1H-benzo[d]imidazol-5-yl)-5-(2,6-dichlorophenyl)imidazolidin-2-one | 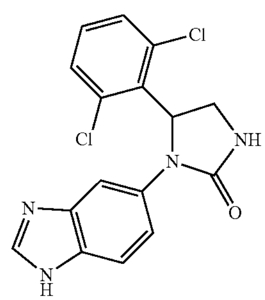 [SMILES: O=C1NCC(c2c(Cl)cccc2Cl)N1c1ccc2[nH]cnc2c1] | $C_{16}H_{12}Cl_2N_4O$ | 347.199 |
| 39 | 1-(1H-benzo[d]imidazol-5-yl)-5-(2,3-dichlorophenyl)imidazolidin-2-one | 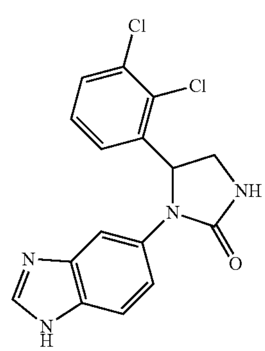 [SMILES: O=C1NCC(c2cccc(Cl)c2Cl)N1c1ccc2[nH]cnc2c1] | $C_{16}H_{12}Cl_2N_4O$ | 347.199 |

| Example | Chemical Name | Structure | Formula | Mol Weight |
|---|---|---|---|---|
| 40 | 1-(1H-benzo[d]imidazol-5-yl)-5-(3,4-dichlorophenyl)imidazolidin-2-one | 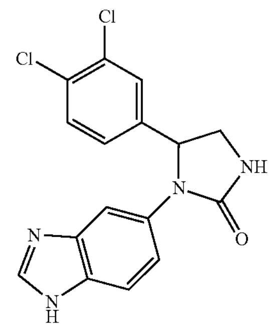 [SMILES: O=C1NCC(c2ccc(Cl)c(Cl)c2)N1c1ccc2[nH]cnc2c1] | $C_{16}H_{12}Cl_2N_4O$ | 347.199 |
| 41 | (S)-1-(1H-benzo[d]imidazol-5-yl)-5-(3,4-dichlorophenyl)imidazolidin-2-one | 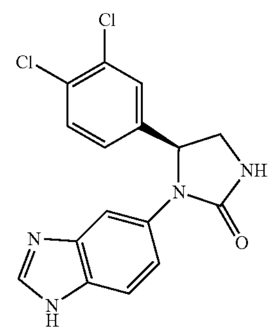 [SMILES: O=C1NC[C@H](c2ccc(Cl)c(Cl)c2)N1c1ccc2[nH]cnc2c1] | $C_{16}H_{12}Cl_2N_4O$ | 347.199 |
| 42 | 1-(1H-1,3-benzodiazol-5-yl)-5-(4-biphenyl)imidazolidin-2-one | 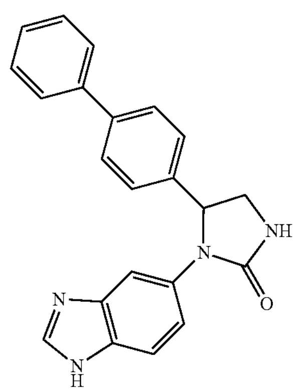 | $C_{22}H_{18}N_4O$ | 354.405 |
| 43 | (S)-1-(1H-1,3-benzodiazol-5-yl)-5-(4-biphenyl)imidazolidin-2-one | 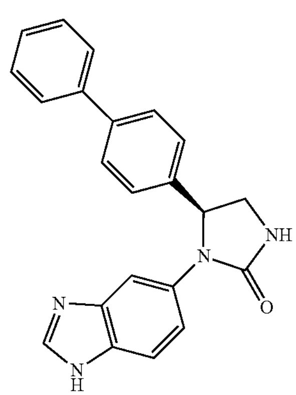 [SMILES: O=C1NC[C@H](c2ccc(-c3ccccc3)cc2)N1c1ccc2[nH]cnc2c1] | $C_{22}H_{18}N_4O$ | 354.405 |

-continued

| Example | Chemical Name | Structure | Formula | Mol Weight |
|---|---|---|---|---|
| 44 | (R)-1-(1H-1,3-benzodiazol-5-yl)-5-(4-biphenyl)imidazolidin-2-one | 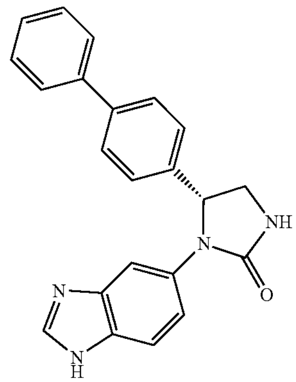 [SMILES: O=C1NC[C@@H](c2ccc(-c3ccccc3)cc2)N1c1ccc2[nH]cnc2c1] | $C_{22}H_{18}N_4O$ | 354.405 |
| 45 | 1-(1H-1,3-benzodiazol-5-yl)-5-(3-fluoro-4-biphenyl)imidazolidin-2-one | 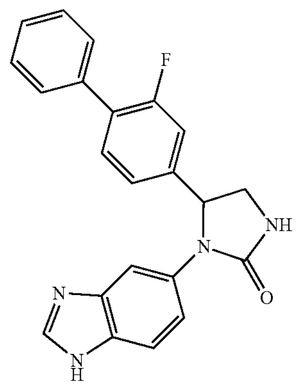 [SMILES: O=C1NCC(c2ccc(-c3ccccc3)c(F)c2)N1c1ccc2[nH]cnc2c1] | $C_{22}H_{17}FN_4O$ | 372.395 |
| 46 | 1-(1H-benzo[d]imidazol-5-yl)-5-[4-(3-chlorophenyl)phenyl]imidazolidin-2-one | 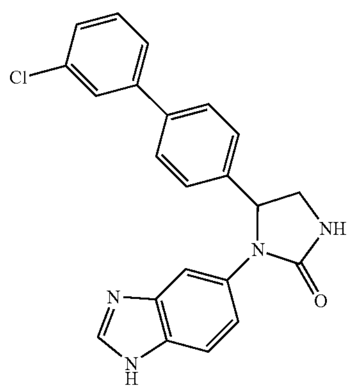 [SMILES: O=C1NCC(c2ccc(-c3cccc(Cl)c3)cc2)N1c1ccc2[nH]cnc2c1] | $C_{22}H_{17}ClN_4O$ | 388.85 |
| 47 | 1-(1H-benzo[d]imidazol-5-yl)-5-(3',4'-dichloro-4-biphenyl)imidazolidin-2-one | 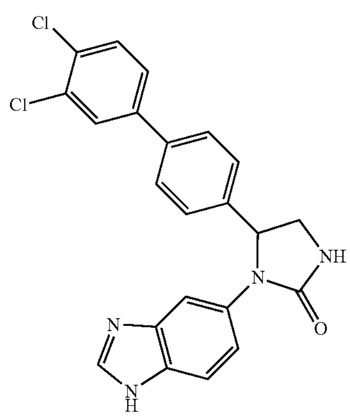 [SMILES: O=C1NCC(c2ccc(-c3ccc(Cl)c(Cl)c3)cc2)N1c1ccc2[nH]cnc2c1] | $C_{22}H_{16}Cl_2N_4O$ | 423.295 |

-continued

| Example | Chemical Name | Structure | Formula | Mol Weight |
|---|---|---|---|---|
| 48 | 1-(1H-benzo[d]imidazol-5-yl)-5-(3-phenylphenyl)imidazolidin-2-one | 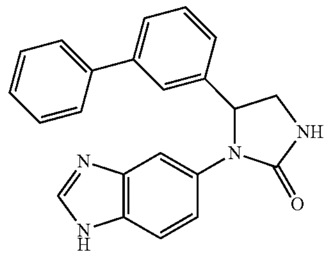 [SMILES: O=C1NCC(c2cccc(-c3ccccc3)c2)N1c1ccc2[nH]cnc2c1] | $C_{22}H_{18}N_4O$ | 354.405 |
| 49 | 1-(1H-benzo[d]imidazol-5-yl)-5-[3-(3-chlorophenyl)phenyl]imidazolidin-2-one | 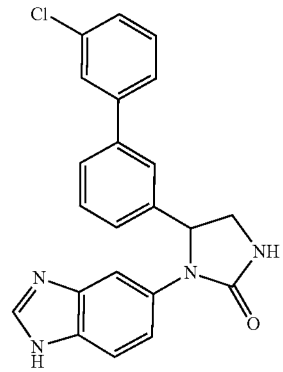 [SMILES: O=C1NCC(c2cccc(-c3cccc(Cl)c3)c2)N1c1ccc2[nH]cnc2c1] | $C_{22}H_{17}ClN_4O$ | 388.85 |
| 50 | 1-(1H-benzo[d]imidazol-5-yl)-5-(3-chloro-4-morpholinophenyl)imidazolidin-2-one | 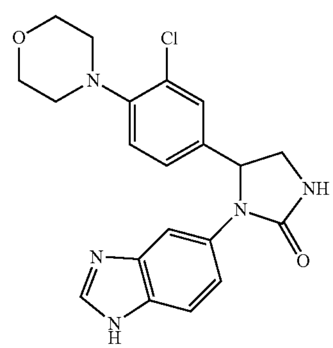 [SMILES: O=C1NCC(c2ccc(N3CCOCC3)c(Cl)c2)N1c1ccc2[nH]cnc2c1] | $C_{20}H_{20}ClN_5O_2$ | 397.858 |
| 51 | 1-(1H-benzo[d]imidazol-5-yl)-5-(4-(4-phenylpiperazin-1-yl)phenyl)imidazolidin-2-one | 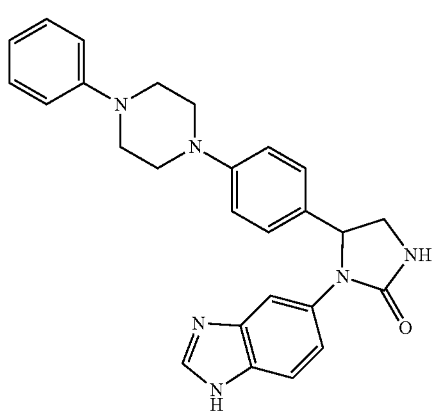 [SMILES: O=C1NCC(c2ccc(N3CCN(c4ccccc4)CC3)cc2)N1c1ccc2[nH]cnc2c1] | $C_{26}H_{26}N_6O$ | 438.524 |

-continued

| Example | Chemical Name | Structure | Formula | Mol Weight |
|---|---|---|---|---|
| 52 | 1-(1H-benzo[d]imidazol-5-yl)-5-(2-chloro-6-(4-ethylpiperazin-1-yl)phenyl)imidazolidin-2-one | 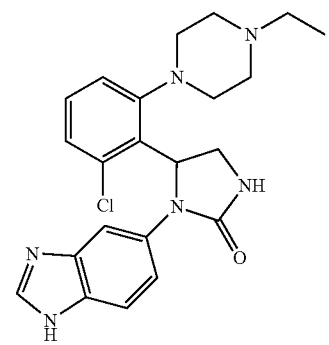 [SMILES: CCN1CCN(c2cccc(Cl)c2C2CNC(=O)N2c2ccc3[nH]cnc3c2)CC1] | $C_{22}H_{25}ClN_6O$ | 424.927 |
| 53 | 1-(H-imidazo[1,2-a]pyridin-7-yl)-5-phenylimidazolidin-2-one | 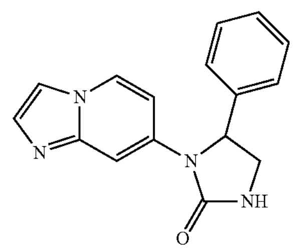 [SMILES: O=C1NCC(c2ccccc2)N1c1ccn2ccnc2c1] | $C_{16}H_{14}N_4O$ | 278.309 |
| 54 | 1-(H-imidazo[1,2-a]pyridin-7-yl)-5-(4-propoxyphenyl)imidazolidin-2-one | 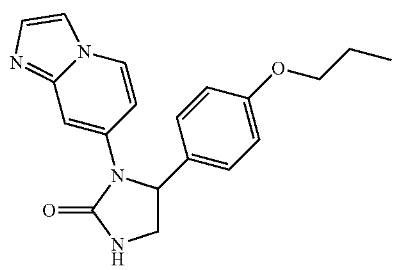 [SMILES: CCCOc1ccc(C2CNC(=O)N2c2ccn3ccnc3c2)cc1] | $C_{19}H_{20}N_4O_2$ | 336.388 |
| 55 | 5-(4-butoxyphenyl)-1-(H-imidazo[1,2-a]pyridin-7-yl)imidazolidin-2-one | 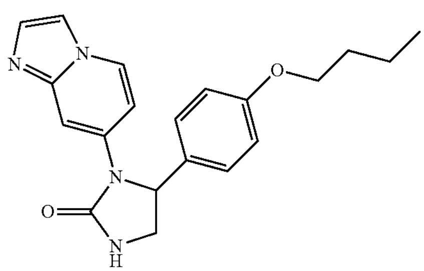 [SMILES: CCCCOc1ccc(C2CNC(=O)N2c2ccn3ccnc3c2)cc1] | $C_{20}H_{22}N_4O_2$ | 350.414 |
| 56 | 5-(2,6-difluoro-4-methoxyphenyl)-1-(H-imidazo[1,2-a]pyridin-7-yl)imidazolidin-2-one | 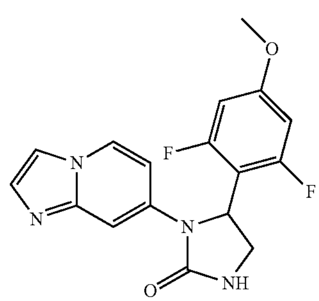 [SMILES: COc1cc(F)c(C2CNC(=O)N2c2ccn3ccnc3c2)c(F)c1] | $C_{17}H_{14}F_2N_4O_2$ | 344.315 |

-continued

| Example | Chemical Name | Structure | Formula | Mol Weight |
|---|---|---|---|---|
| 57 | 1-(H-imidazo[1,2-a]pyridin-7-yl)-5-(4-methoxybenzo[d][1,3]dioxol-6-yl)imidazolidin-2-one | 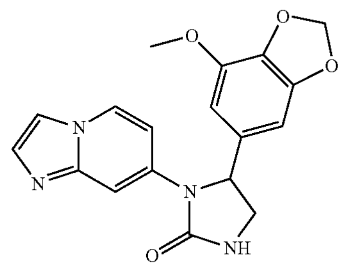 [SMILES: COc1cc(C2CNC(=O)N2c2ccn3ccnc3c2)cc2c1OCO2] | $C_{18}H_{16}N_4O_4$ | 352.344 |
| 58 | 5-(4-(2-morpholinoethoxy)phenyl)-1-(H-imidazo[1,2-a]pyridin-7-yl)imidazolidin-2-one | 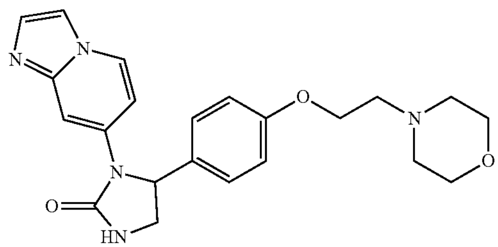 [SMILES: O=C1NCC(c2ccc(OCCN3CCOCC3)cc2)N1c1ccn2ccnc2c1] | $C_{22}H_{25}N_5O_3$ | 407.466 |
| 59 | 5-(2,6-difluorophenyl)-1-(H-imidazo[1,2-a]pyridin-7-yl)imidazolidin-2-one | 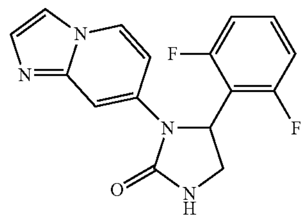 [SMILES: O=C1NCC(c2c(F)cccc2F)N1c1ccn2ccnc2c1] | $C_{16}H_{12}F_2N_4O$ | 314.28 |
| 60 | 5-(biphenyl)-1-(H-imidazo[1,2-a]pyridin-7-yl)imidazolidin-2-one | 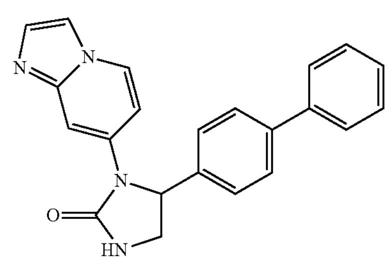 [SMILES: O=C1NCC(c2ccc(-c3ccccc3)cc2)N1c1ccn2ccnc2c1] | $C_{22}H_{18}N_4O$ | 354.405 |
| 61 | 5-(3-fluorobiphenyl)-1-(H-imidazo[1,2-a]pyridin-7-yl)imidazolidin-2-one | 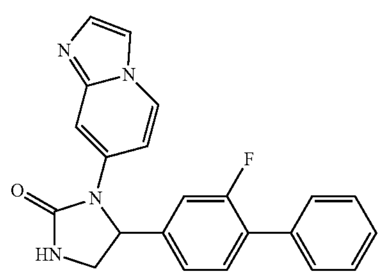 [SMILES: O=C1NCC(c2ccc(-c3ccccc3)c(F)c2)N1c1ccn2ccnc2c1] | $C_{22}H_{17}FN_4O$ | 372.395 |

-continued

| Example | Chemical Name | Structure | Formula | Mol Weight |
|---|---|---|---|---|
| 62 | 1-(H-imidazo[1,2-a]pyridin-7-yl)-5-(4-(4-phenylpiperazin-1-yl)phenyl)imidazolidin-2-one | 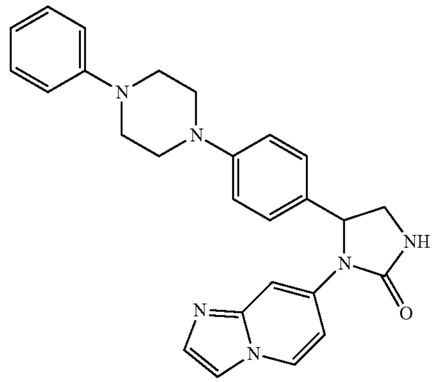 [SMILES: O=C1NCC(c2ccc(N3CCN(c4ccccc4)CC3)cc2)N1c1ccn2ccnc2c1] | $C_{26}H_{26}N_6O$ | 438.22 |
| 63 | 1-(1H-benzo[d]imidazol-5-yl)-5-phenylimidazolidin-4-one | 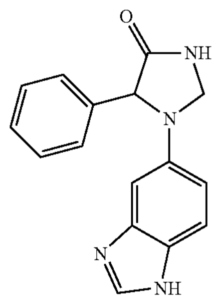 [SMILES: O=C1NCN(c2ccc3[nH]cnc3c2)C1c1ccccc1] | $C_{16}H_{14}N_4O$ | 278.30 |
| 64 | 1-(1H-benzo[d]imidazol-5-yl)-5-(2,3,5-trifluorophenyl)imidazolidin-4-one | 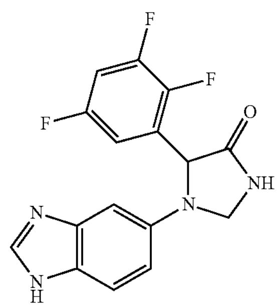 [SMILES: O=C1NCN(c2ccc3[nH]cnc3c2)C1c1cc(F)cc(F)c1F] | $C_{16}H_{11}F_3N_4O$ | 332.27 |
| 65 | 1-Amino-3-(1H-benzo[d]imidazol-5-yl)-4-(4-methoxyphenyl)imidazolidin-2-one | 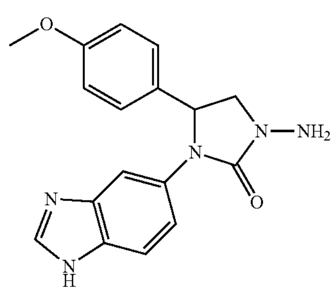 [SMILES: COc1ccc(C2CN(N)C(=O)N2c2ccc3[nH]cnc3c2)cc1] | $C_{17}H_{17}N_5O_2$ | 323.34 |
| 66 | (S)-3-(1H-benzo[d]imidazol-6-yl)-4 phenyloxazolidin-2-one | 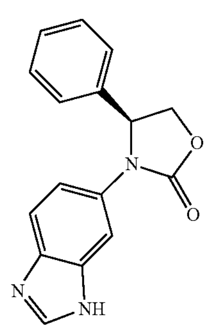 [SMILES: O=C1OC[C@H](c2ccccc2)N1c1ccc2nc[nH]c2c1] | $C_{16}H_{13}N_3O_2$ | 279.293 |

-continued

| Example | Chemical Name | Structure | Formula | Mol Weight |
|---|---|---|---|---|
| 67 | (R)-3-(1H-benzo[d]imidazol-6-yl)-4-phenyloxazolidin-2-one | 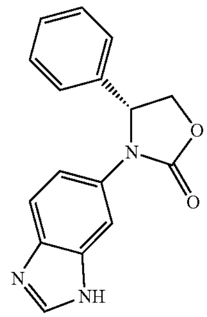 [SMILES: O=C1OC[C@@H](c2ccccc2)N1c1ccc2nc[nH]c2c1] | $C_{16}H_{13}N_3O_2$ | 279.293 |
| 68 | (S)-3-(1H-benzo[d]imidazol-5-yl)-4-isopropyloxazolidin-2-one | 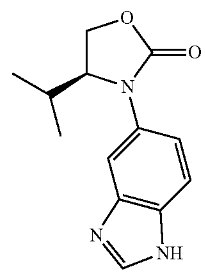 [SMILES: CC(C)[C@H]1COC(=O)N1c1ccc2[nH]cnc2c1] | $C_{13}H_{15}N_3O_2$ | 245.27 |
| 69 | (S)-3-(1H-benzo[d]imidazol-5-yl)-4-benzyloxazolidin-2-one | 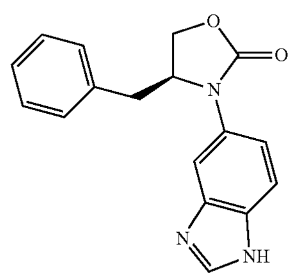 [SMILES: O=C1OC[C@H](Cc2ccccc2)N1c1ccc2[nH]cnc2c1] | $C_{17}H_{15}N_3O_2$ | 293.31 |
| 70 | (4S,5R)-3-(1H-benzo[d]imidazol-6-yl)-4,5-diphenyloxazolidin-2-one | 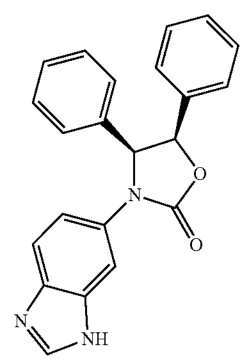 [SMILES: O=C1O[C@H](c2ccccc2)[C@H](c2ccccc2)N1c1ccc2nc[nH]c2c1] | $C_{22}H_{17}N_3O_2$ | 355.389 |
| 71 | (4S,5S)-3-(1H-benzo[d]imidazol-6-yl)-5-methyl-4-phenyloxazolidin-2-one | 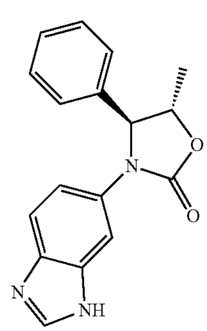 [SMILES: C[C@@H]1OC(=O)N(c2ccc3nc[nH]c3c2)[C@H]1c1ccccc1] | $C_{17}H_{15}N_3O_2$ | 293.32 |

-continued

| Example | Chemical Name | Structure | Formula | Mol Weight |
|---|---|---|---|---|
| 72 | (S)-3-(1H-benzo[d]imidazol-6-yl)-5,5-dimethyl-4-phenyloxazolidin-2-one | 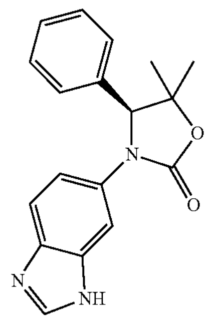 [SMILES: CC1(C)OC(=O)N(c2ccc3nc[nH]c3c2)[C@H]1c1ccccc1] | $C_{18}H_{17}N_3O_2$ | 307.346 |
| 73 | (S)-3-(1H-benzo[d]imidazol-6-yl)-4-(4-propoxyphenyl)oxazolidin-2-one | 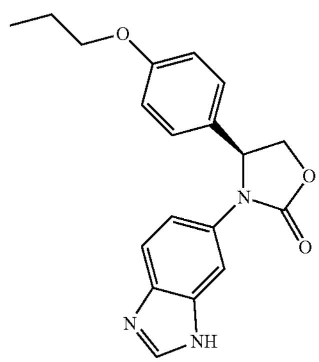 [SMILES: CCCOc1ccc([C@H]2COC(=O)N2c2ccc3nc[nH]c3c2)cc1] | $C_{19}H_{19}N_3O_3$ | 337.372 |
| 74 | (S)-3-(1H-benzo[d]imidazol-6-yl)-4-(2,3-dihydrobenzo[b][1,4]dioxin-7-yl)oxazolidin-2-one | 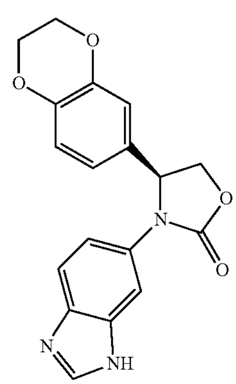 [SMILES: O=C1OC[C@H](c2ccc3c(c2)OCCO3)N1c1ccc2nc[nH]c2c1] | $C_{18}H_{15}N_3O_4$ | 337.11 |
| 75 | (S)-4-(benzo[d][1,3]dioxol-6-yl)-3-(1H-benzo[d]imidazol-6-yl)oxazolidin-2-one | 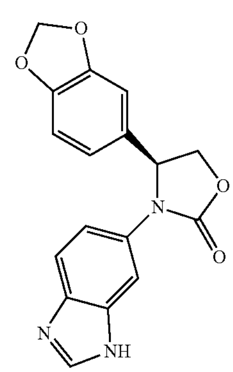 [SMILES: O=C1OC[C@H](c2ccc3c(c2)OCO3)N1c1ccc2nc[nH]c2c1] | $C_{17}H_{13}N_3O_4$ | 323.09 |

| Example | Chemical Name | Structure | Formula | Mol Weight |
|---|---|---|---|---|
| 76 | (4S,5R)-3-(1H-benzo[d]imidazol-6-yl)-4,5-bis(4-propoxyphenyl)oxazolidin-2-one | diastereomer 1 | $C_{28}H_{29}N_3O_4$ | 471.22 |
| 77 | (4S,5R)-3-(1H-benzo[d]imidazol-6-yl)-4,5-bis(4-propoxyphenyl)oxazolidin-2-one | diastereomer 2 | $C_{28}H_{29}N_3O_4$ | 471.22 |
| 78 | 3-(1H-benzo[d]imidazol-6-yl)-5-phenyl-4-(4-propoxyphenyl)oxazolidin-2-one | diastereomer 1 | $C_{25}H_{23}N_3O_3$ | 413.17 |

-continued
| Example | Chemical Name | Structure | Formula | Mol Weight |
|---|---|---|---|---|
| 79 | -(1H-benzo[d]imidazol-6-yl)-5-phenyl-4-(4-propoxyphenyl)oxazolidin-2-one | 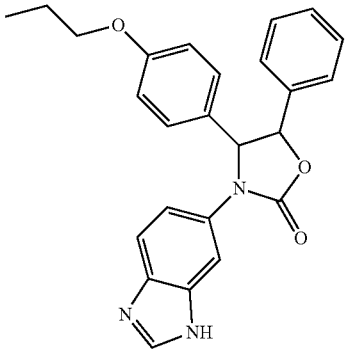 diastereomer 2 | $C_{25}H_{23}N_3O_3$ | 413.17 |
| 80 | (S)-4-(4-(2-(piperazin-1-yl)ethoxy)phenyl)-3-(1H-benzo[d]imidazol-6-yl)oxazolidin-2-one | 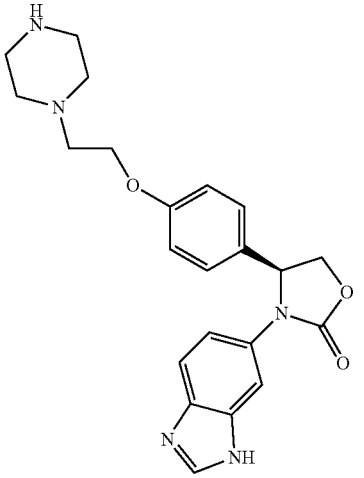 [SMILES: O=C1OC[C@H](c2ccc(OCCN3CCNCC3)cc2)N1c1ccc2nc[nH]c2c1] | $C_{22}H_{25}N_5O_3$ | 407.2 |
| 81 | (S)-4-(4-(2-morpholinoethoxy)phenyl)-3-(1H-benzo[d]imidazol-6-yl)oxazolidin-2-one | 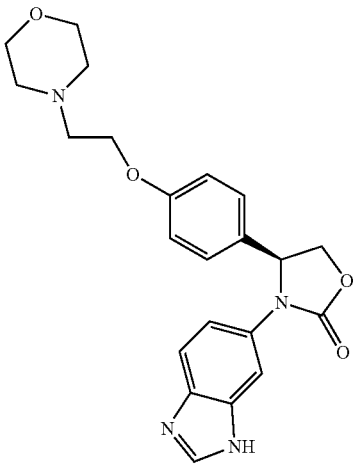 [SMILES: O=C1OC[C@H](c2ccc(OCCN3CCOCC3)cc2)N1c1ccc2nc[nH]c2c1] | $C_{22}H_{24}N_4O_4$ | 408.18 |

-continued

| Example | Chemical Name | Structure | Formula | Mol Weight |
|---|---|---|---|---|
| 82 | (S)-3-(1H-benzo[d]imidazol-6-yl)-4-(2,3-difluorophenyl)oxazolidin-2-one | 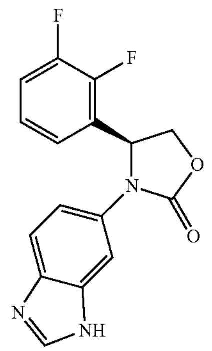 [SMILES: O=C1OC[C@H](c2cccc(F)c2F)N1c1ccc2nc[nH]c2c1] | $C_{16}H_{11}F_2N_3O_2$ | 315.08 |
| 83 | (S)-3-(1H-benzo[d]imidazol-6-yl)-4-(3-fluorophenyl)oxazolidin-2-one | 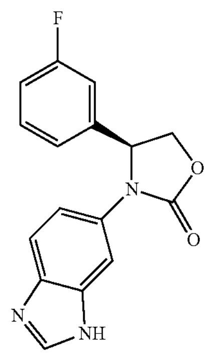 [SMILES: O=C1OC[C@H](c2cccc(F)c2)N1c1ccc2nc[nH]c2c1] | $C_{16}H_{12}FN_3O_2$ | 297.09 |
| 84 | (S)-3-(1H-benzo[d]imidazol-6-yl)-4-(3-fluoro-5-(trifluoromethyl)phenyl)oxazolidin-2-one | 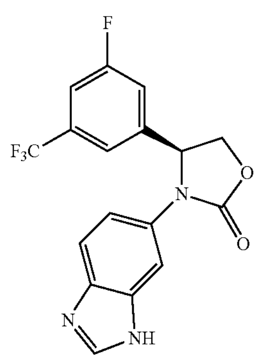 [SMILES: O=C1OC[C@H](c2cc(F)cc(C(F)(F)F)c2)N1c1ccc2nc[nH]c2c1] | $C_{17}H_{11}F_4N_3O_2$ | 365.08 |
| 85 | (S)-3-(1H-benzo[d]imidazol-6-yl)-4-(3-chlorophenyl)oxazolidin-2-one | 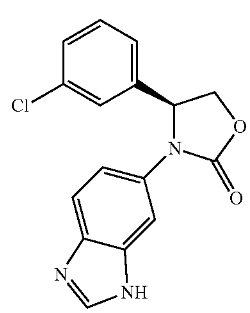 [SMILES: O=C1OC[C@H](c2cccc(Cl)c2)N1c1ccc2nc[nH]c2c1] | $C_{16}H_{12}ClN_3O_2$ | 313.06 |

-continued

| Example | Chemical Name | Structure | Formula | Mol Weight |
|---|---|---|---|---|
| 86 | (S)-3-(1H-benzo[d]imidazol-6-yl)-4-(4-chlorophenyl)oxazolidin-2-one | 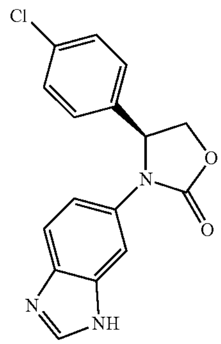 [SMILES: O=C1OC[C@H](c2ccc(Cl)cc2)N1c1ccc2nc[nH]c2c1] | $C_{16}H_{12}ClN_3O_2$ | 313.06 |
| 87 | (S)-3-(1H-benzo[d]imidazol-6-yl)-4-[4-(3-chlorophenyl)phenyl]oxazolidin-2-one | 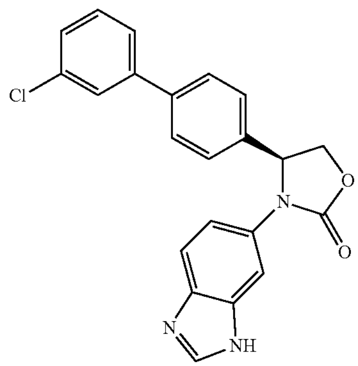 [SMILES: O=C1OC[C@H](c2ccc(-c3cccc(Cl)c3)cc2)N1c1ccc2nc[nH]c2c1] | $C_{22}H_{16}ClN_3O_2$ | 389.09 |
| 88 | (S)-3-(1H-benzo[d]imidazol-6-yl)-4-[3-(3-chlorophenyl)phenyl]oxazolidin-2-one | 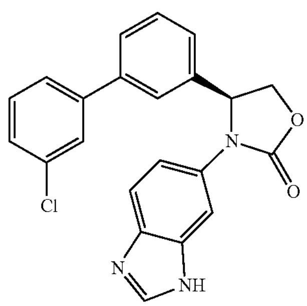 [SMILES: O=C1OC[C@H](c2cccc(-c3cccc(Cl)c3)c2)N1c1ccc2nc[nH]c2c1] | $C_{22}H_{16}ClN_3O_2$ | 389.09 |
| 89 | (S)-3-(1H-benzo[d]imidazol-6-yl)-4-(4-(4-phenylpiperazin-1-yl)phenyl)oxazolidin-2-one | 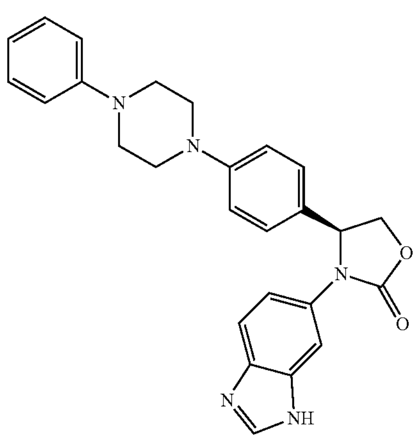 [SMILES: O=C1OC[C@H](c2ccc(N3CCN(c4ccccc4)CC3)cc2)N1c1ccc2nc[nH]c2c1] | $C_{26}H_{25}N_5O_2$ | 439.2 |

-continued

| Example | Chemical Name | Structure | Formula | Mol Weight |
|---|---|---|---|---|
| 90 | (S)-3-(1H-benzo[d]imidazol-6-yl)-4-(4-(4-methylpiperazin-1-yl)phenyl)oxazolidin-2-one | 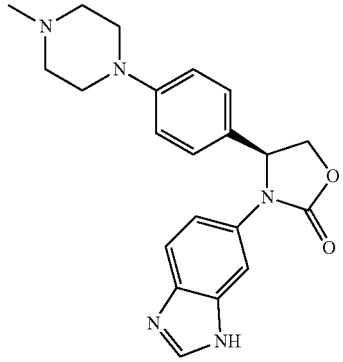 [SMILES: CN1CCN(c2ccc([C@H]3COC(=O)N3c3ccc4nc[nH]c4c3)cc2)CC1] | $C_{21}H_{23}N_5O_2$ | 377.19 |
| 91 | (S)-3-(1H-benzo[d]imidazol-6-yl)-4-(3-(4-phenylpiperazin-1-yl)phenyl)oxazolidin-2-one | 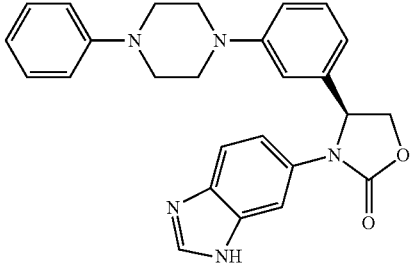 [SMILES: O=C1OC[C@H](c2cccc(N3CCN(c4ccccc4)CC3)c2)N1c1ccc2nc[nH]c2c1] | $C_{26}H_{25}N_5O_2$ | 439.50 |
| 92 | (S)-3-(2-methyl-1H-benzo[d]imidazol-6-yl)-4-phenyloxazolidin-2-one | 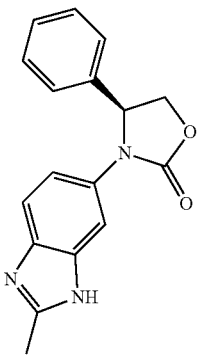 [SMILES: Cc1nc2ccc(N3C(=O)OC[C@@H]3c3ccccc3)cc2[nH]1] | $C_{17}H_{15}N_3O_2$ | 293.31 |
| 93 | (S)-4-(1H-benzo[d]imidazol-6-yl)-5-(4-propoxyphenyl)morpholin-3-one | 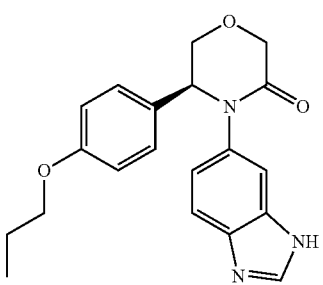 [SMILES: CCCOc1ccc([C@H]2COCC(=O)N2c2ccc3nc[nH]c3c2)cc1] | $C_{20}H_{21}N_3O_3$ | 351.39 |
| 94 | 3-(1H-benzo[d]imidazol-6-yl)-4-(4-propoxyphenyl)-1,3-oxazinan-2-one | 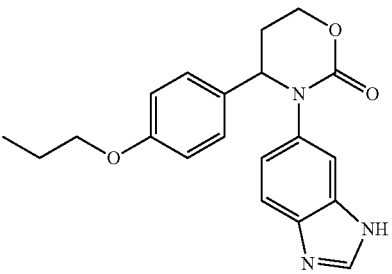 [SMILES: CCCOc1ccc(C2CCOC(=O)N2c2ccc3nc[nH]c3c2)cc1] | $C_{20}H_{21}N_3O_3$ | 351.39 |

-continued
| Example | Chemical Name | Structure | Formula | Mol Weight |
|---|---|---|---|---|
| 95 | (S)-3-(H-imidazo[1,2-a]pyridin-7-yl)-4-phenyloxazolidin-2-one | 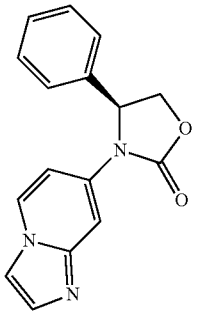 [SMILES: O=C1OC[C@H](c2ccccc2)N1c1ccn2ccnc2c1] | $C_{16}H_{13}N_3O_2$ | 279.293 |
| 96 | (4S,5R)-3-(H-imidazo[1,2-a]pyridin-7-yl)-4,5-diphenyloxazolidin-2-one | 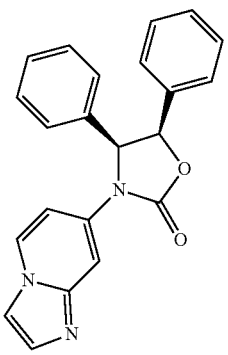 [SMILES: O=C1O[C@H](c2ccccc2)[C@H](c2ccccc2)N1c1ccn2ccnc2c1] | $C_{22}H_{17}N_3O_2$ | 355.389 |
| 97 | (4S,5R)-3-(imidazo[1,2-a]pyridin-6-yl)-4,5-diphenyloxazolidin-2-one | 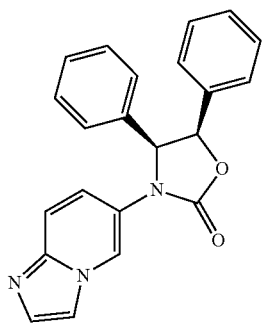 [SMILES: O=C1O[C@H](c2ccccc2)[C@H](c2ccccc2)N1c1ccc2nccn2c1] | $C_{22}H_{17}N_3O_2$ | 355.38 |
| 98 | (S)-3-(H-imidazo[1,2-a]pyridin-7-yl)-4-(4-propoxyphenyl)oxazolidin-2-one | 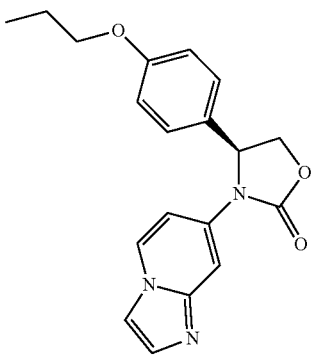 [SMILES: CCCOc1ccc([C@H]2COC(=O)N2c2ccn3ccnc3c2)cc1] | $C_{19}H_{19}N_3O_3$ | 337.372 |

-continued

| Example | Chemical Name | Structure | Formula | Mol Weight |
|---------|---------------|-----------|---------|------------|
| 99 | (S)-4-(4-chlorophenyl)-3-(H-imidazo[1,2-a]pyridin-7-yl)oxazolidin-2-one | 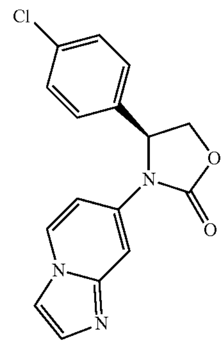 [SMILES: O=C1OC[C@H](c2ccc(Cl)cc2)N1c1ccn2ccnc2c1] | C₁₆H₁₂ClN₃O₂ | 313.06 |
| 100 | 3-(imidazo[1,2-a]pyridin-7-yl)-4-(4-propoxyphenyl)-1,3-oxazinan-2-one | 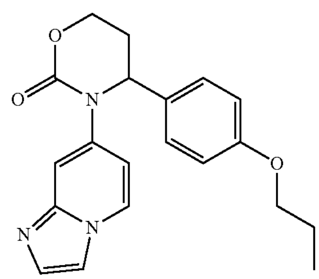 [SMILES: CCCOc1ccc(C2CCOC(=O)N2c2ccn3ccnc3c2)cc1] | C₂₀H₂₁N₃O₃ | 351.39 |
| 101 | 5-(2-phenylpyrrolidin-1-yl)-1H-benzo[d]imidazole | 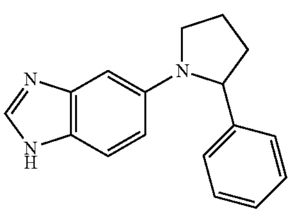 [SMILES: c1ccc(C2CCCN2c2ccc3[nH]cnc3c2)cc1] | C₁₇H₁₇N₃ | 263.33 |
| 102 | 5-(2-(4-methoxyphenyl)pyrrolidin-1-yl)-1H-benzo[d]imidazole | 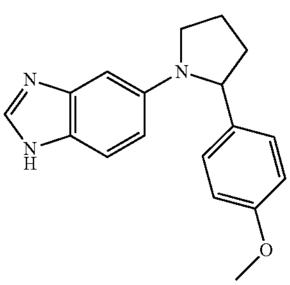 [SMILES: COc1ccc(C2CCCN2c2ccc3[nH]cnc3c2)cc1] | C₁₈H₁₉N₃O | 293.36 |
| 103 | 5-(2-(4-fluorophenyl)pyrrolidin-1-yl)-1H-benzo[d]imidazole | 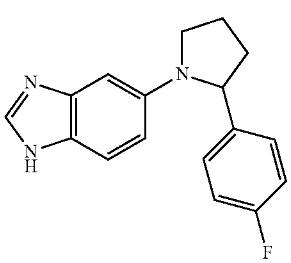 [SMILES: Fc1ccc(C2CCCN2c2ccc3[nH]cnc3c2)cc1] | C₁₇H₁₆FN₃ | 281.32 |

-continued

| Example | Chemical Name | Formula | Mol Weight |
|---------|---------------|---------|------------|
| 104 | 5-(2-(4-chlorophenyl)pyrrolidin-1-yl)-1H-benzo[d]imidazole | $C_{17}H_{16}ClN_3$ | 297.78 |
| 105 | 5-(2-benzylpyrrolidin-1-yl)-1H-benzo[d]imidazole | $C_{18}H_{19}N_3$ | 277.36 |
| 106 | 5-(2-(4-chlorobenzyl)pyrrolidin-1-yl)-1H-benzo[d]imidazole | $C_{18}H_{18}ClN_3$ | 311.80 |
| 107 | 5-(2-(4-fluorobenzyl)pyrrolidin-1-yl)-1H-benzo[d]imidazole | $C_{18}H_{18}FN_3$ | 295.35 |
| 108 | 5-(pyrrolidin-1-yl)-1H-benzo[d]imidazole | $C_{11}H_{13}N_3$ | 187.24 |
| 109 | 5-(2-(4-methoxybenzyl)pyrrolidin-1-yl)-1H-benzo[d]imidazole | $C_{19}H_{21}N_3O$ | 307.38 |
| 110 | 3-(1H-benzo[d]imidazol-6-yl)-2-(4-chlorophenyl)thiazolidin-4-one | $C_{16}H_{12}ClN_3OS$ | 329.80 |

-continued

| Example | Chemical Name | Structure | Formula | Mol Weight |
|---|---|---|---|---|
| 111 | 3-(1H-benzo[d]imidazol-5-yl)-2-phenylthiazolidin-4-one | 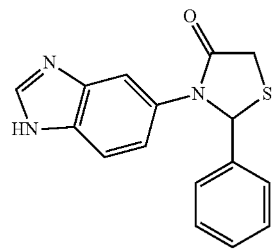 | $C_{16}H_{13}N_3OS$ | 295.35 |
| 112 | 3-(1H-benzo[d]imidazol-6-yl)-2-(4-fluorophenyl)thiazolidin-4-one | 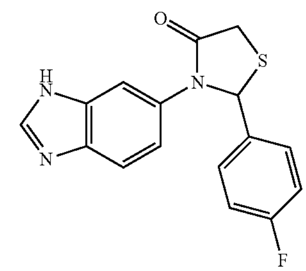 [SMILES: O=C1CSC(c2ccc(Cl)cc2)N1c1ccc2nc[nH]c2c1] | $C_{16}H_{12}FN_3OS$ | 313.34 |
| 113 | 3-(1H-benzo[d]imidazol-6-yl)-2-(naphthalen-1-yl)thiazolidin-4-one | 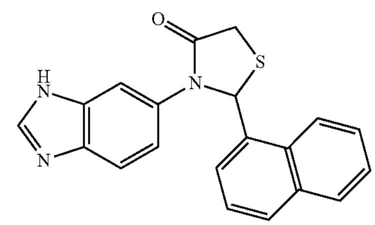 [SMILES: O=C1CSC(c2cccc3ccccc23)N1c1ccc2nc[nH]c2c1] | $C_{20}H_{15}N_3OS$ | 345.41 |
| 114 | 3-(1H-benzo[d]imidazol-6-yl)-2-(4-phenoxyphenyl)thiazolidin-4-one | 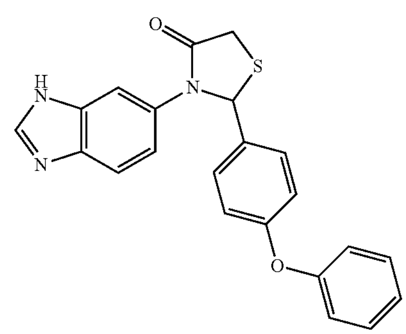 [SMILES: O=C1CSC(c2ccc(Oc3ccccc3)cc2)N1c1ccc2nc[nH]c2c1] | $C_{22}H_{17}N_3O_2S$ | 387.45 |
| 115 | 3-(1H-benzo[d]imidazol-6-yl)-2-(2,6-difluorophenyl)thiazolidin-4-one | 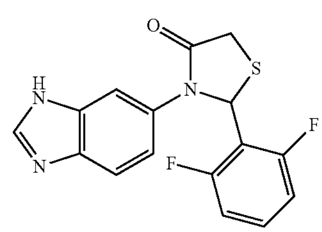 [SMILES: O=C1CSC(c2c(F)cccc2F)N1c1ccc2nc[nH]c2c1] | $C_{16}H_{11}F_2N_3OS$ | 331.33 |
| 116 | 3-(1H-benzo[d]imidazol-6-yl)-2-(thiophen-3-yl)thiazolidin-4-one | 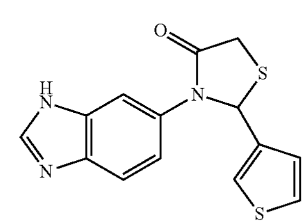 [SMILES: O=C1CSC(c2ccsc2)N1c1ccc2nc[nH]c2c1] | $C_{14}H_{11}N_3OS_2$ | 301.38 |

| Example | Chemical Name | Structure | Formula | Mol Weight |
|---------|---------------|-----------|---------|------------|
| 117 | 3-(1H-benzo[d]imidazol-6-yl)-5-methyl-2-phenylthiazolidin-4-one | 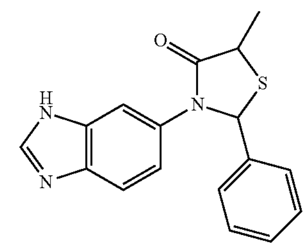 [SMILES: CC1SC(c2ccccc2)N(c2ccc3nc[nH]c3c2)C1=O] | $C_{17}H_{15}N_3OS_2$ | 309.38 |
| 118 | 3-(1H-benzo[d]imidazol-5-yl)-2-phenylthiazolidine-4-thione | 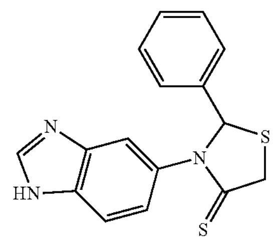 [SMILES: S=C1CSC(c2ccccc2)N1c1ccc2[nH]cnc2c1] | $C_{16}H_{13}N_3S_2$ | 311.42 |
| 119 | 3-(1H-benzo[d]imidazol-6-yl)-2-(4-phenoxyphenyl)thiazolidine-4-thione | 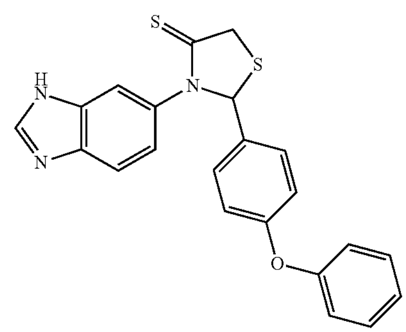 [SMILES: S=C1CSC(c2ccc(Oc3ccccc3)cc2)N1c1ccc2nc[nH]c2c1] | $C_{22}H_{17}N_3OS_2$ | 403.51 |
| 120 | 1-(1H-benzo[d]imidazol-5-yl)-5-(4-fluorophenyl)pyrrolidin-2-one | 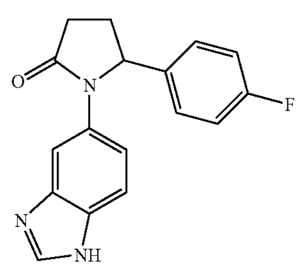 [SMILES: O=C1CCC(c2ccc(F)cc2)N1c1ccc2[nH]cnc2c1] | $C_{17}H_{14}FN_3O$ | 295.31 |
| 121 | 1-(1H-benzo[d]imidazol-5-yl)-5-(4-methoxyphenyl)pyrrolidin-2-one | 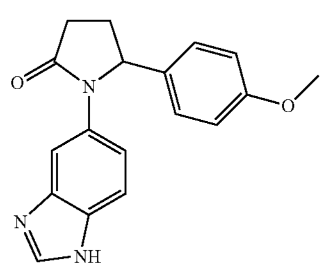 [SMILES: COc1ccc(C2CCC(=O)N2c2ccc3[nH]cnc3c2)cc1] | $C_{18}H_{17}N_3O_2$ | 307.34 |

-continued

| Example | Chemical Name | Structure | Formula | Mol Weight |
|---|---|---|---|---|
| 122 | 1-(1H-benzo[d]imidazol-5-yl)-5-(4-propoxyphenyl)pyrrolidin-2-one | 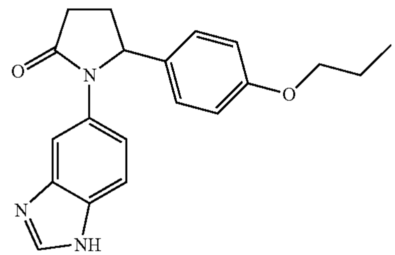 [SMILES: CCCOc1ccc(C2CCC(=O)N2c2ccc3[nH]cnc3c2)cc1] | $C_{20}H_{21}N_3O_2$ | 335.39 |
| 123 | 1-(1H-benzo[d]imidazol-5-yl)-5-(2,3-dihydrobenzo[b][1,4]dioxin-6-yl)pyrrolidin-2-one | 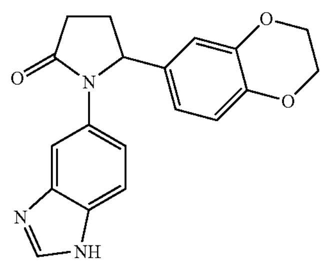 [SMILES: O=C1CCC(c2ccc3c(c2)OCCO3)N1c1ccc2[nH]cnc2c1] | $C_{19}H_{17}N_3O_3$ | 335.35 |
| 124 | 1-(1H-benzo[d]imidazol-5-yl)-5-phenylpyrrolidin-2-one | 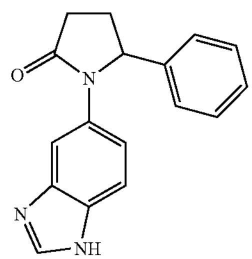 [SMILES: O=C1CCC(c2ccccc2)N1c1ccc2[nH]cnc2c1] | $C_{17}H_{15}N_3O$ | 277.32 |
| 125 | 2-(1H-benzo[d]imidazol-5-yl)-3-phenylisoindolin-1-one | 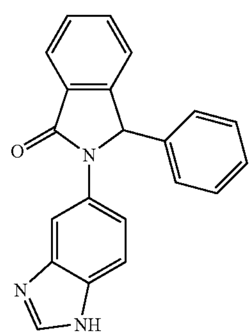 [SMILES: O=C1c2ccccc2C(c2ccccc2)N1c1ccc2[nH]cnc2c1] | $C_{21}H_{15}N_3O$ | 325.36 |
| 126 | 2-(1H-benzo[d]imidazol-5-yl)-3-(4-biphenyl)isoindolin-1-one | 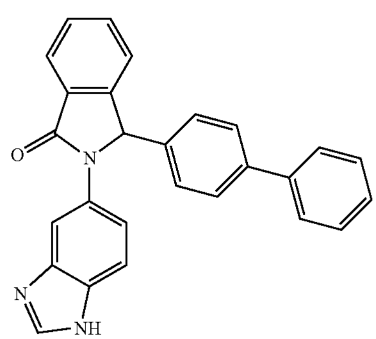 [SMILES: O=C1c2ccccc2C(c2ccc(-c3ccccc3)cc2)N1c1ccc2[nH]cnc2c1] | $C_{27}H_{19}N_3O$ | 401.45 |

-continued

| Example | Chemical Name | Structure | Formula | Mol Weight |
|---|---|---|---|---|
| 127 | 2-(1H-benzo[d]imidazol-5-yl)-3-(4-fluorophenyl)isoindolin-1-one | 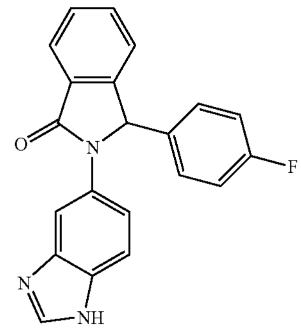 [SMILES: O=C1c2ccccc2C(c2ccc(F)cc2)N1c1ccc2[nH]cnc2c1] | $C_{21}H_{14}FN_3O$ | 343.35 |
| 128 | 2-(1H-benzo[d]imidazol-5-yl)-3-(3-fluorophenyl)isoindolin-1-one | 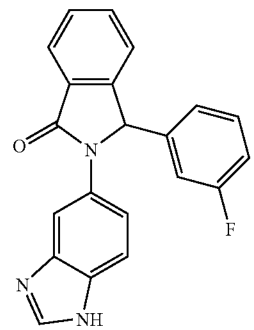 [SMILES: O=C1c2ccccc2C(c2cccc(F)c2)N1c1ccc2[nH]cnc2c1] | $C_{21}H_{14}FN_3O$ | 343.35 |
| 129 | 2-(1H-benzo[d]imidazol-5-yl)-3-(3,5-difluorophenyl)isoindolin-1-one | 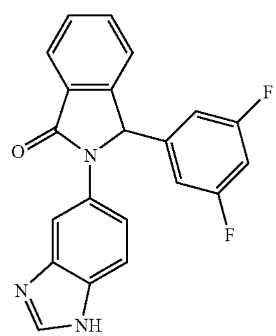 [SMILES: O=C1c2ccccc2C(c2cc(F)cc(F)c2)N1c1ccc2[nH]cnc2c1] | $C_{21}H_{13}F_2N_3O$ | 361.34 |
| 130 | 2-(1H-benzo[d]imidazol-5-yl)-3-(4-chlorophenyl)isoindolin-1-one | 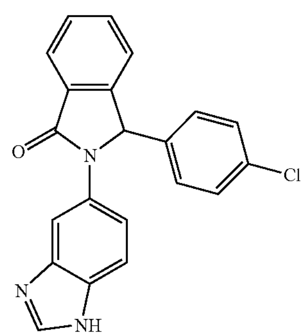 [SMILES: O=C1c2ccccc2C(c2ccc(Cl)cc2)N1c1ccc2[nH]cnc2c1] | $C_{21}H_{14}ClN_3O$ | 359.80 |

-continued

| Example | Chemical Name | Structure | Formula | Mol Weight |
|---|---|---|---|---|
| 131 | 2-(1H-benzo[d]imidazol-5-yl)-3-(3,4-dichlorophenyl)isoindolin-1-one | 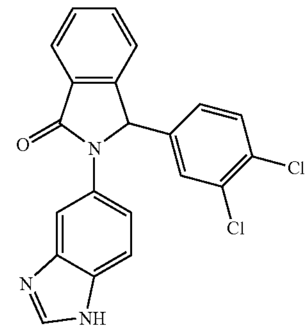 [SMILES: O=C1c2ccccc2C(c2ccc(Cl)c(Cl)c2)N1c1ccc2[nH]cnc2c1] | $C_{21}H_{13}Cl_2N_3O$ | 394.25 |
| 132 | 2-(1H-benzo[d]imidazol-5-yl)-3-(3-chloro-5-fluorophenyl)isoindolin-1-one | 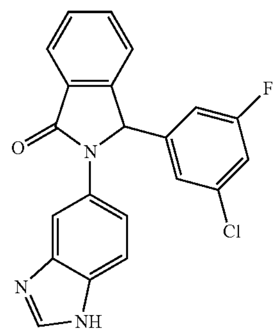 [SMILES: O=C1c2ccccc2C(c2cc(F)cc(Cl)c2)N1c1ccc2[nH]cnc2c1] | $C_{21}H_{13}ClFN_3O$ | 377.79 |
| 133 | 2-(1H-benzo[d]imidazol-5-yl)-3-(4-methoxyphenyl)isoindolin-1-one | 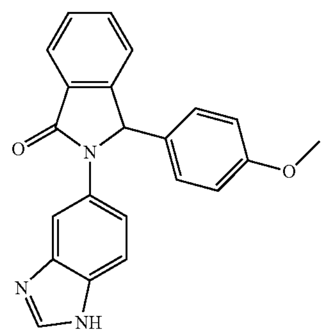 [SMILES: COc1ccc(C2c3ccccc3C(=O)N2c2ccc3[nH]cnc3c2)cc1] | $C_{22}H_{17}N_3O_2$ | 355.38 |
| 134 | 2-(1H-benzo[d]imidazol-5-yl)-3-(4-propoxyphenyl)isoindolin-1-one | 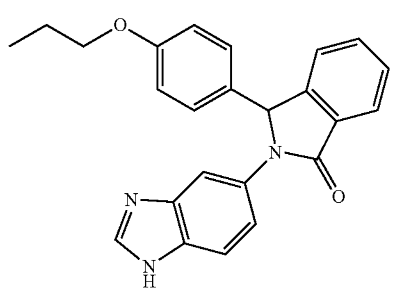 [SMILES: CCCOc1ccc(C2c3ccccc3C(=O)N2c2ccc3[nH]cnc3c2)cc1] | $C_{24}H_{21}N_3O_2$ | 383.44 |
| 135 | 2-(1H-benzo[d]imidazol-5-yl)-3-(3-fluoro-4-methoxyphenyl)isoindolin-1-one | 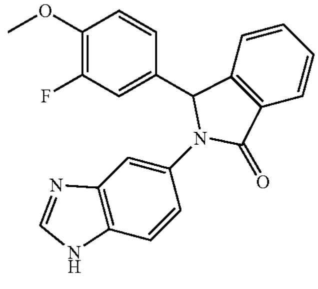 [SMILES: COc1ccc(C2c3ccccc3C(=O)N2c2ccc3[nH]cnc3c2)cc1F] | $C_{22}H_{16}FN_3O_2$ | 373.37 |

-continued

| Example | Chemical Name | Structure | Formula | Mol Weight |
|---|---|---|---|---|
| 136 | 2-(1H-benzo[d]imidazol-5-yl)-3-(3,4-dimethoxyphenyl)isoindolin-1-one | 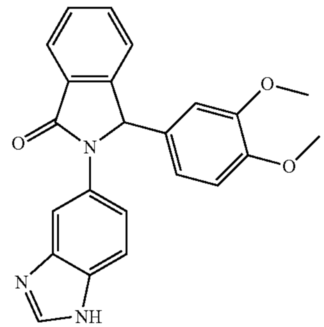 [SMILES: COc1ccc(C2c3ccccc3C(=O)N2c2ccc3[nH]cnc3c2)cc1OC] | $C_{23}H_{19}N_3O_3$ | 385.41 |
| 137 | 3-(benzo[d][1,3]dioxol-6-yl)-2-(1H-benzo[d]imidazol-5-yl)isoindolin-1-one | 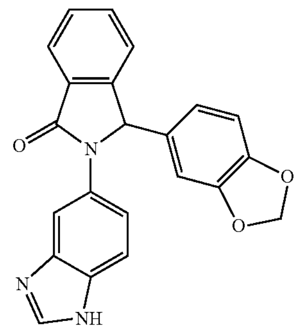 [SMILES: O=C1c2ccccc2C(c2ccc3c(c2)OCO3)N1c1ccc2[nH]cnc2c1] | $C_{22}H_{15}N_3O_3$ | 369.37 |
| 138 | 2-(1H-benzo[d]imidazol-5-yl)-3-(4-phenoxyphenyl)isoindolin-1-one | 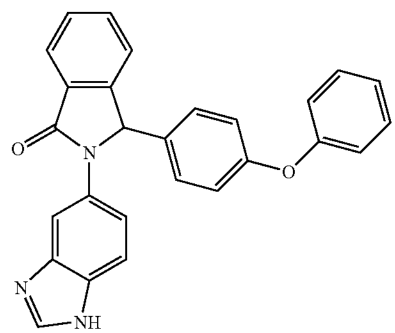 [SMILES: O=C1c2ccccc2C(c2ccc(Oc3ccccc3)cc2)N1c1ccc2[nH]cnc2c1] | $C_{27}H_{19}N_3O_2$ | 417.45 |
| 139 | 2-(1H-benzo[d]imidazol-5-yl)-4,7-dichloro-3-(4-methoxyphenyl)isoindolin-1-one | 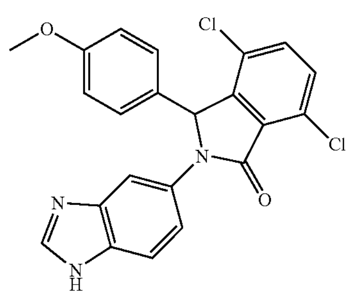 [SMILES: COc1ccc(C2c3c(Cl)ccc(Cl)c3C(=O)N2c2ccc3[nH]cnc3c2)cc1] | $C_{22}H_{15}Cl_2N_3O_2$ | 424.27 |
| 140 | 2-(1H-benzo[d]imidazol-5-yl)-5,6-dichloro-3-(4-methoxyphenyl)isoindolin-1-one | 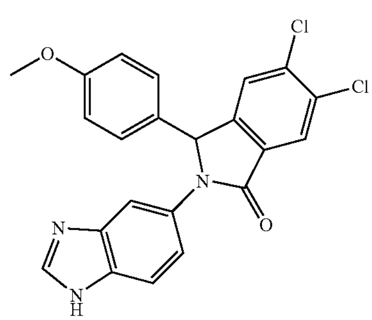 [SMILES: COc1ccc(C2c3cc(Cl)c(Cl)cc3C(=O)N2c2ccc3[nH]cnc3c2)cc1] | $C_{22}H_{15}Cl_2N_3O_2$ | 424.27 |

-continued

| Example | Chemical Name | Structure | Formula | Mol Weight |
|---|---|---|---|---|
| 141 | 2-(1H-benzo[d]imidazol-5-yl)-5,6-dichloro-3-(4-propoxyphenyl)isoindolin-1-one | 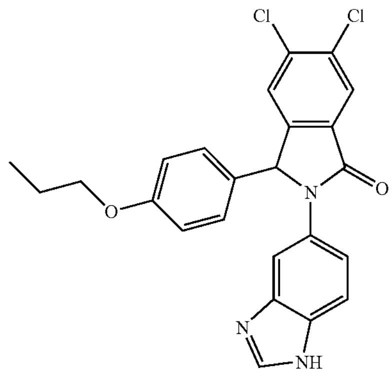 [SMILES: CCCOc1ccc(C2c3cc(Cl)c(Cl)cc3C(=O)N2c2ccc3[nH]cnc3c2)cc1] | $C_{24}H_{19}Cl_2N_3O_2$ | 452.33 |
| 142 | (S)-2-(1H-benzo[d]imidazol-5-yl)-3-(3,4-dimethoxyphenyl)isoindolin-1-one | 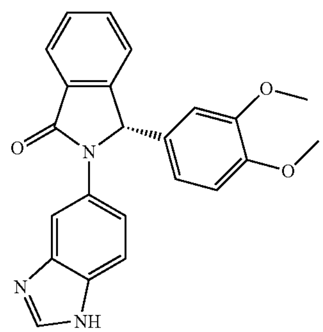 [SMILES: COc1ccc([C@H]2c3ccccc3C(=O)N2c2ccc3[nH]cnc3c2)cc1OC] | $C_{23}H_{19}N_3O_3$ | 385.41 |
| 143 | (R)-2-(1H-benzo[d]imidazol-5-yl)-3-(3,4-dimethoxyphenyl)isoindolin-1-one | 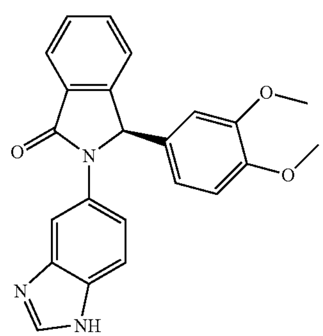 [SMILES: COc1ccc([C@@H]2c3ccccc3C(=O)N2c2ccc3[nH]cnc3c2)cc1OC] | $C_{23}H_{19}N_3O_3$ | 385.41 |
| 144 | (R)-2-(1H-benzo[d]imidazol-5-yl)-3-(4-propoxyphenyl)isoindolin-1-one | 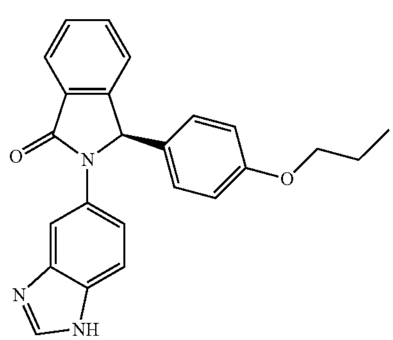 [SMILES: CCCOc1ccc([C@@H]2c3ccccc3C(=O)N2c2ccc3[nH]cnc3c2)cc1] | $C_{24}H_{21}N_3O_2$ | 383.44 |

-continued

| Example | Chemical Name | Structure | Formula | Mol Weight |
|---|---|---|---|---|
| 145 | (S)-2-(1H-benzo[d]imidazol-5-yl)-3-(4-propoxyphenyl)isoindolin-1-one | 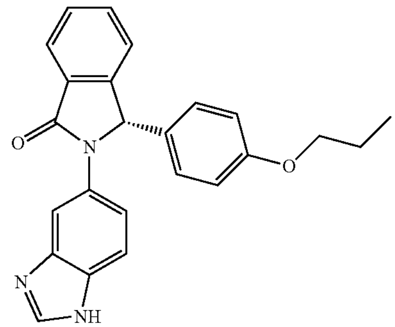 [SMILES: CCCOc1ccc([C@H]2c3ccccc3C(=O)N2c2ccc3[nH]cnc3c2)cc1] | $C_{24}H_{21}N_3O_2$ | 383.44 |
| 146 | (R)-2-(1H-benzo[d]imidazol-5-yl)-3-(4-chlorophenyl)isoindolin-1-one | 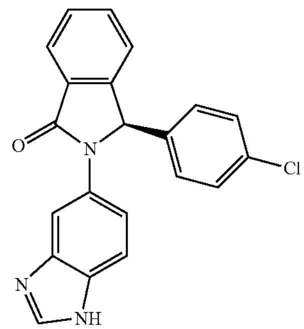 [SMILES: O=C1c2ccccc2[C@@H](c2ccc(Cl)cc2)N1c1ccc2[nH]cnc2c1] | $C_{21}H_{14}ClN_3O$ | 359.80 |
| 147 | (S)-2-(1H-benzo[d]imidazol-5-yl)-3-(4-chlorophenyl)isoindolin-1-one | 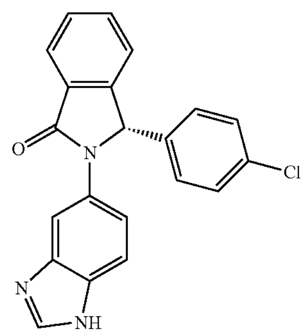 | $C_{21}H_{14}ClN_3O$ | 359.80 |
| 148 | 1-(1H-benzo[d]imidazol-5-yl)-5-(4-phenylcyclohexyl)imidazolidin-2-one | 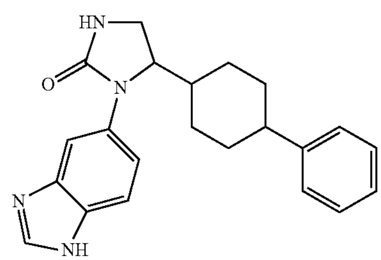 [SMILES: O=C1NCC(C2CCC(c3ccccc3)CC2)N1c1ccc2[nH]cnc2c1] | $C_{22}H_{24}N_4O$ | 360.45 |
| 149 | 1-(1H-benzo[d]imidazol-6-yl)-5-(1-phenylpiperidin-4-yl)imidazolidin-2-one | 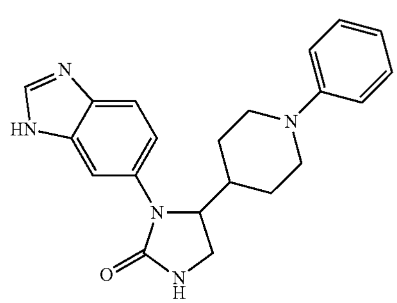 [SMILES: O=C1NCC(C2CCN(c3ccccc3)CC2)N1c1ccc2nc[nH]c2c1] | $C_{21}H_{23}N_5O$ | 361.44 |

| Example | Chemical Name | Structure | Formula | Mol Weight |
|---|---|---|---|---|
| 150 | 1-(1H-benzo[d]imidazol-5-yl)-5-(4-(3-methoxypropyl)phenyl)imidazolidin-2-one | 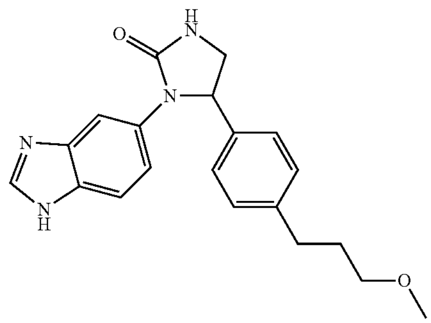 | $C_{20}H_{22}N_4O_2$ | 350.41 |
| 151 | 1-(1H-benzo[d]imidazol-5-yl)-5-(4-hydroxyphenyl)imidazolidin-2-one | 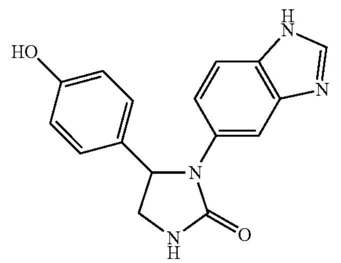 [SMILES: O=C1NCC(c2ccc(O)cc2)N1c1ccc2[nH]cnc2c1] | $C_{16}H_{14}N_4O_2$ | 294.30 |
| 152 | 1-(1H-benzo[d]imidazol-5-yl)-5-(2-hydroxyphenyl)imidazolidin-2-one | 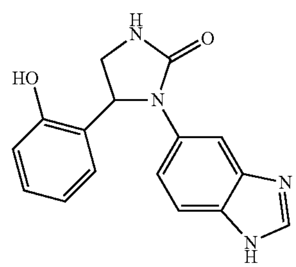 [SMILES: O=C1NCC(c2ccccc2O)N1c1ccc2[nH]cnc2c1] | $C_{16}H_{14}N_4O_2$ | 294.30 |
| 153 | 1-(1H-benzo[d]imidazol-5-yl)-5-(2,4-dihydroxyphenyl)imidazolidin-2-one | 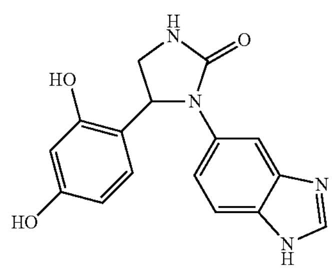 [SMILES: O=C1NCC(c2ccc(O)cc2O)N1c1ccc2[nH]cnc2c1] | $C_{16}H_{14}N_4O_3$ | 310.30 |
| 154 | 1-(1H-benzo[d]imidazol-5-yl)-5-(3,4-dihydroxyphenyl)imidazolidin-2-one | 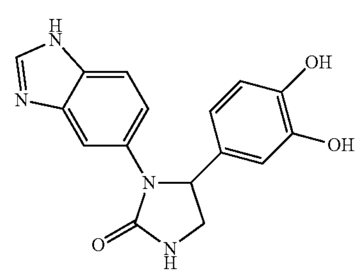 [SMILES: O=C1NCC(c2ccc(O)c(O)c2)N1c1ccc2[nH]cnc2c1] | $C_{16}H_{14}N_4O_3$ | 310.30 |

-continued

| Example | Chemical Name | Structure | Formula | Mol Weight |
|---|---|---|---|---|
| 155 | 1-(1H-benzo[d]imidazol-5-yl)-5-(3-hydroxyphenyl)imidazolidin-2-one | 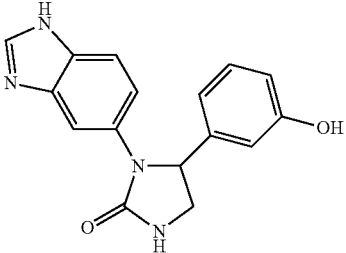 [SMILES: O=C1NCC(c2cccc(O)c2)N1c1ccc2[nH]cnc2c1] | $C_{16}H_{14}N_4O_2$ | 294.30 |
| 156 | 1-(1H-benzo[d]imidazol-5-yl)-5-(4-(cyclohexyloxy)phenyl)imidazolidin-2-one | 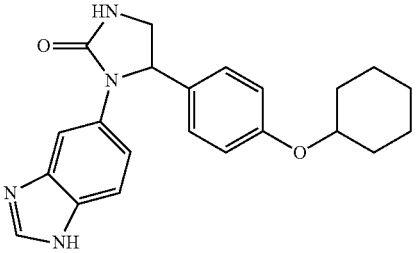 [SMILES: O=C1NCC(c2ccc(OC3CCCCC3)cc2)N1c1ccc2[nH]cnc2c1] | $C_{22}H_{24}N_4O_2$ | 376.45 |
| 157 | 5-(4-(2-methoxyethoxy)phenyl)-1-(1H-benzo[d]imidazol-5-yl)imidazolidin-2-one | 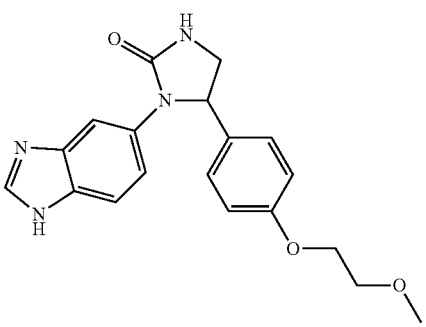 | $C_{19}H_{20}N_4O_3$ | 352.38 |
| 158 | (S)-5-(4-(2-(dimethylamino)ethoxy)phenyl)-1-(1H-benzo[d]imidazol-5-yl)imidazolidin-2-one | 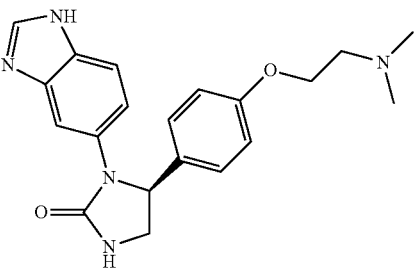 [SMILES: CN(C)CCOc1ccc([C@H]2CNC(=O)N2c2ccc3[nH]cnc3c2)cc1] | $C_{20}H_{23}N_5O_2$ | 365.42 |
| 159 | 3-(1H-benzo[d]imidazol-5-yl)-1-phenethyl-4-(4-propoxyphenyl)imidazolidin-2-one | 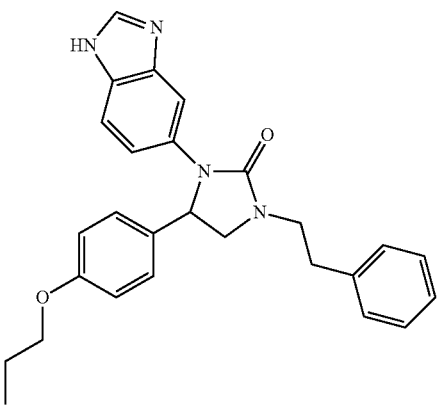 [SMILES: CCCOc1ccc(C2CN(CCc3ccccc3)C(=O)N2c2ccc3[nH]cnc3c2)cc1] | $C_{27}H_{28}N_4O_2$ | 440.53 |

-continued

| Example | Chemical Name | Structure | Formula | Mol Weight |
|---|---|---|---|---|
| 160 | 3-(1H-benzo[d]imidazol-5-yl)-1-((naphthalen-2-yl)methyl)-4-(4-propoxyphenyl)imidazolidin-2-one | 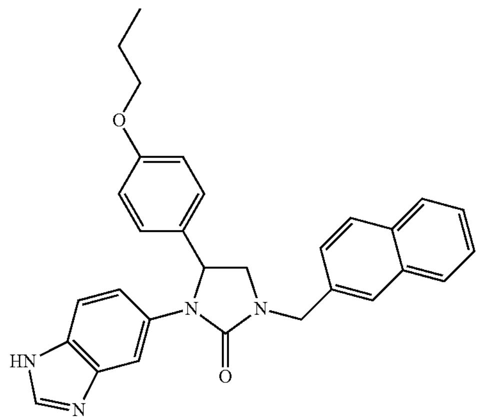 [SMILES: CCCOc1ccc(C2CN(Cc3ccc4ccccc4c3)C(=O)N2c2ccc3[nH]cnc3c2)cc1] | $C_{30}H_{28}N_4O_2$ | 476.56 |
| 161 | 3-(1H-benzo[d]imidazol-5-yl)-1-(3-phenylpropyl)-4-(4-propoxyphenyl)imidazolidin-2-one | 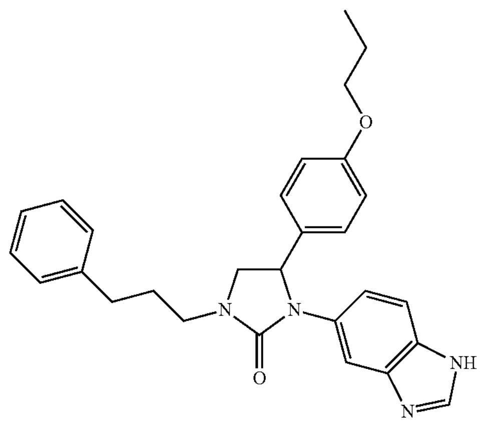 [SMILES: CCCOc1ccc(C2CN(CCCc3ccccc3)C(=O)N2c2ccc3[nH]cnc3c2)cc1] | $C_{28}H_{30}N_4O_2$ | 454.56 |
| 162 | 3-(1H-benzo[d]imidazol-5-yl)-1-benzyl-4-(4-propoxyphenyl)imidazolidin-2-one | 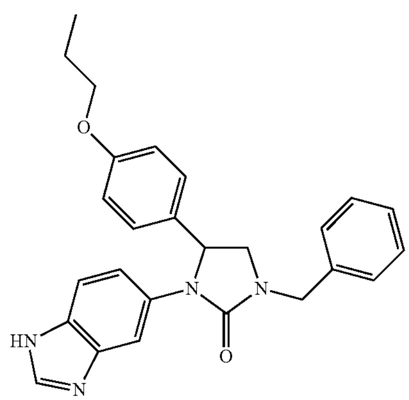 [SMILES: CCCOc1ccc(C2CN(Cc3ccccc3)C(=O)N2c2ccc3[nH]cnc3c2)cc1] | $C_{26}H_{26}N_4O_2$ | 426.51 |
| 163 | 1-(1H-benzo[d]imidazol-5-yl)-5-(4-fluoro-3-methoxyphenyl)imidazolidin-2-one | 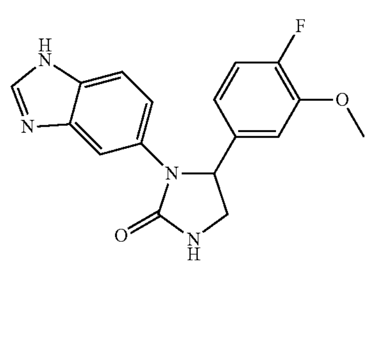 [SMILES: COc1cc(C2CNC(=O)N2c2ccc3[nH]cnc3c2)ccc1F] | $C_{17}H_{15}FN_4O_2$ | 326.32 |

-continued

| Example | Chemical Name | Structure | Formula | Mol Weight |
|---|---|---|---|---|
| 164 | 1-(1H-benzo[d]imidazol-5-yl)-5-(3-fluoro-4-propoxyphenyl) imidazolidin-2-one | 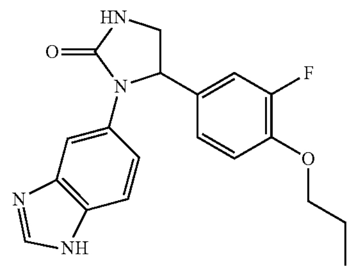 [SMILES: CCCOc1ccc(C2CNC(=O)N2c2ccc3[nH]cnc3c2)cc1F] | $C_{19}H_{19}FN_4O_2$ | 354.37 |
| 165 | 1-(1H-benzo[d]imidazol-5-yl)-5-(2-fluoro-4-propoxyphenyl) imidazolidin-2-one | 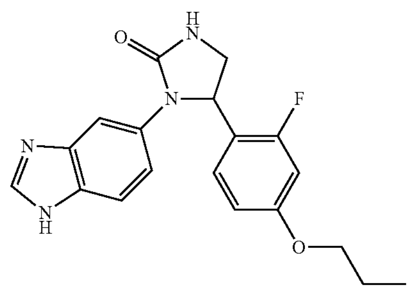 [SMILES: CCCOc1ccc(C2CNC(=O)N2c2ccc3[nH]cnc3c2)c(F)c1] | $C_{19}H_{19}FN_4O_2$ | 354.37 |
| 166 | (S)-1-(1H-benzo[d]imidazol-5-yl)-5-(4-(diethylamino)phenyl) imidazolidin-2-one | 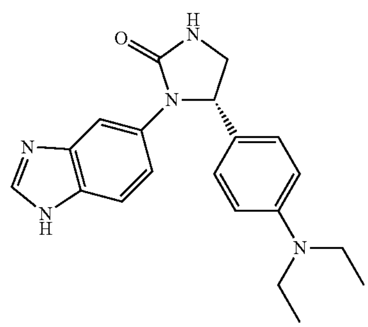 [SMILES: CCN(CC)c1ccc([C@H]2CNC(=O)N2c2ccc3[nH]cnc3c2)cc1] | $C_{20}H_{23}N_5O$ | 349.42 |
| 167 | 1-(1H-benzo[d]imidazol-5-yl)-5-(4-chlorophenyl)imidazolidin-2-one | 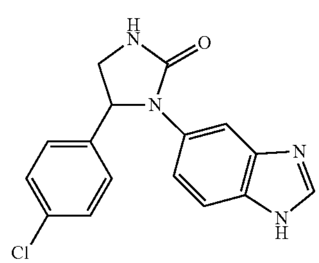 [SMILES: O=C1NCC(c2ccc(Cl)cc2)N1c1ccc2[nH]cnc2c1] | $C_{16}H_{13}ClN_4O$ | 312.75 |
| 168 | 1-(1H-benzo[d]imidazol-5-yl)-5-(4-cyclohexylphenyl) imidazolidin-2-one | 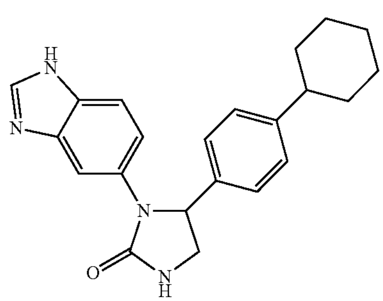 [SMILES: O=C1NCC(c2ccc(C3CCCCC3)cc2)N1c1ccc2[nH]cnc2c1] | $C_{22}H_{24}N_4O$ | 360.45 |

| Example | Chemical Name | Structure | Formula | Mol Weight |
|---|---|---|---|---|
| 169 | 1-(1H-benzo[d]imidazol-5-yl)-5-(4-(4-morpholinocyclohexyl)phenyl)imidazolidin-2-one | 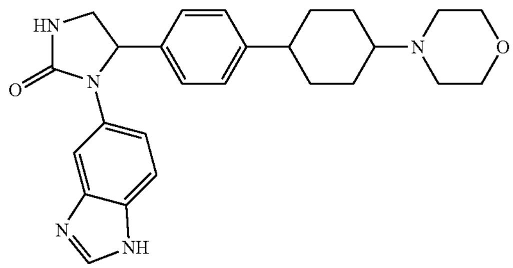 [SMILES: O=C1NCC(c2ccc(C3CCC(N4CCOCC4)CC3)cc2)N1c1ccc2[nH]cnc2c1] | $C_{26}H_{31}N_5O_2$ | 445.55 |
| 170 | (S)-1-(1H-benzo[d]imidazol-5-yl)-5-(4-(1-methylpiperidin-4-yl)phenyl)imidazolidin-2-one | 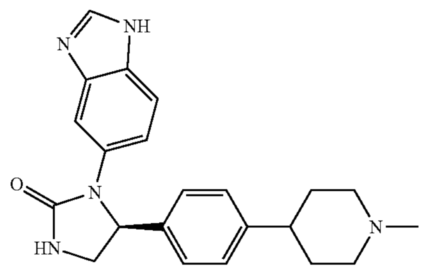 [SMILES: CN1CCC(c2ccc([C@H]3CNC(=O)N3c3ccc4[nH]cnc4c3)cc2)CC1] | $C_{22}H_{25}N_5O$ | 375.46 |
| 171 | 1-(1H-benzo[d]imidazol-5-yl)-5-(4-(tetrahydro-2H-pyran-4-yl)phenyl)imidazolidin-2-one | 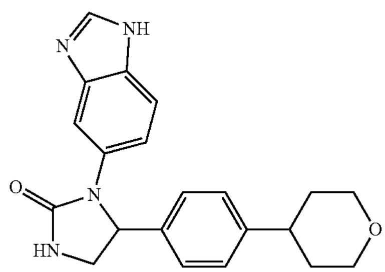 [SMILES: O=C1NCC(c2ccc(C3CCOCC3)cc2)N1c1ccc2[nH]cnc2c1] | $C_{21}H_{22}N_4O_2$ | 362.42 |
| 172 | 1-(1H-benzo[d]imidazol-5-yl)-5-(4-(4-oxocyclohexyl)phenyl)imidazolidin-2-one | 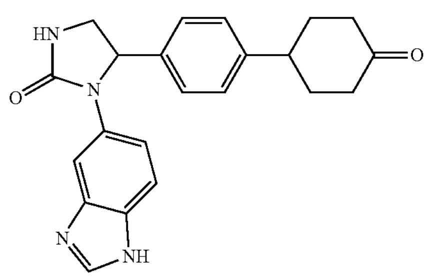 [SMILES: O=C1CCC(c2ccc(C3CNC(=O)N3c3ccc4[nH]cnc4c3)cc2)CC1] | $C_{22}H_{22}N_4O_2$ | 374.43 |
| 173 | (S)-1-(1H-benzo[d]imidazol-5-yl)-5-(4-(4,4-difluorocyclohexyl)phenyl)imidazolidin-2-one | 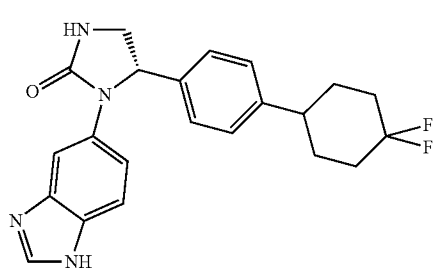 [SMILES: O=C1NC[C@H](c2ccc(C3CCC(F)(F)CC3)cc2)N1c1ccc2[nH]cnc2c1] | $C_{22}H_{22}F_2N_4O$ | 396.43 |

-continued

| Example | Chemical Name | Structure | Formula | Mol Weight |
|---|---|---|---|---|
| 174 | 1-(1H-benzo[d]imidazol-5-yl)-5-(3-(pyrrolidin-1-yl)phenyl)imidazolidin-2-one | 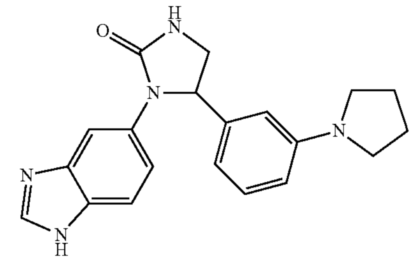 [SMILES: O=C1NCC(c2cccc(N3CCCC3)c2)N1c1ccc2[nH]cnc2c1] | $C_{20}H_{21}N_5O$ | 347.41 |
| 175 | 1-(1H-benzo[d]imidazol-5-yl)-5-(4-(piperidin-1-yl)phenyl)imidazolidin-2-one | 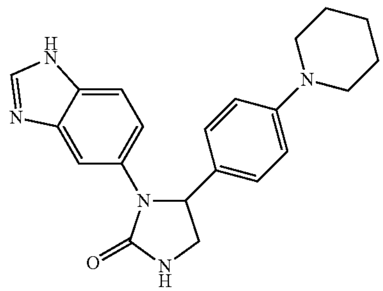 [SMILES: O=C1NCC(c2ccc(N3CCCCC3)cc2)N1c1ccc2[nH]cnc2c1] | $C_{21}H_{23}N_5O$ | 361.44 |
| 176 | 1-(1H-benzo[d]imidazol-5-yl)-5-(3-(piperidin-1-yl)phenyl)imidazolidin-2-one | 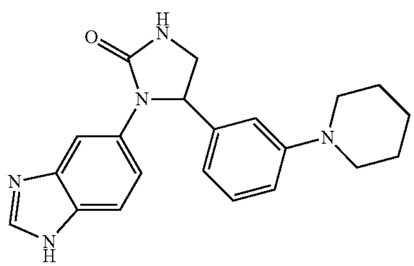 [SMILES: O=C1NCC(c2cccc(N3CCCCC3)c2)N1c1ccc2[nH]cnc2c1] | $C_{21}H_{23}N_5O$ | 361.44 |
| 177 | 1-(1H-benzo[d]imidazol-5-yl)-5-(4-morpholinophenyl)imidazolidin-2-one | 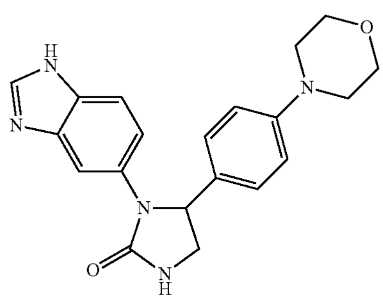 [SMILES: O=C1NCC(c2ccc(N3CCOCC3)cc2)N1c1ccc2[nH]cnc2c1] | $C_{20}H_{21}N_5O_2$ | 363.41 |
| 178 | 5-(4-cyclohexylphenyl)-1-(H-imidazo[1,2-a]pyridin-7-yl)imidazolidin-2-one | 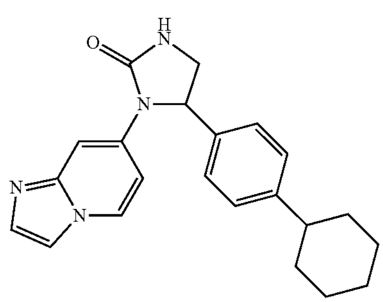 | $C_{22}H_{24}N_4O$ | 360.45 |

| Example | Chemical Name | Structure | Formula | Mol Weight |
|---|---|---|---|---|
| 179 | 1-(H-imidazo[1,2-a]pyridin-7-yl)-5-(4-(pyrrolidin-1-yl)phenyl)imidazolidin-2-one | 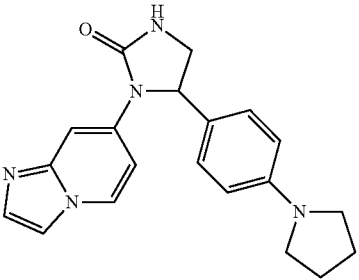 [SMILES: O=C1NCC(c2ccc(N3CCCC3)cc2)N1c1ccn2ccnc2c1] | C$_{20}$H$_{21}$N$_5$O | 347.41 |
| 180 | 1-(H-imidazo[1,2-a]pyridin-7-yl)-5-(3-(pyrrolidin-1-yl)phenyl)imidazolidin-2-one | 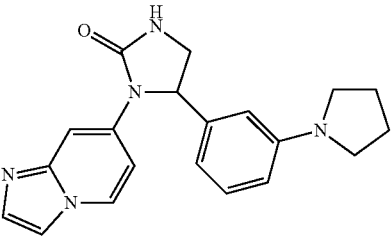 [SMILES: O=C1NCC(c2cccc(N3CCCC3)c2)N1c1ccn2ccnc2c1] | C$_{20}$H$_{21}$N$_5$O | 347.41 |
| 181 | 1-(H-imidazo[1,2-a]pyridin-7-yl)-5-(4-(piperidin-1-yl)phenyl)imidazolidin-2-one | 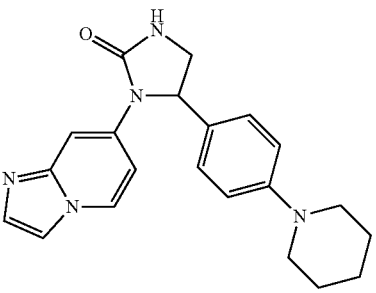 [SMILES: O=C1NCC(c2ccc(N3CCCCC3)cc2)N1c1ccn2ccnc2c1] | C$_{21}$H$_{23}$N$_5$O | 361.44 |
| 182 | 1-(H-imidazo[1,2-a]pyridin-7-yl)-5-(3-(piperidin-1-yl)phenyl)imidazolidin-2-one | 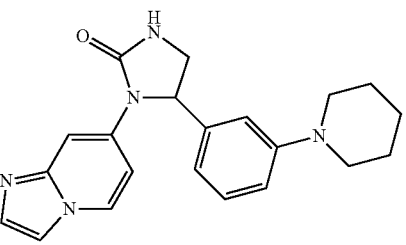 [SMILES: O=C1NCC(c2cccc(N3CCCCC3)c2)N1c1ccn2ccnc2c1] | C$_{21}$H$_{23}$N$_5$O | 361.44 |
| 183 | 1-(H-imidazo[1,2-a]pyridin-7-yl)-5-(1-phenylpiperidin-4-yl)imidazolidin-2-one | 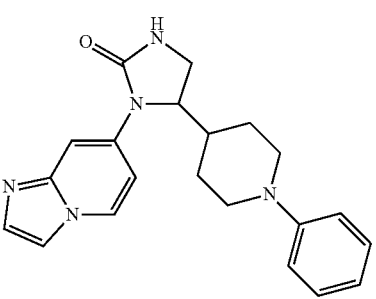 [SMILES: O=C1NCC(C2CCN(c3ccccc3)CC2)N1c1ccn2ccnc2c1] | C$_{21}$H$_{23}$N$_5$O | 361.44 |

-continued

| Example | Chemical Name | Structure | Formula | Mol Weight |
|---------|---------------|-----------|---------|------------|
| 184 | (S)-3-(1H-benzo[d]imidazol-5-yl)-4-(4-(3-methoxypropyl)phenyl)oxazolidin-2-one | 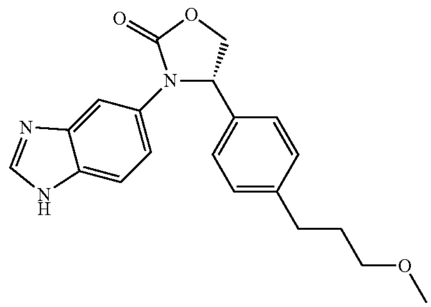 | $C_{20}H_{21}N_3O_3$ | 351.39 |
| 185 | 3-(1H-benzo[d]imidazol-5-yl)-4-(4-(3-(dimethylamino)propyl)phenyl)oxazolidin-2-one | 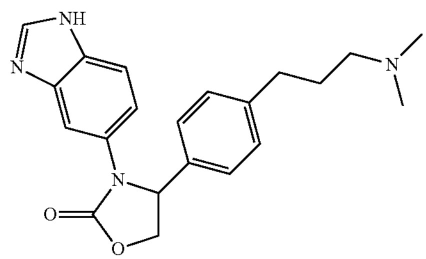 [SMILES: CN(C)CCCc1ccc(C2COC(=O)N2c2ccc3[nH]cnc3c2)cc1] | $C_{21}H_{24}N_4O_2$ | 364.44 |
| 186 | (S)-3-(7-methyl-1H-benzo[d]imidazol-5-yl)-4-phenyloxazolidin-2-one | 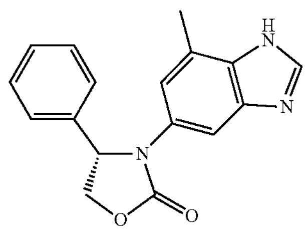 [SMILES: Cc1cc(N2C(=O)OC[C@@H]2c2ccccc2)cc2nc[nH]c12] | $C_{17}H_{15}N_3O_2$ | 293.31 |
| 187 | (S)-3-(6-fluoro-1H-benzo[d]imidazol-5-yl)-4-phenyloxazolidin-2-one | 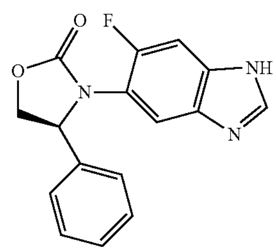 [SMILES: O=C1OC[C@H](c2ccccc2)N1c1cc2nc[nH]c2cc1F] | $C_{16}H_{12}FN_3O_2$ | 297.28 |
| 188 | (S)-3-(7-fluoro-1H-benzo[d]imidazol-5-yl)-4-phenyloxazolidin-2-one | 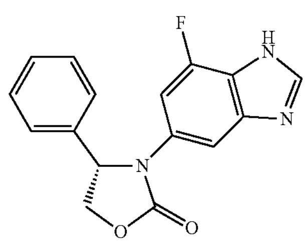 [SMILES: O=C1OC[C@H](c2ccccc2)N1c1cc(F)c2[nH]cnc2c1] | $C_{16}H_{12}FN_3O_2$ | 297.28 |
| 189 | (S)-3-(1H-benzo[d]imidazol-5-yl)-4-(cyclohexylmethyl)oxazolidin-2-one | 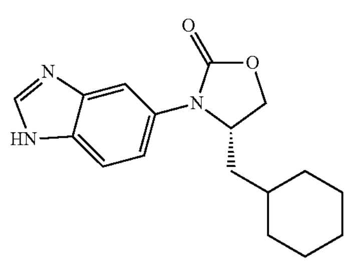 [SMILES: O=C1OC[C@H](CC2CCCCC2)N1c1ccc2[nH]cnc2c1] | $C_{17}H_{21}N_3O_2$ | 299.36 |

| Example | Chemical Name | Structure | Formula | Mol Weight |
|---|---|---|---|---|
| 190 | (S)-3-(1H-benzo[d]imidazol-5-yl)-4-cyclohexyloxazolidin-2-one | 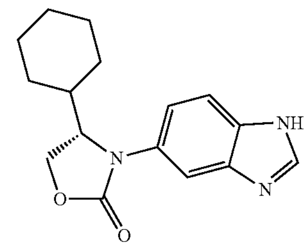 [SMILES: O=C1OC[C@H](C2CCCCC2)N1c1ccc2[nH]cnc2c1] | $C_{16}H_{19}N_3O_2$ | 285.34 |
| 191 | (S)-3-(1H-benzo[d]imidazol-5-yl)-4-(4-phenylcyclohexyl)oxazolidin-2-one | 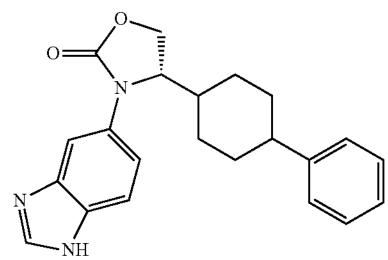 [SMILES: O=C1OC[C@H](C2CCC(c3ccccc3)CC2)N1c1ccc2[nH]cnc2c1] | $C_{22}H_{23}N_3O_2$ | 361.41 |
| 192 | (S)-3-(1H-benzo[d]imidazol-5-yl)-4-(1-phenylpiperidin-4-yl)oxazolidin-2-one | 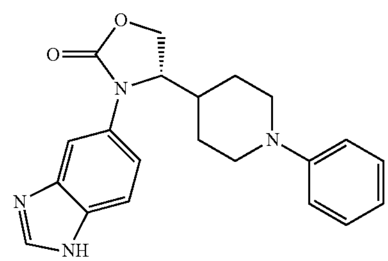 [SMILES: O=C1OC[C@H](C2CCN(c3ccccc3)CC2)N1c1ccc2[nH]cnc2c1] | $C_{21}H_{22}N_4O_2$ | 362.42 |
| 193 | (S)-4-(1-acetylpiperidin-4-yl)-3-(1H-benzo[d]imidazol-5-yl)oxazolidin-2-one | 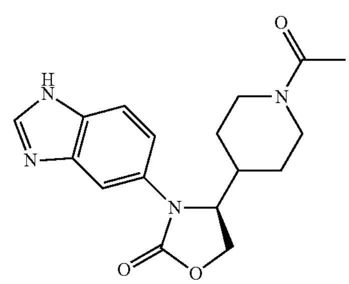 [SMILES: CC(=O)N1CCC([C@H]2COC(=O)N2c2ccc3[nH]cnc3c2)CC1] | $C_{17}H_{20}N_4O_3$ | 328.36 |
| 194 | 3-(1H-benzo[d]imidazol-5-yl)-4-(1-phenylethyl)oxazolidin-2-one | 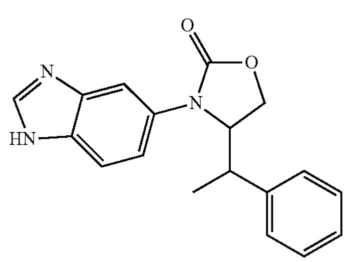 [SMILES: CC(c1ccccc1)C1COC(=O)N1c1ccc2[nH]cnc2c1] | $C_{18}H_{17}N_3O_2$ | 307.34 |
| 195 | (S)-4-(4-propoxybenzyl)-3-(1H-benzo[d]imidazol-5-yl)oxazolidin-2-one | 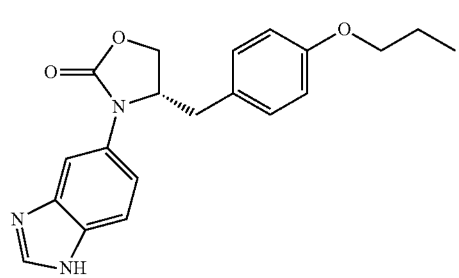 [SMILES: CCCOc1ccc(C[C@H]2COC(=O)N2c2ccc3[nH]cnc3c2)cc1] | $C_{20}H_{21}N_3O_3$ | 351.39 |

-continued

| Example | Chemical Name | Structure | Formula | Mol Weight |
|---|---|---|---|---|
| 196 | (S)-4-(4-isopropoxybenzyl)-3-(1H-benzo[d]imidazol-5-yl)oxazolidin-2-one | 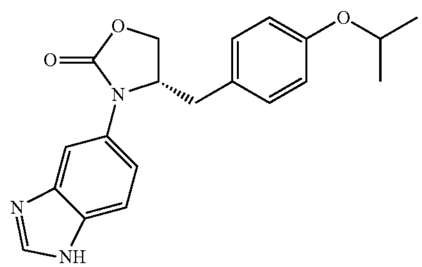 [SMILES: CC(C)Oc1ccc(C[C@H]2COC(=O)N2c2ccc3[nH]cnc3c2)cc1] | $C_{20}H_{21}N_3O_3$ | 351.39 |
| 197 | (S)-4-(4-(cyclohexyloxy)benzyl)-3-(1H-benzo[d]imidazol-5-yl)oxazolidin-2-one | 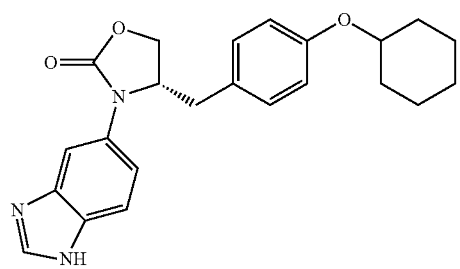 [SMILES: O=C1OC[C@H](Cc2ccc(OC3CCCCC3)cc2)N1c1ccc2[nH]cnc2c1] | $C_{23}H_{25}N_3O_3$ | 391.46 |
| 198 | 4-(4-morpholinobenzyl)-3-(1H-benzo[d]imidazol-5-yl)oxazolidin-2-one | 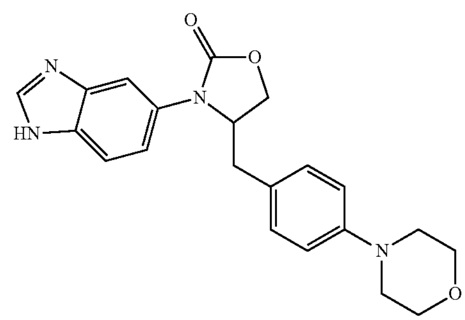 [SMILES: O=C1OCC(Cc2ccc(N3CCOCC3)cc2)N1c1ccc2[nH]cnc2c1] | $C_{21}H_{22}N_4O_3$ | 378.42 |
| 199 | (S)-3-(1H-benzo[d]imidazol-5-yl)-4-phenethyloxazolidin-2-one | 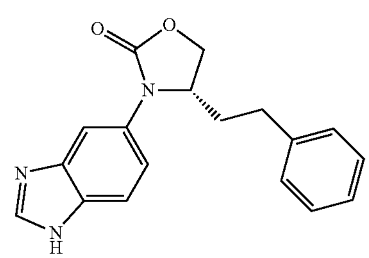 [SMILES: O=C1OC[C@H](CCc2ccccc2)N1c1ccc2[nH]cnc2c1] | $C_{18}H_{17}N_3O_2$ | 307.34 |
| 200 | 3-(1H-benzo[d]imidazol-5-yl)-4-(4-(cyclohexyloxy)phenyl)oxazolidin-2-one | 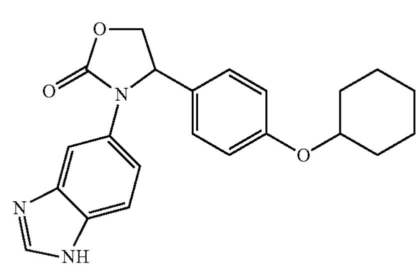 [SMILES: O=C1OCC(c2ccc(OC3CCCCC3)cc2)N1c1ccc2[nH]cnc2c1] | $C_{22}H_{23}N_3O_3$ | 377.43 |

| Example | Chemical Name | Structure | Formula | Mol Weight |
|---|---|---|---|---|
| 201 | (S)-3-(7-methyl-1H-benzo[d]imidazol-5-yl)-4-(4-propoxyphenyl)oxazolidin-2-one | 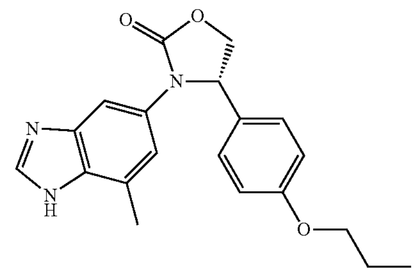 [SMILES: CCCOc1ccc([C@H]2COC(=O)N2c2cc(C)c3[nH]cnc3c2)cc1] | $C_{20}H_{21}N_3O_3$ | 351.39 |
| 202 | (S)-3-(6,7-dimethyl-1H-benzo[d]imidazol-5-yl)-4-(4-propoxyphenyl)oxazolidin-2-one | 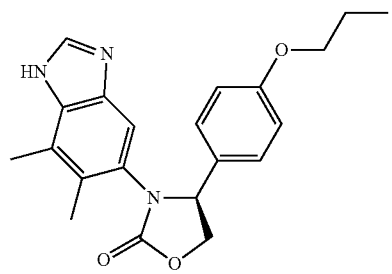 [SMILES: CCCOc1ccc([C@H]2COC(=O)N2c2cc3nc[nH]c3c(C)c2C)cc1] | $C_{21}H_{23}N_3O_3$ | 365.42 |
| 203 | (S)-4-(4-(2-methoxyethoxy)phenyl)-3-(1H-benzo[d]imidazol-5-yl)oxazolidin-2-one | 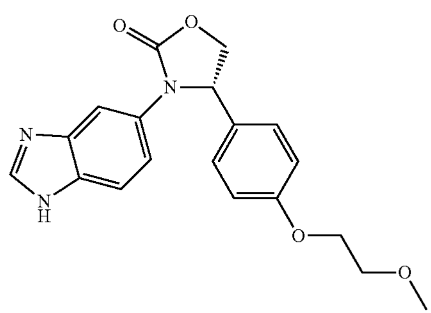 [SMILES: COCCOc1ccc([C@H]2COC(=O)N2c2ccc3[nH]cnc3c2)cc1] | $C_{19}H_{19}N_3O_4$ | 353.37 |
| 204 | (S)-4-(4-(2-(dimethylamino)ethoxy)phenyl)-3-(1H-benzo[d]imidazol-5-yl)oxazolidin-2-one | 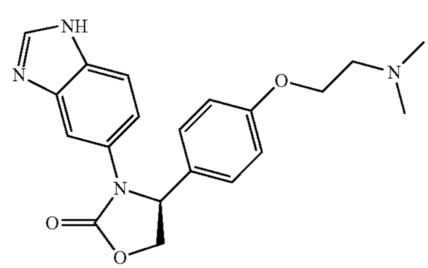 [SMILES: CN(C)CCOc1ccc([C@H]2COC(=O)N2c2ccc3[nH]cnc3c2)cc1] | $C_{20}H_{22}N_4O_3$ | 366.41 |
| 205 | 3-(1H-benzo[d]imidazol-5-yl)-4-(2,6-difluoro-4-methoxyphenyl)oxazolidin-2-one | 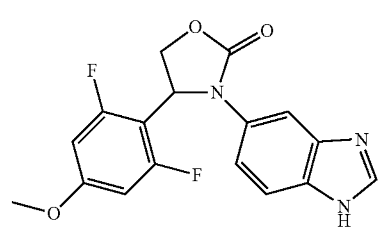 [SMILES: COc1cc(F)c(C2COC(=O)N2c2ccc3[nH]cnc3c2)c(F)c1] | $C_{17}H_{13}F_2N_3O_3$ | 345.30 |

-continued

| Example | Chemical Name | Structure | Formula | Mol Weight |
|---------|---------------|-----------|---------|------------|
| 206 | (S)-3-(1H-benzo[d]imidazol-5-yl)-4-(4-(diethylamino)phenyl)oxazolidin-2-one | 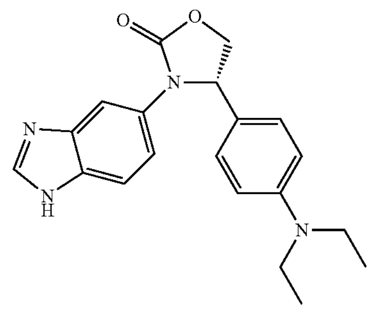 [SMILES: CCN(CC)c1ccc([C@H]2COC(=O)N2c2ccc3[nH]cnc3c2)cc1] | $C_{20}H_{22}N_4O_2$ | 350.41 |
| 207 | (S)-3-(1H-benzo[d]imidazol-5-yl)-4-(4-(bis(2-methoxyethyl)amino)phenyl)oxazolidin-2-one | 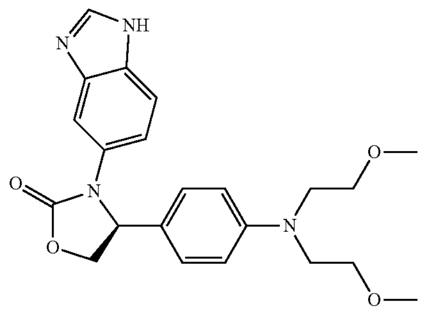 [SMILES: COCCN(CCOC)c1ccc([C@H]2COC(=O)N2c2ccc3[nH]cnc3c2)cc1] | $C_{22}H_{26}N_4O_4$ | 410.46 |
| 208 | (S)-3-(1H-benzo[d]imidazol-5-yl)-4-(4-(dicyclopropylamino)phenyl)oxazolidin-2-one | 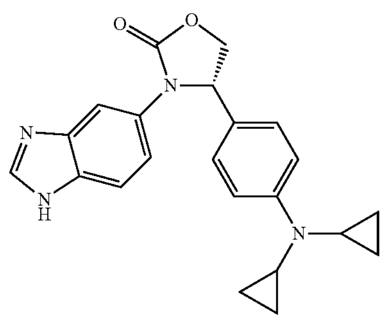 [SMILES: O=C1OC[C@H](c2ccc(N(C3CC3)C3CC3)cc2)N1c1ccc2[nH]cnc2c1] | $C_{22}H_{22}N_4O_2$ | 374.43 |
| 209 | (S)-3-(1H-benzo[d]imidazol-6-yl)-4-(biphenyl-4-yl)oxazolidin 2-one | 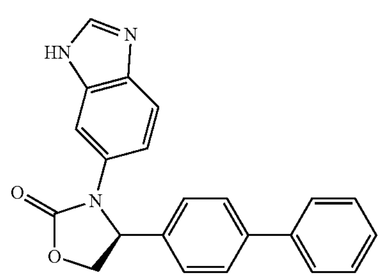 [SMILES: O=C1OC[C@H](c2ccc(-c3ccccc3)cc2)N1c1ccc2nc[nH]c2c1] | $C_{22}H_{17}N_3O_2$ | 355.38 |
| 210 | 3-(1H-benzo[d]imidazol-5-yl)-4-(4-(4-oxocyclohexyl)phenyl)oxazolidin-2-one | 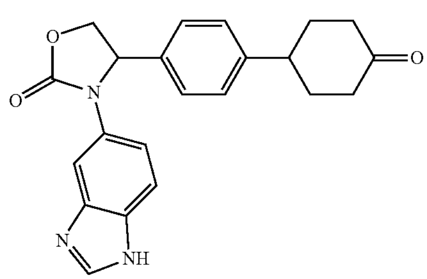 [SMILES: O=C1CCC(c2ccc(C3COC(=O)N3c3ccc4[nH]cnc4c3)cc2)CC1] | $C_{22}H_{21}N_3O_3$ | 375.42 |

-continued

| Example | Chemical Name | Structure | Formula | Mol Weight |
|---|---|---|---|---|
| 211 | 3-(1H-benzo[d]imidazol-5-yl)-4-(4-(4-methoxycyclohexyl)phenyl)oxazolidin-2-one | 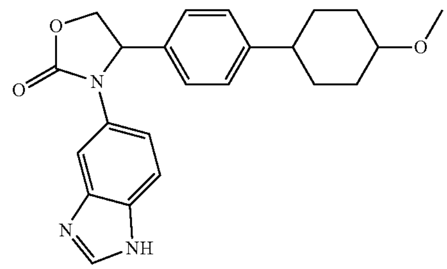 [SMILES: COC1CCC(c2ccc(C3COC(=O)N3c3ccc4[nH]cnc4c3)cc2)CC1] | C₂₃H₂₅N₃O₃ | 391.46 |
| 212 | 3-(1H-benzo[d]imidazol-5-yl)-4-(4-(4-hydroxycyclohexyl)phenyl)oxazolidin-2-one | 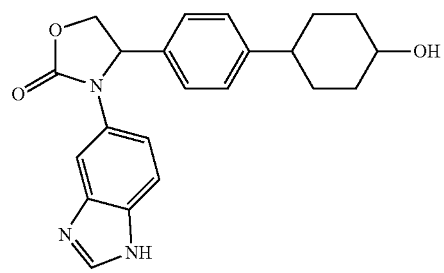 [SMILES: O=C1OCC(c2ccc(C3CCC(O)CC3)cc2)N1c1ccc2[nH]cnc2c1] | C₂₂H₂₃N₃O₃ | 377.43 |
| 213 | 3-(1H-benzo[d]imidazol-5-yl)-4-(4-(4-morpholinocyclohexyl)phenyl)oxazolidin-2-one | 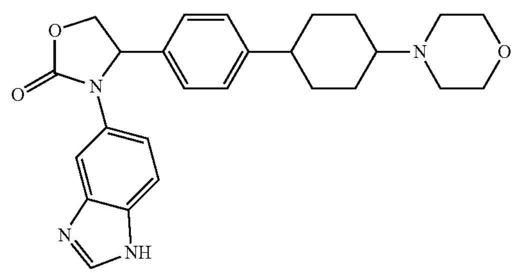 [SMILES: O=C1OCC(c2ccc(C3CCC(N4CCOCC4)CC3)cc2)N1c1ccc2[nH]cnc2c1] | C₂₆H₃₀N₄O₃ | 446.54 |
| 214 | 3-(1H-benzo[d]imidazol-5-yl)-4-(4-(pyrrolidin-1-yl)phenyl)oxazolidin-2-one | 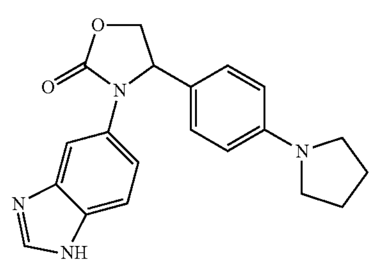 [SMILES: O=C1OCC(c2ccc(N3CCCC3)cc2)N1c1ccc2[nH]cnc2c1] | C₂₀H₂₀N₄O₂ | 348.39 |
| 215 | (S)-3-(1H-benzo[d]imidazol-5-yl)-4-(4-(piperidin-1-yl)phenyl)oxazolidin-2-one | 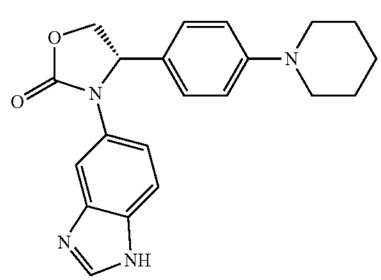 [SMILES: O=C1OC[C@H](c2ccc(N3CCCCC3)cc2)N1c1ccc2[nH]cnc2c1] | C₂₁H₂₂N₄O₂ | 362.46 |

-continued

| Example | Chemical Name | Structure | Formula | Mol Weight |
|---|---|---|---|---|
| 216 | (S)-3-(1H-benzo[d]imidazol-5-yl)-4-(3-(piperidin-1-yl)phenyl)oxazolidin-2-one | 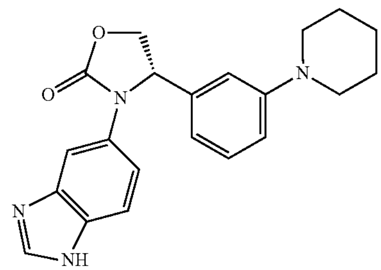 [SMILES: O=C1OC[C@H](c2cccc(N3CCCCC3)c2)N1c1ccc2[nH]cnc2c1] | $C_{21}H_{22}N_4O_2$ | 362.46 |
| 217 | (S)-3-(1H-benzo[d]imidazol-5-yl)-4-(4-morpholinophenyl)oxazolidin-2-one | 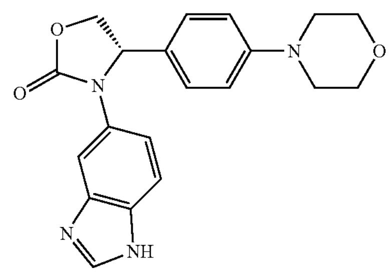 [SMILES: O=C1OC[C@H](c2ccc(N3CCOCC3)cc2)N1c1ccc2[nH]cnc2c1] | $C_{20}H_{20}N_4O_3$ | 364.39 |
| 218 | (S)-3-(1H-benzo[d]imidazol-5-yl)-4-(3-morpholinophenyl)oxazolidin-2-one | 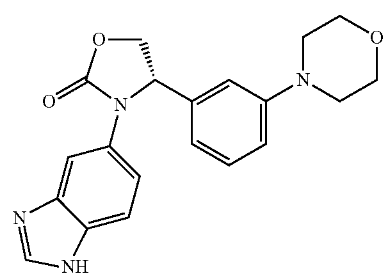 [SMILES: O=C1OC[C@H](c2cccc(N3CCOCC3)c2)N1c1ccc2[nH]cnc2c1] | $C_{20}H_{20}N_4O_3$ | 364.39 |
| 219 | 3-(1H-benzo[d]imidazol-5-yl)-4-(4-(tetrahydro-2H-pyran-4-yl)phenyl)oxazolidin-2-one | 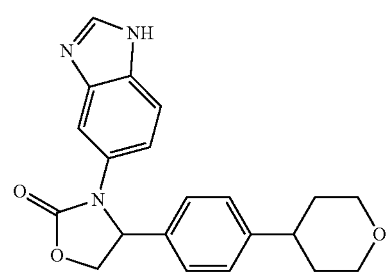 [SMILES: O=C1OCC(c2ccc(C3CCOCC3)cc2)N1c1ccc2[nH]cnc2c1] | $C_{21}H_{21}N_3O_3$ | 363.40 |
| 220 | 3-(1H-benzo[d]imidazol-5-yl)-4-(4-(1-methylpiperidin-4-yl)phenyl)oxazolidin-2-one | 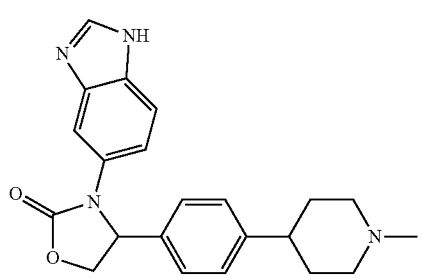 [SMILES: CN1CCC(c2ccc(C3COC(=O)N3c3ccc4[nH]cnc4c3)cc2)CC1] | $C_{22}H_{24}N_4O_2$ | 376.45 |

-continued

| Example | Chemical Name | Structure | Formula | Mol Weight |
|---|---|---|---|---|
| 221 | (S)-3-(1H-benzo[d]imidazol-6-yl)-4-(3-(4-methylpiperazin-1-yl)phenyl)oxazolidin-2-one | 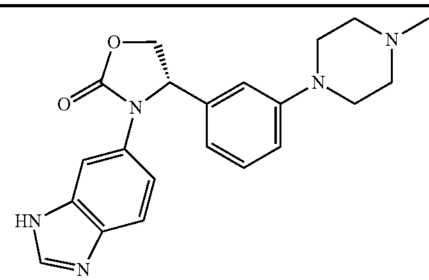 | $C_{21}H_{23}N_5O_2$ | 377.43 |
| 222 | (S)-3-(3-methylH-imidazo[1,2-a]pyridin-7-yl)-4-phenyloxazolidin-2-one | 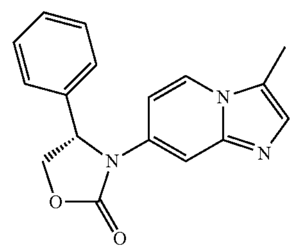 [SMILES: Cc1cnc2cc(N3C(=O)OC[C@@H]3c3ccccc3)ccn12] | $C_{17}H_{15}N_3O_2$ | 293.31 |
| 223 | (S)-3-(3-(trifluoromethyl)H-imidazo[1,2-a]pyridin-7-yl)-4-phenyloxazolidin-2-one | 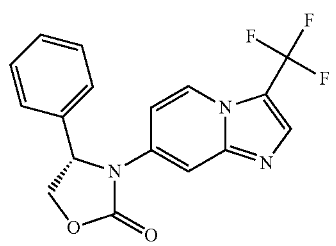 [SMILES: O=C1OC[C@H](c2ccccc2)N1c1ccn2c(C(F)(F)F)cnc2c1] | $C_{17}H_{12}F_3N_3O_2$ | 347.29 |
| 224 | (S)-4-(2,3-dihydrobenzo[b][1,4]dioxin-6-yl)-3-(H-imidazo[1,2-a]pyridin-7-yl)oxazolidin-2-one | 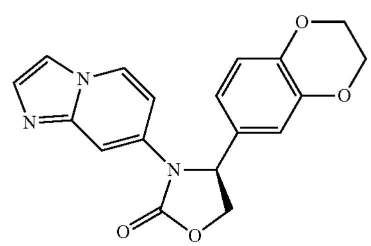 [SMILES: O=C1OC[C@H](c2ccc3c(c2)OCCO3)N1c1ccn2ccnc2c1] | $C_{18}H_{15}N_3O_4$ | 337.32 |
| 225 | (S)-4-(4-cyclohexylphenyl)-3-(H-imidazo[1,2-a]pyridin-7-yl)oxazolidin-2-one | 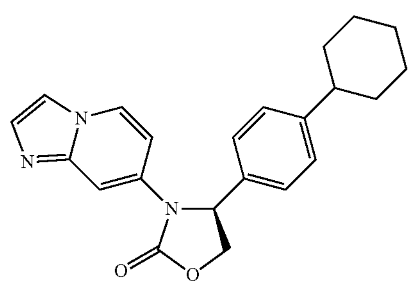 [SMILES: O=C1OC[C@H](c2ccc(C3CCCCC3)cc2)N1c1ccn2ccnc2c1] | $C_{22}H_{23}N_3O_2$ | 361.43 |
| 226 | (S)-3-(H-imidazo[1,2-a]pyridin-7-yl)-4-(4-(piperidin-1-yl)phenyl)oxazolidin-2-one | 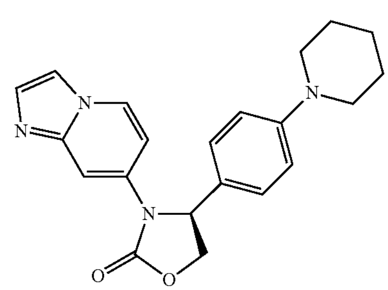 [SMILES: O=C1OC[C@H](c2ccc(N3CCCCC3)cc2)N1c1ccn2ccnc2c1] | $C_{21}H_{22}N_4O_2$ | 362.42 |

-continued

| Example | Chemical Name | Structure | Formula | Mol Weight |
|---|---|---|---|---|
| 227 | (S)-3-(H-imidazo[1,2-a]pyridin-7-yl)-4-(4-morpholinophenyl)oxazolidin-2-one | 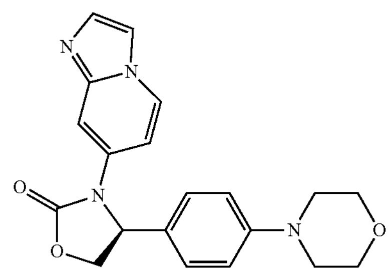 [SMILES: O=C1OC[C@H](c2ccc(N3CCOCC3)cc2)N1c1ccn2ccnc2c1] | $C_{20}H_{20}N_4O_3$ | 364.39 |
| 228 | (S)-3-(H-imidazo[1,2-a]pyridin-7-yl)-4-(4-(4-phenylpiperazin-1-yl)phenyl)oxazolidin-2-one | 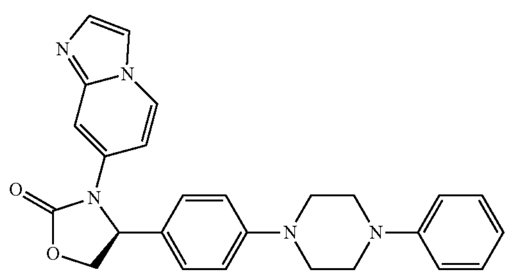 [SMILES: O=C1OC[C@H](c2ccc(N3CCN(c4ccccc4)CC3)cc2)N1c1ccn2ccnc2c1] | $C_{26}H_{25}N_5O_2$ | 439.50 |
| 229 | (S)-1-(1H-benzo[d]imidazol-5-yl)-5-(4-(bis(2-methoxyethyl)amino)phenyl)imidazolidin-2-one | 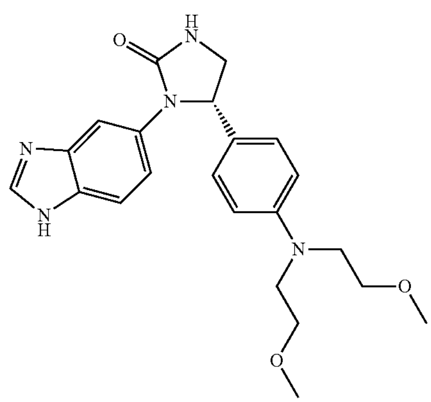 [SMILES: COCCN(CCOC)c1ccc([C@H]2CNC(=O)N2c2ccc3[nH]cnc3c2)cc1] | $C_{22}H_{27}N_5O_3$ | 409.48 |
| 230 | 5-(4-(N-(2-(dimethylamino)ethyl)-N-methylamino)phenyl)-1-(1H-benzo[d]imidazol-5-yl)imidazolidin-2-one | 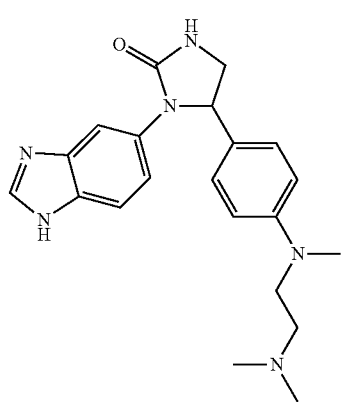 [SMILES: CN(C)CCN(C)c1ccc(C2CNC(=O)N2c2ccc3[nH]cnc3c2)cc1] | $C_{21}H_{26}N_6O$ | 378.47 |

-continued

| Example | Chemical Name | Structure | Formula | Mol Weight |
|---|---|---|---|---|
| 231 | 3-(1H-benzo[d]imidazol-5-yl)-4-(4-(4,4-difluorocyclohexyl)phenyl)oxazolidin-2-one | 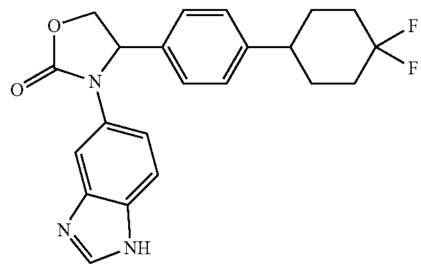 [SMILES: O=C1OCC(c2ccc(C3CCC(F)(F)CC3)cc2)N1c1ccc2[nH]cnc2c1] | $C_{22}H_{21}F_2N_3O_2$ | 397.41 |
| 232 | 2-(1H-benzo[d]imidazol-5-yl)-4,7-difluoro-3-(4-propoxyphenyl)isoindolin-1-one | 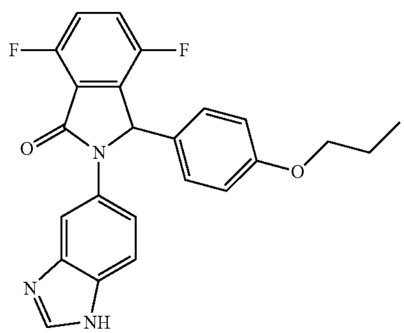 [SMILES: CCCOc1ccc(C2c3c(F)ccc(F)c3C(=O)N2c2ccc3[nH]cnc3c2)cc1] | $C_{24}H_{19}F_2N_3O_2$ | 419.42 |
| 233 | 2-(H-imidazo[1,2-a]pyridin-7-yl)-3-(3,4-dimethoxyphenyl)isoindolin-1-one | 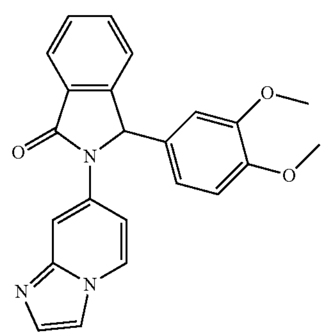 | $C_{23}H_{19}N_3O_3$ | 385.41 |
| 234 | (S)-2-(H-imidazo[1,2-a]pyridin-7-yl)-3-(3,4-dimethoxyphenyl)isoindolin-1-one | 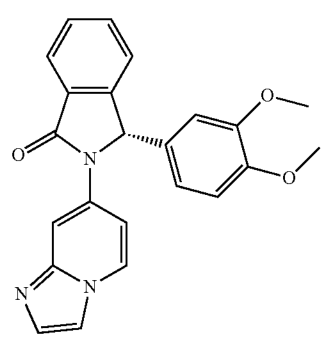 [SMILES: COc1ccc([C@H]2c3ccccc3C(=O)N2c2ccn3ccnc3c2)cc1OC] | $C_{23}H_{19}N_3O_3$ | 385.41 |

-continued

| Example | Chemical Name | Structure | Formula | Mol Weight |
|---|---|---|---|---|
| 235 | (S)-3-(3,4-dimethoxyphenyl)-2-(3-methyl1H-imidazo[1,2-a]pyridin-7-yl)isoindolin-1-one | 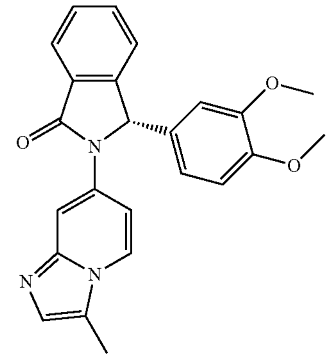 [SMILES: COc1ccc([C@H]2c3ccccc3C(=O)N2c2ccn3c(C)cnc3c2)cc1OC] | $C_{24}H_{21}N_3O_3$ | 399.44 |

General Synthesis Description:

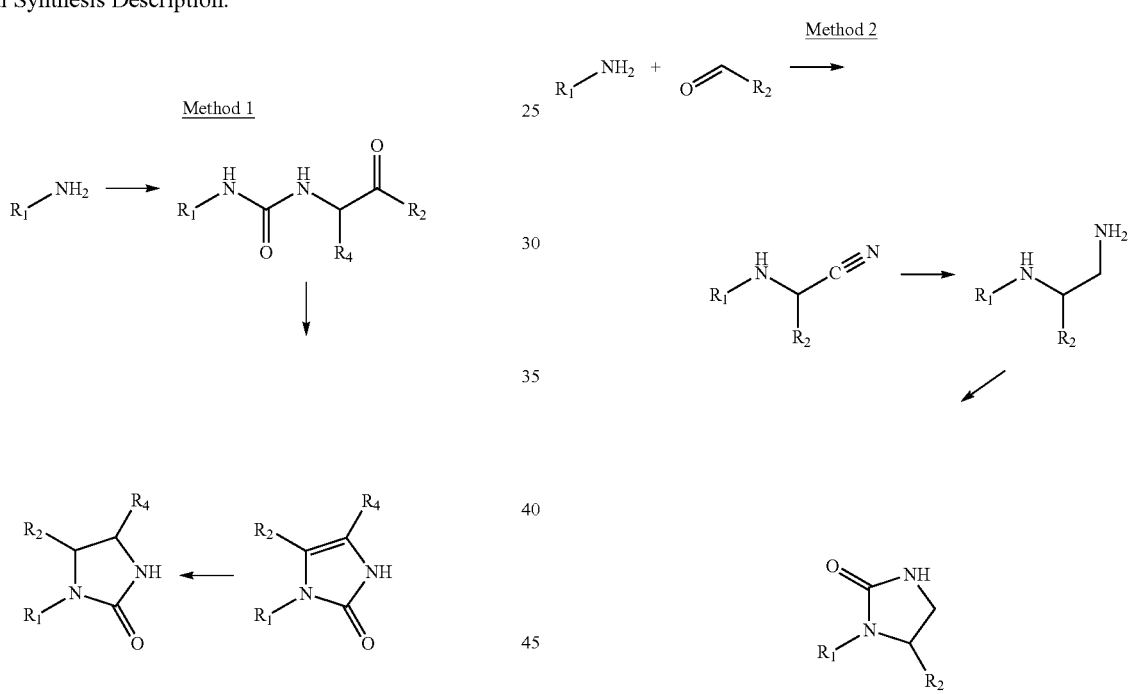

The amine (1 equivalent) was dissolved in $CH_2Cl_2$ and TEA (3 equivalents) were added. Di(1H-imidazol-1-yl)methanone (1 equivalent), dissolved in a small amount of $CH_2Cl_2$, was then added. The mixture was stirred at r.t. for 2 h, then the corresponding aminoalkyl ketone hydrochloride (1 eq), suspended in a small amount of $CH_2Cl_2$ containing 2 equivalents of TEA, was added. The mixture was stirred for 2-3 h until the formation of the urea was complete. The urea was isolated by means of preparative HPLC.

The urea was taken up in a mixture of AcOH and conc. aqueous HCl (40/1, v/v) and kept under reflux for 1 h. The solvent was removed and the remains were re-dissolved in MeOH and little HCl was added (1-2%). The solution was subjected to hydrogenation (PdC, 10% on charcoal, 4 bar, 40° C.) for 4 h. The catalyst was removed by filtration through a pad of CELITE®. The solvent was removed and purified by means of preparative HPLC.

1 equivalent of the aldehyde was dissolved in AcOH (5 mL in case of 4 mmol starting material) and 1.1 equivalents of the amine were added. 1 equivalent of TMSCN was then added to the mixture. The mixture was then stirred for 1.5 h at r.t.

The mixture was then poured on ice/ammonia (containing 12 mL of a 25% $NH_3$ solution in case of 4 mmol starting material). The aqueous layer was extracted 3 times by means of $CH_2Cl_2$ the organic phases were combined and dried. The solvent was removed and remains were taken up in MeOH and 1-2% of conc. HCl were added. The solution was subjected to hydrogenation (PdC 10%, $H_2$ 4 bar, 3 h, RT). After filtration, the solvent was evaporated and the remaining oil was dissolved in $CH_2Cl_2$ and TEA (2.2 equivalents) were added. After addition of carbonyldiimidazole (1.2 eq) the mixture was kept under reflux for 18 h. The solvent was removed and the remaining oil was taken up in $CH_2Cl_2$, washed with water two times and subjected to column chromatography using a $CHCl_3$/MeOH gradient.

Method 3

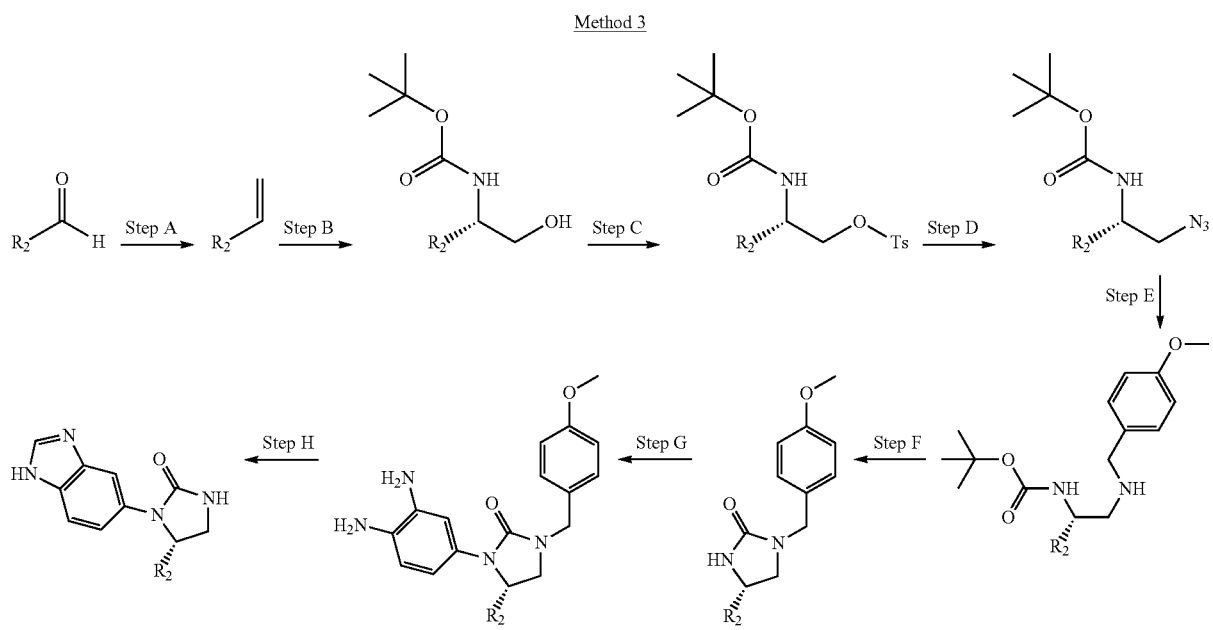

Step A:

1.34 equivalents of a 1M-solution of potassium tert-butoxide or 2 equivalents of n-butyl lithium in THF was added to a suspension of 1.34 equivalents of methyltriphenylphosphonium bromide in THF at 0° C. under argon atmosphere. The reaction was allowed to warm up to ambient temperature and was stirred for 10 minutes. The reaction was then cooled down to 0° C. again, a solution of 1 equivalent 4-propoxybenzaldehyde in THF was added. The reaction was stirred at ambient temperature until the TLC control (heptane/chloroform 1:1) indicated a complete consumption of the aldehyde. The reaction mixture was filtered and the filtrate was concentrated under vacuum. The product was purified via flash-chromatography (hexane/chloroform 8:2).

Step B:

Tert-butyl carbamate (3.1 equiv.) was dissolved in 1-propanol and 0.38 M aqueous NaOH (3.1 eq) was added. The reaction was stirred for 5 minutes at ambient temperature and 1,3-dichloro-5,5-dimethylimidazolidine-2,4-dione (1.535 equiv.) was added and the reaction was stirred for 10 minutes at ambient temperature. The reaction was cooled down to 0° C. and (DHQ)$_2$PHAL (0.06 equiv.) dissolved in 1-propanol was added. After that 1 equiv. of the corresponding styrene dissolved in 1-propanol was added followed by potassium osmate dihydrate (0.04 equiv.) suspended in a small amount of aqueous NaOH. The reaction was stirred at 0° C. until complete consumption of the styrene (TLC control). Water was added and the reaction mixture was extracted three times by means of ethyl acetate. Saturated aqueous sodium chloride solution had to be added until phase separation was observed. The combined organic layer was washed with brine, dried over sodium sulfate, filtered and the solvents were removed under reduced pressure. The product was purified by flash chromatography using a heptane-ethyl acetate gradient (0→30%).

Step C:

The product (1 equiv.) obtained from step B was dissolved in dichloromethane and the solution was cooled down to 0° C. Tosylchloride (1.05 equiv.) and triethylamine (1.4 equiv.) were added to the solution. The reaction was allowed to adopt ambient temperature and was stirred for 14 hours before the reaction mixture was transferred into water. The mixture was extracted three times by means of dichloromethane. The combined organic layers were washed with brine, dried (Na$_2$SO$_4$), filtered and the solvent was removed under reduced pressure. The product was purified by FPLC using a hexane-ethyl acetate gradient (0→30%).

Step D:

The product obtained from step C (1 equiv.) was dissolved in DMF and sodium azide (1.5 equiv.) was added. The reaction was stirred for 2 hours at 70° C. The reaction was cooled down to ambient temperature, before water was added and the mixture was extracted three times with 60 mL ethyl acetate. The combined organic layer was washed with brine, dried over sodium sulfate, filtered and concentrated under reduced pressure. The product was purified via FPLC using hexane-ethyl acetate gradient (0→30%).

Step E:

The product obtained from step D was dissolved in ethanol. The mixture was purged with argon, loaded with palladium on activated carbon (10%) and the mixture was hydrogenated using an autoclave for 14 hours at ambient temperature and 4 bar hydrogen pressure. The catalyst was filtered off through a pad of CELITE® and the filtrate was concentrated under reduced pressure. The product firstly appears as a colorless oil and crystallizes after a few minutes.

The crude product obtained from the hydrogenation was dissolved in ethanol and p-anisaldehyde (1.2 equiv.) was added to the solution. The reaction was stirred for 5 hours at ambient temperature, before the reaction was cooled down to 0° C. and sodium borohydride (2.4 equiv.) was added. The mixture was stirred at ambient temperature for 14 hours. The solvent was removed under reduced pressure. The residue was suspended in saturated aqueous ammonium chloride solution and extracted three times with ethyl acetate. The combined organic layers were washed with brine, dried (Na$_2$SO$_4$), filtered and concentrated under reduced pressure.

Step F:

The crude material obtained from step E was dissolved in dichloromethane and trifluoroacetic acid (20% V/V) was added. The reaction was stirred until the complete consumption of the starting material (TLC control). Toluol was added and the solvents and the trifluoroacetic acid were removed under reduced pressure.

The crude material obtained from the Boc-deprotection was dissolved in dichloromethane and triethylamine (2.2 equiv.) was added. To the stirred solution di(1H-imidazol-1-yl)methanone (1.2 equiv.) was added and the reaction was stirred for 1 hour at reflux. After cooling down the reaction mixture, the solvent was removed and water was added. The aqueous layer was extracted with ethyl acetate three times. The combined organic layer was washed with brine, dried over sodium sulfate, filtered and the solvent was removed under reduced pressure. The product was purified by FPLC (hexane-ethyl acetate 0→100%).

Step G:

The imidazolidin-2-one (1 equiv.), 4-iodobenzene-1,2-diamine (1 equiv.), copper(I) iodide (0.1 equiv.) and cesium fluoride (2 equiv.) were added in a reaction flask purged with argon. Cyclohexane-1,2-diamine (mixture of cis and trans [0.1 equiv.]) was dissolved in dry dioxane and was given to the solids and the mixture was heated at 95° C. under argon atmosphere until TLC indicated consumption of the starting material. The reaction mixture was cooled down to 45° C. and filtered through a pad of CELITE®. The pad was washed with warm dichloromethane several times. The filtrate was concentrated under reduced pressure. The product was purified by FPLC using a chloroform-methanol gradient (0%→10%).

Step H:

The product obtained from step G was dissolved in triethyl orthoformate and the reaction was stirred for 30 minutes at reflux. After cooling the excess of triethyl orthoformate was removed under reduced pressure and the remains were dissolved in trifluoroacetic acid. The reaction was stirred for 14 hours at ambient temperature. The TFA was removed under reduced pressure and the residue was re-dissolved in buffer (pH7) and three times extracted by means of dichloromethane. The combined organic layers were washed with brine, dried over sodium sulfate, filtered and the solvent was removed under reduced pressure. The final product was purified by means of FPLC using a methanol-chloroform gradient (0→10%).

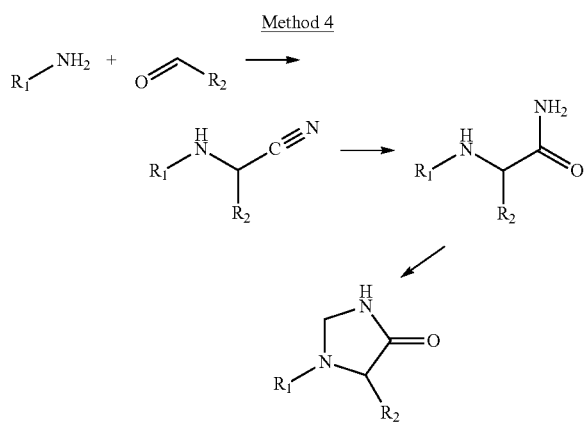

Method 4

1 equivalent of the aldehyde was dissolved in AcOH (5 mL in case of 4 mmol starting material) and 1.1 equivalents of the amine were added. 1 equivalent of TMSCN was then added to the mixture. The mixture was stirred for 1.5 h at r.t.

The mixture was then poured on ice/ammonia (containing 12 mL of a 25% $NH_3$ solution in case of 4 mmol starting material). The aqueous layer was extracted 3 times by means of $CH_2Cl_2$ the organic phases were combined, dried, filtrated and the solvent was removed. The remains were re-dissolved in concentrated HCl and kept at 40° C. overnight. Water was added and the solution was neutralized by adding NaOH. The aqueous phase was extracted three times by means of $CH_2Cl_2$, thereafter the organic phases were combined and dried. The solvent was removed and the remains were taken up in triethyl-ortho formate. The mixture was kept under reflux for 1 h. The orthoester was removed and the remaining oil was dissolved in MeOH and $NaBH_4$ (1.5 equivalents) were added. The mixture was kept at ambient temperature for 1 h, followed by 60° C. for 1 h and the reaction was quenched by addition of an aqueous solution of ammonia (12%). The aqueous layer was extracted three times by means of $CH_2Cl_2$, thereafter the organic phases were combined and dried. The solvent was removed and the remaining mixture was subjected to preparative HPLC.

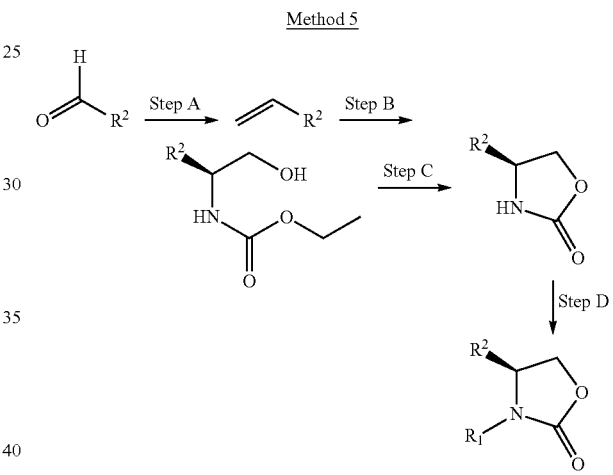

Method 5

Step A:

1.34 equivalents of a 1M-solution of potassium tert-butoxide or 2.0 equivalents of n-butyl-lithium in THF were added to a suspension of 1.34 equivalents of methyltriphenylphosphonium bromide in THF at 0° C. under argon atmosphere. The reaction was allowed to warm up to ambient temperature and was stirred for 10 minutes. The reaction was then cooled down to 0° C. again, a solution of 1 equivalent of the aldehyde in THF was added. The reaction was stirred at ambient temperature until the TLC control (heptane/chloroform 1:1) indicated a complete consumption of the aldehyde. The reaction mixture was filtered and the filtrate was concentrated under vacuum. The product was purified via flash-chromatography (hexane/chloroform 8:2).

Step B:

Ethyl carbamate (3 equiv.) was dissolved in 1-propanol and 0.5 M aqueous NaOH (3 equiv.) was added. The reaction was stirred for 5 minutes at ambient temperature and 1,3-dichloro-5,5-dimethylimidazolidine-2,4-dione (1.5 equiv.) were added and the reaction was stirred for 10 minutes at ambient temperature. $(DHQ)_2PHAL$ (0.06 equiv.) dissolved in 1-propanol were added. After that 1 eq of the corresponding styrene obtained from step A dissolved in 1-propanol were added followed by potassium osmate dihydrate (0.04 equiv.) suspended in small amount of 0.5 M aqueous NaOH. The reaction was stirred at ambient temperature until complete consumption of the styrene. (TLC control) Water was added and the reaction mixture was extracted three times by means of ethyl acetate. The combined organic layer was washed with brine, dried over sodium sulfate, filtered and the solvents were removed under reduced pressure. The product was purified via flash-chromatography using a heptane-ethyl acetate gradient.

Alternative:

T-butyl hypochlorite (3 eq) was added to a stirred solution of benzyl carbamate (3 eq) 0.4M aqueous sodium hydroxide in 1-propanol at 0° C. and stirred for 15 min. A solution of $(DHQ)_2PHAL$ (0.05 eq) in 1-propanol was added. Then the corresponding olefine (1 eq)) in 1-propanol followed by potassium osmate dihydrate (100 mg, 0.025 eq) and the reaction mixture was stirred for 2 h at room temperature. The reaction mixture was quenched into saturated sodium sulphite solution and extracted with ethyl acetate (3×40 mL). The combined organic layer was washed with water, brine, dried over anhydrous sodium sulfate and concentrated under reduced pressure to afford crude product. Purification by column chromatography over silica gel (60-120 mesh) using 10% ethyl acetate in petroleum ether as eluent to afford the product stirred at 95° C. until TLC indicated consumption of the oxazolidin-2-one. After cooling to 45° C. the reaction mixture was filtered through a pad of CELITE®, the pad was washed with warm dichloromethane and the solution was concentrated under reduced pressure. The product was purified via FPLC using a chloroform-methanol gradient (0→10%).

The product obtained from the copper(I)-catalyzed coupling was dissolved in triethyl orthoformate and the reaction was stirred at reflux for 1 h. After cooling the excess of triethyl orthoformate was removed under reduced pressure. The final product was purified via FPLC using a chloroform-methanol gradient (0→10%).

3-(imidazo[1,2-a]pyridin-7-yl)oxazolidin-2-ones 1 equiv. of the oxazolidin-2-one was given together with 7-bromoimidazo[1,2-a]pyridine (1 equiv.), cesium fluoride (2 equiv.) and copper(I) iodide (0.1 equiv.) in a flask. The flask was purged with argon and a solution of cyclohexane-1,2-diamine (0.1 equiv.) in dioxane was added. The reaction was stirred at 95° C. until TLC indicated consumption of the oxazolidin-2-one. After cooling to 45° C. the reaction mixture was filtered through a pad of CELITE®, the pad was washed with warm dichloromethane and the solution was concentrated under reduced pressure. The final product was purified via FPLC using a chloroform-methanol gradient (0→10%).

Method 6

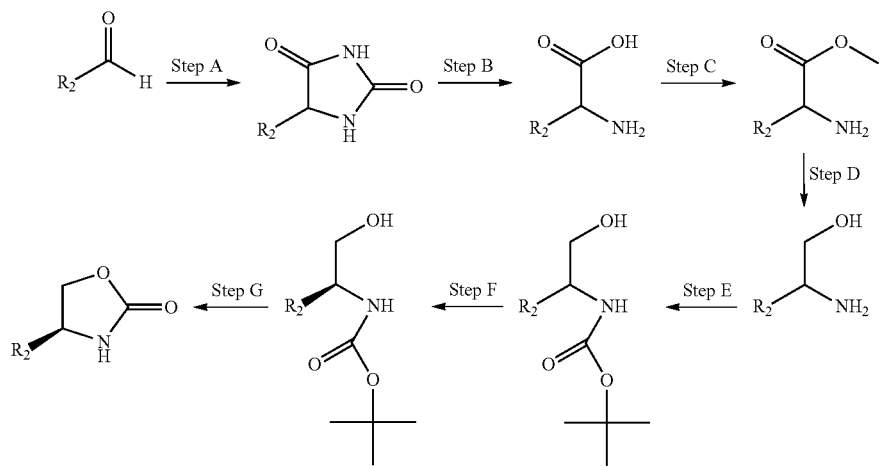

Step C:

The product obtained from step B was dissolved in a 0.2 M solution of sodium hydroxide in methanol. The reaction was stirred at reflux until the TLC control indicated complete consumption. The solvent was removed under reduced pressure and ethyl acetate was added. The organic layer was washed with brine, dried over sodium sulfate, filtered and the solvent was removed under reduced pressure. The product was purified via FPLC using a heptane-ethyl acetate gradient (0→100%).

Step D:

3-(1H-benzo[d]imidazol-5-yl)oxazolidin-2-ones 1 equiv. of the oxazolidin-2-one was given together with 4-iodobenzene-1,2-diamine (1 equiv.), cesium fluoride (2 equiv.) and copper(I) iodide (0.1 equiv.) in a flask. The flask was purged with argon and a solution of cyclohexane-1,2-diamine (0.1 equiv.) in dioxane was added. The reaction was Step A:

Potassium cyanide (1.2 eq) was added to a stirred solution of the corresponding aldehyde (1 eq), ammonium carbonate (3 eq)) in ethanol and water. The reaction mixture was heated at 60° C. overnight. Then the reaction mixture was cooled to 0° C., precipitated solid was filtered and washed with water and petroleum ether. The residue was dried in vacuo.

Step B:

A mixture of the product of step A (1 eq) and 10% NaOH was refluxed overnight. The reaction mixture was extracted with ethyl acetate (3×30 mL) and the aqueous layer was acidified with concentrated HCl up to pH-2. The aqueous layer was extracted with ethyl acetate and the aqueous layer was concentrated under vacuo and co-distilled with toluene. This crude product was taken as such for the next step.

Step C:

Thionyl chloride was added to a stirred solution of the product of step B (1 eq)) in methanol and refluxed overnight.

The reaction mixture was concentrated in vacuo and the residue was dissolved in water and extracted with ethyl acetate. The aqueous layer was basified with solid sodium bicarbonate and extracted with ethyl acetate. The combined organic layer was washed with brine solution, dried over anhydrous sodium sulphate and concentrated in vacuo.

Step D:

Product of step C (1 eq) was added portion wise to a suspension of sodium borohydride (3 eq) in ethanol (100 mL) at 0° C. and stirred at room temperature for 5 h. Excess ethanol was removed in vacuo and the residue was partitioned between water and ethyl acetate. Separated organic layer was washed with water, brine, dried over anhydrous sodium sulphate and concentrated in vacuo.

Step E:

Triethylamine (2 eq), Boc anhydride (1.5 eq) was added successively to a stirred solution of the product of step D (1 eq) in dry dichloromethane and stirred for 4 h at room temperature. The reaction mixture was poured into water and extracted with dichloromethane. The combined organic layer was washed with brine solution, dried over anhydrous sodium sulphate and concentrated in vacuo. This was purified by super fluid chromatography to obtain the R, S enantiomers.

Step F:

Thionyl chloride (8 eq) was added to a stirred solution of compound product of step E (1 eq) in tetrahydrofuran (75 mL) at 0° C. and stirred for 6 h at room temperature. The reaction mixture was concentrated under reduced pressure to give crude compound. The crude product was purified by washing with n-pentane.

Step G:

A mixture of the product of step F (1 eq), 1,2-diamino 4-iodo benzene (1 eq), cesium fluoride (1.5 eq) in 1,4-dioxane were purged with argon gas for 15 min. 1,2-diaminocyclohexane (0.1 eq) and copper iodide (0.1 eq) was added to the reaction mixture, purging continued for another 5 min and stirred over night at 120° C. in a sealed tube. The reaction mixture was quenched with water and extracted with ethyl acetate. The organic layer was washed with brine solution, dried over anhydrous sodium sulphate and concentrated under vacuo to give crude compound. The crude product was purified by column chromatography using neutral alumina using 2% methanol in dichloromethane as eluent.

A mixture of the product of step G (1 eq) and formic acid was heated at 70° C. for 1 h. The reaction mixture was cooled to 0° C. and basified using saturated sodium bicarbonate solution. The aqueous layer was extracted with ethyl acetate, washed with brine solution and dried over anhydrous sodium sulfate. The compound was purified by preparative TLC or HPLC 1M ether-HCl (0.57 mL, 0.57 mmol) was added to a stirred solution of the product (150 mg, 0.47 mmol) in dichloromethane (10 mL) at 0° C. and stirred for 30 min at room temperature. The reaction mixture was filtered and washed with pentane.

Method 7

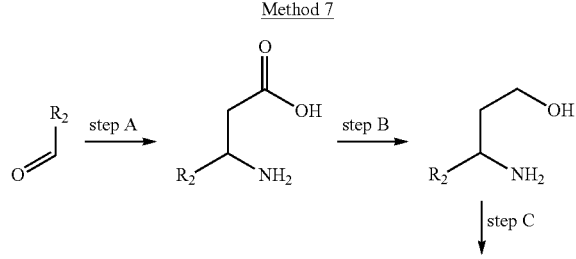

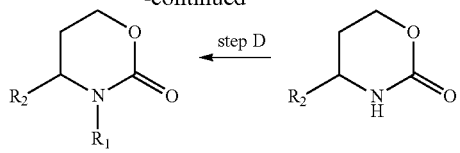

Step A:

Malonic acid (1 equiv.) and ammonium acetate (2 equiv.) were dissolved in methanol. To the stirred solution the corresponding aldehyde (1 equiv.) was added and the reaction was stirred at reflux for 18 hours. The reaction was cooled to 0° C. and the precipitate was filtered off and washed with cold ethanol.

Step B:

To a suspension of the 3-aminopropionic acid obtained from step A in THF, a 2M solution of lithium aluminium hydride (1.5 equiv.) in THF was added slowly. The stirred solution was stirred at 50° C. for 2 hours. The reaction was cooled to 0° C. and the reaction was quenched by addition of water. The solution was extracted with ethyl acetate three times, the organic layers were combined, washed with brine, filtered and the solvents were removed under reduced pressure.

Step C:

Product obtained from step B was dissolved in dichloromethane and di(1H-imidazol-1-yl)methanone (1.2 equiv.) was added to the solution. The reaction was heated at reflux for 1 hour. The reaction was cooled down to ambient temperature and washed with water. The organic layer was dried over sodium sulphate, filtered and the solvent was removed under reduced pressure. The product was purified via FPLC using a heptane-ethyl acetate gradient (0→100%).

Step D:

3-(1H-benzo[d]imidazol-5-yl)-1,3-oxazinan-2-one 1 equiv. of the 1,3-oxazinan-2-one was given together with 4-iodobenzene-1,2-diamine (1 equiv.), potassium carbonate (2 equiv.) and copper(I) iodide (0.1 equiv.) in a flask. The flask was purged with argon and a solution of cyclohexane-1,2-diamine (0.1 equiv.) in dioxane was added. The reaction was stirred at 95° C. until TLC indicated consumption of the 1,3-oxazinan-2-one. After cooling to 45° C. the reaction mixture was filtered through a pad of CELITE®, the pad was washed with warm dichloromethane and the solution was concentrated under reduced pressure. The product was purified via FPLC using a chloroform-methanol gradient (0→10%).

The product obtained from the copper(I)-catalyzed coupling was dissolved in triethyl orthoformate and the reaction was stirred at reflux for 1 h. After cooling the excess of triethyl orthoformate was removed under reduced pressure. The final product was purified via FPLC using a chloroform-methanol gradient (0→10%).

3-(imidazo[1,2-a]pyridin-7-yl)-1,3-oxazinan-2-one 1 equiv. of the 1,3-oxazinan-2-one was given together with 7-bromoimidazo[1,2-a]pyridine (1 equiv.), potassium carbonate (2 equiv.) and copper(I) iodide (0.1 equiv.) in a flask. The flask was purged with argon and a solution of cyclohexane-1,2-diamine (0.1 equiv.) in dioxane was added. The reaction was stirred at 95° C. until TLC indicated consumption of the 1,3-oxazinan-2-one. After cooling to 45° C. the reaction mixture was filtered through a pad of CELITE®, the pad was washed with warm dichloromethane and the solution was concentrated under reduced pressure. The final product was purified via FPLC using a chloroform-methanol gradient (0→10%).

Method 8

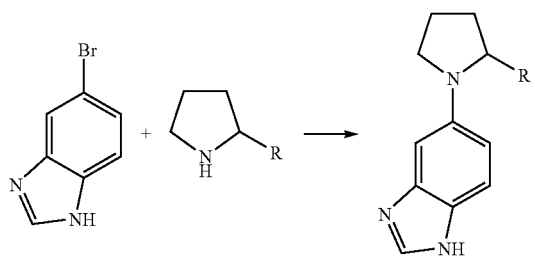

5 (6)-Bromobenzimidazole (200 mg; 1 mmol; 1 eq.), the respective pyrrolidine derivative (1.2 mmol; 1.2 eq.), 2-dicyclohexylphosphino-2'-(N,N-dimethylamino)biphenyl (9 mg; 0.024 mmol; 0.024 eq.; 2.4 mol %) and $Pd_2$ $dba_3$ (9 mg; 0.01 mmol; 0.01 eq.; 1 mol %) were dissolved in THF (1 ml). After addition of lithiumbis(trimethylsilyl)amide (1 M solution in THF; 2.2 ml; 2.2 mmol; 2.2 eq.) the mixture was stirred under argon-atmosphere at 65° C. for 24 h. After cooling to room temperature, 2 N HCl was added until acidic pH and stirred for additional 10 min. The mixture was poured into saturated sodium bicarbonate solution (20 ml) and extracted with EtOAc (3×25 ml). The combined organic layers were dried over $Na_2SO_4$ and evaporated. The remaining residue was purified by flash-chromatography using $Al_2O_3$ and a $CHCl_3$/MeOH gradient.

Method 9

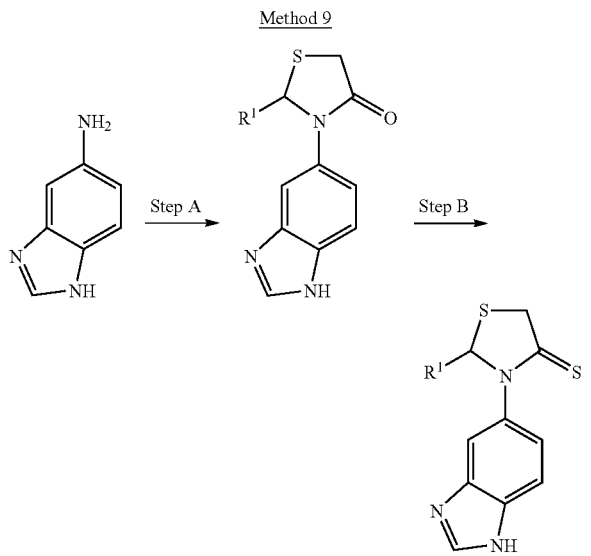

Step A:
5-Aminobenzimidazole (1 eq) was dissolved in EtOH then the corresponding aldehyde (3 eq) and piperidine (catalytic amounts) was added. The solution was stirred at 80° C. in a sealed tube overnight and further at reflux for 1.5 h. Then the solvent was removed and the remains were taken up in toluol and mercapto acetic acid (1.5 eq) or 2-mercapto propionic acid (1.5 eq) was added. The solvent was removed and the product was purified by means of preparative HPLC.

Step B:
The product of step B (1.0 eq) was dissolved in toluol and Lawessons Reagent (5.0 eq) was added. The mixture was kept under reflux for 6 h. The solvent was removed and the remains were taken up in $CHCl_3$ then washed by means of a saturated solution of $NaHCO_3$. The solvent was removed and the product was purified by means of preparative HPLC.

Method 10

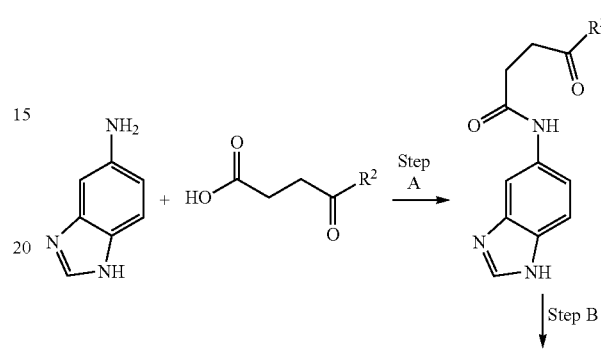

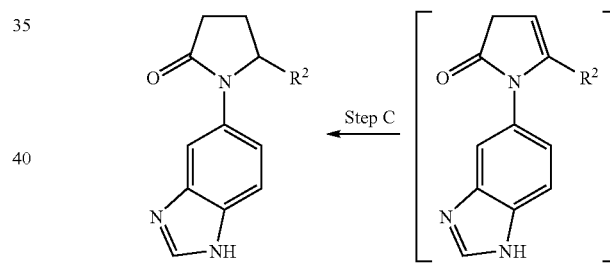

Step A:
The respective 4-oxo-butanoic acid (1 eq.) was dissolved in dichlormethane (10 ml). Carbonyldiimidazole (1 eq.) was added and the mixture was stirred at room temperature for 1 h. After the addition of benzimidazol-5 (6)-amine (1 eq.) the mixture was stirred overnight. The precipitated solid was collected by filtration and washed with dichlormethane to give the title compounds that were used without further purification.

Step B and C:
The respective 4-oxo-butanoicacidamide was dissolved in a mixture of AcOH (3 ml) and toluol (7 ml) and refluxed overnight. After that the solvents were removed by evaporation. The resulting residue was dissolved in AcOH (10 ml) and was hydrogenated over night (PdC 10%; 1-2 bar; r.t.). After filtration through Celite the solvent was evaporated. The remaining residue was taken up with water, brought to basic pH by means of 2 N NaOH and extracted with EtOAc (3×25 ml). The combined organic layers were dried over $Na_2SO_4$, evaporated and the residue was purified by flash-chromatography on silica gel using a $CHCl_3$/MeOH gradient.

Method 11

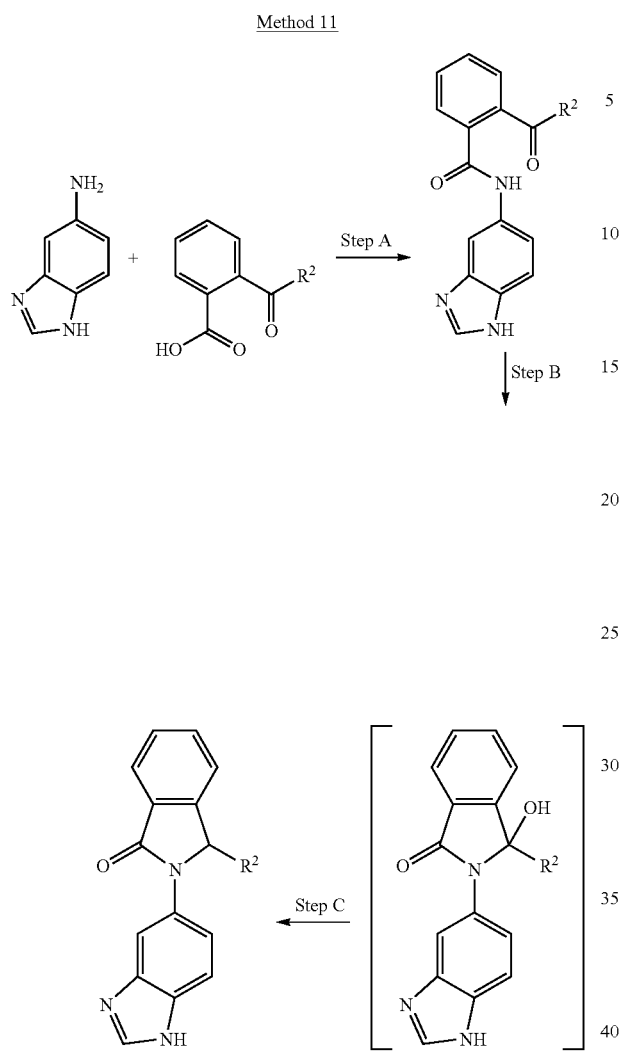

Method 12

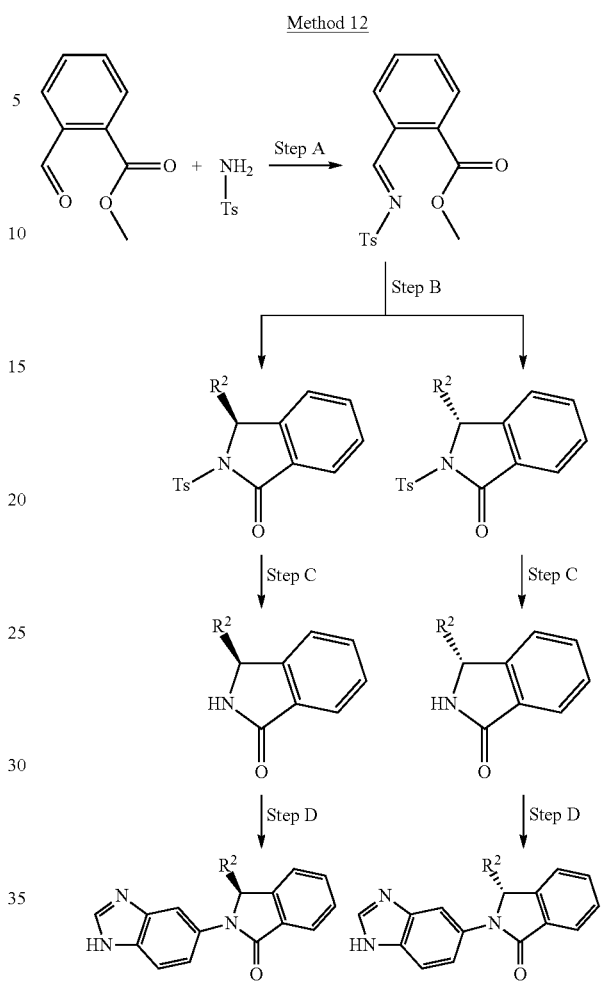

Step A:

Methyl-2-formylbenzoate (3.28 g; 20 mmol; 1 eq.) and para-toluenesulfonamide (3.42 g; 20 mmol; 1 eq.) were suspended in tetraethylorthosilicate (4.69 ml; 21 mmol; 1.05 eq.) and heated to reflux for 6 h. Upon cooling the mixture was diluted with warm EtOAc (70 ml). After treating with n-pentane (250 ml) the mixture was put into a fridge overnight. The precipitate was collected by filtration and washed with n-pentane. Yield: 4.83 g (76.2%); MS m/z: 318.2 [M+H]$^+$ Step B, C:

The respective boronic acid (2 eq.), [RhCl(C$_2$H$_4$)$_2$]$_2$ (0.031 eq.) and (3aS,6aS)-3,6-diphenyl-1,3a,4,6a-tetra-hydropentalen (0.066 eq.), for the preparation of 3S-enantiomers, or (3aR, 6aR)-3,6-diphenyl-1,3a,4,6a-tetrahydropentalen (0.066 eq.), for the preparation of 3R-enantiomers, were dissolved in toluol (2.5 ml) and heated to 55° C. under argon atmosphere. After 1 h, methyl-2-(tosylimino-methyl)benzoate (1 eq.), toluol (6 ml) and TEA (2 eq.) were added sequentially and stirring was continued for 5 h. The mixture was quenched with saturated NaHCO$_3$-solution and extracted with EtOAc (3×25 ml). The combined organic layers were dried over Na$_2$SO$_4$ and evaporated. The resulting residue was dissolved in THF (10 ml). After cooling to 0° C. the solution was treated with SmI$_2$ (1 M solution in THF) until the dark blue color persisted. Stirring was continued for 1 h then the reaction was quenched with saturated sodium bicarbonate solution and extracted with CHCl$_3$ (3×25 ml). The combined Step A, B and C:

The respective 2-oxo benzoic acid (1 eq.) was dissolved in THF (5 ml in case of 1 mmol) and DCC (1 eq.) was added. After stirring at r.t. for 1 h, benzimidazol-5 (6)-amine (1 eq.) was added and stirring at r.t. was continued for 24 h. The mixture was put into the fridge for 2 h and afterwards the precipitated solid was filtered off. The filtrate was concentrated in vacuo, re-dissolved in a mixture of AcOH and toluol (3 ml and 7 ml in case of 1 mmol batch) and refluxed over night. After cooling the solvents were evaporated. The resulting residue was dissolved in CH$_2$Cl$_2$ (10 ml in case of 1 mmol batch), cooled to 0° C. and treated with TFA (1 ml (4 ml) per mmol). After stirring at r.t. for 10 min, triethylsilane (2 eq. (4 eq.)) was added. The reaction was allowed to warm up to room temperature and stirred for 3 h. After that time, the mixture was quenched with saturated sodium bicarbonate solution. The organic layer was separated and the aqueous layer was extracted with EtOAc (3×25 ml). The combined organic layers were dried over Na$_2$SO$_4$, concentrated in vacuo and the remaining residue was purified by flash-chromatography using silica gel and a CHCl$_3$/MeOH gradient.

organic layers were dried over Na$_2$SO$_4$ and concentrated in vacuo. The residue was purified by flash-chromatography using silica gel and a heptane/EtaOAc gradient.
Step D:
4-Iodbenzen-1,2-diamine (1 eq.), the respective 3-phenyl-isoindolinone (1.1 eq.), copper(I)iodide (0.1 eq.), diaminocyclohexane (0.1 eq.) and cesium fluoride (2 eq.) were dissolved in dioxan (5 ml) and heated to 95° C. under argon atmosphere over night. After cooling to room temperature the reaction was quenched with saturated sodium bicarbonate solution and extracted with EtOAc (3×25 ml). The combined organic layers were dried over Na$_2$SO$_4$ and concentrated in vacuo. The remaining residue was dissolved in formic acid orthoethylester (5 ml) and heated to reflux for 2 h. The solvent was evaporated and the residue was purified by semi-preparative HPLC.

SYNTHESIS OF THE EXAMPLES

Example 1

5-tert-butyl-1-(1H-benzo[d]imidazol-5-yl)imidazolidin-2-one

The compound was synthesized as hydrochloride salt by the following procedure.

Phenyl chloroformate (0.98 mL, 7.8 mmol) was dissolved in CH$_2$Cl$_2$, cooled down to 0° C. and 5-aminobenzimidazole (0.865 g, 6.5 mmol) was added slowly. The mixture was kept at 0° C. for 30 min and then the mixture was allowed to adapt ambient temperature. The mixture was stirred at ambient temperature for 2 h. The resulting solid was withdrawn by suction, dried and taken up in a small amount of DMF. To the solution, 1-amino-3,3-dimethylbutan-2-one (0.986, 6.5 mmol) and TEA (2.73 mL, 19.5 mmol) were added. The mixture was kept at 40° C. for 2 h. The solvent was removed and purified by means of preparative HPLC. The remains were re-dissolved in MeOH and a small amount of HCl was added (1-2%). The solution was subjected to hydrogenation (PdC, 10% on charcoal, 4 bar, 60° C.) for 4 h. The catalyst was removed by filtration through a pad of CELITE® and the residue was washed with water. The organic layer was dried, filtrated and the solvent was removed to result in the final product. Yield: 0.087 g (6.3%); MS m/z 259.4 (M+H)$^+$; $^1$H NMR (DMSO, 400 MHz): δ 0.72 (s, 9H); 3.23-3.27 (m, H); 3.46-3.50 (m, H); 4.37-4.41 (m, H); 6.84 (bs, H); 7.56 (dd, H, $^3$J=9.1 Hz, $^4$J=1.7 Hz); 7.70 (d, H, J=9.1 Hz); 7.81 (d, H, $^4$J=1.7 Hz); 9.27 (s, H), HPLC (λ=214 nm, [B]: rt 6.83 min (99%).

Example 2

1-(1H-benzo[d]imidazol-5-yl)-5-cyclohexylimidazolidin-2-one

The compound was synthesized as trifluoroacetate salt starting from 5-aminobenzimidazole (0.59 g, 4.4 mmol), cyclohexanecarbaldehyde (0.45 g, 0.485 mL, 4 mmol), TMSCN (0.5 mL, 4 mmol), PdC (10%, 0.05 g). di-(imidazol-1-yl)methanone (0.64 g, 3.92 mmol), as described in method 2. The product was purified via preparative HPLC using a water-acetonitrile gradient with 0.04% trifluoroacetic acid.

Yield: 0.089 g (5.6%); MS m/z 285.1 (M+H)$^+$; $^1$H NMR (DMSO, 400 MHz): δ 0.82-0.91 (m, H); 0.97-1.16 (m, 4H); 1.39-1.42 (m, H); 1.52-1.69 (m, 5H); 3.24-3.27 (m, H); 3.42-3.46 (m, H); 4.48-4.52 (m, H); 6.92 (s, H); 7.56-7.59 (dd, H, $^3$J=9.1 Hz, $^4$J=2.1 Hz); 7.73-7.75 (d, H, $^3$J=9.1 Hz); 7.94-7.95 (d, H, $^4$J=2.1 Hz); 9.24 (s, H), HPLC (λ=214 nm, [B]: rt 8.64 min (99%).

Example 3

1-(1H-benzo[d]imidazol-5-yl)-5-phenylimidazolidin-2-one

The compound was synthesized starting from 5-aminobenzimidazole (1.46 g, 10 mmol), benzaldehyde (1.06 g, 10 mmol), TMSCN (1.25 mL, 10 mmol), PdC (10%, 0.05 g). di-(imidazol-1-yl)methanone (1.73, 12 mmol), as described in method 2.

Yield: 0.303 g (10.9%); MS m/z 279.3 (M+H)$^+$; $^1$H NMR (DMSO, 400 MHz): δ 3.08-3.11 (m, H); 3.85-3.89 (m, H); 5.54-5.58 (m, H); 7.19-7.33 (m, 6H); 7.51-7.54 (m, H); 7.60 (d, H, J=8.7 Hz); 7.84 (d, H, $^4$J=1.7 Hz); 9.15 (s, H), HPLC (λ=214 nm, [B]: rt 7.36 min (96%).

Example 4

1-(1H-benzo[d]imidazol-5-yl)-5-m-tolylimidazolidin-2-one

The compound was synthesized as hydrochloride salt by the following procedure. 4-Nitrophenyl chloroformate (0.564 g, 3.5 mmol) was dissolved CH$_2$Cl$_2$, cooled down to 0° C. and 5-aminobenzimidazole (0.466 g, 3.5 mmol) was added slowly. The mixture was kept at 0° C. for 30 min and then the mixture was allowed to adapt ambient temperature. The mixture was stirred at ambient temperature for 2 h. The resulted solid was withdrawn by suction, dried and taken up in a small amount of DMF. To the solution aminomethyl-(4-chloro-3-methylphenyl)ketone (0.774, 3.5 mmol) and TEA (1.46 ml, 10.5 mmol) was added. The mixture was kept at 40° C. for 2 h. The solvent was removed and purified by means of preparative HPLC. The remains were re-dissolved in MeOH and a small amount of HCl was added (1-2%). The solution was subjected to hydrogenation (PdC, 10% on charcoal, 4 bar, 60° C.) for 4 h. The catalyst was removed by filtration through a pad of CELITE® and the solvent was removed and purified by means of preparative HPLC.

Yield: 0.008 g (0.6%); MS m/z 293.4 (M+H)$^+$; $^1$H NMR (DMSO, 400 MHz): δ 2.21 (s, 3H); 3.05-3.09 (m, H); 3.83-3.87 (m, H); 5.49-5.53 (m, H); 7.01-7.10 (m, 2H); 7.15 (d, H, J=7.9 Hz); 7.19 (s, H); 7.52-7.55 (m, H); 7.60 (d, H, J=8.7 Hz); 7.84 (s, H); 9.16 (s, H), HPLC (λ=214 nm, [B]: rt 8.05 min (100%).

Example 5

1-(1H-benzo[d]imidazol-5-yl)-5-(4-methoxyphenyl)imidazolidin-2-one

The compound was synthesized as hydrochloride salt starting from 5-aminobenzimidazole (0.266 g, 2 mmol), di(1H-imidazol-1-yl)methanone (0.052 g, 2 mmol), TEA (0.799 mL, 6 mmol), aminomethyl-(4-methoxy)phenyl ketone hydrochloride (0.403 g, 2 mmol), TEA (0.558 mL, 4 mmol), PdC (10%, 0.02 g) as described in method 1.

Yield: 0.234 g (37.8%); MS m/z 309.3 (M+H)$^+$; $^1$H NMR (DMSO, 400 MHz): δ 3.09-3.12 (m, H); 3.67 (s, 3H); 3.84-3.88 (m, H); 5.52-5.55 (m, H); 6.84-6.88 (m, 2H); 7.23 (s, H); 7.25-7.29 (m, 2H); 7.58 (dd, H, $^3$J=9.1 Hz, $^4$J=2.1 Hz); 7.65 (d, H, J=9.1 Hz); 7.90 (s, H); 9.39 (s, H), HPLC (λ=214 nm, [B]: rt 7.84 min (94%).

Example 6

1-(1H-benzo[d]imidazol-5-yl)-5-(4-methoxyphenyl)imidazolidin-2-one

Enantiomer 1

Separation of example 12 by chiral HPLC, column: Nucleocel Alpha RP-S, 250*21 mm (5 μm), eluent: 50/50 acetonitrile/water 30/70, flow 10 mL/min, second eluting enantiomer rt: 20.2 min (99.35) %.

Example 7

1-(1H-benzo[d]imidazol-5-yl)-5-(4-methoxyphenyl)imidazolidin-2-one

Enantiomer 2

Separation of example 12 by chiral HPLC, column: Nucleocel Alpha RP-S, 250*21 mm (5 μm), eluent: 50/50 acetonitrile/water 30/70, flow 10 mL/min, first eluting enantiomer rt: 16.5 min (99.75) %

Example 8

(4R,5S)-1-(1H-benzo[d]imidazol-6-yl)-5-(4-methoxyphenyl)-4-methylimidazolidin-2-one

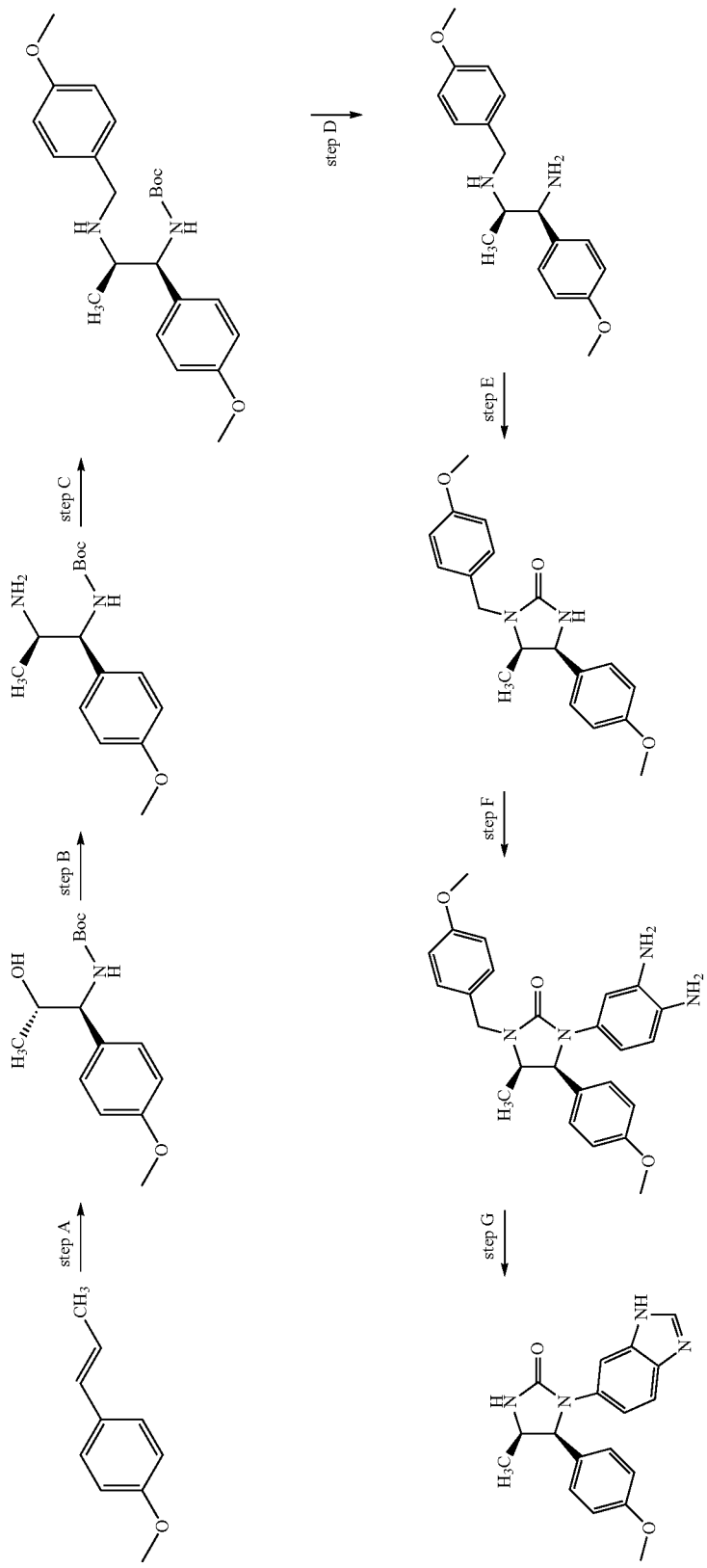

Step A:

Tert-butyl carbamate (3.1 equiv., 4.54 g, 38.75 mmol) was dissolved in 50 mL of 1-propanol and 99 mL of a 0.38 M aqueous NaOH was added. The reaction was stirred for 5 minutes at ambient temperature and 1,3-dichloro-5,5-dimethylimidazolidine-2,4-dione (1.535 equiv., 3.78 g, 19.2 mmol) were added and the reaction was stirred for 10 minutes at ambient temperature. The reaction was cooled down to 0° C. and (DHQ)$_2$PHAL (0.06 equiv., 0.585 g, 0.75 mmol) dissolved in 50 mL 1-propanol were added. After that 1 equiv. of the trans-anethole (1.85 g, 1.875 mL, 12.5 mmol) dissolved in 100 mL of 1-propanol were added followed by potassium osmate dihydrate (0.04 equiv., 0.184 g, 0.5 mmol) suspended in 1 mL 0.38 M aqueous NaOH. The reaction was stirred at 0° C. until complete consumption of the trans-anethole (TLC control). 85 mL of water was added and the reaction mixture was extracted three times by means of 150 mL ethyl acetate. Saturated aqueous sodium chloride solution had to be added until phase separation was observed. The combined organic layer was washed with brine, dried over sodium sulfate, filtrated and the solvents were removed under reduced pressure. The product was purified by FPLC using a heptane-ethyl acetate gradient (0→30%). The product elutes at about 25% of ethyl acetate. Yield: 1.54 g (43.8%)

Step B:

tert-butyl (1S,2S)-2-hydroxy-1-(4-methoxyphenyl)propylcarbamate (1 equiv., 5.5 mmol, 1.54 g) obtained from step B was dissolved in 20 mL of dichloromethane and the solution was cooled down to 0° C. Tosyl chloride (1.05 equiv., 1.10 g, 5.75 mmol) and triethylamine (1.4 equiv., 0.78 g, 1.07 mL, 7.7 mmol) were added to the solution. The reaction was allowed to adopt ambient temperature and was stirred for 18 hours, before the reaction mixture was transferred into 100 mL water. The mixture was extracted three times by means of 100 mL dichloromethane. The combined organic layers were washed with brine, dried (Na$_2$SO$_4$), filtered and the solvent was removed under reduced pressure. The product was purified by FPLC using a heptane-ethyl acetate gradient (0→40%). The product elutes at 25% of ethyl acetate. Yield: 1.79 g (74.7%); MS m/z 436.4 (M+H)$^+$ (1S,2S)-1-(tert-butoxycarbonylamino)-1-(4-methoxyphenyl)propan-2-yl 4-methylbenzene-sulfonate (1 equiv., 1.79 g, 4.1 mmol) was dissolved in 20 mL DMF and sodium azide (1.5 equiv., 0.4 g, 6.2 mmol) was added. The reaction was stirred for 2 hours at 70° C. The reaction was cooled down to ambient temperature before 50 mL water was added and the mixture was extracted three times with 50 mL ethyl acetate. The combined organic layer was washed with brine, dried over sodium sulfate, filtrated and concentrated under reduced pressure. The product was purified via FPLC using heptane-ethyl acetate gradient (0→30%). The product elutes at about 15% ethyl acetate. Yield: 0.75 g (59.6%)

1 equiv. tert-butyl (1S,2R)-2-azido-1-(4-methoxyphenyl) propylcarbamate (0.75 g, 2.45 mmol) was dissolved in 20 mL ethanol. The mixture was purged with argon, loaded with palladium on activated carbon (10%) and the mixture was hydrogenated using an autoclave for 24 hours at ambient temperature and 4 bar hydrogen pressure. The catalyst was filtered off through a pad of celite and the filtrate was concentrated under reduced pressure. The product firstly appears as a colorless oil and crystallizes after a few minutes. Yield: 0.629 g (91.9%)

Step CL:

2.24 mmol of the crude tert-butyl (1S,2R)-2-amino-1-(4-methoxyphenyl)propylcarbamate (1 equiv., 0.629 g) obtained from the hydrogenation was dissolved in 14 mL of ethanol and p-anisaldehyde (1.2 equiv., 0.366 g, 0.326 ml, 2.69 mmol) was added to the solution. The reaction was stirred for 4 hours at ambient temperature before the reaction was cooled down to 0° C. and 5.38 mmol of sodium borohydride (2.4 equiv., 0.203 g) were added. The mixture was stirred at ambient temperature for 14 hours before the solvent was removed under reduced pressure. The residue was suspended in 20 mL saturated aqueous ammonium chloride solution and extracted three times with 40 mL ethyl acetate. The combined organic layers were washed with brine, dried (Na$_2$SO$_4$), filtered and concentrated under reduced pressure. Yield: 0.97 g Step D:

0.97 g of crude tert-butyl (1S,2R)-2-(4-methoxybenzylamino)-1-(4-methoxyphenyl) propylcarbamate (2.4 mmol) was dissolved in 25 mL of dichloromethane and 5 mL of trifluoroacetic acid was added. The reaction was stirred at room temperature until the complete consumption of the starting material (TLC control). Toluol was added and the solvents and the trifluoroacetic acid were removed under reduced pressure. Yield: 1.78 g Step E:

The crude (1S,2R)—N2-(4-methoxybenzyl)-1-(4-methoxyphenyl)propane-1,2-diamine obtained from the Boc-deprotection (step D) was dissolved in 30 mL dichloromethane and triethylamine (2.2 equiv., 1.04 mL, 7.5 mmol) was added. To the stirred solution di(1H-imidazol-1-yl)methanone (1.2 equiv., 0.662 g, 4.08 mmol) was added and the reaction was stirred for 1 hour at reflux. After cooling down the reaction mixture, the solvent was removed and 60 mL water was added. The aqueous layer was extracted with 70 mL of ethyl acetate three times. The combined organic layer was washed with brine, dried over sodium sulfate, filtrated and the solvent was removed under reduced pressure. The product was purified by FPLC (heptane/ethyl acetate 0→100%). The product elutes at about 80 percent of ethyl acetate. Yield: 0.29 g; MS m/z 327.4 (M+H)$^+$ Step F:

The (4S,5R)-1-(4-methoxybenzyl)-4-(4-methoxyphenyl)-5-methylimidazolidin-2-one (1 equiv., 0.29 g, 0.89 mmol), 4-iodobenzene-1,2-diamine (1 equiv., 0.208 g, 0.89 mmol), copper(I) iodide (0.1 equiv., 0.017 g, 0.089 mmol) and cesium fluoride (2 equiv., 0.27 g, 1.78 mmol) were added in a reaction flask and purged with argon. Cyclohexane-1,2-diamine (mixture of cis and trans [0.1 equiv., 0.01 g, 0.011 mL]) was dissolved in 4 mL of dry dioxane was given to the solids and the mixture was heated for 3 days at 95° C. under argon atmosphere. The reaction mixture was cooled down to 45° C. and filtered through a pad of celite. The pad was washed with warm dichloromethane several times. The filtrate was concentrated under reduced pressure. The product was purified by FPLC using a chloroform-methanol gradient (0%→10%). The product elutes at about 4% methanol. Yield: 0.105 g (27.3%); MS m/z 433.5 (M+H)$^+$ Step G:

(4R,5S)-1-(3,4-diaminophenyl)-3-(4-methoxybenzyl)-5-(4-methoxyphenyl)-4-methylimidazolidin-2-one (0.105 g, 0.24 mmol) obtained from step F was dissolved in 3 mL triethyl orthoformate. The reaction was stirred for 30 minutes at reflux. After cooling the solvent was removed and the remains were dissolved in 8 mL trifluoroacetic acid. The reaction was stirred for 14 hours at ambient temperature. The TFA was removed under reduced pressure and the residue was re-dissolved in 20 mL of buffer (pH7) and three times extracted by means of 25 mL dichloromethane. The combined organic layers were washed with brine, dried over sodium sulfate, filtrated and the solvent was removed under reduced pressure. The final product was purified by FPLC using a chloroform-methanol gradient (0→10%). The product elutes at about 5% methanol.

Yield: 0.048 g (62%); MS m/z 323.3 (M+H)$^+$; $^1$H NMR (DMSO, 400 MHz): δ 0.65-0.67 (m, H); 3.67 (s, 3H); 4.06-4.13 (m, 3H); 5.43-5.45 (m, H); 6.83-6.85 (m, 2H); 6.97 (bs, H); 7.12-7.14 (m, 2H); 7.19-7.25 (m, H); 7.30-7.47 (m, H); 7.50-7.69 (m, H); 8.05 (s, H); 12.19-12.24 (m, H), HPLC (λ=214 nm, [B]: rt 8.45 min (98.7%).

Example 9

1-(1H-benzo[d]imidazol-5-yl)-5-(3-methoxyphenyl)imidazolidin-2-one

The compound was synthesized as hydrochloride salt starting from 5-aminobenzimidazole (0.532 g, 4 mmol), di(1H-imidazol-1-yl)methanone (0.713 g, 4.4 mmol), TEA (1.67 mL, 12 mmol), aminomethyl-(3-methoxyphenyl)ketone hydrochloride (0.807 g, 4 mmol), TEA (1.12 mL, 8 mmol), PdC (10%, 0.02 g) as described in method 1.

Yield: 0.087 g (6.3%); MS m/z 309.1 (M+H)$^+$; $^1$H NMR (DMSO, 400 MHz): δ 3.07-3.11 (m, H); 3.66 (s, 3H); 3.83-3.88 (m, H); 5.51-5.55 (m, H, 6.76-6.78 (m, H); 6.85-6.88 (m, 2H); 7.17-7.21 (m, H); 7.24 (bs, H); 7.57 (dd, H, $^3$J=9.2 Hz $^4$J=1.8 Hz); 7.64 (d, H, $^3$J=9.2 Hz); 7.89 (d, H, $^4$J=1.8 Hz); 9.36 (s, H), HPLC (λ=214 nm, [B]: rt 7.79 min (99%).

Example 10

1-(1H-benzo[d]imidazol-5-yl)-5-(2-methoxyphenyl)imidazolidin-2-one

The compound was synthesized starting from 5-aminobenzimidazole (0.585 g, 4.4 mmol), 2-methoxybenzaldehyde (0.484 mL, 4 mmol), TMSCN (0.5 mL, 4 mmol), PdC (10%, 0.02 g), TEA (1.05 mL, 7.55 mmol), di-(imidazol-1-yl)methanone (0.667, 4.12 mmol) as described in method 2.

Yield: 0.184 g (14.9%); MS m/z 309.3 (M+H)$^+$; $^1$H NMR (DMSO, 400 MHz): δ 2.99-3.03 (m, H); 3.84-3.89 (m, 4H); 5.66-5.69 (m, H); 6.79-6.83 (m, H); 6.91 (s, H); 7.02-7.07 (m, 2H); 7.18-7.22 (m, 2H); 7.40 (bs, H); 7.56 (bs, H); 8.06 (s, H); 12.21 (bs, H), HPLC (λ=214 nm, [B]: rt 7.81 min (96%).

Example 11

1-(1H-benzo[d]imidazol-5-yl)-5-(4-ethoxyphenyl)imidazolidin-2-one

The compound was synthesized starting from 5-aminobenzimidazole (0.585 g, 4.4 mmol), 4-ethoxybenzaldehyde (0.601 g, 4 mmol), TMSCN (0.5 mL, 4 mmol), PdC (10%, 0.02 g), TEA (0.98 mL, 7.0 mmol), di-(imidazol-1-yl)methanone (0.622, 3.84 mmol) as described in method 2.

Yield: 0.126 g (9.8%); MS m/z 323.3 (M+H)$^+$; $^1$H NMR (DMSO, 400 MHz): δ 1.21-1.24 (m, 3H); 3.03-3.07 (m, H); 3.75-3.79 (m, H); 3.87-3.92 (m, 2H); 5.37-5.41 (m, H); 6.79 (d, 2H, J=8.7 Hz); 6.86 (s, H); 7.19-7.23 (m, 3H); 7.35 (d, H, J=8.7 Hz); 7.49 (s, H); 8.04 (s, H); 12.19 (bs, H), HPLC (λ=214 nm, [B]: rt 8.40 min (93%).

Example 12

1-(1H-benzo[d]imidazol-5-yl)-5-(4-propoxyphenyl)imidazolidin-2-one

The compound was synthesized starting from 5-aminobenzimidazole (0.585 g, 4.4 mmol), 4-propoxybenzaldehyde (0.632 mL, 4 mmol), TMSCN (0.5 mL, 4 mmol), PdC (10%, 0.02 g), TEA 0.558 mL, 4 mmol), di-(imidazol-1-yl)methanone (0.648, 4 mmol) as described in method 2. Yield: 0.135 g (10.0%); MS m/z 337.0 (M+H)$^+$; $^1$H NMR (DMSO, 400 MHz): δ 0.90-0.93 (m, 3H); 1.61-1.70 (m, 2H); 3.08-3.12 (m, H); 3.81-3.87 (m, 3H); 5.49-5.53 (m, H); 6.85 (d, 2H, J=8.3 Hz); 7.19 (s, H); 7.25 (d, 2H, J=8.7 Hz); 7.55 (dd, H, $^3$J=9.1 Hz, $^4$J=2.1 Hz); 7.62 (d, H, J=9.1 Hz); 7.86 (d, H, $^4$J=2.1 Hz); 9.21 (s, H), HPLC (λ=214 nm, [B]: rt 9.00 min (99%).

Example 13

(R)-1-(1H-benzo[d]imidazol-5-yl)-5-(4-propoxyphenyl)imidazolidin-2-one

Separation of example 12 by chiral HPLC, column: Nucleocel Alpha RP-S, 250*21 mm (5 μm), eluent: 50/50 acetonitrile/water 50/50, flow 10 mL/min, second eluting enantiomer rt: 12.8 min (98.35) %.

Example 14

(S)-1-(1H-benzo[d]imidazol-5-yl)-5-(4-propoxyphenyl)imidazolidin-2-one

Variant 1

The compound was synthesized according to method 3
Step A:
Potassium tert-butoxide (41.7 mL, 41.7 mmol), methyltriphenylphosphonium bromide (14.89 g, 41.7 mmol), 4-propoxybenzaldehyde (4.915 mL, 31.1 mmol), yield: 4.77 g (94.6%)
Step B:
tert-butyl carbamate (9.08 g, 77.5 mmol), 0.38 M aqueous NaOH (200 mL, 76 mmol), 1,3-dichloro-5,5-dimethylimidazolidine-2,4-dione (7.56 g, 38.4 mmol), (DHQ)$_2$PHAL (1.17 g, 1.5 mmol), 1-propoxy-4-vinylbenzene (4.055 g, 25 mmol), potassium osmate dihydrate (0.368 g, 1 mmol)
Yield: 5.49 g (74.4%); MS m/z 296.3 (M+H)$^+$
Step C:
Product obtained from step B (2.95 g, 10 mmol), 4-methylbenzene-1-sulfonyl chloride (2 g, 10.5 mmol), triethylamine (1.95 mL, 14 mmol)
Yield: 2.59 g (57.6%); MS m/z 450.3 (M+H)$^+$
Step D:
Product obtained from step C (2.59 g, 5.76 mmol), sodium azide (0.562 g, 8.64 mmol)
Yield: 1.25 g (67.8%); MS m/z 321.3 (M+H)$^+$
Step E:
Product obtained from step D (1.25 g, 3.9 mmol), PdC (10%, 0.02 g), p-anisaldehyde (0.598 mL, 4.92 mmol), sodium borohydride (0.372 g, 9.84 mmol)
Yield: 1.68 g (crude material)
Step F:
Crude material obtained from step E (1.63 g, 3.94 mmol), trifluoroacetic acid (9.6 mL), triethylamine (1.52 mL, 10.9 mmol), di(1H-imidazol-1-yl)methanone (0.963 g, 5.94 mmol)
Yield: 1.05 g (81.6%); MS m/z 341.1 (M+H)$^+$
Step G:
(S)-1-(4-methoxybenzyl)-4-(4-propoxyphenyl)imidazolidin-2-one obtained from step F (0.28 g, 0.82 mmol), 4-iodobenzene-1,2-diamine (0.192 g, 0.82 mmol), copper(I) iodide (0.016 g, 0.08 mmol), cesium fluoride (0.249 g, 1.64 mmol), cyclohexane-1,2-diamine (mixture of cis and trans [0.01 mL, 0.08 mmol])
Yield: 82 mg (22.4%); MS m/z 447.5 (M+H)$^+$

Step H:
Product obtained from step G (0.082 g, 0.18 mmol), triethyl orthoformate (5 mL), trifluoroacetic acid (10 mL)
Yield: 35 mg (57.9%);
Overall yield: 2.9%; MS m/z 337.2 (M+H)⁺; HPLC (λ=214 nm, [B]: rt 9.00 min (97.4%)

Variant 2

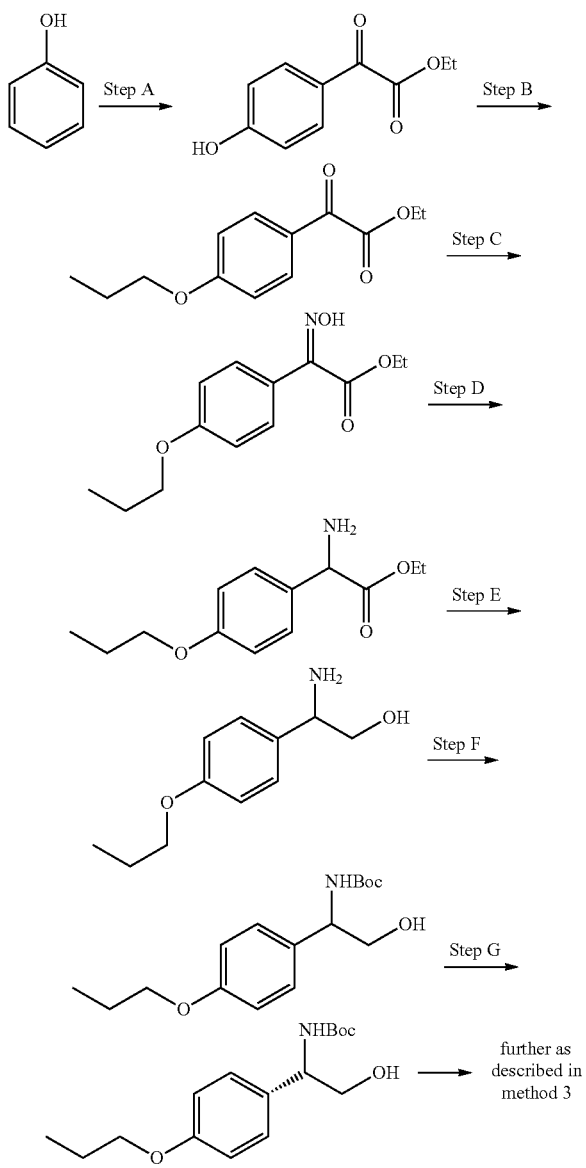

Step A
Phenol (10 g, 106.1 mmol) was added to a solution of powdered aluminium chloride (28.3 g, 212.2 mmol) over a period of 15 min in dichloromethane (100 mL) at 0° C., stirred for 30 min and ethyl oxalyl chloride (14.2 mL, 127.5 mmol) was added to the above reaction mass drop wise over a period of 30 min keeping the temperature at 0° C. Warmed to room temperature and stirred for 15 h. The reaction mass was quenched into cold water and the organic layer separated. The aqueous layer was extracted with dichloromethane. The combined organic layer was washed with water followed by brine solution, dried over anhydrous sodium sulphate and concentrated under reduced pressure to afford crude product. Purification by column chromatography over silica gel (60-120 mesh) using 20-22% ethyl acetate in petroleum ether afforded 7 g (34%) of the product as pale yellow solid.

Step B
1-propyl bromide (4.9 mL, 53.73 mmol) was added to a mixture of the product of step A (6.9 g, 35.82 mmol) and potassium carbonate (9.9 g, 71.65 mmol) in acetonitrile (100 mL) and refluxed for 18 h. The reaction mass was filtered and washed with acetonitrile. The filtrate was concentrated under reduced pressure. The resulting residue was taken in ethyl acetate and washed with water followed by brine solution. Dried over anhydrous sodium sulphate and concentrated under reduced pressure to afford 6 g (71%) of the product as brown oil.

Step C
Hydroxylamine hydrochloride (1.6 g, 22.98 mmol) was added to a mixture of the product of step B (3.6 g, 15.25 mmol) and sodium acetate (2.5 g, 30.50 mmol) in absolute ethanol (50 mL) and refluxed for 18 h. The reaction mass was cooled to 0° C.; filtered and washed with ethanol. The filtrate was concentrated under reduced pressure to afford 3.6 g (94%) of the product as pale yellow oil which on standing converted to cream solid.

Step D
Raney nickel (500 mg) was added to a solution of the product of step C (3.6 g, 14.34 mmol) in ethanol (60 mL), containing catalytic methanolic ammonia and hydrogenated at 85 psi for 20 h in Parr apparatus. The reaction mass was filtered though celite and washed with ethanol. The filtrate was concentrated under reduced pressure to afford 2.7 g (79.5%) of the product as pale brown solid.

Step E
A solution of the product of step D (2.6 g, 10.97 mmol) in tetrahydrofuran (15 mL) was added to a suspension of lithium aluminium hydride (832 mg, 21.94 mmol) in tetrahydrofuran (30 mL) at 0° C. The reaction mass was stirred at 15-20° C. for 1 h. The reaction mass was recooled to 0° C., quenched with saturated sodium sulfate solution and filtered. The filtrate was washed with brine, dried over anhydrous sodium sulfate solution and concentrated in vacuum to afford crude. Triturating with petroleum ether afforded 1.5 g (58%) of the product as yellow solid.

Step F
Triethyl amine (1.42 mL, 10.2 mmol) and di-t-butyldicarbonate (1.4 mL, 6.12 mmol) were added successively to a solution of the product of step F (1.0 g, 5.10 mmol) in dichloromethane at room temperature and stirred for 3 h. The reaction mass was poured into water and extracted with dichloromethane (2×30 mL). The combined organic layer was washed successively with water, brine, dried over anhydrous sodium sulfate and concentrated in vacuum to afford crude compound. Purification by triturating with petroleum ether afforded 750 mg (50%) of the product as yellow solid.

Step G
10.0 g of the product of step F was purified by chiral preparative HPLC using the following conditions: Column: Chiralpak IA (19×250 mm) 10μ; Mobile Phase: Hexane: Ethyl acetate; 92:8; Flow rate: 16 mL/min; UV: 227 nm. The resulting ML's from Chiral preparative HPLC was concentrated in vacuum to afford 3.1 g (31%) of the enantiomer as off white solid.

Variant 3

Separation of example 12 by chiral HPLC, column: Nucleocel Alpha RP-S, 250*21 mm (5 μm), eluent: 50/50 acetonitrile/water 50/50, flow 10 mL/min, first eluting enantiomer rt: 11.6 min (99.15) %.

Example 15

1-(1H-benzo[d]imidazol-5-yl)-5-(4-butoxyphenyl)imidazolidin-2-one

The compound was synthesized as trifluoroacetate salt starting from 5-aminobenzimidazole (0.585 g, 4.4 mmol), 4-butoxybenzaldehyde (0.691 mL, 4 mmol), TMSCN (0.5 mL, 4 mmol), PdC (10%, 0.02 g), TEA (1.03 mL, 7.4 mmol), di-(imidazol-1-yl)methanone (0.658, 4.06 mmol) as described in method 2. The product was purified by means of preparative HPLC.

Yield: 0.08 g (4.3%); MS m/z 351.3 (M+H)$^+$; $^1$H NMR (DMSO, 400 MHz): δ 0.84-0.88 (m, 3H); 1.30-1.40 (m, 2H); 1.56-1.63 (m, 2H); 3.06-3.09 (m, H); 3.80-3.86 (m, 3H); 5.47-5.50 (m, H); 6.82 (d, 2H, J=8.7 Hz); 7.15 (s, H); 7.22 (d, 2H, J=8.7 Hz); 7.51 (d, H, J=9.1 Hz); 7.59 (d, H, J=9.1 Hz); 7.82 (s, H); 9.15 (s, H), HPLC (λ=214 nm, [B]: rt 10.72 min (99%).

Example 16

1-(1H-benzo[d]imidazol-5-yl)-5-(4-(pentyloxy)phenyl)imidazolidin-2-one

The compound was synthesized as trifluoroacetate salt starting from 5-aminobenzimidazole (0.585 g, 4.4 mmol), 4-pentoxybenzaldehyde (0.755 mL, 4 mmol), TMSCN (0.5 mL, 4 mmol), PdC (10%, 0.02 g), TEA (1.05 mL, 7.4 mmol), di-(imidazol-1-yl)methanone (0.667 g, 4.12 mmol) as described in method 2. The product was purified by means of preparative HPLC.

Yield: 0.198 g (13.6%); MS m/z 365.4 (M+H)$^+$; $^1$H NMR (DMSO, 400 MHz): δ 0.80-0.83 (m, 3H); 1.21-1.34 (m, 4H); 1.57-1.64 (m, 2H); 3.03-3.07 (m, H); 3.75-3.79 (m, H); 3.81-3.83 (m, 2H); 5.37-5.41 (m, H); 6.78-6.80 (d, 2H, J=8.7 Hz); 6.86 (s, H); 7.20-7.22 (d, 2H, J=8.7 Hz); 7.28-7.35 (m, 2H); 7.49 (s, H); 8.04 (s, H); 12.18 (bs, H), HPLC (λ=214 nm, [B]: rt 12.64 min (98.2%).

Example 17

1-(1H-benzo[d]imidazol-5-yl)-5-(4-isopropoxyphenyl)imidazolidin-2-one

The compound was synthesized as trifluoroacetate salt starting from 5-aminobenzimidazole (0.585 g, 4.4 mmol), 4-isopropoxybenzaldehyde (0.657 g, 4 mmol), TMSCN (0.5 mL, 4 mmol), PdC (10%, 0.02 g), TEA (0.889 mL, 6.38 mmol), di-(imidazol-1-yl)methanone (0.564, 3.48 mmol) as described in method 2. The product was purified by means of preparative HPLC.

Yield: 0.084 g (4.7%); MS m/z 337.4 (M+H)$^+$; $^1$H NMR (DMSO, 400 MHz): δ 1.18-1.20 (m, 6H); 3.08-3.12 (m, H); 3.82-3.87 (m, H); 4.47-4.53 (m, H); 5.48-5.52 (m, H); 6.82-6.84 (d, 2H, J=8.7 Hz); 7.17 (s, H); 7.23-7.25 (d, 2H, J=8.7 Hz); 7.53-7.55 (dd, H, $^3$J=9.1 Hz, $^4$J=2.1 Hz); 7.61-7.63 (d, H, $^3$J=9.1 Hz); 7.85 (d, H, $^4$J=2.1 Hz); 9.17 (s, H), HPLC (λ=214 nm, [B]: rt 10.11 min (100%).

Example 18

1-(1H-benzo[d]imidazol-5-yl)-5-(4-methoxybenzo[d][1,3]dioxol-6-yl)imidazolidin-2-one The compound was synthesized as trifluoroacetate salt starting from 5-aminobenzimidazole (0.585 g, 4.4 mmol), 7-methoxybenzo[d][1,3]dioxole-5-carbaldehyde (0.721 g, 4 mmol), TMSCN (0.5 mL, 4 mmol), PdC (10%, 0.02 g), TEA (0.521 mL, 3.74 mmol), di-(imidazol-1-yl)methanone (0.331 g, 2.04 mmol) as described in method 2. The product was purified by means of preparative HPLC.

Yield: 0.022 g (1.2%); MS m/z 353.5 (M+H)$^+$; $^1$H NMR (DMSO, 400 MHz): δ 3.09-3.12 (m, H); 3.74 (s, 3H); 3.78-3.83 (m, H); 5.43-5.47 (m, H); 5.87-5.89 (m, 2H); 6.51 (s, H); 6.66 (s, H); 7.17 (s, H); 7.52-7.55 (dd, H, $^3$J=8.7 Hz, $^4$J=1.7 Hz); 7.61-7.63 (d, H, J=8.7 Hz); 7.82 (d, H, $^4$J=1.7 Hz); 9.18 (s, H), HPLC (λ=214 nm, [B]: rt 7.55 min (99.1%).

Example 19

1-(1H-benzo[d]imidazol-5-yl)-5-(2,3-dihydrobenzo[b][1,4]dioxin-6-yl)imidazolidin-2-one The compound was synthesized as hydrochloride salt starting from 5-aminobenzimidazole (0.37 g, 2.78 mmol), di(1H-imidazol-1-yl)methanone (0.496 g, 3.06 mmol), TEA (1.16 mL, 8.34 mmol), aminomethyl-(2,3-dihydrobenzo[b][1,4]dioxin-6-yl)ketone hydrobromide (0.761 g, 2.78 mmol), TEA (0.775 mL, 5.56 mmol), PdC (10%, 0.02 g) as described in method 1.

Yield: 0.014 g (1.4%); MS m/z 337.1 (M+H)$^+$; $^1$H NMR (CD$_3$OD, 400 MHz): δ 3.92-3.96 (t, H, J=9.1 Hz); 4.10-4.16 (m, 5H); 5.41-5.45 (q, H, J=9.1 Hz); 6.51-6.85 (m, 5H); 7.65 (s, 2H); 7.86 (s, H); 9.18 (s, H), HPLC (λ=214 nm, [B]: rt 7.47 min (100%).

Example 20

5-(4-(1,1,2,2-tetrafluoroethoxy)phenyl)-1-(1H-benzo[d]imidazol-5-yl)imidazolidin-2-one The compound was synthesized starting from 5-aminobenzimidazole (0.585 g, 4.4 mmol), 4-(1,1,2,2-tetrafluoroethoxy)benzaldehyde (0.888 g, 4 mmol), TMSCN (0.5 mL, 4 mmol), PdC (10%, 0.02 g), TEA (0.978 mL, 7.0 mmol), di-(imidazol-1-yl)methanone (0.621 g, 3.83 mmol) as described in method 2. The product was purified by means of FPLC.

Yield: 0.265 g (16.8%); MS m/z 395.3 (M+H)$^+$; $^1$H NMR (DMSO, 400 MHz): δ 3.05-3.09 (m, H); 3.25 (s, H); 3.80-3.85 (m, H); 5.52-5.56 (m, H); 6.70-6.72 (m, H); 6.94 (bs, H); 7.17-7.19 (m, 2H); 7.37 (bs, H); 7.41-7.43 (m, 2H); 7.54 (bs, H); 8.05 (s, H); 12.19 (bs, H), HPLC (λ=214 nm, [B]: rt 7.55 min (93.9%).

Example 21

1-(1H-benzo[d]imidazol-5-yl)-5-(2,2-difluorobenzo[d][1,3]-dioxol-5-yl)imidazolidin-2-one The compound was synthesized starting from 5-aminobenzimidazole (0.585 g, 4.4 mmol), 2,2-difluorobenzo[d][1,3]dioxole-5-carbaldehyde (0.744 g, 4 mmol), TMSCN (0.5 mL, 4 mmol), PdC (10%, 0.02 g), TEA (0.81 mL, 5.81 mmol), di-(imidazol-1-yl)methanone (0.514 g, 3.17 mmol) as described in method 2. The product was purified by means of FPLC.

Yield: 0.138 g (9.6%); MS m/z 359.4 (M+H)$^+$; $^1$H NMR (DMSO, 400 MHz): δ 3.10-3.14 (m, H); 3.81-3.85 (m, H); 5.55-5.58 (m, H); 6.99 (s, H); 7.19-7.21 (dd, H, $^3$J=8.3 Hz, $^4$J=2.1 Hz); 7.24-7.26 (dd, H, $^3$J=8.7 Hz, $^4$J=1.7 Hz); 7.30-

7.32 (d, H, $^3$J=8.3 Hz); 7.41-7.43 (m, 2H); 7.56-7.57 (d, H, $^4$J=1.7 Hz); 8.14 (s, H), HPLC (λ=214 nm, [B]: rt 10.25 min (93.1%).

Example 22

1-(1H-benzo[d]imidazol-5-yl)-5-(3-fluoro-4-methoxyphenyl)imidazolidin-2-one

The compound was synthesized starting from 5-aminobenzimidazole (0.585 g, 4.4 mmol), 3-fluoro-4-methoxybenzaldehyde (0.617 g, 4 mmol), TMSCN (0.5 mL, 4 mmol), PdC (10%, 0.02 g), TEA (0.524 mL, 3.76 mmol), di-(imidazol-1-yl)methanone (0.333 g, 2.05 mmol) as described in method 2. The product was purified by means of FPLC.

Yield: 0.04 g (3.1%); MS m/z: 327.5 (M+H)$^+$; $^1$H NMR (DMSO, 400 MHz): δ 3.08-3.12 (m, H); 3.74 (s, 3H); 3.78-3.82 (m, H); 5.43-5.47 (m, H); 6.93 (s, H); 7.04-7.12 (m, 2H); 7.17-7.25 (m, 2H); 7.39-7.41 (m, H); 7.52 (s, H); 8.08 (s, H); 12.22 (bs, H), HPLC (λ=214 nm, [B]: rt 8.54 min (95%).

Example 23

1-(1H-benzo[d]imidazol-5-yl)-5-(2,6-difluoro-4-methoxyphenyl)imidazolidin-2-one

The compound was synthesized starting from 5-aminobenzimidazole (0.585 g, 4.4 mmol), 2,6-difluoro-4-methoxybenzaldehyde (0.688 mL, 4 mmol), TMSCN (0.5 mL, 4 mmol), PdC (10%, 0.02 g), TEA (1.2 mL, 8.6 mmol), di-(imidazol-1-yl)methanone (0.761 g, 4.69 mmol) as described in method 2. The product was purified by means of FPLC.

Yield: 0.113 g (8.2%); MS m/z: 345.3 (M+H)$^+$; $^1$H NMR (DMSO, 400 MHz): δ 3.31-3.35 (m, H); 3.65 (s, 3H); 3.82-3.86 (m, H); 5.74-5.78 (m, H); 6.60 (s, H); 6.63 (s, H); 6.97 (s, H); 7.07 (bs, H); 7.44 (s, 2H); 8.06 (s, H); 12.24 (bs, H), HPLC (λ=214 nm, [B]: rt 8.99 min (93.6%).

Example 24

5-(4-(2-morpholinoethoxy)phenyl)-1-(1H-benzo[d]imidazol-6-yl)imidazolidin-2-one

The compound was synthesized as ditrifluoroacetate salt starting from 5-aminobenzimidazole (0.585 g, 4.4 mmol), 4-(2-morpholinoethoxy)benzaldehyde (0.941 g, 4 mmol), TMSCN (0.5 mL, 4 mmol), PdC (10%, 0.02 g), TEA (1.34 mL, 9.6 mmol), di-(imidazol-1-yl)methanone (0.582 g, 3.6 mmol) as described in method 2. The product was purified by means of preparative HPLC.

Yield: 0.015 g (0.6%); MS m/z: 408.5 (M+H)$^+$; $^1$H NMR (CD$_3$OD, 400 MHz): δ 3.33-3.44 (m, 4H); 3.55-3.58 (m, 2H); 3.79-4.00 (m, 6H); 4.29-4.31 (m, 2H); 5.51-5.55 (m, H); 6.95 (d, 2H, J=8.7 Hz); 7.35 (d, 2H, J=8.7 Hz); 7.58-7.60 (m, 2H); 7.90 (s, H); 9.13 (s, H) HPLC (λ=214 nm, [B]: rt 6.05 min (90.5%).

Example 25

5-(4-(3-morpholinopropoxy)phenyl)-1-(1H-benzo[d]imidazol-5-yl)imidazolidin-2-one The compound was synthesized starting from 5-aminobenzimidazole (1.9 g, 14.45 mmol), 4-(3-morpholinopropoxy)phenyl carbaldehyde (3 g, 12.05 mmol), TMSCN (1.25 g, 12.05 mmol), PdC (10%, 0.40 g), TEA (2.8 mL, 20.25 mmol), di-(imidazol-1-yl)methanone (1.6 g, 10.13 mmol) as described in method 2. The product was purified by means of preparative HPLC.

Yield: 0.03 g (5.79%); MS m/z: 422.3 (M+H)$^+$; $^1$H NMR (400 MHz, CD$_3$OD): δ 8.05 (s, 1H), 7.47 (d, 1H), 7.44 (d, 1H), 7.29-7.22 (m, 3H), 6.83 (d, 2H), 5.38 (t, 1H), 3.97-3.91 (m. 3H), 3.66 (m, 3H), 3.35 (merged with solvent, 2H), 2.52-2.46 (m, 6H), 1.95-1.88 (m, 2H), HPLC (λ=214 nm, [A]: rt 5.00 min (100%).

Example 26

5-(2-(2-morpholinoethoxy)phenyl)-1-(1H-benzo[d]imidazol-5-yl)imidazolidin-2-one

The compound was synthesized starting from 5-aminobenzimidazole (679 mg, 5.11 mmol), 2-(2-morpholinoethoxy)phenyl carbaldehyde (1 g, 4.26 mmol), TMSCN (0.6 mL, 4.26 mmol), PdC (10%, 250 mg), TEA (1.3 mL, 7.80 mmol), di-(imidazol-1-yl)methanone (220 mg, 1.31 mmol) as described in method 2.

Yield: 40 mg (7.5%); MS m/z 408.4 (M+H)$^+$; $^1$H-NMR (400 MHz, DMSO-d$_6$): δ 12.12 (br s, H); 8.07 (s, H); 7.65 (s, H); 7.42 (s, H); 7.36 (s, H); 7.21-7.17 (m, 2H); 7.06-7.04 (m, 2H); 6.94-6.89 (m, H); 6.83-6.79 (m, H); 5.68 (br s, H); 4.19-4.16 (m, 2H); 3.90-3.86 (m, H); 3.60 (s, 4H); 3.09-3.06 (m, H); 2.78-2.73 (m, 2H), HPLC (λ=214 nm, [A]: rt 5.65 min (100%)

Example 27

1-(1H-benzo[d]imidazol-5-yl)-5-(4-fluorophenyl)imidazolidin-2-one

The compound was synthesized as hydrochloride salt starting from 5-aminobenzimidazole (0.665 g, 5 mmol), di(1H-imidazol-1-yl)methanone (0.891 g, 5.5 mmol), TEA (2.09 mL, 15 mmol), aminomethyl-(4-fluorophenyl)ketone hydrochloride (0.948 g, 5 mmol), TEA (1.39 mL, 10 mmol), PdC (10%, 0.02 g) as described in method 1.

Yield: 0.02 g (1.2%); MS m/z: 297.3 (M+H)$^+$; $^1$H NMR (DMSO, 400 MHz): δ 3.07-3.11 (m, H); 3.84-3.88 (m, H); 5.59-5.62 (m, H); 7.12-7.15 (m, 2H); 7.26 (bs, H); 7.35-7.39 (m, 2H); 7.54 (dd, H, $^3$J=9.2 Hz $^4$J=1.8 Hz); 7.63 (d, H, $^3$J=9.2 Hz); 7.89 (d, H, $^4$J=1.8 Hz); 9.35 (s, H), HPLC (λ=214 nm, [B]: rt 7.81 min (97%).

Example 28

1-(1H-benzo[d]imidazol-5-yl)-5-(2-fluorophenyl)imidazolidin-2-one

The compound was synthesized starting from 5-aminobenzimidazole (0.585 g, 4.4 mmol), 2-fluorobenzaldehyde (0.496 g, 4 mmol), TMSCN (0.5 mL, 4 mmol), PdC (10%, 0.02 g), TEA (1.04 mL, 7.5 mmol), di-(imidazol-1-yl)methanone (0.662, 4.08 mmol) as described in method 2.

Yield: 0.155 g (13.1%); MS m/z 365.1 (M+H)$^+$; $^1$H NMR (DMSO, 400 MHz): δ 3.16-3.19 (m, H); 3.88-3.93 (m, H); 5.73-5.76 (m, H); 7.00 (s, H); 7.08-7.20 (m, 2H); 7.24-7.32 (m, 3H); 7.40 (s, H); 7.56 (s, H); 8.08 (s, H); 12.20 (bs, H), HPLC (λ=214 nm, [B]: rt 7.23 min (93%).

Example 29

1-(1H-benzo[d]imidazol-5-yl)-5-(3-fluorophenyl)imidazolidin-2-one

The compound was synthesized as trifluoroacetate salt starting from 5-aminobenzimidazole (0.585 g, 4.4 mmol), 3-fluorobenzaldehyde (0.496 g, 4 mmol), TMSCN (0.5 mL, 4 mmol), PdC (10%, 0.02 g), TEA (0.979 mL, 7.02 mmol), di-(imidazol-1-yl)methanone (0.621, 3.83 mmol) as described in method 2.

Yield: 0.023 g (1.5%); MS m/z 297.4 (M+H)$^+$; $^1$H NMR (DMSO, 400 MHz): δ 3.10-3.13 (m, H); 3.85-3.89 (m, H); 5.59-5.63 (m, H); 7.02-7.07 (m, H); 7.15-7.17 (m, 2H); 7.24 (s, H); 7.31-7.36 (m, H); 7.52-7.55 (dd, H, $^3$J=8.7 Hz, $^4$J=1.7 Hz); 7.61-7.63 (d, H, $^3$J=8.7 Hz); 7.85 (d, H, $^4$J=1.7 Hz); 9.18 (s, H), HPLC (λ=214 nm, [B]: rt 8.25 min (100%).

Example 30

1-(1H-benzo[d]imidazol-5-yl)-5-(2,6-difluorophenyl)imidazolidin-2-one

The compound was synthesized as trifluoroacetate salt starting from 5-aminobenzimidazole (0.585 g, 4.4 mmol), 2,6-difluorobenzaldehyde (0.431 mL, 4 mmol), TMSCN (0.5 mL, 4 mmol), PdC (10%, 0.02 g), TEA (1.15 mL, 8.22 mmol), di-(imidazol-1-yl)methanone (0.730, 4.5 mmol) as described in method 2.

Yield: 0.06 g (3.9%); MS m/z 315.2 (M+H)$^+$; $^1$H NMR (DMSO, 400 MHz): δ 3.38-3.42 (m, H); 3.93-3.98 (m, H); 5.97-6.01 (m, H); 7.02-7.06 (m, 2H); 7.30-7.37 (m, 2H); 7.47-7.50 (dd, H, $^3$J=8.7 Hz, $^4$J=1.7 Hz); 7.64-7.66 (d, H, $^3$J=8.7 Hz); 7.78 (d, H, $^4$J=1.7 Hz); 9.16 (s, H), HPLC (λ=214 nm, [A]: rt 8.24 min (97.3%).

Example 31

1-(1H-benzo[d]imidazol-5-yl)-5-(3,4-difluorophenyl)imidazolidin-2-one

The compound was synthesized as hydrochloride salt starting from 5-aminobenzimidazole (0.585 g, 4.4 mmol), di(1H-imidazol-1-yl)methanone (0.713 g, 4.4 mmol), TEA (1.84 mL, 13.2 mmol), aminomethyl-(3,4-difluorophenyl)ketone hydrochloride (0.911 g, 4.4 mmol), TEA (1.23 mL, 8.8 mmol), PdC (10%, 0.02 g) as described in method 1.

Yield: 0.048 g (3.1%); MS m/z 315.2 (M+H)$^+$; $^1$H NMR (DMSO, 400 MHz): δ 3.10-3.14 (m, H); 3.83-3.87 (m, H); 5.57-5.61 (m, H); 7.16-7.18 (m, H); 7.23 (s, H); 7.32-7.45 (m, 2H); 7.49 (dd, H, $^3$J=8.7 Hz, $^4$J=1.7 Hz); 7.61 (d, H, J=8.7 Hz); 7.82 (d, H, $^4$J=1.7 Hz); 9.14 (s, H), HPLC (λ=214 nm, [B]: rt 7.89 min (96%).

Example 32

1-(1H-benzo[d]imidazol-5-yl)-5-(2-fluoro-5-(trifluoromethyl)phenyl)imidazolidin-2-one The compound was synthesized from 2-fluoro-5-(trifluoromethyl)benzaldehyde (0.565 mL, 4 mmol), 5-aminobenzimidazole (0.585 g, 4.4 mmol), TMSCN (0.5 g, 4 mmol), TEA (0.669 mL, 4.8 mmol), PdC (10%, 0.02 g), di(1H-imidazol-1-yl)methanone (0.778 g, 4.8 mmol) as described in method 2.

Yield: 0.195 g (13.4%); MS m/z 365.2 (M+H)$^+$; $^1$H NMR (DMSO, 400 MHz): δ 3.24-3.28 (m, H); 3.90-3.96 (m, H); 5.83-5.87 (m, H); 7.05-7.17 (m, H); 7.33-7.39 (m, H); 7.41-7.48 (m, 2H); 7.53-7.60 (m, H); 7.63-7.70 (m, 2H); 8.08-8.10 (d, H, J=9.1 Hz); 12.25-12.31 (m, H), HPLC (λ=214 nm, [B]: rt 9.01 min (100%).

Example 33

1-(1H-benzo[d]imidazol-5-yl)-5-(3-fluoro-5-(trifluoromethyl)phenyl)imidazolidin-2-one The compound was synthesized starting from 5-aminobenzimidazole (0.585 g, 4.4 mmol), 3-fluoro-5-(trifluoromethyl)benzaldehyde (0.768 g, 4 mmol), TMSCN (0.5 mL, 4 mmol), PdC (10%, 0.02 g), TEA (0.558 mL, 4 mmol), di-(imidazol-1-yl)methanone (0.648, 4 mmol) as described in method 2.

Yield: 0.143 g (9.8%); MS m/z 365.2 (M+H)$^+$; $^1$H NMR (DMSO, 400 MHz): δ 3.14-3.18 (m, H); 3.85-3.90 (m, H); 5.68-5.72 (m, H); 7.05 (s, H); 7.26 (bs, H); 7.42-7.43 (m, H); 7.51-7.60 (m, 4H); 8.09 (s, H); 12.27 (bs, H), HPLC (λ=214 nm, [B]: rt 9.57 min (95%).

Example 34

1-(1H-benzo[d]imidazol-5-yl)-5-(2-fluoro-4-(trifluoromethyl)phenyl)imidazolidin-2-one The compound was synthesized starting from 5-aminobenzimidazole (0.457 g, 3.44 mmol), 2-fluoro-4-(trifluoromethyl)benzaldehyde (0.600 g, 3.13 mmol), TMSCN (0.39 mL, 3.13 mmol), PdC (10%, 0.02 g), TEA (0.455 mL, 3.26 mmol), di-(imidazol-1-yl)methanone (0.529, 3.26 mmol) as described in method 2.

Yield: 0.100 g (8.8%); MS m/z 365.2 (M+H)$^+$; $^1$H NMR (DMSO, 400 MHz): δ 3.18-3.22 (m, H); 3.89-3.94 (m, H); 5.83-5.87 (m, H); 7.07 (s, H); 7.22-7.24 (m, H); 7.27-7.31 (m, H); 7.39-7.41 (m, H); 7.57 (d, H, $^4$J=2.1 Hz); 7.60-7.64 (m, 2H); 8.07 (s, H); 12.31 (bs, H), HPLC (λ=214 nm, [B]: rt 9.36 min (93%).

Example 35

1-(1H-benzo[d]imidazol-5-yl)-5-(3-fluoro-4-(trifluoromethyl)phenyl)imidazolidin-2-one The compound was synthesized starting from 5-aminobenzimidazole (0.585 g, 4.4 mmol), 3-fluoro-4-(trifluoromethyl)benzaldehyde (0.768 g, 4 mmol), TMSCN (0.5 mL, 4 mmol), PdC (10%, 0.02 g), TEA (0.585 mL, 4.2 mmol), di-(imidazol-1-yl)methanone (0.681, 4.2 mmol) as described in method 2.

Yield: 0.123 g (8.4%); MS m/z 365.1 (M+H)$^+$; $^1$H NMR (DMSO, 400 MHz): δ 3.09-3.13 (m, H); 3.83-3.87 (m, H); 5.63-5.67 (m, H); 7.03 (bs, H); 7.20 (bs, H); 7.36 (d, H, J=7.9 Hz); 7.39 (bs, H); 7.47-7.49 (m, H); 7.56 (bs, H); 7.70 (t, H, J=7.9 Hz); 8.06 (s, H); 12.22 (bs, H), HPLC (λ=214 nm, [B]: rt 9.68 min (91%).

Example 36

1-(1H-benzo[d]imidazol-5-yl)-5-(2-chlorophenyl)imidazolidin-2-one

The compound was synthesized starting from 5-aminobenzimidazole (0.585 g, 4.4 mmol), 2-chloro benzaldehyde (0.448 mL, 4 mmol), TMSCN (0.5 mL, 4 mmol), PdC (10%, 0.02 g), TEA (1.15 mL, 8.25 mmol), di-(imidazol-1-yl)methanone (0.700 g, 4.32 mmol) as described in method 2.

Yield: 0.100 g (8%); MS m/z 313.3 (M+H)$^+$; $^1$H NMR (DMSO, 400 MHz): δ 3.06-3.1 (m, H); 3.94-3.99 (m, H); 5.78-5.81 (m, H); 7.04 (s, H); 7.22-7.29 (m, 4H); 7.41-7.48 (m, 2H); 7.55 (s, H); 8.08 (s, H); 12.29 (bs, H), HPLC (λ=214 nm, [B]: rt 9.16 min (97%).

Example 37

1-(1H-benzo[d]imidazol-5-yl)-5-(3-chlorophenyl)imidazolidin-2-one

The compound was synthesized as trifluoroacetate salt starting from 5-aminobenzimidazole (0.293 g, 2.2 mmol), 3-chloro benzaldehyde (0.227 mL, 2 mmol), TMSCN (0.25 mL, 2 mmol), PdC (10%, 0.01 g), TEA (0.613 mL, 4.4 mmol), di-(imidazol-1-yl)methanone (0.389 g, 2.4 mmol) as described in method 2. The product was purified by means of preparative HPLC.

Yield: 0.049 g (5.7%); MS m/z 313.3 (M+H)$^+$; $^1$H NMR (DMSO, 400 MHz): δ 3.11-3.15 (m, H); 3.87-3-91 (m, H); 5.61-5.65 (m, H); 7.26 (s, H); 7.29-7.37 (m, 3H); 7.42 (s, H); 7.53-7.56 (dd, H, $^3$J=7.1 Hz $^4$J=2.1 Hz); 7.63-7.65 (d, H, J=8.7 Hz); 7.86-7.87 (d, H, $^4$J=2.1 Hz); 9.16 (s, H), HPLC (λ=214 nm, [B]: rt 9.35 min (92%).

Example 38

1-(1H-benzo[d]imidazol-5-yl)-5-(2,6-dichlorophenyl)imidazolidin-2-one

The compound was synthesized as trifluoroacetate salt starting from 5-aminobenzimidazole (0.585 g, 4.4 mmol), 2,6-dichloro-benzaldehyde (0.7 g, 4 mmol), TMSCN (0.5 mL, 4 mmol), PdC (10%, 0.02 g), TEA (0.4 mL, 2.8 mmol), di-(imidazol-1-yl)methanone (0.253 g, 1.56 mmol) as described in method 2. The product was purified by means of preparative HPLC.

Yield: 0.03 g (1.6%); MS m/z 347.1 (M+H)$^+$; $^1$H NMR (DMSO, 400 MHz): δ 3.40-3.44 (m, H); 3.90-3.95 (m, H); 6.34-6.38 (m, H); 7.25-7.29 (m, H); 7.33-7.35 (m, H); 7.40-7.43 (m, 2H); 7.48-7.50 (m, H); 7.63-7.65 (m, H); 7.71 (m, H); 9.15 (s, H), HPLC (λ=214 nm, [B]: rt 8.29 min (93.6%).

Example 39

1-(1H-benzo[d]imidazol-5-yl)-5-(2,3-dichlorophenyl)imidazolidin-2-one

The compound was synthesized starting from 5-aminobenzimidazole (0.585 g, 4.4 mmol), 2,3-dichloro-benzaldehyde (0.700 g, 4 mmol), TMSCN (0.5 mL, 4 mmol), PdC (10%, 0.02 g), TEA (0.5 mL, 3.6 mmol), di-(imidazol-1-yl)methanone (0.308, 1.9 mmol) as described in method 2. Yield: 0.014 g (1%); MS m/z 347.2 (M+H)$^+$; $^1$H NMR (DMSO, 400 MHz): δ 3.08-3.11 (m, H); 3.96-4.01 (m, H); 5.83-5.86 (m, H); 7.09 (s, H); 7.24-7.30 (m, 3H); 7.44 (s, H); 7.52-7.56 (m, 2H); 8.08 (s, H); 12.23 (bs, H), HPLC (λ=214 nm, [B]: rt 9.28 min (94.1%).

Example 40

1-(1H-benzo[d]imidazol-5-yl)-5-(3,4-dichlorophenyl)imidazolidin-2-one

The compound was synthesized as hydrochloride salt starting from 5-aminobenzimidazole (1.18 g, 8.87 mmol), di(1H-imidazol-1-yl)methanone (1.58 g, 9.76 mmol), TEA (3.71, 26.61 mmol), aminomethyl-(3,4-dichlorophenyl)ketone hydrobromide (2.528 g, 8.87 mmol), TEA (2.47 mL, 17.72 mmol), PdC (10%, 0.02 g) as described in method 1.

Yield: 0.054 g (1.6%); MS m/z 347.1 (M+H)$^+$; $^1$H NMR (DMSO, 400 MHz): δ 3.10-3.14 (m, H); 3.84-3.88 (m, H); 5.60-5.64 (m, H); 7.27 (s, H); 7.30 (dd, H, $^3$J=8.3 Hz $^4$J=2.1 Hz); 7.50-7.57 (m, 2H); 7.61-7.64 (m, 2H); 7.85 (s, H); 9.18 (s, H), HPLC (λ=214 nm, [B]: rt 9.79 min (100%).

Example 41

(S)-1-(1H-benzo[d]imidazol-5-yl)-5-(3,4-dichlorophenyl)imidazolidin-2-one

Variant 1

The compound was synthesized from according to method 3.

Step A 2.5M n-Butyl lithium (68.5 mL, 171.42 mmol), triphenylphosphonium methyl bromide (61.2, 171.42 mmol), 3,4-dichloro benzaldehyde (15 g, 85.7 mmol) yield: 10 g (66%)

Step B 1,3 dichloro-5,5-dimethylimidazolidine-2,-dione (14.7 g, 75.0 mmol), t-butyl hypochlorite (15 g, 138.70 mmol), t-butylcarbamate (16.23 g, 138.72 mmol), product of step A (8 g, 46.24 mmol), (DHQ)$_2$PHAL (1.44 g; 1.85 mmol) potassium osmate dihydrate (680 mg, 1.85 mmol), yield: 5 g (35.4%)

Step C

Triethylamine (4.5 mL, 32.67 mmol), p-toluene sulfonyl chloride (3.11 g, 16.33 mmol) product of step B (5 g, 16.33 mmol), in dichloromethane (100 mL). Purification by flash column chromatography over silica gel using 20% ethyl acetate in petroleum ether, yield: 5.6 g (75%).

Step D

Sodium azide (1.5 g, 23.41 mmol) product of step C (5.5 g, 11.95 mmol); yield: 4.0 g (79%)

Step E

Product of step D (2.2 g, 6.65 mmol), zinc dust (1.3 g, 19.96 mmol) yield 3.3 g (89%), para-anisaldehyde (0.78 mL, 6.49 mmol), sodium borohydride (870 mg, 23.6 mmol), yield: 1.88 g (75%)

Step F product of step E (1.8 g, 4.235 mmol), yield 1.1 g (80%) N,N-carbonyl-di-imidazole (300 mg, 1.84 mmol), triethylamine (0.64 mL, 4.615 mmol) yield: 400 mg (74%)

Step G

Product of step F (400 mg, 1.14 mmol), 1,2-diamino 4-bromo benzene (213 mg, 1.14 mmol), cesium fluoride (347 mg, 2.28 mmol), copper iodide (21 mg, 0.11 mmol), 1,2-diaminocyclohexane (13 mg, 0.11 mmol), yield: 400 mg (76%).

Step H

Product of step G (350 mg, 0.738 mmol)

The product was then converted into the HCl-salt

Trifluoroacetic acid (10 mL) was added stirred for 15 h at room temperature. Excess Trifluoroacetic acid was removed in vacuum and the crude compound was extracted with ethyl acetate. The combined organic layer was washed with 10% sodium carbonate, water, brine solution and dried over anhydrous sodium sulphate. The solvent was evaporated under vacuum. Purification by column chromatography over silica gel (100-200 mesh) using gradient 5% methanol in chloroform as eluent afforded 200 mg (76%) product.

1M HCl in ether (0.56 mL) was added to the above product dissolved in acetone (10 mL) at 5° C. and stirred 30 min at room temperature. The reaction mixture was concentrated under reduced pressure, washed with n-pentane and dried in vacuum. Yield: 110 mg (83%), MS m/z 347.1 (M+H)$^+$; $^1$H-NMR (400 MHz, DMSO-d6): δ 9.25 (s, 1H); 7.93 (s, 1H);

7.71-7.66 (m, 2H); 7.58 (d, 1H); 7.48 (d, 1H); 7.35 (dd, 1H); 5.63 (q, 1H); 4.03 (t, 1H); 3.33 (t, 1H, HPLC (λ=214 nm, [A]: rt 10.56 min (97.7%).

Example 42

1-(1H-1,3-benzodiazol-5-yl)-5-(4-biphenyl)imidazolidin-2-one

The compound was synthesized as hydrochloride salt starting from 5-aminobenzimidazole (0.522 g, 3.92 mmol), di(1H-imidazol-1-yl)methanone (0.699 g, 4.31 mmol), TEA (1.64 mL, 11.76 mmol), aminomethyl-(4-biphenyl)ketone hydrobromide (1.14 g, 3.92 mmol), TEA (1.09 mL, 7.8 mmol), PdC (10%, 0.02 g) as described in method 1.

Yield: 0.033 g (2.2%); MS m/z 355.3 (M+H)$^+$; $^1$H NMR (DMSO, 400 MHz): δ 3.15-3.19 (m, H); 3.87-3.96 (m, H); 5.63-5.68 (m, H); 7.22 (s, H); 7.31-7.45 (m, 3H); 7.57-7.62 (m, 7H); 7.88 (s, H); 9.07 (s, H), HPLC (λ=214 nm, [B]: rt 10.96 min (94.1%).

Example 43

(S)-1-(1H-1,3-benzodiazol-5-yl)-5-(4-biphenyl)imidazolidin-2-one

Variant 1

The compound was synthesized according to method 3.
Step A
2.5M n-Butyl lithium (44 mL, 109.89 mmol), triphenylphosphonium methyl bromide (39.23 g, 109.89 mmol) 4-phenyl benzaldehyde (10.0 g, 54.94 mmol) yield: 9.0 g (91%)
Step B
1,3 Dichloro-5,5-dimethylimidazolidine-2,-dione (14.7 g, 75.0 mmol), t-butylcarbamate (17.5 g, 150 mmol), product of step A (9.0 g, 50.0 mmol), (DHQ)$_2$PHAL (970 mg; 1.25 mmol) potassium osmate dihydrate (736 mg, 2.0 mmol), yield: 6.6 g (42.3%)
Step C
Triethylamine (6.2 mL, 44.72 mmol), p-Toluene sulfonyl chloride (6.6 g, 31.94 mmol) product of step B (10.0 g, 31.94 mmol), in dichloromethane (100 mL). Purification by flash column chromatography over silica gel using 20% ethyl acetate in petroleum ether yield: 7.5 g (50.3%).
Step D
Sodium azide (1.46 g, 22.48 mmol) product of step C (7.0 g, 14.98 mmol); yield: 4.0 g (79%)
Step E
Product of step D (4.0 g, 11.83 mmol) 10% PdC (400 mg), yield 3.3 g (89%) Para-Anisaldehyde (1.3 g, 9.61 mmol), sodium borohydride (711 mg, 19.23 mmol), yield: 3.1 g (74%)
Step F
product of step E (3.0 g, 6.94 mmol), yield 2.0 g (86.9%) N,N-carbonyl-di-imidazole (1.46 g, 9.03 mmol), triethylamine (2.5 mL) yield: 1.8 g (83.7%)
Step G
Product of step F (1.0 g, 2.79 mmol), 1,2-diamino 4-bromo benzene (522 mg 2.79 mmol), cesium fluoride (849 mg, 5.58 mmol), copper iodide (53 mg), 1,2-diaminocyclohexane (32 mg, 0.28 mmol), yield: 400 mg (30.8%)
Step H
Product of step G (400 mg, 0.86 mmol), yield: 350 mg (85.7%)
The product was then converted into the HCl-salt Trifluoroacetic acid (10 mL) was added stirred for 15 h at room temperature. Excess trifluoroacetic acid was removed in vacuum and the crude compound was extracted with ethyl acetate. The combined organic layer was washed with 10% sodium carbonate, water, brine solution and dried over anhydrous sodium sulphate. The solvent was evaporated under vacuum. Purification by column chromatography over silica gel (100-200 mesh) using gradient 5% methanol in chloroform as eluent afforded 200 mg (76%) product.

1M HCl in ether (0.56 mL) was added to the above product dissolved in acetone (10 mL) at 5° C. and stirred 30 min at room temperature. The reaction mixture was concentrated under reduced pressure, washed with n-pentane and dried in vacuum. Yield: 190 mg (86%). MS m/z 355.4 (M+H)$^+$; $^1$H-NMR (400 MHz, CD$_3$OD): δ 9.23 (s, H); 7.95 (s, H); 7.74-7.66 (br m, 2H); 7.59-7.41 (br m, 6H); 7.39-7.37 (m, 2H); 7.32-7.28 (m, H); 5.67-5.63 (m, H); 4.08-4.04 (m, H); 3.41-3.39 (m, H), HPLC (λ=214 nm, [B]: rt 10.85 min (97.16%).

Variant 2

Separation of example 42 by chiral HPLC, column: Nucleocel Alpha RP-S, 250*21 mm (5 μm), eluent: 50/50 acetonitrile/water 50/50, flow 10 mL/min, first eluting enantiomer rt: 18.5 min (98.35) %.

Example 44

(R)-1-(1H-1,3-benzodiazol-5-yl)-5-(4-biphenyl)imidazolidin-2-one

Separation of example 42 by chiral HPLC, column: Nucleocel Alpha RP-S, 250*21 mm (5 μm), eluent: 50/50 acetonitrile/water 50/50, flow 10 mL/min, First eluting enantiomer rt: 22 min (99.25) %.

Example 45

1-(1H-1,3-benzodiazol-5-yl)-5-(3-fluoro-4-biphenyl)imidazolidin-2-one

The compound was synthesized starting from 5-aminobenzimidazole (0.585 g, 4.4 mmol), 3-fluoro-4-biphenyl carbaldehyde (0.801 g, 4 mmol), TMSCN (0.5 mL, 4 mmol), PdC (10%, 0.02 g), TEA (0.754 mL, 5.4 mmol), di-(imidazol-1-yl)methanone (0.479 g, 2.95 mmol) as described in method 2.

Yield: 0.219 g (14.7%); MS m/z 373.4 (M+H)$^+$; 1H-NMR (400 MHz, DMSO-d6): δ 3.14-3.18 (m, H); 3.86-3.90 (m, H); 5.59-5.63 (m, H); 7.00 (bs, H); 7.23-7.31 (m, 2H); 7.38-7.45 (m, 7H); 7.57 (bs, H); 7.64 (bs, H); 8.09 (s, H); 12.24 (bs, H); HPLC (λ=214 nm, [B]: rt 10.85 min (96.7%).

Example 46

1-(1H-benzo[d]imidazol-5-yl)-5-[4-(3-chlorophenyl)phenyl]imidazolidin-2-one

The compound was synthesized starting from 5-aminobenzimidazole (0.614 mg, 4.62 mmol), 4-(3-chlorophenyl)phenyl]carbaldehyde (1.0 g, 4.68 mmol), TMSCN (0.93 mL, 6.93 mmol), 10% PdC (200 mg), TEA (1.31 mL, 8.76 mmol), di-(imidazol-1-yl)methanone (460 mg, 2.84 mmol) as described in method 2.

Yield: 0.100 g (5.5%); MS m/z 389.2 (M+H)$^+$; 1H NMR (400 MHz, CD$_3$OD): δ 8.06 (s, 1H), 7.55 (m, 4H), 7.47 (m, 4H), 7.33 (m, 3H), 5.53 (t, 1H), 4.01 (t, 1H), 3.4 (t, 2H). HPLC (λ=214 nm, [B]: rt 13.15 min (95.6%).

Example 47

1-(1H-benzo[d]imidazol-5-yl)-5-(3',4'-dichloro-4-biphenyl)imidazolidin-2-one

The compound was synthesized starting from 5-aminobenzimidazole (0.53 g, 3.98 mmol), 4-3',4'-dichloro-4-biphenyl carbaldehyde (1.0 g, 3.98 mmol), TMSCN (0.8 mL, 5.97 mmol), 10% PdC (200 mg), TEA (1.21 mL, 8.76 mmol), di-(imidazol-1-yl)methanone (426 mg, 2.63 mmol) as described in method 2.

Yield: 0.100 g (5.9%); MS m/z 423.2 (M+H)$^+$; 1H-NMR (400 MHz, CD$_3$OD): δ 8.06 (s, H); 7.69 (s, H); 7.57-7.47 (br m, 8H); 7.32-7.30 (m, H); 5.56-5.52 (m, H); 4.03-3.99 (m, H); 3.40-3.36 (m, H); HPLC (λ=214 nm), [A]: rt 14.35 min (98.7%).

Example 48

1-(1H-benzo[d]imidazol-5-yl)-5-(3-phenylphenyl)imidazolidin-2-one

The compound was synthesized starting from 5-aminobenzimidazole (526 mg, 3.95 mmol), biphenyl-3-carbaldehyde (600 mg, 3.29 mmol), TMSCN (654 mg, 6.59 mmol), 10% PdC (100 mg), TEA (1.5 mL, 11 mmol), di-(imidazol-1-yl)methanone (475 mg, 1.03 mmol) as described in method 2.

Yield: 0.110 g (7.13%); MS m/z 355.2 (M+H)$^+$; $^1$H NMR (400 MHz, DMSO): δ 9.10 (bs, 1H), 7.87 (s, 1H), 7.67-7.30 (m, 11H), 7.25 (s, 1H), 5.65 (q, 1H), 3.92 (t, 1H), 3.22-3.15 (m, 1H), HPLC (λ=214 nm, [B]: rt 11.95 min (97.02%).

Example 49

1-(1H-benzo[d]imidazol-5-yl)-5-[3-(3-chlorophenyl)phenyl]imidazolidin-2-one

The compound was synthesized starting from 5-aminobenzimidazole (614 mg, 4.62 mmol), 3-(3-chlorophenyl)phenyl carbaldehyde (1.0 g, 4.68 mmol), TMSCN (0.93 mL, 6.93 mmol), 10% PdC (200 mg), TEA (1.31 mL, 8.76 mmol), di-(imidazol-1-yl)methanone (460 mg, 2.84 mmol) as described in method 2.

Yield: 0.100 g (6.13%); MS m/z 389.2 (M+H)$^+$; $^1$H NMR (400 MHz, CD$_3$OD): δ 8.056 (s, 1H), 7.61 (s, 1H), 7.56 (s, 2H), 7.55-7.30 (m, 7H), 5.57 (q, 1H), 4.02 (t, 1H), 3.41 (t, 1H), HPLC (λ=214 nm, [B]: rt 13.20 min (95.02%).

Example 50

1-(1H-benzo[d]imidazol-5-yl)-5-(3-chloro-4-morpholinophenyl)imidazolidin-2-one

The compound was synthesized starting from 5-aminobenzimidazole (284 mg, 2.13 mmol), 3-5-(3-chloro-4-morpholinophenyl)carbaldehyde (400 mg, 1.77 mmol), TMSCN (352 mg, 3.55 mmol), 10% PdC (200 mg), TEA (0.82 mL, 5.92 mmol), di-(imidazol-1-yl)methanone (168 mg, 1.03 mmol) as described in method 2.

Yield: 0.04 g (5.5%); MS m/z 398.1 (M+H)$^+$; $^1$H NMR (400 MHz, DMSO-D$_6$): δ 12.24 (bs, 1H), 8.09 (s, 1H), 7.59 (s, 1H), 7.50-7.37 (m, 3H), 7.28 (t, 1H), 7.19 (d, 1H), 7.08 (d, 1H), 6.95 (d, 1H), 5.52-5.48 (q, 1H), 3.81 (t, 1H), 3.68 (t, 4H), 3.09 (t, 1H), 2.89 (t, 4H), HPLC (λ=214 nm, [B]: rt 8.85 min (100%)

Example 51

1-(1H-benzo[d]imidazol-5-yl)-5-(4-(4-phenylpiperazin-1-yl)phenyl)imidazolidin-2-one The compound was synthesized starting from 5-aminobenzimidazole (1.8 g, 13.98 mmol), 5-(4-(4-phenylpiperazin-1-yl)phenyl)carbaldehyde (3.1 g, 11.65 mmol), TMSCN (2.3 mL, 17.48 mmol), 10% PdC (1.0 g), TEA (5.3 mL, 36.64 mmol), di-(imidazol-1-yl)methanone (1.0 g, 6.06 mmol) as described in method 2.

Yield: 0.04 g (0.53%); MS m/z 439.4 (M+H)$^+$; $^1$H NMR (400 MHz, DMSO-D$_6$): δ 12.23 (bs, 1H), 8.01 (s, 1H), 7.53 (s, 1H), 7.38 (s, 1H), 7.19 (t, 5H), 6.97-6.88 (m, 5H), 6.78 (t, 1H), 5.41-5.37 (q, 1H), 3.80 (t, 1H), 3.30-3.16 (m, 8H), 3.09 (t, 1H), HPLC (λ=214 nm), [B]: rt 10.13 min (97.77%).

Example 52

1-(1H-benzo[d]imidazol-5-yl)-5-(2-chloro-6-(4-ethylpiperazin-1-yl)phenyl)imidazolidin-2-one The compound was synthesized starting from 5-aminobenzimidazole (0.95 g, 7.14 mmol), 5-5-(2-chloro-6-(4-ethylpiperazin-1-yl)phenylcarbaldehyde (1.5 g, 5.95 mmol), TMSCN (1.2 g, 11.9 mmol), 10% PdC (0.04 g), TEA (1 mL, 7.53 mmol), di-(imidazol-1-yl)methanone (284 mg, 1.75 mmol) as described in method 2.

Yield: 0.02 g (0.94%); MS m/z 425.4 (M+H)$^+$; $^1$H NMR (400 MHz, DMSO-D$_6$): δ 12.19 (bs, 1H), 8.03 (s, 1H), 7.47 (d, 1H), 7.35 (t, 2H), 7.25-7.03 (m, 5H), 6.32 (d, 1H), 3.90 (t, 1H), 3.55 (d, 1H), 3.33-2.67 (m, 8H), 2.47-2.38 (m, 3H), 1.90 (s, 2H), 1.09-1.05 (t, 3H), HPLC (λ=214 nm), [B]: rt 6.24 min (100.0%).

Example 53

1-(H-imidazo[1,2-a]pyridin-7-yl)-5-phenylimidazolidin-2-one

The compound was synthesized starting from H-imidazo[1,2-a]pyridin-7-yl-amine (0.85 g, 4.4 mmol), benzaldehyde (0.48 g, 4.0 mmol), TMSCN (0.47 g, 4.8 mmol), 10% PdC (0.04 g), TEA (0.307 mL, 2.2 mmol), di-(imidazol-1-yl)methanone (0.195 mg, 1.25 mmol) as described in method 2.

Yield: 0.035 g (2.8%); MS m/z 279.3 (M+H)$^+$; $^1$H NMR (DMSO, 400 MHz): δ 3.12-3.15 (m, 1H), 3.94-3.99 (m, 1H), 5.62-5.65 (m, 1H), 7.27-7.42 (m, 5H), 7.69-7.73 (m, 2H), 7.77 (s, 1H), 7.83-7.85 (m, 1H), 7.99 (m, 1H), 8.58-8.60 (d, 1H, $^3$J=7.47 Hz), HPLC (λ=214 nm), [B]: rt 8.73 min (73.8%).

Example 54

1-(H-imidazo[1,2-a]pyridin-7-yl)-5-(4-propoxyphenyl)imidazolidin-2-one

The compound was synthesized starting from H-imidazo[1,2-a]pyridin-7-yl-amine (0.267 g, 2.0 mmol), 4-propoxy benzaldehyde (0.328 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.057 g (5.7%); MS m/z 337.2 (M+H)+; 1H-NMR (400 MHz, DMSO-d6): δ 0.91-0.95 (t, 3H), 1.65-1.70 (m, 2H), 3.11-3.14 (m, 1H), 3.91-3.93 (t, 2H), 3.94-3.96 (t, 1H), 5.56-5.59 (m, 1H), 6.90-6.93 (d, 2H, J=9 Hz), 7.24-7.27 (d, 2H, J=9 Hz), 7.73-7.75 (dd, 1H, J=2.0; 7.0 Hz), 7.78-7.81 (m, 2H), 7.90-7.91 (d, 1H, J=2.1 Hz), 8.03-8.04 (d, 1H, J=2.3 Hz), 8.62-8.64 (d, 1H, J=7.4 Hz), HPLC (λ=214 nm), ([B]): rt 11.80 min (99%).

Example 55

5-(4-butoxyphenyl)-1-(H-imidazo[1,2-a]pyridin-7-yl)imidazolidin-2-one

The compound was synthesized starting from H-imidazo[1,2-a]pyridin-7-yl-amine (0.267 g, 2.0 mmol), 4-butoxy benzyaldehyde (0.375 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.062 g (6.7%); MS m/z 351.0 (M+H)+; 1H-NMR (DMSO-d6, 400 MHz): δ 0.88-0.91 (t, 3H, J=7.0), 1.36-1.42 (m, 2H), 1.61-1.66 (m, 2H), 3.11-3.14 (dd, 1H, J=3.3, 9.1 Hz), 3.89-3.96 (m, 3H), 5.56-5.59 (dd, 1H, J=3.3, 9.0 Hz), 6.90-6.92 (d, 2H, J=8.7), 7.25-7.27 (d, 2H, J=8.7), 7.74-7.76 (m. 2H), 7.91 (s, 1H), 8.04 (s, 1H), 8.62-8.64 (d, 1H, J=7.4), 13.64 (br s, 0.7H), HPLC (λ=214 nm), [B]: rt 13.00 min (99%)

Example 56

5-(2,6-difluoro-4-methoxyphenyl)-1-(H-imidazo[1,2-a]pyridin-7-yl)imidazolidin-2-one The compound was synthesized starting from H-imidazo[1,2-a]pyridin-7-yl-amine (0.267 g, 2.0 mmol), 2,6-difluoro-4-methoxy benzyaldehyde (0.345 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.067 g (7.3%); MS m/z 345.2 (M+H)+; 1H-NMR (DMSO-d6, 400 MHz): δ 3.35-3.38 (m, 1H), 3.73 (s, 3H), 3.98 (m, 1H), 5.87-5.91 (m, 1H), 6.75-6.78 (d, 2H, J=11.2 Hz), 7.63 (s, 1H), 7.73-7.76 (dd, 1H, J=7.6; 2.4 Hz), 7.93 (d, 1H, J=2.0 Hz), 7.95 (s, 1H), 8.06 (d, 1H, J=2.0 Hz), 8.66-8.68 (d, 1H, J=8.0 Hz), HPLC (λ=214 nm), [B]: rt 9.56 min (99%)

Example 57

1-(H-imidazo[1,2-a]pyridin-7-yl)-5-(4-methoxy-benzo[d][1,3]-dioxol-6-yl)imidazolidin-2-one The compound was synthesized starting from H-imidazo[1,2-a]pyridin-7-yl-amine (0.207 g, 1.554 mmol), (4-methoxybenzo[d][1,3]dioxol-6-yl)carbaldehyde (0.28 g, 1.554 mmol), TMSCN (0.195 mL, 1. 1.554 mmol), 10% PdC (0.04 g), TEA (0.49 mL, 1.554 mmol), di-(imidazol-1-yl)methanone (0.311, 1.554 mmol) as described in method 2.

Yield: 0.033 g (4.5%); MS m/z 353.0 (M+H)+; 1H-NMR (DMSO-d6, 400 MHz) δ 3.14-3.17 (dd, 1H, J=4.0; 9.2 Hz), 3.80 (s, 3H), 3.90-3.94 (t, 1H, J=9 Hz), 5.50-5.54 (dd, 1H, J=9.2; 4.2), 5.94-5.96 (dq, 2H, J=0.8; 7.2 Hz), 6.54 (d, 1H, J=1.2 Hz), 6.70 (d, 1H, J=1.6 Hz), 7.76-7.82 (m, 3H), 7.93 (d, 1H, J=2 Hz), 8.06 (d, 1H, J=2 Hz), 8.64-8.66 (d, 1H, J=7.6 Hz), HPLC (λ=214 nm), [B]: rt 9.20 min (92%)

Example 58

5-(4-(2-morpholinoethoxy)phenyl)-1-(H-imidazo[1,2-a]pyridin-7-yl)imidazolidin-2-one The compound was synthesized starting from H-imidazo[1,2-a]pyridin-7-yl-amine (0.267 g, 2.0 mmol), 2-morpholinoethoxy)phenyl carbaldehyde (0.471 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.016 g (1.48%); MS m/z 408.4 (M+H)+; 1H-NMR (DMSO-d6, 400 MHz): δ 3.09-3.12 (dd, 1H, J=3.3; 9.1 Hz), 3.51-3.53 (t, 2H, J=4.6 Hz), 3.61-4.00 (br m, 9H), 4.28-4.30 (t, 2H, J=9.3 Hz), 5.59-5.62 (dd, 1H, J=8.9; 3.3 Hz), 6.97-6.99 (d, 2H, J=8.8 Hz), 7.30-7.30 (d, 2H, J=8.8 Hz), 7.74-7.77 (d, 1H, J=2; 9.7 Hz), 7.83 (s, 2H), 7.92 (d, 1H, J=2.1 Hz), 8.05 (d, 1H, J=2.1 Hz), 8.64-6.66 (d, 1H, J=7.7 Hz), HPLC (λ=214 nm), [B]: rt 1.40 min (86%)

Example 59

5-(2,6-difluorophenyl)-1-(H-imidazo[1,2-a]pyridin-7-yl)imidazolidin-2-one

The compound was synthesized starting from H-imidazo[1,2-a]pyridin-7-yl-amine (0.267 g, 2.0 mmol), 2,6-difluorobenzaldehyde (0.285 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.0047 g (0.55%); MS m/z 315.1 (M+H)+; 1H-NMR (DMSO-d6, 400 MHz): δ 3.39-3.42 (m, 1H), 3.99-4.04 (t, 1H, J=9.9 Hz), 5.98-6.01 (dd, 1H, J=4.1; 10.4 Hz), 7.12-7.16 (m, 2H), 7.41-7.45 (m, 1H), 7.63 (s, 1H), 7.76-7.78 (dd, 1H, J=2.2; 7.7 Hz), 7.92 (d, 1H, J=2.1 Hz), 7.99 (s, 1H), 8.05 (s, 1H), 8.66-8.68 (d, 1H, J=7.7 Hz), HPLC (λ=214 nm), [B]: rt 8.40 min (100%)

Example 60

5-(biphenyl)-1-(H-imidazo[1,2-a]pyridin-7-yl)imidazolidin-2-one

The compound was synthesized starting from H-imidazo[1,2-a]pyridin-7-yl-amine (0.267 g, 2.0 mmol), biphenyl carbaldehyde (0.365 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.043 g (4.6%); MS m/z 355.2 (M+H)+; 1H-NMR (400 MHz, DMSO-d6): δ 3.19-3.22 (m, H); 3.98-4.03 (m, H); 5.70-5.73 (m, H); 7.32-7.38 (m, H); 7.42-7.46 (m, 4H); 7.61-7.63 (m, 2H); 7.68 (d, J=8.4 Hz, 2H); 7.78-7.81 (m, H); 7.84 (s, H); 7.88 (s, H); 7.92 (d, J=2.0 Hz, H); 8.66 (d, J=8.0 Hz, H), HPLC (λ=214 nm), [31/98]: rt 12.90 min (99%)

Example 61

5-(3-fluorobiphenyl)-1-(H-imidazo[1,2-a]pyridin-7-yl)imidazolidin-2-one

The compound was synthesized starting from H-imidazo[1,2-a]pyridin-7-yl-amine (0.267 g, 2.0 mmol), 3-fluorobiphenyl carbaldehyde (0.401 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.035 g (0.036%); MS m/z 373.0 (M+H)$^+$; 1H-NMR (400 MHz, DMSO-d6): δ 3.22-3.25 (m, H); 3.97-4.02 (m, H); 5.72-5.75 (m, H); 7.24-7.25 (m, H); 7.26-7.57 (m, 7H); 7.80 (dd, J=2.0 Hz 7.6 Hz, H); 7.86 (s, H); 7.90 (s, H); 7.93 (d, J=2.0 Hz, H); 8.06 (d, J=2.4 Hz, H); 6.68 (d, J=7.6 Hz, H) HPLC (λ=214 nm), ([B]) [31/98]): rt 13.20 min (99%)

Example 62

1-(H-imidazo[1,2-a]pyridin-7-yl)-5-(4-(4-phenylpiperazin-1-yl)phenyl)imidazolidin-2-one The compound was synthesized starting from H-imidazo[1,2-a]pyridin-7-yl-amine (0.267 g, 2.0 mmol), 4-(4-phenylpiperazin-1-yl)phenyl carbaldehyde (0.600 g, 2.0 mmol), TMSCN (0.300 mL, 2.4 mmol), 10% PdC (0.04 g), TEA (0.620, 4.9 mmol), di-(imidazol-1-yl)methanone (0.4 g, 2.4 mmol) as described in method 2.

Yield: 0.011 g (0.00126%); MS m/z 439.4 (M+H)$^+$; 1H-NMR (400 MHz, DMSO-d6): δ 3.09-3.12 (m, H); 3.19-3.25 (m, 8H); 3.88-3.93 (m, H); 5.50-5.54 (m, H); 6.75-6.78 (m, H); 6.93-6.97 (m, 4H); 7.17-7.21 (m, 4H); 7.73 (dd, H, $^3$J=7.5 Hz $^4$J=2.1 Hz); 7.78 (s, 2H); 7.89 (d, H, $^4$J=2.1 Hz); 8.01 (d, H, $^4$J=2.1 Hz); 8.61 (d, H, $^3$J=7.5 Hz)
HPLC (λ=214 nm), [31/98]): rt 10.93 min (99%)

Example 63

1-(1H-benzo[d]imidazol-5-yl)-5-phenylimidazolidin-4-one

The compound was synthesized starting from 5-aminobenzimidazole (0.75 g, 5.61 mmol), benzaldehyde (0.52 mL, 5.1 mmol), TMSCN (0.64 mL, 5.1 mmol), conc. aqueous HCl (10 mL), triethyl orthoformate (13 mL, excess), NaBH$_4$ (0.227 g, 6 mmol) as described in method 4. Yield: 0.088 g (6.2%); MS m/z 279.3 (M+H)$^+$; $^1$H NMR (400 MHz, DMSO-D$_6$): δ 4.78-4.80 (m, H); 5.04-5.05 (m, H); 5.17-5.19 (m, H); 6.23 (d, H, J=2.1 Hz); 6.79 (dd, H, $^3$J=9.1 Hz, $^4$J=2.1 Hz); 7.24-7.27 (m, H); 7.30-7.36 (m, 4H); 7.59 (d, H, J=9.1 Hz); 8.89 (s, H); 9.16 (s, H), HPLC (λ=214 nm), [B]: rt 6.43 min (97.8%).

Example 64

1-(1H-benzo[d]imidazol-5-yl)-5-(2,3,5-trifluorophenyl)imidazolidin-4-one

The compound was synthesized starting from 5-aminobenzimidazole (0.732 g, 5.5 mmol), 2,3,5-trifluorobenzaldehyde (0.57 mL, 5 mmol), TMSCN (0.625 mL, 5 mmol), concentrated aqueous HCl (15 mL), triethyl orthoformate (30 mL, excess), NaBH$_4$ (0.157 g, 4.14 mmol) as described in method 4.

Yield: 0.037 g (2.2%); MS m/z 333.2 (M+H)$^+$; $^1$H NMR (400 MHz, DMSO-D$_6$): δ 4.77-4.78 (m, H); 5.19-5.21 (m, H); 5.43 (s, H); 6.67 (d, H, J=1.7 Hz); 6.79-6.82 (m, H); 7.17-7.19 (m, H); 7.48-7.54 (m, H); 7.65 (d, H, J=9.1 Hz); 9.13 (s, H); 9.18 (s, H), HPLC (λ=214 nm), [B]: rt 7.17 min (98%).

Example 65

1-Amino-3-(1H-benzo[d]imidazol-5-yl)-4-(4-methoxyphenyl)imidazolidin-2-one

Example 5 (0.35 mmol) was dissolved in 5 mL of glacial acetic acid and a solution of sodium nitrite (0.46 mmol (1.3 eq.), water 0.25 mL) was added. The solution was stirred for 30 min at r.t. and subsequently cooled to 8° C. After that zinc powder (1.05 mmol, 3 eq) were added in portions under stirring, whereby the reaction temperature was not allowed to exceed 15° C. The mixture was further stirred for 1 h at 12-17° C. Then the solvent was removed and the product was purified by means of semi-preparative HPLC.

yield: 0.02 g (10.3%); MS m/z: 324.5 [M+H]$^+$; $^1$H-NMR (400 MHz, DMSO-d6): δ 3.24-3.27 (m, 1H); 3.64 (s, 3H); 3.91-3.95 (m, 1H); 5.46-5.49 (m, H); 6.84 (d, 2H, J=8.8 Hz); 7.27 (d, 2H, J=8.8 Hz); 7.53 (dd, H, $^3$J=8.8 Hz $^4$J=1.8 Hz); 7.66 (d, H, $^3$J=8.8 Hz); 7.84 (d, H, $^4$J=1.8 Hz); 9.21 (s, H); HPLC (214 nm): rt 6.51 min (95.2%) [B]

Example 66

(S)-3-(1H-benzo[d]imidazol-6-yl)-4-phenyloxazolidin-2-one

The compound was synthesized starting from (S)-4-phenyloxazolidin-2-one (1 equiv., 0.163 g, 1 mmol), 4-bromobenzene-1,2-diamine (1 equiv., 0.187 g, 1 mmol), copper (I) iodide (0.1 equiv., 0.019 g, 0.1 mmol), potassium carbonate (2 equiv., 0.276 g, 2 mmol), cyclohexane-1,2-diamine (0.1 equiv., 0.012 mL, 0.1 mmol). The solids were given together in a reaction flask and the flask was purged with argon. A solution of cyclohexane-1,2-diamine in 5 mL dioxane was added to the flask. The reaction was stirred at reflux for 18 hours, before the reaction was cooled down to 45° C. and filtered through a pad of CELITE®. The pad was washed with warm dichloromethane and the solution was concentrated under reduced pressure. The intermediate product was purified via FPLC using a chloroform-methanol gradient (0→10%, product elutes at about 5%).

The (S)-3-(3,4-diaminophenyl)-4-phenyloxazolidin-2-one was dissolved in 2.5 mL of 5N aqueous hydrochloric acid and 0.25 mL of formic acid was added to the solution. The reaction was stirred at reflux for 1 h before the reaction was cooled down to 0° C. and the reaction mixture was neutralized with buffer (pH7) and conc. ammonia. The aqueous layer was than extracted by means of 25 mL dichloromethane three times. The organic layers were combined, dried, filtered and the solvent was removed under reduced pressure. The final product was purified by means of FPLC using chloroform-methanol gradient (0→10%). The product elutes at about 5% methanol.

Yield: 0.143 g (51.3%); MS m/z 280.3 (M+H)$^+$; $^1$H NMR (400 MHz, DMSO-D$_6$): δ 4.12-4.16 (m, H); 4.81-4.85 (m, H); 5.70-5.74 (m, H); 7.22-7.26 (m, 2H); 7.30-7.33 (m, 2H); 7.37-7.39 (m, 2H); 7.45-7.47 (m, H); 7.58-7.59 (m, H); 8.14 (s, H); 12.37 (bs, H), HPLC (λ=214 nm), [B]: rt 7.87 min (100%).

Example 67

(R)-3-(1H-benzo[d]imidazol-6-yl)-4-phenyloxazolidin-2-one

The compound was synthesized starting from (R)-4-phenyloxazolidin-2-one (1 equiv., 0.163 g, 1 mmol), 4-bromobenzene-1,2-diamine (1 equiv., 0.187 g, 1 mmol), copper (I) iodide (0.1 equiv., 0.019 g, 0.1 mmol), potassium carbonate (2 equiv., 0.276 g, 2 mmol), cyclohexane-1,2-diamine (0.1 equiv., 0.012 mL, 0.1 mmol), 5N HCl (3.4 mL), formic acid (0.343 mL) as described in method 5 step D.

Yield: 0.056 g (20.2%); MS m/z 280.3 (M+H)$^+$; $^1$H NMR (400 MHz, DMSO-D$_6$): δ 4.10-4.13 (m, H); 4.78-4.83 (m, H);

5.68-5.72 (m, H); 7.20-7.23 (m, 2H); 7.27-7.31 (m, 2H); 7.35-7.37 (m, 2H); 7.42-7.45 (m, H); 7.55-7.56 (m, H); 8.12 (s, H); 12.37 (br s, H) HPLC (λ=214 nm), [B]: rt 7.87 min (100%).

Example 68

(S)-3-(1H-benzo[d]imidazol-5-yl)-4-isopropyloxazolidin-2-one

The compound was synthesized starting from (S)-4-isopropyloxazolidin-2-one (0.065 g, 0.5 mmol), 4-iodobenzene-1,2-diamine (0.117 g, 0.5 mmol), copper(I) iodide (0.010 g, 0.05 mmol), cesium fluoride (0.276 g, 1 mmol), cyclohexane-1,2-diamine (0.006 mL, 0.05 mmol), triethyl orthoformate (3 mL) as described in method 5 step D.

Yield: 0.012 g (9.8%); MS m/z 246.3 (M+H)+; 1H NMR (400 MHz, DMSO-D6): δ 0.71-0.72 (m, 3H); 0.79-0.81 (m, 3H); 1.85-1.90 (m, H); 4.20-4.24 (m, H); 4.38-4.42 (m, H); 4.55-4.59 (m, H); 7.25 (bs, H); 7.51-7.66 (m, 2H); 8.20 (s, H); 12.41-12.45 (m, H), HPLC (λ=214 nm), [B]: rt 7.09 min (96.7%).

Example 69

(S)-3-(1H-benzo[d]imidazol-5-yl)-4-benzyloxazolidin-2-one

The compound was synthesized starting from (S)-4-benzyloxazolidin-2-one (0.089 g, 0.5 mmol), 4-iodobenzene-1,2-diamine (0.117 g, 0.5 mmol), copper(I) iodide (0.010 g, 0.05 mmol), cesium fluoride (0.276 g, 1 mmol), cyclohexane-1,2-diamine (0.006 mL, 0.05 mmol), triethyl orthoformate (3 mL) as described in method 5 step D.

Yield: 0.036 g (24.5%); MS m/z 294.2 (M+H)+; 1H NMR (400 MHz, DMSO-D6): δ 2.75-2.91 (m, 2H); 4.11-4.15 (m, H); 4.33-4.37 (m, H); 4.88-4.91 (m, H); 7.13-7.26 (m, 5H); 7.32-7.40 (m, H); 7.54-7.68 (m, H); 7.74-7.79 (m, H); 8.20-8.22 (m, H); 12.43-12.48 (m, H), HPLC (λ=214 nm), [B]: rt 8.93 min (96.5%).

Example 70

(4S,5R)-3-(1H-benzo[d]imidazol-6-yl)-4,5-diphenyloxazolidin-2-one

The compound was synthesized starting from (4S,5R)-4,5-diphenyloxazolidin-2-one (0.479 g, 2 mmol), 4-bromobenzene-1,2-diamine (0.374 g, 2 mmol), copper(I) iodide (0.038 g, 0.2 mmol), potassium carbonate (0.553 g, 4 mmol), cyclohexane-1,2-diamine (0.024 mL, 0.2 mmol), 5N HCl (5.8 mL), formic acid (0.582 mL) as described in method 5 step D Yield: 0.235 g (33.1%); MS m/z 356.2 (M+H)+; 1H NMR (400 MHz, DMSO-D6): δ 6.09 (d, H, J=8.3 Hz); 6.20 (d, H, J=8.3 Hz); 6.95-7.16 (m, 10H); 7.40 (bs, H); 7.49 (d, H, J=8.7 Hz); 7.73 (s, H); 8.15 (s, H); 12.40 (bs, H), HPLC (λ=214 nm), [B]: rt 11.67 min (94.9%).

Example 71

(4S,5S)-3-(1H-benzo[d]imidazol-6-yl)-5-methyl-4-phenyloxazolidin-2-one

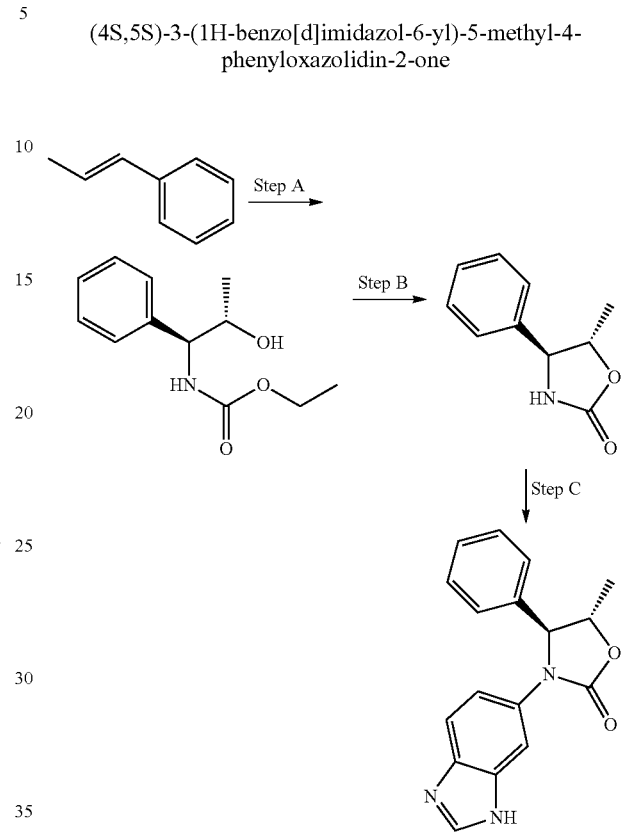

Step A:

Ethyl carbamate (2.14 g, 24 mmol) was dissolved in 27 mL 1-propanol and 47.5 mL 0.5 M freshly prepared aqueous NaOH was added. The reaction was stirred for 5 minutes at ambient temperature and 1,3-dichloro-5,5-dimethylimidazolidine-2,4-dione (2.36 g, 12 mmol) were added and the reaction was stirred for 10 minutes at ambient temperature. (DHQ)2PHAL (0.156 g, 0.2 mmol) and (E)-prop-1-enylbenzene (1.04 mL, 8 mmol) dissolved in 19 mL 1-propanol were added, followed by potassium osmate dihydrate (0.074 g, 0.2 mmol) suspended in 0.56 mL of 0.5 M aqueous NaOH. The reaction was stirred at ambient temperature until complete consumption of the (E)-prop-1-enylbenzene (TLC control). 60 mL water was added and the reaction mixture was extracted three times by means of 60 mL ethyl acetate. The combined organic layer was washed with brine, dried over sodium sulfate, filtered and the solvents were removed under reduced pressure. The product was purified via FPLC using a heptane-ethyl acetate gradient.

Yield: 0.74 g (41.5%); MS m/z 224.3 (M+H)+; HPLC (λ=214 nm), [B]: rt 10.67 min (95.5%).

Step B:

2 mmol of the product (0.446 g) obtained from step A was dissolved in a 0.2 M solution of sodium hydroxide in methanol. The reaction was stirred at reflux until the TLC control indicated complete consumption. The solvent was removed under reduced pressure and ethyl acetate was added. The organic layer was washed with brine, dried over sodium sulfate, filtered and the solvent was removed under reduced pressure.

Yield: 0.335 g (94.5%); MS m/z 178.3 (M+H)+; HPLC (λ=214 nm), [B]: rt 11.41 min (100%).

Step C:

Product (0.335 g, 1.89 mmol) obtained from step B was given together with 4-bromobenzene-1,2-diamine (0.353 g, 1.89 mmol), potassium carbonate (0.522 g, 3.78 mmol) and copper(I) iodide (0.036 g, 0.19 mmol) in a reaction flask. The flask was purged with argon and a solution of cyclohexane-1,2-diamine (0.022 g, 0.19 mmol) in 10 mL dioxane was added. The reaction was stirred at reflux for 14 h. After cooling to 45° C. the reaction mixture was filtered through a pad of CELITE®, the pad was washed with warm dichloromethane and the solution was concentrated under reduced pressure. The product was purified via FPLC using a chloroform-methanol gradient (0→10%).

Yield: 0.362 g (67.7%); MS m/z 284.1 (M+H)+; HPLC (λ=214 nm), [B]: rt 9.53 min (99.7%).

The product obtained from the copper(I)-catalyzed coupling was dissolved in 9.5 mL of 5N aqueous HCl and 0.954 mL of formic acid was added. The reaction was stirred at reflux for 1 hour. After cooling to 0° C. The final product was purified via FPLC using a chloroform-methanol gradient (0→10%).

Yield: 0.288 g (78.7%);

overall yield: 20.9%; MS m/z 294.2 (M+H)+; $^1$H-NMR (400 MHz, DMSO-d6): δ 1.47 (d, 3H, J=5.8 Hz); 4.39-4.45 (m, H); 5.28 (d, H, J=7.1 Hz); 7.14-7.23 (m, 2H); 7.26-7.30 (m, 2H); 7.37-7.46 (m, 3H); 7.52 (s, H); 8.11 (s, H); 12.35 (bs, H); HPLC (λ=214 nm), [B]: rt 9.86 min (100%).

Example 72

(S)-3-(1H-benzo[d]imidazol-6-yl)-5,5-dimethyl-4-phenyloxazolidin-2-one

The compound was synthesized starting from (S)-5,5-dimethyl-4-phenyloxazolidin-2-one (0.25 g, 1.31 mmol), 4-bromobenzene-1,2-diamine (0.245 g, 1.31 mmol), copper(I) iodide (0.025 g, 0.13 mmol), potassium carbonate (0.362 g, 2.62 mmol), cyclohexane-1,2-diamine (0.015 mL, 0.13 mmol), 5N HCl (6.5 mL), formic acid (0.648 mL) as described in method 5 step D Yield: 0.155 g (38.2%); MS m/z 308.2 (M+H)+; $^1$H NMR (400 MHz, DMSO-D$_6$): δ 0.90 (s, 3H); 1.64 (s, 3H); 5.46 (s, H); 7.25-7.34 (m, 5H); 7.41 (s, H); 7.49-7.52 (m, H); 7.64-7.66 (m, H); 8.14 (s, H); 12.36 (bs, H), HPLC (λ=214 nm), [B]: rt 9.65 min (99.6%).

Example 73

(S)-3-(1H-benzo[d]imidazol-6-yl)-4-(4-propoxyphenyl)oxazolidin-2-one

Step A:

The compound was synthesized starting from 4-propoxybenzaldehyde (7.32 g, 44.6 mmol), methyltriphenylphosphonium bromide (21.34 g, 59.75 mmol), 1M solution of potassium tert-butylate in THF (59.8 mL, 59.75 mmol) as described in method 5

Yield: 6.13 g (84.7%)

Step B:

Product obtained from step A (3 g, 18.48 mmol), ethyl carbamate (4.94 g, 27.72 mmol), 5,5-dimethylimidazolidine-2,4-dione (5.46 g, 27.72 mmol), (DHQ)$_2$PHAL (0.72 g, 0.92 mmol), K$_2$OsO$_4$x2H$_2$O (0.274 g, 0.74 mmol), 0.5 M aqueous NaOH (112.8 mL, 56.4 mmol)

Yield: 3 g (61%)

Step C:

Product obtained from step B (3 g, 10.16 mmol), 0.2 M aqueous NaOH (300 mL)

Yield: 1.21 g (46%)

Step D:

Product obtained from step C (1.16 g, 5.25 mmol), 4-bromobenzene-1,2-diamine (0.982 g, 5.25 mmol), copper(I) iodide (0.1 g, 0.525 mmol), potassium carbonate (1.451 g, 10.5 mmol), cyclohexane-1,2-diamine (0.064 mL, 0.525 mmol), 5N HCl (162 mL), formic acid (3.02 mL)

Yield: 0.650 g (47.5%);

Overall yield: 9.2% MS m/z 338.2 (M+H)+; $^1$H NMR (400 MHz, DMSO-D$_6$): δ 0.97 (t, 3H, J=7.5 Hz); 1.69-1.78 (m, 2H); 3.81-3.84 (m, 2H); 4.22-4.26 (m, H); 4.75-4.80 (m, H); 5.32-5.36 (m, H); 6.79-6.81 (m, 2H); 7.16-7.21 (m, 3H); 7.46 (d, H, J=7.5 Hz); 7.60 (d, H, J=2.1 Hz); 7.90 (s, H), HPLC (λ=214 nm), [B]: rt 10.67 min (98%).

Example 74

(S)-3-(1H-benzo[d]imidazol-6-yl)-4-(2,3-dihydrobenzo[b][1,4]dioxin-7-yl)oxazolidin-2-one The compound was synthesized according to method 5.

Step A 1.7M n-Butyl lithium (21.4 mL, 36.5 mmol), triphenyl phosphonium bromide (9.8 g, 27.43 mmol), 2,3-dihydrobenzo[b][1,4]dioxine-6-carbaldehyde (3.0 g, 18.29 mmol), yield: 1.6 g (54.05%)

Step B

Benzylcarbamate (4.3 g, 28.7 mmol), 0.5M aqueous sodium hydroxide (1.1 g in 55 mL), (DHQ)$_2$PHAL (360 mg, 0.46 mmol), potassium osmate dihydrate (130 mg, 0.37 mmol), product from step A (1.5 g, 9.25 mmol), yield 900 mg (33%)

Step C

Thionyl chloride (1.6 mL, 21.88 mmol), product from step B (900 mg, 2.73 mmol), yield: 500 mg (83.33%)

Step D

Product from step C (500 mg, 2.26 mmol, 1,2-diamino-4-iodo benzene (530 mg, 2.26 mmol), cesium fluoride (515 mg, 3.39 mmol), copper iodide (42 mg, 0.22 mmol), 1,2-diaminocyclohexane (27 mg, 0.22 mmol), yield: 180 mg (24.65%), Then the above product (100 mg), formic acid (3 mL), yield 75 mg (75%)

Conversion into HCl-salt: Free base (75 mg, 0.22 mmol) in acetone and 1M HCl in ether (0.22 mL), yield: 45 mg (54.21%), MS m/z 338.2 (M+H)+; $^1$H-NMR (400 MHz, DMSO-d6): δ 9.42 (s, H); 7.91 (s, H); 7.78-7.76 (m, H); 7.60-7.58 (m, H); 6.92 (s, H); 6.87-6.79 (br m, 2H); 5.75-5.72 (m, H); 4.84-4.80 (m, H); 4.15-4.13 (m, 5H), HPLC (λ=214 nm, [A]: rt 9.01 min (99.49%).

Example 75

(S)-4-(benzo[d][1,3]dioxol-6-yl)-3-(1H-benzo[d]imidazol-6-yl)oxazolidin-2-one

The compound was synthesized according to method 5.

Step A 1.5M n-Butyl lithium (28.95 mL, 66.60 mmol), methyl triphenyl phosphonium bromide (23.79 g, 66.60 mmol), piperonal (5.0 g, 33.30 mmol), yield: 3.6 g (73%)

Step B

Benzylcarbamate (6.0 g, 40.5 mmol), 0.5M aqueous sodium hydroxide (30 mL), (DHQ)$_2$PHAL (530 mg, 0.5 mmol), potassium osmate dihydrate (200 mg, 0.4 mmol), product from step A (2.0 g, 13.5 mmol.), yield: 980 mg (23%)

Step C

Thionyl chloride (1.66 mL, 22.85 mmol), product from step B (0.9 g, 2.85 mmol), yield: 450 mg (76.2%)

Step D

Product from step C (450 mg, 2.17 mmol), 1,2-Diamino-4-bromo benzene (406 mg, 2.17 mmol), cesium fluoride (659 mg, 4.34 mmol), copper iodide (62 mg, 0.32 mmol), 1,2-diaminocyclohexane (50 mg, 0.43 mmol), yield: 250 mg (36.7%), Then the above product (230 mg), formic acid (5 mL), yield: (100 mg, 40%)

Conversion into HCl-salt: Free base (100 mg, 0.31 mmol) in acetone and 1M HCl in ether (0.4 mL, 0.37 mmol.), yield: 35 mg, MS m/z 324.2 (M+H)$^+$; $^1$H-NMR (400 MHz, DMSO-d6): δ 9.41 (s, H); 7.90 (s, H); 7.77-7.75 (m, H); 7.59-7.56 (m, H); 7.04 (s, H); 6.91-6.84 (br m, 2H); 5-97-5.96 (m, 2H); 5.78-5.74 (m, H); 4.85-4.81 (m, H); 4.19-4.15 (m, H), HPLC (λ=214 nm, [A]: rt 8.99 min (98.77%).

Example 76, 77

3-(1H-benzo[d]imidazol-6-yl)-4,5-bis(4-propoxyphenyl)oxazolidin-2-one, diastereomer 1 and 2

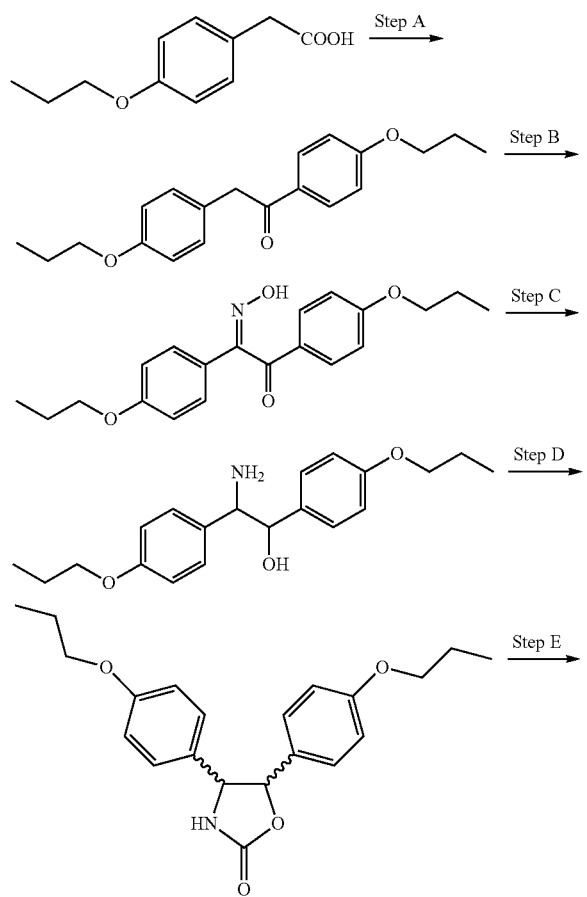

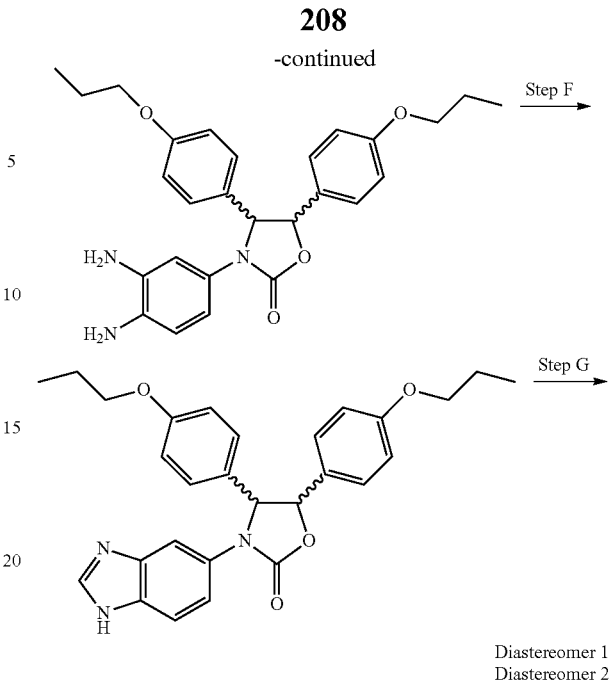

Diastereomer 1
Diastereomer 2

Step A

Thionyl chloride (5.75 mL, 77.30 mmol) was added to a stirred solution of 2-(4-propoxyphenyl)acetic acid (3 g, 15.5 mmol) in chloroform (30 mL) at 0° C. and stirred overnight. The reaction mixture was concentrated under reduced pressure to give acid chloride as oil. A solution of acid chloride (3 g, 14.15 mmol) in dichloromethane was added drop wise to a stirred solution of Aluminum trichloride (2.22 g, 16.7 mmol) and propoxy benzene (1.75 g, 12.86 mmol) in dichloromethane (30 mL) at 0° C. and stirred for 4 h at room temperature. The reaction mixture was poured into ice water and extracted with ethyl acetate. The combined organic layers were washed successively with saturated sodium bi carbonate solution, water, brine solution, dried over anhydrous sodium sulfate and concentrated under reduced pressure to obtain crude compound. This was purified by column chromatography over silica gel (60-120 mesh) using 10% ethyl acetate in petroleum ether as eluent to afford 2.5 g (51.86%) of the product as solid.

Step B t-Butyl nitrite (0.93 mL, 7.76 mmol) was added drop wise to a stirred solution of the product of step A (2 g, 6.41 mmol) in tetrahydrofuran (40 mL) at 0° C. and stirred for 10 min. 5M HCl in iso-1-propanol (10 mL) was added drop wise to the reaction mixture at 0° C. and stirred for 4 h at room temperature. The reaction mixture was concentrated under reduced pressure. The residue was partitioned between saturated sodium bicarbonate solution and ethyl acetate. Separated organic layer was washed with water, brine, dried over anhydrous sodium sulfate and concentrated under reduced pressure to get crude compound. This was purified by column chromatography over silica gel (60-120 mesh) using 20% ethyl acetate in petroleum ether as eluent to afford 1.5 g (68.80%) of the product as solid.

Step C

10% PdC (800 mg) was added to a stirred solution of the product of step B (1.5 g, 4.40 mmol), chloroform (6.6 mL, 88.25 mol) in ethanol (20 mL) were hydrogenated for over night at 75 psi in a par apparatus. The reaction mixture was filtered through celite pad, washed with ethanol and the filtrate was concentrated under reduced pressure to get solid compound. Which was stirred in pentane for 15 min and precipitated solid was filtered and dried in vacuum to afford 1.4 g (97.22%) of the product as solid.

Step D

Triphosgene (800 mg, 2.70 mmol) was added to a stirred solution of the product of step C (1.75 g, 5.40 mmol) in dichloromethane (20 mL) at 10° C. Triethylamine (1.2 mL, 8.12 mmol) was added to the reaction mixture at 0° C. and stirred for 1 h at room temperature. The reaction mixture was poured into ice water and extracted with dichloromethane. The combined organic layers were washed successively with saturated sodium bicarbonate solution, water and brine. Dried over anhydrous sodium sulfate and concentrated under reduced pressure to get 1.2 g (63.82%) of the product as white solid.

Step E

A mixture of the product of step D (750 mg, 2.11 mmol), 1,2-diamino 4-bromo benzene (400 mg, 2.11 mmol), cesium fluoride (650 mg, 4.3 mmol) and copper iodide (60 mg, 0.32 mmol) in 1,4-dioxan (20 mL) were purged with argon gas for 15 min. 1,2-diaminocyclohexane (40 mg, 0.35 mmol) was added to the reaction mixture, purging continued for another 5 min and stirred over night at 110-115° C. in a sealed tube. The reaction mixture was filtered through celite pad, washed with chloroform and concentrated under reduced pressure to give crude compound. This was purified by column chromatography over silica gel (60-120 mesh) using 4% methanol in chloroform as eluent to afford 650 mg (66.80%) of the product as solid.

Step F

A mixture of the product of step E (650 mg) and formic acid (10 mL) were stirred 1 h at 70-80° C. and reaction mixture was concentrated under reduced pressure. The residue was partitioned between saturated sodium bicarbonate and chloroform. Separated organic layer was washed successively with water, brine, dried over anhydrous sodium sulfate and concentrated under reduced pressure to give crude. This was purified by preparative HPLC.

yield: 170 mg

Step G 140 mg of the product of step F were purified by chiral HPLC.

Column: CHIRALPAK IA (250×4.6 mm); 5µ
Mobile phase: Hexane:Ethanol (75:25)
Flow rate: 18 mL/min The obtained prep mL was concentrated under reduced pressure and the residue was dissolved in chloroform, washed with water, brine. Dried over anhydrous sodium sulfate and concentrated under reduced pressure. yield 60 mg (9%) diastereomer 1, 60 mg (9%) of diastereomer 2.

Diastereomer 1* HCl

1M HCl in ether (0.16 mL) was added to a stirred solution of the free base from step G (60 mg, 0.13 mmol) in Acetone (3 mL) at 5° C. and stirred 30 min at room temperature. The reaction mixture was concentrated in vacuum and co-distilled with water. yield: 50 mg (73.52%). MS m/z 472.4 (M+H)$^+$;
$^1$H-NMR (400 MHz, DMSO-d6): δ 14.50 (bs, 1H); 9.41 (s, 1H); 8.06 (d, 1H); 7.77 (d, 1H); 7.66 (d, 1H); 6.98 (d, 2H); 6.87 (d, 2H); 6.73 (d, 2H); 6.64 (d, 2H); 6.15-6.07 (m, 2H); 3.82 (t, 2H); 3.73 (t, 2H); 1.66-1.58 (m, 4H); 0.94-0.85 (m, 6H), HPLC (λ=214 nm, [A]: rt 16.99 min (100%).

Diastereomer 2* HCl

1M HCl in ether (0.16 mL) was added to a stirred solution of the free base from step G (60 mg, 0.13 mmol) in acetone (3 mL) at 5° C. and stirred 30 min at room temperature. The reaction mixture was concentrated in vacuum and co-distilled with water. yield 50 mg (73.52%), MS m/z 472.4 (M+H)$^+$, $^1$H-NMR (400 MHz, DMSO-d6): δ 14.50 (bs, 1H); 9.34 (s, 1H); 8.06 (d, 1H); 7.76 (d, 1H); 7.66 (d, 1H); 6.98 (d, 2H); 6.87 (d, 2H); 6.73 (d, 2H); 6.64 (d, 2H); 6.15-6.07 (m, 2H); 3.82 (t, 2H); 3.73 (t, 2H); 1.66-1.58 (m, 4H); 0.94-0.85 (m, 6H); HPLC (λ=214 nm, [A]: rt 16.96 min (100%)

Example 78, 79

3-(1H-benzo[d]imidazol-6-yl)-5-phenyl-4-(4-propoxyphenyl)oxazolidin-2-one

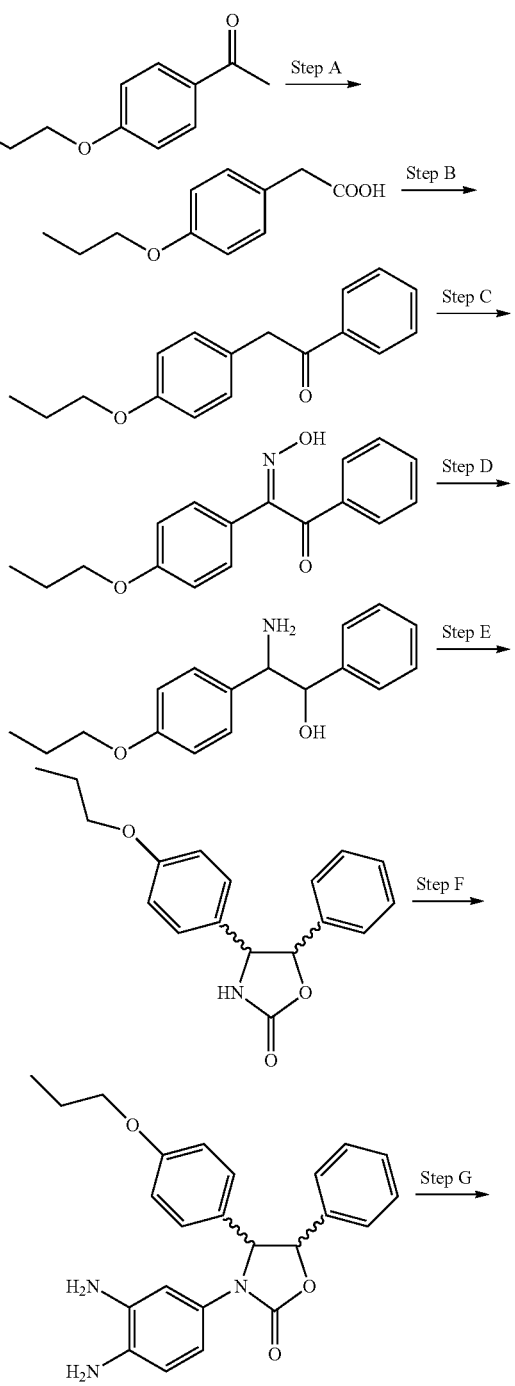

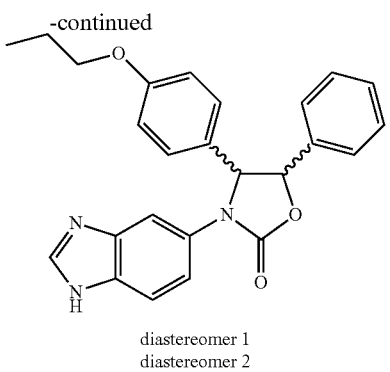

diastereomer 1
diastereomer 2

Step A

A mixture of 4-propoxy acetophenone (20 g, 0.12 mol), sulfur (17.5 g, 0.27 mol), morpholine (75 mL, 0.9 mol) and p-toluene sulfonic acid (2 g) were stirred for 5 h at 130° C. The reaction mixture was poured into 500 mL of ice water and stirred overnight. The precipitated solid was filtered and dried in vacuum to get crude compound. The crude compound and 10% potassium hydroxide in ethanol (400 mL) was refluxed overnight. Ethanol was removed in vacuum. The residue was dissolved in water and acidified (PH~2) using 4N HCl. Precipitated solid was filtered, washed with water, and dried in vacuum to get crude compound. This was purified by column chromatography over silica gel (60-120 mesh) using 20% ethyl acetate in petroleum ether. Yield: 9 g (40.90%)

Step B

Thionyl chloride (9.6 mL, 129 mmol) was added to a stirred solution of the product of step A (5 g, 25.8 mmol) in chloroform (60 mL) at 0° C. and stirred overnight. The reaction mixture was concentrated under reduced pressure to give acid chloride as oil. A solution of acid chloride (5 g, 23.6 mmol) in benzene (20 mL) was added drop wise to a stirred solution of aluminum tri chloride (4 g, 30.66 mmol) in benzene (30 mL) at 0° C. and stirred for 4 h at room temperature. The reaction mixture was poured into ice water and extracted with ethyl acetate. The combined organic layers were washed successively with saturated sodium bi-carbonate solution, water, brine solution, dried over anhydrous sodium sulfate and concentrated under reduced pressure to get crude compound. This was purified by column chromatography over silica gel (60-120 mesh) using 10% ethyl acetate in petroleum ether as eluent to afford 2 g product (30.75%) as solid.

Step C t-Butyl nitrite (1 mL, 8.5 mmol) was added drop wise to a stirred solution of the product of step B (1.8 g, 7.08 mmol) in tetrahydrofuran (40 mL) at 0° C. and stirred for 10 min. 5M HCl in isopropanol (10 mL) was added drop wise to the reaction mixture at 0° C. and stirred for 4 h at room temperature. The reaction mixture was concentrated under reduced pressure. The residue was partitioned between saturated sodium bicarbonate solution and ethyl acetate. Separated organic layer was washed with water, brine, dried over anhydrous sodium sulfate and concentrated under reduced pressure to get crude compound. This was purified by column chromatography over silica gel (60-120 mesh) using 20% ethyl acetate in petroleum ether as eluent to afford 1.4 g (70%) product as solid.

Step D

10% PdC (700 mg) was added to a stirred solution of the product of step C (1.4 g, 4.50 mmol), chloroform (7.5 mL, 90 mmol) in ethanol (20 mL) and hydrogenated over night at 75 psi in a Parr apparatus. The reaction mixture was filtered through celite pad, washed with ethanol and the filtrate was concentrated under reduced pressure to get solid compound. Which was stirred in pentane for 15 min, precipitated solid was filtered and dried in vacuum to afford 1.3 g (97.74%) product as solid.

Step E

Triphosgene (720 mg, 2.34 mmol) was added to a stirred solution of the product of step D (1.3 g, 4.8 mmol) in dichloromethane (20 mL). Triethylamine (1 mL, 7.22 mmol) was added to the reaction mixture at 0° C. and stirred for 1 h at room temperature. The reaction mixture was poured into ice water and extracted with dichloromethane. The combined organic layers were washed successively with saturated sodium bicarbonate solution, water and brine, dried over anhydrous sodium sulfate and concentrated under reduced pressure to get 1 g (70.42%) of the product as white solid.

Step F

A mixture of the product of step F (750 mg, 2.53 mmol), 1,2-diamino 4-bromo benzene (480 mg, 2.53 mmol), cesium fluoride (760 mg, 5 mmol) and copper iodide (80 mg, 0.42 mmol) in 1, 4-dioxane (20 mL) were purged with argon gas for 15 min. 1,2-diaminocyclohexane (50 mg, 0.43 mmol) was added to the reaction mixture, purging continued for another 5 min and stirred over night at 110-115° C. in a sealed tube. The reaction mixture was filtered through celite pad, washed, with chloroform and concentrated under reduced pressure to give crude compound. This was purified by column chromatography over silica gel (60-120 mesh) using 4% methanol in chloroform as eluent to afford 700 mg (70%) of the product as solid.

Step G

A mixture of the product of step F (700 mg) and formic acid (10 mL) were stirred 1 h at 70-80° C. and reaction mixture was concentrated under reduced pressure. The residue was partitioned between saturated sodium bicarbonate and chloroform. Separated organic layer was washed successively with water, brine, dried over anhydrous sodium sulfate and concentrated under reduced pressure to give crude. This was purified by preparative HPLC using following conditions to give the mixed diastereomers.

Column: Gemini C18 (50×30 mm) 10μ
Mobile phase: 10M Ammonium acetate (Aq)
Methanol
T % B: 0/50, 3/50, 12/80, 18/80, 18.1/50
Flow rate: 35 mL/Min.

The obtained prep mL's were concentrated under reduced pressure and the residue was dissolved in chloroform, washed with water, brine. Dried over anhydrous sodium sulfate and concentrated under reduced pressure to afford 200 mg of the product as solid.

Separation of the Diastereomers 150 mg of the mixture of diastereomers was purified by Chiral HPLC using following conditions.

Column: CHIRALPAK IA (250×4.6 mm); 5μ
Mobile phase: Hexane:Ethanol (70:30)
Flow rate: 128 mL/min The obtained prep mL's were concentrated under reduced pressure and the residue was dissolved in chloroform, washed with water, brine. Dried over anhydrous sodium sulfate and concentrated under reduced pressure to afford 70 mg (9.85%) of diastereomere 1 and diastereomere 2 as solid.

Conversion into the HCl-Salt

1M HCl in ether (0.2 mL) was added to a stirred solution of diastereomere 1 (70 mg, 0.17 mmol) in acetone (3 mL) at 5° C. and stirred 30 min at room temperature. The reaction mixture was concentrated in vacuum and co-distilled with water to afford 50 mg (65.87%) of diastereomere 1 HCl as solid.

$^1$H-NMR (400 MHz, DMSO-d6): δ 14.50 (bs, 1H); 9.38 (s, 1H); 8.06 (s, 1H); 7.76 (d, 1H); 7.67 (d, 1H); 7.21-7.09 (m, 4H); 6.88 (d, 2H); 6.60 (d, 2H); 6.22-6.14 (q, 2H); 3.70 (t, 2H); 1.60-1.55 (m, 2H); 0.86 (t, 3H); MS=414 (M+1)

1M HCl in ether (0.2 mL) was added to a stirred solution of diastereomere 2 (70 mg, 0.17 mmol) in Acetone (3 mL) at 5° C. and stirred 30 min at room temperature. The reaction mixture was concentrated in vacuum and co-distilled with water to afford 50 mg (65.87%) of diastereomere 2.HCl as solid.

1H-NMR (400 MHz, DMSO-d6): δ 14.50 (bs, 1H); 9.44 (s, 1H); 8.07 (s, 1H); 7.77 (d, 1H); 7.67 (d, 1H); 7.20-7.09 (m, 5H); 6.88 (d, 2H); 6.60 (d, 2H); 6.22-6.14 (q, 2H); 3.70 (t, 2H); 1.62-1.53 (m, 2H); 0.86 (t, 3H); MS=414 (M+1); HPLC-98.88%.

Example 80

(S)-4-(4-(2-(piperazin-1-ypethoxy)phenyl))-3-(1H-benzo[d]imidazol-6-yl)oxazolidin-2-one The compound was synthesized according to method 5.
Step A
1.5M n-Butyl lithium (5.7 mL, 11.97 mmol), methyl triphenyl phosphonium bromide (3.4 g, 9.58 mmol), 4-(2-(4-tert-butyl-oxycarbonyl-piperazin-1-yl)ethoxy)benzaldehyde (31.6 g, 4.79 mmol), yield: 1.5 g (94.32%)
Step B
t-butyl hypochlorite (1.6 mL, 20.93 mmol), benzylcarbamate (2.1 g, 20.45 mmol), 0.4M aqueous sodium hydroxide (0.55 g in 34 ml), (DHQ)$_2$PHAL (170 mg, 0.22 mmol), potassium osmate dihydrate (66 mg, 0.28 mmol), product from step A (1.50 g, 4.518 mmol), purification by preparative HPLC: column: Chiral pak ADH (19×250 mm) 10μ, mobile phase: hexane: isopropyl alcohol (80:20), flow rate: 15 mL/min, yield: 1.0 g of 76 d (44.3%)
Step C
10% PdC (100 mg), product of step B (600 mg, 1.2024 mmol), hydrogen balloon for 2 h.: 1,1-carbonyldiimadazole (279 mg, 2.3012 mmol.), yield: 420 mg (92.4%)
Step D
Product from step C (420 mg, 1.0632 mmol), 1,2-diamino-4-bromo benzene (200 mg, 1.06 mmol), cesium fluoride (240 mg, 1.59 mmol.), 1,2-diaminocyclohexane (20 mg), copper iodide (20 mg, 4 mol %), yield: 110 mg (22%)
Then the above product (200 mg, 0.40 mmol) was dissolved in formic acid, yield: 150 mg (73.9%)
Conversion into HCl-salt: Free base (60 mg, 0.14 mmol) in acetone and 1M HCl in ether (0.3 mL, 0.3242 mmol) yield: 40 mg, MS m/z 407.1 (M−H)$^+$; 1H-NMR 400 MHz, CD3OD): δ 9.33 (s, 1H); 7.99 (s, 1H); 7.70 (dd, 2H); 7.39 (d, 2H); 7.02 (d, 2H); 5.80 (t, 1H); 4.88 (2H, merged with solvent); 4.39 (s, 2H); 4.26 (t, 1H); 3.68-3.60 (m, 8H), HPLC (λ=214 nm, [A]: rt 1 4.51 min (100%).

Example 81

(S)-4-(4-(2-morpholinoethoxy)phenyl)-3-(1H-benzo[d]imidazol-6-yl)oxazolidin-2-one The compound was synthesized according to method 5
Step A
1.5M n-Butyl lithium (11.4 mL, 17 mmol), methyl triphenyl phosphonium bromide (6.0 g, 17 mmol), 4-(2-morpholinoethoxy benzaldehyde (2 g, 8.51 mmol), yield: 1.6 g (80.8%)
Step B
t-butyl hypochlorite (2.3 mL, 20.93 mmol), Benzylcarbamate (3.20 g, 20.45 mmol), 0.4M aqueous sodium hydroxide (0.1 g in 6.4 mL), (DHQ)$_2$PHAL (270 mg, 0.34 mmol), potassium osmate dihydrate (100 mg, 0.28 mmol), product from step A (1.60 g, 6.87 mmol), yield: 1.0 g (36.23%)
Step C
Thionyl chloride (1.5 mL, 20 mmol), product from step B (1.0 g, 2.5 mmol), yield: 400 mg (54.79%)
Step D
Product from step C (400 mg, 0.73 mmol), 4-bromo 1,2-diamino benzene (140 mg, 0.74 mmol), cesium fluoride (166 mg, 1.09 mmol), 1,2-diaminocyclohexane (0.3 mL), copper iodide (10 mg), yield: 200 mg (37.02%)
Then the above product (150 mg, 0.376 mmol) was dissolved in formic acid, yield: 80 mg (52.28%)
Conversion into HCl-salt: free base (80 mg, 0.2 mmol) in acetone and 1M HCl in ether (0.43 mL, 0.43 mmol), yield: 50 mg (53.76%), MS m/z 409.3 (M+H)$^+$; (400 MHz, DMSO-d6): δ 9.39 (s, 1H); 7.90 (s, 1H); 7.74 (d, 1H); 7.57 (d, 1H); 7.38 (d, 2H); 6.95 (d, 2H); 5.80 (t, 1H); 4.85 (t, 1H); 4.37 (s, 2H); 4.16 (t, 1H); 3.84-3.89 (bs, 5H); 3.48 (t, 3H); 3.16 (bs, 2H), HPLC (λ=214 nm, [A]: rt 4.64 min (94.3%).

Example 82

(S)-3-(1H-benzo[d]imidazol-6-yl)-4-(2,3-difluorophenyl)oxazolidin-2-one

The compound was synthesized according to method 6
Step A
Potassium cyanide (5.7 g, 87.96 mmol.), 2,3-difluoro benzaldehyde (10.0 g, 70.368 mmol.), ammonium carbonate (33.14 g, 211.10 mmol.) water (125 mL: 75 mL). yield: 10.0 g (67.0%).
Step B
Product of step A (10 g, 25.64 mmol.), 10% NaOH (100 mL) yield 22.0 g
Step C
Thionyl chloride (8 mL), product of step B (22.0 g crude), methanol (100 mL), yield: 5.0 g (35.15%).
Step D
Product of step C (5 g, 24.87 mmol), sodium borohydride (2.8 g, 74.62 mmol.), ethanol (100 mL), yield: 4.0 g (92.96%).
Step E
Triethylamine (6.4 mL, 46.24 mmol), Boc anhydride (6.8 mL, 30 mmol), product of step D (4.0 g, 23.12 mmol), dichloromethane (100 mL). yield 4.5 g crude.
Step F
Thionyl chloride (3.9 mL, 52.744 mmol) product of step E (1.8 g, 6.593 mmol) tetrahydrofuran (75 mL). yield: 1.2 g (87.0%)
Step G
Product of step F (500 mg, 2.51 mmol), 1,2-diamino 4-iodo benzene (460 mg, 2.51 mmol), cesium fluoride (570 mg, 3.76 mmol), 1,4-dioxane (15 mL), 1,2-diaminocyclohexane (28 mg, 0.25 mmol), copper iodide (45 mg, 0.25 mmol) yield: 350 mg (45.6%).
Product of step G (300 mg, 0.1 mmol), formic acid (5 mL). yield 150 mg (47.6%)

Coversion into Hydrochloride:

1M ether-HCl (0.57 mL, 0.57 mmol) free base (150 mg, 0.47 mmol) in dichloromethane (10 mL), yield: 140 mg (84.9%), MS m/z: 314 [M-1]; $^1$H-NMR (400 MHz, DMSO-d6): δ 9.35 (s, 1H); 7.94 (s, 1H); 7.77 (d, 1H); 7.57 (d, 1H); 7.41-7.14 (m, 3H); 6.12 (t, 1H); 4.92 (t, 1H); 4.37 (m, 1H); HPLC ([A]): rt 9.76 min (100%)

Example 83

(S)-3-(1H-benzo[d]imidazol-6-yl)-4-(3-fluorophenyl)oxazolidin-2-one

The compound was synthesized according to method 5.
Step B
t-butyl hypochlorite (5.6 mL, 49.25 mmol), benzylcarbamate (7.42 g, 49.12 mmol), 0.4M aqueous sodium hydroxide (2.0 g in 125 mL), (DHQ)$_2$PHAL (637 mg, 0.82 mmol), 3-Fluoro styrene (2.0 g, 16.37 mmol.), potassium osmate dihydrate (240 mg, 0.65 mmol), yield 1.01 g (21.13%)
Step C
Thionyl chloride (2.3 mL, 31.50 mmol), product from step B (1.0 g, 3.46 mmol), yield: 510 mg (81.47%)
Step D
Product from step C (500 mg, 2.76 mmol), 4-Bromo-1,2-diamino benzene (516 mg, 2.76 mmol), cesium fluoride (630 mg, 4.14 mmol), 1,2-diaminocyclohexane (47 mg, 0.41 mmol), copper iodide (80 mg, 0.41 mmol), yield: 130 mg (39.39%). Then the above product (450 mg, 1.56 mmol) was dissolved in formic acid, yield: 450 mg (96.77%)

Conversion into HCl-salt: Free base (440 mg, 1.48 mmol) in acetone and 1M HCl in ether (1.8 mL, 1.8 mmol) yield: 60 mg (74%), MS m/z 298.2 (M+H)$^+$; $^1$H-NMR (400 MHz, DMSO-d6): δ 9.35 (bs, 1H); 7.91 (s, 1H); 7.75 (d, 1H); 7.56 (d, 1H); 7.25-7.41 (m, 3H); 7.13-7.09 (m, 1H); 5.88 (t, 1H); 4.88 (t, 1H); 4.21 (q, 1H); HPLC (λ=214 nm, [A]: rt 8.93 min (100%).

Example 84

(S)-3-(1H-benzo[d]imidazol-6-yl)-4-(3-fluoro-5-(trifluoromethyl)phenyl)oxazolidin-2-one The compound was synthesized according to method 6.
Step A
3-Fluoro-5-trifluoromethyl benzaldehyde (200 mg, 1.041 mmol), potassium cyanide (85 mg, 1.301 mmol), ammonium carbonate (490 mg, 3.123 mmol) ethanol (5 mL), water (2 mL). yield: 250 mg (91.58%)
Step B
Compound from step A (250 mg, 0.954 mmol) in 10% aqueous sodium hydroxide (5 mL) yield: 900 mg
Step C
Thionyl chloride (0.2 mL, 2.8489 mmol), compound from step B (225 mg, 0.949 mmol), methanol (5 mL), yield 150 mg (63.03%)
Step D
Sodium borohydride (45 mg, 1.195 mmol), product from Step C (100 mg, 0.398 mmol), methanol (5 mL), yield: 75 mg (85.23%)
Step E
Triethylamine (3.1 mL, 22.422 mmol), di-tert-butyl dicarbonate (2.8 mL, 12.332 mmol), product from Step D (2.5 g, 11.211 mmol), dichloromethane (50 mL), chiral prep HPLC:: Column: ChiralPak AD-H (250×4.6 mm) 5u, mobile phase: hexane: IPA:DEA (95:05:0.1), flow rate: 1.0 mL/min. UV: 265 nm, temp 25° C., yield 310 mg (8.61%)

Step F
Thionyl chloride (0.55 mL, 7.678 mmol), product from step D (310 mg, 0.9598 mmol), tetrahydrofuran (10 mL), yield: 200 mg (83.68%)
Step G
Product from step F (300 mg, 1.205 mmol), 4-Bromo-1,2-diaminobenzene (225 mg, 1.205 mmol), cesium fluoride (275 mg, 1.807 mmol), copper iodide (23 mg, 0.121 mmol), 1,4-dioxan (10 mL), 1,2-diamino cyclohexane (14 mg, 0.121 mmol), yield: 210 mg (49.07%)
Product from step G (210 mg, 0.592 mmol), formic acid (5 mL) yield: 175 mg (81.40%)
Conversion into Hydrochloride:
1M HCl in ether (0.20 mL, 0.247 mmol) free base (75 mg, 0.206 mmol) acetone (3 mL) yield: 75 mg (90.36%). MS m/z: 366 [M+H]$^+$; $^1$H-NMR (DMSO d$_6$, 500 MHz): δ 9.36 (bs, 1H); 7.93 (s, 1H); 7.80-7.75 (m, 3H); 7.74 (d, 1H); 7.58 (d, 1H); 6.07 (t, 1H); 4.91 (t, 1H); 4.25 (t, 1H); HPLC [A]: rt 8.72 min (96.47%)

Example 85

(S)-3-(1H-benzo[d]imidazol-6-yl)-4-(3-chlorophenyl)oxazolidin-2-one

The compound was synthesized according to method 5.
Step A
1.5M n-Butyl lithium (28.5 mL, 42.7 mmol), methyl triphenyl phosphonium bromide (11.44 g, 32.02 mmol), 3-chloro benzaldehyde (3 g, 21.35 mmol), yield: 1.6 g (54.20%)
Step B
Benzylcarbamate (5 g, 33.69 mmol), 0.4M aqueous sodium hydroxide (1.3 g in 79 mL), (DHQ)$_2$PHAL (420 mg, 0.54 mmol), potassium osmate dihydrate (160 mg, 0.43 mmol), product from step A (1.5 g, 10.86 mmol), yield: 850 mg (25.75%)
Step C
Thionyl chloride (1.74 mL, 23.6 mmol), product from step B (900 mg, 2.95 mmol), yield: 450 mg (77.58%)
Step D
Product from step C (330 mg, 1.67 mmol), 1,2-diamino 4-iodo benzene (390 mg, 1.67 mmol), cesium fluoride (380 mg, 2.51 mmol), 1,2-diaminocyclohexane (21 mg, 15 mmol), copper iodide (35 mg, 15 mmol), yield: 110 mg (22%). Then the above product (70 mg, 0.23 mmol) was dissolved in formic acid, yield: 55 mg (76.38%)
Conversion into HCl-salt: Free base (55 mg, 0.17 mmol) in acetone and 1M HCl in ether (0.17 mL) yield: 35 mg (57.37%), MS m/z 314.1 (M+H)$^+$; 1H-NMR (400 MHz, DMSO-d6): δ 9.42 (br s, H); 7.94 (s, H); 7.78-7.76 (m, H); 7.60-7.55 (m 2H); 7.39-7.36 (br m, 3H); 5.91-5.87 (m, H); 4.91-4.86 (m, H); 4.24-4.20 (m, H), HPLC (λ=214 nm, [A]: rt 10.51 min (97.16%).

Example 86

(S)-3-(1H-benzo[d]imidazol-6-yl)-4-(4-chlorophenyl)oxazolidin-2-one

The compound was synthesized according to method 5.
Step A
1.5M n-Butyl lithium (21 mL, 21.135 mmol), methyl triphenyl phosphonium bromide (19.06 g, 53.35 mmol), 4-chloro benzaldehyde (5 g, 35.56 mmol), yield: 2.5 g (50.9%)
Step B
Benzylcarbamate (1.5 g, 10.869 mmol), 0.4M aqueous sodium hydroxide (1.3 g in 81 mL), (DHQ)$_2$PHAL (420 mg, 0.54 mmol), potassium osmate dihydrate (160 mg, 0.43 mmol), product from step A (1.5 g, 10.869 mmol.), yield: 1.2 g (36.19%

Step C

Thionyl chloride (2.3 mL, 31.47 mmol), product from step B (1.2 g, 3.934 mmol), yield: 0.6 g (50.1%)

Step D

Product from step C (400 mg, 2.03 mmol), 1,2-diamino 4-iodo benzene (390 mg, 2.03 mmol), cesium fluoride (460 mg, 3.04 mmol), 1,2-diaminocyclohexane (23 mg, 0.2 mmol), copper iodide (38 mg, 0.203 mmol), yield: 340 mg (55.2%). Then the above product (300 mg, 0.99 mmol) was dissolved in formic acid 5 mL, yield: 170 mg (54.86%)

Conversion into HCl-salt: Free base (170 mg, 0.54 mmol) in acetone and 1M HCl in ether (0.65 mL) yield: 120 mg (63.5%%), MS m/z 314.1 (M+H)$^+$; $^1$H-NMR (400 MHz, DMSO-d6): δ 9.34 (s, H); 7.90 (s, H); 7.75-7.73 (m, H); 7.56-7.54 (m, H); 7.47-7.40 (br m, 4H); 5.89-5.86 (m, H); 4.90-4.86 (m, H); 4.21-4.18 (m, H), HPLC (λ=214 nm, [A]: rt 10.56 min (94.89%).

Example 87

(S)-3-(1H-benzo[d]imidazol-6-yl)-4-[4-(3-chlorophenyl)phenyl]oxazolidin-2-one

The compound was synthesized according to method 5.

Step A 1.5M n-Butyl lithium (31.2 mL, 46 mmol), phenyl magnesium methyl bromide (16.50 g, 46 mmol), 4-(3-chlorophenyl) benzaldehyde (5 g, 23 mmol), yield: 3.5 g (70.99%)

Step B 1,3 dichloro-5,5-dimethylimidazolidine-2-dione (2.8 g, 14.20 mmol), t-butylcarbamate (3.3 g, 28.30 mmol), 0.5M aqueous sodium hydroxide (58 mL), (DHQ)$_2$PHAL (182 mg, 0.25 mmol), potassium osmate dihydrate (140 mg, 0.38 mmol), product from step A (2 g, 9.35 mmol), yield: 600 mg (18.51%)

Step C

Thionyl chloride (0.55 mL, 4.67 mmol), product from step B (300 mg, 0.57 mmol), yield: 150 mg (65.21%)

Step D

Product from step C (260 mg, 0.73 mmol), 1,2-diamino 4-bromo benzene (140 mg, 0.74 mmol) potassium carbonate (250 mg, 1.85 mmol), copper iodide (14 mg) 1, 155 mg (42.34%)

Then the above product (150 mg), triethylorthoformate (1 mL), then purified by chiral Prep HPLC Column: CHIRALPAK 1A (250×4.6 mm); 5μ, mobile phase: hexane: EtOH: DEA (70:30:0.1), flow rate: 18 mL/min, U.V:254 nm, yield: 55 mg (36.66%), MS m/z 390.2 (M+H)$^+$; $^1$H-NMR (400 MHz, DMSO-d6): δ 8.18 (s, H); 1.68-1.66 (m, 4H); 7.59-7.57 (m, H); 7.51-7.49 (m, 3H); 7.47-7.38 (br m, 2H); 7.32-7.30 (m, H); 5.85-5.81 (m, H); 4.89-4.85 (m, H); 4.21-4.17 (m, H), HPLC (λ=214 nm, [A]: rt 14.40 min (100%)

Example 88

(S)-3-(1H-benzo[d]imidazol-6-yl)-4-[3-(3-chlorophenyl)phenyl]oxazolidin-2-one

The compound was synthesized according to method 5.

Step A 1.5M n-Butyl lithium (31 mL, 46 mmol), phenyl magnesium methyl bromide (16.5 mmol, 46 mmol), 3-(3-chlorophenyl)-benzaldehyde (5 g, 23 mmol), yield: 3.6 g (72.72%)

Step B 1,3-dichloro-5,5-dimethylimidazolidine-2,-dione (1.4 g, 7.10 mmol), t-butylcarbamate (1.7 g, 14.50 mmol), 0.5M aqueous sodium hydroxide (29 mL), (DHQ)$_2$PHAL (95 mg, 12 mmol), potassium osmate dihydrate (70 mg), product from step A (1 g, 4.6 mmol), yield: 610 mg (37.62%)

Step C

Thionyl chloride (1 mL, 13.78 mmol), product from step B (600 mg, 1.73 mmol), yield: 420 mg (88.98%))

Step D

Product from step C (300 mg, 1.10 mmol), 1,2-diamino 4-iodo benzene (210 mg, 1.12 mmol), cesium fluoride (340 mg, 2.20 mmol), copper iodide (35 mg, 15 mmol), 1,2-diaminocyclohexane (21 mg, 15 mmol), yield: 250 mg (60%), Then the above product (230 mg), triethylorthoformate (5 mL), yield: 100 mg (41.66%)

Conversion into HCl-salt: Free base (80 mg, 0.2 mmol) in acetone and 1M HCl in ether (0.2 mL), yield: 50 mg (57.47%), MS m/z 390.2 (M+H)$^+$; $^1$H-NMR (400 MHz, DMSO-d6): δ 9.34 (br s, H); 7.94 (s, H); 7.84 (s, H); 7.75-7.73 (m 2H); 7.63-7.61 (m, 3H); 7.51-7.42 (br m, 4H); 5.95-5.91 m, H); 4.94-4.90 (m, H); 4.32-4.28 (m, H), HPLC (λ=214 nm, [A]: rt 14.32 min (100%).

Example 89

(S)-3-(1H-benzo[d]imidazol-6-yl)-4-(4-(4-phenylpiperazin-1-yl)phenyl)oxazolidin-2-one The compound was synthesized according to method 5.

Step A 1.5M n-Butyl lithium (3.2M; 12.9 mL, 41.35 mmol), methyl triphenyl phosphonium bromide (11.0 g, 31.01 mmol), 4-(4-phenylpiperazin-1-yl)phenyl carbaldehyde (5.5 g, 20.67 mmol), yield: 2.6 g (47.7%)

Step B t-butyl hypochlorite (2.9 mL, 25.41 mmol), benzylcarbamate (3.9 g, 25.83 mmol), 0.4M aqueous sodium hydroxide (1.0 g in 58 mL), (DHQ)$_2$PHAL (320 mg, 0.41 mmol), product from step A (2.2 g, 8.33 mmol) potassium osmate dihydrate (100 mg, 0.28 mmol) Further purification by preparative HPLC, yield 550 mg (15.32%)

Step C

Thionyl chloride (0.75 mL, 10.20 mmol), product from step B (550 mg, 1.27 mmol), yield: 280 mg (68.29%)

Step D

Product from step C (250 mg, 0.77 mmol), 1,2-diamino 4-iodo benzene (180 mg, 0.77 mmol), cesium fluoride (170 mg, 1.15 mmol), 1,2-diaminocyclohexane (10 mg, 0.09 mmol), copper iodide (14 mg, 0.07 mmol), yield: 130 mg (39.39%)

Then the above product (120 mg, 0.28 mmol) was dissolved in formic acid, yield: 80 mg (66.66%)

Conversion into HCl-salt: Free base (70 mg, 0.16 mmol) in acetone and 1M HCl in ether (0.2 mL, 0.20 mmol) yield: 60 mg (74%), 1H-NMR (400 MHz, DMSO-d6): 9.48 (s, 1H); 7.92 (s, 1H); 7.80 (d, 1H); 7.62 (d, 1H); 7.25-7.30 (m, 4H); 7.02-6.97 (m, 5H); 5.74 (t, 1H); 4.84 (t, 1H); 4.18 (t, 3H); 3.29 (s, 7H); MS=440 (M+1)

Example 90

(S)-3-(1H-benzo[d]imidazol-6-yl)-4-(4-(4-methylpiperazin-1-yl)phenyl)oxazolidin-2-one The compound was synthesized according to method 5.

Step A 1.5M n-Butyl lithium (20 mL, 29.42 mmol), methyl triphenyl phosphonium bromide (110.50 g, 29.42 mmol), 4-(4-methylpiperazin-1-yl)phenyl carbaldehyde (3 g, 14.70 mmol), yield: 2 g (67.3%)

Step B

Benzylcarbamate (4.48 g, 29.70 mmol), 0.4M aqueous sodium hydroxide (60.5 mL, 30.2 mmol)), (DHQ)$_2$PHAL (385 mg, 0.50 mmol), product from step A (2 g, 9.90 mmol.) potassium osmate dihydrate (145 mg, 0.40 mmol) Further purification by preparative HPLC, yield 1 g (27.39%)

Step C

Thionyl chloride (0.8 mL, 10.84 mmol), product from step B (0.5 g, 1.35 mmol), yield: 170 mg (48.57%)

Step D

Product from step C (350 mg, 1.34 mmol), 1,2-diamino 4-iodo benzene (250 mg, 1.34 mmol), cesium fluoride (300 mg, 2.01 mmol), 1,2-diaminocyclohexane (12 mg, 0.34 mmol), copper iodide (25 mg, 0.134 mmol), yield: 130 mg (26.53%)

Then the above product (120 mg, 0.32 mmol) was dissolved in formic acid, yield: 70 mg (58.33%)

Conversion into HCl-salt: Free base (70 mg, 0.18 mmol) in acetone and 1M HCl in ether (0.4 mL, 0.408 mL) yield: 55 mg (67.07%), MS m/z 378.4 (M+H)$^+$, $^1$H-NMR (400 MHz, CDCl$_3$): δ 2.51 (s, 3H); 2.76 (s, 2H); 3.05-3.07 (m, 2H); 3.42 (s, 2H); 3.75-3.77 (m, 2H); 4.14-4.18 (m, H); 4.82-4.86 (m, H); 5.74-5.78 (m, H); 6.94-6.96 (m, 2H); 7.29-7.31 (m, 2H); 7.59-7.61 (m, H); 7.76-7.78 (m, H); 7.92-7.93 (m, H); 9.55 (s, H); 11.25 (bs, H), HPLC (λ=214 nm), [A]: rt 5.23 min (96.7%)

Example 91

(S)-3-(1H-benzo[d]imidazol-6-yl)-4-(3-(4-phenylpiperazin-1-yl)phenyl)oxazolidin-2-one The compound was synthesized according to method 5.

Step A n-Butyl lithium (1.3M; 12 mL, 15.13 mmol), methyl triphenyl phosphonium bromide (5.40 g, 15.13 mmol), 3-(4-phenylpiperazin-1-yl)phenyl) carbaldehyde (2.0 g, 7.52 mmol), yield: 1.8 g (92.78%)

Step B t-butyl hypochlorite (2.3 mL, 20.45 mmol), benzylcarbamate (3.10 g, 20.45 mmol), 0.4M aqueous sodium hydroxide (830 mg in 54 mL), (DHQ)$_2$PHAL (265 mg, 0.34 mmol), product from step A (1.80 g, 6.80 mmol) potassium osmate dihydrate (100 mg, 0.28 mmol) Further purification by preparative HPLC, yield; 425 mg (14%)

Step C

Thionyl chloride (0.81 mL, 10.81 mmol), product from step B (400 mg, 1.35 mmol), yield: 200 mg (68.96%)

Step D

Product from step C (200 mg, 0.62 mmol), 1,2-diamino 4-iodo benzene (115 mg, 0.62 mmol), cesium fluoride (190 mg, 1.24 mmol)), 1,2-diaminocyclohexane (10 mg, 0.09 mmol), copper iodide (17 mg, 0.09 mmol), yield: 130 mg (50%)

Then the above product (120 mg, 0.28 mmol) was dissolved in formic acid, yield: 100 mg (81.96%)

Conversion into HCl-salt: Free base (100 mg, 0.23 mmol) in acetone and 1M HCl in ether (0.5 mL, 0.5 mmol) yield: 65 mg (56.53%), MS m/z 440.4 (M+H)$^+$, $^1$H-NMR (400 MHz, DMSO-d$_6$): δ 9.52 (s, 1H); 7.96 (s, 1H); 7.78 (d, 1H); 7.65 (t, 3H); 7.77-7.20 (m, 5H); 7.02-6.96 (m, 2H); 6.87 (d, 1H); 5.79 (t, 1H); 4.86 (t, 1H); 4.19 (t, 1H); 3.42 (bs, 8H), HPLC (λ=214 nm), [A]: rt 11.36 min (100%)

Example 92

(S)-3-(2-methyl-1H-benzo[d]imidazol-6-yl)-4-phenyloxazolidin-2-one

The compound was synthesized as trifluoroacetate salt starting from (S)-4-phenyloxazolidin-2-one (1 equiv., 0.163 g, 1 mmol), 4-iodobenzene-1,2-diamine (1 equiv., 0.234 g, 1 mmol), copper(I) iodide (0.1 equiv., 0.019 g, 0.1 mmol), cesium fluoride (2 equiv., 0.304 g, 2 mmol), cyclohexane-1,2-diamine (0.1 equiv., 0.012 mL, 0.1 mmol). The solids were given together in a reaction flask and the flask was purged with argon. A solution of cyclohexane-1,2-diamine in 4 mL dioxane was added to the flask. The reaction was stirred at 95° C. for 20 hours, before the reaction was cooled down to 45° C. and filtered through a pad of celite. The pad was washed with warm dichloromethane and the solution was concentrated under reduced pressure. The intermediate product was purified via FPLC using a chloroform-methanol gradient (0→10%, product elutes at about 5%). Yield: 0.215 g (80%); MS m/z 270.3 (M+H)$^+$ The (S)-3-(3,4-diaminophenyl)-4-phenyloxazolidin-2-one was dissolved in 12 mL of triethyl orthoacetate and the reaction was stirred at 150° C. for 0.5 h before the reaction was cooled down. The excess of triethyl orthoacetate was removed under reduced pressure. The final product was purified by means of FPLC using chloroform-methanol gradient (0→10%), followed by preparative HPLC using a water-acetonitrile gradient with 0.04% trifluoroacetic acid.

Yield: 0.095 g (23.3%); MS m/z 294.2 (M+H)$^+$; $^1$H NMR (400 MHz, DMSO-D$_6$): δ 2.67 (s, 3H); 4.16-4.20 (m, H); 4.85-4.89 (m, H); 5.79-5.83 (m, H); 7.24-7.40 (m, 5H); 7.49 (dd, H, $^3$J=9.1 Hz, $^4$J=2.1 Hz); 7.63 (d, H, $^3$J=9.1 Hz); 7.76 (d, H, $^4$J=2.1 Hz), HPLC (λ=214 nm), [B]: rt 8.69 min (100%).

Example 93

(S)-4-(1H-benzo[d]imidazol-6-yl)-5-(4-propoxyphenyl)morpholin-3-one

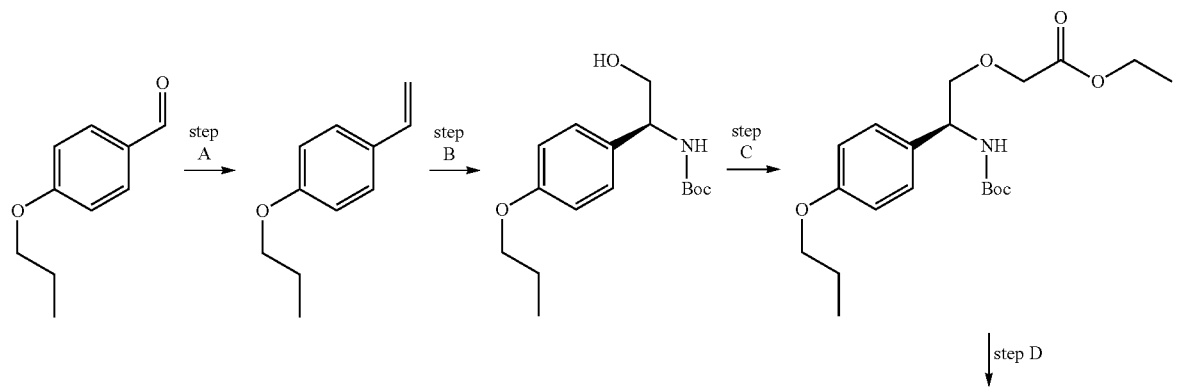

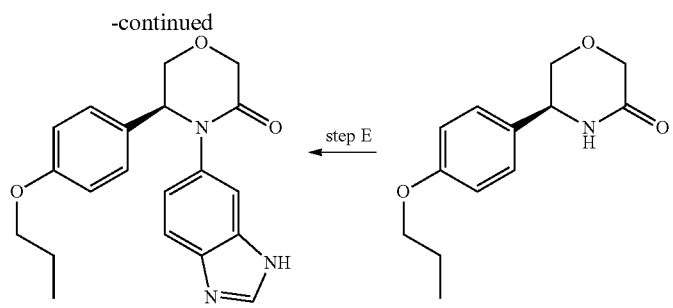

Step A:

A 1M-solution of potassium tert-butoxide (41.7 mL, 41.7 mmol) in THF was added to a suspension of methyltriphenylphosphonium bromide (14.89 g, 41.7 mmol) in 100 mL THF at 0° C. under argon atmosphere. The reaction was allowed to warm up to ambient temperature and was stirred for 10 minutes. After that the reaction was cooled down to 0° C. again, a solution of 4-propoxybenzaldehyde (4.92 mL, 31.1 mmol) in 70 mL THF was added. The reaction was stirred at ambient temperature until the TLC control (heptane/chloroform 1:1) indicated a complete consumption of the aldehyde. The reaction mixture was filtered and the filtrate was concentrated under vacuum. The product was purified via flash-chromatography (hexane/chloroform 8:2).

Yield: 16.5 g (94.6%)

Step B:

Tert-butyl carbamate (9.08 g, 77.5 mmol) was dissolved in 100 mL 1-propanol and 0.38 M aqueous NaOH (198 mL, 75.2 mmol) was added. The reaction was stirred for 5 minutes at ambient temperature before 1,3-dichloro-5,5-dimethylimidazolidine-2,4-dione (7.56 g, 38.4 mmol) was added and the reaction was stirred for 10 minutes at ambient temperature. $(DHQ)_2PHAL$ (1.17 g, 1.5 mmol) dissolved in 100 mL 1-propanol was added. After that 1-propoxy-4-vinylbenzene (4.055 g, 25 mmol) obtained from step A dissolved in 200 mL 1-propanol was added followed by potassium osmate dihydrate (0.368 g, 1 mmol) suspended in 2 mL of 0.38 M aqueous NaOH (0.76 mmol). The reaction was stirred at ambient temperature until complete consumption of the styrene (TLC control). Water (170 mL) was added and the reaction mixture was extracted three times by means of 250 mL ethyl acetate. The combined organic layer was washed with brine (50 mL), dried over sodium sulfate, filtered and the solvents were removed under reduced pressure. The product was purified via flash chromatography using a heptane-ethyl acetate gradient. The product elutes at about 25 percent ethyl acetate.

Yield: 5.49 g (74.4%); MS m/z 296.3 (M+H)$^+$

Step C:

(S)-tert-butyl 2-hydroxy-1-(4-propoxyphenyl)ethylcarbamate (0.47 g, 1.59 mmol) and cesium carbonate (0.673 g, 1.91 mmol) were given into a reaction flask and 15 mL of acetonitrile was added. The mixture was stirred and ethyl 2-bromoacetate (0.332 mL, 3 mmol) was added. The reaction was stirred at 100° C. for 2 hours. The reaction was cooled down to ambient temperature, before 50 mL water and 15 mL buffer (pH7) were added. The mixture was neutralized using 1N aqueous hydrochloric acid. The aqueous layer was extracted three times with 50 mL ethyl acetate. The organic layers were combined, washed with brine, dried over sodium sulfate, filtered and the solvents were removed under reduced pressure. The product was purified via FPLC using a hexane-ethyl acetate gradient (0→40%).

Yield: 0.11 g (18.1%); MS m/z 382.4 (M+H)$^+$

Step D: (S)-ethyl 2-(2-(tert-butoxycarbonylamino)-2-(4-propoxyphenyl)ethoxy)acetate (0.11 g, 0.29 mmol) obtained from step C was dissolved in 3 mL of dichchloromethane and 0.6 mL trifluoroacetic acid was added to the stirred solution. The Boc-deprotection was monitored by TLC. After the deprotection was complete the solvent was removed and the oil was readopt in 3 mL THF, 0.725 mL diisopropylethylamine and a excess of potassium carbonate were added to the solution. The reaction was stirred at 50° C. for 18 hours. The solvent was removed and the oil was readopt in 10 mL dichloromethane and washed with brine (5 mL). The organic layer was dried over sodium sulfate, filtered and the solvent was removed under reduced pressure. The product was purified via FPLC using a heptane-ethyl acetate gradient (0→100%).

Yield: 0.044 g (64.5%); MS m/z 236.2 (M+H)$^+$

Step E:

The final product was synthesized as trifluoroacetate salt starting from (S)-5-(4-propoxyphenyl)morpholin-3-one (0.044 g, 0.19 mmol), 4-iodobenzene-1,2-diamine (0.044 g, 0.19 mmol), copper(I) iodide (0.004 g, 0.019 mmol), cesium fluoride (0.058 g, 0.38 mmol), cyclohexane-1,2-diamine (0.0025 mL, 0.019 mmol). The solids were given together in a reaction flask and the flask was purged with argon. A solution of cyclohexane-1,2-diamine in 2 mL dioxane was added to the flask. The reaction was stirred at 95° C. for 4 days, before the reaction was cooled down to 45° C. and filtered through a pad of celite. The pad was washed with warm dichloromethane and the solution was concentrated under reduced pressure. The intermediate product was purified via FPLC using a chloroform-methanol gradient (0→10%)

Yield: 0.01 g (15%); MS m/z 342.2 (M+H)$^+$

The (S)-4-(3,4-diaminophenyl)-5-(4-propoxyphenyl)morpholin-3-one was dissolved in 0.5 mL of triethyl orthoformate and the reaction was stirred at 150° C. for 0.5 h before the reaction was cooled down. The excess of triethyl orthoacetate was removed under reduced pressure. The final product was purified by means of HPLC using water-acetonitrile gradient with 0.04% trifluoroacetic acid.

Yield: 0.003 g (0.26%); MS m/z 352.4 (M+H)$^+$; HPLC (λ=214 nm), [B]: rt 10.57 min (100%).

Example 94

3-(1H-benzo[d]imidazol-6-yl)-4-(4-propoxyphenyl)-1,3-oxazinan-2-one

The compound was synthesized according to method 7.

Step A:

The compound was synthesized as a trifluoroacetate salt starting from 4-propoxybenzaldehyde (3.16 mL, 20 mmol), malonic acid (2.08 g, 20 mmol), ammonium acetate (3.08 g, 40 mmol). yield: 2.17 g (48.6%)

Step B:

Product obtained from step A (2.15 g, 9.6 mmol), 2M solution of lithium aluminium hydride (7.2 mL, 14.4 mmol), yield: 1.61 g (80.1%)

Step C:

Product obtained from step B (1.61 g, 7.7 mmol), di(1H-imidazol-1-yl)methanone (1.622 g, 10 mmol), yield: 0.9 g (49.7%)

Step D:

Product obtained from step C (0.45 g, 1.91 mmol), 4-iodobenzene-1,2-diamine (0.448 g, 1.91 mmol), copper(I) iodide (0.036 g, 0.19 mmol), potassium carbonate (0.528 g, 3.82 mmol), cyclohexane-1,2-diamine (0.023 mL, 0.19 mmol), triethyl orthoformate (10 mL), Yield: 0.018 g (2.7%);

Overall yield: 0.52%; MS m/z 352.4 (M+H)$^+$; $^1$H NMR (400 MHz, DMSO-D$_6$): δ 0.89-0.93 (m, 3H); 1.60-1.69 (m, 2H); 2.02-2.09 (m, H); 2.51-2.58 (m, H); 3.80-3.83 (m, 2H); 4.25-4.31 (m, H); 4.36-4.41 (m, H); 5.23-5.25 (m, H); 6.80 (d, 2H, J=8.7 Hz); 7.24 (d, 2H, J=8.7 Hz); 7.37-7.39 (m, H); 7.61-7.67 (m, 2H); 9.08 (s, H), HPLC (λ=214 nm), [B]: rt 10.63 min (100%).

Example 95

(S)-3-(H-imidazo[1,2-a]pyridin-7-yl)-4-phenyloxazolidin-2-one

The compound was synthesized starting from 7-bromoimidazo[1,2-a]pyridine (0.099 g, 0.5 mmol), copper(I) iodide (0.010 g, 0.05 mmol), cesium fluoride (0.152 g, 1 mmol), cyclohexane-1,2-diamine (0.006 mL, 0.05 mmol) as described in method 5 step D.

Yield: 0.045 g (32.2%); MS m/z 280.1 (M+H)$^+$; $^1$H NMR (400 MHz, DMSO-D$_6$): δ 4.12-4.16 (m, H); 4.82-4.86 (m, H); 5.76-5.79 (m, H); 7.24-7.41 (m, 8H); 7.76 (s, H); 8.41 (d, H, J=7.5 Hz), HPLC (λ=214 nm), [B]: rt 7.73 min (100%).

Example 96

(4S,5R)-3-(H-imidazo[1,2-a]pyridin-7-yl)-4,5-diphenyloxazolidin-2-one

The compound was synthesized starting from 7-bromoimidazo[1,2-a]pyridine (0.099 g, 0.5 mmol), copper(I) iodide (0.010 g, 0.05 mmol), potassium carbonate (0.138 g, 1 mmol), cyclohexane-1,2-diamine (0.006 mL, 0.05 mmol) as described in method 5 step D.

Yield: 0.057 g (32.1%); MS m/z 356.2 (M+H)$^+$; $^1$H NMR (400 MHz, DMSO-D$_6$): δ 6.15 (d, H, J=7.9 Hz); 6.24 (d, H, J=7.9 Hz); 6.97-6.99 (m, 2H); 7.03-7.16 (m, 8H); 7.38 (s, H); 7.43-7.45 (m, 2H); 7.81 (s, H); 8.48 (d, H, J=7.1 Hz), HPLC (λ=214 nm), [B]: rt 12.07 min (99.5%).

Example 97

(4S,5R)-3-(imidazo[1,2-a]pyridin-6-yl)-4,5-diphenyloxazolidin-2-one

The compound was synthesized starting from 6-bromoimidazo[1,2-a]pyridine (0.197 g, 1 mmol), copper(I) iodide (0.019 g, 0.1 mmol), cesium fluoride (0.304 g, 2 mmol), cyclohexane-1,2-diamine (0.012 mL, 0.1 mmol) as described in method 5 step D.

Yield: 0.033 g (9.3%); MS m/z 356.3 (M+H)$^+$; $^1$H NMR (400 MHz, DMSO-D$_6$): δ 6.06 (d, H, J=8.3 Hz); 6.25 (d, H, J=8.3 Hz); 6.96-6.98 (m, 2H); 7.01-7.16 (m, 8H); 7.4 (s, H); 7.45-7.52 (m, 2H); 8.00 (s, H); 8.96 (bs, H), HPLC (λ=214 nm), [B]: rt 11.28 min (93.9%).

Example 98

(S)-3-(H-imidazo[1,2-a]pyridin-7-yl)-4-(4-propoxyphenyl)oxazolidin-2-one

The compound was synthesized according to method 5.

Step A:

The compound was synthesized starting from 4-propoxybenzaldehyde (7.32 g, 44.6 mmol), methyltriphenylphosphonium bromide (21.34 g, 59.75 mmol), 1M solution of potassium tert-butylate in THF (59.8 mL, 59.75 mmol). yield: 6.13 g (84.7%)

Step B:

Product obtained from step A (3 g, 18.48 mmol), ethyl carbamate (4.94 g, 27.72 mmol), 5,5-dimethylimidazolidine-2,4-dione (5.46 g, 27.72 mmol), (DHQ)$_2$PHAL (0.72 g, 0.92 mmol), K$_2$OsO$_4$x2H$_2$O (0.274 g, 0.74 mmol), 0.5 M aqueous NaOH (112.8 mL, 56.4 mmol), yield: 3 g (61%)

Step C:

Product obtained from step B (3 g, 10.16 mmol), 0.2 M aqueous NaOH (300 mL), yield: 1.21 g (46%)

Step D:

Product obtained from step C (0.376 g, 1.7 mmol), 7-bromoimidazo[1,2-a]pyridine (0.335 g, 1.7 mmol), copper(I) iodide (0.033 g, 0.17 mmol), cesium fluoride (0.52 g, 3.4 mmol), cyclohexane-1,2-diamine (0.021 mL, 0.17 mmol), yield: 0.335 g (58.4%)

Overall yield: 8.7%; MS m/z 338.2 (M+H)$^+$; $^1$H NMR (400 MHz, DMSO-D$_6$): δ 0.92 (t, 3H, J=7.5 Hz); 1.62-1.70 (m, 2H); 3.83-3.87 (m, 2H); 4.12-4.16 (m, H); 4.80-4.84 (m, H); 5.71-5.74 (m, H); 6.89 (d, 2H, J=8.7); 7.26 (d, H, J=7.5 Hz); 7.31-7.38 (m, 3H); 7.48 (br s, H); 7.83 (br s, H); 8.46 (br s, H), HPLC (λ=214 nm), [B]: rt 11.20 min (95%).

Example 99

(S)-4-(4-chlorophenol)-3-(H-imidazo[1,2-a]pyridin-7-yl)oxazolidin-2-one

The compound was synthesized according to method 5.

Step A:

The compound was synthesized starting from 4-chlorobenzaldehyde (0.42 g, 3 mmol), methyltriphenylphosphonium bromide (1.428 g, 4 mmol), 1M solution of potassium tert-butylate in THF (4 mL, 4 mmol)

Yield: 0.12 g (28.9%)

Step B:

Product obtained from step A (0.12 g, 0.869 mmol), ethyl carbamate (0.24 g, 2.695 mmol), 5,5-dimethylimidazolidine-2,4-dione (0.261 g, 1.326 mmol), (DHQ)$_2$PHAL (0.034 g, 0.043 mmol), K$_2$OsO$_4$x2H$_2$O (0.034 g, 0.034 mmol), 0.41 M aqueous NaOH (6.5 mL, 2.652 mmol)

Yield: 0.12 g (56.8%)

Step C:

Product obtained from step B (0.1 g, 0.411 mmol), 0.2 M methanol. NaOH (11.25 mL, 2.25 mmol), yield: 0.07 g (86.2%)

Step D:

Product obtained from step C (0.07 g, 0.355 mmol), 7-bromoimidazo[1,2-a]pyridine (0.07 g, 0.355 mmol), copper(I) iodide (0.007 g, 0.036 mmol), cesium fluoride (0.108 g, 0.71 mmol), cyclohexane-1,2-diamine (0.005 mL, 0.036 mmol), yield: 0.098 g (88%)

Overall yield: 12.5%; MS m/z 314.0 (M+H)+; 1H NMR (400 MHz, DMSO-D6): δ 4.12-4.15 (m, H); 4.80-4.85 (m, H); 5.78-5.82 (m, H); 7.23-7.25 (m, H); 7.30 (s, H); 7.38-7.44 (m, 5H); 7.77 (s, H); 8.42 (d, H, J=7.5 Hz), HPLC (λ=214 nm), [B]: rt 10.35 min (96.8%).

Example 100

3-(imidazo[1,2-a]pyridin-7-yl)-4-(4-propoxyphenyl)-1,3-oxazinan-2-one

The compound was synthesized according to method 7.
Step A:
The compound was synthesized starting from 4-propoxybenzaldehyde (3.16 mL, 20 mmol), malonic acid (2.08 g, 20 mmol), ammonium acetate (3.08 g, 40 mmol). yield: 2.17 g (48.6%)
Step B:
Product obtained from step A (2.15 g, 9.6 mmol), 2M solution of lithium aluminium hydride (7.2 mL, 14.4 mmol), yield: 1.61 g (93.8%)
Step C:
Product obtained from step B (1.61 g, 7.7 mmol), di(1H-imidazol-1-yl)methanone (1.499 g, 9.2 mmol), yield: 0.9 g (49.7%)
Step D:
Product obtained from step C (0.45 g, 1.91 mmol), 7-bromoimidazo[1,2-a]pyridine (0.376 g, 1.91 mmol), copper(I) iodide (0.036 g, 0.19 mmol), potassium carbonate (0.528 g, 3.82 mmol), cyclohexane-1,2-diamine (0.023 mL, 0.19 mmol), yield: 0.210 g (31.3%)
Overall yield: 6.1%; MS m/z 352.3 (M+H)+; 1H-NMR (400 MHz, DMSO-d6): δ 0.87-0.91 (m, 3H); 1.58-1.67 (m, 2H); 2.05-2.12 (m, H); 2.49-2.57 (m, H); 3.79-3.82 (m, 2H); 4.20-4.26 (m, H); 4.35-4.40 (m, H); 5.45-5.47 (m, H); 6.81 (d, 2H, J=8.7 Hz); 7.24 (d, 2H, J=8.7 Hz); 7.47 (d, H, J=7.9 Hz); 7.75 (s, H); 7.96 (s, H); 8.10 (s, H); 8.65 (d, H, J=7.9 Hz), HPLC (λ=214 nm), [B]: rt 9.73 min (100%).

Example 101

5-(2-phenylpyrrolidin-1-yl)-1H-benzo[d]imidazole

The compound was synthesized according to method 8 starting from 5 (6)-bromobenzimidazole (200 mg; 1 mmol; 1 eq.), 2-dicyclohexylphosphino-2'-(N, N-dimethylamino)biphenyl (9 mg; 0.024 mmol; 0.024 eq.; 2.4 mol %), Pd2 dba3 (9 mg; 0.01 mmol; 0.01 eq.; 1 mol %) and 4-phenylpyrrolidine (176 mg; 1.2 mmol; 1.2 eq.); yield: 0.071 g (27.0%); MS m/z: 264.4 [M+H]+; 1H-NMR (DMSO d6, 500 MHz): δ 1.76-1.81 (m, 1H); 1.93-1.98 (m, 2H); 2.35-2.44 (m, 1H); 3.34-3.39 (m, 1H); 3.71-3.75 (m, 1H); 4.73-4.75 (m, 1H); 6.39 (br s, 1H); 6.42-6.44 (m, 1H); 7.17-7.35 (m, 6H); 7.83 (s, 1H); 11.80 (br s, 1H); HPLC ([A]): rt 13.23 min (95.7%)

Example 102

5-(2-(4-methoxyphenyl)pyrrolidin-1-yl)-1H-benzo[d]imidazole

The compound was synthesized according to method 8 starting from 5 (6)-bromobenzimidazole (200 mg; 1 mmol; 1 eq.), 2-Dicyclohexylphosphino-2'-(N, N-dimethylamino)biphenyl (9 mg; 0.024 mmol; 0.024 eq.; 2.4 mol %), Pd2 dba3 (9 mg; 0.01 mmol; 0.01 eq.; 1 mol %) and 2-(4-Methoxyphenyl)-pyrrolidine (214 mg; 1.2 mmol; 1.2 eq.); yield: 0.060 g (20.5%); MS m/z: 294.2 [M+H]+; 1H-NMR (DMSO d6, 500 MHz): δ 1.74-1.77 (m, 1H); 1.92-1.97 (m, 2H); 2.32-2.38 (m, 1H); 3.33-3.36 (m, 1H); 3.68-3.72 (m, 4H); 4.67-4.69 (m, 1H); 6.39 (br s, 1H); 6.43-6.44 (m, 1H); 6.81-6.88 (m, 2H); 7.13-7.15 (m, 2H); 7.27-7.29 (m, 1H); 7.83 (s, 1H); 11.80 (br s, 1H); HPLC ([A]): rt 13.39 min (91.3%)

Example 103

5-(2-(4-fluorophenyl)pyrrolidin-1-yl)-1H-benzo[d]imidazole

The compound was synthesized according to method 8 starting from 5 (6)-bromobenzimidazole (200 mg; 1 mmol; 1 eq.), 2-dicyclohexylphosphino-2'-(N, N-dimethylamino)biphenyl (9 mg; 0.024 mmol; 0.024 eq.; 2.4 mol %), Pd2 dba3 (9 mg; 0.01 mmol; 0.01 eq.; 1 mol %) and 2-(4-Fluorphenyl)-pyrrolidine (199 mg; 1.2 mmol; 1.2 eq.); yield: 0.103 mg (36.7%); MS m/z: 282.5 [M+H]+; 1H-NMR (DMSO d6, 500 MHz): δ 1.73-1.79 (m, 1H); 1.91-1.97 (m, 2H); 2.35-2.43 (m, 1H); 3.33-3.38 (m, 1H); 3.71-3.74 (m, 1H); 4.74-4.76 (m, 1H); 6.38 (br s, 1H); 6.41-6.43 (m, 1H); 7.08-7.12 (m, 2H); 7.25-7.28 (m, 2H); 7.33-7.35 (m, 1H); 7.83 (s, 1H); 11.81 (br s, 1H); HPLC ([A]): rt 13.69 min (95.6%)

Example 104

5-(2-(4-chlorophenyl)pyrrolidin-1-yl)-1H-benzo[d]imidazole

The compound was synthesized according to method 8 starting from 5 (6)-bromobenzimidazole (200 mg; 1 mmol; 1 eq.), 2-dicyclohexylphosphino-2'-(N, N-dimethylamino)biphenyl (9 mg; 0.024 mmol; 0.024 eq.; 2.4 mol %), Pd2 dba3 (9 mg; 0.01 mmol; 0.01 eq.; 1 mol %) and 2-(4-chlorphenyl)-pyrrolidine (220 mg; 1.2 mmol; 1.2 eq.); yield: 0.083 g (27.9%); MS m/z: 293.3 [M+H]+; 1H-NMR (DMSO d6, 500 MHz): δ 1.76-1.80 (m, 1H); 1.91-2.00 (m, 2H); 2.36-2.42 (m, 1H); 3.33-3.38 (m, 1H); 3.71-3.74 (m, 1H); 4.73-4.75 (m, 1H); 6.42-6.44 (m, 2H); 7.25-7.27 (m, 2H); 7.30-7.32 (m, 1H); 7.33-7.35 (m, 2H); 7.88 (s, 1H); 11.90 (br s, 1H); HPLC ([A]): rt 14.66 min (94.8%)

Example 105

5-(2-benzylpyrrolidin-1-yl)-1H-benzo[d]imidazole

The compound was synthesized according to method 8 starting from 5 (6)-Bromobenzimidazole (200 mg; 1 mmol; 1 eq.), 2-dicyclohexylphosphino-2'-(N, N-dimethylamino)biphenyl (9 mg; 0.024 mmol; 0.024 eq.; 2.4 mol %), Pd2 dba3 (9 mg; 0.01 mmol; 0.01 eq.; 1 mol %) and 2-benzylpyrrolidine (194 mg; 1.2 mmol; 1.2 eq.); yield: 0.101 g (36.5%); MS m/z: 278.2 [M+H]+; 1H-NMR (DMSO d6, 500 MHz): δ 1.78-1.83 (m, 2H); 1.88-1.90 (m, 2H); 2.53-2.55 (m, 1H); 2.96-2.99 (m, 1H); 3.11-3.16 (m, 1H); 3.36-3.40 (m, 1H); 3.91-3.94 (m, 1H); 6.65-6.67 (m, 2H); 7.21-7.24 (m, 1H); 7.28-7.34 (m, 4H); 7.45-7.46 (m, 1H); 7.90 (s, 1H); 11.89 (br s, 1H); HPLC ([A]): rt 13.93 min (90.4%)

Example 106

5-(2-(4-chlorobenzyl)pyrrolidin-1-yl)-1H-benzo[d]imidazole

The compound was synthesized starting from 5 (6)-bromobenzimidazole (200 mg; 1 mmol; 1 eq.), 2-dicyclohexylphosphino-2'-(N,N-dimethylamino)biphenyl (9 mg; 0.024 mmol; 0.024 eq.; 2.4 mol %), Pd₂ dba₃ (9 mg; 0.01 mmol; 0.01 eq.; 1 mol %) and 2-(4-chlorobenzyl)-pyrrolidine (234 mg; 1.2 mmol; 1.2 eq.); yield: 0.04 g (1.3%); MS m/z: 312.1 [M+H]⁺; HPLC [A]: rt 15.49 (92.2%)

Example 107

5-(2-(4-fluorobenzyl)pyrrolidin-1-yl)-1H-benzo[d]imidazole

The compound was synthesized according to method 8 starting from 5 (6)-bromobenzimidazole (200 mg; 1 mmol; 1 eq.), 2-dicyclohexylphosphino-2'-(N,N-dimethylamino)biphenyl (9 mg; 0.024 mmol; 0.024 eq.; 2.4 mol %), Pd₂ dba₃ (9 mg; 0.01 mmol; 0.01 eq.; 1 mol %) and 2-(4-fluorobenzyl)-pyrrolidine (216 mg; 1.2 mmol; 1.2 eq.); yield: 0.086 g (29.1%); MS m/z: 296.6 [M+H]⁺; ¹H-NMR (DMSO d₆, 500 MHz): δ 1.76-1.90 (m, 4H); 2.54-2.59 (m, 1H); 2.92-2.95 (m, 1H); 3.10-3.15 (m, 1H); 3.35-3.38 (m, 1H); 3.91-3.94 (m, 1H); 6.68-6.69 (m, 2H); 7.11-7.15 (m, 2H); 7.29-7.32 (m, 2H); 7.43-7.45 (m, 1H); 7.92 (s, 1H); 11.91 (br s, 1H); HPLC ([A]): rt 15.18 (96.3%)

Example 108

5-(pyrrolidin-1-yl)-1H-benzo[d]imidazole

The compound was synthesized according to method 8 starting from 5 (6)-bromobenzimidazole (200 mg; 1 mmol; 1 eq.), 2-dicyclohexylphosphino-2'-(N,N-dimethylamino)biphenyl (9 mg; 0.024 mmol; 0.024 eq.; 2.4 mol %), Pd₂ dba₃ (9 mg; 0.01 mmol; 0.01 eq.; 1 mol %) and pyrrolidine (91 mg; 0.077 ml; 1.2 mmol; 1.2 eq.); yield: 0.054 g (28.9%); MS m/z: 188.3 [M+H]⁺; ¹H-NMR (DMSO d₆, 500 MHz): δ 1.95-1.97 (m, 4H); 3.21-3.24 (m, 4H); 6.55-6.56 (m, 2H); 7.38-7.40 (m, 1H); 7.96 (s, 1H); HPLC [A]: rt 8.72 min (82.3%)

Example 109

5-(2-(4-methoxybenzyl)pyrrolidin-1-yl)-1H-benzo[d]imidazole

The compound was synthesized starting from 5 (6)-bromobenzimidazole (200 mg; 1 mmol; 1 eq.), 2-dicyclohexylphosphino-2'-(N,N-dimethylamino)biphenyl (9 mg; 0.024 mmol; 0.024 eq.; 2.4 mol %), Pd₂ dba₃ (9 mg; 0.01 mmol; 0.01 eq.; 1 mol %) and 2-(4-methoxybenzyl)-pyrrolidine oxalate (337 mg; 1.2 mmol; 1.2 eq.) and lithiumbis(trimethylsilyl)amide (1 M solution in THF; 3.3 ml; 3.3 mmol; 3.3 eq.); yield: 0.06 g (1.9%); MS m/z: 308.2 [M+H]⁺; HPLC (Gradient 3): rt 14.07 (98.9%)

Example 110

3-(1H-benzo[d]imidazol-6-yl)-2-(4-chlorophenyl)thiazolidin-4-one

The compound was synthesized starting from 5-aminobenzimidazole (0.133 g, 1.0 mmol), pchloro-benzaldehyde (0.141 mL, 1.0 mmol), mercapto acetic acid (0.138 g, 1.5 mmol), piperidine, according to method 9 step A. yield: 194 mg (58%), MS m/z: 330.3 (M+H)⁺, HPLC [A]: rt 5.82 min (91%)

Example 111

3-(1H-benzo[d]imidazol-5-yl)-2-phenylthiazolidin-4-one

The compound was synthesized starting from 5-aminobenzimidazole (0.133 g, 1.0 mmol), benzaldehyde (0.306 mL, 3.0 mmol), mercapto acetic acid (0.276 g, 2.0 mmol), piperidine, according to method 9 step A. yield: 118 mg (40%), MS m/z: 296.3 (M+H)⁺, HPLC [A]: rt 5.72 min (96%)

Example 112

3-(1H-benzo[d]imidazol-6-yl)-2-(4-fluorophenyl)thiazolidin-4-one

The compound was synthesized starting from 5-aminobenzimidazole (0.133 g, 1.0 mmol), 4-fluoro-benzaldehyde (0.108 mL, 1.0 mmol), mercapto acetic acid (0.138 g, 1.5 mmol), piperidine, according to method 9 step A. yield: 69 mg (22%), MS m/z: 314.3 (M+H)⁺, HPLC [A]: rt 5.86 min (97%)

Example 113

3-(1H-benzo[d]imidazol-6-yl)-2-(naphthalen-1-yl)thiazolidin-4-one

The compound was synthesized starting from 5-aminobenzimidazole (0.133 g, 1.0 mmol), 4-naphthalen-1-yl carbaldehyde (0.157 mL, 1.0 mmol), mercapto acetic acid (0.157 g, 1.5 mmol), piperidine, according to method 9 step A yield: 54 mg (15.6%), MS m/z: 346.3 (M+H)⁺, HPLC [A]: rt 6.86 min (95%)

Example 114

3-(1H-benzo[d]imidazol-6-yl)-2-(4-phenoxyphenyl)thiazolidin-4-one

The compound was synthesized starting from 5-aminobenzimidazole (0.133 g, 1.0 mmol), 4-4-phenoxyphenyl carbaldehyde (0.175 mL, 1.0 mmol), mercapto acetic acid (0.157 g, 1.5 mmol), piperidine, according to method 9 step A. yield: 173 mg (44.7%), MS m/z: 388.3 (M+H)⁺, HPLC [A]: rt 5.86 min (99%)

Example 115

3-(1H-benzo[d]imidazol-6-yl)-2-(2,6-difluorophenyl)thiazolidin-4-one

The compound was synthesized starting from 5-aminobenzimidazole (0.133 g, 1.0 mmol), 2,6-difluoro-benzaldehyde (0.142 mg, 1.0 mmol), mercapto acetic acid (0.157 g, 1.5 mmol), piperidine, according to method 9 step A. yield: 208 mg (62.8%), MS m/z: 332.3 (M+H)⁺, HPLC [A]: rt 5.76 min (97%)

Example 116

3-(1H-benzo[d]imidazol-6-yl)-2-(thiophen-3-yl)thiazolidin-4-one

The compound was synthesized starting from 5-aminobenzimidazole (0.133 g, 1.0 mmol), 2, 6-2-thienyl carbaldehyd (0.092 mL, 1.0 mmol), mercapto acetic acid (0.157 g, 1.5 mmol), piperidine, according to method 9 step A. yield: 203 mg (70.7%), MS m/z: 302.3 (M+H)$^+$, HPLC [A]): rt 5.68 min (97%)

Example 117

3-(1H-benzo[d]imidazol-6-yl)-5-methyl-2-phenylthiazolidin-4-one

The compound was synthesized starting from 5-aminobenzimidazole (0.133 g, 1.0 mmol), 2,6-benzaldehyd (0.204 mL, 2.0 mmol), 2-mercapto propionic acid (0.280 g, 3.0 mmol), DCC (0.248 mg, 1.2 mmol), according to method 9 step A. yield: 115 mg (37.2%), MS m/z: 310.3 (M+H)$^+$, HPLC [A]): rt 6.32 min (100%)

Example 118

3-(1H-benzo[d]imidazol-5-yl)-2-phenylthiazolidine-4-thione

The compound was synthesized starting from example 110 (0.122 g, 0.29 mmol), Lawesson Reagent (0.6 g, 1.45 mmol), according to method 9 step B. yield: 44 mg (48.7%), MS m/z: 312.3 (M+H)$^+$, HPLC [A]): rt 7.32 min (87%)

Example 119

3-(1H-benzo[d]imidazol-6-yl)-2-(4-phenoxyphenyl)thiazolidine-4-thione

The compound was synthesized starting from example 113 (0.122 g, 0.284 mmol), Lawesson Reagent (0.575 g, 1.42 mmol), according to method 9 step B. yield: 58 mg (50.7%), MS m/z: 404.3 (M+H)$^+$, HPLC [A]): rt 6.45 min (87%)

Example 120

1-(1H-benzo[d]imidazol-5-yl)-5-(4-fluorophenyl)pyrrolidin-2-one

The compound was synthesized according to method 10.
Step A
4-(4-Fluorophenyl)-4-oxobutanoic acid (196 mg; 1 mmol; 1 eq.), carbonyldiimidazol (162 mg; 1 mmol; 1 eq.) and benzimidazol-5 (6)-amine (133 mg; 1 mmol; 1 eq.); yield: 0.189 g (60.8%); MS m/z: 312.2 [M+H]$^+$; HPLC ([A]): rt 10.45 min (81.9%)
Step B, C
yield: 0.048 g (26.8%); MS m/z: 296.2 [M+H]$^+$; $^1$H-NMR (CD$_3$OD, 400 MHz): δ 2.02-2.10 (m, 1H); 2.67-2.82 (m, 3H); 5.39-5.43 (m, 1H); 6.95-6.99 (m, 2H); 7.21 (dd, 1H, $^4$J=2.1 Hz, $^3$J=8.7 Hz); 7.29-7.33 (m, 2H); 7.47 (d, 1H, $^3$J=8.7 Hz); 7.53 (d, 1H, $^4$J=2.1 Hz); 8.10 (s, 1H); HPLC [A]): rt 11.47 min (97.4%)

Example 121

1-(1H-benzo[d]imidazol-5-yl)-5-(4-methoxyphenyl)pyrrolidin-2-one

The compound was synthesized according to method 10.
Step A
4-(4-Methoxy)-4-oxobutanoic acid (208 mg; 1 mmol; 1 eq.), Carbonyldiimidazol (162 mg; 1 mmol; 1 eq.) and Benzimidazol-5 (6)-amine (133 mg; 1 mmol; 1 eq.); yield: 0.207 g (64.1%); MS m/z: 324.2 [M+H]$^+$; HPLC ([A]): rt 10.30 min (93.5%)
Step B, C
Additional purification by semi-preparative HPLC; yield: 0.019 g (9.7%); MS m/z: 308.2 [M+H]$^+$; $^1$H-NMR (CD$_3$OD, 400 MHz): δ 2.03-2.11 (m, 1H); 2.64-2.83 (m, 3H); 3.69 (s, 3H); 5.42-5.45 (m, 1H); 6.79-6.82 (m, 2H); 7.20-7.23 (m, 2H); 7.58 (dd, 1H, $^4$J=2.1 Hz, $^3$J=9.1 Hz); 7.67 (d, 1H, $^3$J=9.5 Hz); 7.86 (d, 1H, $^4$J=2.1 Hz); 9.17 (s, 1H); HPLC ([A]): rt 9.65 min (100%)

Example 122

1-(1H-benzo[d]imidazol-5-yl)-5-(4-propoxyphenyl)pyrrolidin-2-one

The compound was synthesized according to method 10.
Step A
4-Oxo-4-(4-propoxyphenyl)butanoic acid (236 mg; 1 mmol; 1 eq.), carbonyldiimidazol (162 mg; 1 mmol; 1 eq.) and benzimidazol-5 (6)-amine (133 mg; 1 mmol; 1 eq.); yield: 0.215 g (61.3%); MS m/z: 352.3 [M+H]$^+$; HPLC ([A]): rt 13.13 min (100%)
Step B, C
Additional purification by semi-preparative HPLC; yield: 0.023 g (11.2%); MS m/z: 336.1 [M+H]$^+$; $^1$H-NMR (CD$_3$OD, 400 MHz): δ 0.97 (t, 3H, $^3$J=7.5 Hz); 1.67-1.75 (m, 2H); 2.05-2.08 (m, 1H); 2.66-2.80 (m, 3H); 3.82 (t, 2H, $^3$J=6.2 Hz); 5.41-5.44 (m, 1H); 6.78-6.81 (m, 2H); 7.18-7.21 (m, 2H); 7.56 (dd, 1H, $^4$J=2.1 Hz, $^3$J=9.1 Hz); 7.67 (d, 1H, $^3$J=9.1 Hz); 7.85 (d, 1H, $^4$J=2.1 Hz); 9.13 (s, 1H); HPLC ([A]): rt 12.44 min (100%)

Example 123

1-(1H-benzo[d]imidazol-5-yl)-5-(2,3-dihydrobenzo[b][1,4]dioxin-6-yl)pyrrolidin-2-one The compound was synthesized according to method 10.
Step A
4-(2,3-Dihydro-1,4-benzodioxin-6-yl)-4-oxobutanoic acid (236 mg; 1 mmol; 1 eq.), Carbonyldiimidazol (162 mg; 1 mmol; 1 eq.) and Benzimidazol-5 (6)-amine (133 mg; 1 mmol; 1 eq.); yield: 0.209 g (59.5%); MS m/z: 352.3 [M+H]$^+$; HPLC ([A]): rt 10.25 min (94.8%)
Step B, C
Additional purification by semi-preparative HPLC; yield: 0.028 g (14.1%); MS m/z: 336.1 [M+H]$^+$; $^1$H-NMR (CD$_3$OD, 400 MHz): δ 2.00-2.08 (m, 1H); 2.64-2.83 (m, 3H); 4.13 (s, 4H); 5.36-5.39 (m, 1H); 6.70-6.72 (m, 1H); 6.74-6.76 (m, 2H); 7.60 (dd, 1H, $^4$J=1.7, $^3$J=9.1 Hz); 7.69 (d, 1H, $^3$J=9.1 Hz); 7.89 (d, 1H, $^4$J=1.7 Hz); 9.19 (s, 1H); HPLC ([A]): rt 9.77 min (96.1%)

Example 124

1-(1H-benzo[d]imidazol-5-yl)-5-phenylpyrrolidin-2-one

The compound was synthesized according to method 10.
Step A
4-Oxo-4-phenylbutanoic acid (178 mg; 1 mmol; 1 eq.), Carbonyldiimidazol (162 mg; 1 mmol; 1 eq.) and Benzimidazol-5 (6)-amine (133 mg; 1 mmol; 1 eq.); yield: 0.198 g (67.6%); MS m/z: 294.2 [M+H]$^+$; HPLC ([A]): rt 10.66 min (87.9%)

Step B, C yield: 0.015 g (7.4%); MS m/z: 278.1 [M+H]+; 1H-NMR (CD3OD, 400 MHz): δ 2.94-2.10 (m, 1H); 2.70-2.79 (m, 3H); 5.41-5.42 (m, 1H); 7.17-7.19 (m, 1H); 7.23-7.29 (m, 6H); 7.54-7.55 (m, 1H); 8.09 (s, 1H); HPLC ([A]): rt 9.64 min (91.5%)

Example 125

2-(1H-benzo[d]imidazol-5-yl)-3-phenylisoindolin-1-one

The compound was synthesized according to method 10.
2-Benzoylbenzoic acid (226 mg; 1 mmol), DCC (206 mg; 1 mmol), benzimidazol-5 (6)-amine (133 mg; 1 mmol), TFA (1 ml) and triethylsilane (0.322 ml; 2 mmol; 2 eq.); yield: 0.074 g (22.8%); MS m/z: 326.2 [M+H]+; 1H-NMR (DMSO d6, 400 MHz): δ 6.63 (s, 1H); 7.15-7.19 (m, 1H); 7.22-7.32 (m, 5H); 7.48-7.50 (m, 2H); 7.53-7.62 (m, 2H); 7.84-7.86 (m, 2H); 8.16 (s, 1H); 12.42 (br s, 1H); HPLC (Gradient 3): rt 11.89 min (96.2%)

Example 126

2-(1H-benzo[d]imidazol-5-yl)-3-(4-biphenyl)isoindolin-1-one

The compound was synthesized according to method 11.
2-(4-Phenylbenzoyl)benzoic acid (1.0 g; 3.3 mmol), DCC (680 mg; 3.3 mmol), benzimidazol-5 (6)-amine (440 mg; 3.3 mmol), TFA (3.92 ml) and triethylsilane (0.624 ml; 3.92 mmol; 4 eq.) and was additional purified by semi-preparative HPLC; yield: 0.120 g (9.1%); MS m/z: 402.1 [M+H]+; 1H-NMR (DMSO d6, 400 MHz): δ 6.79 (s, 1H); 7.28-7.32 (m, 1H); 7.36-7.40 (m, 5H); 7.53-7.60 (m, 5H); 7.63-7.66 (m, 1H); 7.72-7.74 (d, 1H, 3J=8.7 Hz); 7.76-7.79 (dd, 1H, 4J=1.7 Hz, 3J=8.7 Hz); 7.89-7.91 (m, 1H); 8.17-8.18 (d, 1H, 4J=1.7 Hz); 9.06 (s, 1H); HPLC (Gradient 3): rt 15.20 min (97.0%)

Example 127

2-(1H-benzo[d]imidazol-5-yl)-3-(4-fluorophenyl)isoindolin-1-one

The compound was synthesized according to method 11
2-(4-Fluorobenzoyl)benzoic acid (244 mg; 1 mmol), DCC (206 mg; 1 mmol), benzimidazol-5 (6)-amine (133 mg; 1 mmol), TFA (1 ml) and triethylsilane (0.322 ml; 2 mmol; 2 eq.); yield: 0.055 g (16.0%); MS m/z: 344.1 [M+H]+; 1H-NMR (DMSO d6, 400 MHz): δ 6.65 (s, 1H); 7.04-7.09 (m, 2H); 7.30-7.33 (m, 2H); 7.37-7.51 (m, 2H); 7.54-7.63 (m, 3H); 7.84-7.86 (m, 2H); 8.17 (s, 1H); 12.43 (br s, 1H); HPLC (Gradient 3): rt 12.44 min (95.9%)

Example 128

2-(1H-benzo[d]imidazol-5-yl)-3-(3-fluorophenyl)isoindolin-1-one

The compound was synthesized according to method 11
2-(4-Fluorbenzoyl)benzoic acid (225 mg; 0.92 mmol), DCC (189 mg; 0.92 mmol), benzimidazol-5 (6)-amine (122 mg; 0.92 mmol), TFA (0.25 ml) and triethylsilane (0.08 ml; 0.5 mmol; 2 eq.); yield: 0.010 g (2.7%); MS m/z: 343.1 [M+H]+; 1H-NMR (DMSO d6, 400 MHz): δ 6.67-6.68 (m, 1H); 6.99-7.02 (m, 1H); 7.11-7.12 (m, 1H); 7.16-7.18 (m, 1H); 7.27-7.31 (m, 1H); 7.36-7.37 (m, 1H); 7.40-7.47 (m, 1H); 7.53-7.58 (m, 2H); 7.60-7.63 (m, 1H); 7.85-7.86 (m, 2H); 8.17-8.18 (m, 1H); 12.44-12.45 (m, 1H); HPLC (Gradient 3): rt 12.53 min (93.6%)

Example 129

2-(1H-benzo[d]imidazol-5-yl)-3-(3,5-difluorophenyl)isoindolin-1-one

The compound was synthesized according to method 11
2-(3,5-Difluorbenzoyl)benzoic acid (900 mg; 3.4 mmol), DCC (701 mg; 3.4 mmol), benzimidazol-5 (6)-amine (453 mg; 3.4 mmol), TFA (12 ml) and triethylsilane (1.9 ml; 12 mmol; 4 eq.) and was additional purified by semi-preparative HPLC; yield: 0.020 g (1.6%); MS m/z: 361.3 [M+H]+; 1H-NMR (DMSO d6, 400 MHz): δ 6.77 (s, 1H); 7.06-7.11 (m, 1H); 7.13-7.15 (m, 2H); 7.44 (d, 1H, 3J=7.5 Hz); 7.58-7.61 (m, 1H); 7.64-7.68 (m, 1H); 7.76-7.79 (m, 2H); 7.89 (d, 1 H, 3J=7.5 Hz); 8.18 (s, 1H); 9.20 (s, 1H); HPLC (Gradient 3): rt 13.07 min (99.6%)

Example 130

2-(1H-benzo[d]imidazol-5-yl)-3-(4-chlorophenyl)isoindolin-1-one

The compound was synthesized according to method 11
2-(4-Chlorbenzoyl)benzoic acid (261 mg; 1 mmol), DCC (206 mg; 1 mmol), benzimidazol-5 (6)-amine (133 mg; 1 mmol), TFA (1 ml) and triethylsilane (0.322 ml; 2 mmol; 2 eq.); yield: 0.032 g (8.9%); MS m/z: 360.2 [M+H]+; 1H-NMR (DMSO d6, 400 MHz): δ 6.66 (s, 1H); 7.30-7.33 (m, 4H); 7.39-7.58 (m, 2H); 7.54-7.63 (m, 3H); 7.85-7.87 (m, 2H); 8.17 (s, 1H); 12.44 (br s, 1H); HPLC (Gradient 3): rt 13.43 min (100%)

Example 131

2-(1H-benzo[d]imidazol-5-yl)-3-(3,4-dichlorophenyl)isoindolin-1-one

The compound was synthesized according to method 11
2-(3,4-Dichlorobenzoyl)benzoic acid (720 mg; 2.44 mmol), DCC (503 mg; 2.44 mmol), benzimidazol-5 (6)-amine (325 mg; 2.44 mmol), TFA (9.6 ml) and triethylsilane (1.53 ml; 9.6 mmol; 4 eq.) and was additional purified by semi-preparative HPLC; yield: 0.007 g (0.73%); MS m/z: 396.0 [M+H]+; 1H-NMR (DMSO d6, 400 MHz): δ 6.77 (s, 1H); 7.24-7.27 (m, 1H); 7.41 (d, 1H, 3J=7.5 Hz); 7.49-7.51 (m, 1H); 7.58-7.61 (m, 1H); 7.64-7.68 (m, 1H); 7.74-7.77 (m, 3H); 7.89 (d, 1H, 3J=7.5 Hz); 8.14 (br s, 1H); 9.15 (s, 1H); HPLC (Gradient 3): rt 14.24 min (100%)

Example 132

2-(1H-benzo[d]imidazol-5-yl)-3-(3-chloro-5-fluorophenyl)isoindolin-1-one

The compound was synthesized according to method 11
The compound was synthesized starting from 2-(3-chloro-5-fluorobenzoyl)benzoic acid (920 mg; 3.3 mmol), DCC (681 mg; 3.3 mmol), benzimidazol-5 (6)-amine (439 mg; 3.3 mmol), TFA (12 ml) and triethylsilane (1.9 ml; 12 mmol; 4 eq.) and was additional purified by semi-preparative HPLC; yield: 0.004 g (0.3%); MS m/z: 378.2 [M+H]+; 1H-NMR (DMSO d6, 400 MHz): δ 6.76 (s, 1H); 7.22-7.29 (m, 2H); 7.35 (s, 1H); 7.42-7.44 (m, 1H); 7.58-7.62 (m, 1H); 7.64-7.68 (m, 1H); 7.73-7.76 (m, 2H); 7.88-7.90 (m, 1H); 8.13 (s, 1H); 9.06 (s, 1H); HPLC (Gradient 3): rt 14.24 min (100%)

Example 133

2-(1H-benzo[d]imidazol-5-yl)-3-(4-methoxyphenyl)isoindolin-1-one

The compound was synthesized according to method 11
2-(4-Methoxybenzoyl)benzoic acid (820 mg; 3.2 mmol), DCC (660 mg; 3.2 mmol), benzimidazol-5 (6)-amine (426 mg; 3.2 mmol), TFA (12 ml) and triethylsilane (1.9 ml; 12 mmol; 4 eq.) and was additional purified by semi-preparative HPLC; yield: 0.044 g (3.9%); MS m/z: 356.1 [M+H]$^+$; $^1$H-NMR (DMSO d$_6$, 400 MHz): δ 3.63 (s, 3H); 6.65 (s, 1H); 6.78-6.81 (m, 2H); 7.18-7.20 (m, 2H); 7.32 (d, 1H, $^3$J=7.5 Hz); 7.54-7.65 (m, 1H); 7.61-7.65 (m, 1H); 7.72-7.73 (m, 2H); 7.87 (d, 1H, $^3$J=7.5 Hz); 8.12 (br s, 1H); 9.15 (s, 1H); HPLC (Gradient 3): rt 12.39 min (100%)

Example 134

2-(1H-benzo[d]imidazol-5-yl)-3-(4-propoxyphenyl)isoindolin-1-one

The compound was synthesized according to method 11
2-(4-Propoxybenzoyl)benzoic acid (430 mg; 1.5 mmol), DCC (309 mg; 1.5 mmol), benzimidazol-5 (6)-amine (200 mg; 1.5 mmol), TFA (1.5 ml) and triethylsilane (0.239 ml; 1.5 mmol; 4 eq.) and was additional purified by semi-preparative HPLC; yield: 0.030 g (5.2%); MS m/z: 384.0 [M+H]$^+$; $^1$H-NMR (DMSO d$_6$, 400 MHz): δ 0.84-0.91 (m, 3H); 1.58-1.67 (m, 2H); 3.77-3.80 (m, 2H); 6.64 (s, 1H); 6.77-6.80 (m, 2H); 7.16-7.19 (m, 2H); 7.31 (d, 1H, $^3$J=7.5 Hz); 7.54-7.58 (m, 1H); 7.61-7.65 (m, 1H); 7.72 (br s, 2H); 7.87 (d, 1H, $^3$J=7.5 Hz); 8.11 (br s, 1H); 9.12 (s, 1H); HPLC (Gradient 3): rt 14.00 min (100%)

Example 135

2-(1H-benzo[d]imidazol-5-yl)-3-(3-fluoro-4-methoxyphenyl)isoindolin-1-one

The compound was synthesized according to method 11
2-(3-Fluoro-4-methoxybenzoyl)benzoic acid (390 mg; 1.42 mmol), DCC (293 mg; 1.42 mmol), benzimidazol-5 (6)-amine (189 mg; 1.42 mmol), TFA (0.8 ml) and triethylsilane (0.127 ml; 0.8 mmol; 4 eq.); yield: 0.020 g (3.8%); MS m/z: 374.2 [M+H]$^+$; $^1$H-NMR (DMSO d$_6$, 400 MHz): δ 3.68 (s, 3H); 6.54 (s, 1H); 6.97-7.02 (m, 2H); 7.07-7.10 (m, 1H); 7.30 (d, 1H, $^3$J=7.5 Hz); 7.36-7.49 (m, 2H); 7.51-7.54 (m, 1H); 7.56-7.60 (m, 1H); 7.81-7.83 (m, 2H); 8.15 (s, 1H); 12.04 (br s, 1H); Yield: 0.020 g (25.0%); HPLC (Gradient 3): rt 12.94 min (94.4%)

Example 136

2-(1H-benzo[d]imidazol-5-yl)-3-(3,4-dimethoxyphenyl)isoindolin-1-one

The compound was synthesized according to method 11
2-(3,4-Dimethoxybenzoyl)benzoic acid (1.16 g; 4 mmol), DCC (825 mg; 4 mmol), benzimidazol-5 (6)-amine (533 mg; 4 mmol), TFA (15 ml) and triethylsilane (2.88 ml; 15 mmol; 4 eq.) and was additional purified by semi-preparative HPLC; yield: 0.140 g (9.1%); MS m/z: 385.4 [M+H]$^+$; $^1$H-NMR (DMSO d$_6$, 400 MHz): δ 3.62 (s, 3H); 3.64 (s, 3H); 6.61 (s, 1H); 6.79-6.81 (m, 2H); 6.88 (s, 1H); 7.37-7.39 (m, 1H); 7.54-7.58 (m, 1H); 7.62-7.65 (m, 1H); 7.76-7.79 (m, 2H); 7.86-7.88 (m, 1H); 8.13-8.14 (m, 1H); 9.19 (s, 1H); HPLC (Gradient 3): rt 11.51 min (100%)

Example 137

3-(benzo[d][1,3]-dioxol-6-yl)-2-(1H-benzo[d]imidazol-5-yl)isoindolin-1-one

The compound was synthesized according to method 11
2-(Benzo[d][1,3]dioxol-6-yl)benzoic acid (1.44 g; 4.2 mmol), DCC (870 mg; 4.2 mmol), benzimidazol-5 (6)-amine (560 mg; 4.2 mmol), TFA (5.4 ml) and triethylsilane (0.86 ml; 5.4 mmol; 4 eq.) and was additional purified by semi-preparative HPLC; yield: 0.125 g (25.0%); MS m/z: 370.0 [M+H]$^+$; $^1$H-NMR (DMSO d$_6$, 400 MHz): δ 5.89-5.90 (m, 2H); 6.62 (s, 1H), 6.76-6.77 (m, 1H); 6.78-6.80 (m, 1H); 6.85-6.88 (m, 1H); 7.33-7.35 (m, 1H); 7.54-7.58 (m, 1H); 7.62-7.66 (m, 1H); 7.75-7.76 (m, 2H); 7.85-7.87 (m, 1H); 8.14 (br s, 1H); 9.21 (s, 1H); HPLC (Gradient 3): rt 13.00 min (100%)

Example 138

2-(1H-benzo[d]imidazol-5-yl)-3-(4-phenoxyphenyl)isoindolin-1-one

The compound was synthesized according to method 11
2-(4-Phenoxybenzoyl)benzoic acid (1.0 g; 3.14 mmol), DCC (648 mg; 3.14 mmol), benzimidazol-5 (6)-amine (418 mg; 3.14 mmol), TFA (12 ml) and triethylsilane (1.9 ml; 12 mmol; 4 eq.) and was additional purified by semi-preparative HPLC; yield: 0.040 g (3.1%); MS m/z: 418.3 [M+H]$^+$; $^1$H-NMR (DMSO d$_6$, 400 MHz): δ 6.71 (s, 1H); 6.84-6.86 (m, 2H); 6.90-6.92 (m, 2H); 7.10-7.14 (m, 1H); 7.29-7.35 (m, 5H); 7.55-7.59 (m, 1H); 7.64-7.67 (m, 1H); 7.75-7.76 (m, 2H); 7.88 (d, 1H, $^3$J=7.5 Hz); 8.16 (s, 1H); 9.19 (s, 1H); HPLC (Gradient 3): rt 15.53 min (100%)

Example 139

2-(1H-benzo[d]imidazol-5-yl)-4,7-dichloro-3-(4-methoxyphenyl)isoindolin-1-one

The compound was synthesized according to method 11.
2-(4-Methoxybenzoyl)-3,6-dichlorobenzoic acid (430 mg; 1.32 mmol), DCC (272 mg; 1.32 mmol), benzimidazol-5 (6)-amine (176 mg; 1.32 mmol), TFA (0.36 ml) and triethylsilane (0.057 ml; 0.36 mmol; 4 eq.); yield: 0.010 g (1.8%); MS m/z: 424.1 [M+H]$^+$; $^1$H-NMR (DMSO d$_6$, 400 MHz): δ 3.60 (s, 3H); 6.47-6.49 (m, H); 6.70-6.72 (m, 2H); 7.09-7.11 (m, 2H); 7.27-7.53 (m, 2H); 7.61-7.62 (m, 2H); 7.65-7.72 (m, H); 8.15 (s, H); 12.41 (br s, H)

Example 140

2-(1H-benzo[d]imidazol-5-yl)-5,6-dichloro-3-(4-methoxyphenyl)isoindolin-1-one

The compound was synthesized according to method 11.
2-(4-Methoxybenzoyl)-4,5-dichlorobenzoic acid (495 mg; 1.52 mmol), DCC (313 mg; 1.52 mmol), benzimidazol-5 (6)-amine (202 mg; 1.52 mmol), TFA (0.36 ml) and triethylsilane (0.057 ml; 0.36 mmol; 4 eq.); yield: 0.010 g (1.6%); MS m/z: 424.1 [M+H]$^+$; $^1$H-NMR (DMSO d$_6$, 400 MHz): δ

3.61 (s, 3H); 6.54 (s, H); 6.76-6.78 (m, 2H); 7.15-7.17 (m, 2H); 7.37-7.51 (m, 2H); 7.56 (s, H); 7.77 (s, H); 8.04 (s, H); 8.15 (s, H); 12.43 (br s, H)

Example 141

2-(1H-benzo[d]imidazol-5-yl)-5,6-dichloro-3-(4-propoxyphenyl)isoindolin-1-one

The compound was synthesized according to method 11.
2-(4-Propoxybenzoyl)-4,5-dichlorobenzoic acid (15 mg; 0.04 mmol), DCC (10 mg; 0.04 mmol), benzimidazol-5 (6)-amine (5 mg; 0.04 mmol), TFA (0.08 ml) and triethylsilane (0.013 ml; 0.08 mmol; 4 eq.); yield: 0.005 (27.7%); MS m/z: 452.0 [M+H]$^+$; $^1$H-NMR (DMSO d$_6$, 400 MHz): δ 0.82-0.88 (m, 3H); 1.51-1.63 (m, 2H); 3.80-3.82 (m, 2H); 6.53 (s, H); 6.74-6.76 (m, 2H); 7.13-7.15 (m, 2H); 7.34-7.54 (m, 2H); 7.56 (s, H); 7.76 (s, H); 8.04 (s, H); 8.15 (s, H)

Example 142

(S)-2-(1H-benzo[d]imidazol-5-yl)-3-(3,4-dimethoxyphenyl)isoindolin-1-one

The compound was synthesized according to method 12
Step B, C
3,4-Dimethoxyphenylboronic acid (724 mg; 4 mmol); [RhCl(C$_2$H$_4$)$_2$]$_2$ (12 mg; 0.031 mmol), (3aS,6aS)-3,6-Diphenyl-1,3a,4,6a-tetra-hydropentalen (17 mg; 0.066 mmol), Methyl-2-(tosylimino-methyl)benzoat (634 mg; 2 mmol) and TEA (0.56 ml; 4 mmol); yield: 40 mg (7.4%); MS m/z: 270.4 [M+H]$^+$; 539.4 [2M+H]$^+$; HPLC (Gradient 3): rt 13.41 min (94.4%)
Step D
4-Iodbenzen-1,2-diamine (23 mg; 0.1 mmol); 3-(3,4-Dimethoxyphenyl)isoindolinon (29 mg; 0.11 mmol), copper (I)iodide (2 mg; 0.01 mmol), Diaminocyclohexane (1 mg; 0.01 mmol) and cesiumfluoride (30 mg; 0.2 mmol); yield: 0.015 g (39.0%); MS m/z: 384.4 [M+H]$^+$; $^1$H-NMR (DMSO d$_6$, 400 MHz): δ 3.60 (s, 3H); 3.61 (s, 3H); 6.57 (s, 1H); 6.75-6.77 (m, 2H); 6.85-6.86 (m, 1H); 7.35 (d, 1H, $^3$J=7.1 Hz); 7.51-7.55 (m, 1H); 7.58-7.62 (m, 1H); 7.67-7.68 (m, 2H); 7.84 (d, 1H, $^3$J=7.5 Hz); 8.04 (s, 1H); 8.94 (br s, 1H); HPLC (Gradient 3): rt 11.52 min (99.6%)

Example 143

(R)-2-(1H-benzo[d]imidazol-5-yl)-3-(3,4-dimethoxyphenyl)isoindolin-1-one

The compound was synthesized according to method 12
Step B, C
3,4-Dimethoxyphenylboronic acid (724 mg; 4 mmol); [RhCl(C$_2$H$_4$)$_2$]$_2$ (12 mg; 0.031 mmol), (3aR,6aR)-3,6-diphenyl-1,3a,4,6a-tetra-hydropentalen (17 mg; 0.066 mmol), methyl-2-(tosylimino-methyl)benzoat (634 mg; 2 mmol) and TEA (0.56 ml; 4 mmol); yield: 150 mg (27.9%); MS m/z: 270.3 [M+H]$^+$; 539.5 [2M+H]$^+$; HPLC (Gradient 3): rt 13.57 min (95.8%)
Step D
4-Iodobenzen-1,2-diamine (117 mg; 0.5 mmol); 3-(3,4-dimethoxyphenyl)isoindolinone (148 mg; 0.55 mmol), copper(I)iodide (10 mg; 0.05 mmol), diaminocyclohexane (6 mg; 0.05 mmol) and cesium fluoride (152 mg; 1 mmol); yield: 0.032 g (16.6%); MS m/z: 386.3 [M+H]$^+$; $^1$H-NMR (DMSO d$_6$, 400 MHz): δ 3.60 (s, 3H); 3.62 (s, 3H); 6.58 (s, 1H); 6.77-6.79 (m, 2H); 6.86 (s, 1H); 7.35 (d, 1H, $^3$J=7.5 Hz); 7.52-7.55 (m, 1H); 7.59-7.63 (m, 1H); 7.73-7.75 (m, 2H); 7.84 (d, 1H, $^3$J=7.5 Hz); 8.11 (s, 1H); 9.15 (br s, 1H); HPLC (Gradient 3): rt 11.46 min (99.5%)

Example 144

(R)-2-(1H-benzo[d]imidazol-5-yl)-3-(4-propoxyphenyl)isoindolin-1-one

The compound was synthesized according to method 12
Step B, C
4-Propoxyphenylboronic acid (720 mg; 4 mmol); [RhCl(C$_2$H$_4$)$_2$]$_2$ (12 mg; 0.031 mmol), (3aR, 6aR)-3,6-diphenyl-1,3a,4,6a-tetra-hydropentalen (17 mg; 0.066 mmol), methyl-2-(tosylimino-methyl)benzoat (634 mg; 2 mmol) and TEA (0.56 ml; 4 mmol); yield: 152 mg (28.5%); MS m/z: 268.3 [M+H]$^+$; 535.6 [2M+H]$^+$; HPLC (Gradient 3): rt 18.67 min (89.7%)
Step D
4-Iodbenzen-1,2-diamine (117 mg; 0.5 mmol); 3-(4-propoxyphenyl)isoindolinone (147 mg; 0.55 mmol), copper(I) iodide (10 mg; 0.05 mmol), diaminocyclohexane (6 mg; 0.05 mmol) and cesium fluoride (152 mg; 1 mmol); yield: 0.052 g (27.2%); MS m/z: 384.4 [M+H]$^+$; $^1$H-NMR (DMSO d$_6$, 400 MHz): δ 0.85-0.89 (m, 3H); 1.59-1.63 (m, 2H); 3.76-3.78 (m, 2H); 6.62 (s, 1H); 6.76-6.78 (m, 2H); 7.15-7.17 (m, 2H); 7.29-7.30 (m, 1H); 7.54-7.61 (m, 2H); 7.72 (s, 2H); 7.84-7.86 (m, 1H); 8.10 (s, 1H); 9.15 (s, 1H); HPLC (Gradient 3): rt 14.56 min (99.3%)

Example 145

(S)-2-(1H-benzo[d]imidazol-5-yl)-3-(4-propoxyphenyl)isoindolin-1-one

The compound was synthesized according to method 12
Step B, C
The compound was synthesized starting from 4-propoxyphenylboronic acid (720 mg; 4 mmol); [RhCl(C$_2$H$_4$)$_2$]$_2$ (12 mg; 0.031 mmol), (3aS,6aS)-3,6-diphenyl-1,3a,4,6a-tetra-hydropentalene (17 mg; 0.066 mmol), Methyl-2-(tosylimino-methyl)benzoate (634 mg; 2 mmol) and TEA (0.56 ml; 4 mmol); yield: 72 mg (13.5%); MS m/z: 268.3 [M+H]$^+$; 535.4 [2M+H]$^+$; HPLC (Gradient 3): rt 18.57 min (97.8%)
Step D
4-Iodobenzen-1,2-diamine (47 mg; 0.2 mmol); 3-(4-propoxyphenyl)isoindolinon (59 mg; 0.22 mmol), copper(I)iodide (4 mg; 0.02 mmol), diaminocyclohexane (2 mg; 0.02 mmol) and cesium fluoride (60 mg; 0.4 mmol); yield: 0.016 g (20.5%); MS m/z: 384.4 [M+H]$^+$; $^1$H-NMR (DMSO d$_6$, 400 MHz): δ 0.84-0.88 (m, 3H); 1.55-1.64 (m, 2H); 3.74-3.77 (m, 2H); 6.51 (s, H); 6.73-6.76 (m, 2H); 7.10-7.13 (m, 2H); 7.26 (d, 1H, $^3$J=7.5 Hz); 7.40-7.42 (m, 1H); 7.47-7.59 (m, 3H); 7.80-7.82 (m, 2H); 8.15 (s, 1H); 12.41 (br s, 1H); HPLC (Gradient 3): rt 14.35 min (100%)

Example 146

(R)-2-(1H-benzo[d]imidazol-5-yl)-3-(4-chlorophenyl)isoindolin-1-one

The compound was synthesized according to method 12
Step B, C
4-Chlorophenylboronic acid (624 mg; 4 mmol), [RhCl(C$_2$H$_4$)$_2$]$_2$ (12 mg; 0.031 mmol), (3aR, 6aR)-3,6-diphenyl-1,3a,4,6a-tetra-hydropentalen (17 mg; 0.066 mmol), methyl-2-(tosylimino-methyl)benzoate (634 mg; 2 mmol) and TEA (0.56 ml; 4 mmol); yield: 113 mg (23.3%); MS m/z: 244.4 [M+H]⁺; 487.5 [2M+H]⁺; HPLC (Gradient 3): rt 17.05 min (100%)

Step D

4-Iodobenzen-1,2-diamine (94 mg; 0.4 mmol); 3-(4-chlorophenyl)isoindolinone (107 mg; 0.44 mmol), copper(I)iodide (8 mg; 0.04 mmol), diaminocyclohexane (5 mg; 0.04 mmol) and cesium fluoride (121 mg; 0.8 mmol); yield: 0.020 g (13.9%); MS m/z: 360.2 [M+H]⁺; ¹H-NMR (DMSO d₆, 400 MHz): δ 6.75 (s, 1H); 7.30-7.37 (m, H); 7.56-7.60 (m, 1H); 7.63-7.67 (m, 1H); 7.73-7.75 (m, 2H); 7.89 (d, 1H, ³J=7.5 Hz); 8.13 (s, 1H); 9.15 (s, 1H); HPLC (Gradient 3): rt 13.60 min (100%)

Example 147

(S)-2-(1H-benzo[d]imidazol-5-yl)-3-(4-chlorophenyl)isoindolin-1-one

The compound was synthesized according to method 12
Step B, C

4-Chlorphenylboronic acid (624 mg; 4 mmol), [RhCl (C₂H₄)₂]₂ (12 mg; 0.031 mmol), (3aS, 6aS)-3,6-diphenyl-1,3a,4,6a-tetra-hydropentalen (17 mg; 0.066 mmol), methyl-2-(tosylimino-methyl)benzoate (634 mg; 2 mmol) and TEA (0.56 ml; 4 mmol); yield: 112 mg (23.0%); MS m/z: 244.3 [M+H]⁺; 487.4 [2M+H]⁺; HPLC (Gradient 3): rt 17.24 min (100%)

Step D

4-Iodobenzen-1,2-diamine (94 mg; 0.4 mmol); 3-(4-chlorophenyl)isoindolinone (107 mg; 0.44 mmol), copper(I)iodide (8 mg; 0.04 mmol), diaminocyclohexane (5 mg; 0.04 mmol) and cesium fluoride (121 mg; 0.8 mmol); yield: 0.029 g (20.3%); MS m/z: 360.2 [M+H]⁺; ¹H-NMR (DMSO d₆, 400 MHz): δ 6.72 (s, 1H); 7.28-7.34 (m, 5H); 7.54-7.57 (m, 1H); 7.60-7.64 (m, 1H); 7.68-7.73 (m, 2H); 7.86 (d, 1H, ³J=7.1 Hz); 8.11 (s, 1H); 9.11 (br s, 1H); HPLC (Gradient 3): rt 13.50 min (99.1%)

Example 148

1-(1H-benzo[d]imidazol-5-yl)-5-(4-phenylcyclohexyl)imidazolidin-2-one

The compound was synthesized as the trifluoroacetate salt starting from 5-aminobenzimidazole (848 mg, 6.38 mmol), phenylcyclohexyl carbaldehyde (1.0 g, 5.31 mmol)), TMSCN (1.39 mL, 10.63 mmol), PdC (10%, 0.02 g). di-(imidazol-1-yl)methanone (812 mg, 5.01 mmol), as described in method 2. The product was purified via preparative HPLC using a water-acetonitrile gradient with 0.04% trifluoroacetic acid.

Yield: 0.092 g (4.0%); MS m/z 361.2 (M+H)⁺; ¹H NMR (DMSO, 400 MHz): δ 8.53 (d, 1H); 8.07 (d, 1H); 7.29-7.14 (m, 5H); 4.27 (t, 1H); 4.15-4.10 (m, 2H); 2.42 (t, 1H); 1.83-1.62 (m, 5H); 1.50-1.41 (m, 2H); 1.37-1.21 (m, 1H), HPLC (λ=214 nm, [A]: rt 13.01 min (98.6%).

Example 149

1-(1H-benzo[d]imidazol-6-yl)-5-(1-phenylpiperidin-4-yl)imidazolidin-2-one

The compound was synthesized starting from 1H-benzo[d]imidazol-5-amine (0.400 g, 3 mmol), 1-phenylpiperidine-4-carbaldehyde (0.570 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.082 g (7.6%); MS m/z 362.3 (M+H)⁺, 181.7 (M+2H)²⁺; 1H-NMR (DMSO, 400 MHz): 1.63-1.80 (m, 3H); 1.81-1.89 (m, H); 2.03-2.15 (m, H); 2.90-3.00 (m, H); 3.03-3.15 (m, H); 3.42-3.49 (m, H); 3.59-3.73 (m, 3H); 4.70-4.77 (m, H); 7.12-7.18 (m, H); 7.24 (d, 2H, ³J=8.3 Hz); 7.35 (t, 2H, J=7.5 Hz); 7.66 (dd, H; ³J=9.1 Hz, ⁴J=1.7 Hz); 7.79 (d, H, ³J=9.1 Hz); 7.98 (s, H); 9.14 (s, H); HPLC (λ=214 nm, [A]: rt. 5.87 min (99%)

Example 150

1-(1H-benzo[d]imidazol-5-yl)-5-(4-(3-methoxypropyl)phenyl)imidazolidin-2-one

The compound was synthesized according to method 2 starting from 4-(3-methoxypropyl)benzaldehyde (1.5 g, 8.42 mmol), trimethyl silylcyanide (1.6 mL, 16.84 mmol), 5-amino benzimidazole (1.23 g, 9.26 mmol), 10% Pd—C (300 mg), triethylamine (5.8 mL, 41.97 mmol), 1,1'-carbonyldiimidazole (0.84 g, 5.24 mmol). Yield: 0.055 g (0.6%); MS m/z 293.4 (M+H)⁺; ¹H NMR (DMSO, 400 MHz): δ 2.21 (s, 3H); 3.05-3.09 (m, H); 3.83-3.87 (m, H); 5.49-5.53 (m, H); 7.01-7.10 (m, 2H); 7.15 (d, H, J=7.9 Hz); 7.19 (s, H); 7.52-7.55 (m, H), 7.60 (d, H, J=8.7 Hz); 7.84 (s, H); 9.16 (s, H), HPLC (λ=214 nm, [B]: rt 8.05 min (100%).

Example 151

1-(1H-benzo[d]imidazol-5-yl)-5-(4-hydroxyphenyl)imidazolidin-2-one 1-(1H-Benzo[d]imidazol-5-yl)-5-(4-methoxyphenyl)imidazolidin-2-one (308 mg; 1 mmol; 1 eq.) was dissolved in dry CH₂Cl₂ (20 ml) under Argon atmosphere and cooled to 0° C. BBr₃ (0.285 ml; 3 mmol; 3 eq.) was added dropwise. After complete addition, the mixture was stirred for 1 h at 0° C. and then allowed to warm to room temperature. The reaction was quenched with water and the organic layer was separated. The aqueous layer was neutralized by addition of 1N NaOH. The resulting precipitate was filtered off, dried and used without further purification. Yield: 0.174 g (59.2%); MS m/z: 295.1 [M+H]⁺; ¹H-NMR (400 MHz, DMSO d6): 3.04-3.06 (m, 1H); 3.72-3.77 (m, 1H); 5.30-5.33 (m, 1H); 6.62-6.64 (m, 2H); 6.84 (s, 1H); 7.09-7.11 (m, 2H); 7.17-7.19 (m, 1H); 7.34-7.36 (d, 1H, ³J=8.7 Hz); 7.46 (s, 1H); 8.03 (s, 1H); HPLC(P31/98): rt 6.66 min (100%)

Example 152

1-(1H-benzo[d]imidazol-5-yl)-5-(2-hydroxyphenyl)imidazolidin-2-one

The compound was synthesized starting from 1-(1H-benzo[d]imidazol-5-yl)-5-(2-methoxyphenyl)imidazolidin-2-one (0.075 g, 0.243 mmol) by treating with borontribromide (0.069 mL, 0.73 mmol) as described for Example 151.

Yield: 0.014 g (19.6%); MS m/z 295.2 (M+H)⁺, ¹H-NMR (DMSO, 400 MHz): 3.01-3.06 (m, H); 3.86 (t, H, ³J=8.7 Hz); 5.65 (q, H, J=4.6 Hz); 6.63 (t, H; ³J=7.9 Hz); 6.83 (d, H; ³J=7.9 Hz); 6.92-6.95 (m, H); 6.98-7.04 (m, H); 7.06 (s, H); 7.44 (dd, H; ³J=9.1 Hz, ⁴J=1.7 Hz); 7.53 (d, H; ³J=9.1 Hz); 7.77 (d, H, ⁴J=1.7 Hz); 1.82 (s, H); 9.84 (s, H); HPLC (λ=214 nm, [A]: rt. 8.14 min (100%)

Example 153

1-(1H-benzo[d]imidazol-5-yl)-5-(2,4-dihydroxyphenyl)imidazolidin-2-one

The compound was synthesized starting from 1H-benzo[d]imidazol-5-amine (0.400 g, 3 mmol), 2,4-dimethoxybenzaldehyde (0.5 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2 to give 1-(1H-benzo[d]imidazol-5-yl)-5-(2,4-dimethoxyphenyl)imidazolidin-2-one (yield: 0.305 g, 0.9 mmol, 30%). Treating with borontribromide (0.512 mL, 5.41 mmol) as described for Example 151 gives the title compound.

Yield: 0.050 g (17.9%, 5.4% over all steps); MS m/z 311.1 (M+H)$^+$, $^1$H-NMR (DMSO, 400 MHz): 3.03-3.08 (m, H); 3.80 (t, H, $^3$J=8.7 Hz); 5.54 (dd, H, $^3$J=9.1 Hz, $^4$J=5 Hz); 6.07 (dd, H, $^3$J=8.3 Hz, $^4$J=2.5 Hz); 6.31 (d, H, $^4$J=2.1 Hz); 6.75 (d, H, $^3$J=8.3 Hz); 7.04 (s, H); 7.47 (dd, H, $^3$J=9.1 Hz, $^4$J=2.1 Hz); 7.57 (d, H, $^3$J=9.1 Hz); 1.79 (d, H, J=1.7 Hz); 8.94 (s, H); 9.19 (s, H); HPLC ($\lambda$=214 nm, [A]: rt. 6.16 min (98%)

Example 154

1-(1H-benzo[d]imidazol-5-yl)-5-(3,4-dihydroxyphenyl)imidazolidin-2-one

The compound was synthesized starting from 1H-benzo[d]imidazol-5-amine (0.400 g, 3 mmol), 3,4-dimethoxybenzaldehyde (0.5 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2 to give 1-(1H-benzo[d]imidazol-5-yl)-5-(3,4-dimethoxyphenyl)imidazolidin-2-one (yield: 0.3 g, 0.89 mmol, 29.7%). Treating with borontribromide (0.505 mL, 5.34 mmol) as described for example 151 gives the title compound.

Yield: 0.011 g (3.98%, 1.18% over all steps); MS m/z 311.1 (M+H)$^+$, 621.4 (2M+H); HPLC ($\lambda$=214 nm, [A]: rt. 6.42 min (99%)

Example 155

1-(1H-benzo[d]imidazol-5-yl)-5-(3-hydroxyphenyl)imidazolidin-2-one

The compound was synthesized starting from 1-(1H-benzo[d]imidazol-5-yl)-5-(3-methoxyphenyl)imidazolidin-2-one (0.182 g, 0.59 mmol) by treating with borontribromide (0.224 mL, 2.36 mmol) as described for example 151.

Yield: 0.009 g (4.95%); MS m/z 295.2 (M+H)$^+$; $^1$H-NMR (DMSO, 400 MHz): 3.03-3.08 (m, H); 3.83 (t, H, $^3$J=9.5 Hz); 5.40-5.47 (m, H); 6.56-6.60 (m, H); 6.68 (s, H); 6.73 (d, H, $^3$J=7.9 Hz); 7.07 (t, H, $^3$J=7.9); 7.14 (s, H); 7.50 (m, H); 7.55-7.59 (m, H); 7.79 (s, H); 9.01 (s, H); 9.39 (s, H); HPLC ($\lambda$=214 nm, [A]: rt. 7.30 min (100%)

Example 156

1-(1H-benzo[d]imidazol-5-yl)-5-(4-(cyclohexyloxy)phenyl)imidazolidin-2-one

The compound was synthesized as the trifluoroacetate salt starting from 5-aminobenzimidazole (2.35 g, 17.64 mmol), cyclohexyloxy)phenyl carbaldehyde (3.0 g, 14.70 mmol), TMSCN (2.91 g, 29.40 mmol), PdC (10%, 0.2 g), TEA (9.6 mL, 69.36 mmol), di-(imidazol-1-yl)methanone (1.40 g, 8.67 mmol) as described in method 2. The product was purified by means of preparative HPLC.

Yield: 0.11 g (1.7%); MS m/z 377.4 (M+H)$^+$; $^1$H NMR (400 MHz, CDCl3): $\delta$ 7.88 (s, 1H); 7.63 (s, 1H); 7.47 (s, 1H); 7.25-7.21 (merged with CDCl3, 3H); 6.80 (d, 2H); 5.28 (t, 2H); 4.70 (s, 1H); 4.16 (d, 1H); 3.93 (t, 1H); 3.39 (t, 1H); 1.93-1.75 (m, 4H); 1.55-1.28 (m, 6H), HPLC ($\lambda$=214 nm, [A]: rt 12.75 min (97.3%).

Example 157

5-(4-(2-methoxyethoxy)phenyl))-1-(1H-benzo[d]imidazol-5-yl)imidazolidin-2-one

The compound was synthesized as trifluoroacetate salt starting from 5-aminobenzimidazole (1.3 gmg, 9.99 mmol), 4-(2-methoxyethoxy)benzaldehyde (1.5 g, 8.33 mmol), TMSCN (1.64 mL, 16.66 mmol) 10% Pd—C (200 mg), TEA (2.5 mL, 18.40 mmol), di-(imidazol-1-yl)methanone (1.192 g, 7.36 mmol), as described in method 2. The product was purified by means of preparative HPLC.

Yield: 0.04 g (1.3%); MS m/z 353.3 (M+H)$^+$; $^1$H NMR (400 MHz, DMSO-d6): $\delta$ 12.24 (s, 1H); 8.08 (d, 1H); 7.55-7.24 (m, 5H); 6.96-6.84 (m, 3H); 5.44 (s, 1H); 3.99 (d, 2H); 3.81 (s, 1H); 3.58 (s, 2H); 3.30 (merged with DMSO moisture, 3H); 3.08 (s, 1H); HPLC ($\lambda$=214 nm, [A]: rt 7.97 min (92.93%).

Example 158

(S)-5-(4-(2-(dimethylamino)ethoxy)phenyl)-1-(1H-benzo[d]imidazol-5-yl)imidazolidin-2-one The compound was synthesized as trifluoroacetate salt starting from trimethyl silyl cyanide (1.88 mL, 20.72 mmol), 5-amino benzimidazole (0.82 g, 6.21 mmol), 4-(3-(dimethylamino)propoxy)benzaldehyde (1.0 g, 5.18 mmol), 10% Pd—C (250 mg), triethylamine (7.5 mL, 51.91 mmol), 1,1'-carbonyldiimidazole (1 g, 6.48 mmol). The product was further purified by prep HPLC using the following conditions: Column: Chiralpak AD-HMobile phase: Hexane: Ethanol (0.1% DEA); Flow rate: 32 mL/min, UV: 210 nm, Diluent: Mobile phase The prep fractions were concentrated in vacuum and partitioned between water and chloroform. The separated organic layer was washed with brine solution. Dried over anhydrous sodium sulphate and concentrated in vacuum to afford 50 mg of the product as brown solid.

Yield: 0.050 g (2.6%); MS m/z 366.3 (M+H)$^+$; $^1$H NMR (400 MHz, CDCl3): $\delta$ 10.40 (Bs, 1H); 7.86 (s, 1H); 7.54 (s, 1H); 7.32-7.16 (merged with CDCl3, 5H); 6.80 (d, 2H); 5.25 (t, 1H); 4.83 (s, 1H); 4.00-3.90 (m, 3H); 3.38 (t, 1H); 2.68 (d, 2H); 2.35-2.15 (m, 6H); HPLC ($\lambda$=214 nm, [A]: rt 5.12 min (88.53%).

Example 159

3-(1H-benzo[d]imidazol-5-yl)-1-phenethyl-4-(4-propoxyphenyl)imidazolidin-2-one

Step A:
The compound was synthesized starting from 1-(1H-benzo[d]imidazol-5-yl)-5-(4-propoxyphenyl)imidazolidin-2-one (6.73 g, 20 mmol), triethylamine (3.33 ml, 24 mmol) and trityl chloride (6.7 g, 24 mmol) in 50 ml THF as described in method 13.

Yield: 10.2 g (86%)

Step B:
Product obtained from step A (0.145 g, 0.25 mmol), sodium hydride (0.13 g, 5.42 mmol), (2-bromoethyl)benzene (0.14 ml, 1 mmol). The product was purified by flash chromatography using chloroform as eluent.
Yield: 0.13 g (77%)
Step C:
Product obtained from step B (0.13 g, 0.19 mmol), TFA (4 ml in 20 ml methanol)
Yield: 0.039 g (46.6%)
Overall yield: 30.9% MS m/z 441.4 (M+H)$^+$; $^1$H NMR (400 MHz, DMSO-D$_6$): δ 0.87-0.91 (m, 3H); 1.56-1.67 (m 2H); 2.78-2.82 (m, 2H); 3.05-3.09 (m, H); 3.36-3.55 (m, 2H); 3.77-3.81 (m, 3H); 5.29-5.32 (m, H); 6.75-6.78 (m, 2H); 7.12-7.27 (m, 8H); 7.34-7.36 (m, H); 7.47 (s, H); 8.04 (s, H); 12.24 (br s, H), HPLC (λ=214 nm), [B]: rt 14.97 min (96%).

Example 160

3-(1H-benzo[d]imidazol-5-yl)-1-((naphthalen-2-yl)methyl)-4-(4-propoxyphenyl)imidazolidin-2-one Step A:
The compound was synthesized starting from 1-(1H-benzo[d]imidazol-5-yl)-5-(4-propoxyphenyl)imidazolidin-2-one (6.73 g, 20 mmol), triethylamine (3.33 ml, 24 mmol) and trithyl chloride (6.7 g, 24 mmol) in 50 ml THF as described in method 13.
Yield: 10.2 g (86%)
Step B:
Product obtained from step A (0.145 g, 0.25 mmol), sodium hydride (0.13 g, 5.42 mmol), 2-(bromomethyl)naphthalene (0.055 g, 0.25 mmol)
Step C:
crude product obtained from step B, TFA (4 ml in 20 ml methanol)
Yield: 0.005 g (3.9% step B+C)
Overall yield: 3.3% MS m/z 477.4 (M+H)$^+$; $^1$H NMR (400 MHz, DMSO-D$_6$): δ 0.91-0.95 (m, 3H); 1.60-1.71 (m, 2H); 3.17-3.21 (m, H); 3.76-3.83 (m, 3H); 4.65 (s, 2H); 5.23-5.27 (m, H); 6.74 (d, 2H, J=8.7 Hz); 7.17 (d, 2H, J=8.7 Hz); 7.27-7.29 (m, H); 7.43-7.47 (m, 4H); 7.55 (bs, H); 7.76-7.85 (m, 4H); 8.07 (br s, H), HPLC (λ=214 nm), [B]: rt 16.16 min (95.4%).

Example 161

3-(1H-benzo[d]imidazol-5-yl)-1-(3-phenylpropyl)-4-(4-propoxyphenyl)imidazolidin-2-one Step A:
The compound was synthesized starting from 1-(1H-benzo[d]imidazol-5-yl)-5-(4-propoxyphenyl)imidazolidin-2-one (6.73 g, 20 mmol), triethylamine (3.33 ml, 24 mmol) and trithyl chloride (6.7 g, 24 mmol) in 50 ml THF as described in method 13.
Yield: 10.2 g (86%)
Step B:
Product obtained from step A (0.145 g, 0.25 mmol), sodium hydride (0.13 g, 5.42 mmol), (3-bromopropyl)benzene (0.038 ml, 0.25 mmol)
Step C:
crude product obtained from step B, TFA (4 ml in 20 ml methanol)
Yield: 0.063 g (55.4% step B+C)
Overall yield: 42.7% MS m/z 455.4 (M+H)$^+$; $^1$H NMR (400 MHz, DMSO-D$_6$): δ 0.86-0.90 (m, 3H); 1.58-1.66 (m, 2H); 1.73-1.80 (m, 2H); 2.54-2.58 (m, 2H); 3.08-3.12 (m, H); 3.21-3.24 (m, 2H); 3.78-3.85 (m, 3H); 5.31-5.35 (m, H); 6.80 (d, 2H, J=8.7 Hz); 7.12-7.25 (m, 8H); 7.35-7.37 (m, H); 7.50 (s, H); 8.04 (s, H); 12.22 (br s, H), HPLC (λ=214 nm), [B]: rt 15.73 min (99.3%).

Example 162

3-(1H-benzo[d]imidazol-5-yl)-1-benzyl-4-(4-propoxyphenyl)imidazolidin-2-one

Step A:
The compound was synthesized starting from 1-(1H-benzo[d]imidazol-5-yl)-5-(4-propoxyphenyl)imidazolidin-2-one (6.73 g, 20 mmol), triethylamine (3.33 ml, 24 mmol) and trithyl chloride (6.7 g, 24 mmol) in 50 ml THF as described in method 13.
Yield: 10.2 g (86%)
Step B:
Product obtained from step A (0.145 g, 0.25 mmol), sodium hydride (0.13 g, 5.42 mmol), benzyl bromide (0.03 ml, 0.25 mmol)
Step C:
crude product obtained from step B, TFA (4 ml in 20 ml methanol)
Yield: 0.062 g (58.1% step B+C)
Overall yield: 50% MS m/z 427.3 (M+H)$^+$; $^1$H NMR (400 MHz, DMSO-D$_6$): δ 0.86-0.89 (m, 3H); 1.57-1.66 (m, 2H); 2.97-3.00 (m, H); 3.69-3.74 (m, H); 3.76-3.80 (m, 2H); 4.40 (s, 2H); 5.36-5.40 (m, H); 6.77 (d, 2H, J=8.7 Hz); 7.18 (d, 2H, J=8.7 Hz); 7.23-7.34 (m, 6H); 7.37-7.39 (m, H); 7.54 (s, H); 8.06 (s, H); 12.24 (br s, H), HPLC (λ=214 nm), [B]: rt 14.43 min (99.8%).

Example 163

1-(1H-benzo[d]imidazol-5-yl)-5-(4-fluoro-3-methoxyphenyl)imidazolidin-2-one

The compound was synthesized starting from 5-aminobenzimidazole (0.585 g, 4.4 mmol), 4-fluoro-3-methoxybenzaldehyde (0.616 g, 4 mmol), TMSCN (0.5 mL, 4 mmol), PdC (10%, 0.02 g), TEA 1.21 mL, 8.7 mmol), di-(imidazol-1-yl)methanone (0.767 g, 4.7 mmol) as described in method 2.
Yield: 0.15 g (11.5%); MS m/z 327.5 (M+H)$^+$; $^1$H NMR (DMSO, 400 MHz): δ 3.08-3.12 (m, H); 3.75 (s, 3H); 3.77-3.82 (m, H); 5.43-5.47 (m, H); 6.83-6.86 (m, H); 6.91 (s, H); 7.04-7.09 (m, H); 7.14-7.16 (m, H); 7.21 (s, H); 7.37 (s, H); 7.51 (s, H); 8.05 (s, H); 12.21 (br s, H), HPLC (λ=214 nm, [B]: rt 8.97 min (94.8%).

Example 164

1-(1H-benzo[d]imidazol-5-yl)-5-(3-fluoro-4-propoxyphenyl)imidazolidin-2-one

3-Fluoro-4-propoxybenzaldehyde was synthesized starting from 3-fluoro-4-hydroxybenzaldehyde (0.83 g, 5.95 mmol) and 1-iodopropane (1.16 ml, 11.9 mmol) according to reaction conditions described by Liou et al., *J. Med. Chem.* 2004, 47 (11), 2903.
The compound was further synthesized starting from 5-aminobenzimidazole (0.806 g, 6.1 mmol), 3-fluoro-4-propoxybenzaldehyde (1.0 g, 5.5 mmol), TMSCN (0.69 mL, 5.5 mmol), PdC (10%, 0.02 g), TEA 1.44 mL, 10.3 mmol), di-(imidazol-1-yl)methanone (0.92 g, 5.6 mmol) as described in method 2.

Yield: 0.106 g (5%); MS m/z 355.2 (M+H)+; 1H NMR (CD3OD, 400 MHz): δ 0.96-1.00 (m, 3H); 1.68-1.78 (m, 2H); 3.32-3.36 (m, H); 3.89-3.97 (m, 3H); 5.37-5.41 (m, H); 6.93-6.97 (m, H); 7.07-7.09 (m, H); 7.11-7.14 (m, H); 7.24-7.26 (m, H); 7.46-7.50 (m, 2H); 8.06 (s, H), HPLC (λ=214 nm, [B]: rt 10.73 min (96%).

Example 165

1-(1H-benzo[d]imidazol-5-yl)-5-(2-fluoro-4-propoxyphenyl)imidazolidin-2-one

2-Fluoro-4-propoxybenzaldehyde was synthesized starting from 3-fluoro-4-hydroxybenzaldehyde (0.1 g, 0.7 mmol) and 1-iodopropane (0.24 g, 1.4 mmol) under reaction conditions described by Liou et al., *J. Med. Chem.* 2004, 47 (11), 2903

The compound was synthesized starting from 5-aminobenzimidazole (0.09 g, 0.67 mmol), 2-fluoro-4-propoxybenzaldehyde (0.11 g, 0.6 mmol), TMSCN (0.084 mL, 0.67 mmol), PdC (10%, 0.02 g), TEA 0.184 mL, 1.32 mmol), di-(imidazol-1-yl)methanone (0.117 g, 0.72 mmol) as described in method 2.

Yield: 0.012 g (4.8%); MS m/z 355.4 (M+H)+; 1H NMR (CD3OD, 400 MHz): δ 0.96-0.99 (m, 3H); 1.68-1.76 (m, 2H); 3.39-3.42 (m, H); 3.83-3.86 (m, 2H); 3.97-4.02 (m, H); 5.71-5.75 (m, H); 6.63-6.65 (m, 2H); 7.22-7.27 (m, H); 7.46-7.49 (m, H); 7.57-7.59 (m, H); 7.73 (s, H); 8.72 (s, H), HPLC (λ=214 nm, [B]: rt 10.95 min (95.1%).

Example 166

(S)-1-(1H-benzo[d]imidazol-5-yl)-5-(4-(diethylamino)phenyl)imidazolidin-2-one

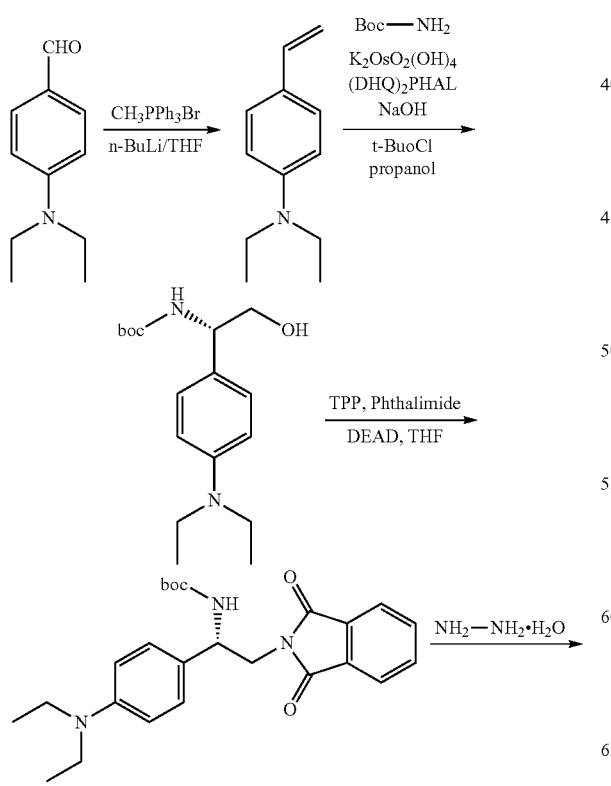

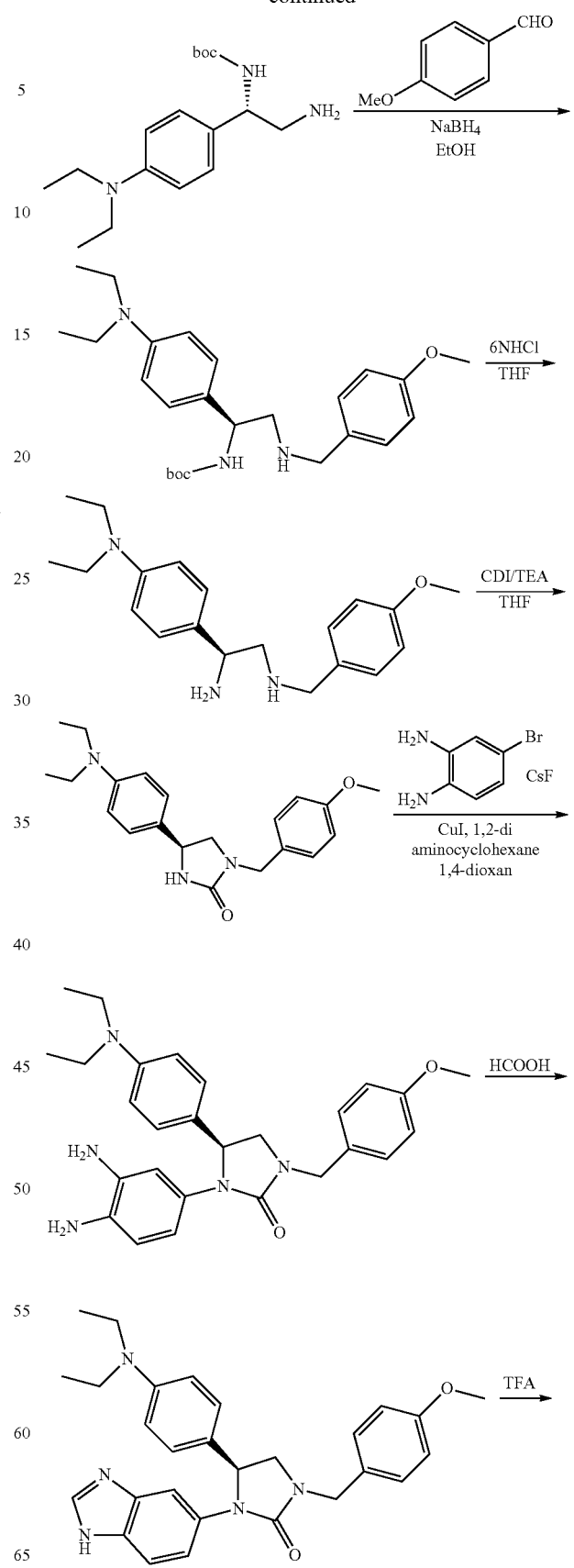

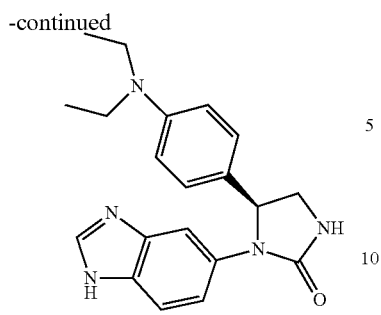

The compound was synthesized according to a modified method 3 shown above starting from 4-(diethylamino)benzaldehyde (2 g, 11.29 mmol), 2.3M n-butyl lithium (t-butyl hypochlorite (1.9 mL, 17.42 mmol), t-butyl carbamate (2 g, 17.14 mmol), sodium hydroxide (0.696 g in 25 mL water), (DHQ)$_2$PHAL (222 mg, 0.285 mmol), potassium osmate dihydrate (83 mg, 0.228 mmol), diethyl azo dicarboxylate (1.5 mL, 9.496 mmol), phthalimide (1.023 g, 6.96 mmol), triphenylphosphine (2.48 g, 9.49 mmol), hydrazine hydrate (20 mL), P-anisaldehyde (0.3 mL, 2.768 mmol), sodium borohydride (366 mg, 9.68 mmol), 6N HCl solution (15 mL), triethyl amine (0.7 mL) and CDI (433 mg, 2.67 mmol), 1,2-diamino-4-bromo benzene (349 mg, 1.869 mmol), cesium fluoride (516 mg, 3.398 mmol), copper iodide (48 mg), 2-diaminocyclohexane (0.03 ml, 0.254 mmol), formic acid (5 mL), in trifluoro acetic acid (5 ml). Yield: 0.07 g (1.6%); MS m/z 350.5 (M+H)$^+$; $^1$H-NMR (400 MHz, DMSO-d6): δ 12.26 (Bs, 1H); 8.08 (s, 1H); 7.52 (s, 1H); 7.39 (d, 1H); 7.25 (s, 1H); 7.12 (d, 2H); 6.88 (d, 3H); 6.52 (d, 2H); 5.32 (q, 1H); 3.73 (t, 1H); 3.39-3.32 (m, 4H); 3.07 (t, 1H); 1.10-0.99 (m, 6H); HPLC (λ=214 nm, [A]: rt 4.44 min (95.4%)

Example 167

1-(1H-benzo[d]imidazol-5-yl)-5-(4-chlorophenyl)imidazolidin-2-one

The compound was synthesized starting from 5-aminobenzimidazole (0.585 g, 4.4 mmol), 4-chlorobenzaldehyde (0.56 g, 4 mmol), TMSCN (0.5 mL, 4 mmol), PdC (10%, 0.02 g), TEA 1.93 mL, 13.9 mmol), di-(imidazol-1-yl)methanone (1.12 g, 6.9 mmol) as described in method 2. Yield: 0.045 g (3.6%); MS m/z 313.1 (M+H)$^+$; $^1$H NMR (400 MHz, DMSO-D$_6$): δ 3.04-3.08 (m, H); 3.79-3.84 (m, H); 5.49-5.52 (m, H); 6.93 (s, H); 7.33-7.38 (m, 5H); 7.19-7.22 (m, H); 7.51 (d, H, J=1.7 Hz); 8.05 (s, H); 12.22 (br s, H), HPLC (λ=214 nm, [B]: rt 9.62 min (99.7%).

Example 168

1-(1H-benzo[d]imidazol-5-yl)-5-(4-cyclohexylphenyl)imidazolidin-2-one

The compound was synthesized starting from 1H-benzo[d]imidazol-5-amine (0.400 g, 3 mmol), 4-cyclohexylbenzaldehyde (0.565 g, 3 mmol), TMSCN (0.375 mL, 3 mmol), Pd/C (10%, 0.02 g), TEA 1.05 mL, 7.5 mmol), di-(imidazol-1-yl) methanone (0.730 g, 4.5 mmol) as described in method 2.
Yield: 0.023 g (2.1%); MS m/z 361.0 (M+H)$^+$; 1H-NMR (DMSO, 400 MHz): 1.05-1.19 (m, H); 1.20-1.34 (m, 4H); 1.59-1.76 (m, 5H); 2.34-2.41 (m, H); 3.04 (t, H, J=7.9 Hz); 3.78 (q, H, J=6.2 Hz); 5.43 (t, H, J=8.3 Hz); 6.83 (s, 0.5H); 6.90 (s, 0.5H); 7.10 (d, 2H, $^3$J=7.9 Hz); 7.13-7-18 (m, 0.6H); 7.19-7.25 (m, 2H); 7.28-7.37 (m, 2H); 7.40 (d, 0.6H, $^3$J=8.7 Hz); 7.46 (s, 0.4H); 7.56 (s, 0.5H); 8.04 (d, H, J=10.8 Hz); 12.14-12-25 (m, 0.9H); HPLC (λ=214 nm, [A]: rt. 15.00 min (95%)

Example 169

1-(1H-benzo[d]imidazol-5-yl)-5-(4-(4-morpholinocyclohexyl)phenyl)imidazolidin-2-one The compound was synthesized starting from 5-aminobenzimidazole (486 mg, 3.66 mmol), 34-(4-morpholinocyclohexyl)phenyl carbaldehyde (1 g, 3.66 mmol), TMSCN (0.98 mL, 7.32 mmol), 10% Pd—C (200 mg), TEA (9.16 mL, 90.60 mmol), di-(imidazol-1-yl)methanone (1.76 g, 10.88 mmol) as described in method 2.

Yield: 0.040 g (2.4%); MS m/z 446.5 (M+H)$^+$; $^1$H NMR (400 MHz, CDCl3): δ 7.91 (s, 1H); 7.64 (s, 1H); 7.55 (s, 1H); 7.25-7.15 (merged with CDCl3, 5H); 5.35 (t, 1H); 4.81 (t, 1H); 3.99 (t, 1H); 3.57 (s, 4H); 3.56-3.32 (m, 2H); 2.85 (s, 1H); 2.45 (s, 4H); 2.21 (S, 1H); 1.99-1.82 (m, 4H); 1.69-1.55 (m, 4H), HPLC (λ=214 nm, [A]: rt 5.84 min (99.4%).

Example 170

(S)-1-(1H-benzo[d]imidazol-5-yl)-5-(4-(1-methylpiperidin-4-yl)Phenyl)imidazolidin-2-one

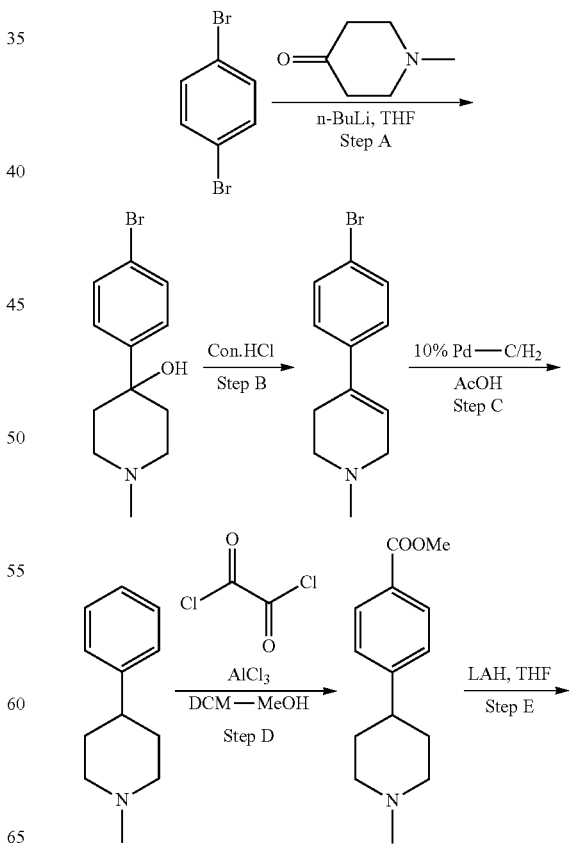

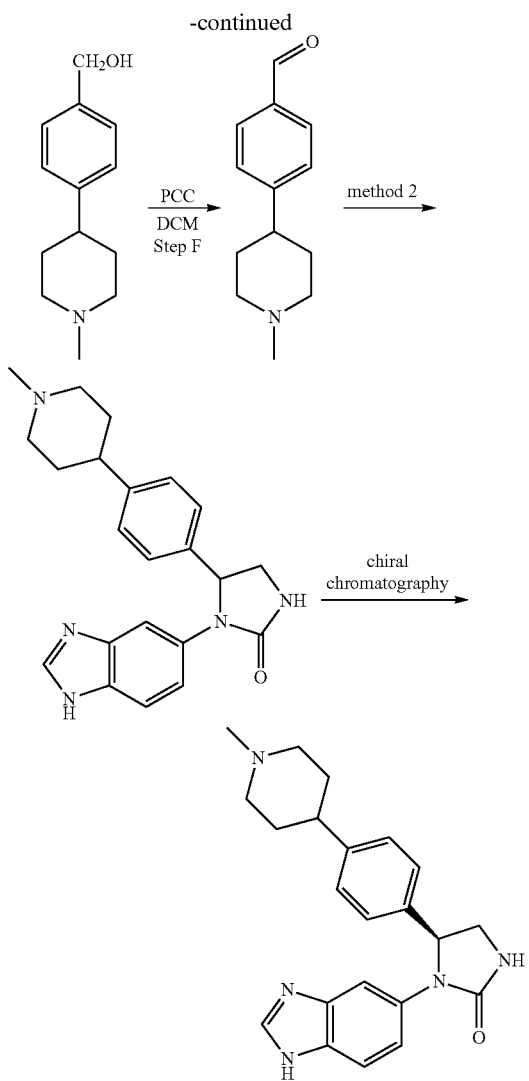

Step A n-BuLi (2.3M in hexane; 18.4 mL, 42.39 mmol) was added to a solution of 1,4-dibromobenzene (10 g, 42.39 mmol) in THF (100 mL) at −78° C. over a period of 10 min (solid separates while adding n-BuLi). Stirred for 30 min at the same temperature and added n-methyl, 4-piperidone (4.9 mL, 42.39 mmol) and slowly warmed to room temperature and stirred for 1 hr at RT. The Reaction mass was quenched with ammonium chloride solution and diluted with ethyl acetate. Separated organic layer and washed with water followed by brine solution. Dried over anhydrous sodium sulphate and concentrated to afford 8.5 g (74%) of the product as an oily liquid which was used without further characterization.

Step B

6N HCl (10 mL) was added to the product of Step A (500 mg, 1.85 mmol) and stirred at reflux for 16 h. The RM was concentrated and the residue was basified with saturated ammonium bicarbonate solution and extracted with ethyl acetate. The combined organic layers were washed with water followed by brine solution, dried over anhydrous sodium sulphate and concentrated to afford 350 mg (75%) of the product as white solid which was used without further characterization.

Step C

10% Pd—C (2 g) was added to a solution of the product of step B (8 g, 31.74 mmol) in AcOH (80 mL) and hydrogenated in par apparatus for 19 h. The RM was filtered through celite bed and washed with ethyl acetate. The filtrate was concentrated to afford 7.5 g (90%) of the product as an oily liquid which was used without further characterization.

Step D

Oxalyl chloride (4.1 mL, 45.71 mmol) was added to a solution of the product of step C (2 g, 11.42 mmol) in DCM (20 mL) at −30° C. followed by AlCl$_3$ (6 g, 45.71 mmol) at the same temperature. Stirred for 1 h at −30° C. and slowly warmed to RT, stirred for 2 h. The RM was cooled to 0° C. and added methanol (30 mL) slowly (exothermic) for 15 min (Note: salts will form and to stir the RM added more of methanol until the solution is clear). Slowly warmed to RT and stirred for 18 h. The RM was quenched into Aq.Na$_2$CO$_3$ solution and diluted with ethyl acetate. The salts were filtered off and washed with ethyl acetate until there is no compound in the salts. Organic layer was separated form the filtrate and washed with water followed by brine solution. Dried over anhydrous sodium sulphate and concentrated to afford 1.3 g (50%) of the product as brown oil which was used without further characterization.

Step E

LiAlH$_4$ (211 mg, 5.57 mmol) was added to a solution of the product of step D (1.3 g, 5.57 mmol) in THF (20 mL) at −0° C. over a period of 15 min. Slowly warmed to RT and stirred for 1 h. The RM was quenched with saturated sodium sulphate solution and diluted with ethyl acetate. The salts were filtered off and washed with ethyl acetate. Combined organic layers and washed with water followed by brine solution. Dried over anhydrous sodium sulphate and concentrated to afford 850 mg (74.5%) of the product as an oil which was used without further characterization.

Step F

PCC (1.05 g, 4.87 mmol) was added to a solution of the product of step E (1 g, 4.87 mmol) in DCM (10 mL) and stirred for 30 min. The reaction mass was dissolved by adding a little of methanol and purified by column chromatography over neutral alumina using 5% methanol in chloroform as eluent to afford 750 mg (75%) of 4-(1-methylpiperidin-4-yl) phenyl) carbaldehyde as an oily liquid which slowly precipitates on long standing which was used without further characterization.

The title compound was synthesized starting from 5-aminobenzimidazole (393 mg, 2.95 mmol), 3-54-(1-methylpiperidin-4-yl)phenyl) carbaldehyde (500 mg, 2.46 mmol), TMSCN (0.5 mL, 4.92 mmol), 10% Pd—C (150 mg), TEA (2.23 mL, 16.04 mmol), di-(imidazol-1-yl)methanone (334 mg, 2.06 mmol) as described in method 2.

The product was further purified by Prep HPLC by the following chiral conditions:

| Column: Chiralpak ADH | Mobile phase: Hexane:Ethanol:0.1% Diethyl amine |
|---|---|
| Flow rate: 32 mL/min | UV: 210 nm   Diluents: Mobile phase |

Solvent was evaporated and co-distilled with toluene and washed with pentane to afford 25 mg of the product as brown solid Yield: 0.025 g (2.2%); MS m/z 376.4 (M+H)$^+$; $^1$H NMR 400 MHz, CDCl3): δ 9.56 (bs, 1H); 7.89 (s, 1H); 7.66 (s, 1H); 7.51 (s, 1H); 7.27-7.13 (merged with CDCl$_3$, 7H); 5.35-5.31 (q, 1H); 5.01-4.90 (m, 1H); 4.69 (s, 1H); 3.95 (t, 1H); 3.37 (t, 1H); 2.94 (d, 2H); 2.50-2.31 (m, 1H); 2.30 (s, 3H); 2.04-1.98 (m, 3H); 1.86-1.65 (m, 4H), HPLC (λ=214 nm, [B]: rt 5.04 min (97.7%)

Example 171

1-(1H-benzo[d]imidazol-5-yl)-5-(4-(tetrahydro-2H-pyran-4-yl)phenyl)imidazolidin-2-one

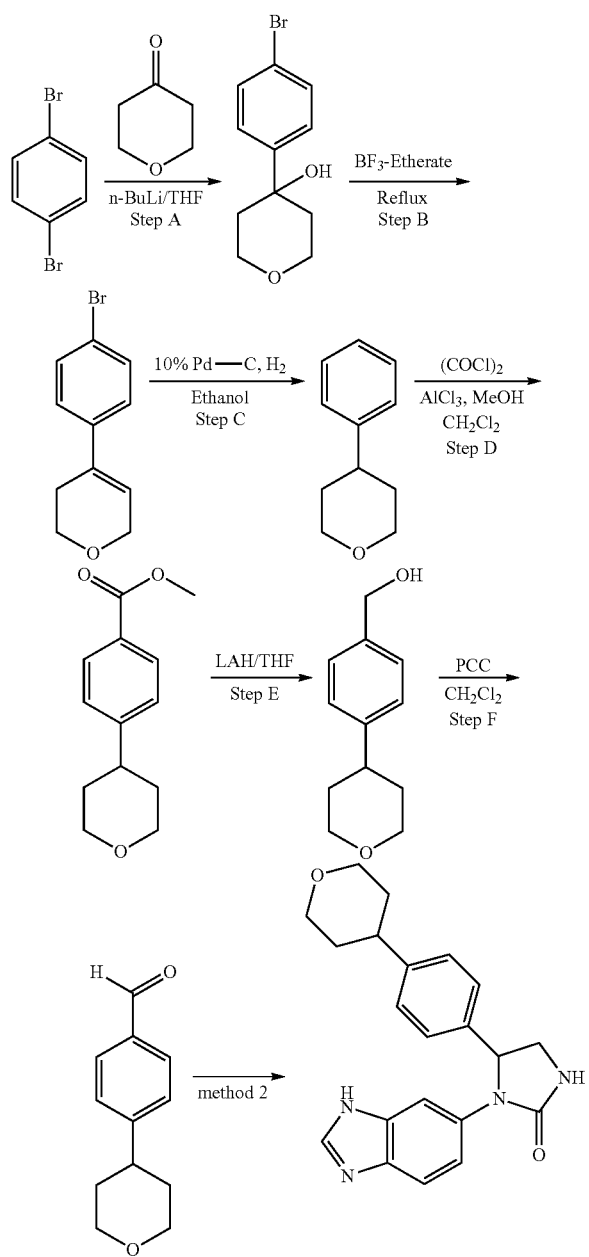

Step A n-Butyl lithium (2.3M in hexane; 1.83 mL, 4.23 mmol) was added to a solution of 1,4-dibromobenzene (1 g, 4.23 mmol) in dry THF at −78° C. The reaction mixture was stirred for 20 min, then the 1H-tetrahydro 4-one (0.4 mL, 4.23 mmol) was added at the same temperature. Slowly the reaction mixture was allowed to reach room temperature over 2 h, the reaction mixture quenched with 5% citric acid solution (10 mL) and extracted with ethyl acetate (3×25 mL) and combined organic layers dried over anhydrous sodium sulfate and concentrated in vacuum to give 900 mg (91.8%) of the product as colorless liquid, which was used without further characterization.

Step B

A suspension of the product of step A (2 g, 7.78 mmol) in BF3-etherate (10 mL) was stirred at room temperature for 2 h. Then the reaction mixture was basified with saturated NaHCO3 solution and extracted with ethyl acetate (3×50 mL) and combined organic layers dried over anhydrous sodium sulfate and concentrated in vacuum to give 1.5 g (81%) of the product which was used without further characterization.

Step C

To a solution of 10% Pd—C (60 0 mg, 10%) in ethanol (50 mL) the product of step B was added (6.0 g, 25.01 mmol) in hydrogenated vessel at 80 Psi for 16 h. Then the reaction mixture was filtered through celite bed and evaporated the solvent and dried to afford 3.42 g (83.7%) of the product as a light yellow color liquid, which was used without further characterization.

Step D

Oxalylchloride (9 mL, 98.76 mmol) was added to a solution of the product of step C (4.0 g, 24.69 mmol) in dichloromethane (50 mL) at −20° C. This reaction mixture was stirred for 30 min and added AlCl3 (32.8 g, 246.9 mmol) at the same temperature and stirred for another 1 h then allowed to reach room temperature over 2 h. Then to the reaction methanol (25 mL) was added and left overnight. The reaction mixture was basified with saturated with NaHCO3 solution and filtered and washed with ethyl acetate (100 mL) the solution was partitioned between two layers and separated the organic layer and washed with brine solution and evaporated the organic layers to afford 4.0 g (74%) of the product as a colorless liquid which was used without further characterization.

Step E

Lithium aluminum hydride (860 mg, 20.45 mmol) was added to a solution of the product of step D (4.5 g, 20.45 mmol) in dry THF (40 mL) at 0° C. Then the reaction mixture was warmed to room temperature for 2 h, and the reaction mixture cooled to 0° C. and quenched with saturated NH4Cl solution (25 mL), and filtered the mixture and washed with ethyl acetate (100 mL). The solution was partitioned between two layers and separated the organic layer and washed with brine solution and evaporated the organic layers to afford 3.2 g (82%) of the product as a light yellow solid which was used without further characterization.

Step F

Pyridinium chlorochromate (4.1 g, 19.27 mmol) was added to a solution of the product of step E (3.7 g, 19.27 mmol) in dichloromethane (40 mL) at room temperature. The reaction mixture stirred for 1 h and added neutral alumina (10 g) and passed through a filter column with 10% ethyl acetate in pet ether to give 2.2 g (60.01%) of the product as a white color solid which was used without further characterization.

The title compound was synthesized starting from 5-aminobenzimidazole (840 mg, 6.32 mmol), 3-(4-(tetrahydro-2H-pyran-4-yl)phenyl carbaldehyde (1.0 g, 5.25 mmol), TMSCN (1.15 mL, 10.52 mmol), 10% Pd—C (250 mg), TEA (3.6 mL, 26.7 mmol), di-(imidazol-1-yl)methanone (434 mg, 2.67 mmol) as described in method 2.

Yield: 0.05 g (2.1%); MS m/z 363.1 (M+H)$^+$; $^1$H NMR (400 MHz, CDCl3): δ 12.25 (d, 1H); 8.07 (d, 1H); 7.59-7.17 (m, 6H); 6.90 (d, 1H); 5.50 (d, 1H); 3.87 (t, 2H); 3.39-3.11

(merged with DMSO moisture, 2H); 3.08 (t, 1H); 2.67 (d, 1H); 1.59 (d, 4H), HPLC (λ=214 nm, [A]: rt 10.03 min (99.38%)

Example 172

1-(1H-benzo[d]imidazol-5-yl)-5-(4-(4-oxocyclohexyl)phenyl)imidazolidin-2-one

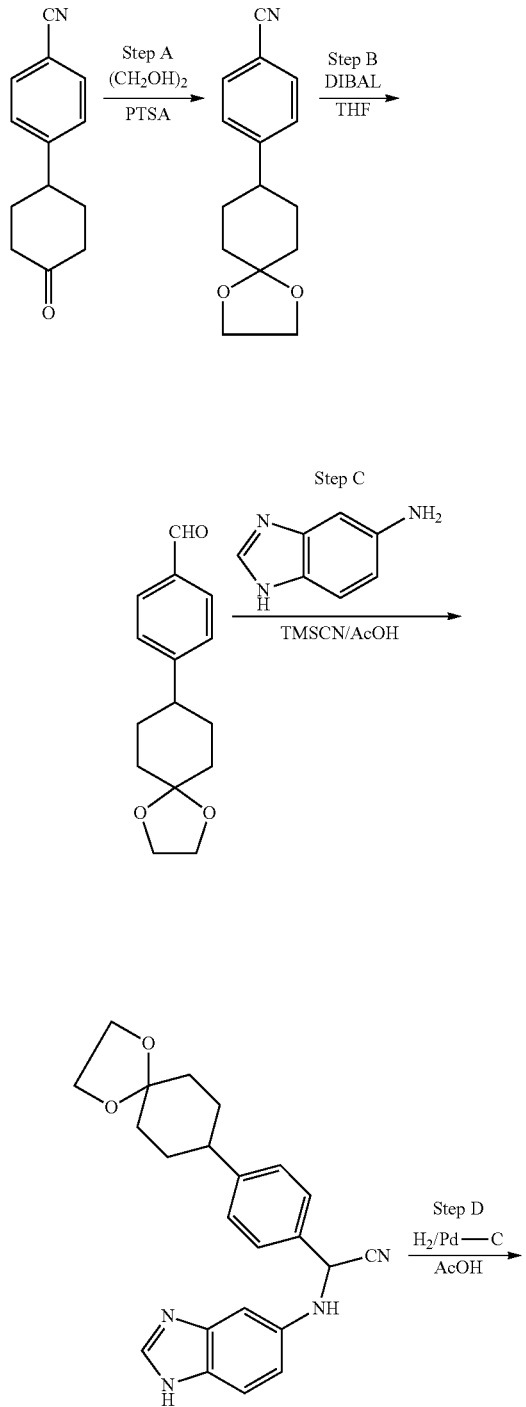

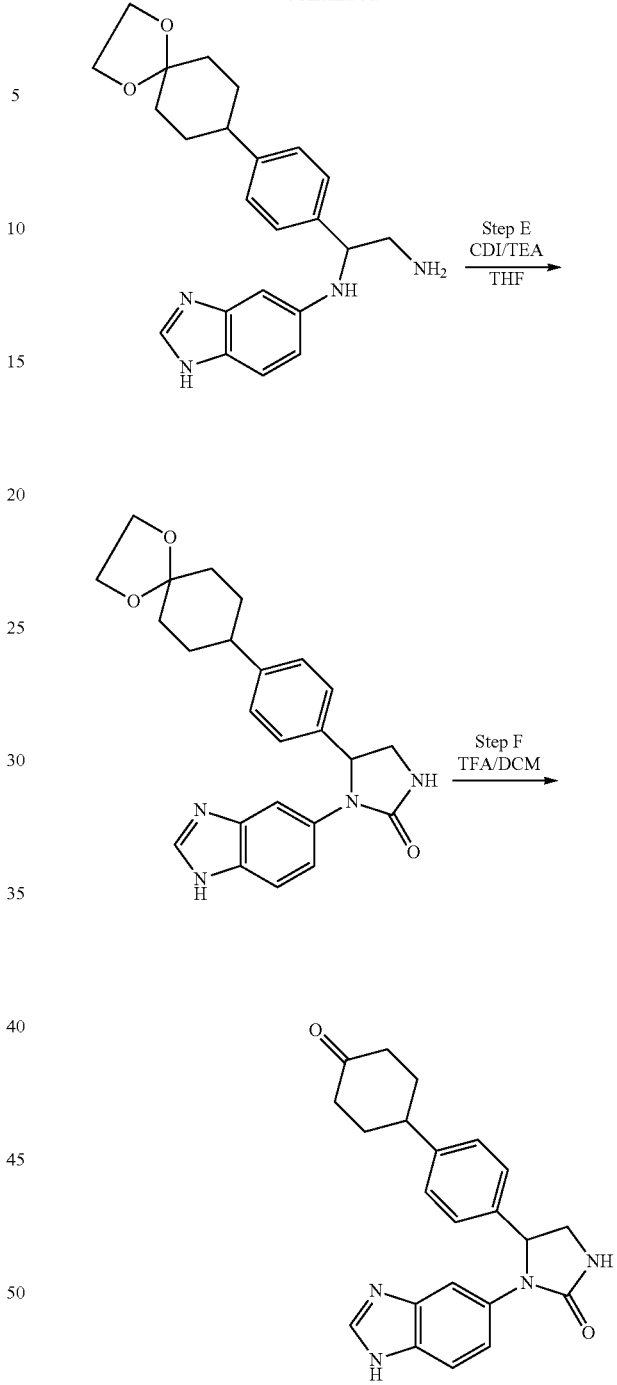

Step A

A mixture of 4-(4-cyano phenyl)cyclo hexanone (3.0 g, 15.05 mmol), ethylene glycol (2.1 mL, 37.64 mmol) and catalytic p-toluene sulfonic acid (430 mg, 2.26 mmol) in toluene (50 mL) was heated at 125-130° C. for 24 h. The reaction mass was cooled to room temperature, diluted with toluene and washed successively with saturated sodium bicarbonate solution, water, brine dried over anhydrous sodium sulfate and concentrated in vacuum to afford crude. Purification by column chromatography over silica gel (60-120 mesh) using 5% ethyl acetate in pet ether as eluent afforded 3.36 g of the product as white solid.

Step B

25% Di isobutyl aluminium hydride in toluene (17.3 mL, 27.65 mmol) was added to a solution of the product of step A (3.36 g, 13.83 mmol) in dry tetrahydrofuran (60 mL) at −40° C. The reaction mass was warmed to room temperature and stirred for 3.5 h. The reaction mass was cooled to 0° C. and quenched with saturated ammonium chloride solution. Filtered the salts and washed with ethyl acetate. The combined filtrate and washings was washed with brine, dried over anhydrous sodium sulfate and concentrated in vacuum to afford 3.36 g of the crude product as pale yellow syrup. This was taken for the next step without purification.

Step C

Trimethylsilylcyanide (0.87 mL, 6.50 mol) was added to a solution of 5-amino benzimidazole (433 mg, 3.25 mmol), the product of step B (800 g, 3.25 mmol) in acetic acid (20 mL) and stirred for 1 h 40 min. The reaction mass was quenched with cold aqueous ammonia solution and extracted with ethyl acetate (2×30 mL). The combined organic layer was washed with water, brine, dried over anhydrous sodium sulfate and concentrated in vacuum to afford 1.0 g of crude the product as yellowish brown solid.

Step D

A solution of the product of step C (1.0 g, 2.58 mmol) in acetic acid (50 mL) was hydrogenated over 10% Pd—C (250 mg) in Parr apparatus for 20 h under 80 psi pressure. The reaction mass was filtered through celite and washed with acetic acid. The combined filtrate and washings was concentrated in vacuum to afford 2.56 g of crude the product as brown liquid. This crude was directly taken for next step without any purification.

Step E

Triethylamine (9.8 mL, 70.4 mmol), carbonyldiimidazole (1.14, 7.04 mmol) were successively added to a solution of crude product of step D (2.76 g, 7.04 mmol) in tetrahydrofuran (50 mL) and refluxed for 18.5 h. The reaction mass was cooled to room temperature, poured into water and extracted with ethyl acetate (2×50 mL). The combined organic layer was washed with water, brine, dried over anhydrous sodium sulphate and concentrated in vacuum to afford crude. Purification by column chromatography over neutral alumina using 6-7% methanol in chloroform as eluent afforded 270 mg of the product as pale yellow solid. This was taken as such to the next step.

Step F

Trifluoroacetic acid (2.5 mL) was added to a solution of the product of step E (200 mg, 0.48 mmol) in dichloromethane (10 mL) at 0° C. and stirred at room temperature for 3.5 h. The volatiles were evaporated in vacuum; the resulting residue was dissolved in dichloromethane and washed successively with saturated sodium bicarbonate solution, water, brine, dried over anhydrous sodium sulfate and concentrated in vacuum to afford crude. Purification by preparative TLC using 5% methanol in chloroform as eluent and afforded 70 mg (35.52%) of the product as pale yellow solid.

Yield: 70 mg (35.52%); MS m/z 375.2 (M+H)+, 174.9 (M+2H)2+; 1H-NMR (DMSO, 400 MHz): δ 12.24 (Bs, 1H); 8.06 (s, 1H); 7.57-7.21 (m, 6H); 6.91 (s, 1H); 5.49 (t, 1H); 3.82 (t, 1H); 3.40 (t, 1H); 3.16-2.98 (m, 2H); 2.55 (merged with DMSO, 1H); 2.37-2.19 (m, 2H); 2.15-0.9 (m, 2H); 0.95-0.85 (m, 2H); HPLC (λ=214 nm, [A]: rt. 9.93 min (94.77%)

Example 173

(S)-1-(1H-benzo[d]imidazol-5-yl)-5-(4-(4,4-difluorocyclohexyl)phenyl)imidazolidin-2-one

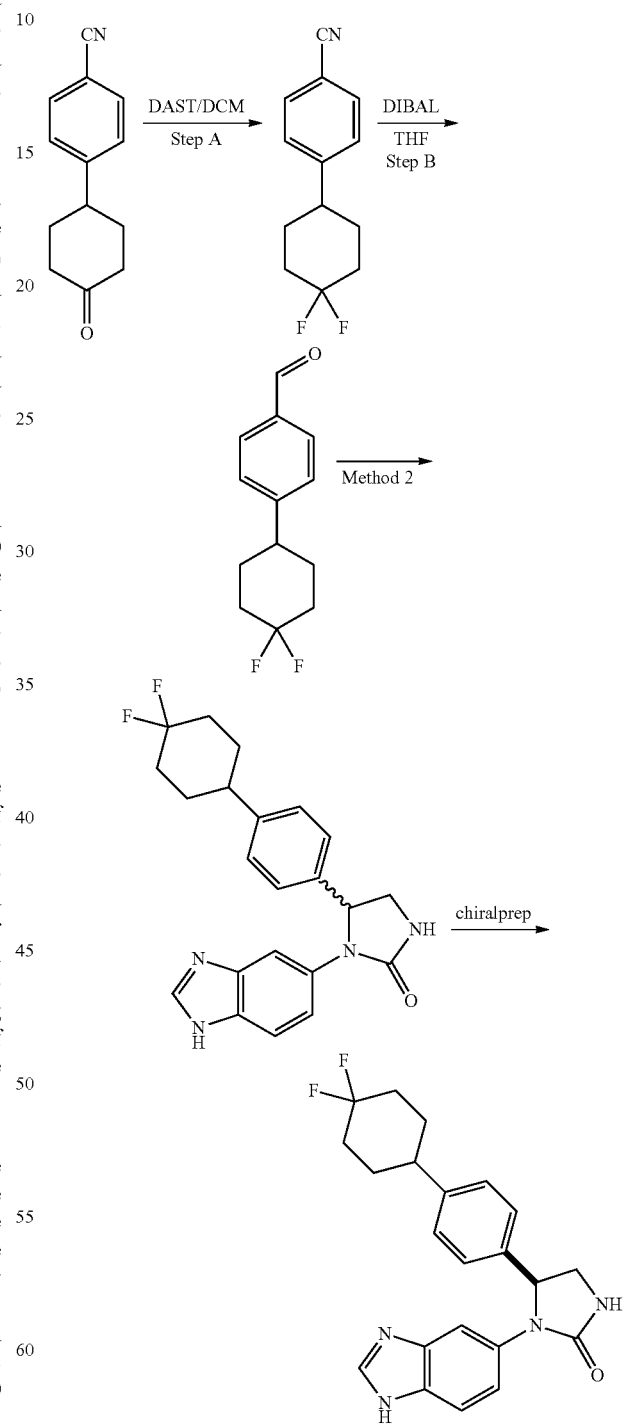

Step A

DAST (2.6 mL, 19.84 mmol) was added to a solution of 4-(4-cyano phenyl)cyclohexanone (2.0 g, 10.04 mmol) in dichloromethane (50) at 0° C. The reaction mass was warmed to room temperature and stirred for 2.5 h. The reaction mass was quenched into ice water and the organic layer was separated. The aqueous layer was extracted with dichloromethane (1×30 mL). The combined organic layer was washed with water (1×50 mL), brine (1×50 mL), dried over anhydrous sodium sulfate and concentrated in vacuum to afford crude. Purification by column chromatography over silica gel (60-120 mesh) using 10-12% ethyl acetate in pet ether as eluent afforded 1.5 g (67.63%) of the product as an off white solid which was used without further characterization.

Step B

Di isobutyl aluminium hydride (8.5 mL, 13.37 mmol) was added to a solution of the product of step A (1.5 g, 6.79 mmol) in dry tetrahydrofuran (50 mL) at −70° C. The reaction mass was warmed to room temperature and stirred for 3 h. The reaction mass was cooled to 0° C. and quenched with saturated ammonium chloride solution. The salts were filtered and washed with chloroform. The combined filtrate and washings were washed with brine, dried over anhydrous sodium sulfate and concentrated in vacuum to afford 1.5 g (96.68%) of 4-(4,4-difluorocyclohexyl)phenyl carbaldehyde as a pale yellow syrup which was used without further characterization.

The title compound was synthesized starting from 5-aminobenzimidazole (297 mg, 2.23 mmol), 3-4-(4,4-difluorocyclohexyl)phenyl carbaldehyde (500 mg, 2.23 mmol), TMSCN (0.6 mL, 2.23 mmol), 10% Pd—C (200 mg), TEA (2.8 mL, 20.0 mmol), di-(imidazol-1-yl)methanone (486 mg, 3.0 mmol) as described in method 2.

Further purification of the title compound by chiral preparative HPLC was conducted using the following chiral area conditions:

| Column: CHIRALPAK ADH (30 × 250 mm): 5µ, Flow rate: 35 mL/min, | Mobile phase: HEXANE:IPA:DEA (80:20:0.1), λmax: 225 nm, Solubility: Mobile phase. |
|---|---|

The fractions were concentrated under reduced pressure. The resulting residue was dissolved in chloroform, washed with water, brine, dried over anhydrous sodium sulphate and concentrated under reduced pressure.

Yield: 0.04 g (4.5%); MS m/z 397.2 (M+H)$^+$; $^1$H NMR DMSO-d$_6$): δ: 12.29 (d, 1H); 8.09 (d, 1H); 7.60-7.17 (m, 7H); 6.96 (d, 1H); 5.49 (s, 1H); 3.82 (d, 1H); 3.07 (t, 1H); 2.62 (t, 1H); 2.62 (s, 1H); 2.04-1.56 (m, 8H) HPLC (λ=214 nm, [A]: rt 12.69 min (100%)

Example 174

1-(1H-benzo[d]imidazol-5-yl)-5-(3-(pyrrolidin-1-yl)phenyl)imidazolidin-2-one

The compound was synthesized starting from 1H-benzo[d]imidazol-5-amine (0.400 g, 3 mmol), 3-(pyrrolidin-1-yl)benzaldehyde (0.526 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.061 g (6.2%); MS m/z 348.2 (M+H)$^+$, 174.9 (M+2H)$^{2+}$; 1H-NMR (DMSO, 400 MHz): 1.83-1.95 (m, 4H); 3.04-3.20 (m, 5H); 3.81 (t, H, J=9.1 Hz); 5.38 (q, H; J=8.7 Hz); 6.32-6.37 (m, H); 6.50 (s, H); 6.54 (d, H, J=7.5 Hz); 6.87 (s, H); 7.04 (t, H, J=7.9 Hz); 7.24-7.34 (m, H); 7.39 (d, H, J=8.7 Hz); 7.51-7.55 (m, H); 8.06 (s, H); 12.23 (br s, 0.6H); HPLC (λ=214 nm, [A]: rt. 9.68 min (99%)

Example 175

1-(1H-benzo[d]imidazol-5-yl)-5-(4-(piperidin-1-yl)phenyl)imidazolidin-2-one

The compound was synthesized starting from 1H-benzo[d]imidazol-5-amine (0.400 g, 3 mmol), 4-(piperidin-1-yl)benzaldehyde (0.570 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.006 g (0.5%); MS m/z 362.4 (M+H)$^+$, 181.7 (M+2H)$^{2+}$; $^1$H-NMR (DMSO, 400 MHz): 1.44-1.51 (m, 6H); 3.00-3.06 (m, 5H); 3.75 (t, H, 8.7 Hz); 5.35 (q, H, J=8.7 Hz); 6.78 (d, 2H, J=8.7 Hz); 7.13 (d, 2H, J=8.7 Hz); 7.21-7.23 (m, 0.6H); 7.35 (d, H, J=8.7 Hz); 7.5 (s, H); 8.06 (br s, 0.6H); HPLC (λ=214 nm, [A]: rt. 5.47 min (90%)

Example 176

1-(1H-benzo[d]imidazol-5-yl)-5-(3-(piperidin-1-yl)phenyl)imidazolidin-2-one

The compound was synthesized starting from 1H-benzo[d]imidazol-5-amine (0.400 g, 3 mmol), 3-(piperidin-1-yl)benzaldehyde (0.570 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.085 g (8.3%); MS m/z 362.2 (M+H)$^+$, 181.7 (M+2H)$^{2+}$; $^1$H-NMR (DMSO, 400 MHz): 1.40-1.57 (m, 6H); 2.95-3.09 (m, 5H); 3.73-3.83 (m, H); 5.37 (q, H, J=9.1 Hz); 6.63-6.73 (m, 2H); 6.79-6.91 (m, 2H); 7.05 (t, H; J=7.8 Hz); 7.13-7.19 (m, 0.5H); 7.27-7.37 (m, H); 7.38-7.43 (m, 0.5H); 7.44-7.49 (m, 0.5H); 7.53 (s, 0.5H); 8.04 (d, H; J=9.1 Hz); 12.15-12.25 (m, H); HPLC (λ=214 nm, [A]: rt. 5.89 min (99%)

Example 177

1-(1H-benzo[d]imidazol-5-yl)-5-(4-morpholinophenyl)imidazolidin-2-one

The compound was synthesized starting from 1H-benzo[d]imidazol-5-amine (0.333 g, 2.5 mmol), 4-morpholinobenzaldehyde (0.473 g, 2.5 mmol), TMSCN (0.375 mL, 3 mmol), Pd/C (10%, 0.02 g), TEA 1 mL, 7.2 mmol), di-(imidazol-1-yl)methanone (0.600 g, 3.7 mmol) as described in method 2.

Yield: 0.048 g (4.16%); MS m/z 364.0 (M+H)$^+$, 182.9 (M+2H)$^{2+}$; $^1$H-NMR (400 MHz, DMSO-D$_6$): 3.01-3.04 (m, 4H); 3.08-3.11 (m, H); 3.66-3.68 (m, 4H); 3.82-3.86 (m, H); 5.46-5.50 (m, H); 6.85-6.87 (m, 2H); 7.19-7.21 (m, 3H); 7.57-7.66 (m, 2H); 7.89 (d, H, J=2.1 Hz); 9.33 (s, H); HPLC (λ=214 nm, [A]: rt 8.02 min (89%)

Example 178

5-(4-cyclohexylphenyl)-1-(H-imidazo[1,2-a]pyridin-7-yl)imidazolidin-2-one

The compound was synthesized starting from H-imidazo[1,2-a]pyridin-7-amine (0.400 g, 3 mmol), 4-cyclohexylbenzaldehyde (0.565 g, 3 mmol), TMSCN (0.450 mL, 3.6 mmol), Pd/C (10%, 0.02 g), TEA 1.05 mL, 7.5 mmol), di-(imidazol-1-yl)methanone (0.730 g, 4.5 mmol) as described in method 2.

Yield: 0.067 g (6.2%); MS m/z 361.0 (M+H)$^+$; 1H-NMR (DMSO, 400 MHz): 1.10-1.23 (m, H); 1.24-1.38 (m, 4H); 1.6-1.76 (m, 5H); 2.39-2.42 (m, H); 3.05-3.15 (m, H); 3.91 (t, H, $^3$J=9.1 Hz); 5.58 (dd, H, $^3$J=5.4 Hz, $^4$J=9.1 Hz); 7.17-7.24 (m, 4H); 7.73 (dd, H, $^3$J=7.5 Hz, $^4$J=2.1 Hz); 7.76-7.79 (m, 2H); 7.87 (d, H, $^4$J=2.1 Hz); 8.00 (d, H, $^4$J=2.1 Hz); 8.61 (d, H, $^3$J=7.9 Hz); HPLC (λ=214 nm, [A]: rt. 15.73 min (99%)

Example 179

1-(H-imidazo[1,2-a]pyridin-7-yl)-5-(4-(pyrrolidin-1-yl)phenyl)imidazolidin-2-one The compound was synthesized starting from H-imidazo[1,2-a]pyridin-7-amine (0.400 g, 3 mmol), 4-(pyrrolidin-1-yl)benzaldehyde (0.530 g, 3 mmol), TMSCN (0.455 mL, 3.6 mmol), Pd/C (10%, 0.02 g), TEA (1.05 mL, 7.5 mmol), di-(imidazol-1-yl)methanone (0.730 g, 4.5 mmol) as described in method 2.

Yield: 0.019 g (1.8%); MS m/z 348.2 (M+H)$^+$, 174.9 (M+2H)$^{2+}$; $^1$H-NMR (DMSO, 400 MHz): 1.74-1.91 (m, 4H); 3.06-3.17 (m, 5H); 3.88 (t, H; J=9.1 Hz); 5.42-5.47 (m, H); 6.46 (d, 2H, $^3$J=8.3 Hz); 7.12 (d, 2H, $^3$J=8.3 Hz); 7.70-7.76 (m, 2H); 7.85 (d, H, $^4$J=2.1 Hz); 7.99 (d, H, $^4$J=2.1 Hz); 8.57-8.60 (m, H); HPLC (λ=214 nm, [A]: rt. 9.40 min (94%)

Example 180

1-(H-imidazo[1,2-a]pyridin-7-yl)-5-(3-(pyrrolidin-1-yl)phenyl)imidazolidin-2-one The compound was synthesized starting from H-imidazo[1,2-a]pyridin-7-amine (0.400 g, 3 mmol), 3-(pyrrolidin-1-yl)benzaldehyde (0.530 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.01 g (0.8%); MS m/z 348.2 (M+H)$^+$, 174.9 (M+2H)$^{2+}$; $^1$H-NMR (DMSO, 400 MHz): 1.81-1.91 (m, 4H); 3.03-3.20 (m, 5H); 3.83 (t, H, J=9.1 Hz); 5.39 (q, H, J=9.1 Hz); 6.35-6.39 (m, H); 6.50 (d, 2H, J=7.9 Hz); 7.04-7.09 (m, 2H); 7.23 (s, H); 7.31-7.34 (m, H); 7.50 (dd, H, $^3$J=7.9 Hz, $^4$J=2.5 Hz); 7.67 (s, H); 8.30 (d, H, J=7.9 Hz); HPLC (λ=214 nm, [A]: rt. 10.62 min (100%)

Example 181

1-(H-imidazo[1,2-a]pyridin-7-yl)-5-(4-(piperidin-1-yl)phenyl)imidazolidin-2-one

The compound was synthesized starting from H-imidazo[1,2-a]pyridin-7-amine (0.400 g, 3 mmol), 4-(piperidin-1-yl)benzaldehyde (0.570 g, 3 mmol), TMSCN (0.455 mL, 3.6 mmol), Pd/C (10%, 0.02 g), TEA 1.05 mL, 7.5 mmol), di-(imidazol-1-yl)methanone (0.730 g, 4.5 mmol) as described in method 2.

Yield: 0.11 g (10.1%); MS m/z 362.0 (M+H)$^+$, 181.0 (M+2H)$^{2+}$; $^1$H-NMR (DMSO, 400 MHz): 1.67-1.78 (m, 2H); 1.87-2.02 (m, 4H); 3.22-3.28 (m, H); 3.45 (t, 4H, J=5.4 Hz); 4.07 (t, H, 9.1 Hz); 5.63-5.68 (m, H); 7.48-7.54 (m, 4H); 7.76 (d, H, J=2.5 Hz); 7.78-7.80 (m, H); 7.84 (dd, 11H, $^3$J=7.9 Hz, $^4$J=2.1 Hz); 7.91 (d, H, $^4$J=2.5 Hz); 8.51 (d, H, $^3$J=7.9 Hz); HPLC (λ=214 nm, [A]: rt. 5.51 min (96%)

Example 182

1-(H-imidazo[1,2-a]pyridin-7-yl)-5-(3-(piperidin-1-yl)phenyl)imidazolidin-2-one

The compound was synthesized starting from H-imidazo[1,2-a]pyridin-7-amine (0.400 g, 3 mmol), 3-(piperidin-1-yl)benzaldehyde (0.570 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.019 g (1.7%); MS m/z 362.3 (M+H)$^+$, 181.7 (M+2H)$^{2+}$; $^1$H-NMR (DMSO, 400 MHz): 1.40-1.61 (m, 6H); 3.05-3.18 (m, 4H); 3.89-3.96 (m, H); 5.53 (dd, H; $^3$J=9.5 Hz; $^4$J=3.3 Hz); 6.67-6.73 (m, H); 6.87-6.92 (m, H); 7.01 (s, H); 7.18 (t, H; J=7.9 Hz); 7.74 (dd, H; $^3$J=7.5 Hz, $^4$J=2.1 Hz); 7.77 (s, H); 7.80 (s, H); 7.89 (d, H, J=2.1 Hz); 8.02 (d, H, J=2.1 Hz); 8.62 (d, H; $^3$J=7.9 Hz); HPLC (λ=214 nm, [A]: rt. 6.20 min (100%)

Example 183

1-(H-imidazo[1,2-a]pyridin-7-yl)-5-(1-phenylpiperidin-4-yl)imidazolidin-2-one

The compound was synthesized starting from H-imidazo[1,2-a]pyridin-7-amine (0.400 g, 3 mmol), 1-phenylpiperidine-4-carbaldehyde (0.570 g, 3 mmol), TMSCN (0.375 mL, 3 mmol), Pd/C (10%, 0.02 g), TEA 1.05 mL, 7.5 mmol), di-(imidazol-1-yl)methanone (0.730 g, 4.5 mmol) as described in method 2.

Yield: 0.007 g (0.6%); MS m/z 362.3 (M+H)$^+$, 181.7 (M+2H)$^{2+}$; $^1$H-NMR (DMSO, 400 MHz): 1.38-1.49 (m, 3H); 1.64-1.72 (m, H); 1.90-2.01 (m, H); 2.40-2.43 (m, H); 2.52-2.65 (m, H); 3.63-3.74 (m, 2H); 4.64-4.69 (m, H); 6.70-6.76 (m, H); 6.89 (d, 2H, $^3$J=7.5 Hz); 7.15 (t, 2H, $^2$J=7.9 Hz); 7.62 (s, H); 7.83 (dd, H, $^3$J=7.5 Hz, $^4$J=2.1 Hz); 7.94 (d, H, $^4$J=2.1 Hz); 8.08 (d, H, $^4$J=2.1 Hz); 8.16 (d, H, $^4$J=2.1 Hz); 8.72 (d, H, $^3$J=7.9 Hz); HPLC (λ=214 nm, [A]: rt. 7.02 min (95%)

Example 184

(S)-3-(1H-benzo[d]imidazol-5-yl)-4-(4-(3-methoxypropyl)phenyl)oxazolidin-2-one

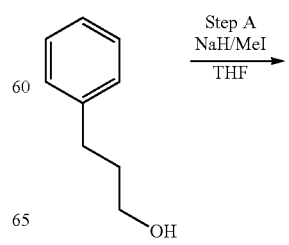

Step A
NaH/MeI
THF

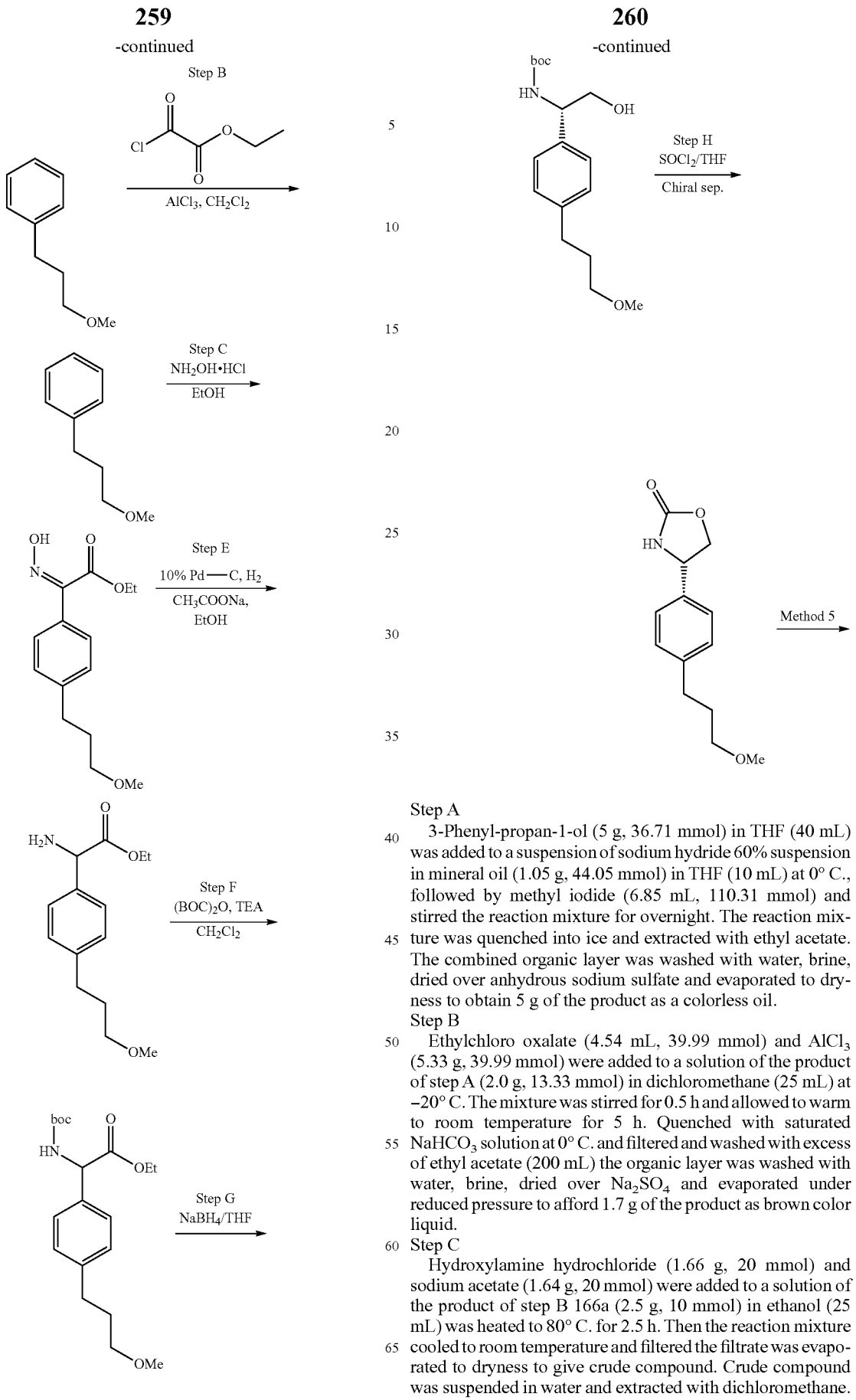

Step A

3-Phenyl-propan-1-ol (5 g, 36.71 mmol) in THF (40 mL) was added to a suspension of sodium hydride 60% suspension in mineral oil (1.05 g, 44.05 mmol) in THF (10 mL) at 0° C., followed by methyl iodide (6.85 mL, 110.31 mmol) and stirred the reaction mixture for overnight. The reaction mixture was quenched into ice and extracted with ethyl acetate. The combined organic layer was washed with water, brine, dried over anhydrous sodium sulfate and evaporated to dryness to obtain 5 g of the product as a colorless oil.

Step B

Ethylchloro oxalate (4.54 mL, 39.99 mmol) and $AlCl_3$ (5.33 g, 39.99 mmol) were added to a solution of the product of step A (2.0 g, 13.33 mmol) in dichloromethane (25 mL) at −20° C. The mixture was stirred for 0.5 h and allowed to warm to room temperature for 5 h. Quenched with saturated $NaHCO_3$ solution at 0° C. and filtered and washed with excess of ethyl acetate (200 mL) the organic layer was washed with water, brine, dried over $Na_2SO_4$ and evaporated under reduced pressure to afford 1.7 g of the product as brown color liquid.

Step C

Hydroxylamine hydrochloride (1.66 g, 20 mmol) and sodium acetate (1.64 g, 20 mmol) were added to a solution of the product of step B 166a (2.5 g, 10 mmol) in ethanol (25 mL) was heated to 80° C. for 2.5 h. Then the reaction mixture cooled to room temperature and filtered the filtrate was evaporated to dryness to give crude compound. Crude compound was suspended in water and extracted with dichloromethane.

Combined organic layer was dried over anhydrous sodium sulfate and evaporated to dryness to get 2.7 g of the product as a colorless liquid.

Step D

To a solution of 10% Pd—C (300 mg, 10%) in ethanol was added the product of step C (2.7 g, 10.18 mmol) and hydrogenated at 80 Psi at room temperature for overnight. Then the catalyst was filtered through celite bed and evaporated the solvent to give 2.2 g of the product as a colorless liquid.

Step E

Boc anhydride (2.1 g, 9.63 mmol) was added to a solution of the product of step D (2.2 g, 8.76 mmol) and triethylamine (1.06 mL, 14.44 mmol) in dichloromethane (30 mL), and stirred for 1 h at room temperature. The reaction mixture was washed with water (30 mL) and extracted with dichloromethane (3×50 mL). The combined organic layer was washed with brine (20 mL), dried over anhydrous sodium sulfate and evaporated to dryness to get crude. The crude compound was triturated with n-pentane and dried to give 2.9 g of the product as brown oil.

Step F

Sodium borohydride (1.25 g, 33.04 mmol) was added to a solution of the product of step E (2.9 g, 8.26 mmol) in ethanol (30 mL) at RT and heated at 50° C. for 2 h. Evaporated the solvent under reduced pressure to get crude. Crude was quenched with saturated NH$_4$Cl solution (25 mL), diluted with water and extracted with dichloromethane. The combined organic layer and washed with brine solution and evaporated to dryness to afford 2.2 g of the product as a solid. Chiral prep HPLC purification using following conditions: Column: Chiral pak IC (30×250 mm) 10μ, Mobile phase: Hexane:ethanol (85:15); Flow rate: 34 mL/min, UV: 210 nm, Diluent: Mobile phase The prep fractions were concentrated in vacuum and partitioned between water and chloroform. The separated organic layer was washed with brine solution. Dried over anhydrous sodium sulphate and concentrated in vacuum to afford 670 mg of the product as brown solid.

Step G

Thionyl chloride (1.27 mL, 17.34 mmol) was added to a solution of the product of step F (0.67 g, 2.16 mmol) in tetrahydrofuran (10 mL) at 0° C. Then the reaction mixture allowed to room temperature for 12 h. The solvent was evaporated and basified with saturated NaHCO$_3$ solution (10 mL) and extracted with chloroform (3×25 mL) and combined organic layers dried over anhydrous sodium sulfate and concentrated in vacuum to give 0.35 g of the product as off white solid.

The product was further synthesized according to method 5 step D, starting from the product of step G (350 mg, 1.48 mmol), 1,2-diamino 4-bromo benzene (306 mg, 1.78 mmol), cesium fluoride (450 mg, 2.96 mmol) and copper iodide (42 mg, 0.22 mmol), 1,2-diaminocyclohexane (25 mg, 0.22 mmol), formic acid (7 mL).

Yield: 0.280 g (53.9.3%); MS m/z 352.2 (M+H)$^+$; $^1$H NMR (400 MHz, CDCl3): δ 10.26 (Bs, 1H); 7.88 (s, 1H); 7.62 (s, 1H); 7.46 (s, 1H); 7.23-7.12 (m, 4H); 5.39 (q, 1H); 4.81 (t, 1H); 4.26 (q, 1H); 3.35-3.30 (m, 4H); 2.61 (t, 2H); 1.85-1.78 (m, 2H), HPLC (λ=214 nm), [A]: rt 11.38 min (96.6%), Chiral HPLC-96.40%.

Example 185

3-(1H-benzo[d]imidazol-5-yl)-4-(4-(3-(dimethylamino)propyl)phenyl)oxazolidin-2-one

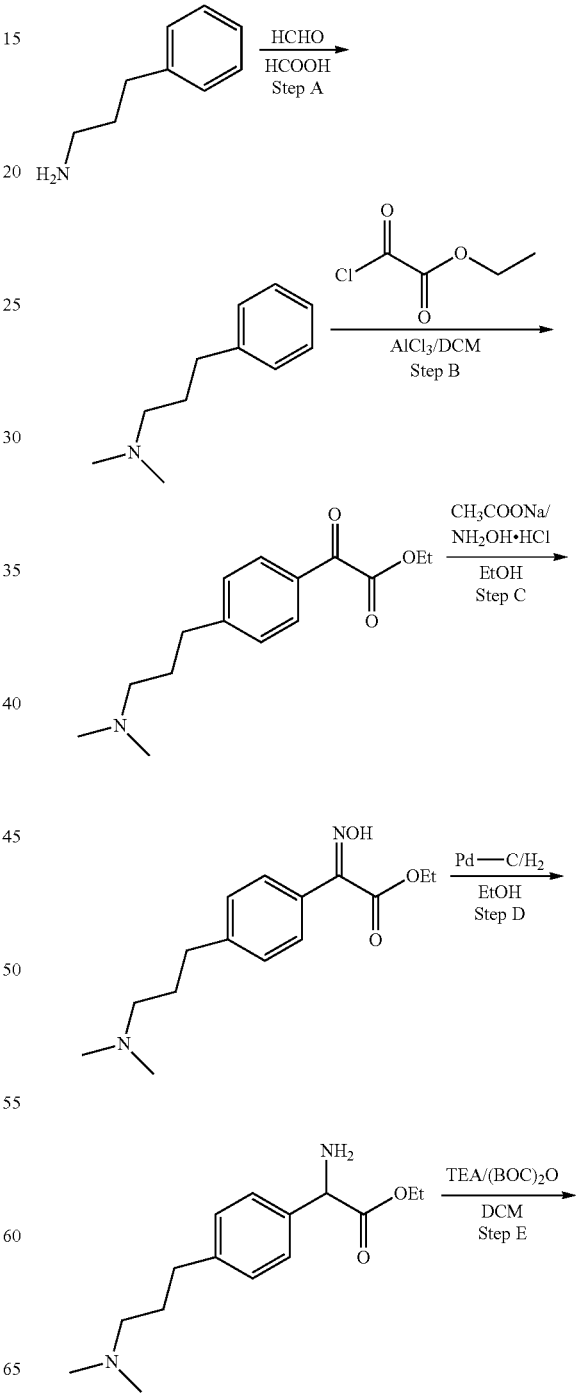

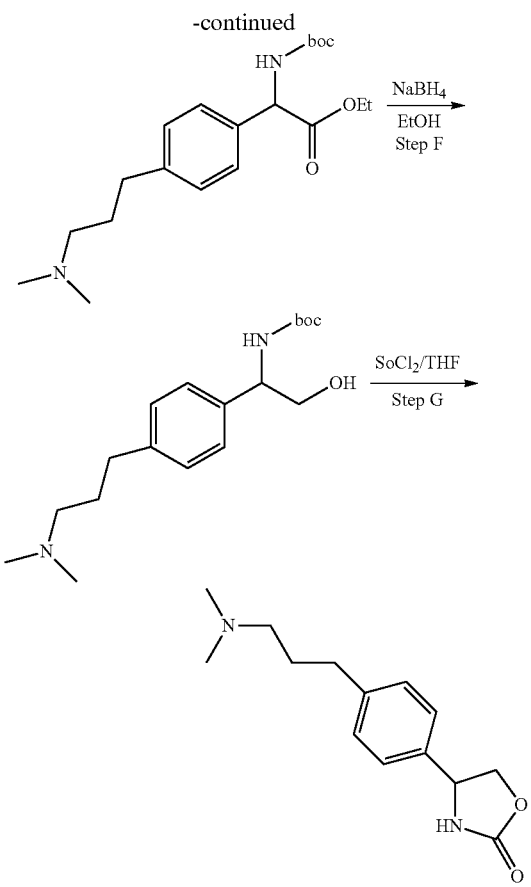

Step A

Formaldehyde (75 mL) was added to a solution of 3-phenylpropyl amine (5 g, 36.97 mmol) in formic acid (50 mL) and stirred at reflux for 18 hr. Concentrated the RM and basified the residue with saturated bicarbonate solution and extracted with ethyl acetate. Combined organic layers and washed with water followed by brine solution. Dried over anhydrous sodium sulphate and concentrated to afford 3.4 g (56%) of the product as oily liquid.

Step B

Ethyloxalyl chloride (7 mL, 61.34 mmol) was added to a solution of the product of step A (2.5 g, 15.33 mmol) in DCM (30 mL) at −30° C. over a period of 10 min. AlCl$_3$ (8.18 g, 61.34 mmol) was added to the above clear solution in three lots over a period of 15 min at −30° C. Stirred for 1 hr at −20° C. to −30° C. Slowly warmed to RT and stirred for 2 hr. The reaction mass was quenched into Aq.Na$_2$CO$_3$ solution and extracted with ethyl acetate The salts were filtered and washed with ethyl acetate until there is no compound in the precipitate. Organic layer was separated from the filtrate and washed with water followed by brine solution. Dried over anhydrous sodium sulphate and concentrated to afford 1.2 g (29.7%) of the product as colorless oil.

Step C

Sodium acetate (748 mg, 9.12 mmol) was added to a suspension of the product of step B (1.2 g, 4.56 mmol), hydroxylamine HCl (634 mg, 9.12 mmol) in ethanol (15 mL) and stirred at reflux for 4 hr. Cooled to RT and filtered off the salts and washed the cake with ethanol. The filtrate was concentrated to afford 1.48 g of the product as white semisolid.

Step D

10% Pd—C (280 mg) was added to a solution of the product of step C (1.4 g, 5.03 mmol) in ethanol (30 mL) and hydrogenated in par apparatus for 16-18 hr at 80 psi. Filtered the RM through celite and washed with ethanol. The filtrate was concentrated to afford 1.2 g (90%) of the product as oily liquid.

Step E

Boc anhydride (1.2 mL, 5.49 mmol) was added to a solution of the product of step D (1.2 g, 4.58 mmol) in TEA (0.95 mL, 6.87 mmol), DCM (20 mL) and stirred for 2 hr. Added water and separated the organic layer. Organic layer was washed with water followed by brine solution. Dried over anhydrous sodium sulphate and concentrated to afford 1.2 g (72%) of the product as colorless oil.

Step F

NaBH$_4$ (713 mg, 4.69 mmol) was added to a solution of the product of step E (1.7 g, 4.69 mmol) in ethanol (20 mL) and slowly warmed to 50° C. and stirred to dissolve. Cooled to RT and stirred for 3 hr. Concentrated the RM and added water to the residue, extracted with ethyl acetate. Combined organic layers and washed with water followed by brine solution. Dried over anhydrous sodium sulphate and concentrated to afford g of the product as oil.

Step G

Thionyl chloride (2.5 mL, 29.81 mmol) was added to a solution of the product of step F (1.2 g, 3.72 mmol) in THF (10 mL) and stirred for hr at RT. Concentrated the RM and the residue was basified with saturated bicarbonate solution. Extracted with ethyl acetate and the organic layer was washed with water followed by brine solution. Dried over anhydrous sodium sulphate and concentrated to afford 610 mg of crude product as oil. Proceeded as such for the next step with out any purification.

The compound was further synthesized according to method 5 step D, starting from the product of step G (600 mg, 2.41 mmol), 4-bromo 1,2-diamino benzene (497 mg, 2.66 mmol), and copper iodide (69 mg, 0.36 mmol), 1,2-diaminocyclohexane (41 mg, 0.362 mmol), formic acid (3 mL)

Yield: 0.025 g (2.8%); MS m/z 365.2 (M+H)$^+$; $^1$H NMR (400 MHz, CD3OD): δ 8.11 (s, 1H); 7.60 (s, 1H); 7.49 (d, 1H); 7.33 (d, 3H); 7.20 (d, 2H); 5.63 (q, 1H); 4.25 (q, 1H); 2.77 (t, 2H); 2.63-2.51 (m, 7H); 2.04-1.83 (m, 3H); HPLC (λ=214 nm), [A]: rt 6.77 min (96.6%).

Example 186

(S)-3-(7-methyl-1H-benzo[d]imidazol-5-yl)-4-phenyloxazolidin-2-one

The compound was synthesized starting from (S)-4-phenyloxazolidin-2-one (1 equiv., 0.326 g, 2 mmol), 5-bromo-3-methylbenzene-1,2-diamine (1 equiv., 0.402 g, 2 mmol), copper(I) iodide (0.1 equiv., 0.038 g, 0.2 mmol), cesium fluoride (2 equiv., 0.605 g, 4 mmol), cyclohexane-1,2-diamine (0.1 equiv., 0.024 mL, 0.2 mmol). The solids were given together in a reaction flask and the flask was purged with argon. A solution of cyclohexane-1,2-diamine in 10 mL dioxane was added to the flask. The reaction was stirred at 95° C. for 48 hours, before the reaction was cooled down to 45° C. and filtered through a pad of CELITE®. The pad was washed with warm dichloromethane and the solution was concentrated under reduced pressure. The intermediate product was purified via FPLC using a chloroform-methanol gradient (0→10%, product elutes at about 5%).

The (S)-3-(3,4-diamino-5-methylphenyl)-4-phenyloxazolidin-2-one was dissolved in triethyl orthoformate and was refluxed for 30 minutes. After cooling the excess of triethyl orthoformate was removed under reduced pressure. The final product was purified via FPLC using a chloroform-methanol gradient (0→10%).

Yield: 0.014 g (2.4%); MS m/z 294.1 (M+H)+; 1H NMR (400 MHz, DMSO-D6): δ 2.40-2.43 (m, 3H); 4.11-4.14 (m, H); 4.79-4.84 (m, H); 5.68-5.74 (m, H); 7.06-7.16 (m, H); 7.21-7.27 (m, H); 7.30-7.39 (m, 5H); 8.08-8.14 (m, H); 12.40 (br s, H), HPLC (λ=214 nm), [B]: rt 9.57 min (99.6%).

Example 187

(S)-3-(6-fluoro-1H-benzo[d]imidazol-5-yl)-4-phenyloxazolidin-2-one

The compound was synthesized starting from (S)-4-phenyloxazolidin-2-one (1 equiv., 0.328 g, 2 mmol), 4-bromo-5-fluorobenzene-1,2-diamine (1 equiv., 0.412 g, 2 mmol), copper(I) iodide (0.1 equiv., 0.040 g, 0.2 mmol), cesium fluoride (2 equiv., 0.608 g, 4 mmol), cyclohexane-1,2-diamine (0.1 equiv., 0.024 mL, 0.2 mmol). The dried solids were given together in a reaction flask and the flask was purged with argon. A solution of cyclohexane-1,2-diamine in 4 mL dioxane was added to the flask. The reaction was stirred at 95° C. for 48 hours, before the reaction was cooled down to 45° C. and filtered through a pad of CELITE®. The pad was washed with warm dichloromethane and the solution was concentrated under reduced pressure. The intermediate product was purified via FPLC using a chloroform-methanol gradient (0→10%, product elutes at about 5%).

Yield: 0.078 g (13.6%)

The (S)-3-(4,5-diamino-2-fluorophenyl)-4-phenyloxazolidin-2-one was dissolved in triethyl orthoformate and was refluxed for 30 minutes. After cooling the excess of triethyl orthoformate was removed under reduced pressure. The final product was purified via FPLC using a chloroform-methanol gradient (0→10%). Further purification by means of semi-preparative HPLC (acetonitrile/water gradient with 0.04% TFA) was necessary.

Overall yield: 0.003 g (1.5%, calc. for TFA salt); MS m/z 298.0 (M+H)+; HPLC (λ=214 nm), [B]: rt 9.06 min (100%).

Example 188

(S)-3-(7-fluoro-1H-benzo[d]imidazol-5-yl)-4-phenyloxazolidin-2-one

The compound was synthesized starting from (S)-4-phenyloxazolidin-2-one (1 equiv., 0.082 g, 0.5 mmol), 5-bromo-3-fluorobenzene-1,2-diamine (1 equiv., 0.103 g, 0.5 mmol), copper(I) iodide (0.1 equiv., 0.010 g, 0.05 mmol), cesium fluoride (2 equiv., 0.152 g, 1 mmol), cyclohexane-1,2-diamine (0.1 equiv., 0.006 mL, 0.05 mmol). The dried solids were given together in a reaction flask and the flask was purged with argon. A solution of cyclohexane-1,2-diamine in 4 mL dioxane was added to the flask. The reaction was stirred at 95° C. for 48 hours, before the reaction was cooled down to 45° C. and filtered through a pad of CELITE®. The pad was washed with warm dichloromethane and the solution was concentrated under reduced pressure. The intermediate product was purified via FPLC using a chloroform-methanol gradient (0→10%, product elutes at about 5%).

The (S)-3-(3,4-diamino-5-fluorophenyl)-4-phenyloxazolidin-2-one was dissolved in triethyl orthoformate and was refluxed for 30 minutes. After cooling the excess of triethyl orthoformate was removed under reduced pressure. The final product was purified via FPLC using a chloroform-methanol gradient (0→10%). Further purification by means of semi-preparative HPLC (acetonitrile/water gradient with 0.04% TFA) was necessary.

Yield: 0.008 g (3.9%, calc. for TFA salt); MS m/z 298.0 (M+H)+; 1H NMR (400 MHz, DMSO-D6): δ 4.11-4.15 (m, H); 4.80-4.85 (m, H); 5.72-5.76 (m, H); 7.21-7.25 (m, H); 7.29 (s, H); 7.31-7.32 (m, 2H); 7.36-7.38 (m, 2H); 7.44 (s, H); 8.46 (s, H), HPLC (λ=214 nm), [B]: rt 9.92 min (100%).

Example 189

(S)-3-(1H-benzo[d]imidazol-5-yl)-4-(cyclohexylmethyl)oxazolidin-2-one

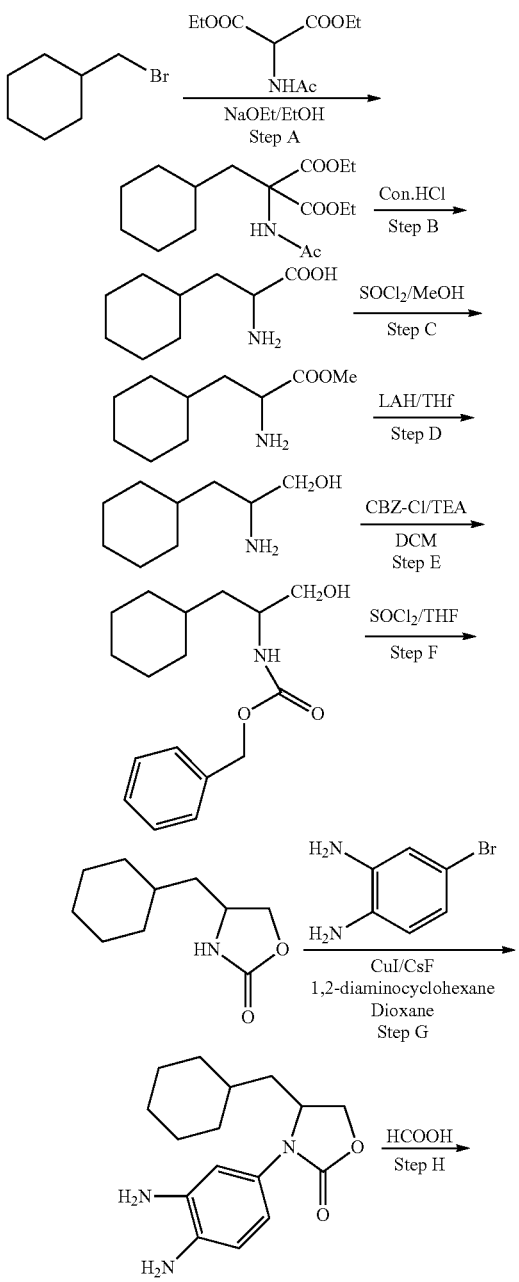

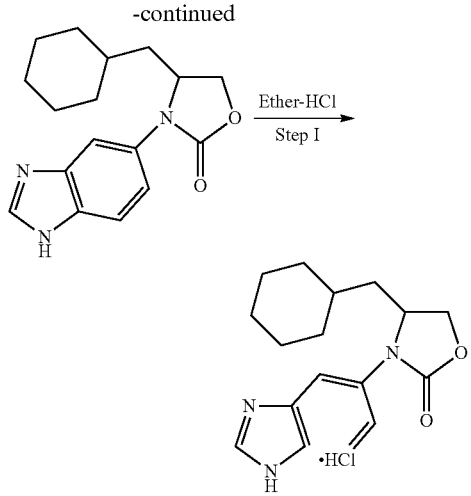

Step A

Diethylacetamidomalonate (10 g, 5.72 mmol) was added to a freshly prepared sodium ethoxide solution by dissolving sodium metal (1.26 g, 5.72 mmol) in ethanol (20 mL) at 0° C. and stirred for 30 min at room temperature. A solution of bromo methyl cyclohexane (5 g, 2.82 mmol) in tetrahydrofuran (25 mL) was added drop wise to the reaction mixture at 0° C. and stirred overnight at room temperature. The reaction mixture was concentrated under reduced pressure and the residue was partitioned between ethyl acetate and water. The separated organic layer was washed with brine, dried over anhydrous sodium sulfate and concentrated under reduced pressure to give crude compound which was purified by column chromatography over silica gel (100-200 mesh) by eluting with 30% ethyl acetate in pet ether to give 5.1 g (35%) of the product as a gummy solid which was used without further characterization.

Step B

A mixture of the product of step A (5 g, 10.7 mmol) and conc.HCl (100 mL) were refluxed overnight. The reaction mixture was concentrated under reduced pressure to afford 1.55 g (71.5%) of the product as the HCl salt which was used without further characterization.

Step C

Thionyl chloride (1.1 mL, 15.1 mmol) was added to a reaction mixture of the product of step B (1.5 g, 7.3 mmol) in methanol (30 mL) at 0° C. and refluxed overnight. The reaction mixture was concentrated under reduced pressure to give crude compound which was partitioned between ethyl acetate and sat.NaHCO$_3$ solution. The separated organic layer was washed successively with water, brine, dried over anhydrous sodium sulfate, concentrated under reduced pressure and dried to afford 1.15 g (85.18%) of the product which was used without further characterization as a solid.

Step D

A solution of the product of step C (1.1 g, 5.3 mmol) in tetrahydrofuran (10 mL) was added to a stirred solution of lithium aluminum hydride (340 mg, 8.7 mmol) in tetrahydrofuran (20 mL) at −15° C. and stirred for 2 h at room temperature. The reaction mixture was quenched with sat. sodium sulfate solution, filtered through a celite pad and washed with ethyl acetate and the filtrate was extracted with ethyl acetate. The combined organic layer was washed with water, brine, dried over anhydrous sodium sulfate and concentrated under reduced pressure to afford 500 mg (60%) of the product as a yellow solid which was used without further characterization.

Step E

Benzyl chloroformate (3.65 g, 21.3 mmol) was added to a stirred solution of the product of step D (2 g, 14.2 mmol), triethylamine (4 mL, 28.4 mmol) in dichloromethane (15 mL) and stirred for 1 h at room temperature. The reaction mixture was poured into water and extracted with dichloromethane. The combined organic layer was washed with brine, dried over anhydrous sodium sulfate and concentrated under reduced pressure to give crude which was purified by column chromatography over silica-gel (100-200 mesh) using 50% ethyl acetate in pet ether as eluent to afford 1 g (25.6%) of the product as a gummy solid which was used without further characterization.

Step F

Thionyl chloride (2.2 mL, 28.4 mmol) was added to a stirred solution of the product of step E (1 g, 3.6 mmol) in tetrahydrofuran (15 mL) at 0° C. and stirred for 3 h at room temperature. The reaction mixture was concentrated in vacuo to give crude compound. This was purified by column chromatography over silica gel (60-120 mesh) using 25% ethyl acetate in pet ether as eluent to afford 500 mg (75.75%) of the product as a solid which was used without further characterization.

Step G

A mixture of the product of step F (450 mg, 2.4 mmol), 1,2-diamino 4-iodo benzene (620 mg, 3.3 mmol), cesium fluoride (730 mg, 4.8 mmol) in 1,4-dioxane (15 mL) were purged with argon gas for 15 min. 1,2-diaminocyclohexane (20 mg) and copper iodide (35 mg) was added to the reaction mixture, purging continued for another 5 min and stirred over night at 120° C. in a sealed tube. The reaction mixture was filtered through a celite pad, washed with dioxan and concentrated under reduced pressure to give crude. This was purified by preparative TLC using 2% methanol in chloroform as eluent to afford 200 mg (29%) of the product as a solid which was used without further characterization.

Step H

A mixture of the product of step G (190 mg, 6.57 mmol) in formic acid (2 mL) was heated at 70° C. for 2 hours. The reaction mixture was cooled to 0° C. and basified using a sodium bicarbonate solution. The compound was extracted with ethyl acetate (3×20 mL), washed with brine solution, dried over anhydrous sodium sulfate and concentrated under reduced pressure. The compound was triturated with ether to afford 120 mg (61.22%) of the product which was used without further characterization as a solid.

Step I

1M HCl in ether (0.4 mL) was added to a stirred solution of the product of step H (110 mg, 0.36 mmol) in acetone (3 mL) at 0° C. and stirred for 30 min at room temperature. The reaction mixture was filtered, washed with pentane and dried in vacuum, to afford the product as solid.

Yield: 96 mg (78%), MS m/z 300.2 (M+H)$^+$; $^1$H-NMR (400 MHz, DMSO-d6): δ 9.43 (d, 1H); 7.88 (t, 2H); 7.61 (d, 1H); 4.71 (s, 1H); 4.62 (d, 1H); 4.20 (d, 1H); 1.80 (d, 1H);

1.75-1.41 (m, 6H); 1.38-1.07 (m, 4H); 0.86-0.80 (m, 2H); HPLC (λ=214 nm), [A]: rt 11.89 min (100%); Chiral HPLC: 99.27%

Example 190

(S)-3-(1H-benzo[d]imidazol-5-yl)-4-cyclohexylox-azolidin-2-one

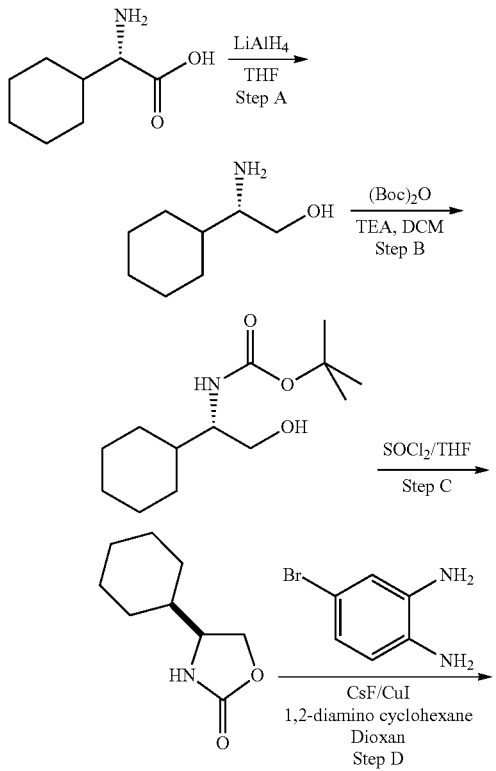

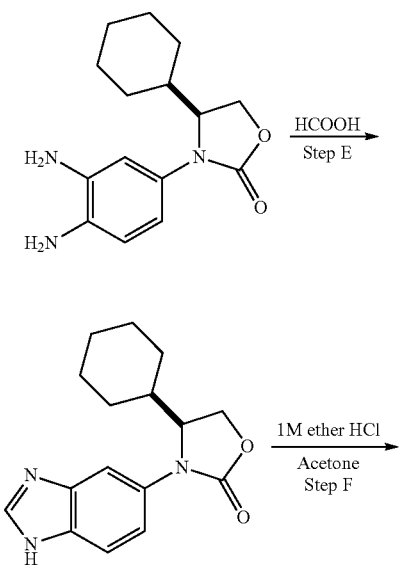

-continued

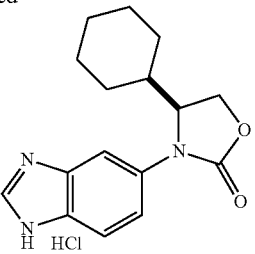

Step A

To a solution of L-(+) cyclohexyl glycine (1.0 g, 6.369 mmol) in dry tetrahydrofuran (15 ml) was added lithium aluminum hydride (0.84 g, 22.292 mmol) under nitrogen at 0° C. in one portion. The reaction mass was slowly heated to reflux at 70° C. for 5 hrs. The reaction mass was quenched with ethyl acetate and successively washed with water and brine solution. The organic layer was dried over anhydrous sodium sulphate and concentrated in vacuum to afford 0.6 g (65.9%) of the product as an off white solid which was used without further characterization.

Step B

To a solution of the product of step A (0.6 g, 4.198 mmol) in dichloromethane (6 ml) was added triethyl amine (0.93 g, 9.23 mmol) and di-ter-butyl dicarbonate (1.189 g, 5.454 mmol) at 0° C. The reaction mass was stirred at room temperature for 4 hrs. The reaction mass was diluted with dichloromethane and washed with water, brine, dried over anhydrous sodium sulphate and concentrated in vacuum to give crude compound. Purification by column chromatography over silica gel (60-120 mesh) using 15% ethyl acetate in pet ether as eluent to afford 0.6 g (60%) of the product as a white solid which was used without further characterization.

Step C

Thionyl chloride (1.77 ml, 24.69 mmol) was added to the product of step B (0.6 g, 2.469 mmol) slowly drop wise at 0° C. and stirred at room temperature for 4 hrs. Excess thionyl chloride was removed in vacuum, co distilled twice with pet ether to afford crude compound. Purification by column chromatography over silica gel (60-120 mesh) using 15% ethyl acetate in pet ether as eluent to afford 0.2 g (47.9%) of the product as a yellow solid which was used without further characterization.

Step D

A mixture of the product of step C (200 mg, 1.1834 mmol), 1,2-diamino-4-bromo benzene (220 mg, 1.1834 mmol), cesium fluoride (350 mg, 2.366 mmol) and copper iodide (22 mg, 0.1183 mmol) in 1,4-dioxan (5 ml) were purged with argon gas for 10 min. 1,2-diaminocyclohexane (13 mg, 0.1183 mmol) was added to the reaction mixture and continued purging for another 10 min. The reaction mass was stirred at 95-100° C. in a sealed tube for 18 h. The reaction mixture was filtered through celite, washed with dichloromethane and concentrated under reduced pressure to afford 300 mg of crude compound. By LC-MS the crude compound was showing 34.9% of the product. The crude compound was taken as such for the next step.

Step E

A solution of the product of step D (300 mg), formic acid (5 mL) was stirred for 30 min at 70° C. and reaction mixture was concentrated under reduced pressure. The resulting residue was partitioned between saturated sodium bicarbonate solution and ethyl acetate. The organic layer was separated and the aqueous layer was extracted with ethyl acetate. The combined organic layer was washed successively with water, brine, dried over anhydrous sodium sulfate and concentrated in vacuum to afford crude compound. The crude compound was purified by column chromatography over silica gel (100-200 mesh) using 3% methanol in chloroform as eluent to afford 100 mg of the product 100 with 84% purity. Further purified by prep HPLC. The obtained prep mL's were concentrated under reduced pressure and portioned between chloroform and water. The separated organic layer was dried over anhydrous sodium sulfate and concentrated in vacuo to afford 40 mg (37.3%) of the product as an off white solid.

Step F

1M HCl in ether (0.16 ml, 0.16 mmol) was added to a stirred solution of the product of step E (40 mg, 0.14 mmol) in acetone (5 mL) at 0° C. and stirred for 30 min at room temperature. The solid precipitated out. The solvent was distilled off completely under vacuum. The solid was dissolved in distilled water and lyophilized to afford 40 mg of the product as off white solid. Yield: 0.040 g MS m/z 286.2 (M+H)$^+$; $^1$H-NMR (400 MHz, D$_2$O): δ 9.12 (d, 1H); 7.93-7.87 (m, 2H); 7.64 (d, 1H); 4.95-4.60 (merged with D2O, 3H); 4.58-4.46 (m, 1H); 1.65-1.50 (m, 5H); 1.14-0.93 (m, 5H); HPLC (λ=214 nm), [A]: rt 8.85 min (100%). Chiral HPLC: 99.61%

Example 191

(S)-3-(1H-benzo[d]imidazol-5-yl)-4-(4-phenylcyclohexyl)oxazolidin-2-one

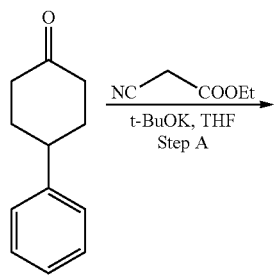

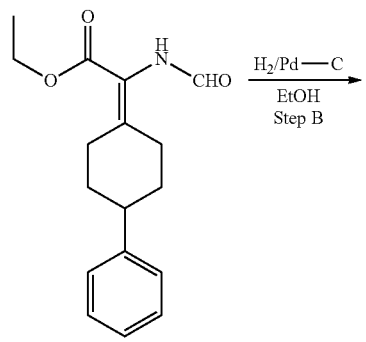

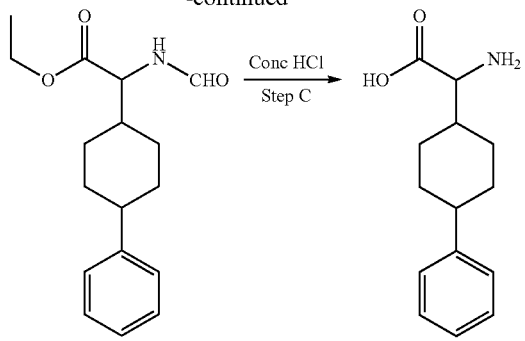

Step A

To a cooled solution of potassium t-butoxide (2.3 g, 20.68 mmol), in THF (50 mL) was added ethyl isocyano acetate (2 g, 20.68 mmol) on drop wise over a period of 20 min at 0° C. stirred for 30 min at room temperature. Then added 4-phenylcyclohexanone (3.0 g; 17.24 mmol) in THF (50 mL) on drop wise over a period of 30 min then stirred over night at room temperature. On completion of reaction, reaction mixture was quenched with crushed ice then extracted in ethyl acetate. The combined ethyl acetate extracts were washed with water (3×100 mL) followed by brine (2×100 mL) and dried over anhydrous sodium sulfate to get crude product. The crude product was purified by column chromatography by using neutral alumina, eluted with 50% ethyl acetate in pet ether to give (2.5 g, 62.5%) as a brown colored liquid, which was used without further characterization.

Step B

A solution of the product of step A (2.5 g, 8.73 mmol) in ethanol (200 mL) was hydrogenated over 10% Pd—C (2 g) in Parr apparatus for 18 h under 80 psi pressure. The reaction mass was filtered through celite and washed with ethanol. The combined filtrate and washings were concentrated in vacuum to afford the product (2 g, 79.68%) as a brown syrup which was used without further characterization.

Step C

The compound of the product of step B (2 g, 6.97 mmol) in hydrochloric acid (35%) (150 mL) was refluxed for 16 h. Then the reaction mixture was co distilled with toluene for 2 times then washed with diethyl ether to remove organic impurities and concentrated in vacuo to get 4 g of the product (1.5 g, 83.33%) as an off-white solid which was used for the further steps as such.

The title compound was further synthesized starting from thionylchloride (1 mL, 12.87 mmol), triethylamine (1.2 mL, 8.86 mmol), di-tert-butyl dicarbonate (0.75 mL, 3.5 mmol), sodium borohydride (2.7 g, 47.32 mmol) according to method 6 starting with Step C. Then concentrated in vacuo to get mixed stereoisomers 1.2 g (76.15%) as a pale yellow oily liquid. The isomers separated by chiral prep HPLC to get each isomer 600 mg.

Chiral Prep HPLC Conditions

| Column: Chiralpak ADH (250 × 20 mm) 5μ | Mobile Phase: Hexane:Ethanol:DEA (95:5) |
|---|---|
| Flow rate: 18 mL/min | Wave length: 210 nm | Diluents: EtOH-Hexane |

After that the first eluting isomer was treated further according to method 6 starting from chloride (0.44 g, 3.76 mmol), 4-bromo-1,2,diaminobenzene (0.358 g, 1.91 mmol), cesium fluoride (0.58 g, 3.8 mmol) and copper (II) iodide (54 mg, 0.28 mmol), formic acid (5 mL)

Yield: 0.20 g (8.6%); MS m/z 362.3 (M+H)+; $^1$H NMR 400 MHz, DMSO-d6): δ 12.45 (s, 1H); 8.24 (d, 1H); 7.75-7.56 (m, 2H); 7.30-7.11 (m, 6H); 4.65 (d, 1H); 4.49-4.37 (m, 2H); 2.49-2.42 (m, 1H); 1.77-1.62 (m, 5H); 1.35-1.19 (m, 4H), HPLC (λ=214 nm), [A]: rt 14.57 min (95.25%).

Example 192

(S)-3-(1H-benzo[d]imidazol-5-yl)-4-(1-phenylpiperidin-4-yl)oxazolidin-2-one

The compound was synthesized according to method 6 starting from 1-phenylpiperidine-4-carbaldehyde (5 g, 26.4 mmol), potassium cyanide (2.57 g, 3.96 mmol), ammonium carbonate (12.5 g, 79.3 mmol), thionyl chloride (5 mL, 61.8 mmol), ditertiary butyl di carbonate (2 g, 2 mL, 9.6 mmol), triethyl amine (2.5 mL, 17.6 mmol), LAH (0.98 g, 25.86 mmol).

On step E the 1.5 q of the racemate was separated into the isomers using Chiral Prep HPLC.

| Column: Chiralpak ADH (250 × 20 mm) 5µ | Mobile Phase: Hexane:Ethanol:DEA (90:10:0.1) |
|---|---|
| Flow rate: 40 mL/min | Wave length: 210 nm | Diluents: EtOH-Hexane |

0.35 g of the first eluting enantiomer was treated further according to method 6 starting from thionyl chloride (1.57 g, 2 mL, 13.24 mmol), 1,2-diamino-4-bromo benzene (0.25 g, 1.34 mmol), cesium fluoride (0.37 g, 5.58 mmol) and copper (I) iodide (35 mg), formic acid (4 mL) Yield: 0.060 g (0.6%); MS m/z 363.2 (M+H)+; $^1$H NMR 400 MHz, DMSO-d6): δ 12.65 (Bs, 1H); 8.28 (s, 1H); 7.59 (s, 1H); 7.62 (d, 1H); 7.36-7.33 (q, 1H); 7.16 (t, 2H); 6.87-6.70 (m, 3H); 4.73 (t, 1H); 4.48 (q, 1H); 4.2 (q, 1H); 3.66 (s, 2H); 2.54-2.34 (merged with DMSO, 2H); 1.57-1.17 (m, 5H), HPLC (λ=214 nm), [A]: rt 4.80 min (95.0%).

Example 193

(S)-4-(1-acetylpiperidin-4-yl)-3-(1H-benzo[d]imidazol-5-yl)oxazolidin-2-one

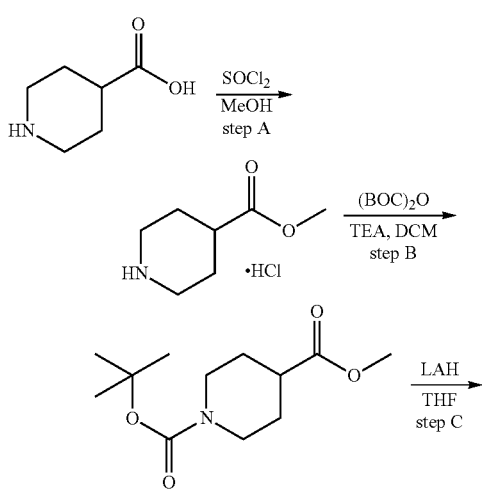

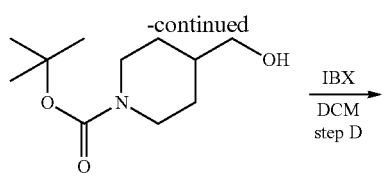

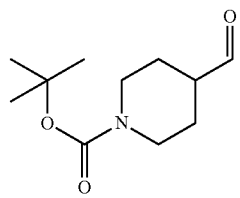

Step A

To a stirred solution of piperidine-4-carboxylic acid (4 g, 30.96 mmol) in MeOH (40 mL) was added SOCl$_2$ (6.7 mL, 92.90 mmol) drop wise at 0° C., resulting reaction mixture was heated to reflux for 16 hrs. The reaction mixture was concentrated under reduced pressure to afford the product (4.7 g, 85%) as an off white solid.

Step B

To a stirred suspension of the product of step A (3.7 g, 20.67 mmol) in DCM (75 mL) was added Et$_3$N (14.4 mL, 103.35 mmol) at 0° C. followed by drop wise addition of BOC anhydride (13.3 mL, 62.01 mmol), resulting reaction mixture was stirred at room temperature for 16 hrs. Water (50 mL) was added to the reaction mixture, organic layer was separated and aqueous layer was extracted with dichloromethane. Combined organic layer was washed with brine, dried over sodium sulfate and concentrated under reduced pressure. The crude compound was purified by column chromatography over silica gel (100-200 mesh) using 2% methanol in chloroform as eluent to afford the product (5 g, 99%) as a colorless liquid.

Step C

To a stirred suspension of lithium aluminium hydride (937 mg, 24.69 mmol) in dry tetrahydrofuran (25 mL) was added the product of step B (5 g, 20.57 mmol) in dry tetrahydrofuran (25 mL) drop wise at 0° C., resulting reaction mixture was stirred at 0° C. for 2 hrs. The reaction mixture was quenched with sat. sodium sulfate, resulting reaction mixture was stirred at room temperature for 1 hr, filtered through a celite bed, washed with ethyl acetate. Combined filtrate was dried over sodium sulfate, concentrated under reduced pressure to afford compound the product (3.5 g, 79%) as a white solid was used in next step without further purifications.

Step D

To a stirred solution of the compound of step C (3.5 g, 16.279 mmol) in DCM (70 mL) was added IBX (9.1 g, 32.55 mmol), resulting reaction mixture was stirred at room temperature for 48 h. The reaction mixture was filtered, filtrate was washed with water, brine, dried over sodium sulfate, concentrated under reduced pressure to give crude compound. This was purified by column chromatography over silica gel (100-200 mesh) using 50% ethyl acetate in pet ether to afford 2 g (58%) of the product as a colorless gummy compound.

The compound was the further synthesized according to method 6.

Example 194

3-(1H-benzo[d]imidazol-5-yl)-4-(1-phenylethyl)oxazolidin-2-one

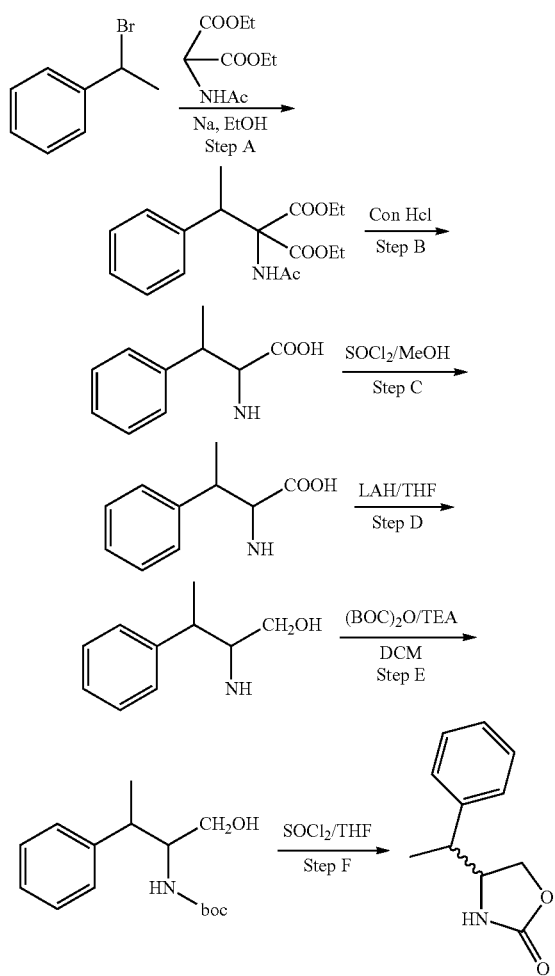

Step A

To a solution of sodium metal (1.86 g, 80.86 mmol) in ethanol was added diethyl acetamido malonate (12.95 g, 59.6 mmol) and allowed to stir at room temp for 30 minutes, after cooling the above reaction mass to 0° C. and added phenyl methyl bromide (10 g, 54.2 mmol) slowly for 15 minutes and the reaction mass heated to 75° C. for 14 hrs. The reaction mass was concentrated under reduced pressure. The residue was dissolved in ethyl acetate, washed with water, brine, dried over anhydrous sodium sulfate and concentrated under reduced pressure to afford 8.0 g (64%) of the product as brown color liquid.

Step B

A mixture of the product of step A (0.5 g, 2.16 mmol) in 70% HCl 5.0 ml, 10.0 vol) was heated to 100° C. for 14 hrs and the reaction mass evaporated under reduced pressure to afford 0.28 g (77%) of the product.

Step C

Thionyl chloride (0.75 g, 5.02 mmol) was added to a solution of the product of step B (0.3 g, 1.6 mmol) in methanol (3 mL) at 0° C. and heated at reflux for 15 h. The volatiles were removed in vacuo and the resulting residue was partitioned between chloroform and saturated sodium bicarbonate solution. The organic layer was separated and the aqueous layer was extracted with ethyl acetate. The combined organic layer was washed with water, brine, dried over anhydrous sodium sulfate and concentrated in vacuo to afford 0.26 g (81.2%) of the product as pale yellow liquid.

Step D

A solution of the product of step C (0.2 g, 1.0 mmol) in tetrahydrofuran (2 mL) was added to a suspension of lithium aluminium hydride (43 mg, 1.1 mmol) in tetrahydrofuran (3 mL) at 0° C. and stirred 15 min. at room temperature. The reaction mixture was quenched with saturated sodium sulfate solution and filtered over celite, washed with chloroform. The filtrate was washed with brine, dried over anhydrous sodium sulfate and concentrated in vacuo to afford 150 mg (88.18%) of the product as pale brown liquid.

Step E

Triethylamine (2.6 mL, 16.6 mmol) and di-ter-butyldicarbonate (2.08 mL, 9.08 mmol) were added successively to a solution of the product of step D (1.5 g, 9.0 mmol) in dichloromethane (20 mL) at room temperature and stirred for 15 h. The RM was poured into water and extracted with dichloromethane (2×30 mL). The combined organic layer was washed successively with water, brine, dried over anhydrous sodium sulfate and concentrated in vacuum to afford crude compound. This was purified by flash column chromatography over neutral alumina using 25% ethyl acetate in pet ether as eluent to afford 1.65 g (66.5%) of the product as pale yellow syrup.

Step F

Thionyl chloride (1.64 mL, 17.8 mmol) was added to a solution of the product of step E (0.56 g, 2.12 mmo) in tetrahydrofuran (10 mL) at 0° C. and stirred at room temperature and stirred for 15 h. The volatiles were removed in vacuum, co-distilled twice with toluene to afford crude compound. Purification by column chromatography over silica gel (60-120 mesh) using 50% ethyl acetate in pet ether as eluent to afford 340 mg (86.8%) of the product as pale brown syrup which crystallized to cream solid upon standing.

The compound was further synthesized according to method 5 starting with step D

Product of step F (200 mg, 1.0 mmol), 1,2-diamino-4-bromo benzene (230 mg, 1.2 mmol), cesium fluoride (228 mg, 1.5 mmol) and copper iodide (13 mg, 0.15 mmol), 1,2-diaminocyclohexane (17 mg, 0.15 mmol), Formic acid (5 mL).

Yield: 0.055 g (17.7.1%); MS m/z 308.2 (M+H)$^+$; $^1$H NMR (400 MHz, DMSO-D$_6$): δ 14.5 (s, 1H); 9.50 (s, 1H); 8.10 (d, 1H); 7.90 (s, 1H); 7.78 (d, 1H); 7.30 (d, 6H); 7.22 (s, 2H); 7.04

(d, 1H); 5.02 (s, 1H); 4.37-4.29 (m, 2H); 3.19 (s, 1H); 1.26 (d, 1H), 1.17 (d, 3H); HPLC (λ=214 nm), [A]: rt 9.84 min (100%).

Example 195

(S)-4-(4-propoxybenzyl)-3-(1H-benzo[d]imidazol-5-yl)oxazolidin-2-one

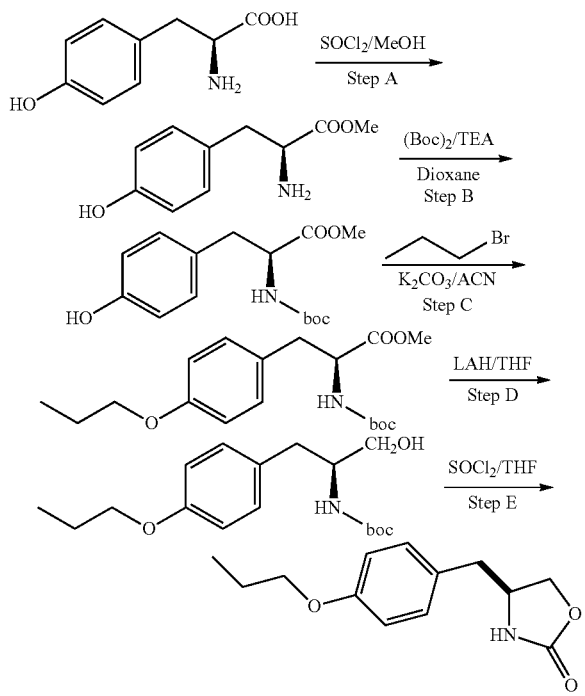

Step A

Thionyl chloride (8 mL, 110.3 mmol) was added to a stirred solution of compound 2-amino-3-(4-hydroxy-phenyl)-propionic acid (10 g, 55.19 mmol) in methanol (100 mL) and refluxed overnight. The reaction mixture was concentrated in vacuo and the residue was dissolved in water and extracted with ethyl acetate. The aqueous layer was basified with solid sodium bicarbonate and extracted with ethyl acetate. The combined organic layer was washed with brine solution, dried over anhydrous sodium sulfate and concentrated in vacuo to afford 10 g (78%) of the product as white color solid.

Step B

Triethylamine (5.4 mL, 38.87 mmol), BOC anhydride (2.9 mL, 12.95 mmol) was added successively to a stirred solution of compound the product of step A (3 g, 12.95 mmol) in dry dioxin (40 mL) and stirred for 4 h at room temperature. The reaction mixture was poured into water and extracted with ethyl acetate. The combined organic layer was washed with brine solution, dried over anhydrous sodium sulphate and concentrated in vacuo to afford 2 g of the product (52%) as solid.

Step C

Bromo propane (0.4 mL, 4.40 mmol), potassium carbonate (935 mg, 6.77 mmol) were added successively to stirred solution of the product of step A (1 g, 3.38 mmol) in acetonitrile and refluxed overnight. The reaction mixture was filtered, washed with ethyl acetate and the filtrate was concentrated under reduced pressure. The residue was partitioned between water and ethyl acetate. The separated organic layer was washed successively with water, brine, dried over anhydrous sodium sulfate and concentrated under reduced to afford 1 g (87%) of the product as oil.

Step D

The product of step C (900 mg, 2.67 mmol) in tetrahydrofuran (10 mL) was added drop wise to a suspension of lthium aluminium hydride (300 mg, 8.01 mmol.) in tetrahydrofuran (10 mL) at 0° C. and stirred at room temperature for 5 h. The reaction mixture was quenched with sat. sodium sulfate and extracted with ethyl acetate. The separated organic layer was washed with water, brine, dried over anhydrous sodium sulphate and concentrated in vacuo to afford 800 mg (96%) of the product as off white solid.

Step E

Thionyl chloride (1.4 mL, 19.41 mmol) was added to a stirred solution of compound the product of step D (750 mg, 2.42 mmol) in tetrahydrofuran (75 mL) at 0° C. and stirred for 6 h at room temperature. The reaction mixture was concentrated under reduced pressure to give crude compound. The crude was purified by washed with n-pentane to afford 505 mg (87%) of the product as light brown color solid.

The compound was further synthesized as a hydrochloride salt according to method 5 starting with step D starting from the product of step E (500 mg, 2.12 mmol), 1,2-diamino 4-iodo benzene (480 mg, 2.55 mmol), cesium fluoride (580 mg, 3.82 mmol), 1,2-diaminocyclohexane (29 mg, 0.25 mmol) and copper iodide (49 mg, 0.25 mmol), formic acid (5 mL)

Yield: 0.037 g (4.1%); MS m/z 352.3 (M+H)$^+$; $^1$H NMR 400 MHz, DMSO-d6): δ 9.53 (d, 1H); 8.10 (s, 1H); 7.91 (d, 1H); 7.77 (d, 2H); 7.06 (d, 2H); 6.81 (d, 2H); 5.00 (s, 1H); 4.43 (t, 1H); 4.22 (q, 1H); 3.86 (t, 2H); 2.89-2.77 (m, 2H); 1.73-1.65 (m, 2H); 0.98-0.94 (m, 3H), HPLC (λ=214 nm), [A]: rt 11.33 min (100%).

Example 196

(S)-4-(4-isopropoxybenzyl)-3-(1H-benzo[d]imidazol-5-yl)oxazolidin-2-one

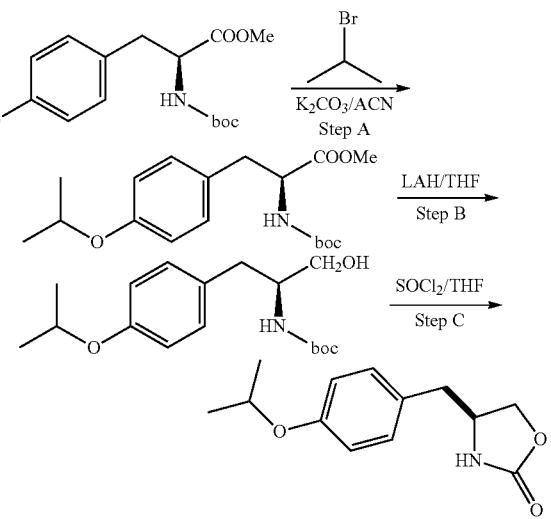

Step A

2-Iodo propane (0.45 mL, 4.40 mmol), potassium carbonate (1 g, 6.77 mmol) were added successively to stirred solution of tert-butyl (S)-1-(methoxycarbonyl)-2-(4-hydroxyphenyl)ethylcarbamate (1 g, 3.38 mmol) in acetonitrile and refluxed overnight. The reaction mixture was filtered, washed with ethyl acetate and the filtrate was concentrated under reduced pressure. The residue was partitioned between water and ethyl acetate. The separated organic layer was washed successively with water, brine, dried over anhydrous sodium sulfate and concentrated under reduced to afford 900 g (78%) of the product as an oil.

Step B

The product of step A (600 mg, 2.61 mmol) in tetrahydrofuran (10 mL) was added drop wise to a suspension of lithium aluminium hydride (300 g, 8.01 mmol.) in tetrahydrofuran (10 mL) at 0° C. and stirred at room temperature for 5 h. The reaction mixture was quenched with sat. sodium sulfate and extracted with ethyl acetate. The separated organic layer was washed with water, brine, dried over anhydrous sodium sulphate and concentrated in vacuo to afford 600 g (75%) of the product off white solid.

Step C

Thionyl chloride (1.13 mL, 15.53 mmol) was added to a stirred solution of compound 180b (600 mg, 1.94 mmol) in Tetrahydrofuran (15 mL) at 0° C. and stirred for 6 h at room temperature. The reaction mixture was concentrated under reduced pressure to give crude compound. The crude was purified by washed with n-pentane to afford 415 mg (91%) of 180 c as light brown color solid.

The compound was further synthesized as a hydrochlorid salt according to method 5 starting with step D starting from the product of step C 400 mg, 1.70 mmol), 1,2-diamino 4-iodo benzene (397 mg, 2.12 mmol), cesium fluoride (485 mg, 3.19 mmol), 1,2-diaminocyclohexane (24 mg, 0.21 mmol), copper iodide (40 mg, 0.21 mmol), formic acid (5 mL), 1M ether-HCl (0.18 mL, 0.18 mmol)

Yield: 0.45 g (7.5%); MS m/z 352.4 (M+H)+; $^1$H NMR (400 MHz, DMSO-d6): δ 9.53 (d, 1H); 8.09 (s, 1H); 7.91 (d, 1H); 7.76 (d, 1H); 7.05 (d, 2H); 6.77 (d, 2H); 5.00 (s, 1H); 4.55-4.42 (m, 2H); 4.23 (s, 1H); 2.89-2.76 (m, 2H); 1.22 (s, 6H) HPLC (λ=214 nm), [A]: rt 10.45 min (100%), Chiral HPLC: 88.05%;

Example 197

(S)-4-(4-(cyclohexyloxy)benzyl)-3-(1H-benzo[d]imidazol-5-yl)oxazolidin-2-one

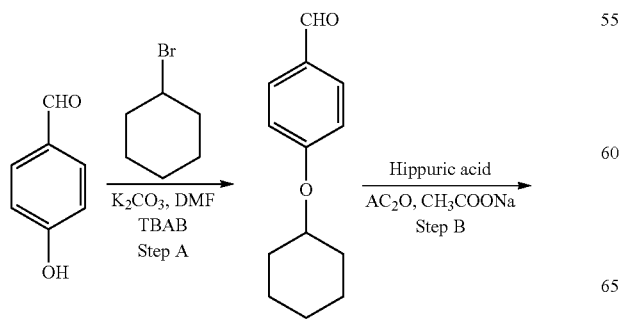

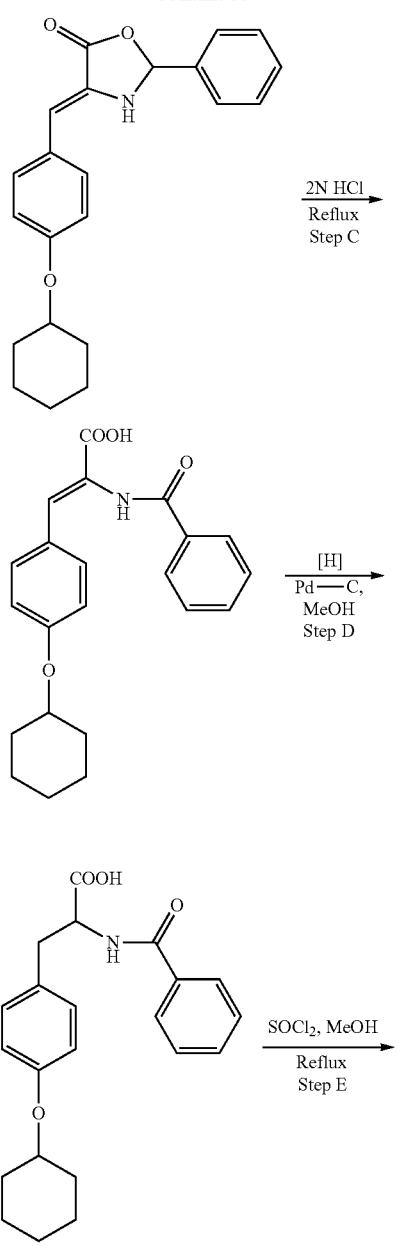

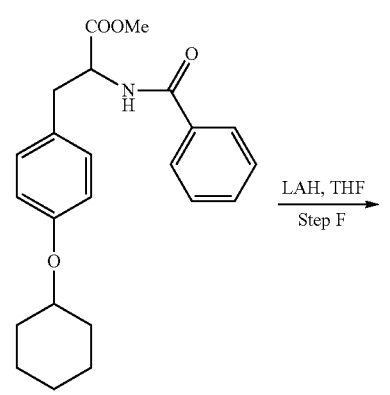

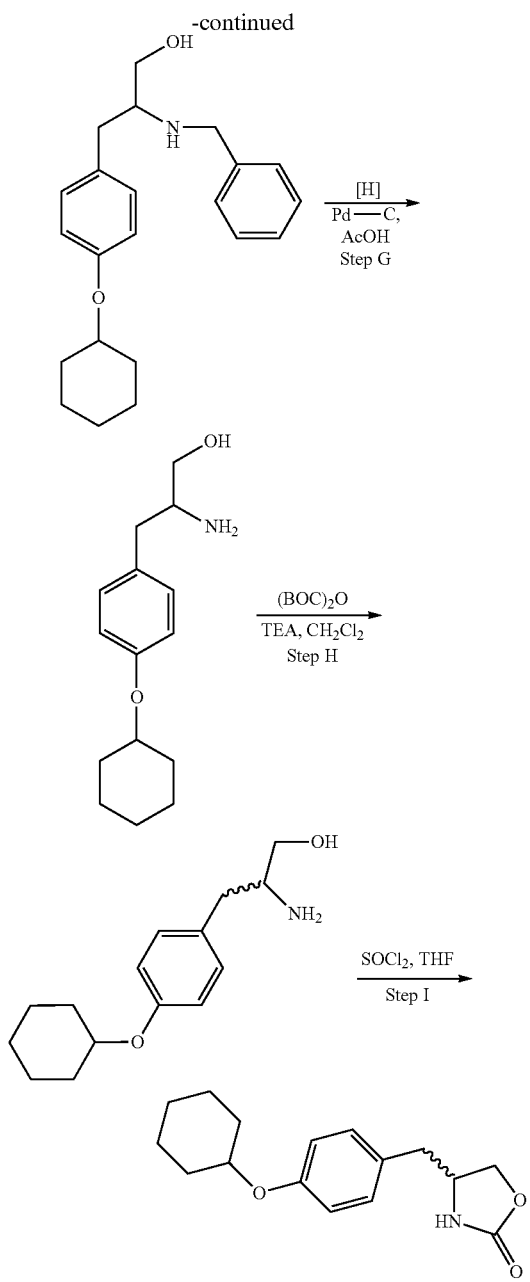

Step A

A mixture of cyclohexyl bromide (30 mL, 163.06 mmol), p-hydroxy benzaldehyde (20 g, 163.7 mmol), catalytic amount of tetrabutylammonmium iodide (500 mg) and potassium carbonate (113 g, 138.21 mmol) in N,N-Dimethylformamide (200 mL) and stirred at 140° C. for 18 h. The reaction mixture was poured into ice water and extracted with diethyl ether. The combined organic layer was washed with water, brain, dried over sodium sulfate and concentrated under reduced pressure to afford 18 g (53.8%) of the product.

Step B

Hippuric acid (3.17 g, 17.72 mmol), anhydrous sodium acetate (1.45 g, 17.72 mmol) were added subsequently to a solution of the product of step A (3.6 g, 17.72 mmol) in acetic anhydride (20 mL) and refluxed for 18 h. The reaction mixture was cooled to 0° C. and added ethanol (20 mL) allowed to stand for 2 h. Precipitated solid was filtered and washed with ethanol and hot water and dried in vacuo to afford 2.6 g (42.5%) of the product as white solid.

Step C

A mixture of the product of step B (10 g, 28.82 mmol) and 3N hydrochloric acid (100 mL) was heated at reflux temperature for 12 h. The reaction mixture was concentrated under reduced pressure and dried in vacuo to afford 10 g (95%) of the product of step C as a brown color solid.

Step D

A solution of the product of step C (10 g, 27.39 mmol) in ethanol (120 mL) was hydrogenated over 10% Pd—C (2 g) for 6 h at 60 psi in a Parr apparatus. The reaction mass was filtered through celite and washed with ethanol. The filtrate was concentrated under reduced pressure to afford 5 g (50%) of the product as brown color solid.

Step E

Thionyl chloride (3 mL, 40.87 mmol) was added to solution of the product of step D (5.0 g, 13.62 mmol.) in methanol (50 ml) under argon atmosphere at 0° C. and heated at 65° C. for 12 h. The reaction mixture was concentrated under reduced pressure and the residue was basified with aq. saturated sodium bicarbonate and extracted with ethyl acetate (3×25 ml). The combined organic layer was washed with brine solution, dried over sodium sulfate and concentrated in vacuo to afford the product (5.0 g, 96%) as a white color solid.

Step F

Lithium aluminum hydride (550 mg, 13.12 mmol) was added in three portions to a solution of the product of step E (5 g, 13.12 mmol) in dry THF (60 mL) at 0° C. and stirred 12 h at room temperature. The reaction mixture was cooled to 0° C. and quenched with saturated $NH_4Cl$ solution and extracted with ethyl acetate. The combined organic layer was washed with brine, dried over anhydrous sodium sulfate and concentrated in vacuum. The crude compound was purified by column chromatography using 60-120 silica mesh the pure compound elute at 2% methanol in chloroform to afford 3 g (68.3%) of the product as a brown color solid.

Step G

To a solution of 10% Pd—C (300 mg, 10%) in acetic acid (50 mL) was added the product of step F (3.0 g, 8.84 mmol) and hydrogenated at 80 Psi in par apparatus for 36 h. The catalyst was filtered through celite pad and concentrated in vacuo and dried to afford 1.5 g (68.3%) of the product as a colorless liquid.

Step H

Boc anhydride (0.56 mL, 2.46 mmol) was added to a solution of the product of step G (500 mg, 2.00 mmol) and triethylamine (0.54 mL, 4.00 mmol) in dichloromethane (10 mL), and stirred for 3 h. The reaction mixture was washed with water (10 mL) and extracted with dichloromethane (3×20 mL). The combined organic layer was washed with brain, dried over anhydrous sodium sulfate and concentrated in vacuo to afford 350 mg (50%) of the product as a yellow color liquid.

Step I

Thionyl chloride (0.6 mL, 8.02 mmol) was added to a solution of the product of step H (350 mg, 1.00 mmol) in tetrahydrofuran (10 mL) at 0° C. and stirred 12 h room temperature. The reaction mixture was concentrated in vacuo and basified with saturated $NaHCO_3$ solution and extracted with chloroform. The combined organic layer was washed with water, brain, dried over anhydrous sodium sulfate and concentrated in vacuo to afford 200 mg (72.7%) of the product as a colorless liquid.

The compound was further synthesized as a hydrochloride salt according to method 5 starting with step D starting from the product of step I (200 mg, 0.727 mmol), 1,2-diamino 4-bromo benzene (152 mg, 0.872 mmol), cesium fluoride (165 mg, 1.08 mmol) and copper iodide (20 mg, 0.109 mmol), 1,2-diaminocyclohexane (12 mg, 0.108 mmol), formic acid (10 mL) Yield: 0.100 g (35.1%); MS m/z 392.2 (M+H)+; $^1$H NMR (400 MHz, DMSO-d6): δ 12.54 (s, bs); 8.25 (s, 1H); 7.79 (s, 1H); 7.79 (s, 1H); 7.61 (s, 1H); 7.39 (d, 1H); 7.05 (d, 2H); 6.81 (d, 2H); 4.86 (s, 1H); 4.40-4.14 (m, 3H); 2.82-2.74 (m, 2H); 1.87 (s, 2H); 1.69 (s, 2H); 1.36-1.23 (m, 6H); HPLC (λ=214 nm), [B]: rt 14.61 min (96.4%).

Example 198

4-(4-morpholinobenzyl)-3-(1H-benzo[d]imidazol-5-yl)oxazolidin-2-one

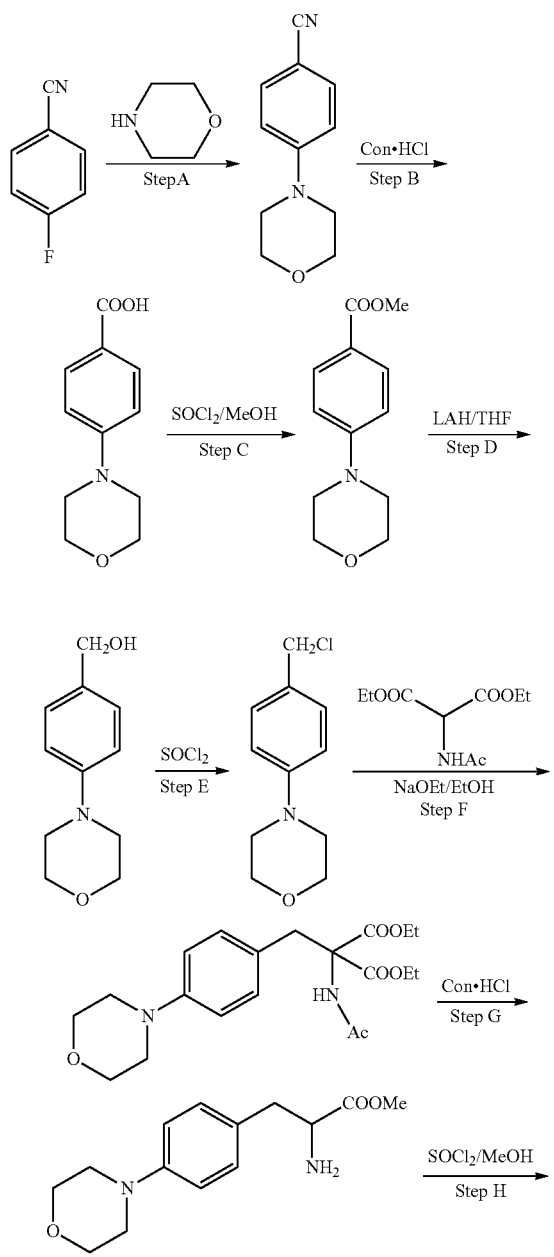

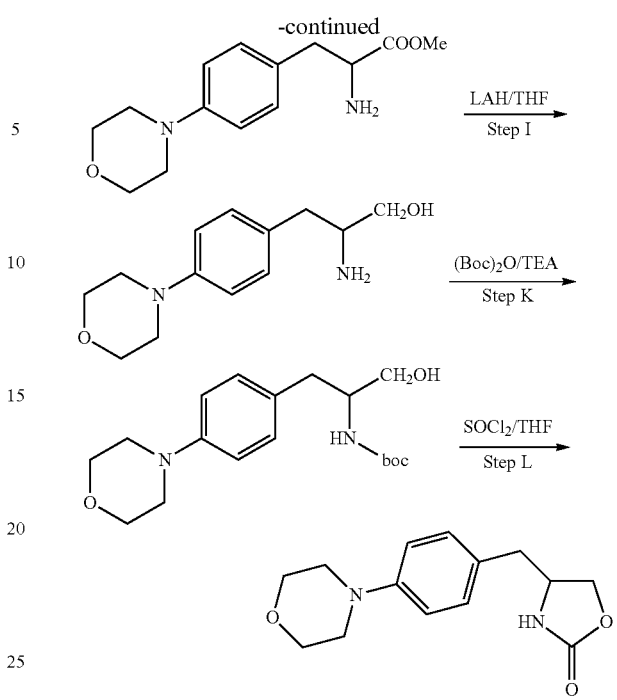

Step A

A mixture of 4-fluoro benzonitrile (10 g, 0.82 mmol) and morpholine (50 mL) were stirred overnight in a steal bomb at 100° C. The reaction mixture was poured into water and extracted with diethyl ether. The combined organic layer was washed successively with water, brine, dried over anhydrous sodium sulfate and concentrated under reduced pressure to afford 7 g of the product as gummy solid.

Step B

A mixture of the product of step A (7 g, 37.23 mmol) and con.HCl were refluxed overnight. The reaction mixture was concentrated under reduced pressure to give 8.3 g (96.3%) of the product as HCl salt.

Step C

Thionyl chloride (5.8 mL, 80.30 mmol) was added to a reaction mixture of the product of step B (8.3 g, 40.19 mmol) in methanol (80 mL) at 0° C. and refluxed overnight. The reaction mixture was concentrated under reduced pressure to give crude compound which was partitioned between EtOAC and sat.NaHCO$_3$ solution. Separated organic layer was washed successively with water, brine, dried over anhydrous sodium sulfate, concentrated under reduced pressure and dried to afford 6 g (67.5%) of the product as solid.

Step D

A solution of the product of step C (6 g, 27.32 mmol) in tetrahydrofuran (50 mL) was added to a suspension of lithium aluminium hydride (2 g, 54.21 mmol) in tetrahydrofuran (20 mL) at −15° C. and stirred 2 h at room temperature. The reaction mixture was quenched with sat. sodium sulfate solution, filtered through celite pad and washed with ethyl acetate and the filtrate was extracted with ethyl acetate. The combined organic layer was washed successively with water, brine, dried over anhydrous sodium sulfate and concentrated under reduced pressure to afford 4.12 g (78.58%) of the product as yellow solid.

Step E

A mixture of the product of step D (4.1 g, 21.2 mmol), thionyl chloride (4.5 mL, 63.8 mmol) in chloroform (25 mL)

were stirred at reflux for over night. The reaction mixture was concentrated under reduced pressure and dried to afford 4 g (91.3%) of the product as oil.

Step F

Diethylacetamidomalonate (12.64 g, 0.058 mmol) was added to a freshly prepared sodium ethoxide solution by dissolving sodium metal (890 mg, 38.80 mmol) in ethanol (20 mL) at 0° C. and stirred 30 min at room temperature. A solution of the product of step E (4 g, 19.42 mmol) in tetrahydrofuran (25 mL) was added dropwise to the reaction mixture at 0° C. and stirred overnight at room temperature. The reaction mixture was concentrated under reduced pressure and the residue was partitioned between ethyl acetate and water. The separated organic layer was washed with brine, dried over anhydrous sodium sulfate and concentrated under reduced pressure to give crude compound which was purified by column chromatography over silica gel (100-200 mesh) by eluting with 30% ethyl acetate in pet ether to give 6 g (81%) of the product as gummy solid.

Step G

A mixture of the product of step F (6 g, 15.3 mmol) and con.HCl were refluxed overnight. The reaction mixture was concentrated under reduced pressure to afford 3.5 g (91.6%) of the product as HCl salt.

Step H

Thionyl chloride (1.56 mL, 21 mmol) was added to a reaction mixture of the product of step G (3.5 g, 14 mmol) in methanol (30 mL) at 0° C. and refluxed overnight. The reaction mixture was concentrated under reduced pressure to give crude compound which was partitioned between EtOAC and sat.NaHCO$_3$ solution. Separated organic layer was washed successively with water, brine, dried over anhydrous sodium sulfate, concentrated under reduced pressure and dried to afford 3 g (81%) of the product as solid.

Step I

A solution of the product of step H (2 g, 7.57 mmol) in tetrahydrofuran (10 mL) was added to a stirred solution of lithium aluminium hydride (370 g, 9.84 mmol) in tetrahydrofuran (20 mL) at −15° C. and stirred 2 h at room temperature. The reaction mixture was quenched with sat. sodium sulfate solution, filtered through celite pad and washed with ethyl acetate and the filtrate was extracted with ethyl acetate. The combined organic layer was washed with water, brine, dried over anhydrous sodium sulfate and concentrated under reduced pressure to afford 1.6 g (89.8%) of the product as yellow solid.

Step K

Boc anhydride was added to a stirred solution of the product of step I (1.6 g, 6.77 mmol), triethylamine (1.4 mL, 13.54 mmol) in dichloromethane (15 mL) and stirred 1 h at room temperature. The reaction mixture was poured into water and extracted with dichloromethane. The combined organic layer was washed with brine, dried over anhydrous sodium sulfate and concentrated under reduced pressure to afford 700 mg (30.83%) of the product as gummy solid.

Step L

Thionyl chloride (0.7 mL, 0.96 mmol) was added to a stirred solution of the product of step K (700 mg, 0.48 mmol) in tetrahydrofuran (15 mL) at 0° C. and stirred 3 h at room temperature. The reaction mixture was concentrated in vacuo and basified with saturated NaHCO$_3$ solution and extracted with chloroform. The combined organic layer was washed with water, brine, dried over anhydrous sodium sulfate and concentrated under reduced pressure to give crude compound. This was purified by column chromatography over silica gel (60-120 mesh) using 25% ethyl acetate in pet ether as eluent to afford 200 mg (38%) of the product as solid. The compound was further synthesized as a hydrochloride salt according to method 5 starting with step D starting from the product of step L (175 mg, 0.67 mmol), 1,2-diamino 4-iodo benzene (140 mg, 0.8 mmol), cesium fluoride (200 mg, 1.32 mmol), 1,2-diaminocyclohexane (20 mg) and copper iodide (35 mg), formic acid (2 mL), 1M HCl in ether (0.2 mL)

Yield: 0.035 g (13.8%); MS m/z 379.4 (M+H)$^+$; $^1$H NMR (400 MHz, DMSO-d6): δ 9.58 (s, 1H); 8.08 (s, 1H); 7.87 (d, 1H); 7.72 (d, 1H); 4.98 (q, 1H); 4.42 (t, 2H); 4.20 (q, 2H); 3.75 (s, 4H); 3.09 (s, 4H); 2.85-2.78 (m, 2H); HPLC (λ=214 nm), [A]: rt 6.59 min (99.18%)

Example 199

(S)-3-(1H-benzo[d]imidazol-5-yl)-4-phenethyloxazolidin-2-one

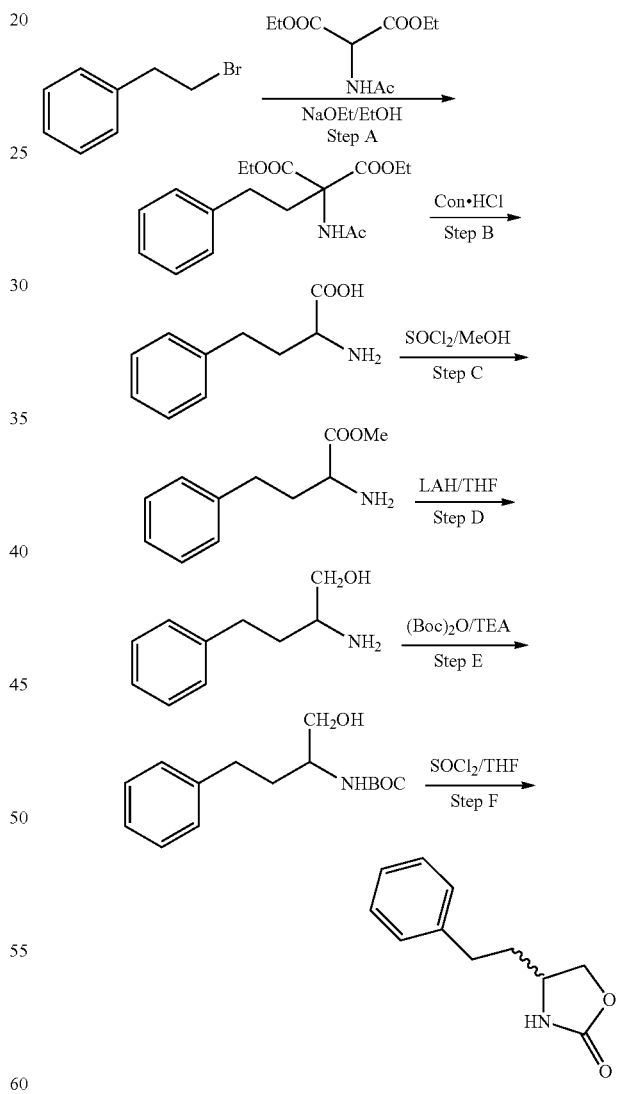

Step A

Diethylacetamidomalonate (9.39 g, 43.22 mmol) was added to the freshly prepared sodium ethoxide obtained by adding sodium (2.49 g, 108.05 mmol) to absolute ethanol (80 mL) at 0° C. The RM was warmed to room temperature and stirred for 25 min. Cooled to 0° C. and a solution of (2-bromoethyl)benzene (8.0 g, 43.22 mmol) was added. The reaction mass was warmed to room temperature and stirred for 1 h, heated at reflux for 15 h. The solvent was evaporated in vacuo and the resulting residue was partitioned between water and ethyl acetate. The organic layer was separated and the aqueous layer was extracted with ethyl acetate. The combined organic layer was washed successively with water, brine, dried over anhydrous sodium sulfate and concentrated in vacuo to afford crude compound. Purification by column chromatography over silica gel (60-120 mesh) using 25% ethyl acetate in pet ether as eluent afforded 2.89 g (20.83%) of the product as cream solid.

Step B

A suspension of the product of step A (2.88 g, 8.97 mmol) in concentrated hydrochloric acid (20 mL) was heated at reflux for 26 h. The volatiles were evaporated in vacuo and co evaporated with toluene and dried under reduced pressure to afford 1.46 g (90.96%) of the product as off white solid.

Step C

Thionyl chloride (1.2 mL, 16.44 mmol) was added to a solution of the product of step B (1.45 g, 8.10 mmol) in methanol (20 mL) at 0° C. The reaction mixture was heated at reflux for 15 h. The volatiles were evaporated in vacuo and the resulting residue was partitioned between chloroform and saturated sodium bicarbonate solution. The organic layer was separated and the aqueous layer was extracted with ethyl acetate. The combined organic layer was washed with water, brine dried over anhydrous sodium sulfate and concentrated in vacuum to afford 1.36 g (87.2%) of the product as pale yellow liquid.

Step D

A solution of the product of step C (1.05 g, 5.44 mmol) in tetrahydrofuran (10 mL) was added to a suspension of lithium aluminium hydride (206 mg, 5.44 mmol) in tetrahydrofuran (30 mL) at 0° C. The reaction mass was stirred for 15 min. Recooled to 0° C. and quenched with saturated sodium sulfate solution. Filtered over celite, washed with chloroform. The combined filtrate and washings was washed with brine, dried over anhydrous sodium sulfate and concentrated in vacuo to afford 800 mg (89.18%) of the product as pale brown liquid.

Step E

Triethyl amine (1.4 mL, 10.04 mmol) and di-ter-butyl dicarbonate (1.4 mL, 6.10 mmol) were added successively to a solution of the product of step D (800 mg, 4.84 mmol) in dichloromethane (20 mL) at room temperature and stirred for 15 h. The RM was poured into water and extracted with dichloromethane (2×30 mL). The combined organic layer was washed successively with water, brine, dried over anhydrous sodium sulfate and concentrated in vacuum to afford crude compound. Purification by flash column chromatography over neutral alumina using 25% ethyl acetate in pet ether as eluent afforded 800 mg (62.5%) of the product as pale yellow syrup.

Step F

Thionyl chloride (2.0 mL, 27.39 mmol) was added to a solution of the product of step E (800 mg, 3.02 mmol) in tetrahydrofuran (20 mL) at 0° C. The Reaction mass was warmed to room temperature and stirred for 15 h. The volatiles were evaporated in vacuum, co distilled twice with toluene to afford crude. Purification by column chromatography over silica gel (60-120 mesh) using 50% ethyl acetate in pet ether as eluent to afford 500 mg (86.8%) of the product of step F as pale brown syrup which crystallized to cream solid upon standing. The compound was further synthesized as a hydrochloride salt according to method 5 starting with step D starting from the product of step F (480 mg, 2.51 mmol), 1,2-diamino-4-bromo benzene (470 mg, 2.51 mmol), cesium fluoride (572 mg, 3.76 mmol) and copper iodide (72 mg, 0.376 mmol) 1,2-diaminocyclohexane (43 mg, 0.376 mmol) formic acid (5 mL) 1M HCl in ether (0.39 mL, 0.39 mmol).

Yield: 0.235 g (10.3%); MS m/z 308.4 (M+H)$^+$; $^1$H NMR (400 MHz, DMSO-d6): δ 9.47 (s, 1H); 7.99 (s, 1H); 7.85 (d, 1H); 7.58 (d, 1H); 7.22 (t, 2H); 7.16-7.10 (m, 3H); 4.76-4.75 (m, 1H); 4.60 (t, 1H); 4.36-4.32 (m, 1H); 2.61-2.50 (merged with DMSO, 2H); 1.90-1.81 (m, 2H); HPLC (λ=214 nm), [A]: rt 9.20 min (100%).

Example 200

3-(1H-benzo[d]imidazol-5-yl)-4-(4-(cyclohexyloxy) phenyl)oxazolidin-2-one

The compound was synthesized according to Method 6 starting from 4-(cyclohexyloxy)benzaldehyde (4 g, 19.60 mmol), potassium cyanide (1.60 g, 24.50 mmol), ammonium carbonate (5.64 g, 58.8 mmol), 10% aqueous sodium hydroxide (80 mL), 10% aqueous sodium hydroxide solution (120 mL), di tert-butyl dicarbonate (14.47 g, 66 mmol), potassium carbonate (1.78 g, 129.94 mmol), methyl iodide (1.46 g, 10.31 mmol), sodium borohydride (1.13 g, 29.76 mmol), thionyl chloride (20 mL, 273.9 mmol), 4-bromo-1,2-diamino benzene (561 mg, 3.0 mmol), cesium fluoride (912 mg, 6.0 mmol), copper iodide (85 mg, 0.45 mmol), formic acid (5 mL). Yield: 120 mg (1.6%), MS m/z 378.4 (M+H)$^+$; $^1$H-NMR (400 MHz, CDCl3): δ 7.91 (s, 1H); 7.62 (s, 1H); 7.48 (d, 1H); 7.19 (d, 3H); 6.81 (d, 2H); 5.33 (t, 2H); 4.79 (t, 1H); 4.17 (t, 1H); 4.14 (s, 1H); 1.9 (t, 2H); 1.75 (d, 2H); 1.56-1.25 (m, 6H); HPLC (λ=214 nm, [A]: rt 14.40 min (100%).

Example 201

(S)-3-(7-methyl-1H-benzo[d]imidazol-5-yl)-4-(4-propoxyphenyl)oxazolidin-2-one (S)-4-(4-propoxyphenyl)oxazolidin-2-one was used as starting material and the synthesis was already described above.

The compound was synthesized starting from (S)-4-phenyloxazolidin-2-one (1 equiv., 0.1 g, 0.45 mmol), 5-bromo-3-methylbenzene-1,2-diamine (1 equiv., 0.091 g, 0.45 mmol), copper(I) iodide (0.1 equiv., 0.009 g, 0.045 mmol), cesium fluoride (2 equiv., 0.137 g, 0.9 mmol), cyclohexane-1,2-diamine (0.1 equiv., 0.006 mL, 0.05 mmol). The dried solids were given together in a reaction flask and the flask was purged with argon. A solution of cyclohexane-1,2-diamine in 4 mL dioxane was added to the flask. The reaction was stirred at 95° C. for 48 hours, before the reaction was cooled down to 45° C. and filtered through a pad of CELITE®. The pad was washed with warm dichloromethane and the solution was concentrated under reduced pressure. The intermediate product was purified via FPLC using a chloroform-methanol gradient (0→10%).

Yield: 0.092 g (59.9%)

The (S)-3-(3,4-diamino-5-methylphenyl)-4-(4-propoxyphenyl)oxazolidin-2-one was dissolved in triethyl orthoformate and was refluxed for 30 minutes. After cooling the excess of triethyl orthoformate was removed under reduced pressure. The final product was purified via FPLC using a chloroform-methanol gradient (0→10%).

Yield: 0.016 g (16.9%)

Overall yield: 10.1%; MS m/z 352.3 (M+H)$^+$; $^1$H NMR (400 MHz, DMSO-D$_6$): δ 0.89-0.92 (m, 3H); 1.60-1.71 (m, 2H); 2.40-2.42 (m, 3H); 3.81-3.84 (m, 2H); 4.08-4.12 (m, H); 4.75-4.79 (m, H); 5.60-5.64 (m, H); 6.83-6.86 (m, 2H); 7.04-

7.13 (m, H); 7.26-7.35 (m, 3H); 8.08-8.14 (m, H); 12.40 (br s, H), HPLC (λ=214 nm), [B]: rt 11.99 min (93.8%).

Example 202

(S)-3-(6,7-dimethyl-1H-benzo[d]imidazol-5-yl)-4-(4-propoxyphenyl)oxazolidin-2-one (S)-4-(4-propoxyphenyl)oxazolidin-2-one was used as starting material and the synthesis was already described above.

The compound was synthesized starting from (S)-4-phenyloxazolidin-2-one (1 equiv., 0.1 g, 0.45 mmol), 5-bromo-3,4-dimethylbenzene-1,2-diamine (1 equiv., 0.097 g, 0.45 mmol), copper(I) iodide (0.1 equiv., 0.009 g, 0.045 mmol), cesium fluoride (2 equiv., 0.137 g, 0.9 mmol), cyclohexane-1,2-diamine (0.1 equiv., 0.006 mL, 0.05 mmol). The dried solids were given together in a reaction flask and the flask was purged with argon. A solution of cyclohexane-1,2-diamine in 4 mL dioxane was added to the flask. The reaction was stirred at 95° C. for 48 hours, before the reaction was cooled down to 45° C. and filtered through a pad of CELITE®. The pad was washed with warm dichloromethane and the solution was concentrated under reduced pressure. The intermediate product was purified via FPLC using a chloroform-methanol gradient (0→10%).

Yield: 0.020 g (12.5%)

The (S)-3-(4,5-diamino-2,3-dimethylphenyl)-4-(4-propoxyphenyl)oxazolidin-2-one was dissolved in triethyl orthoformate and was refluxed for 30 minutes. After cooling the excess of triethyl orthoformate was removed under reduced pressure. The final product was purified via FPLC using a chloroform-methanol gradient (0→10%).

Yield: 0.008 g (39.1%)

Overall yield: 4.9%; MS m/z 366.4 (M+H)$^+$; $^1$H NMR (400 MHz, DMSO-D$_6$): δ 0.89-0.93 (m, 3H); 1.61-1.69 (m, 2H); 2.16 (br s, 3H); 2.39 (br s, 3H); 3.78-3.86 (m, 2H); 4.30-4.34 (m, H); 4.77-4.86 (m, H); 5.57-5.63 (m, H); 6.82-6.83 (m, 2H); 7.29-7.31 (m, 2H); 7.40-7.49 (m, H); 8.09 (br s, H); 12.36 (br s, H), HPLC (λ=214 nm), [B]: rt 11.71 min (90.9%).

Example 203

(S)-4-(4-(2-methoxyethoxy)phenyl)-3-(1H-benzo[d]imidazol-5-yl)oxazolidin-2-one

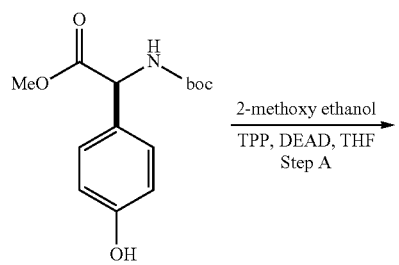

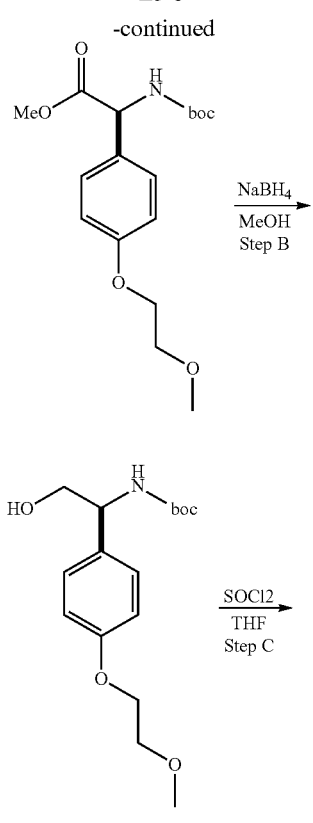

Step A 2-methoxy ethanol (0.389 mg, 5.12 mmol), triphenyl phosphine (1.68 g, 6.4 mmol) was added to a solution of tert-butyl (methoxycarbonyl)(4-hydroxyphenyl)methylcarbamate (1.2 g, 4.27 mmol) in THF (20 mL), stirred for 10 min. DEAD (1.16 g, 6.4 mmol) was added. Then heated to reflux for over night. On completion of starting material, reaction mixture was cooled to room temperature. Then diluted with water extracted in ethyl acetate 3 times. The combined ethyl acetate extracts were washed with water (3×100 mL) followed by brine (2×100 mL) and dried over anhydrous sodium sulfate. Then concentrated in vacuo to get 800 mg (57.14%) of the product as a pale yellow oily liquid.

Step B

To a solution of the product of step A (800 mg, 3.31 mmol) in methanol (20 mL) at 0° C. was added sodium borohydride (500 mg, 13.27 mmol) in portions and stirred well at RT for 16 h. Then methanol was distilled out and the residue obtained was extracted in ethyl acetate. The combined ethyl acetate extracts were washed with water (3×100 mL) followed by brine (2×100 mL) and dried over anhydrous sodium sulfate. Then concentrated in vacuo to get 700 mg (97.22%) of the product as a pale yellow oily liquid.

Step C

To a solution of the product of step B (700 mg, 2.25 mmol) in dry THF (20 ml) at 0° C. was added thionyl chloride (0.32 mL, 4.5 mmol) and stirred well at RT for 16 h. Then the RM was concentrated in vacuo to get 450 mg (84%) of the product as a pale yellow solid.

The compound was further synthesized according to method 6 starting from the product of step C (0.45 g, 1.89 mmol), 4-bromo-1,2,diaminobenzene (0.355 g, 1.89 mmol), cesium fluoride (0.577 g, 3.79 mmol) and copper (II) iodide (54 mg, 0.28 mmol), 2-diamino cyclohexane (32 mg, 0.28 mmol), formic acid (5 mL). Yield: 0.2 g (29.9%); MS m/z 354.3 (M+H)+; $^1$H NMR (400 MHz, DMSO-d6): δ 10.10 (Bs, 1H); 7.91 (d, 1H); 7.55 (d, 1H); 7.26-7.20 (merged with CDCl3, 3H); 6.85 (d, 2H); 5.35 (q, 1H); 4.79 (t, 1H); 4.26 (q, 1H); 4.05 (t, 2H); 3.71 (t, 2H) 3.43 (d, 3H), HPLC (λ=214 nm), [A]: rt 9.98 min (96.48%).

Example 204

(S)-4-(4-(2-(dimethylamino)ethoxy)phenyl)-3-(1H-benzo[d]imidazol-5-yl)oxazolidin-2-one The compound was synthesized according to method 5 starting from 4-(2-(dimethylamino)ethoxy)benzaldehyde (3 g, 15.70 mmol), 2.3 M n-butyl lithium (13.65 mL, 15.7 mmol), triphenyl phosphonium methyl bromide (11.21 g, 17 mmol) T-butyl hypochlorite (2.7 mL, 22.32 mmol), t-butyl carbamate (2.66 g, 22.72 mmol) 0.4M aqueous sodium hydroxide (0.9 g in 57 mL water), osmate dihydrate (100 mg, 0.29 mmol), thionyl chloride (1.2 mL, 16.49 mmol), 4-bromo 1,2-diamino benzene (0.31 mg, 0.1.672 mmol), and copper iodide (44 mg, 0.228), 1,2-diaminocyclohexane (26 mg, 0.228), formic acid (3 mL). Yield: 0.110 g (2.0%); MS m/z 367.2 (M+H)+; $^1$H NMR (400 MHz, CDCl3): δ10.40 (Bs, 1H); 7.89 (s, 1H); 7.53 (s, 1H); 7.26-7.19 (merged with CDCl3, 5H); 6.81 (d, 2H); 5.33 (t, 1H); 4.79 (q, 1H); 4.25 (t, 1H); 4.00 (t, 2H); 2.70 (t, 2H); 2.34-2.25 (m, 6H); HPLC (λ=214 nm), [A]: rt 5.79 min (94.7%).

Example 205

3-(1H-benzo[d]imidazol-5-yl)-4-(2,6-difluoro-4-methoxyphenyl)oxazolidin-2-one

The compound was synthesized according to method 6 starting from 2,6-difluoro-4-methoxybenzaldehyde (4 g, 23.25 mmol), potassium cyanide (1.8 mg, 27.90 mmol), ammonium carbonate (10.95 g, 69.76 mmol), 10% aqueous sodium hydroxide (50 mL), thionyl chloride (2.6 mL, 36.86 mmol), sodium borohydride (2.31 g, 64.37 mmol), triethylamine (2.4 mL, 17.73 mmol), di-tert-butyl dicarbonate (1.5 mL, 7.09 mmol), thionyl chloride (3.3 mL, 46.2 mmol), 4-bromo-1,2,diaminobenzene (0.734 g, 3.93 mmol), cesium fluoride (1.19 g, 7.86 mmol) and copper (II) iodide (112 mg, 5.89 mmol), 1,2-diamino cyclohexane (67 mg, 5.89 mmol), formic acid (5 mL). Yield: 175 mg (2.2%). MS m/z 346.3 (M+H)+; $^1$H-NMR (400 MHz, CDCl3): δ 9.45 (bs, 1H); 7.97 (s, 1H); 7.72 (bs, 1H); 7.39 (s, 1H); 7.26 (s, 1H); 6.37 (d, 1H); 5.87 (s, 1H); 4.83 (t, 1H); 4.47 (t, 1H); 3.70 (s, 3H), HPLC (λ=214 nm), [A]: rt 9.17 min (100%).

Example 206

(S)-3-(1H-benzo[d]imidazol-5-yl)-4-(4-(diethylamino)phenyl)oxazolidin-2-one

The compound was synthesized according to method 6 starting from tert-butyl (R)-1-(4-(diethylamino)phenyl)-2-hydroxyethylcarbamate (0.500 g, 21.623 mmol), thionyl chloride (0.95 mL, 12.98 mmol, 4-bromo1,2-diamino benzene (219 mg, 1.175 mmol), cesium fluoride (324 mg, 2.136 mmoles) and copper iodide (30 mg, 0.160 mmoles), 1,2-diaminocyclohexane (0.02, 0.1602 mmoles), formic acid (5 mL). Yield: 0.05 g (0.6%). MS m/z 351.4 (M+H)+; $^1$H-NMR (400 MHz, DMSO-d6): δ 12.44 (d, 1H); 8.17 (d, 1H); 7.56- 7.13 (m, 5H); 6.55 (d, 2H); 5.54 (t, 1H); 4.75 (t, 1H); 4.09 (t, 1H); 3.39-3.20 (m, 4H); 1.23-0.98 (m, 6H), HPLC (λ=214 nm, [A]: rt 6.04 min (97.7%).

Example 207

(S)-3-(1H-benzo[d]imidazol-5-yl)-4-(4-(bis(2-methoxyethyl)amino)phenyl)oxazolidin-2-one The compound was synthesized according to method 6 starting from tert-butyl (R)-1-(4-(bis(2-methoxyethyl)amino)phenyl)-2-hydroxyethylcarbamate (0.350 g, 0.951 mmol), thionyl chloride (0.55 mL, 7.608 mmol), 4-bromo-1,2-diamino benzene (111 mg, 0.598 mmol), cesium fluoride (165 mg, 1.08 mmoles) and copper iodide (15 mg, 0.081 mmoles), 1,2-diaminocyclohexane (0.06, 0.598 mmoles) formic acid (5 mL). Yield: 0.04 g (10.8%). MS m/z 411.4 (M+H)+; $^1$H-NMR 400 MHz, CDCl3): δ 7.89 (d, 1H); 7.60-7.45 (m, 2H); 7.26-7.11 (merged with CDCl3, 3H); 6.61 (d, 2H); 5.60 (t, 1H); 4.77 (t, 1H); 4.33 (t, 1H); 3.60-3.49 (m, 8H); 3.32 (s, 6H), HPLC (λ=214 nm, [A]: rt 10.09 min (96%).

Example 208

(S)-3-(1H-benzo[d]imidazol-5-yl)-4-(4-(dicyclopropylamino)phenyl)oxazolidin-2-one

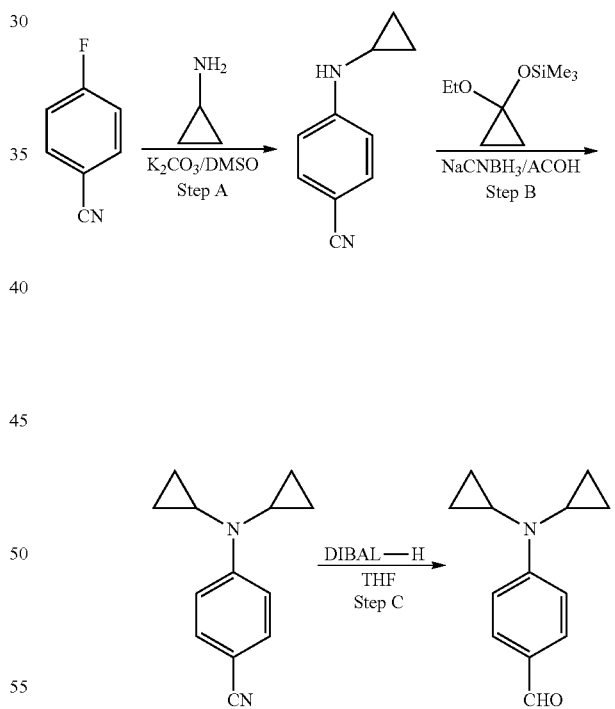

Step A

A suspension of 4-fluorobenzonitrile (6 g, 0.0495 moles), cyclopropyl amine (10.3 ml, 0.1487 moles) and potassium carbonate (34.21 g, 0.198 moles) in DMSO (50 mL) was refluxed for 6 hours. The reaction mass was cooled and poured into ice water (100 ml) and extracted with ethyl acetate. The separated organic layer was washed with brine solution, dried over anhydrous sodium sulphate and concentrated under reduced pressure to afford crude compound, purified by column chromatography over silica gel (60-120 mesh) using 10% ethyl acetate in pet ether as eluent to afford 5 g of the product as white solid.

Step B

Sodium cyanoborohydride (2.98 g, 47.4 mmol) was added to a stirred solution of the product of step A (5 g, 31.64 mmol) in acetic acid (40 ml) and 1-ethoxy cyclopropyloxy trimethylsilane at room temperature and heated to 85° C. for 3 hours. Cooled to room temperature diluted with dichloromethane and washed with saturated sodium bicarbonate solution & brine solution. Dried over anhydrous sodium sulfate and concentrated under reduced pressure gave crude compound. This was purified by column chromatography over neutral alumina using 8% ethyl acetate in pet ether as eluent to afford 3 g of the product white crystalline solid.

Step C

25% DIBAL in toluene (11.47 ml, 20.2 mmol) was added drop wise to a solution of the product of step B (2 g, 10 mmol) in dry DCM (20 ml) at −45° C. and allowed to stir for 1.5 h, the reaction mixture was quenched with saturated ammonium chloride solution (50 ml) and extracted with ethyl acetate (200 ml). The organic layer was separated and washed with water, brine solution. Dried over anhydrous sodium sulphate and concentrated under reduced pressure to afford crude compound, which was purified by column chromatography over alumina using 40% ethyl acetate in pet ether as eluent to afford 2 g of the product as yellow liquid.

The compound was further synthesized according to method 5 starting from the product of step C (1.6 g, 7.96 mmol), 2.3M n-butyl lithium in hexane (6.19 mL, 14.92 mmol), triphenyl phosphonium methyl bromide (6.68 g, 15.92 mmol), T-butyl hypochloride (2 mL, 18.85 mmol), Boc carbamate (2.17 g, 18.60 mmol), (DHQ)$_2$PHAL (240 mg, 0.309 mmol), potassium osmate dihydrate (90 mg, 0.247 mmol), Thionyl chloride (0.439 mL, 6.024 mmol), 4-bromo-1,2-diamino benzene (130 mg, 0.697 mmol), cesium fluoride (212 mg, 1.395 mmoles) and copper iodide (20 mg, 0.104 mmoles), 1,2-diaminocyclohexane (1 mL), formamidine acetate (23 mg, 0.219 mmoles). Yield: 0.03 g (0.6%). MS m/z 375.3 (M+H)$^+$; $^1$H-NMR 400 MHz, CDCl3): δ 7.94 (s, 1H); 7.67 (s, 1H); 7.52 (s, 1H); 7.15 (d, 3H); 6.96 (d, 2H); 5.34 (q, 1H); 4.77 (t, 1H); 4.27 (q, 1H); 2.40-2.38 (t, 1H); 0.88-0.80 (m, 4H); 0.64-0.63 (m, 4H); HPLC (λ=214 nm, [A]: rt 14.39 min (95%).

Example 209

(S)-3-(1H-benzo[d]imidazol-6-yl)-4-(biphenyl-4-yl)oxazolidin-2-one

The compound was synthesized starting from 4-vinylbiphenyl (1.55 g 8.6 mmol), ethyl carbamate (2.38 g, 26.7 mmol), 5,5-dimethylimidazolidine-2,4-dione (2.6 g, 13.2 mmol), (DHQ)$_2$PHAL (0.402 g, 0.52 mmol), K$_2$OsO$_4$x2H$_2$O (0.127 g, 0.34 mmol), 0.38 M aqueous NaOH (74 mL, 28 mmol), 4-iodobenzene-1,2-diamine (0.35 g, 1.5 mmol), copper(I) iodide (0.029 g, 0.15 mmol), cesium fluoride (0.456 g, 3 mmol), cyclohexane-1,2-diamine (0.018 mL, 0.15 mmol), triethyl orthoformate (10 ml) as described in method 5.

Yield: 0.011 g (0.4%); MS m/z 356.3 (M+H)$^+$; $^1$H NMR (400 MHz, DMSO-D$_6$): δ 4.19-4.30 (m, H); 4.73-4.84 (m, H); 5.25-5.51 (m, H); 7.29-7.68 (m, 12H); 7.94-8.22 (m, H), HPLC (λ=214 nm), [B]): rt 12.22 min (100%).

Examples 210, 211, 212

3-(1H-benzo[d]imidazol-5-yl)-4-(4-(4-oxocyclohexyl)phenyl)oxazolidin-2-one, 3-(1H-benzo[d]imidazol-5-yl)-4-(4-(4-methoxycyclohexyl)phenyl)oxazolidin-2-one, and 3-(1H-benzo[d]imidazol-5-yl)-4-(4-(4-hydroxycyclohexyl)phenyl)oxazolidin-2-one

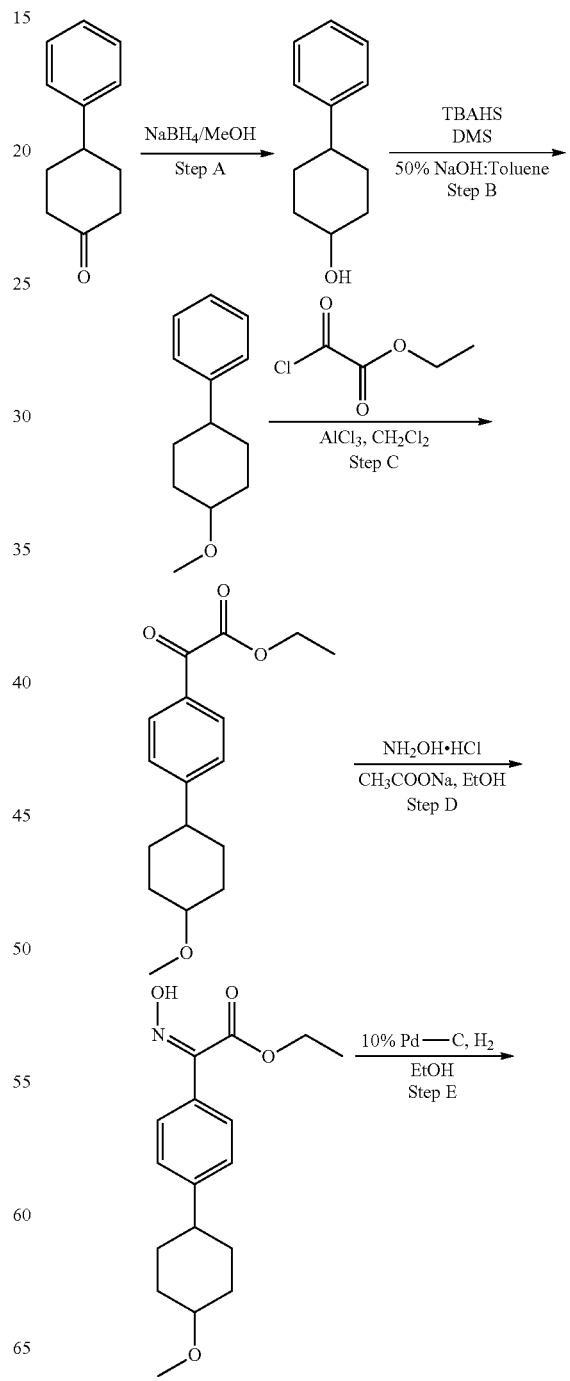

295
-continued
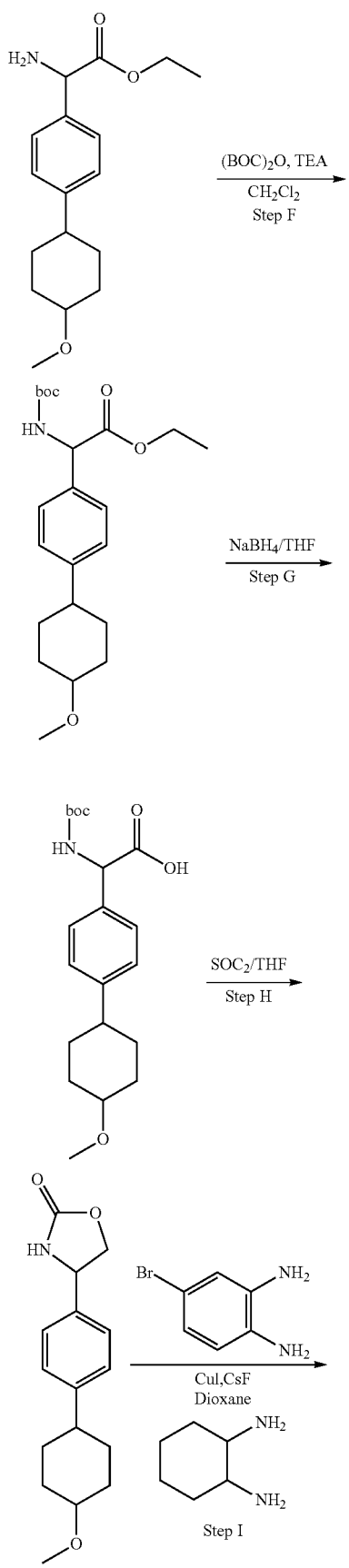
296
-continued
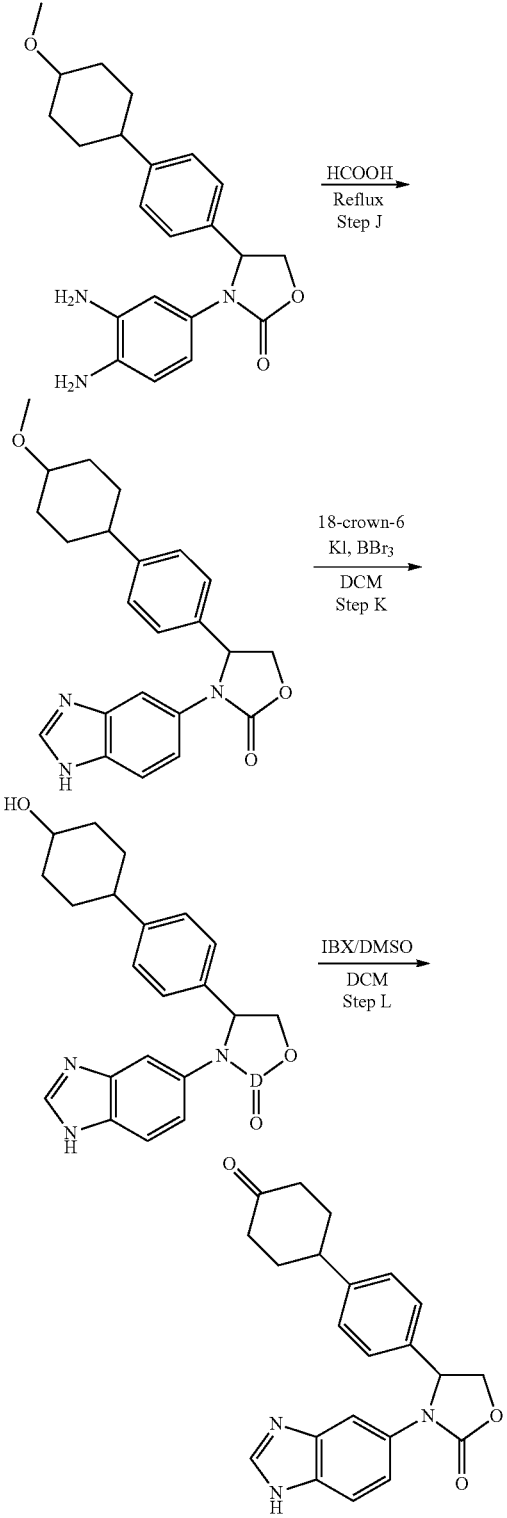
Step A
Sodium borohydride (0.54 g, 14.36 mmol) was added to a solution of 4-phenyl cyclohexanone (5.0 g, 28.73 mmol) in ethanol (50 mL) at RT and stirred for 0.5 h. Evaporated the reaction mixture and quenched the reaction mixture with ammonium chloride solution and extracted with dichloromethane. Combined organic layer was washed with water, brine, dried over anhydrous sodium sulfate and evaporated to dryness to get 5.0 g of the product as white color solid.

Step B

Tetra butyl ammonium hydrogen sulfate (1.42 g, 4.21 mmol) followed by dimethyl sulphate (14.15 g, 112.35 mmol) were added to a solution of the product of step A (5.0 g, 28.08 mmol) in a mixture of 1:1 ratio of 50% NaOH:Toluene (100 mL) and heated at 80° C. for 48 h. Diluted the reaction mixture with water, acidified with 10% HCl and extracted with ethyl acetate. Combined organic layer was washed with water, brine, dried over anhydrous sodium sulfate and evaporated to dryness to get crude compound. Crude compound was purified by column chromatography over silica gel (60-120 mesh) by eluting in 2-4% ethyl acetate in pet ether to get 4.0 g of the product as colorless oil.

Step C

Ethylchloro oxalate (7.16 mL, 63.15 mmol) and $AlCl_3$ (8.42 g, 63.15 mmol) were added to a solution of the product of step B (2.0 g, 13.33 mmol) in dichloromethane (60 mL) at −20° C. The mixture was stirred for 1 h and allow to room temperature for 2 h. Quenched with saturated $NaHCO_3$ solution at 0° C. and filtered and washed with excess of ethyl acetate (200 mL) and the organic layer separated, washed with water, brine, dried over $Na_2SO_4$ and evaporated under reduced pressure to afford 3.0 g of the product as brown color liquid.

Step D

Hydroxylamine hydrochloride (1.44 g, 20.68 mmol) and sodium acetate (1.69 g, 20.68 mmol) were added to a solution of the product of step C (2.5 g, 10 mmol) in ethanol (30 mL) was heated at 80° C. for 2 h. Then the reaction mixture cooled to room temperature and filtered the filtrate was evaporated to dryness to give crude compound. Crude compound was suspended in water and extracted with dichloromethane. Combined organic layer was dried over anhydrous sodium sulfate and evaporated to dryness to get 3.1 g of the product as a colorless liquid.

Step E

To a solution of 10% Pd—C (0.62 g, 20%) in ethanol was added the product of step D (3.1 g, 10.16 mmol) and hydrogenated at 80 Psi at room temperature for overnight. Then the catalyst was filtered through celite bed and evaporated the solvent to give 3.0 g of the product as a colorless liquid.

Step F

Boc anhydride (2.23 g, 10.3 mmol) was added to a solution of the product of step E (3.0 g, 10.30 mmol) and triethylamine (1.6 mL, 12.37 mmol) in dichloromethane (30 mL), and stirred overnight at room temperature. The reaction mixture was washed with water (30 mL) and extracted with dichloromethane (3×50 mL). The combined organic layer was washed with brine (20 mL), dried over anhydrous sodium sulfate and evaporated to dryness to get crude 2.9 g of the product as brown oil.

Step G

Sodium borohydride (0.82 g, 21.48 mmol) was added to a solution of the product of step F (2.1 g, 5.37 mmol) in ethanol (30 mL) at RT and heated at 50° C. for 3 h. Evaporated the solvent under reduced pressure to get crude. Crude was quenched with saturated $NH_4Cl$ solution (25 mL), diluted with water and extracted with dichloromethane. The combined organic layer and washed with brine solution and evaporated to dryness to afford 1.5 g of the product as gummy mass.

Step H

Thionyl chloride (2.5 mL, 34.38 mmol) was added to a solution of the product of step G (1.5 g, 4.29 mmol) in tetrahydrofuran (20 mL) at 0° C. Then the reaction mixture allowed to room temperature for 12 h. The solvent was evaporated and basified with saturated $NaHCO_3$ solution (10 mL) and extracted with chloroform (3×25 mL) and combined organic layers dried over anhydrous sodium sulfate and concentrated in vacuo to give 1.0 g of the product as off white solid.

Step I

A mixture of the product of step H (1 g, 3.63 mmol), 1,2-diamino 4-bromo benzene (0.74 g, 3.99 mmol), cesium fluoride (1.1 g, 7.26 mmol) and copper iodide (0.1 g, 0.54 mmol) in 1,4-dioxane (15 mL) were purged with argon gas for 15 min. 1,2-diamino cyclohexane (61 mg, 0.22 mmol) was added to the reaction mixture and continued purging for another 15 min. The reaction mass was stirred 24 h at 120° C. in a sealed tube. The reaction mixture was filtered through celite, washed with Dioxane and evaporated to dryness under reduced pressure. The crude product was purified by column chromatography over neutral alumina by eluting in 3% methanol in chloroform as a eluent and to afford 1 g of the product as pale brown solid.

Example 211

A mixture of the product of step I (1.1 g, 2.62 mmol), formic acid (10 mL) was stirred for 1 h at 90° C. and the reaction mixture was concentrated under reduced pressure to get crude. Crude was basified with saturated sodium bicarbonate solution and extracted with chloroform. The combined organic layer was washed with water, brine, dried over anhydrous sodium sulfate and evaporated under reduced pressure to afford crude. Crude compound was triturated with n-pentane and dried to afford 1 g of Example 211. MS m/z 392.5 $(M+H)^+$, HPLC [A]: rt 12.00 min (92.96%).

Example 212

A solution of 18-crown-6 (4.46 g, 16.87 mmol) saturated with potassium iodide in dry dichloromethane (30 mL) was added to a solution of Example 211 (1.1 g, 2.81 mmol), cooled to −30° C., to this was added boron tribromide (0.8 mL, 8.43 mmol) and stirred at RT for 3 hours. Quenched the reaction mixture with sodium bicarbonate solution, diluted with water and extracted with dichloromethane. Combined organic layer was washed with water, brine, dried over anhydrous sodium sulfate and evaporated to dryness to get crude compound. Crude compound was purified over neutral alumina by eluting in 3-4% methanol in chloroform to afford 450 mg of Example 212. MS m/z 378.4 $(M+H)^+$; HPLC [A]: rt 9.95 min (93.81%)

Example 210

A solution of Example 212 (0.4 g, 1.06 mmol) in dichloromethane (20 mL) was added to a suspension of IBX (0.89 g, 3.18 mmol) in DMSO (7 mL) and stirred at room temperature for overnight. Filtered the reaction mixture, washed with saturated sodium bicarbonate solution, water, brine, dried over anhydrous sodium sulphate and evaporated the solvent under reduced pressure to get 300 mg of PQPL-188 (HPLC-93%) as off white solid. 80 mg was further purified by preparative TLC by eluting in 4% methanol in chloroform to get 50 mg of Example 153 as off white solid.

Yield: 0.05 g (12.0%), MS m/z 376.4 $(M+H)^+$; $^1$H-NMR (400 MHz, DMSO-d6): δ 12.39 (d, 1H); 8.15 (d, 1H); 7.61-7.20 (m, 7H); 5.73 (d, 1H); 4.80 (t, 1H); 4.22 (t, 1H); 2.98 (t, 1H); 2.56 (merged with DMSO, 1H); 2.21 (d, 2H); 1.99 (d, 2H); 1.78 (d, 2H), HPLC [A]: rt 10.69 min (94.8%)

Example 213

3-(1H-benzo[d]imidazol-5-yl)-4-(4-(4-morpholinocyclohexyl)phenyl)oxazolidin-2-one The compound was synthesized according to method 5 starting from n-butyl lithium (2.3M in hexane; 3.66 mL, 7.32 mmol), tri phenyl phosphonium bromide (2.6 g, 7.32 mmol), 4-(4-morpholinocyclohexyl)benzaldehyde (1 g, 3.66 mmol), t-butyl hypochlorite (1.13 mL, 8.85 mmol), Boc carbamate (1.03 g, 8.85 mmol) 0.4M aqueous sodium hydroxide (360 mg in 10 mL), (DHQ)$_2$PHAL (114 mg, mmol), potassium osmate dihydrate (40 mg, 0.12 mmol), thionyl chloride (0.6 mL, 8 mmol), 1,2-diamino-4-bromobenzene (160 mg, 0.84 mmol) and cesium fluoride (190 mg, 1.26 mmol), copper iodide (25 mg, 0.13 mmol) and 1,2-diaminocyclohexane (15 mg, 0.13 mmol), formic acid (10 mL). Yield: 40 mg (2.4%), MS m/z 447.4 (M+H)$^+$; $^1$H-NMR (400 MHz, DMSO-d6): δ 12.38 (s, 1H); 8.15 (s, 1H); 7.60-7.16 (m, 6H); 5.69 (t, 1H); 4.8 (t, 1H); 4.13-4.10 (q, 1H); 3.57 (t, 4H); 2.56 (merged with DMSO, 1H); 2.33 (s, 4H); 2.11 (s, 1H); 1.91-1.67 (m, 5H); 1.45-1.38 (m, 4H), HPLC (λ=214 nm, [A]: rt 7.95 min (97.87%)

Example 214

3-(1H-benzo[d]imidazol-5-yl)-4-(4-(pyrrolidin-1-yl)phenyl)oxazolidin-2-one

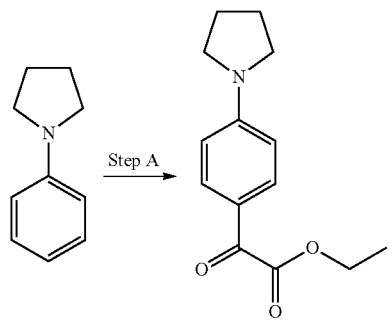

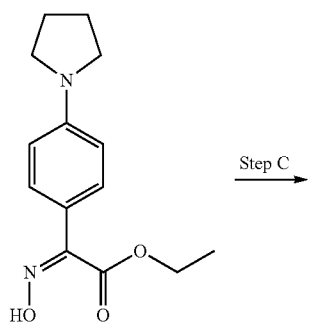

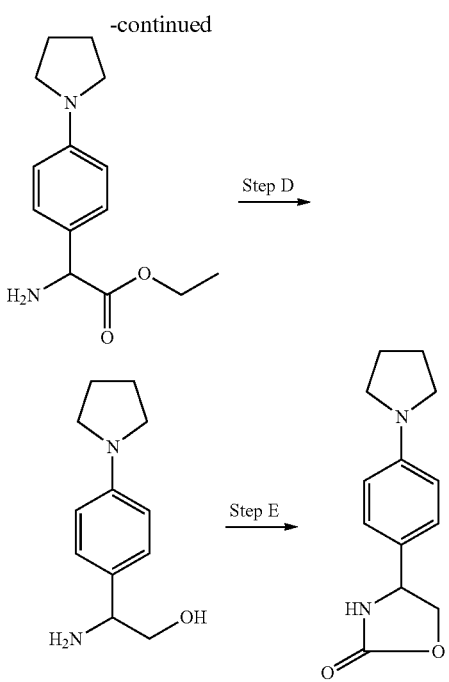

The compound was synthesized as described above starting from:

Step A
1-Phenylpyrrolidine (1 g, 6.8 mmol), ethyl 2-chloro-2-oxoacetate (0.84 mL, 7.5 mmol), aluminium chloride (1.81 g, 13.6 mmol).

Step B
Hydroxylamine hydrochloride (0.17 g, 2.49 mmol); sodium acetate (0.27 g, 3.32 mmol), Step C
PdC (10%, 0.02 g), Step D
2M solution of lithium aluminium hydride in THF (1.3 mL, 2.62 mmol), Step E
di-(imidazol-1-yl)methanone (0.2 g, 1.23 mmol), further according to method 5 step D starting from 4-iodobenzene-1,2-diamine (0.066 g, 0.28 mmol), copper(I) iodide (0.006 g, 0.028 mmol), cesium fluoride (0.085 g, 0.56 mmol), cyclohexane-1,2-diamine (0.004 mL, 0.028 mmol), triethyl orthoformate (1 ml), yield: 0.007 g (0.6%); MS m/z 349.2 (M+H)$^+$, 175.4 (M+2H)$^{2+}$; $^1$H NMR (400 MHz, CD$_3$OD): δ 1.63-1.72 (m, 2H); 1.90-1.98 (m, 4H); 3.32-3.36 (m, 4H); 4.29-4.33 (m, H); 4.85-4.89 (m, H); 5.61-5.65 (m, H); 7.42-7.44 (m, 2H); 7.51-7.55 (m, 3H); 7.61 (d, H, J=2.1 Hz); 7.94 (s, H); 8.21 (d, H, J=7.7 Hz); 8.49-8.51 (m, H), HPLC (λ=214 nm), [A]: rt 10.69 min (84.7%).

Example 215

(S)-3-(1H-benzo[d]imidazol-5-yl)-4-(4-(piperidin-1-yl)phenyl)oxazolidin-2-one

The compound was synthesized according to method 5.
Step A:
The compound was synthesized starting from 4-(piperidin-1-yl)benzaldehyde (2 g, 10.6 mmol), methyltriphenylphosphonium bromide (5.1 g, 14.3 mmol), 1.6M solution of butyllithium in THF (8.9 mL, 14.3 mmol),
yield: 1.5 g (75.7%)

Step B:
Product obtained from step A (1.5 g, 8 mmol), ethyl carbamate (2.22 g, 24.9 mmol), 5,5-dimethylimidazolidine-2,4-dione (2.41 g, 12.23 mmol), (DHQ)$_2$PHAL (0.312 g, 0.4 mmol), K$_2$OsO$_4$x2H$_2$O (0.118 g, 0.32 mmol), 0.41 M aqueous NaOH (60.2 mL, 24.5 mmol),
yield: 0.38 g (16.2%)

Step C:
Product obtained from step B (0.38 g, 1.3 mmol), 0.2 M aqueous NaOH (35.75 ml),
yield: 0.24 g (75%)

Step D:
Product obtained from step C (0.24 g, 1 mmol), 4-iodobenzene-1,2-diamine (0.234 g, 1 mmol), copper(I) iodide (0.019 g, 0.1 mmol), cesium fluoride (0.304 g, 2 mmol), cyclohexane-1,2-diamine (0.013 mL, 0.1 mmol), triethyl orthoformate (4 ml),
yield: 0.010 g (6.9%)
Overall yield: 0.010 g (0.7%); MS m/z 363.2 (M+H)$^+$, 182.2 (M+2H)$^{2+}$; $^1$H NMR (400 MHz, CDCl$_3$): δ 1.52-1.54 (m, 2H); 1.63 (br s, 4H); 3.08-3.10 (m, 4H); 4.22-4.26 (m, H); 4.73-4.77 (m, H); 5.30 (br s, H); 6.79-6.81 (m, 2H); 7.13-7.19 (m, 3H); 7.50 (br s, H); 7.61 (br s, H); 7.95 (br s, H), HPLC (λ=214 nm), [A]: rt 6.54 min (97.8%).

Example 216

(S)-3-(1H-benzo[d]imidazol-5-yl)-4-(3-(piperidin-1-yl)phenyl)oxazolidin-2-one

The compound was synthesized according to method 5.
Step A:
The compound was synthesized starting from 3-(piperidin-1-yl)benzaldehyde (1.5 g, 7.9 mmol), methyltriphenylphosphonium bromide (3.83 g, 10.7 mmol), 1.6M solution of butyllithium in THF (6.7 mL, 10.7 mmol),
yield: 1.1 g (74%)

Step B:
Product obtained from step A (1.1 g, 5.9 mmol), ethyl carbamate (1.62 g, 18.21 mmol), 5,5-dimethylimidazolidine-2,4-dione (1.76 g, 8.96 mmol), (DHQ)$_2$PHAL (0.229 g, 0.29 mmol), K$_2$OsO$_4$x2H$_2$O (0.087 g, 0.23 mmol), 0.41 M aqueous NaOH (44 mL, 17.9 mmol),
yield: 0.2 g (11.6%)

Step C:
Product obtained from step B (0.2 g, 0.68 mmol), 0.2 M aqueous NaOH (18.8 ml),
yield: 0.15 g (89%)

Step D:
Product obtained from step C (0.15 g, 0.61 mmol), 4-iodobenzene-1,2-diamine (0.142 g, 0.61 mmol), copper(I) iodide (0.011 g, 0.06 mmol), cesium fluoride (0.183 g, 1.22 mmol), cyclohexane-1,2-diamine (0.008 mL, 0.06 mmol), triethyl orthoformate (10 ml),
yield: 0.010 g (4.5%)
Overall yield: 0.010 g (0.3%); MS m/z 363.2 (M+H)$^+$, 182.2 (M+2H)$^{2+}$; $^1$H NMR (400 MHz, CDCl$_3$): δ 1.51-1.55 (m, 2H); 1.60-1.64 (m, 4H); 3.04-3.12 (m, 4H); 4.23-4.26 (m, H); 4.76-4.80 (m, H); 5.30-5.34 (m, H); 6.70-6.72 (m, H); 6.78-6.80 (m, 2H); 7.12-7.16 (m, H); 7.29 (br s, H); 7.46 (br s, H); 7.66 (br s, H); 7.96 (br s, H), HPLC (λ=214 nm), [A]: rt 4.43 min (88%).

Example 217

(S)-3-(1H-benzo[d]imidazol-5-yl)-4-(4-morpholinophenyl)oxazolidin-2-one

The compound was synthesized according to method 5.
Step A:
The compound was synthesized starting from 4-morpholinobenzaldehyde (2 g, 10.5 mmol), methyltriphenylphosphonium bromide (5.04 g, 14.12 mmol), 1.6M solution of butyllithium in THF (8.8 mL, 14.12 mmol),
yield: 0.78 g (58.6%)

Step B:
Product obtained from step A (0.78 g, 4.1 mmol), ethyl carbamate (1.14 g, 12.7 mmol), 5,5-dimethylimidazolidine-2,4-dione (1.24 g, 6.3 mmol), (DHQ)$_2$PHAL (0.16 g, 0.21 mmol), K$_2$OsO$_4$x2H$_2$O (0.06 g, 0.16 mmol), 0.41 M aqueous NaOH (30.7 mL, 12.5 mmol),
yield: 0.4 g (33.1%)

Step C:
Product obtained from step B (0.4 g, 1.4 mmol), 0.2 M NaOH in methanol (37.5 ml),
yield: 0.285 g (60.1%)

Step D:
Product obtained from step C (0.14 g, 0.56 mmol), 4-iodobenzene-1,2-diamine (0.13 g, 0.56 mmol), copper(I) iodide (0.011 g, 0.06 mmol), cesium fluoride (0.17 g, 1.13 mmol), cyclohexane-1,2-diamine (0.008 mL, 0.06 mmol), triethyl orthoformate (4 ml),
yield: 0.062 g (30.2%)
Overall yield: 3.5%; MS m/z 365.3 (M+H)$^+$, 183.4 (M+2H)$^{2+}$; $^1$H NMR (400 MHz, CDCl$_3$): δ 3.07-3.09 (m, 4H); 3.77-3.79 (m, 4H); 4.21-4.25 (m, H); 4.74-4.79 (m, H); 5.30-5.34 (m, H); 6.78-6.80 (m, 2H); 7.17-7.19 (m, 3H); 7.42 (br s, H); 7.58 (br s, H), 7.87 (br s, H) HPLC (λ=214 nm), [A]: rt 7.31 min (98.8%).

Example 218

(S)-3-(1H-benzo[d]imidazol-5-yl)-4-(3-morpholinophenyl)oxazolidin-2-one

The compound was synthesized according to method 5.
Step A:
The compound was synthesized starting from 3-morpholinobenzaldehyde (2 g, 10.5 mmol), methyltriphenylphosphonium bromide (5.04 g, 14.12 mmol), 2M solution of butyllithium in THF (8.8 mL, 14.12 mmol),
yield: 1.16 g (58.6%)

Step B:
Product obtained from step A (1.16 g, 6.14 mmol), ethyl carbamate (1.7 g, 19 mmol), 5,5-dimethylimidazolidine-2,4-dione (1.84 g, 9.36 mmol), (DHQ)$_2$PHAL (0.239 g, 0.31 mmol), K$_2$OsO$_4$x2H$_2$O (0.09 g, 0.25 mmol), 0.41 M aqueous NaOH (46.2 mL, 18.7 mmol),
yield: 0.27 g (14.9%)

Step C:
Product obtained from step B (0.27 g, 0.92 mmol), 0.2 M aqueous NaOH (25.3 ml),
yield: 0.180 g (80%)

Step D:
Product obtained from step C (0.07 g, 0.28 mmol), 4-iodobenzene-1,2-diamine (0.066 g, 0.28 mmol), copper(I) iodide (0.006 g, 0.03 mmol), cesium fluoride (0.085 g, 0.56 mmol), cyclohexane-1,2-diamine (0.004 mL, 0.03 mmol), triethyl orthoformate (2 ml),
yield: 0.010 g (10%)
Overall yield: 0.010 g (0.7%); MS m/z 365.2 (M+H)$^+$, 183.4 (M+2H)$^{2+}$; $^1$H NMR (400 MHz, CD$_3$OD): δ 3.00-3.10 (m, 4H); 3.74-3.76 (m, 4H); 4.22-4.26 (m, H); 4.81-4.87 (m, H); 5.55-5.59 (m, H); 6.83-6.84 (m, 2H); 6.93 (s, H); 7.16-7.20 (m, H); 7.37 (s, H); 7.87 (br s, H), HPLC (λ=214 nm), [A]: rt 8.56 min (93.9%).

Example 219

3-(1H-benzo[d]imidazol-5-yl)-4-(4-(tetrahydro-2H-pyran-4-yl)phenyl)oxazolidin-2-one

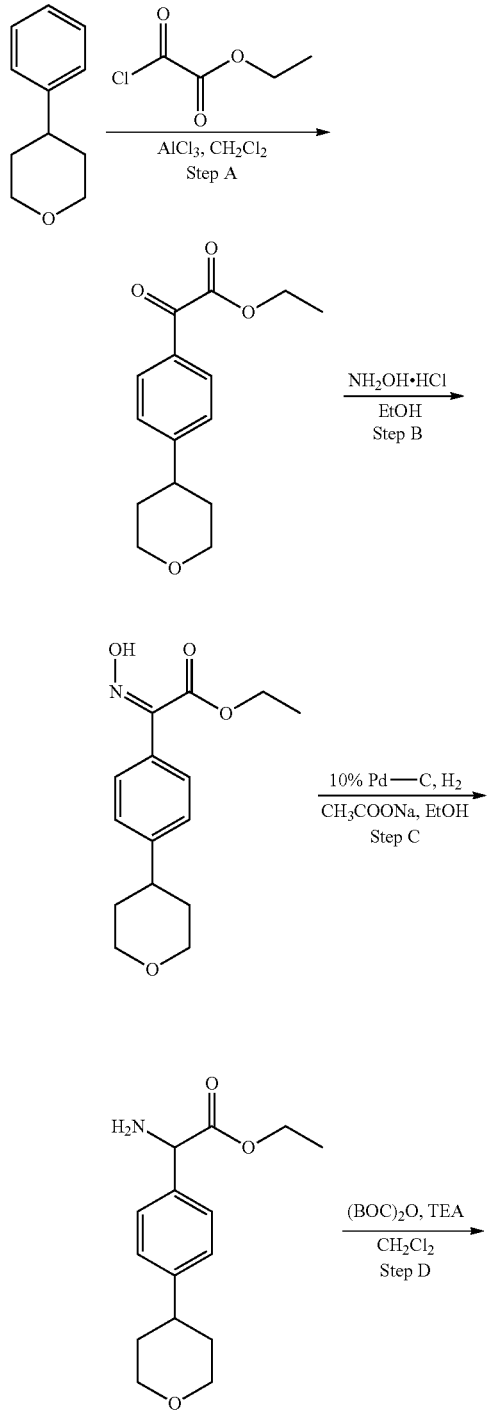

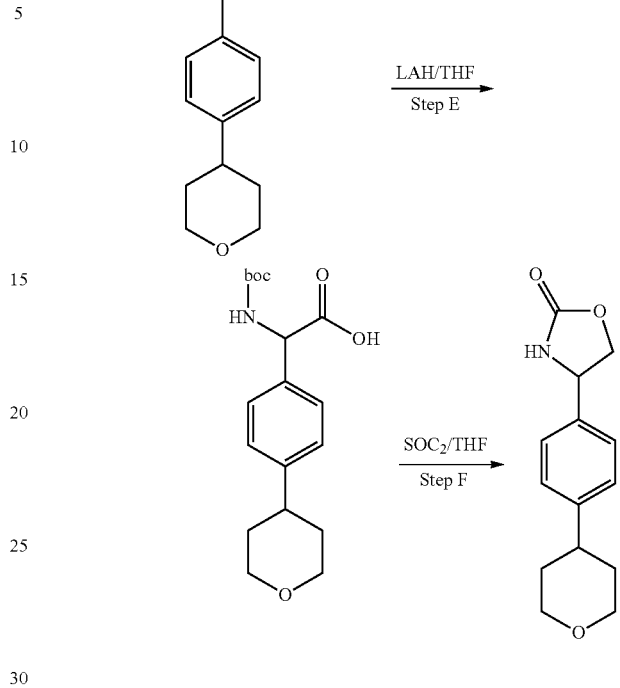

Step A

Ethyl chloro oxalate (5.5 mL, 49.38 mmol) and AlCl₃ (6.5 g, 49.38 mmol) were added to a solution of tetrahydro-4-phenyl-2H-pyran (2.0 g, 12.34 mmol) in dichloromethane (25 mL) at −20° C. The mixture was stirred for 1 h and allow to room temperature for 2 h. Then the mixture were quenched with saturated NaHCO₃ solution at 0° C. and filtered and washed with excess of ethyl acetate (200 mL) and the organic layer separated and dried with Na₂SO₄ and evaporated under reduced pressure to afford 2.0 g (62.5%) the product as a brown color liquid.

Step B

Hydroxylaminehydrochloride (1.65 g, 23.86 mmol) and sodium acetate (1.95 g, 23.86 mmol) were added to a solution of the product of step B (2.5 g, 9.54 mmol) in ethanol (25 mL) was heated to 80° C. for 12 h. Then the reaction mixture cooled to room temperature and filtered the filtrate was evaporated to dryness to give 2.42 g (91%) of the product as a colorless liquid.

Step C

To a solution of 10% Pd—C (350 mg, 10%) in ethanol was added to the product of step B (3.5 g, 12.63 mmol) in hydrogenated vessel at 80 Psi at room temperature for 24 h. Then the catalyst was filtered through celite bed and evaporated the solvent to give 1.7 g (51.5%) of the product as a colorless liquid.

Step D

Boc-anhydride (2.5 mL, 11.40 mmol) was added to a solution of the product of step C (3.0 g, 11.40 mmol) and triethylamine (2.4 mL, 11.40 mmol) in dichloromethane (40 mL), and stirred for 3 h. The reaction mixture was washed with water (30 mL) and extracted with dichloromethane (3×50 mL). The combined organic layer was washed with brine (20 mL), dried over anhydrous sodium sulfate and concentrated. The crude compound purified by column chromatography using neutral alumina the pure product elute at 15% of ethyl acetate in pet ether as solvent to give 2.3 g (56%) of the product as a yellow color liquid.

Step E

Lithium aluminum hydride (150 mg, 3.57 mmol) was added to a solution of the product of step C (1.3 g, 3.57 mmol) in dry THF (40 mL) at 0° C. Then the reaction mixture was warmed to room temperature for 2 h, and reaction mixture cool 0° C. and quenched with saturated NH$_4$Cl solution (25 mL), and filtered the mixture and washed with ethyl acetate (100 mL). The solution was partitioned between two layers and separated the organic layer and washed with brine solution and evaporated the organic layers to afford 900 mg (81.8%) of the product as a light yellow solid.

Step F

Thionyl chloride (1.5 mL, 19.93 mmol) was added to a solution of the product of step E (800 mg, 2.49 mmol) in tetrahydrofuran (10 mL) at 0° C. Then the reaction mixture allowed to room temperature for 12 h. the solvent was evaporated and basified with saturated NaHCO$_3$ solution (10 mL) and extracted with chloroform (3×25 mL) and combined organic layers dried over anhydrous sodium sulfate and concentrated in vacuo to give 480 mg (78%) of the product as a light yellow solid.

The compound was further synthesized according to method 5 step D starting from the product of step F (400 mg, 1.617 mmol), 1,2-diamino 4-bromo benzene (333 mg, 1.78 mmol), cesium fluoride (490 mg, 3.22 mmol), copper iodide (45 mg, 0.241 mmol), formic acid (5 mL). Yield: 150 mg (25.5%), MS m/z 364.3 (M+H)$^+$; $^1$H-NMR (400 MHz, DMSO-d6): δ 12.38 (s, 1H); 8.15 (s, 1H); 7.60 (s, 1H); 7.55 (bs, 1H); 7.33-7.20 (m, 5H); 5.72 (t, 1H); 4.80 (t, 1H): 4.12 (t, 1H); 3.88 (d, 2H); 3.37-3.29 (merged with DMSO moisture, 2H); 2.60 (d, 1H); 1.60-1.23 (m, 4H), HPLC (λ=214 nm, [A]: rt 10.93 min (98.93%).

Example 220

3-(1H-benzo[d]imidazol-5-yl)-4-(4-(1-methylpiperidin-4-yl)phenyl)oxazolidin-2-one

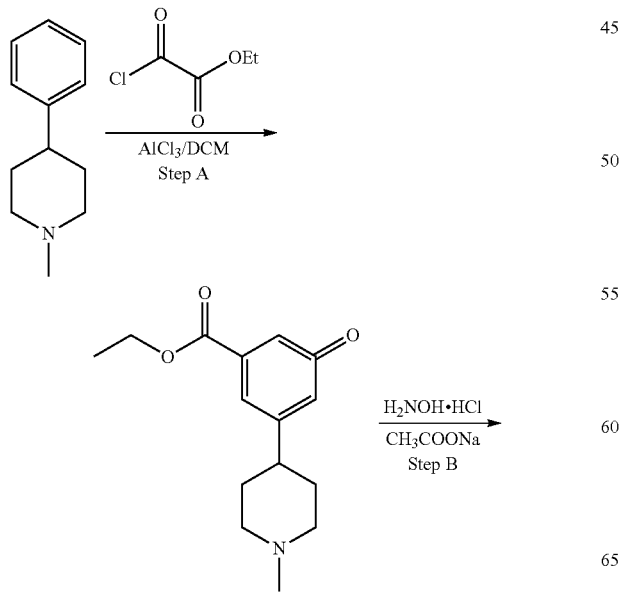

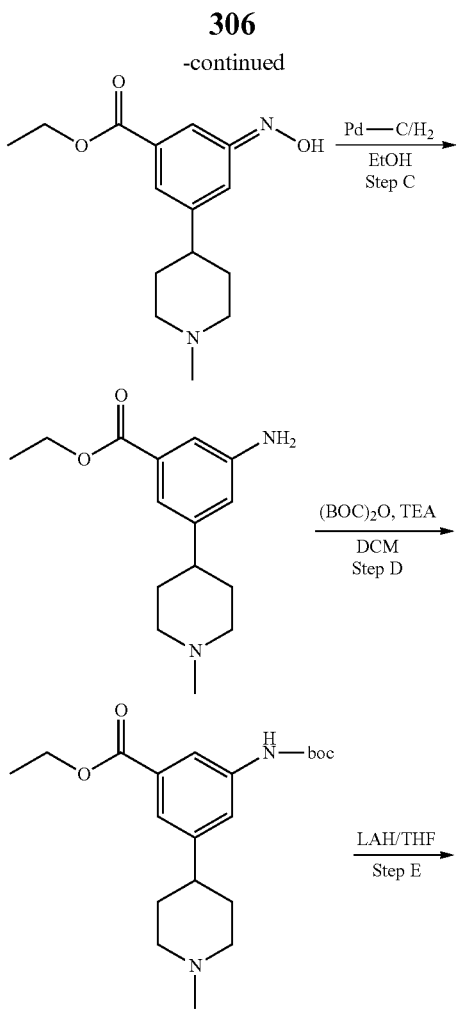

Step A

Ethyl oxalyl chloride (13 mL, 114.28 mmol) was added to a solution of 1-methyl-4-phenylpiperidine (5 g, 28.57 mmol) in DCM (50 mL) at −30° C. over a period of 5 min. Added aluminium chloride (15.2 g, 114.28 mmol) to the above solution in 3 lots over a period of 15 min. Stirred the RM at −30° C. for 1 h. Slowly warmed the RM to room temperature and stirred for 2 h at room temperature. The reaction mass was quenched into Aq. Na$_2$CO$_3$ solution and extracted into ethyl acetate. The salts were filtered off and washed with ethyl acetate. Separated the organic layer form the filtrate and washed with water followed by brine solution. Dried over anhydrous sodium sulphate and concentrated o afford 2.8 g (35.8%) of the product as brown oily liquid

Step B

Sodium acetate (596 mg, 7.27 mmol), hydroxylamine.HCl (505 mg, 7.27 mmol) were added successively to the product of step A (1 g, 3.6 mmol) in ethanol (8 mL) and stirred at reflux for 2 h. The salts were separated and washed with ethanol. The filtrate was concentrated to afford 1.5 g of the product crude.

Step C

10% Pd—C (200 mg) was added to a solution of the product of step B (1.5 g, 5.17 mmol) in ethanol (25 mL) and hydrogenated at 80 psi for 15 h. The RM was filtered through celite and washed with ethanol. The filtrate was concentrated to afford 1 g (70.4%) of the product as thick oil.

Step D

Triethylamine (0.6 mL, 4.34 mmol) was added to a solution of the product of step C (1 g, 3.62 mmol) in DCM (10 mL) and stirred for 15 min. Added (Boc)$_2$O (0.95 mL, 4.34 mmol) and stirred for 1 hr at RT. Added water and extracted into ethyl acetate. Combined organic layers and washed with water followed by brine solution. Dried over anhydrous sodium sulphate and concentrated to afford 700 mg of the crudeproduct as oil which was used without further characterization.

Step E

LAH(90 mg, 2.39 mmol) was added to solution of the product of step D (900 mg, 2.39 mmol) in THF (15 mL) at 0° C. slowly over period of 5 min. Stirred for 2 h at 0° C.-5° C. and the RM was quenched with saturated sodium sulphate solution and diluted with ethyl acetate. The salts were filtered off and washed with ethyl acetate. Combined organic layers and washed with water followed by brine solution. Dried over anhydrous sodium sulphate and concentrated to afford 550 mg of the product as oil.

Step F

Thionyl chloride (1 mL, 14.37 mmol) was added to solution of the product of step E (600 mg, 14.37 mmol) In THF (10 mL) at 0° C. and slowly warmed to RT and stirred for 18 hr. Concentrated the RM at below 45° C. and basified with saturated sodium bicarbonate solution and extracted with ethyl acetate. Combined organic layers and washed with water followed by brine solution. Dried over anhydrous sodium sulphate and concentrated to afford 290 mg of the product as yellow solid.

The compound was further synthesized according to method 5 step D starting from the product of step F (290 mg, 1.11 mmol), 2-diamino-4-bromo benzene (229 mg, 1.22 mmol), cesium fluoride (339 mg, 2.23 mmol) and copper (I) iodide (31 mg, 0.167 mmol), 1,2-diamino cyclohexane (19 mg, 0.167 mmol), formic acid (3 mL). Yield: 50 mg (11.9%), MS m/z 377.4 (M+H)$^+$; $^1$H-NMR 400 MHz, CDCl3): δ 7.95 (s, 1H); 7.67 (s, 1H); 7.51 (s, 2H); 7.25-7.15 (merged with CDCl3, 5H); 5.42-5.39 (q, 1H); 4.79 (t, 1H); 4.25-4.22 (q, 1H); 2.95 (d, 2H); 2.49-2.39 (m, 2H); 2.30 (s, 3H); 2.06-1.99 (m, 2H); 1.77-1.65 (m, 4H), HPLC (λ=214 nm, [A]: rt 5.63 min (94.45%).

Example 221

(S)-3-(1H-benzo[d]imidazol-6-yl)-4-(3-(4-methylpiperazin-1-yl)Phenyl)oxazolidin-2-one The compound was synthesized according to method 6 starting from 3-(4-methylpiperazin-1-yl)benzaldehyde (11 g, 53.92 mmol), KCN (3.5 g, 53.9 mmol), ammonium carbonate (4.381 g, 67.40 mmol), NaOH (12 g, 775.32 mmol), thionyl chloride (22.74 g, 313.25 mmol), di tertiary butyl dicarbonate (1.8 g, 11.59 mmol), triethylamine (3.23 mL, 23.18 mmol), sodium borohydride (2.45 g, 65.01 mmol), thionyl chloride (0.864 mL, 11.54 mmol), 1,2-diamino-4-bromo benzene (181 mg, 0.969 mmol), cesium fluoride (267 mg, 1.762 mmol), cis-1,2-diamino cyclo hexane (0.015 mL, 0.132 mmol), formic acid (5 mL). Yield: 50 mg (0.25%), MS m/z 378.3 (M+H)$^+$, $^1$H-NMR (400 MHz, DMSO-d6): δ 12.39 (d, 1H); 8.16 (d, 1H); 7.59-7.11 (m, 4H); 6.95 (d, 1H); 6.28-6.72 (m, 2H); 5.63-5.61 (q, 1H); 4.8 (t, 1H); 4.12 (t, 1H); 3.07 (d, 4H); 2.49-2.40 (m, 4H); 2.19 (s, 3H), HPLC (λ=214 nm), [A]: rt 6.53 min (93.54%)

Example 222

(S)-3-(3-methylH-imidazo[1,2-a]pyridin-7-yl)-4-phenyloxazolidin-2-one

The compound was synthesized according to method 5 step D starting from 7-bromo-3-methylH-imidazo[1,2-a]pyridine (84 mg; 0.4 mmol; 1 eq.) dioxane (5 ml), (S)-4-phenyloxazolidin-2-one (72 mg; 0.44 mmol; 1.1 eq.), copper(I) iodide (8 mg; 0.04 mmol; 0.1 eq.), cesium fluoride (121 mg; 0.8 mmol; 2 eq.), diaminocyclohexane (5 mg; 0.04 mmol; 0.1 eq)

Yield: 57 mg (48%); MS m/z 294.2 (M+H)$^+$; $^1$H NMR (400 MHz, DMSO-D$_6$): δ 2.37 (s, 3H); 4.17 (dd, 1H, $^3$J=8.7 Hz, $^2$J=2.9 Hz); 4.86 (t, 1H, $^3$J=8.7 Hz); 5.81 (dd, 1H, $^3$J=8.7 Hz, $^2$J=2.9 Hz); 7.23-7.37 (m, 6H); 7.40-7.42 (m, 2H); 8.17 (d, 1H, $^3$J=7.5 Hz); HPLC (λ=214 nm), [B]: rt 10.78 min (99.7%).

Example 223

(S)-3-(3-(trifluoromethyl)H-imidazo[1,2-a]pyridin-7-yl)-4-phenyloxazolidin-2-one The compound was synthesized according to method 5 step D starting from 7-bromo-3-(trifluoromethyl)H-imidazo[1,2-a]pyridine (80 mg; 0.3 mmol; 1 eq.), dioxane (5 ml), (S)-4-phenyloxazolidin-2-one (54 mg; 0.33 mmol; 1.1 eq.), copper(I) iodide (6 mg; 0.03 mmol; 0.1 eq.), cesium fluoride (91 mg; 0.6 mmol; 2 eq.), diaminocyclohexane (4 mg; 0.04 mmol; 0.1 eq).

Yield: 39 mg (37%); MS m/z 348.0 (M+H)$^+$; $^1$H NMR (400 MHz, DMSO-D$_6$): δ 4.21 (dd, 1H, $^3$J=8.7 Hz, $^2$J=3.3 Hz); 4.90 (t, 1H, $^3$J=8.7 Hz); 5.88 (dd, 1H, $^3$J=8.7 Hz, $^2$J=3.7 Hz); 7.29-7.33 (m, 1H); 7.36-7.40 (m, 2H); 7.42-7.44 (m, 2H); 7.56 (d, 1H, $^4$J=2.1 Hz); 7.67 (dd, 1H, $^3$J=7.5 Hz, $^2$J=2.1 Hz); 8.15 (s, 1H); 8.52 (d, 1H, $^3$J=7.5 Hz); HPLC (λ=214 nm), [B]: rt 14.43 min (98.6%).

Example 224

(S)-4-(2,3-dihydrobenzo[b][1,4]dioxin-6-yl)-3-(H-imidazo[1,2-a]pyridin-7-yl)oxazolidin-2-one The compound was synthesized according to method 5.

Step A:

The compound was synthesized starting from 2,3-dihydrobenzo[b][1,4]dioxine-6-carbaldehyde (0.5 g, 3.05 mmol), methyltriphenylphosphonium bromide (1.47 g, 4.11 mmol), 2M solution of butyllithium in THF (2.06 mL, 4.11 mmol), yield: 0.41 g (82.9%)

Step B:

Product obtained from step A (0.41 g, 2.4 mmol), tert-butyl carbamate (0.91 g, 7.75 mmol), 5,5-dimethylimidazolidine-2,4-dione (0.75 g, 3.8 mmol), (DHQ)$_2$PHAL (0.12 g, 0.15 mmol), K$_2$OsO$_4$x2H$_2$O (0.037 g, 0.1 mmol), 0.38 M aqueous NaOH (20 mL, 7.6 mmol),
yield: 0.3 g (40.6%)

Step C:

Product obtained from step B (0.3 g, 1.3 mmol) was dissolved in 40 mL dichloromethane and 5 mL of TFA were added. After stirring for 1 hour at ambient temperature the solvent was removed under reduced pressure. The residue was readopted in THF. Di(1H-imidazol-1-yl)methanone (0.2 g, 1.22 mmol) and triethylamine (0.17 mL, 1.22 mmol) was added. The reaction was stirred for 48 hours at 50° C. before the solvent was removed under reduced pressure. The remaining residue was readopted in ethyl acetate and washed with water. The organic layer was dried over sodium sulfate, filtrated and the solvent was removed using a rotary evaporator. The product was purified by means of flash chromatography (ethyl acetate/heptane gradient).
yield: 0.12 g (53.4%)
Step D:
Product obtained from step C (0.12 g, 0.54 mmol), 7-bromoimidazo[1,2-a]pyridine (0.11 g, 0.55 mmol), copper(I) iodide (0.011 g, 0.055 mmol), cesium fluoride (0.17 g, 1.1 mmol), cyclohexane-1,2-diamine (0.007 mL, 0.055 mmol),
yield: 0.030 g (16.5%)
Overall yield: 0.010 g (3%); MS m/z 388.2 (M+H)$^+$; $^1$H NMR (400 MHz, DMSO-D$_6$): δ 4.08-4.12 (m, H); 4.15 (s, 4H); 4.75-4.79 (m, H); 5.63-5.66 (m, H); 6.78-6.89 (m, 3H); 7.25-7.29 (m, 2H); 7.43 (s, H); 7.77 (s, H); 8.42 (d, H, J=7.5 Hz), HPLC (λ=214 nm), [A]: rt 7.55 min (98.5%).

Example 225

(S)-4-(4-cyclohexylphenyl)-3-(H-imidazo[1,2-a]pyridin-7-yl)oxazolidin-2-one

The compound was synthesized according to method 5.
Step A:
The compound was synthesized starting from 4-cyclohexylbenzaldehyde (2.3 g, 12.2 mmol), methyltriphenylphosphonium bromide (5.9 g, 16.5 mmol), 2M solution of butyllithium in THF (8.25 mL, 16.5 mmol),
yield: 2.08 g (91.4%)
Step B:
Product obtained from step A (2.08 g, 11.17 mmol), ethyl carbamate (3.08 g, 34.61 mmol), 5,5-dimethylimidazolidine-2,4-dione (3.35 g, 17.03 mmol), (DHQ)$_2$PHAL (0.434 g, 0.56 mmol), K$_2$OsO$_4$x2H$_2$O (0.165 g, 0.45 mmol), 0.41 M aqueous NaOH (84 mL, 34.05 mmol),
yield: 1.35 g (41.5%)
Step C:
Product obtained from step B (1.35 g, 4.64 mmol), 0.2 M aqueous NaOH (128 ml),
yield: 0.675 g (59.3%)
Step D:
Product obtained from step C (0.2 g, 0.82 mmol), 7-bromoimidazo[1,2-a]pyridine (0.16 g, 0.82 mmol), copper(I) iodide (0.016 g, 0.082 mmol), cesium fluoride (0.25 g, 1.63 mmol), cyclohexane-1,2-diamine (0.010 mL, 0.082 mmol),
yield: 0.160 g (54%)
Overall yield: 12.1%; MS m/z 362.2 (M+H)$^+$; $^1$H NMR (400 MHz, DMSO-D$_6$): δ 1.13-1.31 (m, 6H); 1.60-1.70 (m, 4H); 2.38-2.42 (m, H); 4.10-4.14 (m, H); 4.78-4.82 (m, H); 5.71-5.75 (m, H); 7.17-7.19 (m, 2H); 7.28-7.30 (m, 4H); 7.41 (br s, H); 7.76 (s, H); 8.40-8.42 (m, H), HPLC (λ=214 nm), [A]: rt 15.01 min (98.3%).

Example 226

(S)-3-(H-imidazo[1,2-a]pyridin-7-yl)-4-(4-(piperidin-1-yl)phenyl)oxazolidin-2-one The compound was synthesized according to method 5.
Step A:
The compound was synthesized starting from 4-(piperidin-1-yl)benzaldehyde (1.17 g, 6.18 mmol), methyltriphenylphosphonium bromide (2.98 g, 8.35 mmol), 1.6M solution of butyllithium in THF (5.22 mL, 8.35 mmol),
yield: 0.72 g (62.2%)
Step B:
Product obtained from step A (0.72 g, 3.85 mmol), ethyl carbamate (1.14 g, 12.7 mmol), 5,5-dimethylimidazolidine-2,4-dione (1.24 g, 6.3 mmol), (DHQ)$_2$PHAL (0.16 g, 0.21 mmol), K$_2$OsO$_4$x2H$_2$O (0.06 g, 0.16 mmol), 0.41 M aqueous NaOH (30.7 mL, 12.5 mmol),
yield: 0.2 g (17.8%)
Step C:
Product obtained from step B (0.2 g, 0.69 mmol), 0.2 M aqueous NaOH (18.8 ml),
yield: 0.165 g (97.8%)
Step D:
Product obtained from step C (0.09 g, 0.37 mmol), 7-bromoimidazo[1,2-a]pyridine (0.07 g, 0.37 mmol), copper(I) iodide (0.007 g, 0.037 mmol), cesium fluoride (0.11 g, 0.73 mmol), cyclohexane-1,2-diamine (0.005 mL, 0.037 mmol),
yield: 0.02 g (15.1%)
Overall yield: 1.6%; MS m/z 363.2 (M+H)$^+$; $^1$H NMR (400 MHz, CDCl$_3$): δ 1.63-1.72 (m, 2H); 1.90-1.98 (m, 4H); 3.32-3.36 (m, 4H); 4.29-4.33 (m, H); 4.85-4.89 (m, H); 5.61-5.65 (m, H); 7.42-7.44 (m, 2H); 7.51-7.55 (m, 3H); 7.61 (d, H, J=2.1 Hz); 7.94 (s, H); 8.21 (d, H, J=7.7 Hz); 8.49-8.51 (m, H), HPLC (λ=214 nm), [A]: rt 3.87 min (98%).

Example 227

(S)-3-(H-imidazo[1,2-a]pyridin-7-yl)-4-(4-morpholinophenyl)oxazolidin-2-one

The compound was synthesized according to method 5.
Step A:
The compound was synthesized starting from 4-morpholinobenzaldehyde (2 g, 10.5 mmol), methyltriphenylphosphonium bromide (5.04 g, 14.1 mmol), 1.6M solution of butyllithium in THF (8.8 mL, 14.1 mmol),
yield: 0.78 g (39.4%)
Step B:
Product obtained from step A (0.78 g, 4.1 mmol), ethyl carbamate (1.14 g, 12.7 mmol), 5,5-dimethylimidazolidine-2,4-dione (1.24 g, 6.3 mmol), (DHQ)$_2$PHAL (0.16 g, 0.21 mmol), K$_2$OsO$_4$x2H$_2$O (0.06 g, 0.16 mmol), 0.41 M aqueous NaOH (30.6 mL, 12.5 mmol),
yield: 0.4 g (33.1%)
Step C:
Product obtained from step B (0.4 g, 1.36 mmol), 0.2 M aqueous NaOH (37.5 ml),
yield: 0.29 g (84.5%)
Step D:
Product obtained from step C (0.14 g, 0.56 mmol), 7-bromoimidazo[1,2-a]pyridine (0.11 g, 0.56 mmol), copper(I) iodide (0.011 g, 0.06 mmol), cesium fluoride (0.17 g, 1.13 mmol), cyclohexane-1,2-diamine (0.008 mL, 0.06 mmol),
yield: 0.05 g (24.3%)
Overall yield: 2.7%; MS m/z 365.3 (M+H)$^+$; $^1$H NMR (400 MHz, CDCl$_3$): δ 3.10-3.12 (m, 4H); 3.79-3.81 (m, 4H); 4.19-4.22 (m, H); 4.74-4.79 (m, H); 5.30-5.33 (m, H); 6.83 (d, 2H, J=8.7 Hz); 7.08 (s, H); 7.20 (d, 2H, J=8.7 Hz); 7.44 (s, H); 7.47 (s, H); 7.59-7.61 (m, H); 7.99-8.01 (m, H), HPLC (λ=214 nm), [A]: rt 7.23 min (95.1%).

Example 228

(S)-3-(H-imidazo[1,2-a]pyridin-7-yl)-4-(4-(4-phenylpiperazin-1-yl)phenyl)oxazolidin-2-one The compound was synthesized according to method 5.

Step A:

The compound was synthesized starting from 4-(4-phenylpiperazin-1-yl)benzaldehyde (1.03 g, 3.87 mmol), methyltriphenylphosphonium bromide (1.86 g, 5.22 mmol), 2M solution of butyllithium in THF (2.61 mL, 5.22 mmol), yield: 0.66 g (64.5%)

Step B:

Product obtained from step A (0.66 g, 2.5 mmol), tert-butyl carbamate (0.91 g, 7.75 mmol), 5,5-dimethylimidazolidine-2,4-dione (0.75 g, 3.83 mmol), (DHQ)$_2$PHAL (0.117 g, 0.15 mmol), K$_2$OsO$_4$x2H$_2$O (0.037 g, 0.1 mmol), 0.38 M aqueous NaOH (20 mL, 7.68 mmol), yield: 0.26 g (26.2%)

Step C:

Product obtained from step B (0.26 g, 0.66 mmol) was dissolved in 40 mL dichloromethane and 5 mL of TFA were added. After stirring for 1 hour at ambient temperature the solvent was removed under reduced pressure. The residue was readopted in dichloromethane. Di(1H-imidazol-1-yl)methanone (0.13 g, 0.79 mmol) and triethylamine (0.11 mL, 0.79 mmol) was added. The reaction was stirred for 90 minutes at ambient temperature before the solvent was removed under reduced pressure. The remaining residue was readopted in ethyl acetate and washed with water. The organic layer was dried over sodium sulfate, filtrated and the solvent was removed using a rotary evaporator. The product was purified by means of flash chromatography (ethyl acetate/hexane gradient).

yield: 0.08 g (37.8%)

Step D:

Product obtained from step C (0.08 g, 0.25 mmol), 7-bromoimidazo[1,2-a]pyridine (0.049 g, 0.25 mmol), copper(I) iodide (0.005 g, 0.025 mmol), cesium fluoride (0.076 g, 0.5 mmol), cyclohexane-1,2-diamine (0.003 mL, 0.025 mmol), yield: 0.004 g (3.8%)

Overall yield: 0.2%; MS m/z 440.4 (M+H)$^+$, 220.9 (2M+H)$^{2+}$; $^1$H NMR (400 MHz, CD$_3$OD): δ 3.33-3.34 (m, 8H); 4.28-4.31 (m, H); 4.89-4.92 (m, H); 5.68-5.70 (m, H); 6.92-6.95 (m, H); 7.05-7.08 (m, 4H); 7.27-7.33 (m, 4H); 7.76-7.78 (m, H); 7.84 (d, H, J=2.1 Hz); 7.93 (d, H, J=2.1 Hz); 7.99 (d, H, J=2.1 Hz); 8.61 (d, H, J=7.6 Hz), HPLC (λ=214 nm), [A]: rt 12.38 min (93.6%).

Example 229

(S)-1-(1H-benzo[d]imidazol-5-yl)-5-(4-(bis(2-methoxyethyl)amino)phenyl)imidazolidin-2-one

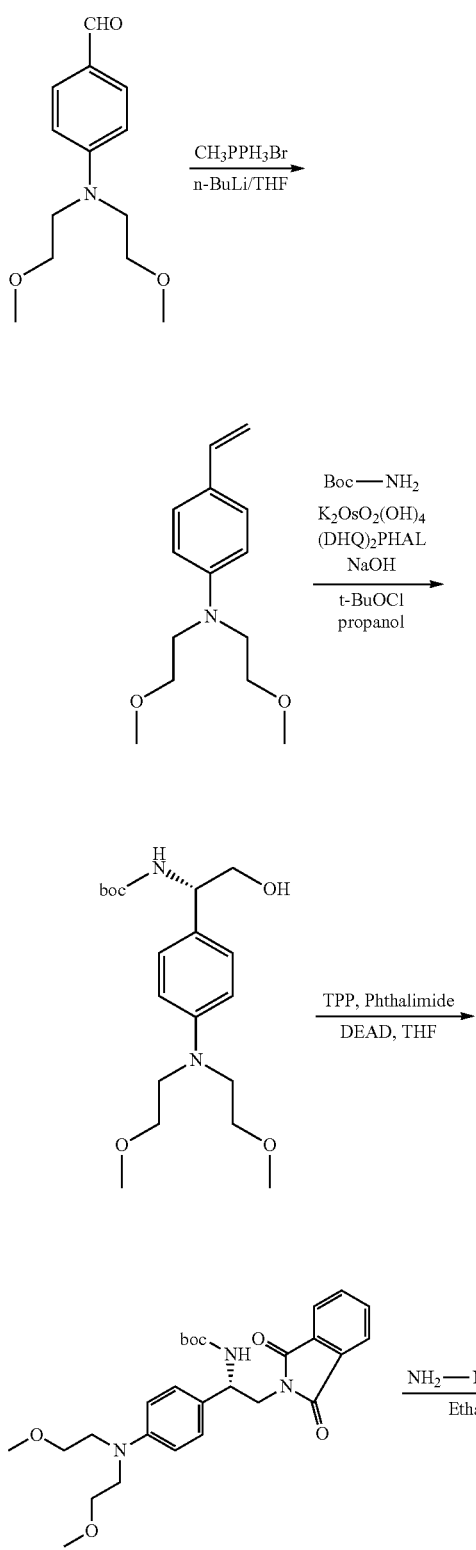

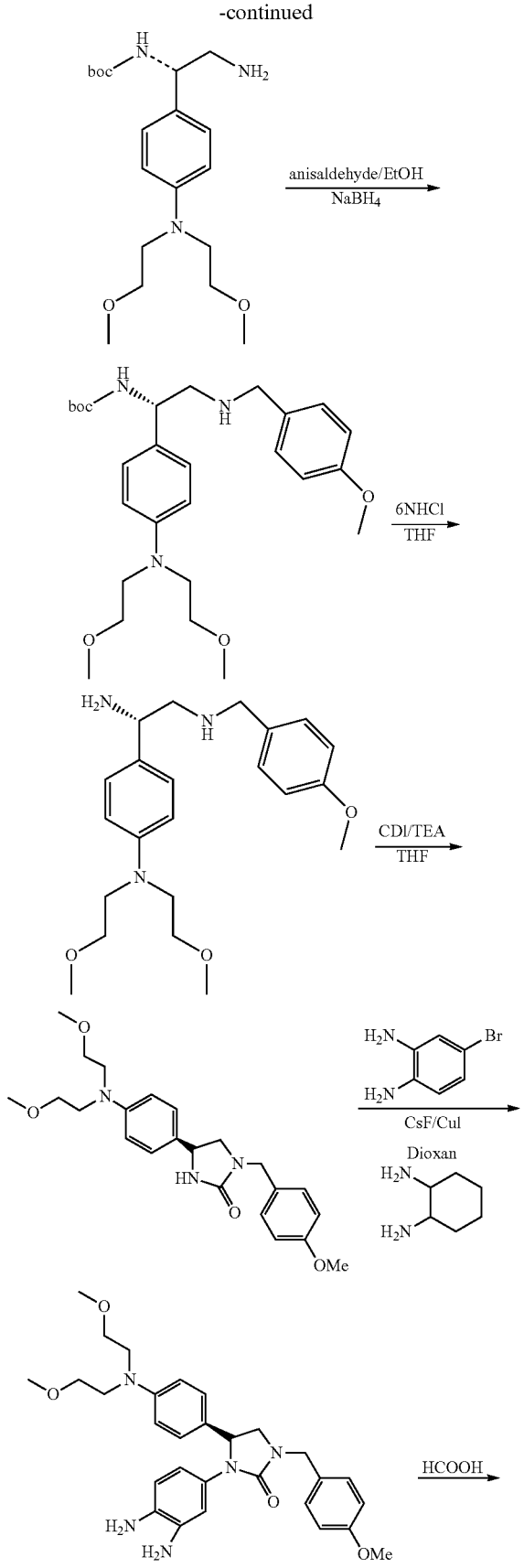

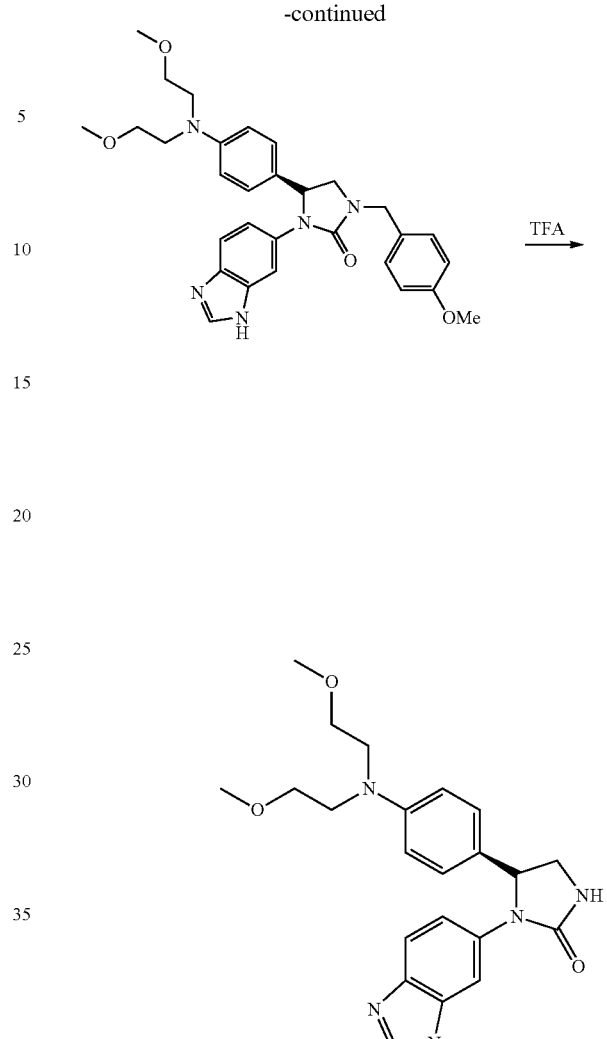

The compound was synthesized according to a modified method 3 shown above starting from 4-(bis(2-methoxyethyl)amino)benzaldehyde (1.180 g, 4.97 mmol), 2.3M n-butyl lithium (4.3 mL, 9.95 mmol), triphenyl phosphonium methyl bromide (3.5 g, 9.95 mmol), t-butyl hypochlorite (1 mL, 9.342 mmol), t-butyl carbamate (1.075 g, 9.191 mmol), sodium hydroxide (0.373 g in 22 mL water), (DHQ)$_2$PHAL (119 mg, 0.153 mmol), potassium osmate dihydrate (45 mg, 0.122 mmol), pthalimide (1.318 g, 8.967 mmol), triphenyl phosphine (3.2 g, 12.28 mmol), diethylazo dicarboxylate (2 ml, 12.28 mmol), hydrazine hydrate (30 mL), P-anisaldehyde (0.32 ml, 2.656 mmol), sodium borohydride (350 mg, 9.296 mmol), triethyl amine (0.539 mL) and CDI (0.301 g, 1.86 mmol), 1,2-dibromo 4-bromo benzene (200 mg, 1.065 mmol), cesium fluoride (300 mg, 1.936 mmol), copper iodide (50 mg), 1,2-diaminocyclohexane (16 mg, 0.145 mmol), formic acid (5 mL), trifluoroacetic acid (5 mL). Yield: 0.040 g (1.96%); MS m/z 410.6 (M+H)$^+$; 1H NMR (400 MHz, CDCl3): δ 7.89 (d, 1H); 7.60-7.45 (m, 2H); 7.26-7.11 (merged with CDCl3, 3H); 6.61 (d, 2H); 5.60 (t, 1H); 4.77 (t, 1H); 4.33 (t, 1H); 3.60-3.49 (m, 8H); 3.32 (s, 6H); HPLC (λ=214 nm, [A]: rt 8.46 min (98.3%).
Example 230
5-(4-(N-(2-(dimethylamino)ethyl)-N-methylamino)phenyl)-1-(1H-benzo[d]imidazol-5-yl)imidazolidin-2-one
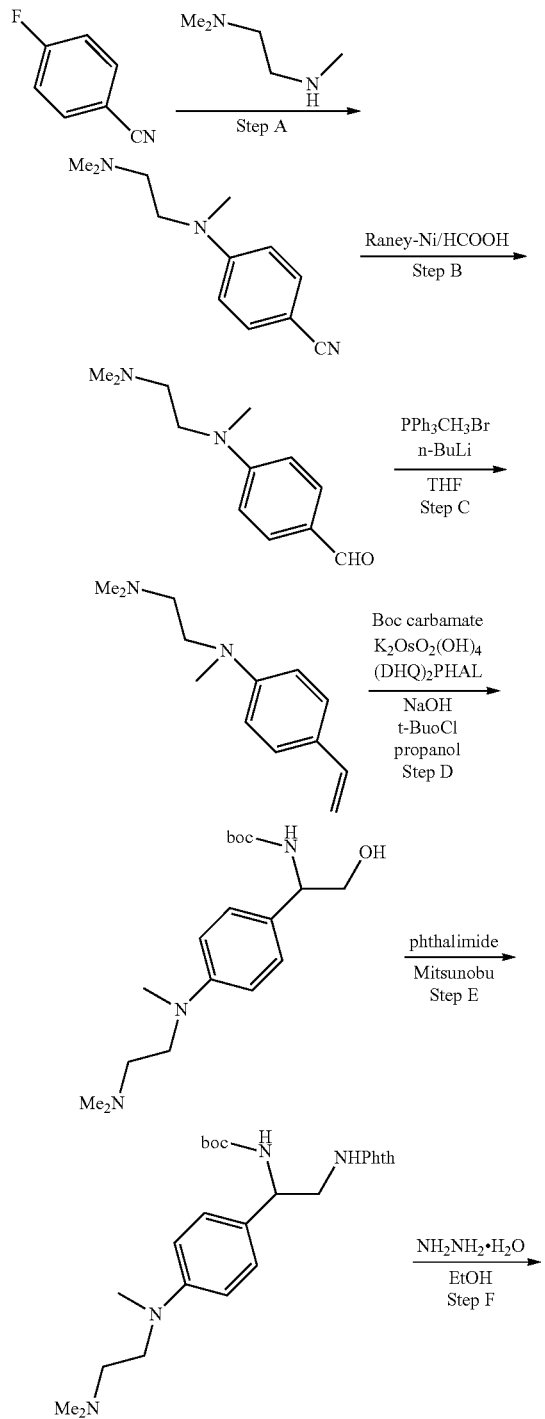
-continued
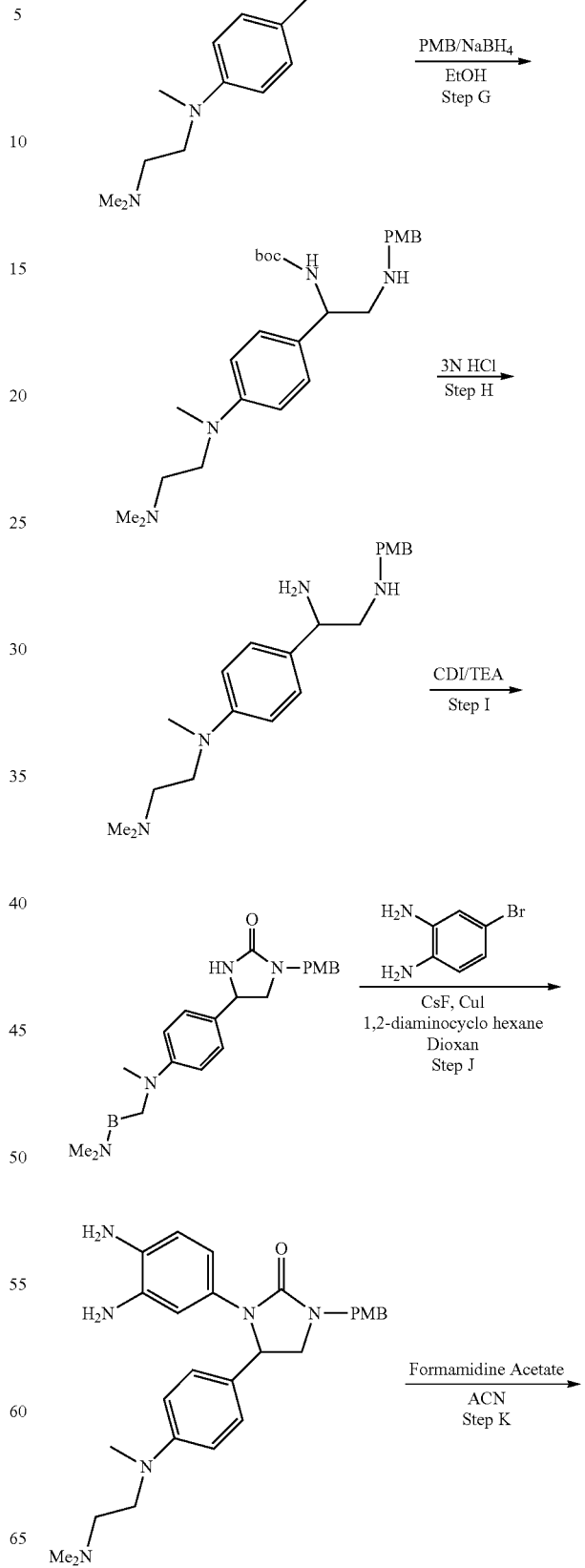

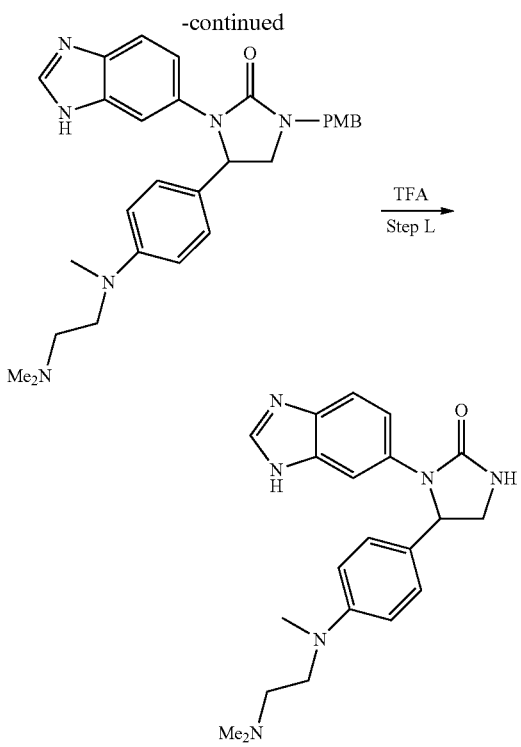

Step A

A suspension of 4-fluorobenzonitrile (5 g, 41.3 mmoles), trimethyl ethylamine (6 ml, 1.2 vol) was refluxed for 16 hours. The reaction mass was cooled and diluted in cold water (100 ml), and extracted with ethyl acetate (3×100 mL) and dried over anhydrous sodium sulphate and concentrated under vacuum to afford 5 g (58.8%) of the product as a colorless liquid.

Step B

A suspension of the product of step A (5 g, 24.27 mmol) in 85% formic acid (10 vol, 50 mL) was added Raney Ni (1-vol, 5 g) at room temperature for 12 h. Then the reaction mixture filtered through celite bed and washed with ethyl acetate (50 mL). The mixture was basified with saturated NaHCO$_3$ solution extracted with ethyl acetate (3×50 mL). And dried over anhydrous sodium sulphate and concentrated under vacuum to afford 4 g (78.8%) of 196b as a colorless liquid.

Step C 2.3 M n-Butyl lithium (25.65 mL, 58.2 mmol) was added to a stirred solution of triphenyl phosphonium methyl bromide (20.78 g, 58.2 mmol) in tetrahydrofuran (110 mL) at −10° C. and stirred for 30 min. A solution of the product of step B (6 g, 29.12 mmol) in tetrahydrofuran (30 mL) was added drop wise to the reaction mixture at −10° C. and stirred for 3 h at room temperature. The reaction mixture was quenched with saturated ammonium chloride solution (50 mL) and extracted with ethyl acetate (3×50 mL). The organic layer was washed with brine solution, dried over anhydrous sodium sulfate and concentrated under reduced pressure to give crude; this was purified by column chromatography over neutral alumina using 20% ethyl acetate in pet ether as eluent afforded 3.2 g (54.2) of the product as colorless liquid.

Step D

T-butyl hypochlorite (8.1 mL, 74.72 mmol) was added to a stirred solution of t-butyl carbamate (8.8 g, 75.98 mmol) in 1-propanol (90 mL) and 0.4M aqueous sodium hydroxide (2.98 g in 157 mL water) at 0° C. and stirred for 15 min. A solution of (DHQ) 2PHAL (954 mg, 1.22 mmol) in 1-propanol (90 mL) was added. Then the product of step C (5.0 g, 24.50 mmol) in 1-propanol (90 mL) followed by potassium osmate dihydrate (360 mg, 0.98 mmol) were added and the reaction mixture was stirred for 0.5 h at room temperature. The reaction mixture was quenched with saturated sodium sulphite solution (50 mL) and extracted with ethyl acetate (3×100 mL). The combined organic layer was washed with water, brine, dried over anhydrous sodium sulfate and concentrated under reduced pressure to afford crude 3.0 g of the product.

Step E

Diethylazo dicarboxylate (0.63 mL, 4.0 mmol) was added to a mixture of pthalimide (431 mg, 2.93 mmol), triphenylphospine (1.04 g, 4.0 mmol) and the product of step D (900 mg, 2.67 mmol) in dry THF (200 mL) at 0° C. and heated at 90° C. overnight. The solvent was evaporated in vacuum to afford crude which was purified by column chromatography over silica gel (60-120 mesh) using 20% ethyl acetate in pet ether as eluent to afford 900 mg (72.5%) of the product as light yellow solid.

Step F

Hydrazine hydrate (10 mL) was added to a solution of the product of step E (900 mg, 1.934 mmol) in ethanol (5 mL) in room temperature. Then the reaction mass stirred at 80° C. for 2 h, reaction mass was cooled to room temperature and evaporated to dryness and the RM was diluted with water (50 mL) and extracted with ethyl acetate (3×50 mL). The organic layer was separated and dried over anhydrous sodium sulphate concentrated to afford crude compound column purified by 4% methanol in DCM as eluent in neutral alumina to afford 550 mg (84.5%) of the product as light yellow solid.

Step G

P-anisaldehyde (0.4 mL, 3.27 mmol) was added to a stirred solution of the product of step F (1.0 g, 2.97 mmol) in absolute ethanol (10 mL) and stirred for 5 h at room temperature. Cooled to 0° C., sodium borohydride (395 mg, 10.4 mmol) was added and the reaction mass was stirred for 10 h at room temperature. The reaction mass was poured into saturated ammonium chloride solution and extracted with ethyl acetate (2×75 mL). The combined organic layer was washed successively with water, brine, dried over anhydrous sodium sulfate and concentrated in vacuo to afford 750 mg (55.59%) of the product as white solid.

Step H

3N HCl solution (10 mL) was added to a solution of the product of step G (750 mg, 1.64 mmol) in tetrahydrofuran (10 mL) at 0° C. The reaction mass was warmed to room temperature and stirred for 15 h. THF was evaporated in vacuo and the residue made alkaline using saturated sodium bicarbonate solution (20 mL). The mixture was extracted with dichloromethane (3×50 mL). The combined organic layer was washed successively with water (20 mL), brine (20 mL), dried over anhydrous sodium sulfate, and concentrated in vacuo to afford 500 mg (85.47%) of the product as viscous liquid.

Step I

Triethylamine (0.57 mL, 4.20 mmol) and CDI (327 mg, 2.02 mmol) were added successively to a solution of the product of step H (600 mg, 1.68 mmol) in tetrahydrofuran (10 mL) at room temperature. The reaction mass was heated to 70° C. and maintained for 2 h. The solvent was evaporated in vacuo, the residue dissolved in ethyl acetate (50 mL) and washed successively with water, brine, dried over anhydrous sodium sulfate and concentrated in vacuo to afford crude. The crude compound was purified by column using neutral alumina. The pure compound elute in 2% methanol in chloroform as mobile phase to afford 260 mg (39.1%) of the product as viscous liquid.

Step J

A mixture of the product of step I (200 mg, 0.523 mmol), 1,2-diamino-4-bromobenzene (107 mg, 0.575 mmol), cesium fluoride (159 mg, 1.04 mmol) and copper iodide (15 mg, 0.08 mmol) in 1,4-dioxan (5 ml) was purged with argon gas for 15 min. 1,2-diaminocyclohexane (9 mg, 0.08 mmol) was added to the reaction mixture and purging continued for another 10 min. The reaction mass was stirred at 110-115° C. in a sealed tube for 38 h. The reaction mixture was filtered though celite, washed with dioxan and concentrated under reduced pressure to afford crude. The crude compound was purified by column chromatography over neutral alumina using 2-3% methanol in chloroform as eluent to afford 80 mg (31.3%) of the product as brown solid.

Step K

Formamidine acetate (25 mg, 0.245 mmol) was added to a solution of the product of step J (80 mg, 0.163 mmol) in ACN (5 mL) was heated at 70-75° C. for 2 h. The reaction mixture was concentrated under reduced pressure. The RM was dissolved in 50 mL of 10% methanol in chloroform and organic layer was washed with water, brine, dried over anhydrous sodium sulfate and concentrated in vacuo to afford 60 mg (74%) of the product as a brown solid.

Step L

A solution of the product of step K (60 mg, 0.12 mmol) in trifluoroacetic acid (4 mL) was heated to 4 h at 70° C. then cooled to room temperature. TFA was distilled; the crude compound was dissolved in ethyl acetate, washed with 10% sodium bicarbonate solution, water and brine solution. Dried over anhydrous sodium sulfate and evaporated in vacuo to afford crude which was purified by Prep. TLC using 6% methanol in chloroform as eluent to afford 25 mg (56.4%) of the product as brown solid.

Yield: 0.025 g (55%); MS m/z 379.5 (M+H)$^+$; $^1$H NMR (400 MHz, DMSO-d6): δ 12.28 (s, 1H); 8.11 (s, 1H); 7.80-7.33 (m, 4H); 7.21 (d, 2H); 6.69-(d, 2H); 4.72 (t, 1H); 4.23 (t, 1H); 3.60 (t, 1H); 3.41 (t, 2H); 2.88 (s, 3H); 2.35 (t, 2H); 2.17 (s, 6H) HPLC (λ=214 nm, [A]: rt 7.43 min (91.9%).

Example 231

3-(1H-benzo[d]imidazol-5-yl)-4-(4-(4,4-difluorocyclohexyl)phenyl)oxazolidin-2-one The compound was synthesized from example 210.

Diethyl amino sulpfhur triflouride (0.25 g, 0.31 mL, 1.6 mmol) was added to a solution of Example 210 (0.15 g, 0.4 mmol) in dichloromethane (5 mL) at 0° C. and heated at reflux for 48 hours. The reaction mixture was quenched with ice, basified with saturated bicarbonate solution and extracted with dichloromethane. Combined organic layer was washed with water, brine, dried over anhydrous sodium sulfate and evaporated to dryness to get 140 mg of the product as brown solid. Yield: 0.02 g (15.0%), MS m/z 398.4 (M+H)$^+$; $^1$H-NMR (400 MHz, CDCl3): δ 7.98 (s, 1H), 7.70 (s, 1H), 7.52 (s, 1H), 7.21-7.1 (Merged with CDCl3, 4H), 5.45-5.41 (q, 1H), 4.81 (t, 1H), 4.25-4.22 (q, 1H), 2.53 (d, 1H), 2.17-2.02 (m, 2H), 1.86-1.25 (m, 7H), HPLC (λ=214 nm, [A]: rt 14.79 min (99.3%)

Example 232

2-(1H-benzo[d]imidazol-5-yl)-4,7-difluoro-3-(4-propoxyphenyl)isoindolin-1-one

The compound was synthesized according to method 11.

2-(4-Propoyxbenzoyl)-3,6-difluorobenzoic acid (577 mg; 1.8 mmol), DCC (371 mg; 1.8 mmol), benzimidazol-5 (6)-amine (239 mg; 1.8 mmol), TFA (1.28 ml) and triethylsilane (0.204 ml; 1.28 mmol; 4 eq.) and was additional purified by semipreparative HPLC.

Yield: 0.043 g (5.6%); MS m/z: 420.3 [M+H]$^+$; $^1$H-NMR (DMSO d$_6$, 400 MHz): 0.86 (t, 3H, $^3$J=7.5 Hz); 1.55-1.64 (m, 2H); 3.74-3.77 (m, 2H); 6.65 (s, 1H); 6.72-6.74 (m, 2H); 7.14-7.16 (m, 2H); 7.31-7.48 (br m, 4H); 7.707-7.711 (m, 1H); 8.15 (s, 1H); 12.41 (br s, 1H); HPLC (λ=214 nm), [B]: rt 14.98 min (99.3%).

Example 233

2-(H-imidazo[1,2-a]pyridin-7-yl)-3-(3,4-dimethoxyphenyl)isoindolin-1-one

7-BromoH-imidazo[1,2-a]pyridine (39 mg; 0.2 mmol; 1 eq.) was dissolved in dioxane (5 ml). 3-(3,4-dimethoxyphenyl)isoindolin-1-one (59 mg; 0.22 mmol; 1.1 eq.), copper(I) iodide (4 mg; 0.02 mmol; 0.1 eq.), cesium fluoride (60 mg; 0.4 mmol; 2 eq.) and diaminocyclohexane (3 mg; 0.02 mmol; 0.1 eq) were added and the mixture was stirred at 100° C. under argon over night. The reaction was quenched with sat. NaHCO$_3$-solution and extracted with EtOAc (3×25 ml). The combined organic layers were dried over Na$_2$SO$_4$, evaporated and purified by flashchromatography on silica with a CHCl$_3$/MeOH gradient.

Yield: 24 mg (31%); MS m/z 386.3 (M+H)$^+$; $^1$H NMR (400 MHz, DMSO-D$_6$): δ 3.61 (s, 3H); 3.64 (s, 3H); 6.56 (s, 1H); 6.76-6.82 (m, 2H); 6.908-6.913 (m, 1H); 7.35 (d, 1H, $^3$J=7.5 Hz); 7.45-7.62 (br m, 5H); 7.68-7.69 (m, 1H); 7.84 (d, 1H, $^3$J=7.5 Hz); 8.44 (d, 1H, $^3$J=7.5 Hz); HPLC (λ=214 nm), [B]: rt 11.93 min (91.4%).

Example 234

(S)-2-(H-imidazo[1,2-a]pyridin-7-yl)-3-(3,4-dimethoxyphenyl)isoindolin-1-one

7-BromoH-imidazo[1,2-a]pyridine (39 mg; 0.2 mmol; 1 eq.) was dissolved in dioxane (5 ml). (S)-3-(3,4-dimethoxyphenyl)isoindolin-1-one (59 mg; 0.22 mmol; 1.1 eq.), copper(I) iodide (4 mg; 0.02 mmol; 0.1 eq.), cesium fluoride (60 mg; 0.4 mmol; 2 eq.) and diaminocyclohexane (3 mg; 0.02 mmol; 0.1 eq) were added and the mixture was stirred at 100° C. under argon over night. The reaction was quenched with sat. NaHCO$_3$-solution and extracted with EtOAc (3×25 ml). The combined organic layers were dried over Na$_2$SO$_4$, evaporated and purified by semi-preparative HPLC.

Yield: 21 mg (27%); MS m/z 386.1 (M+H)$^+$; $^1$H NMR (400 MHz, DMSO-D$_6$): δ 3.64 (s, 3H); 3.67 (s, 3H); 6.59 (s, 1H); 6.81-6.86 (m, 2H); 6.93 (br s, 1H); 7.37-7.38 (m, 1H); 7.48-7.57 (m, 4H); 7.61-7.65 (m, 1H); 7.71 (br s, 1H); 7.81 (s, 1H); 7.85-7.87 (m, 1H); HPLC (λ=214 nm), [B]: rt 11.61 min (98.4%).

Example 235

(S)-3-(3,4-dimethoxyphenyl)-2-(3-methylH-imidazo[1,2-a]pyridin-7-yl)isoindolin-1-one 7-Bromo-3-methylH-imidazo[1,2-a]pyridine (42 mg; 0.2 mmol; 1 eq.) was dissolved in dioxane (5 ml). (S)-3-(3,4-dimethoxyphenyl)isoindolin-1-one (59 mg; 0.22 mmol; 1.1 eq.), copper(I) iodide (4 mg; 0.02 mmol; 0.1 eq.), cesium fluoride (60 mg; 0.4 mmol; 2 eq.) and diaminocyclohexane (3 mg; 0.02 mmol; 0.1 eq) were added and the mixture was stirred at 100° C. under argon over night. The reaction was quenched with sat. NaHCO$_3$-solution and extracted with EtOAc (3×25 ml). The combined organic layers were dried over Na$_2$SO$_4$, evaporated and purified by semi-preparative HPLC.

Yield: 21 mg (27%); MS m/z 400.2 (M+H)$^+$; $^1$H NMR (400 MHz, DMSO-D$_6$): δ 2.39 (s, 3H); 3.64 (s, 3H); 3.66 (s, 3H); 6.60 (s, 1H); 6.81-6.82 (m, 2H); 6.91-6.93 (m, 1H); 7.27 (s, 1H); 7.35-7.38 (m, 1H); 7.50-7.57 (m, 3H); 7.69-7.79 (m, 1H); 7.85-7.87 (m, 1H); 8.18-8.20 (m, 1H); HPLC (λ=214 nm), [B]: rt 12.13 min (92.9%).

Activity Screening
Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Hφorsholm, Denmark) in 0.2 M Tris/HCl, pH 8.0 containing 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-ββNA from H-Gln-βNA per minute under the described conditions.

In a second fluorometric assay, QC was activity determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 µl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 K$_M$. For detailed investigations of the inhibition and determination of K$_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Results

Examples 2, 3, 5, 7-12, 14-30, 32-43, 45-51, 53-62, 65-66, 68, 70-92, 95-96, 98, 99, 102, 116, 118, 121-123, 125-151, 156-173, 175, 177-179, 181-182, 184-186, 188-192, 194-197, 199-201, 203-221, 224-228 and 232-234 were tested and gave hQC IC$_{50}$ values of less than 10 µM. Certain specific values are given in the table below:

| Example no. | hQC IC$_{50}$ [µM] | hQC K$_i$ [µM] |
|---|---|---|
| 12 | 0.482 | 0.0625 |
| 13 | 30.2 | 7.25 |
| 14 | 0.238 | 0.0374 |
| 43 | 0.254 | 0.0408 |
| 55 | 0.397 | 0.075 |
| 60 | 0.882 | 0.149 |
| 73 | 0.170 | 0.0336 |
| 89 | 0.160 | 0.0125 |
| 142 | 0.297 | 0.0535 |
| 145 | 0.240 | 0.0588 |

Analytical Methods
HPLC:

Method [A]: The analytical HPLC-system consisted of a Merck-Hitachi device (model LaChrom®) utilizing a LUNA® RP 18 (5 µm), analytical column (length: 125 mm, diameter: 4 mm), and a diode array detector (DAD) with λ=214 nm as the reporting wavelength. The compounds were analyzed using a gradient at a flow rate of 1 mL/min; whereby eluent (A) was acetonitrile, eluent (B) was water, both containing 0.1% (v/v) trifluoro acetic acid applying the following gradient:: 0 min-5 min→5% (A), 5 min-17 min→5-15% (A), 15 min-27 min→15-95% (A) 27 min-30 min→95% (A), Method [B]: 0 min-15 min→5-60% (A), 15 min-20 min→60-95% (A), 20 min-23 min→95% (A), Method [C]: 0 min-20 min→5-60% (A), 20 min-25 min→60-95% (A). 25 min-30 min→95% (A).

Method [B]: The analytical HPLC-system consisted of a Agilent MSD 1100 utilizing a Waters SunFire RP 18 (2.5 µm), analytical column (length: 50 mm, diameter: 2.1 mm), and a diode array detector (DAD) with λ=254 nm as the reporting wavelength. The compounds were analyzed using a gradient at a flow rate of 0.6 mL/min; whereby eluent (A) was acetonitrile, eluent (B) was water and eluent (C) 2% formic acid in acetonitrile applying the following gradient:

| Time min | % Solvent B | % Solvent C |
|---|---|---|
| 0 | 90 | 5 |
| 2.5 | 10 | 5 |
| 4 | 10 | 5 |
| 4.5 | 90 | 5 |
| 6 | 90 | 5 |

The purities of all reported compounds were determined by the percentage of the peak area at 214 nm.

Mass-Spectrometry, NMR-Spectroscopy:

ESI-Mass spectra were obtained with a SCIEX API 365 spectrometer (Perkin Elmer) utilizing the positive ionization mode.

The $^1$H NMR-Spectra (500 MHz) were recorded at a BRUKER AC 500. The solvent was DMSO-D$_6$, unless otherwise specified. Chemical shifts are expressed as parts per million (ppm) downfiled from tetramethylsilan. Splitting patterns have been designated as follows: s (singulet), d (doublet), dd (doublet of doublet), t (triplet), m (multiplet) and br (broad signal).

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals are recorded and filtered using LeCroy 9350M digital storage oscilloscope linked to a personal computer. Samples (5 μl) were mixed with equal volumes of the matrix solution. For matrix solution DHAP/DAHC was used, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 μl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of Glu$^1$-cyclization, Aβ-derived peptides were incubated in 100 μl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC is added all 24 hours. In case of Aβ(3-21)a, the assays contained 1% DMSO. At different times, samples are removed from the assay tube, peptides extracted using ZipTips (Millipore) according to the manufacturer's recommendations, mixed with matrix solution (1:1 v/v) and subsequently the mass spectra recorded. Negative controls either contain no QC or heat deactivated enzyme. For the inhibitor studies the sample composition was the same as described above, with exception of the inhibitory compound added (5 mM or 2 mM of a test compound of the invention).

---

What is claimed is:

1. A compound of formula (I):

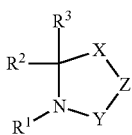

(I)

or a pharmaceutically acceptable salt, solvate or polymorph thereof, including all tautomers and stereoisomers thereof, wherein:

(a) $R^1$ represents heteroaryl, -carbocyclyl-heteroaryl, —$C_{2-6}$alkenylheteroaryl, —$C_{1-6}$alkylheteroaryl, or $(CH_2)_aCR^5R^6(CH_2)_b$heteroaryl wherein a and b independently represent integers 0-5 provided that a+b=0-5 and $R^5$ and $R^6$ are alkylene which together with the carbon to which they are attached form a $C_3$-$C_5$ cycloalkyl group;

in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —$C(O)OH$, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —$C(O)NH(C_{3-10}$cycloalkyl); and in which any of aforesaid carbocyclyl groups may optionally be substituted by one or more groups selected from $C_{1-4}$alkyl, oxo, halogen and $C_{1-4}$alkoxy;

(b) $R^2$ and $R^3$ are independently selected as follows, (i) $R^2$ represents (1) H, $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl;

in which any of aforesaid aryl and heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, $C_{1-6}$alkoxy-$C_{1-6}$alkoxy-, nitro, halogen, halo$C_{1-6}$alkyl, halo$C_{1-6}$alkoxy, cyano, hydroxyl, —C(O)OH, —$NH_2$, —NH$C_{1-4}$ alkyl, —N($C_{1-4}$alkyl)($C_{1-4}$alkyl), —N($C_{1-4}$alkyl)($C_{1-4}$alkyl)-N($C_{1-4}$alkyl)($C_{1-4}$ alkyl), —$C_{1-4}$alkyl-N($C_{1-4}$alkyl)($C_{1-4}$alkyl), —$C_{1-4}$alkoxy-N($C_{1-4}$alkyl)($C_{1-4}$alkyl), —N($C_{3-8}$ cycloalkyl)($C_{3-8}$cycloalkyl), —N(—$C_{1-6}$alkyl-$C_{1-6}$alkoxy)(—$C_{1-6}$alkyl-$C_{1-6}$alkoxy), —C(O)N($C_{1-4}$alkyl)($C_{1-4}$alkyl), —C(O)$NH_2$, —C(O)NH($C_{1-4}$alkyl) and —C(O)NH($C_{3-10}$cycloalkyl); and in which any of aforesaid carbocyclyl and heterocyclyl groups may optionally be substituted by one or more groups selected from $C_{1-4}$alkyl, oxo, halogen, —C(O)$C_{1-6}$alkyl and $C_{1-4}$alkoxy; or (2) phenyl substituted by phenyl, phenyl substituted by a monocyclic heteroaryl group, phenyl substituted by phenoxy, phenyl substituted by heterocyclyl, phenyl substituted by heterocyclyl wherein said heterocyclyl is substituted by phenyl, phenyl substituted by —O—$C_{1-4}$alkyl-heterocyclyl, phenyl substituted by benzyloxy, phenyl substituted by carbocyclyl, phenyl substituted by carbocyclyl wherein said carbocyclyl is substituted by heterocyclyl, phenyl substituted by —O-carbocyclyl, heterocyclyl substituted by phenyl, carbocyclyl substituted by phenyl, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by a monocyclic heterocyclyl group), —$C_{1-4}$alkyl(phenyl substituted by an —O-carbocyclyl group), —$C_{1-4}$alkyl(phenyl substituted by benzyloxy), —$C_{1-4}$alkyl(optionally substituted phenyl fused to optionally substituted carbocyclyl or —$C_{1-4}$alkyl(optionally substituted phenyl fused to optionally substituted heterocyclyl);

in which any of aforesaid phenyl, benzyloxy and heteroaryl groups may optionally be substituted by one or more groups selected from $C_{1-4}$alkyl, halogen and $C_{1-4}$alkoxy, and in which any of aforesaid carbocyclyl and heterocyclyl groups may optionally be substituted by one or more groups selected from methyl, phenyl, oxo, halogen, hydroxyl and $C_{1-4}$alkoxy; and (ii) $R^3$ represents H, —$C_{1-4}$alkyl or aryl;

in which aforesaid aryl may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$ alkyl), —C(O)$NH_2$, —C(O)NH($C_{1-4}$alkyl) and, —C(O)NH($C_{3-10}$cycloalkyl); or (c) $R^2$ and $R^3$ are jointly selected as follows, (1) $R^2$ and $R^3$ are joined to form a carbocyclyl ring which is optionally substituted by one or more $C_{1-2}$alkyl groups;

(2) $R^2$ and $R^3$ are joined to form a carbocyclyl ring which is fused to phenyl, wherein aforesaid carbocyclyl and/or phenyl may optionally be substituted by one or more groups selected from $C_{1-4}$alkyl, halogen and $C_{1-4}$alkoxy; or (3) $R^2$ and $R^3$ are joined to form a carbocyclyl ring which is fused to monocyclic heteroaryl, wherein aforesaid carbocyclyl and/or heteroaryl may optionally be substituted by one or more groups selected from $C_{1-4}$alkyl, halogen and $C_{1-4}$alkoxy;

(d) X and Z are independently selected as follows, (i) X represents C=O, O, $CR^7R^8$, —O—$CH_2$— or —$CH_2$—$CH_2$-; and (ii) Z represents —N—$R^4$, O or $CHR^{10}$, such that when X represents O, Z must represent $CHR^{10}$; or (e) X and Z are jointly selected to represent two adjacent carbon atoms of a phenyl ring which is fused in that position and which is optionally substituted by one or more halogen or $C_{1-2}$alkyl groups; and (f) Y represents $CHR^9$, C=O or C=S;

wherein, $R^4$ represents H, —$C_{1-8}$alkyl, —C(O)$C_{1-6}$alkyl or —$NH_2$;

$R^7$ and $R^8$ independently represent H, —$C_{1-4}$ alkyl or aryl;

in which said aforesaid aryl may be optionally substituted by $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —$NH_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)$NH_2$, —C(O)NH($C_{1-4}$alkyl) and, —C(O)NH($C_{3-10}$cycloalkyl); and $R^9$ and $R^{10}$ independently represent H or methyl;

provided that the moiety —Y—Z—X— represents a moiety other than —C(=O)—N(—$R^4$)—C(=O)— or —C(=S)—N(—$R^4$)—C(=O)—.

2. A compound according to claim 1, wherein $R^1$ represents unsubstituted heteroaryl or heteroaryl optionally substituted by one or more $C_{1-6}$ alkyl, halogen or $C_{1-6}$ haloalkyl groups.

3. A compound according to claim 2, wherein $R^1$ represents a phenyl ring fused to a 5-membered heteroaryl ring wherein $R^1$ is linked to the core of formula (I) through the phenyl ring.

4. A compound according to claim 2 wherein $R^1$ represents

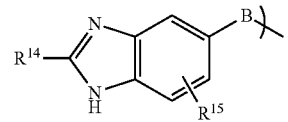

wherein:

B represents a bond, —$CH_2$—, —$CH_2$—$CH_2$—, —CH(Me)—, —CH(Me)-$CH_2$— or —$CH_2$—CH(Me)- and $R^{14}$ and $R^{15}$ independently represent H or $C_{1-2}$alkyl.

5. A compound according to claim 4 wherein $R^1$ represents

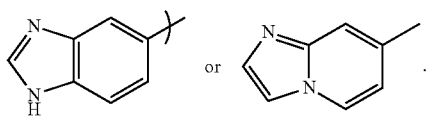

6. A compound according to claim 5 wherein $R^1$ represents

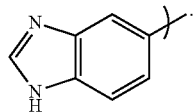

7. A compound according to claim 1, wherein $R^2$ represents aryl, heteroaryl, phenyl substituted by phenyl, phenyl fused to heterocyclyl or $R^2$ and $R^3$ are joined to form a carbocyclyl ring which is fused to phenyl; the aforesaid aryl, heteroaryl, phenyl, heterocyclyl and carbocyclyl optionally being substituted.

8. A compound according to claim 7 wherein $R^2$ represents aryl, heteroaryl, phenyl substituted by phenyl or phenyl fused to heterocyclyl; the aforesaid aryl, heteroaryl, phenyl and heterocyclyl optionally being substituted.

9. A compound according to claim 8 wherein $R^2$ represents optionally substituted aryl.

10. A compound according to claim 9 wherein $R^2$ represents phenyl substituted by one or more groups selected from $C_{1-6}$ alkyl, $C_{1-6}$ alkoxy, hydroxyl, halo$C_{1-6}$ alkyl, halo$C_{1-6}$ alkoxy, halogen, $C_{1-6}$alkoxy-$C_{1-6}$alkyl-, $C_{1-6}$alkoxy-$C_{1-6}$alkoxy-, —N($C_{1-4}$alkyl)($C_{1-4}$alkyl)-N($C_{1-4}$alkyl)($C_{1-4}$alkyl), —N($C_{1-4}$alkyl)($C_{1-4}$alkyl), —N($C_{3-8}$cycloalkyl)($C_{3-8}$cycloalkyl), —$C_{1-4}$alkyl-N($C_{1-4}$alkyl)($C_{1-4}$alkyl), —$C_{1-4}$ alkoxy-N($C_{1-4}$alkyl)($C_{1-4}$alkyl), —N(—$C_{1-6}$alkyl-$C_{1-6}$alkoxy)(—$C_{1-6}$alkyl-$C_{1-6}$alkoxy).

11. A compound according to claim 10 wherein $R^2$ represents phenyl substituted by one or more groups selected from methyl, methoxy, ethoxy, propoxy, butoxy, pentoxy, isopropyloxy, hydroxyl, trifluoromethyl, tetrafluoroethyloxy, chlorine, fluorine, —(CH$_2$)$_3$—OMe, —O—(CH$_2$)$_2$—OMe, —N(Me)-(CH$_2$)$_2$—N(Me)$_2$, —N(ethyl)(ethyl)), —N(cyclopropyl)(cyclopropyl)), —(CH$_2$)$_3$—N(methyl)(methyl), —O(CH$_2$)$_2$—N(methyl)(methyl)), —N((CH$_2$)$_2$OMe)(CH$_2$)$_2$OMe)).

12. A compound according to claim 11 wherein $R^2$ represents phenyl substituted by one or more $C_{1-6}$ alkoxy groups.

13. A compound according to claim 12 wherein $R^2$ represents phenyl substituted by one or more groups selected from methoxy, ethoxy, propoxy, butoxy, pentoxy or isopropyloxy.

14. A compound according to claim 13 wherein $R^2$ represents phenyl substituted by a propoxy group.

15. A compound according to claim 1, wherein $R^3$ represents H.

16. A compound according to claim 1, wherein $R^4$ represents H.

17. A compound according to claim 1, wherein X represents $CR^7R^8$, Y represents C=O and Z represents —N—$R^4$.

18. A compound according to claim 16, wherein X represents CH$_2$, Y represents C=O and Z represents —NH.

19. A compound according to claim 1, wherein X represents C=O, Y represents CHR$^9$ and Z represents —N—$R^4$.

20. A compound according to claim 1, wherein X represents $CR^7R^8$, Y represents C=O and Z represents O.

21. A compound according to claim 1, wherein X represents $CR^7R^8$, Y represents CHR$^9$ and Z represents CHR$^{10}$.

22. A compound according to claim 1, wherein X represents $CR^7R^8$, Y represents C=O and Z represents CHR$^{10}$.

23. A compound according to claim 1, wherein X and Z represent two adjacent carbon atoms of a phenyl ring which is fused in that position and is optionally substituted by one or more halogen or $C_{1-2}$alkyl groups and Y represents C=O.

24. A compound according to claim 1, wherein X represents —O—CH$_2$—, Y represents CO and Z represents CHR$^{10}$.

25. A compound according to claim 1, wherein X represents —CH$_2$—CH$_2$—, Y represents CO and Z represents O.

26. A compound according to any one of examples 1 to 109, 120 to 235 or a pharmaceutically acceptable salt, solvate or polymorph thereof, including all tautomers and stereoisomers.

27. A compound according to any one of examples 12 to 14 or a pharmaceutically acceptable salt, solvate or polymorph thereof, including all tautomers and stereoisomers.

28. A pharmaceutical composition comprising a compound of claim 1 optionally in combination with one or more therapeutically acceptable diluents or carriers.

29. The pharmaceutical composition of claim 28, which comprises additionally at least one compound, selected from the group consisting of neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

30. The pharmaceutical composition of claim 28, which comprises additionally at least one compound, selected from the group consisting of PEP-inhibitors, LiCl, inhibitors of inhibitors of DP IV or DP IV-like enzymes, acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors, interferon-tau (trophoblastin) and SAIK-MS.

31. A process for preparation of a compound of formula (I) according to claim 1, which comprises:
(a) preparing a compound of formula (I) from a compound of formula (II):

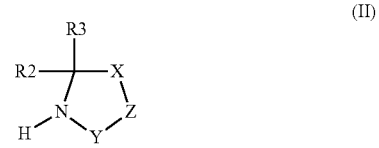

(II)

wherein $R^2$, $R^3$, X, Y and Z are as defined in claim 1;
(b) preparing a compound of formula (I) wherein $R^3$ represents hydrogen, Y represents CO, Z represents —N—$R^4$ and X represents $CR^7R^8$ and $R^8$ represents hydrogen by hydrogenation of a compound of formula (III):

(III)

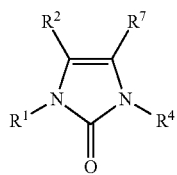

wherein $R^1$, $R^2$, $R^4$ and $R^7$ are as defined in claim 1;
(c) preparing a compound of formula (I) wherein $R^3$ represents hydrogen, Y represents CO, Z represents $CH_2$ and X represents $CH_2$ by hydrogenation of a compound of formula (IV):

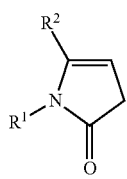

(IV)

wherein $R^1$ and $R^2$ are as defined in claim 1;
(d) preparing a compound of formula (I) wherein $R^3$ represents hydrogen, Y represents CO, Z represents —N—$R^4$ and X represents $CH_2$ from a compound of formula (V):

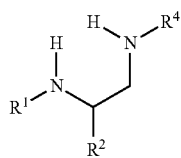

(V)

wherein $R^1$, $R^2$ and $R^4$ are as defined in claim 1;
(e) preparing a compound of formula (I) wherein $R^3$ represents hydrogen, Y represents $CH_2$, Z represents —N—$R^4$ and X represents CO from a compound of formula (VI):

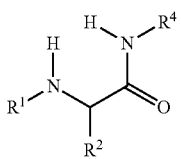

(VI)

wherein $R^1$, $R^2$ and $R^4$ are as defined in claim 1;
(f) preparing a compound of formula (I) wherein $R^1$ represents 1H-benzo[d]imidazol-5-yl, $R^3$ represents hydrogen, Y represents CO, Z represents —NH and X represents $CH_2$ from a compound of formula (VII):

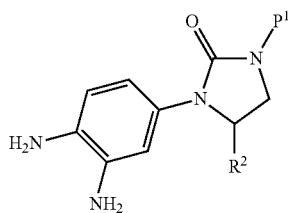

(VII)

wherein $R^2$ is as defined in claim 1;
(g) preparing a compound of formula (I) wherein $R^3$ represents hydrogen, Y represents CO
and X and Z are joined to form a carbocyclic ring or else X and Z represent two adjacent
carbon atoms of a phenyl ring which is fused in that position and is optionally substituted by
one or more halogen or $C_{1-2}$alkyl groups, from a compound of formula (VIII):

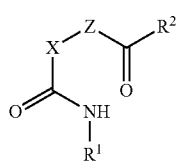

(VIII)

wherein $R^1$, $R^2$, X and Z are as defined in claim 1;
(h) preparing a compound of formula (I) wherein X represents S, for example a compound of formula (I) wherein $R^3$ represents hydrogen, Y represents CO, Z represents —$CH_2$ and X represents S from a corresponding compound in which X represents O;
(i) preparing a compound of formula (I) wherein $R^4$ represents —$NH_2$ from a corresponding compound of formula (I) wherein $R^4$ represents H by treatment with nitrite followed by reduction;
(j) preparing a compound of formula (I) wherein $R^4$ represents —$C_{1-8}$alkyl or —C(O)$C_{1-6}$alkyl from a corresponding compound of formula (I) wherein $R^4$ represents H by treatment with an alkylating or alkanoylating agent;
(k) interconversion of compounds of formula (I); or
(l) deprotecting a compound of formula (I) which is protected.

32. A compound according to claim 2, wherein $C_{1-6}$ alkyl is methyl, halogen is fluorine, or $C_{1-6}$ haloalkyl is trifluoromethyl.

33. A compound according to claim 23, wherein the one or more $C_{1-2}$alkyl groups comprise 2,5-dichlorophenyl or 3,4-dichlorophenyl.

* * * * *

UNITED STATES PATENT AND TRADEMARK OFFICE
CERTIFICATE OF CORRECTION

PATENT NO. : 8,486,940 B2
APPLICATION NO. : 12/880369
DATED : July 16, 2013
INVENTOR(S) : Ulrich Heiser et al.

It is certified that error appears in the above-identified patent and that said Letters Patent is hereby corrected as shown below:

In the Claims:

Column 340, line 55-57:

"33. A compound according to claim 23, wherein the one or more C1-2alkyl groups comprise 2,5-dichlorophenyl or 3,4-dichlorophenyl."

should be

--33. A compound according to claim 23, wherein the optionally substituted phenyl ring comprises 2,5-dichlorophenyl or 3,4-dichlorophenyl.--

Signed and Sealed this
First Day of October, 2013

Teresa Stanek Rea
*Deputy Director of the United States Patent and Trademark Office*

SEQUENCE LISTING

```
<160> NUMBER OF SEQ ID NOS: 20

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40
```

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 5

Gln Gly Pro Trp Leu Glu Glu Glu Glu Ala Tyr Gly Trp Met Asp
1               5                   10                  15

Phe

<210> SEQ ID NO 6
<211> LENGTH: 13
<212> TYPE: PRT
<213> ORGANISM: Homo sapiens

<400> SEQUENCE: 6

Gln Leu Tyr Glu Asn Lys Pro Arg Arg Pro Tyr Ile Leu
1               5                   10

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 7

Gln His Trp Ser Tyr Gly Leu Arg Pro Gly
1               5                   10

<210> SEQ ID NO 8
<211> LENGTH: 97
<212> TYPE: PRT
<213> ORGANISM: Homo sapiens

<400> SEQUENCE: 8

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
        35                  40                  45

Asn Arg Glu Val Cys Thr Asn Pro Asn Asp Asp Trp Val Gln Glu Tyr
    50                  55                  60

```
Ile Lys Asp Pro Asn Leu Pro Leu Leu Pro Thr Arg Asn Leu Ser Thr
 65                  70                  75                  80

Val Lys Ile Ile Thr Ala Lys Asn Gly Gln Pro Gln Leu Leu Asn Ser
                 85                  90                  95

Gln

<210> SEQ ID NO 9
<211> LENGTH: 76
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
  1               5                  10                  15

Asn Arg Lys Ile Pro Ile Gln Arg Leu Glu Ser Tyr Thr Arg Ile Thr
                 20                  25                  30

Asn Ile Gln Cys Pro Lys Glu Ala Val Ile Phe Lys Thr Lys Arg Gly
             35                  40                  45

Lys Glu Val Cys Ala Asp Pro Lys Glu Arg Trp Val Arg Asp Ser Met
 50                  55                  60

Lys His Leu Asp Gln Ile Phe Gln Asn Leu Lys Pro
 65                  70                  75

<210> SEQ ID NO 10
<211> LENGTH: 76
<212> TYPE: PRT
<213> ORGANISM: Homo sapiens

<400> SEQUENCE: 10

Gln Pro Asp Ala Ile Asn Ala Pro Val Thr Cys Cys Tyr Asn Phe Thr
  1               5                  10                  15

Asn Arg Lys Ile Ser Val Gln Arg Leu Ala Ser Tyr Arg Arg Ile Thr
                 20                  25                  30

Ser Ser Lys Cys Pro Lys Glu Ala Val Ile Phe Lys Thr Ile Val Ala
             35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75

<210> SEQ ID NO 11
<211> LENGTH: 68
<212> TYPE: PRT
<213> ORGANISM: Homo sapiens

<400> SEQUENCE: 11

Gln Val Gly Thr Asn Lys Glu Leu Cys Cys Leu Val Tyr Thr Ser Trp
  1               5                  10                  15

Gln Ile Pro Gln Lys Phe Ile Val Asp Tyr Ser Glu Thr Ser Pro Gln
                 20                  25                  30

Cys Pro Lys Pro Gly Val Ile Leu Leu Thr Lys Arg Gly Arg Gln Ile
             35                  40                  45

Cys Ala Asp Pro Asn Lys Lys Trp Val Gln Lys Tyr Ile Ser Asp Leu
 50                  55                  60

Lys Leu Asn Ala
 65

<210> SEQ ID NO 12
```

```
<211> LENGTH: 373
<212> TYPE: PRT
<213> ORGANISM: Homo sapiens

<400> SEQUENCE: 12

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
                100                 105                 110

Ser Leu Glu Pro Thr Pro Ser Ser Gln Glu Ala Gln Arg Ala Leu Gly
            115                 120                 125

Thr Ser Pro Glu Leu Pro Thr Gly Val Thr Gly Ser Ser Gly Thr Arg
130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
            195                 200                 205

Ser Pro Ala Pro Glu Glu Asn Ala Pro Ser Glu Gly Gln Arg Val Trp
210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Pro Val Ser Ser Glu Gly Thr
            260                 265                 270

Pro Ser Arg Glu Pro Val Ala Ser Gly Ser Trp Thr Pro Lys Ala Glu
            275                 280                 285

Glu Pro Ile His Ala Thr Met Asp Pro Gln Arg Leu Gly Val Leu Ile
290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
            355                 360                 365

Val Leu Val Pro Val
            370

<210> SEQ ID NO 13
```

```
<211> LENGTH: 76
<212> TYPE: PRT
<213> ORGANISM: Homo sapiens

<400> SEQUENCE: 13

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 14
<211> LENGTH: 33
<212> TYPE: PRT
<213> ORGANISM: Homo sapiens

<400> SEQUENCE: 14

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
                20                  25                  30

Leu

<210> SEQ ID NO 15
<211> LENGTH: 11
<212> TYPE: PRT
<213> ORGANISM: Homo sapiens

<400> SEQUENCE: 15

Arg Pro Lys Pro Gln Gln Phe Phe Gly Leu Met
1               5                   10

<210> SEQ ID NO 16
<211> LENGTH: 32
<212> TYPE: PRT
<213> ORGANISM: Artificial sequence
<220> FEATURE:
<223> OTHER INFORMATION: Synthetic peptide

<400> SEQUENCE: 16

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
                20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic peptide

<400> SEQUENCE: 17

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
                20                  25                  30
```

```
<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 19
<211> LENGTH: 34
<212> TYPE: PRT
<213> ORGANISM: Artificial sequence
<220> FEATURE:
<223> OTHER INFORMATION: Synthetic peptide

<400> SEQUENCE: 19

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gln Tyr Asn Ala Asp
1               5
```